US011427558B1

(12) United States Patent
Garofalo et al.

(10) Patent No.: US 11,427,558 B1
(45) Date of Patent: Aug. 30, 2022

(54) INDAZOLES AND AZAINDAZOLES AS LRRK2 INHIBITORS

(71) Applicant: ESCAPE Bio, Inc., South San Francisco, CA (US)

(72) Inventors: Albert W. Garofalo, South San Francisco, CA (US); Stéphane De Lombaert, Brisbane, CA (US); Jacob Bradley Schwarz, South San Francisco, CA (US); Daniele Andreotti, San Giovanni Lupatoto (IT); Fabio Maria Sabbatini, Verona (IT); Elena Serra, Lecce (IT); Silvia Bernardi, Verona (IT); Marco Migliore, Verona (IT); Federica Budassi, Urbino (IT); Claudia Beato, Verona (IT)

(73) Assignee: ESCAPE Bio, Inc., South San Francisco, CA (US)

( * ) Notice: Subject to any disclaimer, the term of this patent is extended or adjusted under 35 U.S.C. 154(b) by 0 days.

(21) Appl. No.: 16/925,398

(22) Filed: Jul. 10, 2020

Related U.S. Application Data

(60) Provisional application No. 62/937,979, filed on Nov. 20, 2019, provisional application No. 62/872,891, filed on Jul. 11, 2019.

(51) Int. Cl.
| | |
|---|---|
| *C07D 401/12* | (2006.01) |
| *C07D 471/04* | (2006.01) |
| *C07D 405/14* | (2006.01) |
| *C07D 401/14* | (2006.01) |
| *C07D 417/14* | (2006.01) |
| *C07D 403/12* | (2006.01) |
| *C07D 405/12* | (2006.01) |
| *C07D 413/14* | (2006.01) |
| *C07D 405/04* | (2006.01) |

(52) U.S. Cl.
CPC ......... *C07D 401/12* (2013.01); *C07D 401/14* (2013.01); *C07D 403/12* (2013.01); *C07D 405/04* (2013.01); *C07D 405/12* (2013.01); *C07D 405/14* (2013.01); *C07D 413/14* (2013.01); *C07D 417/14* (2013.01); *C07D 471/04* (2013.01)

(58) Field of Classification Search
CPC combination set(s) only.
See application file for complete search history.

(56) References Cited

U.S. PATENT DOCUMENTS

| 6,258,822 B1 * | 7/2001 | Geyer ............... C07C 257/18 514/275 |
| 7,872,039 B2 | 1/2011 | Dorsch et al. |
| 10,005,720 B2 | 6/2018 | Sexton et al. |
| 2003/0134836 A1 | 7/2003 | Elbaum et al. |
| 2003/0203922 A1 | 10/2003 | Patel et al. |
| 2006/0270686 A1 | 11/2006 | Kelly et al. |
| 2008/0280891 A1 | 11/2008 | Kelly et al. |
| 2009/0054397 A1 | 2/2009 | Ohi et al. |
| 2009/0270394 A1 | 10/2009 | Galemmo et al. |
| 2011/0263612 A1 | 10/2011 | Whitten et al. |
| 2013/0109661 A1 | 5/2013 | Hermann et al. |
| 2014/0154805 A1 | 6/2014 | Shi et al. |
| 2014/0200227 A1 | 7/2014 | Xue et al. |
| 2016/0024071 A1 | 1/2016 | Garofalo et al. |
| 2016/0113931 A1 | 4/2016 | Lee et al. |
| 2021/0261553 A1 | 8/2021 | Garofalo et al. |
| 2021/0386721 A1 | 12/2021 | Zhu et al. |

FOREIGN PATENT DOCUMENTS

| CN | 107176932 | 6/2020 |
| DE | 102004051277 | 4/2006 |
| DE | 102005014089 | 9/2006 |
| EP | 3889150 | 10/2021 |
| FR | 2889526 | 2/2012 |
| WO | WO 9730119 | 8/1997 |
| WO | WO 9809961 | 3/1998 |
| WO | WO 2000/006173 | 2/2000 |
| WO | WO 2002055501 | 7/2002 |
| WO | WO 2002066470 | 8/2002 |
| WO | WO 2002068406 | 9/2002 |
| WO | WO 2004078723 | 9/2004 |
| WO | WO 2004078746 | 9/2004 |
| WO | WO 2004098518 | 11/2004 |
| WO | WO 2004108133 | 12/2004 |
| WO | WO 2005074642 | 8/2005 |
| WO | WO 2005123688 | 12/2005 |
| WO | WO 2006032851 | 3/2006 |
| WO | WO 2006053109 | 5/2006 |
| WO | WO 2006053227 | 5/2006 |
| WO | WO 2006081230 | 8/2006 |
| WO | WO 2006099379 | 9/2006 |
| WO | WO 2006100100 | 9/2006 |
| WO | WO 2006132914 | 12/2006 |
| WO | WO 2007017577 | 2/2007 |

(Continued)

OTHER PUBLICATIONS

Atzrodt et al., "The renaissance of H/D exchange," Angew. Chem. Int. Ed., 2007, 46(41):7744-7765.
Berge et al., "Pharmaceutical Salts," J Pham Sci., 1977, 66(1):1-19.
CAS Accession No. 1808785-20-7, dated Sep. 29, 2015, 10 pages.
Fell et al., "Mli-2, a potent, selective, and centrally active compound for exploring the therapeutic potential and safety of LRRK2 kinase inhibition," J Pharma Exp Ther., 2015, 355(3):397-409.
Herdemann et al., "Optimization of ITK inhibitors through successive iterative design cycles," Bioorganic & Medicinal Chemistry letters, 2011, 21(6):1852-1856.
Kaela et al., "The G2019S mutation in LRRK2 imparts resiliency to kinase inhibition," Experimental Neurology, 2018, 309:1-13.

(Continued)

*Primary Examiner* — Heidi Reese

(74) *Attorney, Agent, or Firm* — Fish & Richardson P.C.

(57) ABSTRACT

The present invention is directed to indazole and azaindazole compounds which are inhibitors of LRRK2 and are useful in the treatment of CNS disorders.

18 Claims, No Drawings

(56) References Cited

FOREIGN PATENT DOCUMENTS

| | | |
|---|---|---|
| WO | WO 2007048070 | 4/2007 |
| WO | WO 2007058626 | 5/2007 |
| WO | WO 2007087443 | 8/2007 |
| WO | WO 2007093402 | 8/2007 |
| WO | WO 2007095124 | 8/2007 |
| WO | WO 2007109362 | 9/2007 |
| WO | WO 2007112093 | 10/2007 |
| WO | WO 2008048991 | 4/2008 |
| WO | WO 2008137027 | 11/2008 |
| WO | WO 2009024341 | 2/2009 |
| WO | WO 2009035951 | 3/2009 |
| WO | WO 2009038775 | 3/2009 |
| WO | WO 2009038784 | 3/2009 |
| WO | WO 2009046842 | 4/2009 |
| WO | WO 2009062.258 | 5/2009 |
| WO | WO 2009061730 | 5/2009 |
| WO | WO 2009073788 | 6/2009 |
| WO | WO 2009112445 | 9/2009 |
| WO | WO 2009158571 | 12/2009 |
| WO | WO 2010010190 | 1/2010 |
| WO | WO 2010029300 | 3/2010 |
| WO | WO 2010112124 | 10/2010 |
| WO | WO 2011035324 | 3/2011 |
| WO | WO 2011039735 | 4/2011 |
| WO | WO 2011123937 | 10/2011 |
| WO | WO 2011133750 | 10/2011 |
| WO | WO 2011133882 | 10/2011 |
| WO | WO 2011133920 | 10/2011 |
| WO | WO 2011137219 | 11/2011 |
| WO | WO 2012025638 | 3/2012 |
| WO | WO 2012036573 | 3/2012 |
| WO | WO 2012/135631 | 10/2012 |
| WO | WO 2012135799 | 10/2012 |
| WO | WO 2012/162254 | 11/2012 |
| WO | WO 2013102145 | 7/2013 |
| WO | WO 2013106432 | 7/2013 |
| WO | WO 2013151938 | 10/2013 |
| WO | WO 2014/134774 | 9/2014 |
| WO | WO 2014/150981 | 9/2014 |
| WO | WO 2014165816 | 10/2014 |
| WO | WO 2014194127 | 12/2014 |
| WO | WO 2014195400 | 12/2014 |
| WO | WO 2014202741 | 12/2014 |
| WO | WO 2015/026683 | 2/2015 |
| WO | WO 2015015378 | 2/2015 |
| WO | WO 2015095701 | 6/2015 |
| WO | WO 2016036586 | 3/2016 |
| WO | WO 2016081599 | 5/2016 |
| WO | WO 2016083433 | 6/2016 |
| WO | WO 2016133935 | 8/2016 |
| WO | WO 2016144702 | 9/2016 |
| WO | WO 2017012576 | 1/2017 |
| WO | WO 2017027400 | 2/2017 |
| WO | WO 2017049172 | 3/2017 |
| WO | WO 2017049409 | 3/2017 |
| WO | WO 2017157885 | 9/2017 |
| WO | WO 2017163078 | 9/2017 |
| WO | WO 2018115383 | 6/2018 |
| WO | WO 2018137573 | 8/2018 |
| WO | WO 2018137607 | 8/2018 |
| WO | WO 2018137619 | 8/2018 |
| WO | WO 2018140513 | 8/2018 |
| WO | WO 2018208985 | 12/2018 |
| WO | WO 2019002624 | 1/2019 |
| WO | WO 2019036534 | 2/2019 |
| WO | WO 2019/074810 | 4/2019 |
| WO | WO 2019074809 | 4/2019 |
| WO | WO 2019087129 | 5/2019 |
| WO | WO 2019222173 | 11/2019 |
| WO | WO 2020092136 | 5/2020 |
| WO | WO 2020135513 | 7/2020 |
| WO | WO 2020/191261 | 9/2020 |
| WO | WO 202.0228649 | 11/2020 |
| WO | WO 2020247298 | 12/2020 |
| WO | WO 2021050688 | 3/2021 |
| WO | WO 2021088859 | 5/2021 |
| WO | WO 2021222789 | 11/2021 |

OTHER PUBLICATIONS

Kerekes et al., "Aurora kinase inhibitors based on the imidazo[1,2-a]pyrazine core: fluorine and deuterium incorporation improve oral absorption and exposure," J Med Chem., 2011, 54(1):201-210.

Lennox et al., "Selection of boron reagents for Suzuki-Miyaura coupling," Chem. Soc. Rev. 2014, 43:412-43.

Lewis et al., "LRRK2 and human disease: a complicated question or a question of complexes?," Sci. Signal., 2012, 5(207): pe2.

PCT International Preliminary Report on Patentability in International Appln. No. PCT/US2019/032163, dated Nov. 17, 2020, 7 pages.

PCT International Search Report and Written Opinion in International Appln. No. PCT/US2019/032163, dated Aug. 2, 2019, 11 pages.

PCT International Search Report and Written Opinion in International Appln. No. PCT/US2020/023763, dated May 12, 2020, 10 pages.

PCT International Search Report and Written Opinion in International Appln. No. PCT/US2020/041506, dated Sep. 24, 2020, 15 pages.

Peturssion et al., "Protecting Groups in Carbohydrate Chemistry," J Chem. Educ., 1997, 74(11):1297.

Simon-Sanchez et al., "LRRK2 is expressed in areas affected by Parkinson's disease in the adult mouse brain," Eur. J Neurosci. 2006, 23(3):659.

STN Accession No. 2129527-41-7, dated Sep. 22, 2017, 1 page.
STN Accession No. 2129840-05-5, dated Sep. 22, 2017, 1 page.
STN Accession No. 2129896-08-6, dated Sep. 22, 2017, 1 page.
STN Accession No. 2190570-67-1, dated Mar. 13, 2018, 4 pages.
STN Accession No. 2191450-42-5, dated Mar. 14, 2018, 10 pages.
STN Accession No. 2191450-42-5, dated Mar. 14, 2018, 4 pages.
STN Accession No. 2221963-04-6, dated Apr. 30, 2018, 8 pages.
STN Accession No. 2253752-25-7, dated Dec. 18, 2018, 23 pages.
STN Accession No. 2253752-25-7, dated Dec. 18, 2018, 27 pages.
STN Accession No. 2253892-33-8, dated Dec. 19, 2018, 13 pages.
STN Accession No. 2253892-33-8, dated Dec. 19, 2018, 6 pages.
STN Accession No. 2379707-93-2, dated Nov. 14, 2019, 17 pages.
STN Accession No. 45703-61-614, dated Jul. 19, 2013, 1 page.
STN International Transcript, dated May 16, 2019, 21 pages.
STN International Transcript, dated Nov. 14, 2018, 21 pages.

Suzuki, "Recent advances in the cross-coupling reactions of organoboron derivatives with organic electrophiles, 1995-1998," J. Organomet. Chem, 1999, 57:147-168.

Valeur et al., "Amide bond formation: beyond the myth of coupling reagents," Chem. Soc. Rev., 2009, 38(2):606-631.

Xu et al., "Design, synthesis and biological evaluation of deuterated nintedanib for improving pharmacokinetic properties," J Label Compd Radiopharm., 2015, 58(7):308-312.

International Preliminary Report on Patentability in International Appln. No. PCT/US2020/023763, dated Sep. 16, 2021, 8 pages.

International Search Report and Written Opinion in International Appln. No. PCT/US2021/021054, dated Apr. 16, 2021, 12 pages.

International Preliminary Report on Patentability in International Appln. No. PCT/US2020/041506, dated Jan. 20, 2022, 7 pages.

* cited by examiner

INDAZOLES AND AZAINDAZOLES AS LRRK2 INHIBITORS

FIELD OF THE INVENTION

The present invention is directed to indazole and azaindazole compounds which are inhibitors of LRRK2 and are useful in the treatment of CNS disorders.

BACKGROUND OF THE INVENTION

Parkinson's disease ("PD") is the most common form of parkinsonism, a movement disorder, and the second most common, age-related neurodegenerative disease estimated to affect 1-2% of the population over age 65. PD is characterized by tremor, rigidity, postural instability, impaired speech, and bradykinesia. It is a chronic, progressive disease with increasing disability and diminished quality of life. In addition to PD, parkinsonism is exhibited in a range of conditions such as progressive supranuclear palsy, corticobasal degeneration, multiple system atrophy, and dementia with Lewy bodies.

Current therapeutic strategies for PD are primarily palliative and focus on reducing the severity of symptoms using supplemental dopaminergic medications. At present, there is no disease-modifying therapy that addresses the underlying neuropathological cause of the disease, thus constituting a significant unmet medical need.

It has long been known that family members of PD patients have an increased risk of developing the disease compared to the general population. Leucine-rich repeat kinase 2 ("LRRK2," also known as dardarin) is a 286 kDa multi-domain protein that has been linked to PD by genome-wide association studies. LRRK2 expression in the brain is highest in areas impacted by PD (*Eur. J. Neurosci.* 2006, 23(3):659) and LRRK2 has been found to localize in Lewy Bodies, which are intracellular protein aggregates considered to be a hallmark of the disease. Patients with point mutations in LRRK2 present disease that is nearly indistinguishable from idiopathic patients. While more than 20 LRRK2 mutations have been associated with autosomal-dominantly inherited parkinsonism, the G2019S mutation located within the kinase domain of LRRK2 is by far the most common. This particular mutation is found in >85% of LRRK2-linked PD patients. It has been shown that the G2019S mutation in LRRK2 leads to an enhancement in LRRK2 kinase activity and inhibition of this activity is a therapeutic target for the treatment of PD.

In addition to PD, LRRK2 has been linked to other diseases such as cancer, leprosy, and Crohn's disease (*Sci. Signal.*, 2012, 5(207), pe2). As there are presently limited therapeutic options for treating PD and other disorders associated with aberrant LRRK2 kinase activity, there remains a need for developing LRRK2 inhibitors.

SUMMARY OF THE INVENTION

The present invention is directed to a compound of Formula I:

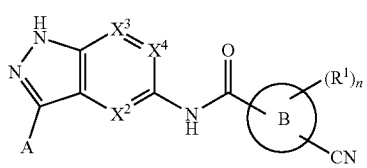

or a pharmaceutically acceptable salt thereof, wherein constituent members are defined herein.

The present invention is further directed to a pharmaceutical composition comprising a compound of Formula I, or a pharmaceutically acceptable salt thereof, and at least one pharmaceutically acceptable carrier.

The present invention is further directed to a method of inhibiting LRRK2 activity, comprising contacting a compound of Formula I, or a pharmaceutically acceptable salt thereof, with LRRK2.

The present invention is further directed to a method of treating a disease or disorder associated with elevated expression or activity of LRRK2, or a functional variant thereof, said method comprising administering to a patient in need thereof a therapeutically effective amount of a compound of Formula I, or a pharmaceutically acceptable salt thereof.

The present invention is further directed to a method for treating a neurodegenerative disease in a patient comprising administering to the patient a therapeutically effective amount of the compound of Formula I, or a pharmaceutically acceptable salt thereof.

The present invention is further directed to a compound of Formula I, or a pharmaceutically acceptable salt thereof, for use in therapy.

The present invention is further directed to a use of a compound of Formula I, or a pharmaceutically acceptable salt thereof, for the preparation of a medicament for use in therapy.

DETAILED DESCRIPTION

The present invention is directed to an inhibitor of LRRK2 which is a compound of Formula I:

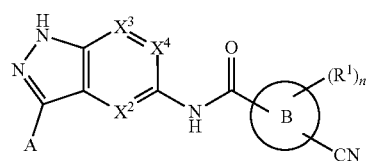

or a pharmaceutically acceptable salt thereof, wherein:

A is $Cy^1$, $Cy^1$-$C_{1-4}$ alkyl-, $Cy^1$-$C_{2-4}$ alkenyl-, $Cy^1$-$C_{2-4}$ alkynyl-, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, $S(O)_2NR^cR^d$, or $P(O)R^cR^d$; wherein said $C_{1-6}$ alkyl, $C_{2-6}$ alkenyl, $C_{2-6}$ alkynyl, and $C_{1-6}$ haloalkyl of A are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, $S(O)_2NR^cR^d$, and $P(O)R^cR^d$;

Ring B is phenyl or 5-10 membered heteroaryl, wherein said 5-10 membered heteroaryl comprises 1, 2, or 3 ring-forming heteroatoms independently selected from N, O, and S;

$X^2$ is N or $CR^2$;
$X^3$ is N or $CR^3$;

$X^4$ is N or $CR^4$; wherein not more than two of $X^2$, $X^3$, and $X^4$ are simultaneously N;

$Cy^1$ is selected from $C_{6-10}$ aryl, $C_{3-10}$ cycloalkyl, 5-14 membered heteroaryl, and 4-14 membered heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $CC(O)R^b$, $NR^cC(O)OR^a$, $N^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$, wherein said substituents $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl are each optionally substituted by 1, 2, or 3 further substituents independently selected from halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $N^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each $R^1$ is independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $N^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^e)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^1$ are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

or two $R^1$ groups together with the atoms to which they are attached form a $C_{5-7}$ cycloalkyl group which is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^2$ and $R^4$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$ and $S(O)_2NR^{c2}R^{d2}$, wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^2$ and $R^4$ are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^3$ is selected from H, halo, $C_{1-6}$ alkyl, $C_{2-6}$ alkenyl, $C_{2-6}$ alkynyl, $C_{1-6}$ haloalkyl, $C_{3-4}$ cycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{c3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, wherein said $C_{1-6}$ alkyl, $C_{2-6}$ alkenyl, $C_{2-6}$ alkynyl, $C_{1-6}$ haloalkyl, and $C_{3-4}$ cycloalkyl of $R^3$ are each optionally substituted with 1, 2, or 3 substituents independently selected from halo, $C_{1-4}$ alkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

each $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^a$, $R^b$, $R^c$, $R^d$, $R^{a1}$, $R^{b1}$, $R^{c1}$, $R^{d1}$, $R^{a2}$, $R^{b2}$, $R^{c2}$, and $R^{d2}$ is optionally substituted with 1, 2, 3, 4, or 5 substituents independently selected from halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$ and $S(O)_2NR^{c3}R^{d3}$;

each $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-6 membered heteroaryl, and 4-7 membered heterocycloalkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-6 membered heteroaryl, and 4-7 membered heterocycloalkyl are each optionally substituted with 1, 2, or 3 substituents independently selected from OH, CN, amino, halo, $C_{1-6}$alkyl, $C_{1-6}$alkoxy, $C_{1-6}$haloalkyl, and $C_{1-6}$haloalkoxy;

each $R^e$, $R^{e1}$, $R^{e2}$, and $R^{e3}$ is independently selected from H, $C_{1-4}$ alkyl, and CN; and n is 0, 1, 2, or 3;

wherein when $X^2$ is $CR^2$, $X^3$ is $CR^3$; and $X^4$ is $CR^4$, then A is other than —C(=O)OH or —C(=O)OCH$_3$; and wherein the compound is other than:

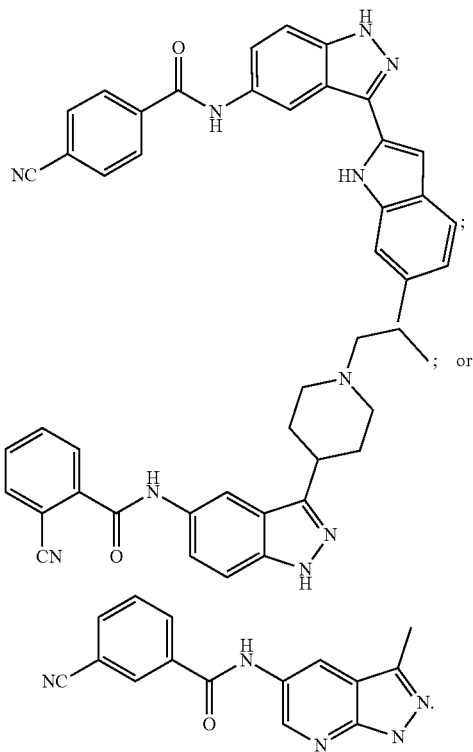

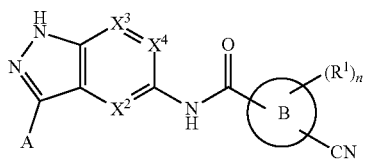

The present invention is directed to an inhibitor of LRRK2 which is a compound of Formula I:

or a pharmaceutically acceptable salt thereof, wherein:

A is $Cy^1$, $Cy^1$-$C_{1-4}$ alkyl-, halo, $C_{1-6}$ alkyl, $C_{2-6}$ alkenyl, $C_{2-6}$, alkynyl, $C_{1-6}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, C(=NR$^e$) NR$^c$R$^d$, NR$^c$C(=NR$^e$)NR$^c$R$^d$, NR$^c$R$^d$, NR$^c$C(O)R$^b$, NR$^c$C (O)OR$^a$, NR$^c$C(O)NR$^c$R$^d$, NR$^c$S(O)R$^b$, NR$^c$S(O)$_2$R$^b$, NR$^c$S (O)$_2$NR$^c$R$^d$, S(O)R$^b$, S(O)NR$^c$R$^d$, S(O)$_2$R$^b$, and S(O)$_2$NR$^c$R$^d$; wherein said $C_{1-6}$ alkyl, $C_{2-6}$ alkenyl, $C_{2-6}$ alkynyl, and $C_{1-6}$ haloalkyl of A are each optionally substituted with 1, 2, 3, 4, or 5 substituents independently selected from $C_{1-6}$ alkyl, $C_{2-6}$ alkenyl, $C_{2-6}$ alkynyl, $C_{1-6}$ haloalkyl, $C_{3-7}$ cycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, C(=NR$^e$)NR$^c$R$^d$, NR$^c$C(=NR$^e$)NR$^c$R$^d$, NR$^c$R$^d$, NR$^c$C(O)R$^b$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;

Ring B is phenyl or 5-10 membered heteroaryl, wherein said 5-10 membered heteroaryl comprises 1, 2, or 3 ring-forming heteroatoms independently selected from N, O, and S;

$X^2$ is N or $CR^2$;

$X^3$ is N or $CR^3$;

$X^4$ is N or $CR^4$; wherein not more than two of $X^2$, $X^3$, and $X^4$ are simultaneously N;

$Cy^1$ is selected from $C_{6-10}$ aryl, $C_{3-10}$ cycloalkyl, 5-14 membered heteroaryl, and 4-14 membered heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, NO$_2$, OR$^a$, SR$^a$, C(O)R$^b$, C(O) NR$^c$R$^d$, C(O)OR$^a$, OC(O)R$^b$, OC(O)NR$^c$R$^d$, NR$^c$R$^d$, NR$^c$C (O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S (O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$, wherein said substituents $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl are each optionally substituted by 1, 2, or 3 further substituents independently selected from halo, $C_{1-6}$ alkyl, $C_{2-6}$ alkenyl, $C_{2-6}$ alkynyl, $C_{1-6}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O) OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$ NR$^c$R$^d$, S(O)R$^b$, S(O)NR$^c$R$^d$, S(O)$_2$R$^b$, and S(O)$_2$NR$^c$R$^d$.

each $R^1$ is independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, NO$_2$, OR$^{a1}$, SR$^{a1}$, C(O) R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O) NR$^{c1}$R$^{d1}$, C(=NR$^{e1}$)R$^{b1}$, C(=NR$^{e1}$)NR$^{c1}$R$^{d1}$, NR$^{c1}$C (=NR$^{e1}$)NR$^{c1}$R$^{d1}$, NR$^{c1}$S(O)R$^{b1}$, NR$^{c1}$S(O)$_2$R$^{b1}$, NR$^{c1}$S (O)$_2$NR$^{c1}$R$^{d1}$, S(O)R$^{b1}$, S(O)NR$^{c1}$R$^{d1}$, S(O)$_2$R$^{b1}$, and S(O)$_2$ NR$^{c1}$R$^{d1}$; wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^1$ are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{c1}$)NR$^{c1}$R$^{d1}$, NR$^{c1}$C(=NR$^{e1}$) NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C (O)NR$^{c1}$R$^{d1}$, NR$^{c1}$S(O)R$^{b1}$, NR$^{c1}$S(O)$_2$R$^{b1}$, NR$^{c1}$S(O)$_2$ NR$^{c1}$R$^{d1}$, S(O)R$^{b1}$, S(O)NR$^{c1}$R$^{d1}$, S(O)$_2$R$^{b1}$, and S(O)$_2$ NR$^{c1}$R$^{d1}$;

or two $R^1$ groups together with the atoms to which they are attached form a $C_{5-7}$ cycloalkyl group which is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c}$, S(O)$_2$NR$^{c1}$R$^{d1}$, S(O)R$^{b1}$, S(O)NR$^{c1}$R$^d$S(O)$_2$R$^{b1}$, and S(O)$_2$NR$^{c1}$R$^{d1}$;

R$^2$ and R$^4$ are each independently selected from H, halo, C$_{1-6}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, C(=NR$^{e2}$)R$^{b2}$, C(=NR$^{e2}$)NR$^{c2}$R$^{d2}$, NR$^{c2}$C(=NR$^{e2}$)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$, wherein said C$_{1-6}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{14}$ alkyl, 5-10 membered heteroaryl-C$_{1-4}$ alkyl, and 4-10 membered heterocycloalkyl-C$_{1-4}$ alkyl of R$^2$ and R$^4$ are each optionally substituted with 1, 2, 3, 4, or 5 substituents independently selected from halo, C$_{1-6}$ alkenyl, C$_{2-6}$ alkynyl, C$_{1-6}$ haloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, C(=NR$^{e2}$)R$^{b2}$, C(=NR$^{e2}$)NR$^{c2}$R$^{d2}$, NR$^{c2}$C(=NR$^{e2}$)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$;

R$^3$ is selected from H, halo, C$_{1-6}$ alkyl, C$_{2-6}$ alkenyl, C$_{2-6}$ alkynyl, C$_{1-6}$ haloalkyl, C$_{3-4}$ cycloalkyl, CN, NO$_2$, OR$^{a3}$, SR$^{a3}$C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^d$C(=NR$^{e3}$)R$^b$C(=NR$^{c3}$)NR$^{c3}$R$^{d3}$, NR$^{c3}$C(=NR$^{e3}$)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$, wherein said C$_{1-6}$ alkyl, C$_{2-6}$ alkenyl, C$_{2-6}$ alkynyl, C$_{1-6}$ haloalkyl, and C$_{3-4}$ cycloalkyl of R$^3$ are each optionally substituted with 1, 2, or 3 substituents independently selected from halo, C$_{1-4}$ alkyl, CN, NO$_2$, OR$^{a3}$, SR$^{a3}$C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^d$, NR$^{c3}$C(O)R$^{b3}$, NR$^{c3}$C(O)OR$^{a3}$, NR$^{c3}$C(O)NR$^{c3}$R$^{d3}$, C(=NR$^{e3}$)R$^{b3}$, C(=NR$^{e3}$)NR$^{c3}$R$^d$, NR$^{c3}$C(=NR$^{e3}$)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^d$S(O)$_2$R$^{b3}$ and S(O)$_2$NR$^{c3}$R$^{d3}$;

each R$^a$, R$^b$, R$^c$, R$^d$, R$^{a1}$, R$^{b1}$, R$^{c1}$, R$^{d1}$, R$^{a2}$, R$^{b2}$, R$^{c2}$, R$^{d2}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl, wherein said C$_{1-6}$ alkyl, C$_{2-6}$ alkenyl, C$_{2-6}$ alkynyl, C$_{6-10}$ aryl, C$_{3-7}$cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl of R$^a$, R$^b$, R$^c$, R$^d$, R$^{a1}$, R$^{b1}$, R$^{c1}$, R$^{d1}$, R$^{a2}$, R$^{b2}$, R$^{c2}$, and R$^{d2}$ is optionally substituted with 1, 2, 3, 4, or 5 substituents independently selected from halo, C$_{1-4}$ alkyl, C$_{1-4}$ haloalkyl, C$_{1-6}$ haloalkyl, C$_{2-6}$ alkenyl, C$_{2-6}$ alkynyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, C(=NR$^{e3}$)NR$^{c3}$R$^d$, NR$^{c3}$C(=NR$^{e3}$) NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$;

each R$^{a3}$, R$^{b3}$, R$^{c3}$, and R$^{d3}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-6 membered heteroaryl, and 4-7 membered heterocycloalkyl, wherein said C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-6 membered heteroaryl, and 4-7 membered heterocycloalkyl are each optionally substituted with 1, 2, or 3 substituents independently selected from OH, CN, amino, halo, C$_{1-6}$ alkyl, C$_{1-6}$ alkoxy, C$_{1-6}$ haloalkyl, and C$_{1-6}$ haloalkoxy;

each R$^c$, R$^{c1}$, R$^{c2}$, and R$^{c3}$ is independently selected from H, C$_{1-4}$ alkyl, and CN; and n is 0, 1, 2, or 3;

wherein when X$^2$ is CR$^2$; X$^3$ is CR; and X$^4$ is CR$^4$, then A is other than —C(=O)OH or —C(=O)OCH$_3$; and wherein the compound is other than:

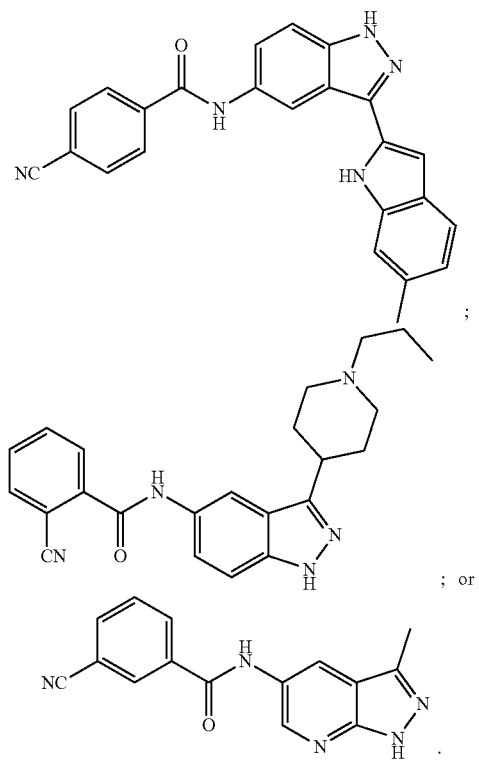

; or

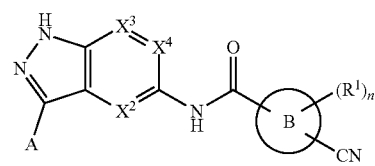

.

The present invention is directed to an inhibitor of LRRK2 which is a compound of Formula I:

$$\text{I}$$

or a pharmaceutically acceptable salt thereof, wherein:

A is Cy$^1$, Cy$^1$-C$_{1-4}$ alkyl-, halo, C$_{1-6}$ alkyl, C$_{2-6}$ alkenyl, C$_{2-6}$ alkynyl, C$_{1-6}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, C(=NR$^e$) NR$^c$R$^d$, NR$^c$C(=NR$^e$)NR$^c$R$^d$, NR$^c$R$^d$, NR$^c$C(O)R$^b$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said C$_{1-6}$ alkyl, C$_{2-6}$ alkenyl, C$_{2-6}$ alkynyl, and C$_{1-6}$ haloalkyl of A are each optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, CN, NO$_2$, OW, SR$^a$, C(O)R$^b$, C(O)NR$^c$R$^d$, C(O)OR$^a$, OC(O)R$^b$, OC(O)NR$^c$R$^d$, C(=NR$^e$)NR$^c$R$^d$, NR$^c$C(=NR$^e$)NR$^c$R$^d$, NR$^c$R$^d$, NR$^c$C(O)R$^b$, NR$^c$1C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;

Ring B is phenyl, 5-membered heteroaryl, or 6-membered heteroaryl, wherein said 5- or 6-membered heteroaryl comprises 1, 2, or 3 ring-forming heteroatoms independently selected from N, O, and S;

$X^2$ is N or CR$^2$;

$X^3$ is N or CR$^3$;

$X^4$ is N or CR$^4$; wherein not more than two of $X^2$, $X^3$, and $X^4$ are simultaneously N;

Cy$^1$ is selected from C$_{6-10}$ aryl, C$_{3-10}$ cycloalkyl, 5-14 membered heteroaryl, and 4-14 membered heterocycloalkyl, each optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-14 membered heteroaryl, 4-14 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$, wherein said substituents C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-14 membered heteroaryl, 4-14 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl are each optionally substituted by 1, 2, or 3 further substituents independently selected from halo, C$_{1-6}$ alkyl, C$_{2-6}$ alkenyl, C$_{2-6}$ alkynyl, C$_{1-6}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;

each R$^1$ is independently selected from H, halo, C$_{1-6}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, C(=NR$^{e1}$)R$^{b1}$, C(=NR$^{e1}$)NR$^{c1}$R$^{d1}$, NR$^{c1}$C(=NR$^{e1}$)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$, wherein said C$_{1-6}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl of R$^1$ are each optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$;

R$^2$ and R$^4$ are each independently selected from H, halo, C$_{1-6}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, C(=NR$^{e2}$)R$^{b2}$, C(=NR$^{e2}$)NR$^{c2}$R$^{d2}$, NR$^{c2}$C(=NR$^{e2}$)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$, wherein said C$_{1-6}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl of R$^2$ and R$^4$ are each optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, C(=NR$^{e2}$)R$^{b2}$, C(=NR$^{e2}$)NR$^{c2}$R$^{d2}$, NR$^{c2}$C(=NR$^{e2}$)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$;

R$^3$ is selected from H, halo, C$_{1-6}$ alkyl, C$_{2-6}$ alkenyl, C$_{2-6}$ alkynyl, C$_{1-6}$ haloalkyl, C$_{3-4}$ cycloalkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, C(=NR$^{e3}$)R$^{b3}$, C(=NR$^{e3}$)NR$^{c3}$R$^{d3}$, NR$^{c3}$C(=NR$^{e3}$)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$ wherein said C$_{1-6}$ alkyl, C$_{2-6}$ alkenyl, C$_{2-6}$ alkynyl, C$_{1-6}$ haloalkyl, and C$_{3-4}$ cycloalkyl of R$^3$ are each optionally substituted with 1, 2, or 3 substituents independently selected from halo, C$_{1-4}$ alkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, C(=NR$^{c3}$)R$^{b3}$, C(=NR$^{c3}$)NR$^{c3}$R$^{d3}$, NR$^{c3}$C(=NR$^{e3}$)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$S(O)NR$^{c3}$R$^{d3}$, S(O)$_2$$^{b3}$, and S(O)$_2$NR$^{c3}$R$^{d3}$;

each R$^a$, R$^b$, R$^c$, R$^d$, R$^{a1}$, R$^{b1}$, R$^{c1}$, R$^{d1}$, R$^{a2}$, R$^{b2}$, R$^{c2}$, R$^{d2}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl, wherein said C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl of R$^a$, R$^b$, R$^c$, R$^d$, R$^{a1}$, R$^{b1}$, R$^{c1}$, R$^{d1}$, R$^{a2}$, R$^{b2}$, R$^{c2}$, and R$^{d2}$ is optionally substituted with 1, 2, 3, 4, or 5 substituents independently selected from halo, C$_{1-4}$ alkyl, C$_{1-4}$ haloalkyl, C$_{1-6}$ haloalkyl, C$_{2-6}$ alkenyl, C$_{2-6}$ alkynyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{c3}$)NR$^{c3}$R$^d$NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$;

each R$^{a3}$, R$^{b3}$, R$^{c3}$, and R$^{d3}$ is independently selected from H, C$_{1-6}$ alkyl, C$_{1-6}$ haloalkyl, C$_{2-6}$ alkenyl, C$_{2-6}$ alkynyl, $C_{6-10}$ aryl, $C_{3-7}$ cycloalkyl, 5-6 membered heteroaryl, and 4-7 membered heterocycloalkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-6 membered heteroaryl, and 4-7 membered heterocycloalkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

each $R^e$, $R^{e1}$, $R^{e2}$, and $R^{e3}$ is independently selected from H, $C_{1-4}$ alkyl, and CN; and n is 0, 1, 2, or 3;

wherein when $X^2$ is $CR^2$; $X^3$ is $CR^3$; and $X^4$ is $CR^4$, then A is other than —C(=O)OH or —C(=O)OCH$_3$; and wherein the compound is other than:

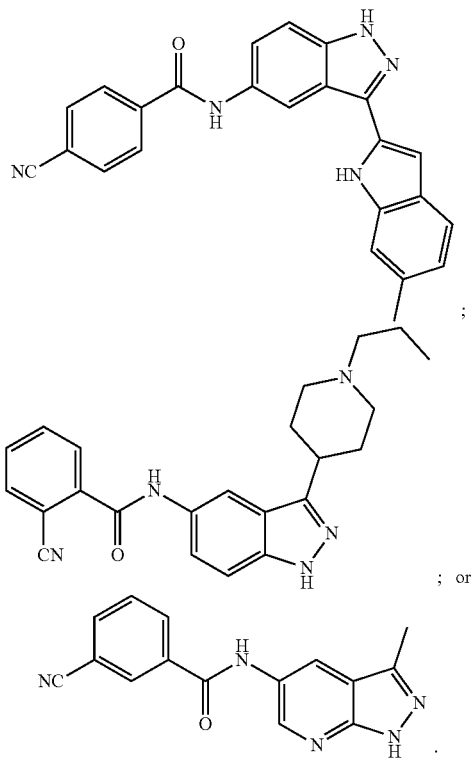

In some embodiments, $X^2$ is $CR^2$; $X^3$ is $CR^3$; and $X^4$ is $CR^4$.

In some embodiments, $X^2$ is N; $X^3$ is $CR^3$; and $X^4$ is $CR^4$.
In some embodiments, $X^2$ is $CR^2$; $X^3$ is N; and $X^4$ is $CR^4$.
In some embodiments, $X^2$ is $CR^2$; $X^3$ is $CR^3$; and $X^4$ is N.
In some embodiments, $X^2$ is N; $X^3$ is $CR^3$; and $X^4$ is N.
In some embodiments, $X^2$ is N; $X^3$ is N; and $X^4$ is $CR^4$.
In some embodiments, $X^2$ is $CR^2$; $X^3$ is N; and $X^4$ is N.
In some embodiments, $R^2$, $R^3$, and $R^4$ are each H.

In some embodiments, $R^2$ is H or halo. In some embodiments, $R^2$ is halo. In some embodiments, $R^2$ is H.

In some embodiments, $R^3$ is H or halo. In some embodiments, $R^3$ is halo. In some embodiments, $R^3$ is H or fluoro. In some embodiments, $R^3$ is H. In some embodiments, $R^3$ is fluoro.

In some embodiments, $R^4$ is H or halo. In some embodiments, $R^4$ is halo. In some embodiments, $R^4$ is H.

In some embodiments, A is $Cy^1$, $Cy^1$-$C_{2-4}$ alkenyl-, halo, CN, $C_{1-6}$ alkyl, $C_{2-6}$ alkenyl, $C_{1-6}$ haloalkyl, $OR^a$, $SR^a$, $NR^cC(O)R^b$, or $S(O)_2R^b$, wherein said $C_{1-6}$ alkyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, NO$_2$, $OR^a$, $SR^a$, $C(O)R^b$, $C(O)NR^cR^d$, $C(O)OR^a$, OC(O)$R^b$, OC(O)NR$^c$R$^d$, C(=NR$^e$)NR$^c$R$^d$, N$^c$C(=NR$^e$)NR$^c$R$^d$, NR$^c$R$^d$, NR$^c$C(O)R$^b$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

In some embodiments, A is $Cy^1$, halo, $C_{1-6}$ alkyl, or NR$^c$C(O)R$^b$, wherein said $C_{1-6}$ alkyl is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, NO$_2$, OR, SR$^a$, C(O)R$^b$, C(O)NR$^c$R$^d$, C(O)OR$^a$, OC(O)R$^b$, OC(O)NR$^c$R$^d$, C(=NR$^e$)NR$^c$R$^d$, NR$^c$C(=NR$^e$) NR$^c$R$^d$, NR$^c$R$^d$, NR$^c$C(O)R$^b$, NR$^c$C(O)OR$^a$, NR$^c$C(O)NR$^c$ R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

In some embodiments, A is $Cy^1$, halo, or $C_{1-6}$ alkyl optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, C(=NR$^e$) NR$^c$R$^d$, NR$^c$C(=NR$^e$)NR$^c$R$^d$, NR$^c$R$^d$, NR$^c$C(O)R$^b$, NR$^{c1}$C (O)OR$^a$, NR$^c$C(O)NR$^c$R$^d$, NR$^c$S(O)R$^b$, NR$^c$S(O)$_2$R$^b$, NR$^c$S (O)$_2$NR$^c$R$^d$, S(O)R$^b$, S(O)NR$^c$R$^d$, S(O)$_2$R$^b$, and S(O)$_2$ NR$^c$R$^d$.

In some embodiments, A is methyl.
In some embodiments, A is halo.
A is iodo, bromo, chloro, or fluoro.
In some embodiments, A is iodo or bromo.
In some embodiments, A is iodo. In some embodiments, A is bromo.
In some embodiments, $Cy^1$-$C_{2-4}$ alkenyl-.
In some embodiments, A is $Cy^1$.

In some embodiments, $Cy^1$ is $C_{6-10}$ aryl or 5-14 membered heteroaryl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$ NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S (O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$, wherein said substituents $C_{1-6}$ alkyl, $C_{2-6}$ alkenyl, $C_{2-6}$ alkynyl, $C_{1-6}$ haloalkyl, $C_{6-10}$ aryl, $C_{3-10}$cycloalkyl, 5-14 membered heteroaryl, 4-14 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl are each optionally substituted by 1, 2, or 3 further substituents independently selected from halo, $C_{1-6}$ alkyl, $C_{2-6}$ alkenyl, $C_{2-6}$ alkynyl, $C_{1-6}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$ NR$^c$R$^d$, NR$^c$C(O)R$^b$, NR$^c$C(O) OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$ NR$^c$R$^d$, S(O)R$^b$, S(O)NR$^c$R$^d$, S(O)$_2$R$^b$, and S(O)$_2$NR$^c$R$^d$.

In some embodiments, $Cy^1$ is phenyl or 5-, 6-, or 8-membered heteroaryl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^c$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$, wherein said substituents C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-14 membered heteroaryl, 4-14 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl are each optionally substituted by 1, 2, or 3 further substituents independently selected from halo, C$_{1-6}$ alkyl, C$_{2-6}$ alkenyl, C$_{2-6}$ alkynyl, C$_{1-6}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

In some embodiments, Cy$^1$ is selected from C$_{3-10}$ cycloalkyl and 4-14 membered heterocycloalkyl, each optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-14 membered heteroaryl, 4-14 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)CR$^d$, C(=NR$^e$)R$^b$, C(=NR$^e$)NR$^c$R$^d$, NR$^c$C(=NR$^c$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$, wherein said substituents C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-14 membered heteroaryl, 4-14 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl are each optionally substituted by 1, 2, or 3 further substituents independently selected from halo, C$_{1-6}$ alkyl, C$_{2-6}$ alkenyl, C$_{2-6}$ alkynyl, C$_{1-6}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$ NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NS(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

In some embodiments, Cy$^1$ is selected from C$_{3-7}$ cycloalkyl and 4-6 membered heterocycloalkyl, each optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-14 membered heteroaryl, 4-14 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$, wherein said substituents C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-14 membered heteroaryl, 4-14 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl are each optionally substituted by 1, 2, or 3 further substituents independently selected from halo, C$_{1-6}$ alkyl, C$_{2-6}$ alkenyl, C$_{2-6}$ alkynyl, C$_{1-6}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$ NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

In some embodiments, Cy$^1$ is phenyl, furanyl, pyridyl, pyrazolyl, isoxazolyl, thienyl, benzoxazolyl, thiazolyl, oxazolyl, imidazolyl, oxodihydropyridinyl, isothiazolyl, pyrrolyl, cyclopropyl, pyrimidinyl, triazolyl, oxooxazolyl, azetidinyl, oxetanyl, piperidinyl, dihydrofuranyl, tetrahydropyranyl, cyclobutyl, thieno[2,3-c]pyridinyl, or pyridazinyl, each optionally substituted by 1, 2, or 3 substituents independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-14 membered heteroaryl, 4-14 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$, wherein said substituents C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-14 membered heteroaryl, 4-14 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl are each optionally substituted by 1, 2, or 3 further substituents independently selected from halo, C$_{1-6}$ alkyl, C$_{2-6}$ alkenyl, C$_{2-6}$ alkynyl, C$_{1-6}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, N$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

In some embodiments, Cy$^1$ is phenyl, furanyl, pyridyl, pyrazolyl, isoxazolyl, thienyl, benzoxazolyl, thiazolyl, oxazolyl, imidazolyl, oxodihydropyridinyl, isothiazolyl, pyrrolyl, cyclopropyl, or pyrimidinyl, each optionally substituted by 1, 2, or 3 substituents independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-14 membered heteroaryl, 4-14 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$ NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$, wherein said substituents C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-14 membered heteroaryl, 4-14 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl are each optionally substituted by 1, 2, or 3 further substituents independently selected from halo, C$_{1-6}$ alkyl, C$_{2-6}$ alkenyl, C$_{2-6}$ alkynyl, C$_{1-6}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$ NR$^c$C(O)R$^b$, NR$^{c1}$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

In some embodiments, Cy$^1$ is phenyl, furanyl, pyridyl, pyrazolyl, isoxazolyl, thienyl, or benzoxazolyl, each optionally substituted by 1, 2, or 3 substituents independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-14 membered heteroaryl, 4-14 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$, wherein said substituents C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-14 membered heteroaryl, 4-14 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl are each optionally substituted by 1, 2, or 3 further substituents independently selected from halo, C$_{1-6}$ alkyl, C$_{2-6}$ alkenyl, C$_{2-6}$ alkynyl, C$_{1-6}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, N$^c$C(O)R$^b$, NR$^c$C(O)OR$^a$, CC(O)NR$^c$R$^d$, C(=NR$^e$)R$^b$, C(=NR$^e$)NR$^c$R$^d$, NR$^c$C(=NR$^e$))R$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

In some embodiments, Cy$^1$ is phenyl, furanyl, pyridyl, pyrazolyl, isoxazolyl, thienyl, benzoxazolyl, thiazolyl, oxazolyl, imidazolyl, oxodihydropyridinyl, isothiazolyl, pyrrolyl, cyclopropyl, or pyrimidinyl.

In some embodiments, Cy$^1$ is phenyl, furanyl, pyridyl, or oxazolyl.

In some embodiments, Cy$^1$ is phenyl, furanyl, or pyridyl.
In some embodiments, Cy$^1$ is furanyl.
In some embodiments, Cy$^1$ is oxazolyl.
In some embodiments, Cy$^1$ is cyclopropyl.
In some embodiments, Ring B is 5-membered heteroaryl or 6-membered heteroaryl, wherein said 5- or 6-membered heteroaryl comprises 1, 2, or 3 ring-forming heteroatoms independently selected from N, O, and S.

In some embodiments, Ring B is 6-membered heteroaryl, wherein said 6-membered heteroaryl comprises 1, 2, or 3 ring-forming N atoms.

In some embodiments, Ring B is phenyl, pyridyl, pyrimidinyl, thiazolyl, pyrrolyl, furanyl, pyrazolyl, imidazolyl, isothiazolyl, isoxazolyl, pyrazinyl, pyridazinyl, oxodihydropyridinyl, thienopyridyl, or indazolyl.

In some embodiments, Ring B is phenyl, pyridyl, pyrimidinyl, thiazolyl, pyrrolyl, furanyl, pyrazolyl, imidazolyl, isothiazolyl, or isoxazolyl.

In some embodiments, Ring B is phenyl, pyridyl, pyrimidinyl, thiazolyl, pyrrolyl, furanyl, pyrazolyl, imidazolyl, isothiazolyl, isoxazolyl, pyrazinyl, pyridazinyl, oxodihydropyridinyl, thienopyridyl, indazolyl, dihydro-5H-cyclopenta[c]pyridinyl, or quinolinyl.

In some embodiments, Ring B is phenyl, pyridyl, pyrimidinyl, thiazolyl, pyrrolyl, or furanyl.

In some embodiments, Ring B is phenyl.
In some embodiments, Ring B is pyridyl.
In some embodiments, Ring B is pyrimidinyl.
In some embodiments, Ring B is thiazolyl.
In some embodiments, Ring B is pyrolyl.
In some embodiments, Ring B is furanyl.
In some embodiments, Ring B is pyrazolyl.
In some embodiments, Ring B is imidazolyl.
In some embodiments, Ring B is isothiazolyl.
In some embodiments, Ring B is isoxazolyl.
In some embodiments, each R$^1$ is independently selected from H, halo, C$_{1-6}$ alkyl, C$_{2-6}$ alkenyl, C$_{1-6}$ haloalkyl, and OR$^{a1}$.

In some embodiments, each R$^1$ is independently selected from H, halo, and C$_{1-6}$ alkyl.

In some embodiments, R$^1$ is independently selected from H, F, Cl, Br, I, CH$_3$, CH$_2$CH$_3$, isopropyl, isopropenyl, —CH=CH$_2$, C≡CH, CHF$_2$, CF$_3$, OH, methoxy, OCF$_3$, and cyclopropyl.

In some embodiments, each R$^1$ is independently selected from H, F, Cl, Br, I, CH$_3$, CH$_2$CH$_3$, isopropyl, isopropenyl, —CH=CH$_2$, C≡CH, CHF$_2$, CF$_3$, OH, methoxy, and OCF$_3$.

In some embodiments, each R$^1$ is independently selected from H, F, Cl, Br, I, CH$_3$, —CH=CH$_2$, CHF$_2$, CF$_3$, OH, and methoxy.

In some embodiments, each R$^1$ is independently selected from H, F, Cl, Br, I, and CH$_3$.

In some embodiments, two R$^1$ groups together with the atoms to which they are attached form a C$_{5-7}$ cycloalkyl group which is optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^d$, S(O)$_2$R$^{b1}$, and S(O)$_2$NR$^{c1}$R$^{d1}$.

In some embodiments, two R$^1$ groups together with the atoms to which they are attached form a cyclopentane group.

In some embodiments, n is 0, 1, or 2.
In some embodiments, n is 0 or 1.
In some embodiments, n is 0.
In some embodiments, n is 1.
In some embodiments, n is 2.
In some embodiments, n is 1 or 2.
In some embodiments, the compound is a compound of Formula I, or a pharmaceutically acceptable salt thereof, wherein:

A is Cy$^1$;
Ring B is phenyl, pyridyl, pyrimidinyl, thiazolyl, pyrrolyl, furanyl, pyrazolyl, imidazolyl, isothiazolyl, isoxazolyl, pyrazinyl, pyridazinyl, oxodihydropyridinyl, thienopyridyl, indazolyl, dihydro-5H-cyclopenta[c]pyridinyl, or quinolinyl;
X$^2$ is N or CR$^2$;
X$^3$ is CR$^3$;
X$^4$ is CR$^4$;
Cy$^1$ is phenyl, furanyl, pyridyl, pyrazolyl, isoxazolyl, thienyl, benzoxazolyl, thiazolyl, oxazolyl, imidazolyl, oxodihydropyridinyl, isothiazolyl, pyrrolyl, cyclopropyl, pyrimidinyl, triazolyl, oxooxazolyl, azetidinyl, oxetanyl, piperidinyl, dihydrofuranyl, tetrahydropyranyl, cyclobutyl, thieno[2,3-c]pyridinyl, or pyridazinyl, each optionally substituted by 1, 2, or 3 substituents independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-14 membered heteroaryl, 4-14 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$, wherein said substituents C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-14 membered heteroaryl, 4-14 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl are each optionally substituted by 1, 2, or 3 further substituents independently selected from halo, C$_{1-6}$ alkyl, C$_{2-6}$ alkenyl, C$_{2-6}$ alkynyl, C$_{1-6}$ haloalkyl, CN, NO$_2$, OR$^a$, SR$^a$, C(O)R$^b$, C(O) NR$^c$R$^d$, C(O)OR$^a$, OC(O)R$^b$, OC(O)NR$^c$R$^d$, NR$^c$R$^d$ NR$^c$C(O)R$^b$, NR$^c$C(O)OR$^a$, NR$^c$C(O)NR$^c$R$^d$, C(=NR$^e$)R$^{b1}$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;

each R$^1$ is independently selected from H, F, Cl, Br, I, CH$_3$, CH$_2$CH$_3$, isopropyl, isopropenyl, —CH=CH$_2$, C≡CH, CHF$_2$, CF$_3$, OH, methoxy, OCF$_3$, and cyclopropyl;

R$^2$, R$^3$, and R$^4$ are each H;

each R$^a$, R$^b$, R$^c$, and R$^d$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl, wherein said C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl of R$^a$, R$^b$, R$^c$, R$^d$, and R$^{a1}$ is optionally substituted with 1, 2, 3, 4, or 5 substituents independently selected from halo, C$_{1-4}$ alkyl, C$_{1-4}$ haloalkyl, C$_{1-6}$ haloalkyl, C$_{2-6}$ alkenyl, C$_{2-6}$ alkynyl, CN, OR$^{a3}$, SR$^{a3}$, C(O)R$^{b3}$, C(O)NR$^{c3}$R$^{d3}$, C(O)OR$^{a3}$OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$S(O)NR$^{c3}$R$^{d3}$, S(O)$_2$R$^{b3}$, NR$^{c3}$S(O)$_2$R$^{b3}$NR$^{c3}$S(O)$_2$NR$^{c3}$R$^{d3}$, and S(O)$_2$NR$^{c3}$R$^{d3}$;

each R$^{a3}$, R$^{b3}$, R$^{c3}$, and R$^3$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-6 membered heteroaryl, and 4-7 membered heterocycloalkyl, wherein said C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-6 membered heteroaryl, and 4-7 membered heterocycloalkyl are each optionally substituted with 1, 2, or 3 substituents independently selected from OH, CN, amino, halo, C$_{1-6}$ alkyl, C$_{1-6}$ alkoxy, C$_{1-6}$ haloalkyl, and C$_{1-6}$ haloalkoxy;

each R$^c$ and R$^{c3}$ is independently selected from H, C$_{1-4}$ alkyl, and CN; and n is 0, 1, 2, or 3.

In some embodiments, the compound is a compound of Formula I, or a pharmaceutically acceptable salt thereof, wherein:

A is Cy$^1$;

Ring B is phenyl, pyridyl, pyrimidinyl, thiazolyl, pyrrolyl, furanyl, pyrazolyl, imidazolyl, isothiazolyl, isoxazolyl, pyrazinyl, pyridazinyl, oxodihydropyridinyl, thienopyridyl, or indazolyl;

X$^2$ is N or CR$^2$;

X$^3$ is CR$^3$;

X$^4$ is CR$^4$;

Cy$^1$ is phenyl, furanyl, pyridyl, pyrazolyl, isoxazolyl, thienyl, benzoxazolyl, thiazolyl, oxazolyl, imidazolyl, oxodihydropyridinyl, isothiazolyl, pyrrolyl, cyclopropyl, or pyrimidinyl, each optionally substituted by 1, 2, or 3 substituents independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-14 membered heteroaryl, 4-14 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$ NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$, wherein said substituents C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-14 membered heteroaryl, 4-14 membered heterocycloalkyl. C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl are each optionally substituted by 1, 2, or 3 further substituents independently selected from halo, C$_{1-6}$ alkyl, C$_{2-6}$ alkenyl, C$_{2-6}$ alkynyl, C$_{1-6}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;

each R$^1$ is independently selected from H, halo, C$_{1-6}$ alkyl, C$_{2-6}$ alkenyl, C$_{2-6}$ alkynyl, C$_{1-6}$ haloalkyl, and OR$^{a1}$;

R$^2$, R$^3$, and R$^4$ are each H;

each R$^a$, R$^b$, R$^c$, R$^d$, and R$^{a1}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl, wherein said C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl of R$^a$, R$^b$, R$^c$, R$^d$, and R$^{a1}$ is optionally substituted with 1, 2, 3, 4, or 5 substituents independently selected from halo, C$_{1-4}$ alkyl, C$_{1-4}$ haloalkyl, C$_{1-6}$ haloalkyl, C$_{2-6}$ alkenyl, C$_{2-6}$ alkynyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$;

each R$^{a3}$, R$^{b3}$, R$^{c3}$, and R$^{d3}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-6 membered heteroaryl, and 4-7 membered heterocycloalkyl, wherein said C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-6 membered heteroaryl, and 4-7 membered heterocycloalkyl are each optionally substituted with 1, 2, or 3 substituents independently selected from OH, CN, amino, halo, C$_{1-6}$ alkyl, C$_{1-6}$ alkoxy, C$_{1-6}$ haloalkyl, and C$_{1-6}$ haloalkoxy;

each R$^c$ and R$^{c3}$ is independently selected from H, C$_{1-4}$ alkyl, and CN; and n is 0, 1, 2, or 3.

In some embodiments, the compound is a compound of Formula I, or a pharmaceutically acceptable salt thereof, wherein:

A is Cy$^1$;

Ring B is phenyl, pyridyl, pyrimidinyl, thiazolyl, pyrrolyl, furanyl, pyrazolyl, imidazolyl, isothiazolyl, or isoxazolyl;

X$^2$ is N or CR$^2$;

X$^3$ is CR$^3$;

X$^4$ is CR$^4$;

Cy$^1$ is phenyl, furanyl, pyridyl, pyrazolyl, isoxazolyl, thienyl, or benzoxazolyl, each optionally substituted by 1, 2, or 3 substituents independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-14 membered heteroaryl, 4-14 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, R$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$, wherein said substituents C$_{1-6}$ alkyl, C$_{2-6}$ alkenyl, C$_{2-6}$ alkynyl, C$_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl are each optionally substituted by 1, 2, or 3 further substituents independently selected from halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$ $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each $R^1$ is independently selected from H, halo, $C_{1-6}$ alkyl, $C_{2-6}$ alkenyl, $C_{1-6}$ haloalkyl, and $OR^a$;

$R^2$, $R^3$, and $R^4$ are each H;

each $R^a$, $R^b$, $R^c$, $R^d$, and $R^{a1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^a$, $R^b$, $R^c$, $R^d$, and $R^{a1}$ is optionally substituted with 1, 2, 3, 4, or 5 substituents independently selected from halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-6 membered heteroaryl, and 4-7 membered heterocycloalkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-6 membered heteroaryl, and 4-7 membered heterocycloalkyl are each optionally substituted with 1, 2, or 3 substituents independently selected from OH, CN, amino, halo, $C_{1-6}$alkyl, $C_{1-6}$alkoxy, $C_{1-6}$haloalkyl, and $C_{1-6}$haloalkoxy;

each $R^c$ and $R^{c3}$ is independently selected from H, $C_{1-4}$ alkyl, and CN; and n is 0, 1, 2, or 3.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula I can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chained or branched. The term "Cn-m alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, ethan-1,1-diyl, propan-1,3-diyl, propan-1,2-diyl, propan-1,1-diyl, butan-1,4-diyl, butan-1,3-diyl, butan-1,2-diyl, 2-methyl-propan-1,3-diyl and the like.

The term "alkoxy", employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms. The term "$C_{n-m}$ dialkoxy" refers to a linking group of formula —O—($C_{n-m}$ alkyl)-O—, the alkyl group of which has n to m carbons. Example dialkyoxy groups include —OCH$_2$CH$_2$O— and OCH$_2$CH$_2$CH$_2$O—. In some embodiments, the two O atoms of a $C_{n-m}$ dialkoxy group may be attached to the same B atom to form a 5- or 6-membered heterocycloalkyl group.

The term "amino" refers to a group of formula —NH$_2$.

The term "carbonyl", employed alone or in combination with other terms, refers to a —C(=O)— group, which also may be written as C(O).

The term "cyano" or "nitrile" refers to a group of formula —C≡N, which also may be written as —CN.

The terms "halo" or "halogen", used alone or in combination with other terms, refers to fluoro, chloro, bromo and iodo. In some embodiments, "halo" refers to a halogen atom selected from F, Cl, or Br. In some embodiments, halo groups are F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include CF$_3$, C$_2$F$_5$, CHF$_2$, CH$_2$F, CCl$_3$, CHCl$_2$, C$_2$Cl$_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "sulfido" refers to a sulfur atom as a divalent substituent, forming a thiocarbonyl group (C=S) when attached to carbon.

The term "oxidized" in reference to a ring-forming N atom refers to a ring-forming N-oxide.

The term "oxidized" in reference to a ring-forming S atom refers to a ring-forming sulfonyl or ring-forming sulfinyl.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, and the like. In some embodiments, aryl groups have from 6 to about 10 carbon atoms. In some embodiments aryl groups have 6 carbon atoms. In some embodiments aryl groups have 10 carbon atoms. In some embodiments, the aryl group is phenyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridinyl (pyridyl), pyrimidinyl, pyrazinyl, pyridazinyl, and the like.

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl, isoindolyl, and pyridazinyl.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl.

The term "heterocycloalkyl," employed alone or in combination with other terms, refers to a non-aromatic ring or ring system, which may optionally contain one or more alkenylene groups as part of the ring structure, which has at least one heteroatom ring member independently selected from nitrogen, sulfur, oxygen and phosphorus, and which has 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic (e.g., having two fused or bridged rings) or spirocyclic ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or S(O)$_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

The term, "compound," as used herein is meant to include all stereoisomers, geometric isomers, tautomers and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000). Smith et al., *March's Advanced Organic Chemistry: Reactions, Mechanisms, and Structure*, 6$^{th}$ Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^3$C), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

General Scheme 1

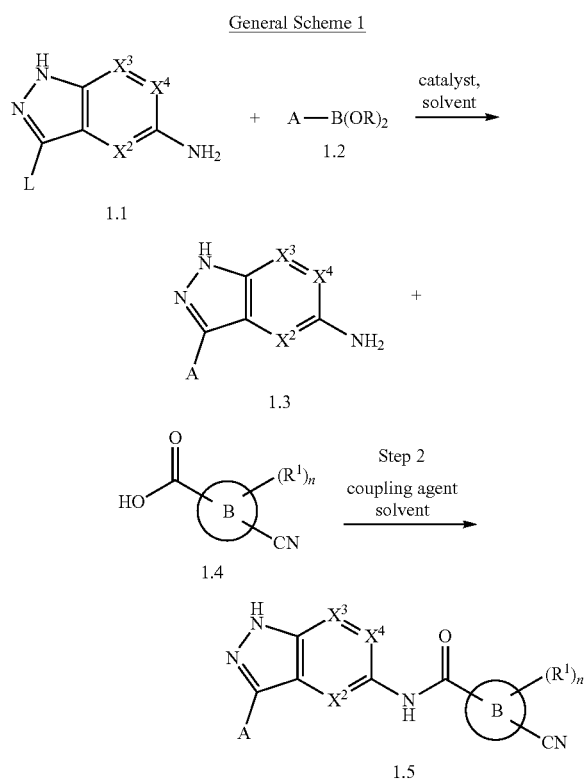

A general synthesis of compounds of the invention comprises a 2-step procedure as shown in General Scheme 1 above. A 5-aminoindazole or aza derivative (1.1) with suitable substitution at C3 (L=leaving group, eg.: Cl, Br, I, OTf) is coupled with a suitable aryl, alkenyl, or alkyl borane (1.2) using a metal-catalyzed cross-coupling reaction employing reagents such as Pd(amphos)Cl$_2$ or PdCl$_2$(dppf)$_2$ (see: Chem. Rev. 1995, 95, 2457; Chem. Soc. Rev. 2014, 43, 412; J. Organomet. Chem. 1999, 576, 147) to afford intermediate 1.3. Combining intermediate 1.3 and carboxylic acid 1.4 with a suitable activating agent such as T3P or EDCI (see: Chem. Soc. Rev. 2009, 38, 606) to form an amide bond will lead to products of type 1.5 (Formula I). Products of type 1.3 and 1.5 can be purified by silica gel chromatography, preparative reverse-phase HPLC, SFC, as well as other purification methods such as crystallization.

General Scheme 2

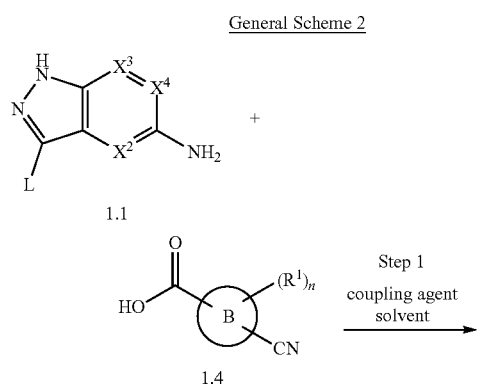

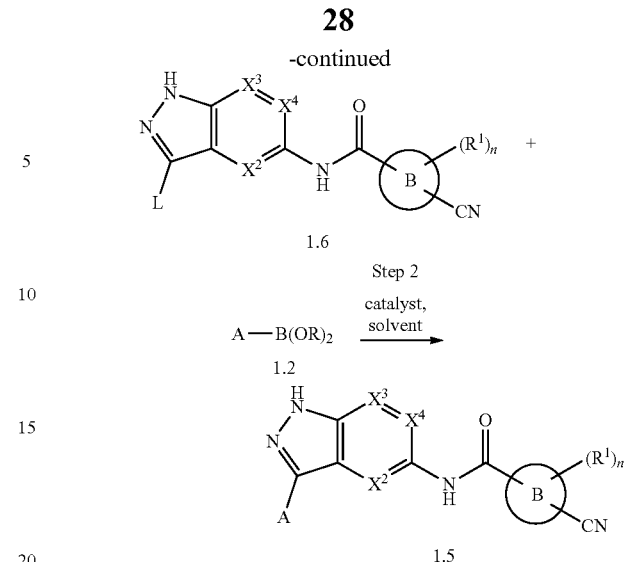

Alternatively, products of type 1.5 may be prepared using the 2-step procedure as shown in General Scheme 2. A 5-aminoindazole or aza derivative thereof (1.1) with substitution at C3 (L=leaving group, eg.: Cl, Br, I, OTf) is coupled with a carboxylic acid using a suitable activating agent such as T3P or EDCI (see: Chem. Soc. Rev. 2009, 38, 606) to form an amide of type 1.6. The amide intermediate (1.6) is then coupled with a suitable aryl, alkenyl, or alkyl borane (1.2) using a metal-catalyzed cross-coupling reaction employing reagents such as Pd(amphos)Cl$_2$ or PdCl$_2$(dppf)$_2$ (see: Chem. Rev. 1995, 95, 2457; Chem. Soc. Rev. 2014, 43, 412; J. Organomet. Chem. 1999, 576, 147) to afford products of type 1.5 (Formula I). Products of type 1.6 and 1.5 can be purified by silica gel chromatography, preparative reverse-phase HPLC, SFC, as well as other purification methods such as crystallization.

Methods of Use

Over-activation of LRRK2 kinase activity, e.g., in kinase mutant G2019S, is a mechanism in alpha-synuclein related neurodegeneration, and is implicated in diseases that are characterized by the formation of Lewy bodies. Compounds as described herein, e.g., compounds of Formula I, exhibit inhibitory activity against LRRK2 kinase, including LRRK2 mutant kinase, such as mutant G2019S. Kinase activity can be determined using a kinase assay, which typically employs a kinase substrate and a phosphate group donor, such as ATP (or a derivative thereof). An exemplary kinase assay is described in Example A.

The present disclosure provides methods of modulating (e.g., inhibiting) LRRK2 activity, by contacting LRRK2 with a compound of the invention, or a pharmaceutically acceptable salt thereof. In some embodiments, the contacting can be administering to a patient, in need thereof, a compound provided herein, or a pharmaceutically acceptable salt thereof. In certain embodiments, the compounds of the present disclosure, or pharmaceutically acceptable salts thereof, are useful for therapeutic administration to treat neurodegenerative disease. For example, a method of treating a disease or disorder associated with inhibition of LRRK2 interaction can include administering to a patient in need thereof a therapeutically effective amount of a compound provided herein, or a pharmaceutically acceptable salt thereof. The compounds of the present disclosure can be used alone, in combination with other agents or therapies or as an adjuvant or neoadjuvant for the treatment of diseases or disorders, including neurodegenerative diseases. For the uses described herein, any of the compounds of the disclosure, including any of the embodiments thereof, may be used.

Compounds and compositions as described herein, e.g., compounds of Formula I are useful in the treatment and/or prevention of LRRK2 kinase mediated disorders, including LRRK2 kinase mutant mediated diseases. LRRK2 kinase mutant G2019S mediated diseases include, but are not limited to, neurological diseases such as Parkinson's disease and other Lewy body diseases such as Parkinson disease with dementia, Parkinson's associated risk syndrome, dementia with Lewy bodies (e.g., diffuse Lewy body disease (DLBD), Lewy body dementia, Lewy body disease, cortical Lewy body disease or senile dementia of Lewy type), Lewy body variant of Alzheimer's disease (i.e., diffuse Lewy body type of Alzheimer's disease), combined Parkinson's disease and Alzheimer's disease, as well as diseases associated with glial cortical inclusions, such as syndromes identified as multiple system atrophy, including striatonigral degeneration, olivopontocerebellar atrophy, and Shy-Drager syndrome, or other diseases associated with Parkinsonism, such as Hallervorden-Spatz syndrome (also referred to as Hallervorden-Spatz disease), fronto-temporal dementia, Sandhoff disease, progressive supranuclear palsy, corticobasal degeneration, autonomic dysfunctions (e.g., postural or orthostatic hypotension), cerebellar dysfunctions, ataxia, movement disorders, cognitive deterioration, sleep disorders, hearing disorders, tremors, rigidity (e.g., joint stiffness, increased muscle tone), bradykinesia, akinesia and postural instability (failure of postural reflexes, along other disease related factors such as orthostatic hypotension or cognitive and sensory changes, which lead to impaired balance and falls); cancers, including melanoma, acute myelogenous leukemia, breast carcinoma, lung adenocarincoma, prostate adenocarcinoma, renal cell carcinoma, and papillary thyroid carcinoma; autoimmune diseases such as Inflammatory Bowel Disease (e.g. Crohn's disease and ulcerative colitis); and leprosy.

In some embodiments, a method of treating a disease is provided comprising administering to a patient in need thereof a therapeutically effective amount of a compound of Formula I, or a pharmaceutically acceptable salt thereof, wherein the disease is selected from the group consisting of Parkinson's disease, Parkinson disease with dementia, Parkinson's associated risk syndrome, dementia with Lewy bodies, Lewy body variant of Alzheimer's disease, combined Parkinson's disease and Alzheimer's disease, multiple system atrophy, striatonigral degeneration, olivopontocerebellar atrophy, Shy-Drager syndrome, Hallervorden-Spatz syndrome, fronto-temporal dementia, Sandhoff disease, progressive supranuclear palsy, corticobasal degeneration, postural hypotension, orthostatic hypotension, cerebellar dysfunctions, ataxia, movement disorders, cognitive deterioration, sleep disorders, hearing disorders, tremors, rigidity, bradykinesia, akinesia, postural instability, melanoma, acute myelogenous leukemia, breast carcinoma, lung adenocarincoma, prostate adenocarcinoma, renal cell carcinoma, papillary thyroid carcinoma, Crohn's disease, ulcerative colitis, and leprosy.

In some embodiments, a method of treating a neurological disease is provided comprising administering to a patient in need thereof a therapeutically effective amount of a compound of Formula I, or a pharmaceutically acceptable salt thereof, wherein the neurological disease is selected from the group consisting of Parkinson's disease, Parkinson disease with dementia, Parkinson's associated risk syndrome, dementia with Lewy bodies, Lewy body variant of Alzheimer's disease, combined Parkinson's disease and Alzheimer's disease, multiple system atrophy, striatonigral degeneration, olivopontocerebellar atrophy, Shy-Drager syndrome, Hallervorden-Spatz syndrome, fronto-temporal dementia, Sandhoff disease, progressive supranuclear palsy, corticobasal degeneration, postural hypotension, orthostatic hypotension, cerebellar dysfunctions, ataxia, movement disorders, cognitive deterioration, sleep disorders, hearing disorders, tremors, rigidity, bradykinesia, akinesia, and postural instability.

In some embodiments, a method of treating a neurological disease is provided comprising administering to a patient in need thereof a therapeutically effective amount of a compound of Formula I, or a pharmaceutically salt thereof, wherein the neurological disease is selected from the group consisting of Parkinson's disease, Parkinson disease with dementia, Parkinson's associated risk syndrome, dementia with Lewy bodies, Lewy body variant of Alzheimer's disease, combined Parkinson's disease and Alzheimer's disease, multiple system atrophy, striatonigral degeneration, olivopontocerebellar atrophy, and Shy-Drager syndrome.

In some embodiments, a method of treating Parkinson's disease is provided comprising administering to a patient in need thereof a therapeutically effective amount of a compound of Formula I, or a pharmaceutically acceptable salt thereof.

In some embodiments, a method of treating a cancer is provided comprising administering to a patient in need thereof a therapeutically effective amount of a compound of Formula I, or a pharmaceutically acceptable salt thereof, wherein the cancer is selected from the group consisting of melanoma, acute myelogenous leukemia, breast carcinoma, lung adenocarincoma, prostate adenocarcinoma, renal cell carcinoma, and papillary thyroid carcinoma.

In some embodiments, a method of treating an autoimmune disease is provided comprising administering to a patient in need thereof a therapeutically effective amount of a compound od Formula I, or a pharmaceutically acceptable salt thereof, wherein the autoimmune disease is selected from the group consisting of Crohn's disease and ulcerative colitis.

In some embodiments, a method of treating leprosy is provided comprising administering to a patient in need thereof a therapeutically effective amount of a compound of Formula I, or a pharmaceutically acceptable salt thereof, or a composition comprising such compound or salt thereof.

In some embodiments, the compounds as described herein, e.g., compounds of Formula I, are inhibitors of LRRK2 kinase activity. In some embodiments, the compounds as described herein, e.g. compounds of Formula I, are inhibitors of LRRK2 mutant kinase activity. In some embodiments, the compounds as described herein, e.g. compounds of Formula I, are inhibitors of LRRK2 mutant G2019S kinase activity.

Compounds as described herein, e.g., compounds of Formula I, exhibit cellular biological activities, including but not limited to reduction in phosphorylation of ser910 or ser935 in HEK-293 cells transfected with either wild-type LRRK2 or LRRK2 G2019S mutant.

In some embodiments, compounds of Formula I are selective LRRK2 G2019S mutant inhibitors as compared to wild-type LRRK2.

As used herein, the term "contacting" refers to the bringing together of the indicated moieties in an in vitro system or an in vivo system such that they are in sufficient physical proximity to interact.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

As used herein, the term "selective" or "selectivity" as it relates to kinase activity, means that a compound as described herein, e.g. a compound of Formula I, is a more potent inhibitor of a particular kinase, such as LRRK2 kinase, when compared to another kinase. While LRRK2 has other enzymatic activities, it is understood that when inhibitory activity or selectivity of LRRK2, or any mutation thereof, is mentioned, it is the LRRK2 kinase activity that is being referred to, unless clearly stated otherwise. As such, selectivity of LRRK2 relative to another kinase indicates a comparison of the $IC_{50}$ of a compound on the kinase activity of LRRK2 to the $IC_{50}$ of the compound on the kinase activity of another kinase. For example, a compound that is 10 fold selective for LRRK2 kinase activity relative to another kinase activity will have a ratio of $IC_{50}$(other kinase)÷$IC_{50}$(LRRK2)=10 (or a ratio of $IC_{50}$(LRRK2)÷$IC_{50}$(other kinase)=0.1).

In some embodiments, a compound as described herein, e.g., a compound of Formula I, is selective for a LRRK2 mutant over wild type LRRK2. Selectivity of LRRK2 mutants relative to wild type LRRK2 indicates a comparison of the $IC_{50}$ of a compound on the kinase activity of the mutant LRRK2 to the $IC_{50}$ of the compound on the kinase activity of wild type LRRK2. For example, a compound that is 10 fold selective for LRRK2 mutant kinase activity relative to wild type LRKK2 kinase activity will have a ratio of $IC_{50}$(wild type LRRK2)÷$IC_{50}$(mutant LRRK2)=10. In some embodiments, a compound provided herein is greater than 1 fold selective, greater than 2 fold selective, greater than 5 fold selective, greater than 10 fold selective, greater than 25 fold selective, or greater than 50 fold selective for LRRK2 mutant kinase over wild type LRRK2. In some embodiments, the LRRK2 mutant is LRRK2 G2019S.

The term "LRRK2-mediated condition", "Leucine-rich repeat kinase 2 mediated disorder" or any other variation thereof, as used herein means any disease or other condition in which LRRK2, including any mutations thereof, is known to play a role, or a disease state that is associated with elevated activity or expression of LRRK2, including any mutations thereof. For example, a "LRRK2-mediated condition" may be relieved by inhibiting LRRK2 kinase activity. Such conditions include certain neurodegenerative diseases, such as Lewy body diseases, including, but not limited to, Parkinson's disease, Lewy body variant of Alzheimer's disease, combined Parkinson's disease and Alzheimer's disease, dementia with Lewy bodies, diffuse Lewy body disease, as well as any syndrome identified as multiple system atrophy; certain cancers, such as melanoma, papillary renal cell carcinoma and papillary thyroid carcinoma; certain autoimmune diseases, such as Inflammatory Bowel Disease (e.g. Crohn's disease and ulcerative colitis); and leprosy.

The term "neurodegenerative diseases" includes any disease or condition characterized by problems with movements, such as ataxia, and conditions affecting cognitive abilities (e.g., memory) as well as conditions generally related to all types of dementia. "Neurodegenerative diseases" may be associated with impairment or loss of cognitive abilities, potential loss of cognitive abilities and/or impairment or loss of brain cells. Exemplary "neurodegenerative diseases" include Alzheimer's disease, Parkinson's disease, amyotrophic lateral sclerosis (ALS), Down syndrome, dementia, multi-infarct dementia, mild cognitive impairment (MCI), epilepsy, seizures, Huntington's disease, neurodegeneration induced by viral infection (e.g. AIDS, encephalopathies), traumatic brain injuries, as well as ischemia and stroke.

"Neurodegenerative diseases" also includes any undesirable condition associated with the disease. For instance, a method of treating a neurodegenerative disease includes methods of treating or preventing loss of neuronal function characteristic of neurodegenerative disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

One or more additional pharmaceutical agents or treatment methods can be used in combination with a compound of Formula I for treatment of LRRK2-associated diseases, disorders, or conditions, or diseases or conditions as described herein. The agents can be combined with the present compounds in a single dosage form, or the agents can be administered simultaneously or sequentially as separate dosage forms. In some embodiments, the additional pharmaceutical agent is a dopamine precursor, including, for example, levodopa, melevodopa, and etilevodopa. In some embodiments, the additional pharmaceutical agent is a dopamine agonist, including, for example, pramipexole, ropinorole, apomorphine, rotigotine, bromocriptine, cabergoline, and pergolide. In some embodiments, the additional pharmaceutical agent is a monamine oxidase B ("MAO B") inhibitor, including, for example, selegiline and rasagiline. In some embodiments, the additional pharmaceutical agent is a catechol O-methyltransferase ("COMT") inhibitor, including, for example, tolcapone and entacapone. In some embodiments, the additional pharmaceutical agent is an anticholinergic agent including, for example, benztropine, trihexyphenidyl, procyclidine, and biperiden. In some embodiments, the additional pharmaceutical agent is a glutamate ("NMDA") blocking drug, including, for example, amantadine. In some embodiments, the additional pharmaceutical agent is an adenosine A2A antagonist, including, for example, istradefylline and preladenant. In some embodiments, the additional pharmaceutical agent is a 5-HT1a antagonist, including, for example, piclozotan and pardoprunox. In some embodiments, the additional pharmaceutical agent is an alpha 2 antagonist, including, for example, atipamezole and fipamezole.

Formulations, Dosage Forms, and Administration

When employed as pharmaceuticals, the compounds of the present disclosure can be administered in the form of pharmaceutical compositions. Thus the present disclosure provides a composition comprising a compound of Formula I or any of the formulas as described herein, a compound as recited in any of the claims and described herein, or a pharmaceutically acceptable salt thereof, or any of the embodiments thereof, and at least one pharmaceutically acceptable carrier. These compositions can be prepared in a manner well known in the pharmaceutical arts, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the present disclosure or a pharmaceutically acceptable salt thereof, in combination with one or more pharmaceutically acceptable carriers. In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In some embodiments, the composition is a sustained release composition comprising at least one compound described herein, or a pharmaceutically acceptable salt thereof, and at least one pharmaceutically acceptable carrier or excipient The compositions can be formulated in a unit dosage form, each dosage containing from about 5 to about 1,000 mg (1 g). The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers.

EXAMPLES

Experimental procedures for compounds of the invention are provided below. Where the preparation of starting materials is not described, these are commercially available, known in the literature, or readily obtainable by those skilled in the art using standard procedures. Where it is stated that compounds were prepared analogously to earlier examples or intermediates, it will be appreciated by the skilled person that the reaction time, number of equivalents of reagents and temperature can be modified for each specific reaction and that it may be necessary or desirable to employ different work-up or purification techniques. Where reactions are carried out using microwave irradiation, the microwave used is a Biotage Initiator. The actual power supplied varies during the course of the reaction in order to maintain a constant temperature.

All solvents used were commercially available and were used without further purification. Reactions were typically run using anhydrous solvents under an inert atmosphere of nitrogen.

Liquid Chromatography-Mass Spectrometry Method A

Instrument Name: MDAP_Fractionlynx; Method Description: Semi preparative MDAP Method; LC/MS System: Fractionlynx (Waters) with ZQ MS detector; LC/MS Conditions: Column: XSelect CSH Prep. C18 5 μm OBD 30×100 mm @ room T; Injection loop: 1 ml; Solvents: A=H$_2$O+0.1% HCOOH; B=MeCN.

| Gradient: | | | | |
|---|---|---|---|---|
| Time (min) | Flow Rate (ml/min) | % A | % B | Curve |
| initial | 40.0 | 60.0 | 40.0 | — |
| 10.0 | 40.0 | 20.0 | 80.0 | 6 |
| 10.5 | 40.0 | 0.0 | 100.0 | 6 |
| 14.5 | 40.0 | 0.0 | 100.0 | 6 |
| 15.0 | 40.0 | 60.0 | 40.0 | 6 |
| 16.1 | 3.0 | 60.0 | 40.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionisation mode: Positive Electrospray (ES+); Scan Range: ES+ 100 to 900 AMU; Scan Duration: 0.50 seconds.

Liquid Chromatography-Mass Spectrometry Method B
Instrument Name: MDAP_Fractionlynx; Method Description: Semi preparative MDAP Method; LC/MS System: Fractionlynx (Waters) with ZQ MS detector; LC/MS Conditions: Column: XSelect CSH Prep. C18 5 μm OBD 30×100 mm @ room T; Injection loop: 1 mL; Solvents: A=H$_2$O+0.1% HCOOH; B=MeCN.

| Gradient: | | | | |
|---|---|---|---|---|
| Time (min) | Flow Rate (ml/min) | % A | % B | Curve |
| initial | 40.0 | 60.0 | 40.0 | — |
| 10.0 | 40.0 | 30.0 | 70.0 | 6 |
| 10.5 | 40.0 | 0.0 | 100.0 | 6 |
| 14.5 | 40.0 | 0.0 | 100.0 | 6 |
| 15.0 | 40.0 | 60.0 | 40.0 | 6 |
| 16.1 | 3.0 | 60.0 | 40.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionisation mode: Positive Electrospray (ES+); Scan Range: ES+ 100 to 900 AMU; Scan Duration: 0.50 seconds.

Liquid Chromatography-Mass Spectrometry Method C
Instrument Name: MDAP_Fractionlynx; Method Description: Semi preparative MDAP Method; LC/MS System: Fractionlynx (Waters) with ZQ MS detector; LC/MS Conditions: Column: XSelect CSH Prep. C18 5 μm OBD 30×100 mm @ room T; Injection loop: 1 mL; Solvents: A=H$_2$O+0.1% HCOOH; B=MeCN.

| Gradient: | | | | |
|---|---|---|---|---|
| Time (min) | Flow Rate (ml/min) | % A | % B | Curve |
| initial | 40.0 | 60.0 | 40.0 | — |
| 6.0 | 40.0 | 35.0 | 65.0 | 6 |
| 7.0 | 40.0 | 0.0 | 100.0 | 6 |
| 10.0 | 40.0 | 0.0 | 100.0 | 6 |
| 10.5 | 40.0 | 60.0 | 40.0 | 6 |
| 11.0 | 3.0 | 60.0 | 40.0 | 6 |

The curve parameter followed Waters definition (6=linear, 11=step); Acquisition stop time: 11 min; UV Conditions: UV detection range: 210 nm to 350 nm; Acquisition rate: 1.0 spectra/s; MS Conditions: Ionisation mode: Positive Electrospray (ES+); Scan Range: ES+ 100 to 900 AMU; Scan Duration: 0.50 seconds.

Liquid Chromatography-Mass Spectrometry Method D
Instrument Name: MDAP_Fractionlynx; Method Description: Semi preparative MDAP Method; LC/MS System: Fractionlynx (Waters) with ZQ MS detector; LC/MS Conditions: Column: XSelect CSH Prep. C18 5 μm OBD 30×100 mm @ room T; Injection loop: 1 mL; Solvents: A=H$_2$O+0.1% HCOOH; B=MeCN.

| Gradient: | | | | |
|---|---|---|---|---|
| Time (min) | Flow Rate (ml/min) | % A | % B | Curve |
| initial | 40.0 | 90.0 | 10.0 | — |
| 10.0 | 40.0 | 40.0 | 60.0 | 6 |
| 10.5 | 40.0 | 0.0 | 100.0 | 6 |
| 14.5 | 40.0 | 0.0 | 100.0 | 6 |
| 15.0 | 40.0 | 90.0 | 10.0 | 6 |
| 16.1 | 3.0 | 90.0 | 10.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionisation mode: Positive Electrospray (ES+); Scan Range: ES+ 100 to 900 AMU; Scan Duration: 0.50 seconds.

Liquid Chromatography Method E
Instrument Name: Gilson GX-281 AutoPurification System
Column: Welch Ultimate AQ-C18, 150×30 mm, 5 um particle size
Solvents: A=H$_2$O+0.1% TFA; B=MeCN
Gradient: 30-60% B depending on compound polarity Liquid Chromatography-Mass Spectrometry Method F
Instrument Name: MDAP_Fractionlynx; Method Description: Semi preparative MDAP Method; LC/MS System: Fractionlynx (Waters) with ZQ MS detector; LC/MS Conditions: Column: XSelect CSH Prep. C18 5 μm OBD 30×100 mm @ room T; Injection loop: 1 ml; Solvents: A=H$_2$O+0.1% HCOOH; B=MeCN.

| Gradient: | | | | |
|---|---|---|---|---|
| Time (min) | Flow Rate (ml/min) | % A | % B | Curve |
| initial | 40.0 | 76.0 | 24.0 | — |
| 10.0 | 40.0 | 66.0 | 34.0 | 6 |
| 10.5 | 40.0 | 0.0 | 100.0 | 6 |
| 14.5 | 40.0 | 0.0 | 100.0 | 6 |
| 15.0 | 40.0 | 76.0 | 24.0 | 6 |
| 15.1 | 3.0 | 76.0 | 24.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionisation mode: Positive Electrospray (ES+); Scan Range: ES+ 100 to 900 AMU; Scan Duration: 0.50 seconds.

Liquid Chromatography-Mass Spectrometry Method G
Instrument Name: MDAP_Fractionlynx; Method Description: Semi preparative MDAP Method; LC/MS System: Fractionlynx (Waters) with ZQ MS detector: LC/MS Conditions: Column: XSelect CSH Prep. C18 5 µm OBD 30×100 mm @ room T; Injection loop: 1 ml; Solvents: A=H$_2$O+0.1% HCOOH; B=MeCN.

| Gradient: | | | | |
|---|---|---|---|---|
| Time (min) | Flow Rate (ml/min) | % A | % B | Curve |
| initial | 40.0 | 33.0 | 67.0 | — |
| 10.0 | 40.0 | 25.0 | 75.0 | 6 |
| 10.5 | 40.0 | 0.0 | 100.0 | 6 |
| 14.5 | 40.0 | 0.0 | 100.0 | 6 |
| 15.0 | 40.0 | 33.0 | 67.0 | 6 |
| 15.1 | 3.0 | 33.0 | 67.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionisation mode: Positive Electrospray (ES+); Scan Range: ES+ 100 to 900 AMU; Scan Duration: 0.50 seconds.

Liquid Chromatography-Mass Spectrometry Method H

Instrument Name: MDAP_Fractionlynx; Method Description: Semi preparative MDAP Method; LC/MS System: Fractionlynx (Waters) with ZQ MS detector; LC/MS Conditions: Column: XSelect CSH Prep. C18 5 µm OBD 30×100 mm @ room T; Injection loop: 1 ml; Solvents: A=H$_2$O+0.1% HCOOH; B=MeCN.

| Gradient: | | | | |
|---|---|---|---|---|
| Time (min) | Flow Rate (ml/min) | % A | % B | Curve |
| initial | 40.0 | 40.0 | 60.0 | — |
| 10.0 | 40.0 | 0.0 | 100.0 | 6 |
| 10.5 | 40.0 | 0.0 | 100.0 | 6 |
| 14.5 | 40.0 | 0.0 | 100.0 | 6 |
| 15.0 | 40.0 | 40.0 | 60.0 | 6 |
| 16.1 | 3.0 | 40.0 | 60.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionisation mode: Positive Electrospray (ES+); Scan Range: ES+ 100 to 900 AMU; Scan Duration: 0.50 seconds.

Liquid Chromatography-Mass Spectrometry Method I

Instrument Name: MDAP_Fractionlynx; Method Description: Semi preparative MDAP Method; LC/MS System: Fractionlynx (Waters) with ZQ MS detector; LC/MS Conditions: Column: XSelect CSH Prep. C18 5 µm OBD 30×100 mm @ room T; Injection loop: 1 ml; Solvents: A=H$_2$O+0.10% HCOOH; B=MeCN.

| Gradient: | | | | |
|---|---|---|---|---|
| Time (min) | Flow Rate (ml/min) | % A | % B | Curve |
| initial | 40.0 | 55.0 | 45.0 | — |
| 10.0 | 40.0 | 40.0 | 60.0 | 6 |
| 10.5 | 40.0 | 0.1 | 99.9 | 6 |
| 14.5 | 40.0 | 0.1 | 99.9 | 6 |
| 15.0 | 40.0 | 55.0 | 45.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionisation mode: Positive Electrospray (ES+); Scan Range: ES+ 100 to 900 AMU; Scan Duration: 0.50 seconds.

Liquid Chromatography-Mass Spectrometry Method J

Instrument Name: MDAP_Fractionlynx; Method Description: Semi preparative MDAP Method; LC/MS System: Fractionlynx (Waters) with ZQ MS detector: LC/MS Conditions: Column: XSelect CSH Prep. C18 5 µm OBD 30×100 mm @ room T; Injection loop: 1 ml; Solvents: A=H$_2$O+0.1% HCOOH; B=MeCN.

| Gradient: | | | | |
|---|---|---|---|---|
| Time (min) | Flow Rate (ml/min) | % A | % B | Curve |
| initial | 40.0 | 50.0 | 50.0 | — |
| 10.0 | 40.0 | 30.0 | 70.0 | 6 |
| 10.5 | 40.0 | 0.1 | 99.9 | 6 |
| 14.5 | 40.0 | 0.1 | 99.9 | 6 |
| 15.0 | 40.0 | 50.0 | 50.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionisation mode: Positive Electrospray (ES+); Scan Range: ES+ 100 to 900 AMU; Scan Duration: 0.50 seconds.

Liquid Chromatography-Mass Spectrometry Method K

Instrument Name: MDAP_Fractionlynx; Method Description: Semi preparative MDAP Method: LC/MS System: Fractionlynx (Waters) with ZQ MS detector; LC/MS Conditions: Column: XSelect CSH Prep. C18 5 µm OBD 30×100 mm @ room T; Injection loop: 1 ml; Solvents: A=H$_2$O+0.1% HCOOH; B=MeCN.

| Gradient: | | | | |
|---|---|---|---|---|
| Time (min) | Flow Rate (ml/min) | % A | % B | Curve |
| initial | 40.0 | 45.0 | 55.0 | — |
| 10.0 | 40.0 | 30.0 | 70.0 | 6 |
| 10.5 | 40.0 | 0.0 | 100.0 | 6 |
| 14.5 | 40.0 | 0.0 | 100.0 | 6 |
| 15.0 | 40.0 | 45.0 | 55.0 | 6 |
| 16.1 | 3.0 | 45.0 | 55.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionisation mode: Positive Electrospray (ES+); Scan Range: ES+ 100 to 900 AMU; Scan Duration: 0.50 seconds.

Liquid Chromatography-Mass Spectrometry Method L

Instrument Name: MDAP_Fractionlynx; Method Description: Semi preparative MDAP Method; LC/MS System: Fractionlynx (Waters) with ZQ MS detector; LC/MS Conditions: Column: Gemini 5 µm C18 110A AXIA (100× 30 mm) @ room T; Injection loop: 1 ml; Solvents: A=10 mM ammonium bicarbonate aqueous solution adjusted to pH 10 with ammonia; B=MeCN.

| Gradient: | | | | |
|---|---|---|---|---|
| Time (min) | Flow Rate (ml/min) | % A | % B | Curve |
| initial | 40.0 | 60.0 | 40.0 | — |
| 10.0 | 40.0 | 20.0 | 80.0 | 6 |
| 10.5 | 40.0 | 0.0 | 100.0 | 6 |
| 14.5 | 40.0 | 0.0 | 100.0 | 6 |
| 15.0 | 40.0 | 60.0 | 40.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionisation mode: Positive Electrospray (ES+); Scan Range: ES+ 100 to 900 AMU; Scan Duration: 0.50 seconds.

Liquid Chromatography-Mass Spectrometry Method M
Instrument Name: MDAP_Fractionlynx; Method Description: Semi preparative MDAP Method; LC/MS System: Fractionlynx (Waters) with ZQ MS detector: LC/MS Conditions: Column: XSelect CSH Prep. C18 5 μm OBD 30×100 mm @ room T; Injection loop: 1 ml; Solvents: A=H$_2$O+0.1% HCOOH; B=MeCN.

| Gradient: | | | | |
|---|---|---|---|---|
| Time (min) | Flow Rate (ml/min) | % A | % B | Curve |
| initial | 40.0 | 40.0 | 60.0 | — |
| 10.0 | 40.0 | 21.0 | 79.0 | 6 |
| 10.5 | 40.0 | 0.0 | 100.0 | 6 |
| 14.5 | 40.0 | 0.0 | 100.0 | 6 |
| 15.0 | 40.0 | 40.0 | 60.0 | 6 |
| 15.1 | 40.0 | 40.0 | 60.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionisation mode: Positive Electrospray (ES+); Scan Range: ES+ 100 to 900 AMU; Scan Duration: 0.50 seconds.

Liquid Chromatography-Mass Spectrometry Method N
Instrument Name: MDAP_Fractionlynx; Method Description: Semi preparative MDAP Method; LC/MS System: Fractionlynx (Waters) with ZQ MS detector; LC/MS Conditions: Column: XSelect CSH Prep. C18 5 μm OBD 30×100 mm @ room T; Injection loop: 1 ml; Solvents: A=H$_2$O+0.1% HCOOH; B=MeCN.

| Gradient: | | | | |
|---|---|---|---|---|
| Time (min) | Flow Rate (ml/min) | % A | % B | Curve |
| initial | 40.0 | 80.0 | 20.0 | — |
| 10.0 | 40.0 | 30.0 | 70.0 | 6 |
| 10.5 | 40.0 | 0.0 | 100.0 | 6 |
| 14.5 | 40.0 | 0.0 | 100.0 | 6 |
| 15.0 | 40.0 | 80.0 | 20.0 | 6 |
| 16.1 | 3.0 | 80.0 | 20.0 | 6 |

The curve parameter followed Waters definition (6=linear, 11=step); Acquisition stop time: 11 min; UV Conditions: UV detection range: 210 nm to 350 nm; Acquisition rate: 1.0 spectra/s; MS Conditions: Ionisation mode: Positive Electrospray (ES+); Scan Range: ES+ 100 to 900 AMU; Scan Duration: 0.50 seconds.

Liquid Chromatography-Mass Spectrometry Method 0
Instrument Name: MDAP_Fractionlynx; Method Description: Semi preparative MDAP Method; LC/MS System: Fractionlynx (Waters) with ZQ MS detector; LC/MS Conditions: Column: XSelect CSH Prep. C18 5 μm OBD 30×100 mm @ room T; Injection loop: 1 ml; Solvents: A=H$_2$O+0.10% HCOOH; B=MeCN.

| Gradient: | | | | |
|---|---|---|---|---|
| Time (min) | Flow Rate (ml/min) | % A | % B | Curve |
| initial | 40.0 | 55.0 | 45.0 | — |
| 10.0 | 40.0 | 15.0 | 85.0 | 6 |
| 10.5 | 40.0 | 0.0 | 100.0 | 6 |
| 14.5 | 40.0 | 0.0 | 100.0 | 6 |
| 15.0 | 40.0 | 55.0 | 45.0 | 6 |
| 15.1 | 40.0 | 55.0 | 45.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionisation mode: Positive Electrospray (ES+); Scan Range: ES+ 100 to 900 AMU; Scan Duration: 0.50 seconds.

Liquid Chromatography-Mass Spectrometry Method P
Instrument Name: MDAP_Fractionlynx; Method Description: Semi preparative MDAP Method; LC/MS System: Fractionlynx (Waters) with ZQ MS detector; LC/MS Conditions: Column: XSelect CSH Prep. C18 5 sum OBD 30×100 mm @ room T; Injection loop: 1 ml; Solvents: A=H$_2$O+0.1°/% HCOOH; B=MeCN.

| Gradient: | | | | |
|---|---|---|---|---|
| Time (min) | Flow Rate (ml/min) | % A | % B | Curve |
| initial | 40.0 | 55.0 | 45.0 | — |
| 10.0 | 40.0 | 10.0 | 90.0 | 6 |
| 10.5 | 40.0 | 0.0 | 100.0 | 6 |
| 14.5 | 40.0 | 0.0 | 100.0 | 6 |
| 15.0 | 40.0 | 55.0 | 45.0 | 6 |
| 15.1 | 40.0 | 55.0 | 45.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionisation mode: Positive Electrospray (ES+); Scan Range: ES+ 100 to 900 AMU; Scan Duration: 0.50 seconds.

Liquid Chromatography-Mass Spectrometry Method O
Instrument Name: MDAP_Fractionlynx; Method Description: Semi preparative MDAP Method; LC/MS System: Fractionlynx (Waters) with ZQ MS detector; LC/MS Conditions: Column: XSelect CSH Prep. C18 5 sum OBD 30×100 mm @ room T; Injection loop: 1 ml; Solvents: A=H$_2$O+0.1°/% HCOOH; B=MeCN.

| Gradient: | | | | |
|---|---|---|---|---|
| Time (min) | Flow Rate (ml/min) | % A | % B | Curve |
| initial | 40.0 | 40.0 | 60.0 | — |
| 10.0 | 40.0 | 30.0 | 70.0 | 6 |
| 10.5 | 40.0 | 0.0 | 100.0 | 6 |

-continued

| Gradient: | | | | |
|---|---|---|---|---|
| Time (min) | Flow Rate (ml/min) | % A | % B | Curve |
| 14.5 | 40.0 | 0.0 | 100.0 | 6 |
| 15.0 | 40.0 | 40.0 | 60.0 | 6 |
| 15.1 | 40.0 | 40.0 | 60.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionisation mode: Positive Electrospray (ES+); Scan Range: ES+ 100 to 900 AMU; Scan Duration: 0.50 seconds.

Liquid Chromatography-Mass Spectrometry Method R
Instrument Name: MDAP_Fractionlynx; Method Description: Semi preparative MDAP Method; LC/MS System: Fractionlynx (Waters) with QDa MS detector; LC/MS Conditions: Column: XSelect CSH Prep. C18 5 sim OBD 30×100 mm @ room T; Injection loop: 1 ml; Solvents: A=$H_2O$+0.10% HCOOH; B=MeCN.

| Gradient: | | | | |
|---|---|---|---|---|
| Time (min) | Flow Rate (ml/min) | % A | % B | Curve |
| initial | 40.0 | 90.0 | 10.0 | — |
| 10.0 | 40.0 | 65.0 | 35.0 | 6 |
| 10.5 | 40.0 | 0.0 | 100.0 | 6 |
| 14.5 | 40.0 | 0.0 | 100.0 | 6 |
| 15.0 | 40.0 | 90.0 | 10.0 | 6 |
| 16.1 | 3.0 | 90.0 | 10.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionisation mode: Positive Electrospray (ES+); Scan Range: ES+ 100 to 900 AMU; Scan Duration: 0.50 seconds.

Liquid Chromatography-Mass Spectrometry Method S
Instrument Name: MDAP_Fractionlynx; Method Description: Semi preparative MDAP Method; LC/MS System: Fractionlynx (Waters) with ZQ MS detector; LC/MS Conditions: Column: XSelect CSH Prep. C18 5 μm OBD 30×100 mm @ room T; Injection loop: 1 ml; Solvents: A=$H_2O$+0.1% HCOOH; B=MeCN.

| Gradient: | | | | |
|---|---|---|---|---|
| Time (min) | Flow Rate (ml/min) | % A | % B | Curve |
| initial | 40.0 | 70.0 | 30.0 | — |
| 10.0 | 40.0 | 52.0 | 48.0 | 6 |
| 10.5 | 40.0 | 0.0 | 100.0 | 6 |
| 14.5 | 40.0 | 0.0 | 100.0 | 6 |
| 15.0 | 40.0 | 70.0 | 30.0 | 6 |
| 16.1 | 3.0 | 70.0 | 30.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionisation mode: Positive Electrospray (ES+); Scan Range: ES+ 100 to 900 AMU; Scan Duration: 0.50 seconds.

Liquid Chromatography-Mass Spectrometry Method T
Instrument Name: MDAP_Fractionlynx; Method Description: Semi preparative MDAP Method; LC/MS System: Fractionlynx (Waters) with ZQ MS detector: LC/MS Conditions: Column: Gemini 5 μm C18 110A AXIA (100× 30 mm) @ room T; Injection loop: 1 ml; Solvents: A=10 mM ammonium bicarbonate aqueous solution adjusted to pH 10 with ammonia; B=MeCN.

| Gradient: | | | | |
|---|---|---|---|---|
| Time (min) | Flow Rate (ml/min) | % A | % B | Curve |
| initial | 40.0 | 70.0 | 30.0 | — |
| 10.0 | 40.0 | 25.0 | 75.0 | 6 |
| 10.5 | 40.0 | 0.0 | 100.0 | 6 |
| 14.5 | 40.0 | 0.0 | 100.0 | 6 |
| 15.0 | 40.0 | 70.0 | 30.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionisation mode: Positive Electrospray (ES+); Scan Range: ES+ 100 to 900 AMU; Scan Duration: 0.50 seconds.

Liquid Chromatography Method U
Column: Welch Xbridge BEH C18 100×30 mm×10 um @ room temperature; mobile phase: water (10 mM $NH_4HCO_3$)-MeCN: 33-53% over 10 minutes.

Liquid Chromatography Method V
Column: Welch Ultimate AQ-C18 150×30 mm×5 um @ room temperature; mobile phase: water (0.1% TFA)-MeCN: 35-65% over 12 minutes.

Liquid Chromatography Method W
Column: Welch Xbridge BEH C18 100×30 mm×10 um @ room temperature; mobile phase: water (10 mM $NH_4HCO_3$)-MeCN: 15-43% over 10 minutes.

Liquid Chromatography Method X
Column: Welch Xbridge BEH C18 100×30 mm×10 um @ room temperature; mobile phase: water (0.4% $NH_3H_2O$+10 mM $NH_4HCO_3$)-MeCN: 28-58% over 10 minutes.

Liquid Chromatography Method Y
Column: Welch Xbridge Prep OBD C18 150×40 mm×5 um @ room temperature; mobile phase: water (0.4% $NH_3H_2O$+10 mM $NH_4HCO_3$)-MeCN: 30-60% over 10 minutes.

Liquid Chromatography Method Z
Column: Welch Xbridge Prep OBD C18 150×40 mm×10 um @ room temperature; mobile phase: water (10 mM $NH_4HCO_3$)-MeCN: 30-55% over 10 minutes.

Liquid Chromatography Method AA
Column: Nano-micro Kromasil C18 100×30 mm×5 um @ room temperature; mobile phase: water (0.1% TFA)-MeCN: 36-46% over 10 minutes.

Liquid Chromatography Method AB
Column: Nano-micro Kromasil C18 80×25 mm×3 um @ room temperature; mobile phase: water (0.1% TFA)-MeCN: 35-55% over 10 minutes.

Liquid Chromatography Method AC
Column: Welch Xbridge BEH C18 100×30 mm×10 um @ room temperature; mobile phase: water (10 mM $NH_4HCO_3$)-MeCN: 35-55% over 10 minutes.

Liquid Chromatography Method AD
Column: Welch Xbridge BEH C18 100×30 mm×10 um @ room temperature; mobile phase: water (10 mM $NH_4HCO_3$)-MeCN: 25-55% over 8 minutes.

Liquid Chromatography Method AE
Column: Nano-micro Kromasil C18 80×25 mm×3 um @ room temperature; mobile phase: water (0.1% TFA)-MeCN: 25-55% over 10 minutes.
Liquid Chromatography Method AF
Column: Welch Xbridge Prep OBD C18 150×40 mm×10 um @ room temperature; mobile phase: water (10 mM $NH_4HCO_3$)-MeCN: 30-60% over 8 minutes.
Liquid Chromatography Method AG
Column: Welch Xbridge Prep OBD C18 150×40 mm×10 um @ room temperature; mobile phase: water (10 mM $NH_4HCO_3$)-MeCN: 35-65% over 8 minutes.
Liquid Chromatography Method AH
Column: Welch Ultimate AQ-C18 150×30 mm×5 um @ room temperature; mobile phase: water (0.1% TFA)-MeCN: 30-60% over 12 minutes.
Liquid Chromatography Method AI
Prep-HPLC column: Phenomenex Luna C18 (150×30 mm, 5 um); mobile phase: [water (0.1% TFA)-MeCN]; B %: 25%-55%, 10 min
Liquid Chromatography Method AJ
Prep-HPLC column: Waters Xbridge BEH C18 (100×30 mm, 10 um); mobile phase: [water (10 mM $NH_4HCO_3$)-MeCN]; B %: 30%-60%, 8 min
Liquid Chromatography Method AK
Prep-HPLC column: Phenomenex Luna C18 (150×30 mm, 5 um); mobile phase: [water (0.1% TFA)-MeCN]; B %: 30%-60%, 10 min
Liquid Chromatography Method AL
SFC column: DAICEL CHIRALPAK AD (250×30 mm, 10 um); mobile phase: [0.1% $NH_3H_2O$ IPA]; B %: 30%-30%, min
Liquid Chromatography Method AM
Prep-HPLC column: Waters Xbridge BEH C18 (100×30 mm, 10 um); mobile phase: [water (10 mM $NH_4HCO_3$)-MeCN]; B %: 27%-57%, 8 min
Liquid Chromatography Method AN
Prep-HPLC column: Phenomenex Synergi C18 (150×25 mm, 10 um); mobile phase: [water (0.1% TFA)-MeCN]; B %: 20%-50%, 10 min
Liquid Chromatography Method AO
Prep-HPLC (column: Phenomenex Luna C18 (100×40 mm, 3 um); mobile phase: [water (0.1% TFA)-MeCN]; B %: 30%-60%, 10 min
Liquid Chromatography Method AP
Prep-HPLC (neutral condition, column: Waters Xbridge BEH C18 (100×25 mm, 5 um); mobile phase: [water (10 mM $NH_4HCO_3$)-MeCN]; B %: 30%-60%, 10 min
Liquid Chromatography Method AQ
Prep-HPLC column: Nano-micro Kromasil C18 (100×40 mm, 10 um); mobile phase: [water (0.1% TFA)-MeCN], B %: 10%-40%, 8 min
Liquid Chromatography Method AR
Prep-HPLC column: Waters Xbridge Prep OBD C18 (150×40 mm, 10 um); mobile phase: [water (10 mM $NH_4HCO_3$)-MeCN]; B %: 15%-45%, 8 min
Liquid Chromatography Method AS
Prep-HPLC basic condition, column: Phenomenex Gemini-NX C18 (75×30 mm, 3 um); mobile phase: [water (0.05% $NH_3H_2O$+10 mM $NH_4HCO_3$)-MeCN]; B %: 25%-55%, 8 min
Liquid Chromatography Method AT
Prep-HPLC neutral condition, column: Waters Xbridge BEH C18 (100×30 mm, 10 um); mobile phase: [water (10 mM $NH_4HCO_3$)-MeCN]; B %: 15%-45%, 8 min
Liquid Chromatography Method AU
Prep-HPLC column: Phenomenex Luna C18 (150×30 mm, 5 um); mobile phase: [water (0.1% TFA)-MeCN]; B %: 35%-65%, 10 min
Liquid Chromatography Method AV
Prep-HPLC neutral condition, column: Waters Xbridge BEH C18 (100×30 mm, 10 um); mobile phase: [water (10 mM $NH_4HCO_3$)-MeCN]; B %: 35%-65%, 8 min
Liquid Chromatography Method AW
Prep-HPLC TFA condition, column: Nano-micro Kromasil C18 (100×40 mm, 10 um); mobile phase: [water (0.1% TFA)-MeCN]; B %: 1%-37%, 8 min
Liquid Chromatography Method AX
Prep-HPLC column: Waters Xbridge BEH C18 (100×30 mm, 10 um); mobile phase: [water (0.1% TFA)-MeCN]; B %: 25%-55%, 8 min
Liquid Chromatography Method AY
Prep-HPLC column: Waters Xbridge BEH C18 (100×30 mm, 10 um); mobile phase: [water (0.05% $NH_3H_2O$-MeCN]; B %: 15%-45%, 12 min
Liquid Chromatography Method AZ
Prep-HPLC column: Waters Xbridge BEH C18 (100×30 mm, 10 um); mobile phase: [water (10 mM $NH_4HCO_3$)-MeCN]; B %: 32%-62%, 8 min
Liquid Chromatography Method BA
Prep-HPLC TFA condition, column: Phenomenex Synergi C18 (150×25 mm, 10 um); mobile phase: [water (0.1% TFA)-MeCN]; B %: 35%-65%, 8 min
Liquid Chromatography Method BB
Prep-HPLC column: Waters Xbridge BEH C18 (100×30 mm, 10 um); mobile phase: [water (10 mM $NH_4HCO_3$)-MeCN]; B %: 15%-45%, 8 min
Liquid Chromatography Method BC
Prep-HPLC TFA condition, column: Welch Ultimate AQ-C18 (150×30 mm, 5 um); mobile phase: [water (0.1% TFA)-MeCN]; B %: 27%-57%, 12 min
Liquid Chromatography Method BD
Prep-HPLC TFA condition, column: Welch Ultimate AQ-C18 (150×30 mm, 5 um); mobile phase: [water (0.1% TFA)-MeCN]; B %: 33%-63%, 12 min
Liquid Chromatography Method BE
Prep-HPLC TFA condition, column: Nano-micro Kromasil C18 (80×25 mm, 3 um); mobile phase: [water (0.1% TFA)-MeCN]; B %: 33%-57%, 7 min
Liquid Chromatography Method BF
Prep-HPLC column: Phenomenex Luna C18 (150×30 mm, 5 um); mobile phase: [water (0.04% HCl)-MeCN]; B %: 30%-60%, 10 min
Liquid Chromatography Method BG
Prep-HPLC column: Nano-micro Kromasil C18 (80×25 mm, 3 um), mobile phase: [water (0.1% TFA)-MeCN]; B %: 40%-60%, 7 min
Liquid Chromatography Method BH
Prep-HPLC column: Waters Xbridge BEH C18 (100×30 mm, 10 um); mobile phase: [water (10 mM $NH_4HCO_3$)-MeCN], B %: 32%-55%, 10 min
Liquid Chromatography Method BI
Prep-HPLC column: Waters Xbridge BEH C18 (100×30 mm, 10 um); mobile phase: [water (10 mM $NH_4HCO_3$)-MeCN]; B %: 27%-47%, 10 min
Liquid Chromatography Method BJ
Prep-HPLC TFA condition, column: Welch Ultimate AQ-C18 (150×30 mm, 5 um); mobile phase: [water (0.1% TFA)-MeCN]; B %: 25%-55%, 12 min
Liquid Chromatography Method BK
Prep-HPLC TFA condition, column: Welch Ultimate AQ-C18 (150×30 mm, 5 um); mobile phase: [water (0.1% TFA)-MeCN]; B %: 15%-45%, 12 min Liquid Chromatography Method BL
Prep-HPLC column: Phenomenex Luna C18 (100×30 mm, 5 um); mobile phase: [water (0.1% TFA)-MeCN]; B %: 40%-55%, 12 min Liquid Chromatography Method BM
Prep-HPLC column: Waters Xbridge Prep OBD C18 (150×40 mm, 10 um); mobile phase: [water (0.04% NH$_3$H$_2$O+10 mM NH$_4$HCO$_3$)-MeCN]; B %: 15%-45%, 10 min Liquid Chromatography Method BN
Prep-HPLC TFA condition, column: Nano-micro Kromasil C18 (80×25 mm, 3 um); mobile phase: [water (0.1% TFA)-MeCN]; B %: 39%-56%, 7 min Liquid Chromatography Method BO
Prep-HPLC column: Nano-micro Kromasil C18 (80×5 mm, 3 um); mobile phase: [water (0.1% TFA)-MeCN]; B %: 35%-55%, 7 min Liquid Chromatography Method BP
Prep-HPLC column: Nano-micro Kromasil C18 (80×25 mm, 3 um); mobile phase: [water (0.1% TFA)-MeCN]; B %: 30%-52%, 7 min Liquid Chromatography Method BQ
Prep-HPLC Waters Xbridge BEH C18 (100×30 mm, 10 um); mobile phase: [water (10 mM NH$_4$HCO$_3$)-MeCN]; B %: 32%-52%, 10 min Liquid Chromatography Method BR
Prep-HPLC TFA condition, column: Nano-micro Kromasil C18 (80×25 mm, 3 um); mobile phase: [water (0.1% TFA)-MeCN]; B %: 45%-61%, 7 min Liquid Chromatography Method BS
Prep-HPLC basic condition, column: Waters Xbridge Prep OBD C18 (150×40 mm, 10 um); mobile phase: [water (0.04% NH$_3$H$_2$O+10 Mm NH$_4$HCO$_3$)-MeCN]; B %: 25%-55%, 8 min Liquid Chromatography Method BT
Prep-HPLC TFA condition, column: Nano-micro Kromasil C18 (80×25 mm, 3 um); mobile phase: [water (0.1% TFA)-MeCN]; B %: 32%-48%, 7 min Liquid Chromatography Method BU
Prep-HPLC neutral condition, column: Waters Xbridge Prep OBD C18 (150×40 mm, 10 um); mobile phase: [water (10 mM NH$_4$HCO$_3$)-MeCN]; B %: 20%-50%, 8 min Liquid Chromatography Method BV
Prep-HPLC column: Nano-micro Kromasil C18 (80×25 mm, 3 um); mobile phase: [water (0.1% TFA)-MeCN]; B %: 30%-45%, 7 min Liquid Chromatography Method BW
Prep-HPLC TFA condition; column: Phenomenex Luna C18 (100×30 mm, 5 um); mobile phase: [water (0.1% TFA)-MeCN]; B %: 35%-60%, 12 min Liquid Chromatography Method BX
Prep-HPLC TFA condition, column: Nano—micro Kromasil C18 (80×25 mm, 3 um); mobile phase: [water (0.1% TFA)-MeCN]; B %: 37%-63%, 7 min Liquid Chromatography Method BY
Prep-HPLC column: Waters Xbridge BEH C18 (100×30 mm, 10 um); mobile phase: [water (10 mM NH$_4$HCO$_3$)-MeCN]; B %: 30%-55%, 10 min Liquid Chromatography Method BZ
Prep-HPLC (column: Waters Xbridge BEH C18 (100×30 mm, 10 um); mobile phase: [water (10 mM NH$_4$HCO$_3$)-MeCN]; B %: 35%-60%, 10 min)

Liquid Chromatography Method CA
Prep-HPLC column: Waters Xbridge BEH C18 (100×30 mm, 10 um); mobile phase: [water (10 mM NH$_4$HCO$_3$)-MeCN]; B %: 5%-25%, 10 min Liquid Chromatography Method CB
Prep-HPLC (column: Waters Xbridge BEH C18 (100×30 mm, 10 um); mobile phase: [water (10 mM NH$_4$HCO$_3$)-MeCN]; B %: 30%-60%, 10 min)

Liquid Chromatography Method CC
Prep-HPLC (TFA condition, column: phenolmenex Luna C18 (100×30 mm, 5 um); mobile phase: [water (0.1% TFA)-MeCN]; B %:25%-55%, 12 min)

Liquid Chromatography Method CD
Prep-HPLC column: Waters Xbridge BEH C18 (100×25 mm, 5 um); mobile phase: [water (10 mM NH$_4$HCO$_3$)-MeCN]; B %: 30%-60%, 8 min Liquid Chromatography Method CE
Prep-HPLC column: Nano-micro Kromasil C18 (80×25 mm, 3 um); mobile phase: [water (0.1% TFA)-MeCN]; B %: 38%-60%, 7 min Liquid Chromatography Method CF
Prep-HPLC neutral condition, column: Waters Xbridge BEH C18 (100×30 mm, 10 um; mobile phase: [water (10 mM NH$_4$HCO$_3$)-MeCN]; B %: 20%-45%, 8 min Liquid Chromatography Method CG
Prep-HPLC column: Waters Xbridge BEH C18 (100×30 mm, 10 um); mobile phase: [water (10 mM NH$_4$HCO$_3$)-MeCN]; B %: 20%-50%, 8 min Liquid Chromatography Method CH
Prep-HPLC column: Waters Xbridge BEH C18 (100×30 mm, 10 um); mobile phase: [water (10 mM NH$_4$HCO$_3$)-MeCN]; B %: 30%-55%, 8 min Liquid Chromatography Method CI
Prep-HPLC column: Waters Xbridge BEH C18 (100×30 mm, 10 um); mobile phase: [water (10 mM NH$_4$HCO$_3$)-MeCN]; B %: 30%-53%, 10 min Liquid Chromatography Method CJ
Prep-HPLC column: Nano-micro C18 (100×40 mm, 3 um); mobile phase: [water (0.1% TFA)-MeCN]; B %: 25%-55%, 8 min Liquid Chromatography Method CK
Prep-HPLC column: Waters Xbridge BEH C18 (100×30 mm, 10 um); mobile phase: [water (10 mM NH$_4$HCO$_3$)-MeCN]; B %: 1%-30%, 10 min Liquid Chromatography Method CL
Prep-HPLC column: Nano-micro Kromasil C18 (100×40 mm, 3 um); mobile phase: [water (0.1% TFA)-MeCN]; B %: 30%-60%, 8 min Liquid Chromatography Method CM
Prep-HPLC column: Nano-micro Kromasil C18 (100×40 mm, 3 um); mobile phase: [water (0.1% TFA)-MeCN]; B %: 13%-43%, 8 min Liquid Chromatography Method CN
Prep-HPLC TFA condition, column: YMC-Actus Triart C18 (100×30 mm, 5 um); mobile phase: [water (0.1% TFA)-MeCN]; B %: 10%-40%, 10 min Liquid Chromatography Method CO
Prep-HPLC TFA condition column: Phenomenex Synergi C18 (150×25 mm, 10 um); mobile phase: [water (0.1% TFA)-MeCN]; B %: 10%-35%, 10 min Liquid Chromatography Method CP
Prep-HPLC TFA condition column: Phenomenex Luna C18 (100×40 mm×3 um); mobile phase: [water (0.1% TFA)-MeCN]; B %: 10%-50%, 10 min Liquid Chromatography Method CQ
Prep-HPLC neutral condition column: Phenomenex Gemini-NX C18 (75×30 mm, 3 um); mobile phase: [water (10 mM NH$_4$HCO$_3$)-MeCN]; B %: 20%-40%, 6 min Liquid Chromatography Method CR
Prep-HPLC neutral condition column: Phenomenex Gemini-NX C18 (75×30 mm, 3 um); mobile phase: [water (10 mM NH$_4$HCO$_3$)-MeCN]; B %: 15%-45%, 12 min Liquid Chromatography Method CS
Prep-HPLC TFA condition column: Phenomenex Luna C18 (100×40 mm, 5 um); mobile phase: [water (0.1% TFA)-MeCN]; B %: 15%-45%, 8 min Liquid Chromatography Method CT
Prep-HPLC basic condition column: Phenomenex Gemini-NX C18 (75×30 mm, 3 um); mobile phase: [water (0.05% $NH_3H_2O$+10 mM $NH_4HCO_3$)-MeCN]; B %: 30%-60%, 8 min Liquid Chromatography Method CU
Semipreparative HPLC conditions and results: Column Chiralpak AD-H (25×2.0 cm, 5µ) Mobile phase n-Hexane/Ethanol 70/30% v/v Flow rate (mL/min) 18 mL/min DAD detection 220 nm Loop 300 µL Total amount 150 mg Solubilization 150 mg in 3 mL MeOH=50 mg/mL Injection 17 mg/injection Liquid Chromatography Method CV
Prep. HPLC Method:
Instrument Name: MDAP_Fractionlynx; Method Description: Semi preparative MDAP Method; LC/MS System: Fractionlynx (Waters) with QDa MS detector; LC/MS Conditions: Column: XSelect CSH Prep. C18 5 µm OBD 30×100 mm @ room T; Injection loop: 1 mL; Solvents: A=$H_2O$+0.1% HCOOH; B=MeCN.

| Gradient: | | | | |
|---|---|---|---|---|
| Time (min) | Flow Rate (ml/min) | % A | % B | Curve |
| initial | 40.0 | 80.0 | 20.0 | — |
| 10.0 | 40.0 | 30.0 | 70.0 | 6 |
| 10.5 | 40.0 | 0.0 | 100.0 | 6 |
| 14.5 | 40.0 | 80.0 | 20.0 | 6 |
| 16.1 | 3.0 | 80.0 | 20.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionization mode: Positive Electrospray (ES+); Scan Range: ES+ 100 to 900 AMU; Scan Duration: 0.50 seconds.

Liquid Chromatography Mass Spectrometry Method CW
Prep. HPLC Method:
Instrument Name: MDAP_Fractionlynx; Method Description: Semi preparative MDAP Method; LC/MS System: Fractionlynx (Waters) with QDa MS detector; LC/MS Conditions: Column: XSelect CSH Prep. C18 5 µm OBD 30×100 mm @ room T; Injection loop: 1 mL; Solvents: A=$H_2O$+0.1% HCOOH; B=MeCN.

| Gradient: | | | | |
|---|---|---|---|---|
| Time (min) | Flow Rate (ml/min) | % A | % B | Curve |
| initial | 40.0 | 65.0 | 45.0 | — |
| 10.0 | 40.0 | 45.0 | 55.0 | 6 |
| 10.5 | 40.0 | 0.1 | 99.9 | 6 |
| 14.5 | 40.0 | 0.1 | 99.9 | 6 |
| 15.0 | 40.0 | 65.0 | 45.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionization mode: Positive Electrospray (ES+); Scan Range: ES+ 100 to 900 AMU; Scan Duration: 0.50 seconds.

Liquid Chromatography-Mass Spectrometry Method CX:
Instrument Name: MDAP_Fractionlynx; Method Description: Semi preparative MDAP Method; LC/MS System: Fractionlynx (Waters) with QDa MS detector; LC/MS Conditions: Column: XSelect CSH Prep. C18 5 µm OBD 30×100 mm @ room T: Injection loop: 1 mL; Solvents: A=$H_2O$+0.1% HCOOH; B=MeCN.

| Gradient: | | | | |
|---|---|---|---|---|
| Time (min) | Flow Rate (ml/min) | % A | % B | Curve |
| initial | 40.0 | 70.0 | 30.0 | — |
| 10.0 | 40.0 | 50.0 | 50.0 | 6 |
| 10.5 | 40.0 | 0.1 | 99.9 | 6 |
| 14.5 | 40.0 | 0.1 | 99.9 | 6 |
| 15.0 | 40.0 | 50.0 | 50.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionization mode: Positive Electrospray (ES+); Scan Range: ES+ 100 to 900 AMU; Scan Duration: 0.50 seconds.

Liquid Chromatography Method CY
Chiral prep. HPLC Method:
Column Chiralpak IC (25×2.0 cm), 5µ
Mobile phase n-Hexane/(Ethanol+0.1% isopropylamine) 60/40% v/v
Flow rate (mL/min) 17 mL/min
DAD detection 220 nm
Loop 1000 µL
Total amount 58 mg
Solubilization 58 mg in 3.0 mL DCM=19.3 mg/mL
Injection 19.3 mg/injection Liquid Chromatography Method CZ
Instrument Name: MDAP_Fractionlynx; Method Description: Semi preparative MDAP Method; LC/MS System: Fractionlynx (Waters) with QDa MS detector; LC/MS Conditions: Column: XSelect CSH Prep. C18 5 µm OBD 30×100 mm @ room T; Injection loop: 1 mL; Solvents: A=$H_2O$+0.1% HCOOH; B=MeCN.

| Gradient: | | | | |
|---|---|---|---|---|
| Time (min) | Flow Rate (ml/min) | % A | % B | Curve |
| initial | 40.0 | 50.0 | 50.0 | — |
| 10.0 | 40.0 | 43.0 | 57.0 | 6 |
| 10.5 | 40.0 | 0.0 | 100.0 | 6 |
| 14.5 | 40.0 | 0.0 | 100.0 | 6 |
| 15.0 | 40.0 | 50.0 | 50.0 | 6 |
| 15.1 | 40.0 | 50.0 | 50.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionization mode: Positive Electrospray (ES+); Scan Range: ES+ 100 to 900 AMU; Scan Duration: 0.50 seconds.

Liquid Chromatography Method DA
Prep-HPLC basic condition 30 g C18 column; mobile phase [water (0.1% $NH_3$)-MeCN]; B % 5%-35%.

Liquid Chromatography Method DB
C-18 chromatography (from 100% water+0.1% formic acid to 90/10 100% water+0.1% formic acid/MeCN+0.1% formic acid in 12CV)

Liquid Chromatography Method DC
Prep HPLC:
Column: XSelect CSH Prep. C18 5 μm OBD 30×100 mm @ room T Injection loop: 1 ml Solvents: A=$H_2O$+0.1% HCOOH B=MeCN

| Gradient: | | | | |
|---|---|---|---|---|
| Time (min) | Flow Rate (ml/min) | % A | % B | Curve |
| initial | 40.0 | 70.0 | 30.0 | — |
| 10.0 | 40.0 | 50.0 | 55.0 | 6 |
| 10.5 | 40.0 | 0.1 | 99.9 | 6 |
| 14.5 | 40.0 | 0.1 | 99.9 | 6 |
| 15.0 | 40.0 | 70.0 | 30.0 | 6 |

The curve parameter followed Waters definition (6=linear, 11=step). Acquisition stop time: 15.0 min UV Conditions: UV detection range: 210 nm to 350 nm Acquisition rate: 1.0 spectra/s MS Conditions: Ionization mode: Positive Electrospray (ES+) Scan Range: ES+ 100 to 900 AMU Scan Duration: 0.50 seconds Liquid Chromatography Method DD
Prep HPLC:
Column: XSelect CSH Prep. C18 5 μm OBD 30×100 mm @ room T Injection loop: 1 mL Solvents: A=$H_2O$+0.1% HCOOH B=Acetonitrile

| Gradient: | | | | |
|---|---|---|---|---|
| Time (min) | Flow Rate (ml/min) | % A | % B | Curve |
| initial | 40.0 | 70.0 | 30.0 | — |
| 10.0 | 40.0 | 60.0 | 40.0 | 6 |
| 10.5 | 40.0 | 0.1 | 99.9 | 6 |
| 15.0 | 40.0 | 0.1 | 99.9 | 6 |
| 15.0 | 40.0 | 70.0 | 30.0 | 6 |

The curve parameter followed Waters definition (6=linear, 11=step). Acquisition stop time: 15.0 min UV Conditions: UV detection range: 210 nm to 350 nm Acquisition rate: 1.0 spectra/s MS Conditions: Ionization mode: Positive Electrospray (ES+) Scan Range: ES+ 100 to 900 AMU Scan Duration: 0.50 seconds Liquid Chromatography Method DE
Prep HPLC:
Column: XSelect CSH Prep. C18 5 μm OBD 30×100 mm @ room T Injection loop: 1 mL Solvents: A=$H_2O$+0.1% HCOOH B=MeCN

| Gradient: | | | | |
|---|---|---|---|---|
| Time (min) | Flow Rate (ml/min) | % A | % B | Curve |
| initial | 40.0 | 55.0 | 45.0 | — |
| 10.0 | 40.0 | 53.0 | 47.0 | 6 |
| 10.5 | 40.0 | 0.0 | 100.0 | 6 |
| 15.0 | 40.0 | 0.0 | 100.0 | 6 |
| 15.1 | 40.0 | 55.0 | 45.0 | 6 |

The curve parameter followed Waters definition (6=linear, 11=step). Acquisition stop time: 15.0 min UV Conditions: UV detection range: 210 nm to 350 nm Acquisition rate: 1.0 spectra/s MS Conditions: Ionization mode: Positive Electrospray (ES+) Scan Range: ES+ 100 to 900 AMU Scan Duration: 0.50 seconds Liquid Chromatography Method DF
Prep HPLC:
Column: XSelect CSH Prep. C18 5 μm OBD 30×100 mm @ room T Injection loop: 1 ml Solvents: A=$H_2O$+0.1% HCOOH B=MeCN

| Gradient: | | | | |
|---|---|---|---|---|
| Time (min) | Flow Rate (ml/min) | % A | % B | Curve |
| initial | 40.0 | 70.0 | 30.0 | — |
| 10.0 | 40.0 | 50.0 | 50.0 | 6 |
| 10.5 | 40.0 | 0.1 | 99.9 | 6 |
| 14.5 | 40.0 | 0.1 | 99.9 | 6 |
| 15.0 | 40.0 | 70.0 | 30.0 | 6 |

The curve parameter followed Waters definition (6=linear, 11=step). Acquisition stop time: 15.0 min UV Conditions: UV detection range: 210 nm to 350 nm Acquisition rate: 1.0 spectra/s MS Conditions: Ionization mode: Positive Electrospray (ES+) Scan Range: ES+ 100 to 900 AMU Scan Duration: 0.50 seconds Liquid Chromatography Method DG
Prep. HPLC Method:
Instrument Name: MDAP_Fractionlynx; Method Description: Semi preparative MDAP Method; LC/MS System: Fractionlynx (Waters) with QDa MS detector; LC/MS Conditions: Column: XSelect CSH Prep. C18 5 μm OBD 30×100 mm @ room T; Injection loop: 1 ml; Solvents: A=$H_2O$+0.1% HCOOH; B=MeCN.

| Gradient: | | | | |
|---|---|---|---|---|
| Time (min) | Flow Rate (ml/min) | % A | % B | Curve |
| initial | 40.0 | 50.0 | 60.0 | — |
| 10.0 | 40.0 | 35.0 | 65.0 | 6 |
| 10.5 | 40.0 | 0.1 | 99.9 | 6 |
| 14.5 | 40.0 | 0.1 | 99.9 | 6 |
| 15.0 | 40.0 | 50.0 | 50.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionisation mode: Positive Electrospray (ES+): Scan Range: ES+ 100 to 900 AMU; Scan Duration: 0.50 seconds.

Liquid Chromatography Method DH
Prep. HPLC Method:
Instrument Name: MDAP_Fractionlynx; Method Description: Semi preparative MDAP Method; LC/MS System: Fractionlynx (Waters) with QDa MS detector; LC/MS Conditions: Column: XSelect CSH Prep. C18 5 μm OBD 30×100 mm @ room T; Injection loop: 1 ml; Solvents: A=$H_2O$+0.1% HCOOH; B=MeCN.

| Gradient: | | | | |
|---|---|---|---|---|
| Time (min) | Flow Rate (ml/min) | % A | % B | Curve |
| initial | 40.0 | 53.0 | 37.0 | — |
| 10.0 | 40.0 | 33.0 | 67.0 | 6 |
| 10.5 | 40.0 | 0.1 | 99.9 | 6 |

-continued

| Gradient: | | | | |
|---|---|---|---|---|
| Time (min) | Flow Rate (ml/min) | % A | % B | Curve |
| 14.5 | 40.0 | 0.1 | 99.9 | 6 |
| 15.0 | 40.0 | 53.0 | 17.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionisation mode: Positive Electrospray (ES+); Scan Range: ES+ 100 to 900 AMU; Scan Duration: 0.50 seconds.
Liquid Chromatography Method DI
Prep. HPLC Method:
Instrument Name: MDAP_Fractionlynx; Method Description: Semi preparative MDAP Method; LC/MS System: Fractionlynx (Waters) with QDa MS detector; LC/MS Conditions: Column: XSelect CSH Prep. C18 5 μm OBD 30×100 mm @ room T; Injection loop: 1 ml; Solvents: A=H$_2$O+0.1% HCOOH; B=MeCN.

| Gradient: | | | | |
|---|---|---|---|---|
| Time (min) | Flow Rate (ml/min) | % A | % B | Curve |
| initial | 40.0 | 50.0 | 50.0 | — |
| 10.0 | 40.0 | 30.0 | 70.0 | 6 |
| 10.5 | 40.0 | 0.1 | 99.9 | 6 |
| 14.5 | 40.0 | 0.1 | 99.9 | 6 |
| 15.0 | 40.0 | 50.0 | 50.0 | 6 |

The curve parameter followed Waters definition (6=linear, 11=step); Acquisition stop time: 15 min; UV Conditions: UV detection range: 210 nm to 350 nm; Acquisition rate: 1.0 spectra/s; MS Conditions: Ionisation mode: Positive Electrospray (ES+); Scan Range: ES+ 100 to 900 AMU; Scan Duration: 0.50 seconds.
Liquid Chromatography Method DJ
Preparative HPLC (neutral condition) column: Waters Xbridge BEH C18 (100×30 mm, 10) um; mobile phase: [water (10 mM NH$_4$HCO$_3$)-MeCN]; B %: 10%-40%, 6 min
Other Analytical Methods
$^1$H Nuclear magnetic resonance (NMR) spectroscopy was carried out using one of the following instruments: a Bruker Avance 400 instrument equipped with probe DUAL 400 MHz S1, a Bruker Avance 400 instrument equipped with probe 6 S1 400 MHz 5 mm $^1$H-$^{13}$C ID, a Bruker Avance III 400 instrument with nanobay equipped with probe Broadband BBFO 5 mm direct, a 400 MHz Agilent Direct Drive instrument with ID AUTO-X PFG probe, all operating at 400 MHz, or an Agilent VNMRS500 Direct Drive instrument equipped with a 5 mm Triple Resonance $^1$H{$^{13}$C/$^{15}$N} cryoprobe operating at 500 MHz. The spectra were acquired in the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; br, broad.
Where thin layer chromatography (TLC) occurs, it refers to silica gel TLC using silica gel F254 (Merck) plates, Rf is the distance travelled by the compound divided by the distance travelled by the solvent on a TLC plate. Column chromatography was performed using an automatic flash chromatography (Biotage SP1 or Isolera) system over Biotage silica gel cartridges (KP-Sil or KP-NH) or in the case of reverse phase chromatography over Biotage C18 cartridges (KP-C18).

Intermediate A-1:
3-(Furan-3-yl)-1H-indazol-5-amine

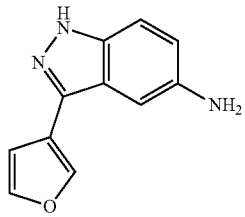 [SMILES: Nc1ccc2[nH]nc(-c3ccoc3)c2c1]

3-Bromo-1H-indazol-5-amine (2.82 g, 13.3 mmol) was dissolved in THF (40 mL). Then a solution of tripotassium phosphate (8.47 g, 39.9 mmol) and 3-furanylboronic acid (1.79 g, 15.96 mmol) in water (15 mL) was added. The resulting mixture was degassed with N$_2$ for 15 minutes. S-Phos Pd G2 (0.96 g, 1.33 mmol) was added and the mixture was stirred at 80° C. under N$_2$ for 15 h. Water was added and the organic solvent was evaporated. The resulting solid was filtered, washed with water and dried. The residue was purified by column chromatography (SiO$_2$, 100 g) using a 0-10% gradient of MeOH in DCM for 10 CV followed by 10% MeOH in DCM for 5 CV giving a solid which was triturated with MeCN to afford the title compound (1.65 g, 8.28 mmol, 62.28% yield) as a pale yellow solid. $^1$H NMR (400 MHz, DMSO-d$_6$) δ 12.60 (s, 1H), 8.14 (t, J=1.2 Hz, 1H), 7.78 (t, J=1.7 Hz, 1H), 7.25 (d, J=8.8 Hz, 1H), 6.98 (d, J=1.9 Hz, 1H), 6.93 (d, J=1.8 Hz, 1H), 6.82 (dd, J=8.8, 2.0 Hz, 1H), 4.79 (s, 2H). MS-ESI (m/z) calc'd for C$_{11}$H$_{10}$N$_3$O [M+H]$^+$: 200.1. Found 200.0.

Intermediate A-2:
3-(Pyridin-4-yl)-1H-indazol-5-amine

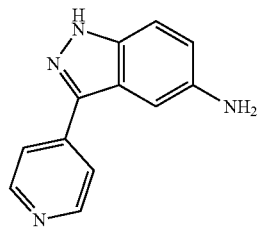 [SMILES: O=[N+]([O-])c1ccc2[nH]nc(-c3ccncc3)c2c1]

Step 1. 5-Nitro-3-(pyridin-4-yl)-1H-indazole

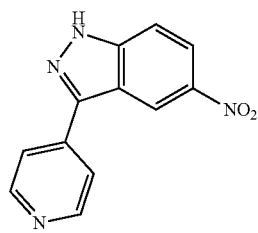

A mixture of 3-bromo-5-nitro-1H-indazole (8 g, 33.05 mmol), 4-pyridylboronic acid (4.88 g, 39.66 mmol), AcOK (9.73 g, 99.16 mmol), and Pd(Amphos)Cl₂ (1.17 g, 1.65 mmol) in EtOH (120 mL) and H₂O (30 mL) was degassed and purged with N₂ (3×). The mixture was stirred at 100° C. for 16 hrs under N₂ atmosphere. The reaction mixture was concentrated to give a residue which was diluted with 2 N HCl (100 mL) and EtOAc (100 mL). A yellow solid formed that was filtered and collected. The solid was dried under vacuum to afford the title compound (5.6 g) as a yellow solid.

Step 2. 3-(Pyridin-4-yl)-1H-indazol-5-amine

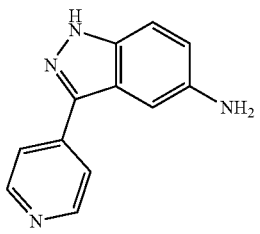 [SMILES: Nc1ccc2[nH]nc(-c3ccncc3)c2c1]

To a solution of 5-nitro-3-(pyridin-4-yl)-1H-indazole (5.6 g, 23.31 mmol) in EtOH (80 mL) and H₂O (20 mL) was added Zn (7.62 g, 116.56 mmol) and NH₄Cl (6.24 g, 116.56 mmol). The mixture was stirred at 80° C. for 12 hrs. The reaction mixture was filtered and the filtrate was concentrated to afford the title compound (1.37 g) as a yellow solid which was used without further purification.

Intermediate A-3: 3-Phenyl-1H-indazol-5-amine

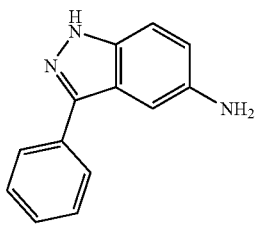

Step 1: 5-Nitro-3-phenyl-1H-indazole

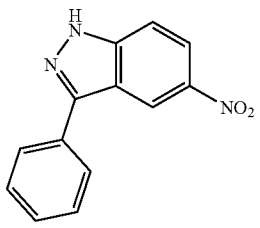 [SMILES: O=[N+]([O-])c1ccc2[nH]nc(-c3ccccc3)c2c1]

To a mixture of 3-bromo-5-nitro-1H-indazole (200 mg, 826 umol), phenylboronic acid (120.91 mg, 991 umol), and AcOK (243.30 mg, 2.48 mmol) in EtOH (5 mL) and H₂O (1.25 mL) was added Pd(AmPhos)Cl₂ (29.26 mg, 41.32 μmol). The resulting mixture was degassed and purged with N₂ (3×), and then the mixture was stirred at 100° C. for 12 hrs under a N₂ atmosphere. The reaction mixture was concentrated under reduced pressure to give a residue. The residue was purified by flash silica gel chromatography (ISCO; 20 g SepaFlash column, 100 mL/min) using a 0-50% EtOAc/petroleum ether gradient eluent to afford the title compound (180 mg, 91% yield) as a yellow solid.

Step 2: 3-Phenyl-1H-indazol-5-amine

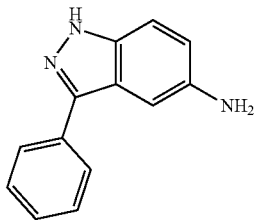

To a solution of 5-nitro-3-phenyl-1H-indazole (180 mg, 752 umol) in EtOH (8 mL) was added SnCl₂.2H₂O (848.90 mg, 3.76 mmol). The mixture was stirred at 70° C. for 3 hrs. The reaction mixture was concentrated under reduced pressure to remove solvent. The residue was diluted with H₂O (10 mL) and the pH adjusted to 8 by addition of sat. aq. NaHCO₃ followed by extraction with EtOAc (20 mL×3). The combined organic layers were dried over Na₂SO₄, filtered and concentrated under reduced pressure to afford the title compound (170 mg) as a brown gum which was used without further purification.

Intermediate A-4:
5-Cyano-1,2-dimethyl-1H-pyrrole-3-carboxylic acid

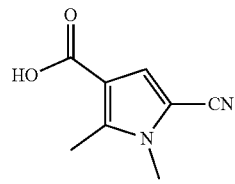

Step 1:
4-Bromo-1,5-dimethyl-1H-pyrrole-2-carbonitrile

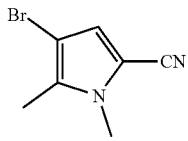

To a solution of 1,5-dimethyl-1H-pyrrole-2-carbonitrile (400 mg, 3.33 mmol) in HOAc (2 mL) was added Br₂ (585.22 mg, 3.66 mmol). The mixture was stirred at 20° C. for 12 hrs and then concentrated under reduced pressure to remove solvent. The reaction mixture was filtered and the solid was washed with 60 mL of H₂O and dried under vacuum to give a residue. The residue was purified by flash silica gel chromatography (ISCO; 12 g SepaFlash column,

Step 2: 5-(Cyano-1,2-dimethyl-1H-pyrrole-3-carboxylic acid

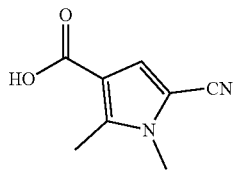

To a solution of 4-bromo-1,5-dimethyl-1H-pyrrole-2-carbonitrile (200 mg, 1.00 mmol) in THF (12 mL) was added n-BuLi (2.5 M, 1.21 mL) at −78° C. and the mixture was stirred for 1 hr under N₂. Dry ice (CO₂ solid, >10 eq) was added and the mixture was stirred at −78° C. for 2 hrs. The reaction mixture was acidified with 1N HCl to pH=3. The resulting precipitate was collected by filtration to afford the title compound (95 mg) as a gray solid. ¹H NMR (400 MHz, DMSO-d₆) δ 7.25 (s, 1H), 3.70 (s, 3H), 2.59 (s, 3H).

Intermediate A-5: Methyl 5-cyano-2-methylfuran-3-carboxylate

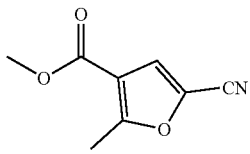

Step 1: Methyl 5-formyl-2-methylfuran-3-carboxylate

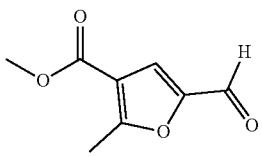

POCl₃ (1.09 g, 7.14 mmol, 663.12 uL) was added to DMF (678.57 mg, 9.28 mmol, 714.29 uL) dropwise at 0° C. After stirring at 0° C. for 15 min, methyl 2-methylfuran-3-carboxylate (1.0 g, 7.14 mmol, 892.86 uL) was added to the mixture at 15° C. The mixture was then stirred at 100° C. for 3 hrs. The mixture was poured onto 20 g of ice and the pH was adjusted to 8 with 10% aq. NaOH at 0-10° C. The mixture was filtered. The filter solid was washed with H₂O (5.0 mL×3) and dried in vacuo to afford the title compound (1.0 g, 83%) as a yellow solid. ¹H NMR (400 MHz, DMSO-d₆) δ 9.56 (s, 1H), 7.47 (s, 1H), 3.87 (s, 3H), 2.69 (s, 3H).

Step 2: Methyl 5-((2,2-dimethylhydrazineylidene)methyl)-2-methylfuran-3-carboxylate

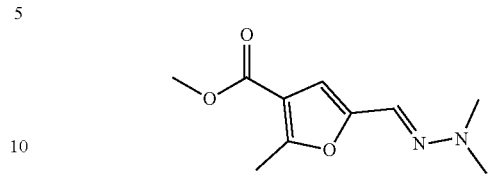

To a stirred solution of methyl 5-formyl-2-methylfuran-3-carboxylate (900 mg, 5.35 mmol) in dry EtOH (10 mL) was added 1,1-dimethylhydrazine hydrochloride (775.24 mg, 8.03 mmol, 978.84 µL) in one portion. Then the mixture was stirred at 80° C. for 12 hrs. TLC (petroleum ether:EtOAc=5/1, R$_f$ (product)=0.32) showed the reaction was complete. The mixture was concentrated in vacuo and purified by silica gel chromatography (petroleum ether:EtOAc=10/1-5/1) to afford the title compound (550 mg, 2.62 mmol, 49% yield) as a yellow oil.

Step 3: Methyl 5-cyano-2-methylfuran-3-carboxylate

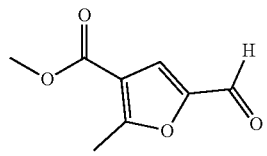

To a stirred solution of methyl 5-((2,2-dimethylhydrazineylidene)methyl)-2-methylfuran-3-carboxylate (550 mg, 2.62 mmol) in DCM (10 mL) was added m-CPBA (1.41 g, 6.54 mmol, 80% purity) in one portion at 0° C. Then the mixture was stirred at 20° C. for 18 hrs. Then K₂CO₃ (1.63 g, 11.77 mmol) was added to the mixture. The mixture was stirred for an additional 2 hrs. TLC (petroleum ether:EtOAc=3/1, Rr (product)=0.39) showed the reaction was complete. The mixture was filtered and the filtrate was concentrated in vacuo to afford the title compound (450 mg) as a yellow solid which was used without further purification.

Intermediate A-6: 5-Chloro-3-iodo-1H-pyrazolo[4,3-b]pyridine

To a stirred solution of 5-chloro-1H-pyrazolo[4,3-b]pyridine (4.0 g, 26.05 mmol) in DMF (100 mL) was added I₂ (26.44 g, 104.19 mmol, 20.99 mL), followed by adding KOH (7.31 g, 130.23 mmol) in portions at 0° C. Then the mixture was stirred at 25° C. for 12 hrs. The mixture was diluted with EtOAc (300 mL), washed with sat. aq. Na₂SO₃ (150 mL×3), dried over Na₂SO₄ and concentrated under vacuum to afford the title compound (4.0 g) as a yellow solid which was used without further purification.

Intermediate A-7:
3-(Isoxazol-4-yl)-1H-indazol-5-amine

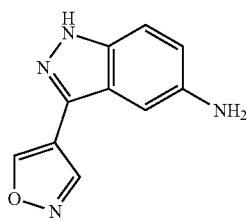 [SMILES: Nc1ccc2[nH]nc(-c3cnoc3)c2c1]

A mixture of 3-bromo-1H-indazol-5-amine (100 mg, 471.59 umol), 4-(4,4,5,5-tetramethyl-1,3,2-dioxaborolan-2-yl)isoxazole (101.17 mg, 518.75 umol), Pd(Amphos)Cl$_2$ (33.39 mg, 47.16 umol) and AcOK (138.85 mg, 1.41 mmol) in EtOH (4 mL) and H$_2$O (0.5 mL) was degassed and purged with N$_2$ (3×), and then the mixture was stirred at 40° C. for 12 hrs under an N$_2$ atmosphere. The process was repeated and the reaction mixtures were combined and concentrated to give a residue. The residue was diluted with 30 mL of H$_2$O, filtered and the filtrate was extracted with EtOAc (10 mL×3). The combined organic phases were dried over Na$_2$SO$_4$, filtered and the filtrate was concentrated. The material was purified by flash silica gel chromatography (ISCO; 4 g SepaFlash column) using a 0-30% EtOAc/petroleum ether gradient eluent to afford the title compound (64 mg, 67%) as a brown oil. MS-ESI (m/z) calcd for C$_{10}$H$_9$N$_4$O [M+H]$^+$: 201.1. Found 201.0.

Intermediate A-8: 5-Cyano-3-methylpyrazine-2-carboxylic acid and Intermediate A-8': 6-Cyano-3-methylpyrazine-2-carboxylic acid

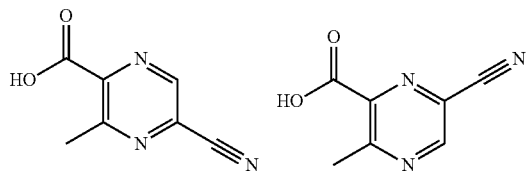

Step 1: 3-(Methoxycarbonyl)-2-methylpyrazine 1-oxide

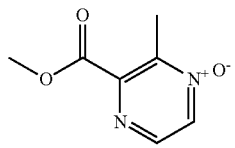

To a suspension of methyl 3-methylpyrazine-2-carboxylate (1.52 g, 10 mmol) in CHCl$_3$ (30.3 mL) was added MCPBA (2.71 g, 11 mmol) and the mixture was stirred at 70° C. for 5 hrs. The solvent was evaporated and the residue was taken up in EtOAc and washed with aqueous K$_2$CO$_3$ (3×). The aqueous layer was extracted with EtOAc (2×) and the combined organic layers were passed through a phase separator and evaporated to give a light orange solid which was purified by silica gel column chromatography using a 0-100% EtOAc/cyclohexane gradient eluent to afford the title compound (500 mg, 30%) as a white solid. $^1$H NMR (400 MHz, DMSO-d$_6$) δ 8.54 (d, J=4.0 Hz, 1H), 8.47 (d, J=4.0 Hz, 1H), 3.92 (s, 3H), 2.47 (s, 3H). MS-ESI (m/z) calc'd for C$_7$H$_9$N$_2$O$_3$[M+H]$^+$: 169.1. Found 168.9.

Step 2: Methyl 5-chloro-3-methylpyrazine-2-carboxylate and Methyl 6-chloro-3-methylpyrazine-2-carboxylate

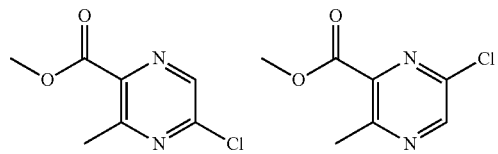

A suspension of 3-(methoxycarbonyl)-2-methylpyrazine 1-oxide (310.0 mg, 1.84 mmol) in POCl$_3$ (10.0 mL, 106.96 mmol) was heated at 100° C. for 2 hrs. The excess POCl$_3$ was evaporated and the residue was purified by silica gel column chromatography using a 0-100% EtOAc/cyclohexane gradient eluent to afford a mixture of the title compounds (171 mg, 49%) as a white solid. $^1$H NMR (400 MHz, DMSO-d$_6$) δ 8.89 (s, 1H), 3.91 (s, 4H), 2.71 (s, 3H). $^1$H NMR (400 MHz, DMSO-d$_6$) δ 8.73 (d, J=0.8 Hz, 1H), 3.90 (s, 3H), 2.70 (d, J=0.7 Hz, 3H). MS-ESI (m/z) calc'd for C$_7$H$_8$ClN$_2$O$_2$ [M+H]$^+$: 187.0. Found 187.0

Step 3: Methyl 3-methyl-5-vinylpyrazine-2-carboxylate and methyl 3-Methyl-6-vinylpyrazine-2-carboxylate

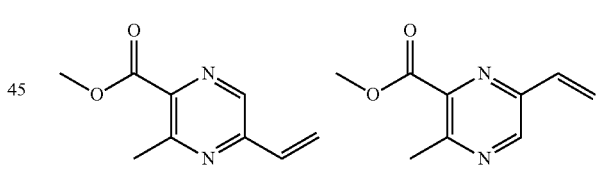

A solution of methyl 5-chloro-3-methylpyrazine-2-carboxylate and methyl 6-chloro-3-methylpyrazine-2-carboxylate (171.0 mg, 0.920 mmol) and tributyl(ethenyl)stannane (0.32 mL, 1.1 mmol) was degassed with N$_2$ for 10 minutes. Bis(triphenylphosphine)palladium(II) dichloride (64.51 mg, 0.090 mmol) was added and the mixture was stirred at 100° C. for 1 hr. The solvent was evaporated and the residue was purified by silica gel column chromatography using a 0-100% EtOAc/cyclohexane gradient eluent to afford a mixture of the title compounds (163.3 mg, 100% yield) as a yellow solid. $^1$H NMR (400 MHz, DMSO-d$_6$) δ 8.87 (s, 1H), 6.89 (dd, J=17.6, 11.0 Hz, 1H), 6.36 (dd, J=17.6, 1.3 Hz, 1H), 5.66 (dd, J=11.0, 1.3 Hz, 1H), 3.91 (s, 3H), 2.67 (s, 3H). $^1$H NMR (400 MHz, DMSO-d$_6$) δ 8.70 (s, 1H), 6.92 (dd, J=17.5, 10.9 Hz, 1H), 6.48 (dd, J=17.5, 1.4 Hz, 1H), 5.76 (dd, J=10.9, 1.4 Hz, 1H), 3.89 (s, 2H), 2.70 (d, J=0.7 Hz, 2H). MS-ESI (m/z) calc'd for C$_9$H$_{11}$N$_2$O$_2$[M+H]$^+$: 179.1. Found 179.0 and 179.0.

Step 4: Methyl 5-formyl-3-methylpyrazine-2-carboxylate and Methyl 6-formyl-3-methylpyrazine-2-carboxylate

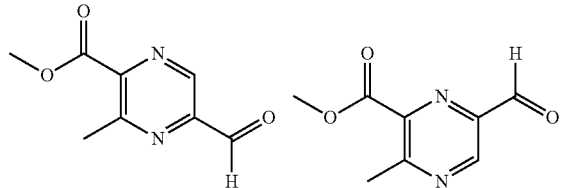

To a solution of methyl 3-methyl-5-vinylpyrazine-2-carboxylate and methyl 3-methyl-6-vinylpyrazine-2-carboxylate (163.3 mg, 0.920 mmol) in 1,4-dioxane (4.582 mL) was added a solution of NaIO$_4$ (392.03 mg, 1.83 mmol) in H$_2$O (4.58 mL). After 5 minutes, a 4% solution of osmium tetroxide (0.29 mL, 0.050 mmol) was added and the mixture was stirred at 25° C. for 2 hrs. The suspension was diluted with water and then extracted with DCM (3×). The combined organic layers were passed through a phase separator and concentrated to afford a mixture of the title compounds (145 mg, 88%) as a black oil. $^1$H NMR (400 MHz, DMSO-d$_6$) δ 10.06 (s, 1H), 9.15 (s, 1H), 3.96 (s, 3H), 2.82 (s, 3H). $^1$H NMR (400 MHz, DMSO-d$_6$) δ 10.07 (s, 1H), 9.01 (d, J=0.8 Hz, 1H), 3.95 (s, 3H), 2.79 (d, J=0.7 Hz, 3H). MS-ESI (m/z) calc'd for C$_8$H$_9$N$_2$O$_3$ [M+H]$^+$: 179.1. Found 181.0 and 181.1.

Step 5: Methyl 5-cyano-3-methylpyrazine-2-carboxylate and Methyl 6-cyano-3-methylpyrazine-2-carboxylate

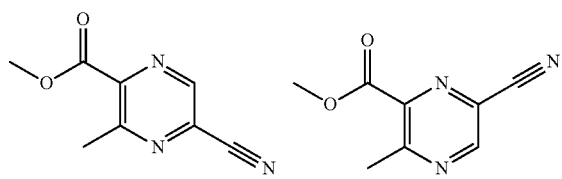

A mixture of methyl 5-formyl-3-methylpyrazine-2-carboxylate and methyl 6-formyl-3-methylpyrazine-2-carboxylate (145.0 mg, 0.800 mmol) and hydroxylamine hydrochloride (55.93 mg, 0.800 mmol) in DMSO (1 mL) was heated at 90° C. for 1 hr. Water was added and the suspension was extracted with EtOAc (3×). The combined organic layers were washed with H$_2$O (2×) and brine, passed through a phase separator and evaporated to obtain a black solid. POCl$_3$ was added and the solution was heated at 90° C. for 2 hrs. The mixture was poured into a solution of K$_2$CO$_3$ and extracted with DCM (3×); the combined organic layers were passed through a phase separator and evaporated to afford a mixture of the title compounds (85 mg, 60%) as a dark solid. $^1$H NMR (400 MHz, DMSO-d$_6$) δ 9.27 (s, 1H), 3.94 (s, 3H), 2.81 (s, 3H). $^1$H NMR (400 MHz, DMSO-d$_6$) δ 9.15 (s, 1H), 3.94 (s, 3H), 2.74 (s, 3H). MS-ESI (m/z) calc'd for C$_8$H$_8$N$_3$O$_2$ [M+H]$^+$: 178.1. Found 178.0

Step 6: 5-Cyano-3-methylpyrazine-2-carboxylic acid and 6-Cyano-3-methylpyrazine-2-carboxylic acid

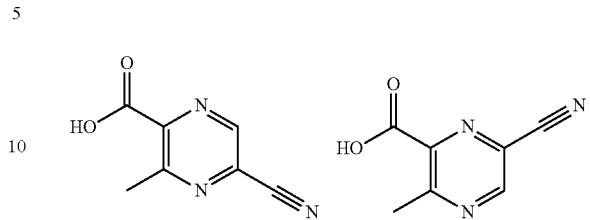

To a solution of methyl 5-cyano-3-methylpyrazine-2-carboxylate and methyl 6-cyano-3-methylpyrazine-2-carboxylate (85.0 mg, 0.480 mmol) in THF (2.399 mL) was added a solution of NaOH (39.35 mg, 0.960 mmol) in H$_2$O (2.399 mL) and the mixture was stirred at 25° C. for 3 hrs. The solvent was evaporated and the residue was taken up in POCl$_3$ (2 mL) and heated at 100° C. for 30 minutes. Excess POCl$_3$ was then evaporated and the residue was taken up in H$_2$O and extracted with EtOAc (3×). The combined organic layers were passed through a phase separator and evaporated to afford a mixture of the title compounds (61 mg, 78%) as a dark oil. $^1$H NMR (400 MHz, DMSO-d$_6$) δ 14.27 (s, 1H), 9.12 (s, 1H), 2.72 (d, J=0.6 Hz, 3H). $^1$H NMR (400 MHz, DMSO-d$_6$) δ 14.27 (s, 1H), 9.04 (s, 1H), 2.74-2.73 (m, 3H). MS-ESI (m/z) calc'd for C$_8$H$_8$N$_3$O$_2$ [M+H]$^+$: 162.0. Found 162.0.

Intermediate A-9: 5-Cyano-3,4-dimethylpicolinic acid

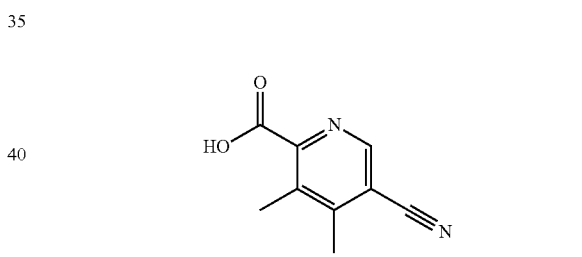

Step 1: 4,5,6-Trimethyl-2-oxo-1,2-dihydropyridine-3-carbonitrile

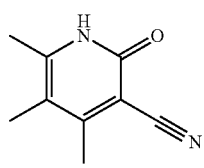

To a solution of (Z)-4-amino-3-methylpent-3-en-2-one (18.2 g, 160.83 mmol) in THF (120 mL) was added dropwise a solution of malononitrile (10.62 g, 160.83 mmol) in THF (40 mL) and the mixture was stirred at 25° C. for 15 hrs. The solid formed was collected by filtration and washed with EtOAc to afford the title compound (17.89 g, 69%) as a white solid. $^1$H NMR (400 MHz, DMSO-d$_6$) δ 12.17 (s, 1H), 2.32 (s, 3H), 2.27-2.24 (m, 3H), 1.93 (s, 3H). MS-ESI (m/z) calc'd for C$_9$H$_{11}$N$_2$O [M+H]$^+$: 163.1. Found 163.0.

Step 2: 2-Chloro-4,5,6-trimethylnicotinonitrile

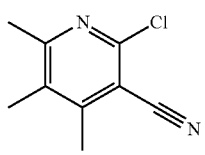

A suspension of 4,5,6-trimethyl-2-oxo-1,2-dihydropyridine-3-carbonitrile (17.89 g, 110.3 mmol) in POCl$_3$ (70.0 mL, 748.71 mmol) was heated at 100° C. for 15 hrs. The reaction mixture was concentrated and then poured into water (1 L). The pH was adjusted to 7 by addition of Na$_2$CO$_3$. The solid was collected by filtration and dried to afford the title compound (18.59 g, 93%) as a yellow solid. $^1$H NMR (400 MHz, DMSO-d$_6$) δ 2.51 (s, 3H), 2.47 (s, 3H), 2.22 (s, 3H). MS-ESI (m/z) calc'd for C$_9$H$_{10}$ClN$_2$ [M+H]$^+$: 181.1. Found 181.0.

Step 3: 4,5,6-Trimethylnicotinonitrile

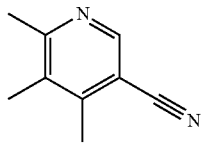

To a solution of 2-chloro-4,5,6-trimethylnicotinonitrile (1.81 g, 10 mmol) in MeOH (50 mL) was added 10% Pd/C (1.06 g, 1 mmol). Ammonium formate (630.6 mg, 10 mmol) was then added and the mixture was stirred at 60° C. for 1 hr. The mixture was filtered through Celite and the filtrate was evaporated to dryness to give a residue that was taken up in water and extracted with DCM (3×). The combined organic layers were passed through a phase separator and concentrated to afford the title compound (1.19 g, 81%) as a yellow solid. $^1$H NMR (400 MHz, DMSO-d$_6$) δ 8.61 (s, 1H), 2.53 (s, 3H), 2.44 (s, 3H), 2.23 (s, 3H). MS-ESI (m/z) calc'd for C$_9$H$_{11}$N$_2$ [M+H]$^+$: 147.1. Found 146.9.

Step 4: 5-Cyano-2,3,4-trimethylpyridine 1-oxide

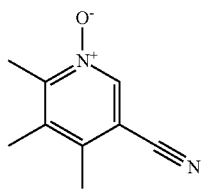

To a solution of 4,5,6-trimethylnicotinonitrile (1.19 g, 8.14 mmol) in DCM (40.7 mL) was added MCPBA (2.01 g, 8.14 mmol) and the mixture was stirred at 25° C. for 5 hrs. The solution was washed with K$_2$CO$_3$ solution (3×) and the aqueous layer was extracted with DCM (3×). The combined organic phases were passed through a phase separator and concentrated to afford the title compound (1.19 g, 90%) as a yellow solid. $^1$H NMR (400 MHz, DMSO-d$_6$) δ 8.73 (s, 1H), 2.44 (s, 3H), 2.39 (s, 3H), 2.28 (s, 3H). MS-ESI (m/z) calc'd for C$_9$H$_{11}$N$_2$O [M+H]$^+$: 163.1. Found 163.0.

Step 5: 6-(Hydroxymethyl)-4,5-dimethylnicotinonitrile

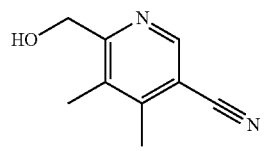

To a solution of 5-cyano-2,3,4-trimethylpyridine 1-oxide (4.15 g, 25.59 mmol) in DCM (39.15 mL) was added dropwise 2,2,2-trifluoroacetic acid (2,2,2-trifluoro-1-oxoethyl) ester (10.67 mL, 76.76 mmol) in DCM (39.15 mL) at 0° C. and the mixture was stirred at 25° C. for 15 h. The solvent was evaporated to dryness and the red oil obtained was dissolved in MeOH (50 mL). Then K$_2$CO$_3$ (3 g) was added and the suspension was stirred for 15 min. The solvent was evaporated to give a residue that was taken up in water and extracted with DCM (3×). The combined organic layers were passed through a phase separator and evaporated to afford the title compound (3.65 g, 88%) as a dark orange solid. $^1$H NMR (400 MHz, DMSO-d$_6$) δ 8.70 (s, 1H), 5.22 (t, J=5.6 Hz, 1H), 4.64 (d, J=5.6 Hz, 2H), 2.46 (s, 3H), 2.29 (s, 3H). MS-ESI (m/z) calc'd for C$_9$H$_{11}$N$_2$O [M+H]$^+$: 163.1. Found 163.0.

Step 6: 5-Cyano-3,4-dimethylpicolinic acid

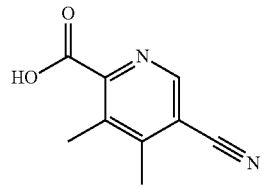

To a solution of 6-(hydroxymethyl)-4,5-dimethylnicotinonitrile (3.65 g, 22.5 mmol) in acetone (62.98 mL) was added dropwise (over 15 min) a solution of KMnO$_4$ (3.91 g, 24.75 mmol) in water (31.49 mL) at 25° C. and the mixture was stirred for 30 minutes. The dark material was filtered and washed with 1 M K$_2$CO$_3$ solution. The filtrate was concentrated to remove the organic solvent and the pH was adjusted to 4-5 by addition of 6 M HCl and the solution was extracted with EtOAc (3×). Then additional 6 M HCl was added until pH=1 was reached and the aqueous phase was further extracted with EtOAc (3×). The combined organic layers were passed through a phase separator and concentrated to afford the title compound (1.75 g, 44%) as a beige solid. $^1$H NMR (400 MHz, DMSO-d$_6$) δ 13.82 (s, 1H), 8.78 (s, 1H), 2.50 (s, 3H), 2.33 (s, 3H). MS-ESI (m/z) calc'd for C$_9$H$_9$N$_2$O$_2$[M+H]$^+$: 177.1. Found 177.1.

Intermediate A-10: 3-(2-Methoxypyridin-4-yl)-1H-indazol-5-amine

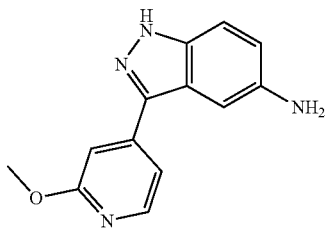 [SMILES: COc1cc(-c2n[nH]c3ccc(N)cc23)ccn1]

3-Bromo-1H-indazol-5-amine (1.0 g, 4.72 mmol), 2-methoxypyridine-4-boronic acid (1081.87 mg, 7.07 mmol) and tripotassium phosphate (3003.11 mg, 14.15 mmol) were dissolved in a mixture of THF (12 mL) and H$_2$O (4 mL). The reaction mixture was degassed with nitrogen for 15 min and then SPhos-Pd-G2 (0.51 g, 0.710 mmol) was added. The mixture was heated to 80° C. and stirred for 20 hrs. Then 0.5 eq of 2-methoxypyridine-4-boronic acid and 0.075 eq of Sphos-Pd-G2 were added and the mixture was stirred at 80° C. for an additional 16 hrs. The reaction was cooled to r.t. and diluted with H$_2$O and EtOAc. The phases were separated and the aqueous layer was extracted with EtOAc (2×). The combined organic layers were concentrated under reduced pressure to give a residue that was purified by preparative HPLC using Method CM to afford the title compound (385 mg, 34%) as a yellow solid. $^1$H NMR (400 MHz, DMSO-d$_6$) δ 13.13 (br. s., 1H) 8.19-8.28 (m, 1H) 7.52 (dd, J=5.39, 1.43 Hz, 1H) 7.35 (d, J=8.80 Hz, 1H) 7.24 (d, J=0.66 Hz, 1H) 7.17 (d, J=1.32 Hz, 1H) 6.86 (dd, J=8.80, 1.98 Hz, 1H) 5.02 (s, 2H) 3.92 (s, 3H). MS-ESI (m/z) calc'd for C$_{13}$H$_{13}$N$_4$O$_2$ [M+H]$^+$: 241.1. Found 241.2.

Intermediate A-11: 3-(1-(Difluoromethyl)-1H-pyrazol-4-yl)-1H-indazol-5-amine

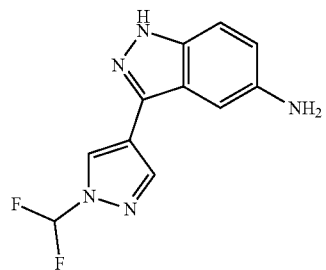

3-Iodo-1H-indazol-5-amine (1.3 g, 5 mmol) was dissolved in THF (28.37 mL) then a solution of tripotassium phosphate (3.18 g, 15 mmol) and 1-(difluoromethyl)-4-(4,4,5,5-tetramethyl-1,3,2-dioxaborolan-2-yl)pyrazole (1.46 g, 6 mmol) in H$_2$O (10.64 mL) was added and the mixture was degassed with N$_2$ for 15 minutes. SPhos-Pd-G2 (0.36 g, 0.500 mmol) was added and the mixture was stirred at 100° C. under N$_2$ for 1 hr. H$_2$O was added and the organic solvent was evaporated. The solid that formed was collected by filtration and washed with water and dried. The filtrate was extracted with EtOAc (3×) and the combined organic layers were concentrated and added to the solid to obtain a residue which was triturated with DCM to afford the title compound (880 mg, 71%) as a grey solid. $^1$H NMR (400 MHz, DMSO-d$_6$) δ 12.70 (s, 1H), 8.61 (s, 1H), 8.22 (s, 1H), 7.88 (t, J=59.1 Hz, 1H), 7.28 (d, J=8.8 Hz, 1H), 7.03 (d, J=2.0 Hz, 1H), 6.84 (dd, J=8.8, 2.0 Hz, 1H), 4.82 (s, 2H). MS-ESI (m/z) calc'd for C$_{11}$H$_{10}$F$_2$N$_5$ [M+H]$^+$: 250.1. Found 250.3.

Intermediate A-12: 4-Cyano-2-fluoro-6-methylbenzoic acid

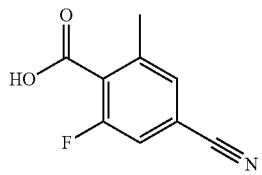

Step 1: Methyl 4-bromo-2-fluoro-6-methylbenzoate

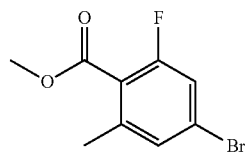

To a solution of 4-bromo-2-fluoro-6-methylbenzoic acid (1.37 g, 5.88 mmol) in DMF (9.798 mL) was added potassium carbonate (2.44 g, 17.64 mmol) and iodomethane (0.73 mL, 11.76 mmol), then the mixture was stirred at 80° C. for 1 hr. The mixture was poured into water (150 mL) and the mixture was extracted with Et$_2$O (3×). The combined organic layers were washed with H$_2$O (2×) and brine, then passed through a phase separator and evaporated to give the title compound (1.452 g, 100%) as a white solid. $^1$H NMR (400 MHz, DMSO-d$_6$) δ 7.54 (ddd, J=9.5, 1.8, 0.7 Hz, 1H), 7.46 (dt, J=1.8, 0.8 Hz, 1H), 3.87 (s, 3H), 2.33 (d, J=0.7 Hz, 3H). MS-ESI (m/z) calc'd for C$_9$H$_9$BrFO$_2$ [M+H]$^+$: 247.0/249.0. Found 247.0/249.0.

Step 2: Methyl 2-fluoro-6-methyl-4-vinylbenzoate

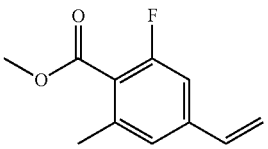

A solution of methyl 4-bromo-2-fluoro-6-methylbenzoate (1.45 g, 5.88 mmol) and tributyl(ethenyl)stannane (2.06 mL, 7.05 mmol) in 1,4-dioxane (58.79 mL) was sparged with N$_2$ for 10 minutes. Triphenylphosphine palladium(II) dichloride (413.84 mg, 0.590 mmol) was added and the mixture was stirred at 100° C. for 1.5 hrs. The solvent was evaporated and the residue was purified by silica gel column chromatography using a 0-10% EtOAc/cyclohexane gradient eluent to afford the title compound (1.142 g, 100%) as yellow oil. $^1$H NMR (400 MHz, DMSO-d$_6$) δ 7.31 (dd, J=11.2, 1.5 Hz, 1H), 7.28-7.26 (m, 1H), 6.79-6.62 (m, 1H), 6.00 (dd, J=17.7, 0.8 Hz, 1H), 5.42 (d, J=10.9 Hz, 1H), 3.86 (s, 3H), 2.33 (d, J=0.8 Hz, 3H). MS-ESI (m/z) calc'd for $C_{11}H_{12}FO_2$ [M+H]$^+$: 195.1. Found 195.0.

Step 3: Methyl 2-fluoro-4-formyl-6-methylbenzoate

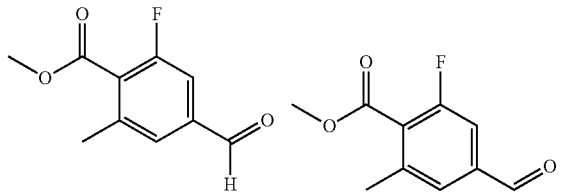

To a solution of methyl 2-fluoro-6-methyl-4-vinylbenzoate (1.14 g, 5.88 mmol) in 1,4-dioxane (29.39 mL) was added a solution of NaIO$_4$ (2.51 g, 11.76 mmol) in H$_2$O (29.39 mL) and the mixture was stirred at 25° C. for 5 minutes. Osmium tetroxide (1.87 mL, 0.290 mmol) was added and the reaction was stirred for 2 hrs. The reaction was diluted with H$_2$O and the mixture was extracted with DCM (3×). The combined organic layers were passed through a phase separator (charged with activated carbon) and concentrated to afford the title compound (1.14 g, 99%) as a dark solid. $^1$H NMR (400 MHz, DMSO-d$_6$) δ 9.99 (d, J=1.7 Hz, 1H), 7.73 (t, J=1.1 Hz, 1H), 7.66 (ddd, J=9.4, 1.4, 0.7 Hz, 1H), 3.92 (s, 3H), 2.41 (t, J=0.7 Hz, 3H). MS-ESI (m/z) calc'd for $C_{10}H_{10}FO_3$ [M+H]$^+$: 197.1. Found 197.0.

Step 4:
3-Fluoro-4-(methoxycarbonyl)-5-methylbenzoic acid

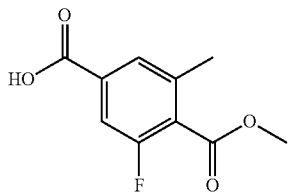

To a solution of methyl 2-fluoro-4-formyl-6-methylbenzoate (1.14 g, 5.81 mmol) in DMSO (5 mL) was added hydroxylamine hydrochloride (403.81 mg, 5.81 mmol) and the mixture was stirred at 90° C. for 2 hrs. Water was added and the mixture was extracted with EtOAc. The organic layer was washed with H$_2$O (3×) then passed through a phase separator and concentrated. The residue was purified by silica gel column chromatography using a 0-50% EtOAc/cyclohexane gradient eluent to afford the title compound (457 mg, 37%) as a yellow oil. $^1$H NMR (400 MHz, DMSO-d$_6$) δ 13.49 (s, 1H), 7.72 (s, 1H), 7.58 (dd, J=9.9, 1.5 Hz, 1H), 3.90 (s, 3H), 2.38 (s, 3H). MS-ESI (m/z) calc'd for $C_{10}H_{10}FO_4$ [M+H]$^+$: 213.1. Found 213.0.

Step 5: Methyl 4-cyano-2-fluoro-6-methylbenzoate

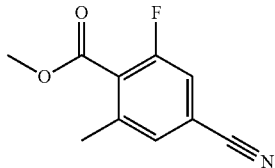

A solution of 3-fluoro-4-(methoxycarbonyl)-5-methylbenzoic acid (457.0 mg, 2.15 mmol) in thionyl chloride (10.0 mL, 137.09 mmol) was heated at 80° C. for 2 hrs. The excess of thionyl chloride was evaporated and the residue was taken up in THF (10 mL). A solution of 0.5 M ammonia (17.23 mL, 8.62 mmol) in dioxane was added and the mixture was stirred at 25° C. for 1 hr. The solvent was evaporated and the residue was taken up in POCl$_3$ (10.0 mL, 106.96 mmol) and the resulting suspension was stirred at 100° C. for 3 hrs. Excess POCl$_3$ was evaporated and the residue was taken up in water and extracted with DCM (3×). The combined organic layers were passed through a phase separator and concentrated to afford the title compound (410 mg, 99%) as a yellow solid. $^1$H NMR (400 MHz, DMSO-d$_6$) δ 7.85 (ddd, J=9.5, 1.4, 0.7 Hz, 1H), 7.74 (dd, J=1.5, 0.7 Hz, 1H), 3.92 (s, 3H), 2.36 (d, J=0.7 Hz, 3H). MS-ESI (m/z) calc'd for $C_{10}H_9FNO_2$ [M+H]$^+$: 194.1. Found 194.1.

Step 6: 4-Cyano-2-fluoro-6-methylbenzoic acid

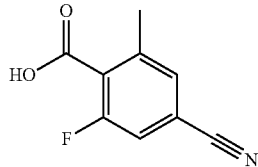

To a solution of methyl 4-cyano-2-fluoro-6-methylbenzoate (410.0 mg, 2.12 mmol) in THF (5.31 mL) was added 1 M NaOH (4.24 mL, 4.24 mmol) and the mixture was stirred at 25° C. for 6 hrs. The organic solvent was evaporated and the mixture was acidified by addition of 1 M HCl and extracted with EtOAc (3×). The combined organic layers were passed through a phase separator and concentrated to afford the title compound (380 mg, 99%) as a brown solid. $^1$H NMR (400 MHz, DMSO-d$_6$) δ 14.08 (s, 1H), 7.80 (dd, J=9.3, 1.4 Hz, 1H), 7.72-7.66 (m, 1H), 2.37 (s, 3H). MS-ESI (m/z) calc'd for $C_9H_5FNO_2$ [M–H]$^-$: 178.1. Found 178.1.

Intermediate A-13:
6-Chloro-5-cyano-3,4-dimethylpicolinic acid

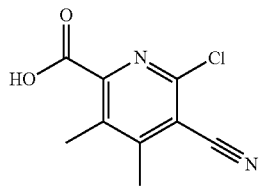

Step 1: 2-Chloro-6-(hydroxymethyl)-4,5-dimethyl-nicotinonitrile

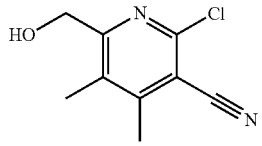

To a solution of 2-chloro-3-cyano-4,5,6-trimethylpyridine 1-oxide (634.0 mg, 3.22 mmol) in DCM (9.86 mL) was added dropwise 2,2,2-trifluoroacetic anhydride (1.34 mL, 9.67 mmol) in DCM (9.86 mL) at 0° C. and the mixture was stirred at 25° C. for 15 hrs. The solvent was evaporated to give a residue that was taken up in water and extracted with DCM (2×). The combined organic layers were passed through a phase separator and concentrated to afford the title compound (650 mg, 100%) as a pale yellow solid. $^1$H NMR (400 MHz, DMSO-$d_6$) δ 5.42 (t, J=5.8 Hz, 1H), 4.60 (d, J=5.4 Hz, 2H), 2.50 (s, 3H), 2.28 (s, 3H). MS-ESI (m/z) calc'd for $C_9H_{10}ClN_2O$ [M+H]$^+$: 197.0. Found 197.0.

Step 2: 6-Chloro-5-cyano-3,4-dimethylpicolinic acid

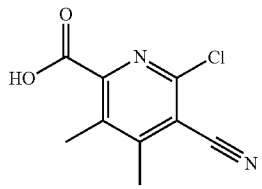

To a solution of 2-chloro-6-(hydroxymethyl)-4,5-dimethylnicotinonitrile (100.0 mg, 0.510 mmol) in acetone (1.5 mL) was added dropwise a solution of KMnO$_4$ (88.41 mg, 0.560 mmol) in H$_2$O (0.750 mL) at r.t. and the mixture was stirred for 2 hrs. The dark mixture was filtered and the solid was washed with 1 M aqueous K$_2$CO$_3$. The filtrate was concentrated to remove acetone and then extracted with EtOAc. The pH was adjusted to pH=2 by addition of 6 M HCl and was extracted with EtOAc (3×). The combined organic layers were passed through a phase separator and concentrated to afford the title compound (78 mg, 73%) as a beige solid. $^1$H NMR (400 MHz, DMSO-$d_6$) δ 2.55 (s, 3H), 2.33 (s, 3H). MS-ESI (m/z) calc'd for $C_9H_8ClN_2O_2$ [M+H]$^+$: 211.0. Found 211.0.

Intermediate A-14: 5-Cyano-3,4,6-trimethylpicolinic acid

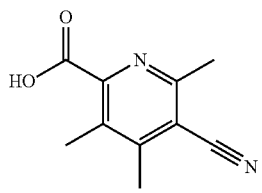

Step 1:6-(Hydroxymethyl)-2,4,5-trimethylnicotinonitrile

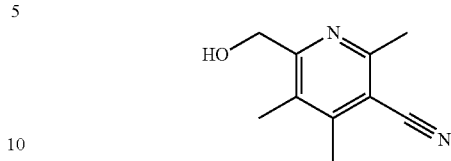

A solution of 2-chloro-6-(hydroxymethyl)-4,5-dimethylnicotinonitrile (150.0 mg, 0.760 mmol), K$_2$CO$_3$ (210.87 mg, 1.53 mmol) and trimethylboroxine (0.21 mL, 1.53 mmol) in 1,4-dioxane (2 mL)/H$_2$O (1 mL) was degassed with N$_2$ for 15 min. Tetrakis(triphenylphosphine)palladium(0) (176.3 mg, 0.150 mmol) was added and the mixture was stirred at 90° C. for 6 hours. The residue was taken up in H$_2$O and extracted with EtOAc (2×). The combined organic layers were passed through a phase separator and evaporated to obtain a residue which was purified by reversed phase column chromatography using a 2-80% MeCN/H$_2$O (0.1% formic acid) gradient eluent to afford the title compound (83 mg, 62%) as a white solid. $^1$H NMR (400 MHz, DMSO-$d_6$) δ 5.19 (t, J=5.5 Hz, 1H), 4.60 (d, J=5.5 Hz, 2H), 2.62 (s, 3H), 2.44 (s, 3H), 2.25 (s, 3H). MS-ESI (m/z) calc'd for $C_{10}H_{13}N_2O$ [M+H]$^+$: 177.1. Found 177.0.

Step 2: 5-Cyano-3,4,6-trimethylpicolinic acid

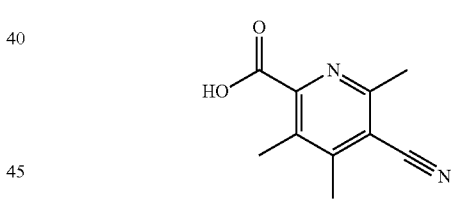

To a solution of 6-(hydroxymethyl)-2,4,5-trimethylnicotinonitrile (83.0 mg, 0.47 mmol) in acetone (1.5 mL) was added dropwise a solution of KMnO$_4$ (81.88 mg, 0.52 mmol) in H$_2$O (0.75 mL) at r.t. and the mixture was stirred for 2 hrs. The dark mixture was filtered and the solid was washed with 1 M aqueous K$_2$CO$_3$. The filtrate was concentrated to remove the organic solvent and extracted with EtOAc. Then the pH was adjusted to pH=2 by addition of 6 M HCl and the solution was extracted with EtOAc (3×). The combined organic layers were passed through a phase separator and evaporated to afford the title compound (90 mg, 100%) as a white solid. $^1$H NMR (400 MHz, DMSO-$d_6$) δ 13.63 (br s, 1H), 2.63 (s, 3H), 2.49 (s, 3H), 2.29 (s, 3H). MS-ESI (m/z) calc'd for $C_{10}H_9N_2O_2$ [M−H]$^-$: 189.1. Found 189.2.

Intermediate A-15: 3-(Thiazol-5-yl)-1H-indazol-5-amine

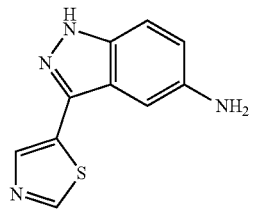

A microwave reactor vial was charged with 3-iodo-1H-indazol-5-amine (500.0 mg, 1.93 mmol), Pd(amphos)Cl$_2$ (137.06 mg, 0.190 mmol), 5-(4,4,5,5-tetramethyl-1,3,2-dioxaborolan-2-yl)thiazole (448.17 mg, 2.12 mmol), 1,4-dioxane (3.281 mL) and H$_2$O (0.750 mL). The vial was flushed with N$_2$ for 5 min after which KOAc (340.96 mg, 3.47 mmol) was added and the vial was sealed and irradiated in a microwave reactor at 100° C. for 30 min. The reaction mixture was partitioned between H$_2$O and EtOAc. The phases were separated and the aqueous layer was extracted with EtOAc (2×). The combined organic phases were washed with brine (1×), dried over Na$_2$SO$_4$ and concentrated to give a residue that was purified by preparative HPLC using Method CN to afford the title compound (93 mg, 22%). MS-ESI (m/z) calc'd for C$_{10}$H$_9$N$_4$S [M+H]$^+$: 217.1. Found 217.1.

Intermediate A-16: 3-Bromo-2-methoxy-6-methyl-N-(3-(oxazol-5-yl)-1H-indazol-5-yl)benzamide

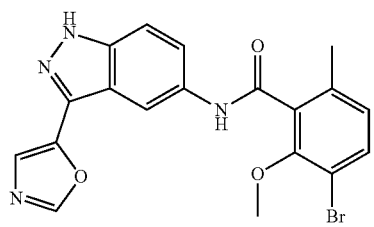 [SMILES: COc1c(Br)ccc(C)c1C(=O)Nc1ccc2[nH]nc(-c3cnco3)c2c1]

To a mixture of 3-bromo-2-methoxy-6-methylbenzoic acid (40.0 mg, 0.160 mmol), 3-(1,3-oxazol-5-yl)-1H-indazol-5-amine (35.94 mg, 0.180 mmol) and Et$_3$N (45.5 uL, 0.330 mmol) in MeCN (2.5 mL) was added HATU (62.06 mg, 0.160 mmol) and the mixture was stirred at r.t. for 1 hr. The reaction mixture was partitioned between H$_2$O and EtOAc and the phases were separated. The aqueous layer was extracted with EtOAc (2×) and the combined organic phases were washed with brine (1×), dried over Na$_2$SO$_4$, and concentrated to afford the title compound (110 mg) which was used without further purification. $^1$H NMR (400 MHz, DMSO-d$_6$) δ 13.50 (s, 1H) 10.59 (s, 1H) 8.59 (d, J=6.60 Hz, 2H) 7.50-7.79 (m, 4H) 6.97-7.14 (m, 1H) 3.82 (s, 3H) 2.29 (s, 3H). MS-ESI (m/z) calc'd for C$_{19}$H$_{16}$BrN$_4$O$_3$ [M+H]$^+$: 427.0/429.0. Found 427.2/429.2.

Intermediate A-17: 4-Cyano-6,7-dihydro-5H-cyclopenta[c]pyridine-1-carboxylic acid

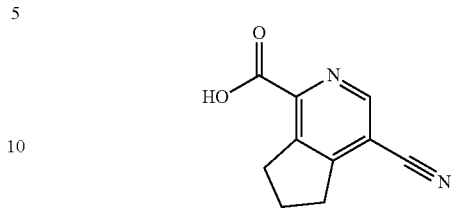

Step 1: 1-Methyl-3-oxo-4,5,6,7-tetrahydro-3H-cyclopenta[c]pyridine-4-carbonitrile and 4-Methyl-2-oxo-2,5,6,7-tetrahydro-1H-cyclopenta[b]pyridine-3-carbonitrile

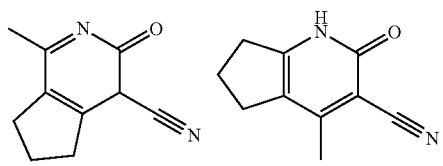

To a solution of 2-acetyl-1-cyclopentanone (5.05 g, 40 mmol) and 2-cyanoacetamide (3.36 g, 40 mmol) was added piperidine (3.95 mL, 40 mmol) and the mixture was stirred at 75° C. for 22 hrs. After cooling the solid formed was collected by filtration and dried to afford a mixture of the title compounds (3.35 g, 48%) as a white solid. $^1$H NMR (400 MHz, DMSO-d$_6$) δ 12.26 (s, 1H), 2.80 (t, J=7.8 Hz, 2H), 2.63 (t, J=7.3 Hz, 2H), 2.27 (s, 3H), 2.07-1.96 (m, 2H). MS-ESI (m/z) calc'd for C$_{10}$H$_{11}$N$_2$O [M+H]$^+$: 175.1. Found 175.0.

Step 2: 3-Chloro-1-methyl-6,7-dihydro-5H-cyclopenta[c]pyridine-4-carbonitrile and 2-Chloro-4-methyl-6,7-dihydro-5H-cyclopenta[b]pyridine-3-carbonitrile

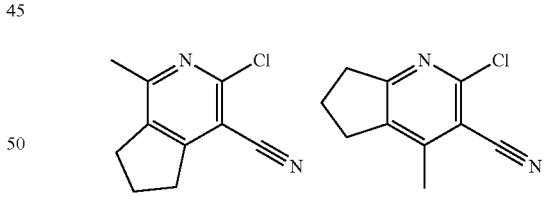

A suspension of 1-methyl-3-oxo-4,5,6,7-tetrahydro-3H-cyclopenta[c]pyridine-4-carbonitrile and 4-methyl-2-oxo-2,5,6,7-tetrahydro-1H-cyclopenta[b]pyridine-3-carbonitrile (3.35 g, 19.23 mmol) in POCl$_3$ (20.0 mL, 213.92 mmol) was heated [upon heating the solid slowly dissolves until complete dissolution] at 100° C. for 17 hrs. The excess of POCl$_3$ was evaporated and the oil that remained was taken up in water and stirred for 30 minutes. The solid that formed was collected by filtration and dried under vacuum to afford a mixture of the title compounds (3.704 g, 19.23 mmol) as an off-white solid. $^1$H NMR (400 MHz, DMSO-d$_6$) δ 3.08 (t, J=7.7 Hz, 2H), 2.94-2.85 (m, 2H), 2.45 (s, 3H), 2.21-2.05 (m, 2H). MS-ESI (m/z) calc'd for C$_{10}$H$_{10}$ClN$_2$ [M+H]$^+$: 193.1. Found 193.0.

Step 3: 1-Methyl-6,7-dihydro-5H-cyclopenta[c]pyridine-4-carbonitrile and 4-Methyl-6,7-dihydro-5H-cyclopenta[b]pyridine-3-carbonitrile

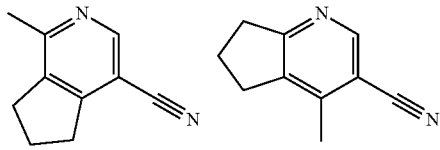

A mixture of 3-chloro-1-methyl-6,7-dihydro-5H-cyclopenta[c]pyridine-4-carbonitrile and 2-chloro-4-methyl-6,7-dihydro-5H-cyclopenta[b]pyridine-3-carbonitrile (0.96 g, 5 mmol), NaOAc.3H$_2$O (685.45 mg, 5 mmol) and 10% Pd/C (532.1 mg, 0.500 mmol) was hydrogenated for 1 hr. The catalyst was filtered through Celite and the filtrate was evaporated to give a residue. The residue was taken up in H$_2$O and extracted with DCM (3×). The combined organic layers were passed through a phase separator and evaporated to afford a mixture of the title compounds (380 mg, 2.402 mmol) as a clear oil. $^1$H NMR (400 MHz, DMSO-d$_6$) δ 8.62 (s, 1H), 3.06 (dd, J=8.1, 7.2 Hz, 2H), 2.96-2.87 (m, 2H), 2.47 (s, 3H), 2.15-2.03 (m, 2H). MS-ESI (m/z) calc'd for C$_{10}$H$_{10}$N, [M+H]$^+$: 159.1. Found 159.0.

Step 4: 4-Cyano-1-methyl-6,7-dihydro-5H-cyclopenta[c]pyridine 2-oxide and 3-Cyano-4-methyl-6,7-dihydro-5H-cyclopenta[b]pyridine 1-oxide

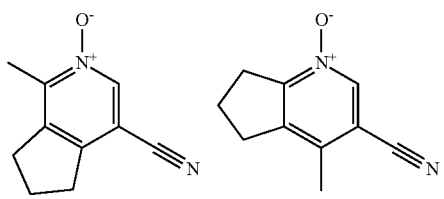

To a solution of 1-methyl-6,7-dihydro-5H-cyclopenta[c]pyridine-4-carbonitrile and 4-methyl-6,7-dihydro-5H-cyclopenta[b]pyridine-3-carbonitrile (380.0 mg, 2.4 mmol) in DCM (24.02 mL) was added MCPBA (592.17 mg, 2.4 mmol) and the mixture was stirred at 25° C. for 5 hrs. The solution was washed with a K$_2$CO$_3$ solution (3×) and the aqueous layers were extracted with DCM (3×). All the organic phases were combined, passed through a phase separator and evaporated to dryness to afford a mixture of the title compounds (355 mg, 85%) as a white solid. $^1$H NMR (400 MHz, DMSO-d$_6$) δ 8.70 (s, 1H), 3.06-2.94 (m, 4H), 2.34 (s, 3H), 2.19-2.06 (m, 2H). MS-ESI (m/z) calc'd for C$_{10}$H$_{10}$N$_2$O [M+H]$^+$: 175.1. Found 175.0.

Step 5: 1-(Hydroxymethyl)-6,7-dihydro-5H-cyclopenta[c]pyridine-4-carbonitrile and 7-Hydroxy-4-methyl-6,7-dihydro-5H-cyclopenta[b]pyridine-3-carbonitrile

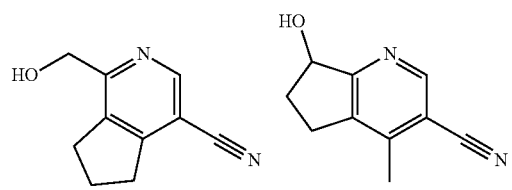

To a solution of 4-cyano-1-methyl-6,7-dihydro-5H-cyclopenta[c]pyridine 2-oxide and 3-cyano-4-methyl-6,7-dihydro-5H-cyclopenta[b]pyridine 1-oxide (355.0 mg, 2.04 mmol) in DCM (6 mL) was added dropwise 2,2,2-trifluoroacetic anhydride (0.85 mL, 6.11 mmol) in DCM (2 mL) at 25° C. and the mixture was stirred at 25° C. for 15 hrs. The solvent was evaporated and the red oil obtained was dissolved in MeOH (10 mL). Then K$_2$CO$_3$ (0.5 g) was added and the suspension was stirred for 15 min. The solvent was evaporated and the residue was taken up in water and extracted with DCM (3×). The combined organic layers were passed through a phase separator and evaporated to afford a mixture of the title compounds (310 mg, 87%) as a dark oil. $^1$H NMR (400 MHz, DMSO-d$_6$) δ 8.69 (s, 1H), 5.31 (t, J=6.0 Hz, 1H), 4.59 (d, J=5.4 Hz, 2H), 3.11-3.01 (m, 4H), 2.10 (p, J=7.6 Hz, 2H). MS-ESI (m/z) calc'd for C$_{10}$H$_{10}$N$_2$O [M+H]$^+$: 175.1. Found 175.0.

Step 6: 4-Cyano-6,7-dihydro-5H-cyclopenta[c]pyridine-1-carboxylic acid

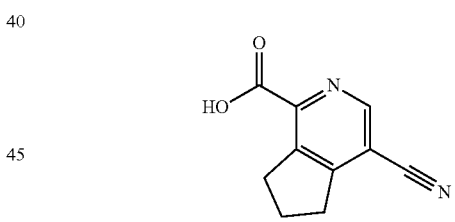

To a solution of 1-(hydroxymethyl)-6,7-dihydro-5H-cyclopenta[c]pyridine-4-carbonitrile and 7-hydroxy-4-methyl-6,7-dihydro-5H-cyclopenta[b]pyridine-3-carbonitrile (310.0 mg, 0.710 mmol) in acetone (8.898 mL) and H$_2$O (8.898 mL) was added KMnO$_4$ (224.98 mg, 1.42 mmol) and the mixture was stirred at 25° C. for 3 hrs. The dark mixture was filtered under vacuum and the solid was washed with acetone and 1 M aqueous K$_2$CO$_3$. The filtrate was concentrated to remove the organic solvent and the remaining aqueous layer was extracted with Et$_2$O (3×). The aqueous layer was adjusted to pH≤1 by addition of conc. HCl and extracted with EtOAc (3×). The combined organic layers were passed through a phase separator and concentrated to afford the title compound (133.9 mg, 99°%) as a dark solid. $^1$H NMR (400 MHz, DMSO-d$_6$) δ 13.51 (bs, 1H), 8.86 (s, 1H), 3.25 (t, J=7.6 Hz, 2H), 3.12 (t, J=7.7 Hz, 2H), 2.16-2.06 (m, 2H). MS-ESI (m/z) calc'd for C$_{10}$H$_9$N$_2$O$_2$ [M+H]$^+$: 189.1. Found 189.0.

Intermediate A-18: 5-Cyano-4-methoxy-3-methylpicolinic acid

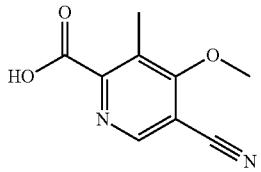

Step 1: 4-Methoxy-2,3-dimethylpyridine 1-oxide

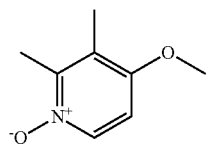

To a suspension of 2,3-dimethyl-4-nitro-1-oxidopyridin-1-ium (5.04 g, 30 mmol) in MeOH (50 mL) was added K$_2$CO$_3$ (4.98 g, 36 mmol) portionwise at 0° C. [Caution: without the ice bath, the reaction can be violently exothermic]. The mixture was heated at 65° C. for 4 hrs, then the solvent was evaporated to dryness and the residue was taken up in CH$_3$CN (100 mL) and stirred at reflux for 30 minutes. The solid was filtered and washed with CH$_3$CN (10 mL, ×3). The filtered solution rapidly became a suspension and was filtered again to remove the solids and concentrated to afford the title compound (3.8 g, 83%) as an orange solid. $^1$H NMR (400 MHz, DMSO-d$_6$) δ 8.10 (d, J=7.5 Hz, 1H), 6.94 (d, J=7.3 Hz, 1H), 3.83 (s, 3H), 2.35 (s, 3H), 2.12 (s, 3H). MS-ESI (m/z) calc'd for C$_8$H$_{12}$NO$_2$ [M+H]$^+$: 154.1. Found 153.0.

Step 2: 5-Bromo-4-methoxy-2,3-dimethylpyridine 1-oxide

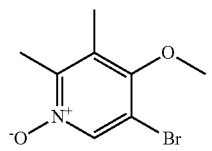

To a solution of 4-methoxy-2,3-dimethylpyridine 1-oxide (4.0 g, 26.11 mmol) in trifluoroacetic acid (5.201 mL) and sulfuric acid (6.96 mL, 130.57 mmol) was added N-bromosuccinimide (9.3 g, 52.23 mmol) portionwise and the mixture was stirred at 25° C. for 15 hrs. The mixture was poured onto cracked ice and quenched with an aqueous Na$_2$S$_2$O$_3$ solution. The pH was adjusted to 7 by addition of 6 M NaOH and then extracted with DCM (3×). The combined organic layers were passed through a phase separator and concentrated to afford the title compound (4.53 g, 75%) as a dark oil. $^1$H NMR (400 MHz, DMSO-d$_6$) δ 8.51-8.49 (m, 1H), 3.76 (s, 3H), 2.32 (d, J=0.6 Hz, 3H), 2.24 (t, J=0.7 Hz, 3H). MS-ESI (m/z) calc'd for C$_8$H$_{11}$BrNO$_2$ [M+H]$^+$: 232.0/234.0. Found 232.0/234.0.

Step 3: (5-Bromo-4-methoxy-3-methylpyridin-2-yl)methanol

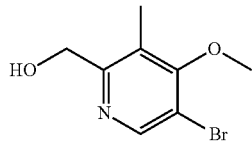

To a solution of 5-bromo-4-methoxy-2,3-dimethylpyridine 1-oxide (4.53 g, 19.52 mmol) in DCM (40 mL) was added dropwise 2,2,2-trifluoroacetic anhydride (8.14 mL, 58.56 mmol) in DCM (20 mL) at 0° C. The mixture was stirred at 0° C. for 5 hrs. The solvent was evaporated and the residue was taken up in MeOH (60 mL). Solid K$_2$CO$_3$ was added and the suspension was stirred at 25° C. for 30 minutes. The solvent was evaporated to give a residue that was taken up in H$_2$O and extracted with DCM (3×). The combined organic layers were passed through a phase separator and concentrated to afford the title compound (4.53 g, 100%) as an orange oil. $^1$H NMR (400 MHz, DMSO-d$_6$) δ 8.48 (d, J=0.7 Hz, 1H), 5.12 (t, J=5.6 Hz, 1H), 4.54 (d, J=5.4 Hz, 2H), 3.81 (s, 3H), 2.28 (d, J=0.6 Hz, 3H). MS-ESI (m/z) calc'd for C$_8$H$_{11}$BrNO$_2$ [M+H]$^+$: 232.0/234.0. Found 232.0/234.0.

Step 4: 5-Bromo-4-methoxy-3-methylpicolinic acid

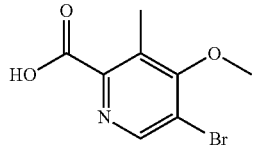

To a solution of (5-bromo-4-methoxy-3-methylpyridin-2-yl)methanol (4.53 g, 19.52 mmol) in acetone (54 mL) was added dropwise a solution of KMnO$_4$ (3.08 g, 19.52 mmol) in H$_2$O (27 mL) at 25° C. and the mixture was stirred for 2 hrs. The dark mixture was filtered and washed with acetone and H$_2$O. The filtrate was concentrated and the pH was adjusted to pH=2 by addition of conc. HCl and the solution was extracted with EtOAc (5×). The combined organic layers were passed through a phase separator and concentrated to afford the title compound (1.6 g, 33%) as a white solid. $^1$H NMR (400 MHz, DMSO-d$_6$) δ 14.91 (s, 1H), 8.61 (s, 1H), 3.86 (s, 3H), 2.38 (s, 3H). MS-ESI (m/z) calc'd for C$_8$H$_9$BrNO$_3$ [M+H]$^+$: 246.0/248.0. Found 246.0/248.0.

Step 5: Methyl 5-bromo-4-methoxy-3-methylpicolinate

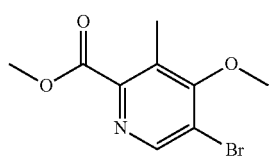

To a solution of 5-bromo-4-methoxy-3-methylpicolinic acid (1.6 g, 6.5 mmol) in DMF (10.84 mL) was added K$_2$CO$_3$ (2.7 g, 19.51 mmol) and iodomethane (0.81 mL, 13 mmol) and the mixture was stirred at 80° C. for 1 hr. The mixture was then poured into H$_2$O (150 mL) and the mixture was extracted with Et$_2$O (3×). The combined organic layers were washed with H$_2$O (2×) and brine then passed through a phase separator and concentrated to afford the title compound (1 g, 59%) as a yellow solid. $^1$H NMR (400 MHz, DMSO-d$_6$) δ 8.63 (d, J=0.7 Hz, 1H), 3.87 (s, 3H), 3.86 (s, 3H), 2.37 (d, J=0.6 Hz, 3H). MS-ESI (m/z) calc'd for C$_9$H$_{11}$BrNO$_3$ [M+H]$^+$: 260.0/262.0. Found 260.0/262.0.

Step 6: Methyl 4-methoxy-3-methyl-5-vinylpicolinate

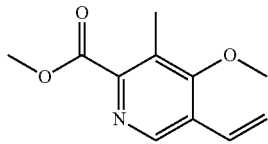

A solution of methyl 5-bromo-4-methoxy-3-methylpicolinate (1.0 g, 3.84 mmol) and tributyl(ethenyl)stannane (1.35 mL, 4.61 mmol) in 1,4-dioxane (38.45 mL) was purged with N$_2$ for 10 minutes. Bis(triphenylphosphine)palladium(II) dichloride (270.65 mg, 0.380 mmol) was added and the mixture was stirred at 100° C. for 15 hrs. The solvent was evaporated and the residue was purified by silica gel column chromatography using a 0-50% EtOAc/cyclohexane gradient eluent to afford the title compound (504 mg, 63%) as a yellow oil. $^1$H NMR (400 MHz, DMSO-d$_6$) δ 8.73-8.56 (m, 1H), 6.89 (ddd, J=17.8, 11.3, 0.6 Hz, 1H), 6.07 (dd, J=17.9, 1.1 Hz, 1H), 5.55 (dd, J=11.3, 1.1 Hz, 1H), 3.86 (s, 3H), 3.76 (s, 3H), 2.32 (d, J=0.6 Hz, 3H). MS-ESI (m/z) calc'd for C$_{11}$H$_{14}$NO$_3$ [M+H]$^+$: 208.1. Found 208.1.

Step 7: Methyl 5-formyl-4-methoxy-3-methylpicolinate

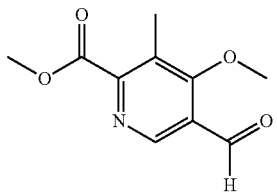

To a solution of methyl 4-methoxy-3-methyl-5-vinylpicolinate (504.0 mg, 2.43 mmol) in 1,4-dioxane (12.16 mL) was added a solution of NaIO$_4$ (1.04 g, 4.86 mmol) in H$_2$O (12.16 mL) and the mixture was stirred at 25° C. for 1 hr. The mixture was diluted with water and extracted with DCM (3×). The combined organic layers were passed through a phase separator and concentrated to afford the title compound (406 mg, 80%) as a dark solid. $^1$H NMR (400 MHz, DMSO-d$_6$) δ 10.32 (s, 1H), 8.74 (s, 1H), 4.01 (s, 3H), 3.90 (s, 3H), 2.32 (d, J=0.6 Hz, 3H). MS-ESI (m/z) calc'd for C$_{10}$H$_{12}$NO$_4$ [M+H]$^+$: 210.1. Found 210.1.

Step 8: Methyl 4-chloro-5-cyano-3-methylpicolinate

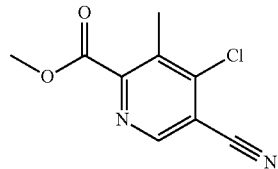

To a solution of methyl 5-formyl-4-methoxy-3-methylpicolinate (406.0 mg, 1.94 mmol) in DMSO (2.4 mL) was added hydroxylamine hydrochloride (134.86 mg, 1.94 mmol) and the mixture was stirred at 90° C. for 1 hr. The mixture was taken up in H$_2$O and extracted with EtOAc (3×). The combined organic layers were washed with H$_2$O, passed through a phase separator, and evaporated to give a black solid which was taken up in POCl$_3$ (3 mL) and heated at 100° C. for 1 hr. Excess POCl$_3$ was evaporated and the residue was taken up in H$_2$O and extracted with EtOAc (3×). The combined organic layers were passed through a phase separator and concentrated to afford the title compound (270 mg, 66%) as a dark solid. $^1$H NMR (400 MHz, DMSO-d$_6$) δ 8.99 (q, J=0.6 Hz, 1H), 3.93 (s, 3H), 2.46 (d, J=0.6 Hz, 3H). MS-ESI (m/z) calc'd for C$_9$H$_8$ClN$_2$O$_2$[M+H]$^+$: 211.0. Found 211.0.

Step 9: 5-Cyano-4-methoxy-3-methylpicolinic acid

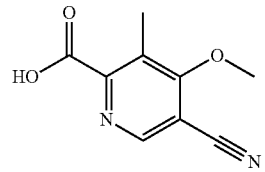

To a solution of methyl 4-chloro-5-cyano-3-methylpicolinate (170.0 mg, 0.810 mmol) in MeOH (8.071 mL) was added 30% NaOMe (0.3 mL, 1.61 mmol) and the mixture was stirred at 25° C. for 15 minutes. The solvent was evaporated and the residue was taken up in H$_2$O and extracted with EtOAc (3×). The combined organic layers were passed through a phase separator and concentrated to afford the title compound (125 mg, 81%) as a dark yellow solid. $^1$H NMR (400 MHz, DMSO-d$_6$) δ 14.74 (s, 1H), 8.74 (d, J=0.7 Hz, 1H), 4.24 (s, 3H), 2.24 (d, J=0.5 Hz, 3H).). MS-ESI (m/z) calc'd for C$_9$H$_9$N$_2$O$_3$ [M+H]$^+$: 193.1. Found 193.1.

Intermediate A-19: 5-Cyano-3-cyclopropylpicolinic acid

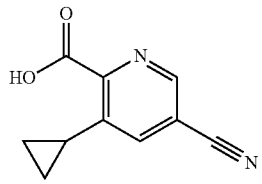 [SMILES: N#Cc1cnc(C(=O)O)c(C2CC2)c1]

Step 1: Methyl 3-chloro-5-cyanopicolinate

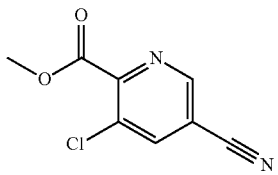

To a solution of 3-chloro-5-cyanopyridine-2-carboxylic acid (50.0 mg, 0.270 mmol) in DMF (0.456 mL) was added $K_2CO_3$ (113.56 mg, 0.820 mmol) and iodomethane (34.1 uL, 0.550 mmol) and the mixture was stirred at 80° C. for 1 hr. The mixture was then partitioned between EtOAc and $H_2O$. The organic phase was separated, dried over $Na_2SO_4$, filtered and concentrated to afford the title compound (58 mg) which was used without further purification. $^1$H NMR (400 MHz, DMSO-$d_6$) δ 9.07 (d, J=1.6 Hz, 1H), 8.82 (d, J=1.7 Hz, 1H), 3.95 (s, 3H). MS-ESI (m/z) calc'd for $CH_8ClN_2O_2$ $[M+H]^+$: 197.0. Found 197.0.

Step 2: Methyl 5-cyano-3-cyclopropylpicolinate

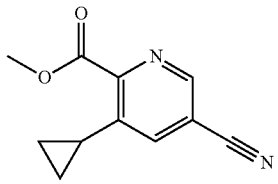

To a microwave vial was added methyl 3-chloro-5-cyanopyridine-2-carboxylate (58.0 mg, 0.280 mmol), cesium carbonate (273.96 mg, 0.840 mmol), potassium cyclopropyl trifluoroborate (62.21 mg, 0.420 mmol), toluene (1 mL) and water (0.100 mL). The vial was capped and degassed with nitrogen (15 min). [1,1'-Bis(diphenylphosphino)ferrocene]dichloropalladium(II), complex with DCM (22.95 mg, 0.030 mmol) was added and the vial was sealed and the reaction mixture was stirred and heated to 100° C. under microwave irradiation for 12 hrs. The mixture was filtered through Celite, then $H_2O$ (200 mL) and EtOAc (200 mL) were added. The organic phase was separated, dried over $Na_2SO_4$, filtered and concentrated. The residue was purified by silica gel column chromatography using a 0-50% EtOAc/cyclohexane gradient eluent to afford the title compound (35 mg, 62%) as a white solid. $^1$H NMR (400 MHz, chloroform-$d_6$) δ 8.73 (d, J=1.9 Hz, 1H), 7.62 (dd, J=1.9, 0.6 Hz, 1H), 4.05 (s, 3H), 2.57 (ddd, J=8.5, 5.3, 3.2 Hz, 1H), 1.24-1.15 (m, 2H), 0.83-0.72 (m, 2H). MS-ESI (m/z) calc'd for $C_{11}H_{11}N_2O_2[M+H]^+$: 203.1. Found 203.1.

Step 3: 5-Cyano-3-cyclopropylpicolinic acid

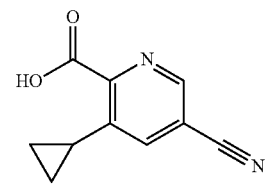 [SMILES: N#Cc1cnc(C(=O)O)c(C2CC2)c1]

A solution of 2 N NaOH (0.17 mL, 0.350 mmol) was added to a solution of methyl 5-cyano-3-cyclopropylpyridine-2-carboxylate (35.0 mg, 0.170 mmol) in EtOH (2 mL) and was stirred at r.t. for 1 hr. 5 N Hydrochloric acid was added to the reaction mixture (until pH=1) at r.t., followed by extraction with EtOAc. The extract was dried over $Na_2SO_4$, filtered and the solvent was concentrated to afford the title compound (20 mg, 61%) which was used without further purification. MS-ESI (m/z) calc'd for $C_{10}H_7N_2O_2$ $[M-H]^-$: 187.1. Found 187.0.

Intermediate A-20:
5-Cyano-3-(prop-1-en-2-yl)picolinic acid

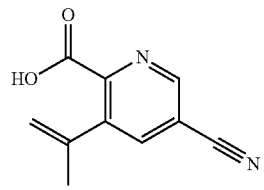

Step 1: Ethyl 5-cyano-3-(prop-1-en-2-yl)picolinate

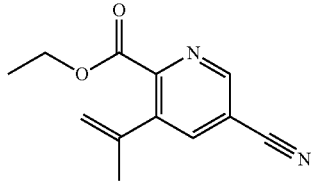 [SMILES: C=C(C)c1cc(C#N)cnc1C(=O)OCC]

To a microwave vial was added cesium carbonate (464.09 mg, 1.42 mmol), ethyl 3-chloro-5-cyanopyridine-2-carboxylate (150.0 mg, 0.710 mmol), 4,4,5,5-tetramethyl-2-(1-methylethenyl)-1,3,2-dioxaborolane (179.51 mg, 1.07 mmol), toluene (1 mL) and $H_2O$ (0.100 mL). The vial was capped and degassed with $N_2$ (15 min). [1,1'-Bis(diphenylphosphino)ferrocene]dichloropalladium(II) (78.38 mg, 0.110 mmol) was added, the vial was sealed and heated in a microwave reactor to 100° C. The reaction was left stirring for 4 hrs at 100° C. The mixture was filtered through Celite, then $H_2O$ (200 mL) and EtOAc (200 mL) were added. The organic phase was separated, dried over $Na_2SO_4$, filtered and concentrated under reduced pressure. The residue was purified by silica gel column chromatography using a 0-50% EtOAc/cyclohexane gradient eluent to afford the title compound (127 mg, 82%) as a colorless oil. $^1$H NMR (400 MHz, DMSO-$d_6$) δ 8.98 (d, J=1.9 Hz, 1H), 8.48 (d, J=1.9 Hz, 1H), 5.29 (t, J=1.5 Hz, 1H), 4.99 (t, J=1.1 Hz, 1H), 4.32 (q, J=7.1 Hz, 2H), 2.07 (dd, J=1.5, 0.9 Hz, 4H), 1.27 (t, J=7.1 Hz, 3H). MS-ESI (m/z) calc'd for $C_{12}H_{13}N_2O_2$ $[M+H]^+$: 217.1. Found 217.0.

Step 2: 5-Cyano-3-(prop-1-en-2-yl)picolinic acid

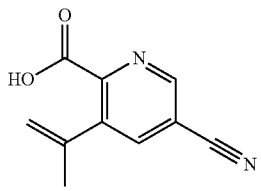

To a solution of ethyl 5-cyano-3-(prop-1-en-2-yl)picolinate (60.0 mg, 0.280 mmol) in EtOH (1 mL) was added a solution of LiOH.H$_2$O (11.64 mg, 0.280 mmol) in H$_2$O (0.600 mL) and the resulting solution was stirred for 15 min at r.t. EtOAc and water were added and the aqueous phase was separated and acidified with 1 M HCl until pH=1 and extracted with EtOAc (2×). The organic phases were combined and concentrated under reduced pressure to afford the title compound (21 mg, 40%) as a white solid which was used without further purification. $^1$H NMR (400 MHz, DMSO-d$_6$) δ 13.77 (s, 1H), 8.94 (d, J=1.9 Hz, 1H), 8.41 (d, J=1.9 Hz, 1H), 5.28 (t, J=1.5 Hz, 1H), 5.07 (d, J=1.4 Hz, 1H), 2.08 (t, J=1.3 Hz, 3H). MS-ESI (m/z) calc'd for C$_{10}$H$_9$N$_2$O$_2$ [M+H]$^+$: 189.1. Found 189.1.

Intermediate A-21:
5-Cyano-6-methoxy-3,4-dimethylpicolinic acid

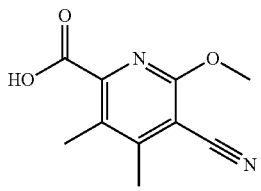

Step 1: 2-Chloro-3-cyano-4,5,6-trimethylpyridine 1-oxide

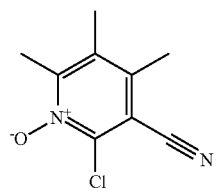

To a solution of 2-chloro-4,5,6-trimethylpyridine-3-carbonitrile (3.0 g, 16.61 mmol) in DCM (83.04 mL) was added MCPBA (8.19 g, 33.22 mmol) and the mixture was stirred at 50° C. for 24 hrs. Another portion of MCPBA (4.09 g, 16.61 mmol) was then added and the reaction was stirred for an additional 15 hrs. The solvent was evaporated and the residue was purified by silica gel column chromatography using a 0-100% EtOAc/cyclohexane gradient eluent to afford the title compound (1.95 g, 60%) as a yellow solid. $^1$H NMR (400 MHz, DMSO-d$_6$) δ 2.51 (s, 3H), 2.45 (s, 3H), 2.29 (s, 3H). MS-ESI (m/z) calc'd for C$_9$H$_{10}$ClN$_2$O [M+H]$^+$: 197.0. Found 197.0.

Step 2: 2-Chloro-6-(hydroxymethyl)-4,5-dimethyl-nicotinonitrile

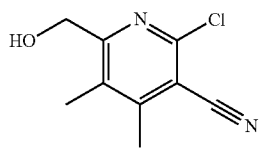

To a solution of 2-chloro-3-cyano-4,5,6-trimethylpyridine 1-oxide (1.95 g, 9.92 mmol) in DCM (49.59 mL) was added dropwise trifluoroacetic acid anhydride (4.14 mL, 29.75 mmol) and the mixture was stirred at 25° C. for 15 hrs. The solvent was evaporate and the residue was taken up in MeOH. Then K$_2$CO$_3$ (2 g) was added and the suspension was stirred at 25° C. for 1 hr. The solvent was evaporated, the residue was taken up in H$_2$O and extracted with DCM (3×). The combined organic layers were passed through a phase separator and evaporated to obtain 2-chloro-6-(hydroxymethyl)-4,5-dimethylpyridine-3-carbonitrile (1.29 g, 66%) as a yellow solid. $^1$H NMR (400 MHz, DMSO-d$_6$) δ 5.41 (t, J=5.9 Hz, 1H), 4.59 (d, J=5.8 Hz, 2H), 2.49 (s, 3H), 2.27 (s, 3H). MS-ESI (m/z) calc'd for C$_9$H$_{10}$ClN$_2$O [M+H]$^+$: 197.0. Found 197.0.

Step 3:
6-Formyl-2-methoxy-4,5-dimethylnicotinonitrile

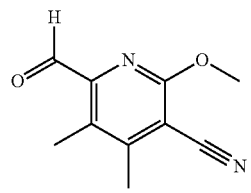

To a solution of 2-chloro-6-(hydroxymethyl)-4,5-dimethylnicotinonitrile (0.39 g, 2 mmol) in MeOH (10 mL) was added NaOMe (0.74 mL, 4 mmol) and the mixture was stirred at 25° C. for 15 hrs. The solvent was evaporated and the residue was taken up in H$_2$O and extracted with DCM (3×). The combined organic layers were passed through a phase separator and concentrated to afford the title compound (166 mg, 44%) as a dark oil. $^1$H NMR (400 MHz, DMSO-d$_6$) δ 10.04 (s, 1H), 4.04 (s, 3H), 2.51 (d, J=1.1 Hz, 3H), 2.47 (s, 3H). MS-ESI (m/z) calc'd for C$_{10}$H$_{11}$N$_2$O$_2$ [M+H]$^+$: 191.0. Found 191.0.

Step 4: 5-Cyano-6-methoxy-3,4-dimethylpicolinic acid

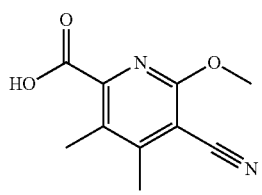

To a solution of 6-formyl-2-methoxy-4,5-dimethylnicotinonitrile (166.0 mg, 0.870 mmol) in acetone (8 mL) was added a solution of KMnO$_4$ (137.92 mg, 0.870 mmol) in H$_2$O (2 mL) and the mixture was stirred at 25° C. for 2 hrs. The organic solvent was evaporated, 1 M K$_2$CO$_3$ was added, and the mixture was filtered through Celite. The H$_2$O layer was washed with EtOAc and then acidified by addition of HCl and extracted with EtOAc (3×). The combined organic layers were passed through a phase separator and concentrated to afford the title compound (82 mg, 46%) as a yellow solid. $^1$H NMR (400 MHz, DMSO-d$_6$) δ 13.68 (s, 1H), 3.95 (s, 3H), 2.46 (s, 3H), 2.22 (s, 3H). MS-ESI (m/z) calc'd for C$_{10}$H$_{11}$N$_2$O$_3$[M+H]$^+$: 207.1. Found 207.0.

Intermediate A-22: 1-(3-(Piperidin-1-yl)propyl)-1H-indazol-5-amine

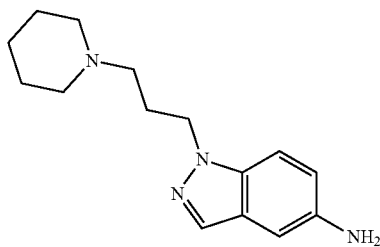 [SMILES: Nc1ccc2c(cnn2CCCN2CCCCC2)c1]

Step 1: 1-(Prop-2-yn-1-yl)piperidine

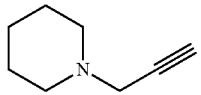

To a solution of piperidine (4.94 mL, 50 mmol) in DCM (10 mL) was added dropwise 3-bromo-1-propyne (2.38 g, 20 mmol) and the mixture was stirred at 25° C. for 15 hrs. The solvent was evaporated and the residue was taken up in Et$_2$O and washed with H$_2$O (3×). The organic layer was passed through a phase separator and evaporated to afford the title compound (2.33 g, 95%) as an orange oil. $^1$H NMR (400 MHz, DMSO-d$_6$) δ 3.20 (d, J=2.4 Hz, 2H), 3.08 (t, J=2.4 Hz, 1H), 2.41-2.33 (m, 4H), 1.61-1.28 (m, 6H).

Step 2: 3-(3-(Piperidin-1-yl)prop-1-yn-1-yl)-1H-indazol-5-amine

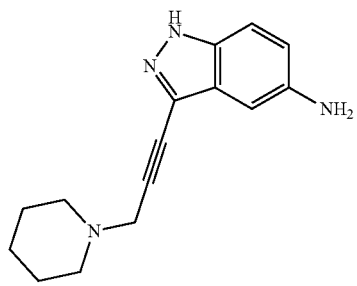 [SMILES: Nc1ccc2[nH]nc(C#CCN3CCCCC3)c2c1]

A mixture of 3-iodo-1H-indazol-5-amine (1.04 g, 4 mmol), 1-(prop-2-yn-1-yl)piperidine (0.74 g, 6 mmol), bis(triphenylphosphine)palladium(II) dichloride (281.56 mg, 0.400 mmol) and copper (I) iodide (38.09 mg, 0.200 mmol) in Et$_3$N (4 mL) was heated at 90° C. for 2 hrs. The solvent was evaporated and the residue was purified by silica gel column chromatography using a 0-50% MeOH/DCM gradient eluent to afford the title compound (160 mg, 16%) as an orange oil. $^1$H NMR (400 MHz, DMSO-d$_6$) δ 12.83 (s, 1H), 7.26 (dd, J=8.7, 0.8 Hz, 1H), 6.80 (dd, J=8.8, 2.1 Hz, 1H), 6.69 (dd, J=2.1, 0.8 Hz, 1H), 4.97 (d, J=2.7 Hz, 2H), 3.54 (s, 2H), 2.64 (t, J=5.3 Hz, 2H), 1.64-1.29 (m, 8H). MS-ESI (m/z) calc'd for C$_{15}$H$_{19}$N$_4$ [M+H]$^+$: 255.2. Found 255.4.

Step 3: 3-(3-(Piperidin-1-yl)propyl)-1H-indazol-5-amine

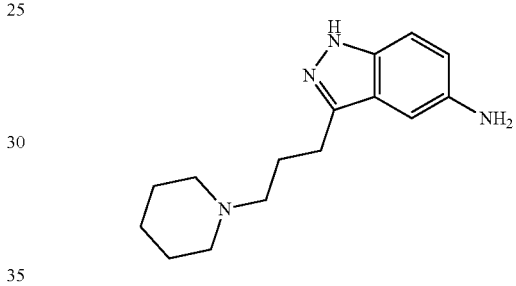

To a solution of 3-(3-(piperidin-1-yl)prop-1-yn-1-yl)-1H-indazol-5-amine (160.0 mg, 0.630 mmol) in EtOH (6.291 mL) was added 10% Pd/C (66.95 mg, 0.060 mmol) and the mixture was hydrogenated at 3 bars for 24 hrs. The catalyst was removed by filtration through Celite and the filtrate evaporated to afford the title compound (116 mg, 71%) as an orange solid. $^1$H NMR (400 MHz, DMSO-d$_6$) δ 12.15 (s, 1H), 7.27-7.13 (m, 1H), 6.79-6.75 (m, 1H), 6.75-6.68 (m, 1H), 4.73 (s, 2H), 3.13-2.97 (m, 2H), 2.78 (t, J=7.4 Hz, 2H), 2.73-2.55 (m, 2H), 1.99-1.83 (m, 2H), 1.74-1.31 (m, 8H). MS-ESI (m/z) calc'd for C$_{15}$H$_{23}$N$_4$ [M+H]$^+$: 259.2. Found 259.5.

Intermediate A-23:
3-Cyclopropyl-1H-indazol-5-amine

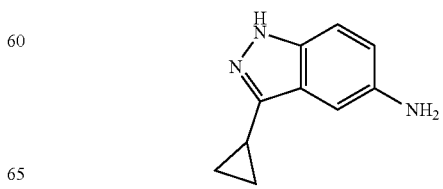

Step 1: 3-Iodo-5-nitro-1-((2-(trimethylsilyl)ethoxy)methyl)-1H-indazole and 3-Iodo-5-nitro-2-((2-(trimethylsilyl)ethoxy)methyl)-2H-indazole

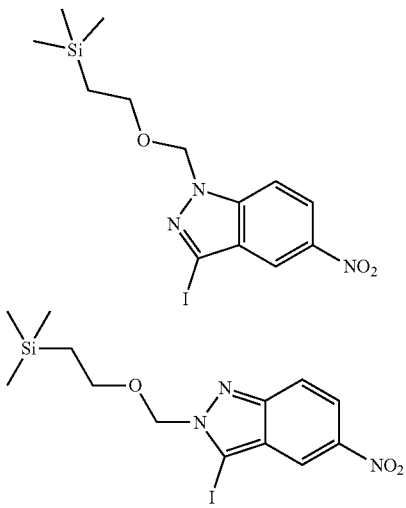

To a solution of NaH (276.79 mg, 6.92 mmol) in THF (6 mL) at 0° C. was added 3-iodo-5-nitro-1H-indazole (1.0 g, 3.46 mmol) in THF (10 mL) dropwise and the mixture was stirred for 20 minutes at r.t. 2-(Chloromethoxy)ethyl-trimethylsilane (0.8 mL, 4.5 mmol) was added slowly to the mixture and stirring was continued for 1 hr at 0° C. The mixture was diluted with H$_2$O and extracted with EtOAc (2×). The combined organic layers were washed with H$_2$O (1×), dried over Na$_2$SO$_4$, filtered and concentrated to give a residue. The residue was purified by silica gel column chromatography using a 0-20% EtOAc/cyclohexane gradient eluent to afford a 3:1 mixture (determined by NMR) respectively of the title compounds (1.23 g, 85%) as a yellow solid. 3-Iodo-5-nitro-1-((2-(trimethylsilyl)ethoxy)methyl)-1H-indazole: $^1$H NMR (400 MHz, DMSO-d$_6$) δ 8.33-8.40 (m, 2H) 8.00-8.05 (m, 1H) 5.85 (s, 2H) 3.51-3.60 (m, 2H) 0.78-0.84 (m, 2H) −0.10 (s, 9H). 3-Iodo-5-nitro-2-((2-(trimethylsilyl)ethoxy)methyl)-2H-indazole: $^1$H NMR (400 MHz, DMSO-d$_6$) δ 8.47 (dd, J=2.20, 0.66 Hz, 1H) 8.07 (d, J=2.20 Hz, 1H) 7.89 (dd, J=9.46, 0.66 Hz, 1H) 5.86 (s, 2H) 3.63-3.70 (m, 2H) 0.85-0.91 (m, 2H) −0.07 (s, 9H). MS-ESI (m/z) calc'd for C$_{13}$H$_{19}$IN$_3$O$_3$Si [M+H]$^+$: 420.1. Found 420.1.

Step 2: 3-Cyclopropyl-5-nitro-1-((2-(trimethylsilyl)ethoxy)methyl)-1H-indazole and 3-Cyclopropyl-5-nitro-2-((2-(trimethylsilyl)ethoxy)methyl)-2H-indazole

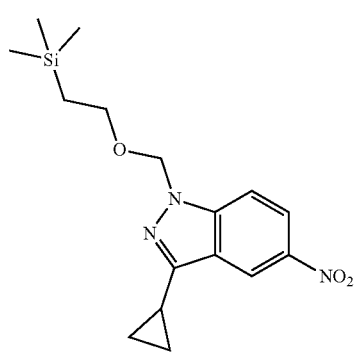

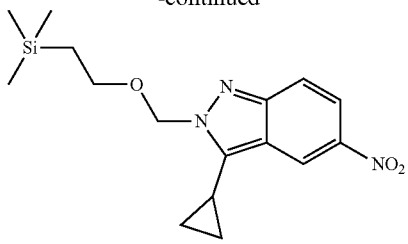

A mixture of 3-iodo-5-nitro-1-((2-(trimethylsilyl)ethoxy)methyl)-1H-indazole and 3-iodo-5-nitro-2-((2-(trimethylsilyl)ethoxy)methyl)-2H-indazole (1.0 g, 2.38 mmol), cyclopropylboronic acid (307.31 mg, 3.58 mmol) and tripotassium phosphate (988.89 mg, 7.15 mmol) were dissolved in 1,4-dioxane (15 mL) and degassed with N$_2$ for 5 minutes. [1,1'-Bis(diphenylphosphino)ferrocene]dichloropalladium(II) (174.51 mg, 0.240 mmol) was then added and the mixture was stirred at 100° C. under N$_2$ for 3 hrs. The reaction mixture was partitioned between H$_2$O and EtOAc. The phases were separated and the aqueous layer was extracted with EtOAc (2×). The combined organic phases were washed with H$_2$O (1×), dried over Na$_2$SO$_4$, and evaporated to dryness. The material was purified by silica gel column chromatography using a 0-20% EtOAc/cyclohexane gradient eluent to afford a 3:1 mixture (determined by NMR) respectively of the title compounds (785 mg, 99%). Methyl 6-chloro-5-cyano-3-methylpicolinate: $^1$H NMR (400 MHz, DMSO-d$_6$) δ 8.58 (s, 1H) 3.92 (s, 3H) 2.48 (d, J=0.66 Hz, 3H). 3-Cyclopropyl-5-nitro-1-((2-(trimethylsilyl)ethoxy)methyl)-1H-indazole: $^1$H NMR (400 MHz, DMSO-d$_6$) δ ppm 8.86-8.91 (m, 1H) 8.27 (dd, J=9.24, 2.20 Hz, 1H) 7.88 (d, J=9.24 Hz, 1H) 5.72 (s, 2H) 3.48-3.55 (m, 2H) 2.52-2.58 (m, 1H) 1.06-1.12 (m, 2H) 0.96-1.04 (m, 2H) 0.75-0.83 (m, 2H) −0.13--0.09 (m, 9H). 3-Cyclopropyl-5-nitro-2-((2-(trimethylsilyl)ethoxy)methyl)-2H-indazole: $^1$H NMR (400 MHz, DMSO-d$_6$) δ 8.66 (d, J=2.20 Hz, 1H) 7.99 (dd, J=9.46, 2.20 Hz, 1H) 7.76 (d, J=9.46 Hz, 1H) 5.87 (s, 2H) 3.64-3.71 (m, 2H) 2.30-2.38 (m, 1H) 1.22-1.30 (m, 2H) 1.13-1.17 (m, 2H) 0.85-0.91 (m, 2H) −0.07--0.03 (m, 9H). MS-ESI (m/z) calc'd for C$_{16}$H$_{24}$N$_3$O$_3$Si [M+H]$^+$: 334.2. Found 334.3.

Step 3: 3-Cyclopropyl-5-nitro-1H-indazole

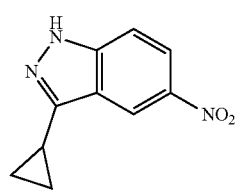

To a solution of 3-cyclopropyl-5-nitro-1-((2-(trimethylsilyl)ethoxy)methyl)-1H-indazole and 3-cyclopropyl-5-nitro-2-((2-(trimethylsilyl)ethoxy)methyl)-2H-indazole, 2-[(3-cyclopropyl-5-nitroindazol-1-yl)methoxy]ethyl-trimethylsilane and 3-cyclopropyl-5-nitro-2-{[2-(trimethylsilyl)ethoxy]methyl}-2H-indazole (785.0 mg, 2.35 mmol) in DCM (25 mL) was added trifluoroacetic acid (1.0 mL, 13.07 mmol). The mixture was stirred at r.t. for 2 hrs. The mixture was concentrated and redissolved in MeOH (20 mL). Aqueous NH$_3$ (5 mL) was added and the mixture was stirred at r.t. for 2 hrs. The reaction mixture was partitioned between H$_2$O and EtOAc and the phases were separated. The aqueous layer was extracted with EtOAc (2×) and the combined organic phases were washed with H$_2$O (1×), dried over Na$_2$SO$_4$ and evaporated to dryness. The residue was purified by reversed phase chromatography on a 12 g C18 column, using a 5-50% CH$_3$CN/H$_2$O (0.1% formic acid) gradient eluent to afford the title compound (65 mg, 14%) as a yellow solid. $^1$H NMR (400 MHz, DMSO-d$_6$) δ 13.25 (br. s., 1H) 8.84 (d, J=2.20 Hz, 1H) 8.17 (dd, J=9.13, 2.09 Hz, 1H) 7.63 (d, J=9.02 Hz, 1H) 2.44-2.49 (m, 1H) 0.93-1.10 (m, 4H). MS-ESI (m/z) calc'd for C10H$_{10}$N$_3$O$_2$ [M+H]$^+$: 204.1. Found 204.0.

Step 4: 3-Cyclopropyl-1H-indazol-5-amine

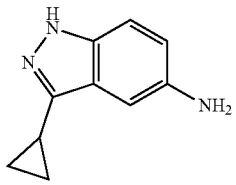 [SMILES: Nc1ccc2[nH]nc(C3CC3)c2c1]

A mixture of 3-cyclopropyl-5-nitro-1H-indazole (65.0 mg, 0.320 mmol), NH$_4$Cl (18.82 mg, 0.350 mmol) and Fe powder (71.46 mg, 1.28 mmol) in EtOH (2 mL) and H$_2$O (2 mL) was stirred at 80° C. for 1.5 hrs. The solids were removed by filtration through Celite and the solid was washed with EtOH. The filtrate was concentrated and re-dissolved in EtOAc. H$_2$O was added and the two phases were separated. The aqueous layer was extracted with EtOAc (2×) and the combined organic layers were washed with H$_2$O (1×), dried over Na$_2$SO$_4$, and the solvent was removed to afford the title compound (50 mg, 90%) as a yellow solid which was used without further purification. $^1$H NMR (400 MHz, DMSO-d$_6$) δ 12.02 (br. s., 1H) 7.05-7.23 (m, 1H) 6.65-6.79 (m, 2H) 4.70 (br. s., 2H) 2.01-2.11 (m, 1H) 0.80-0.95 (m, 4H). MS-ESI (m/z) calc'd for C10H$_{12}$N$_3$ [M+H]$^+$: 174.1. Found 174.1.

Example 1: 5-Cyano-3-fluoro-N-(3-(furan-3-yl)-1H-indazol-5-yl)picolinamide

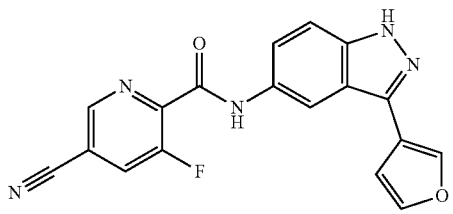 [SMILES: N#Cc1cnc(C(=O)Nc2ccc3[nH]nc(-c4ccoc4)c3c2)c(F)c1]

To a mixture of 5-cyano-3-fluoropyridine-2-carboxylic acid (33 mg, 0.200 mmol), 3-(furan-3-yl)-1H-indazol-5-amine (Intermediate A-1, 39.84 mg, 0.200 mmol) and triethylamine (27.88 µL, 0.200 mmol) was added HATU (76.05 mg, 0.200 mmol) and the mixture was stirred at 25° C. for 15 h. Water was added and the solid that formed was filtered and purified by reverse phase column chromatography on a Biotage Isolera One apparatus (NH, 11 g) using a gradient of 0-5% MeOH in DCM for 10 CV to afford the title compound (20.6 mg, 0.059 mmol, 30.0% yield) as a yellow solid. $^1$H NMR (400 MHz, DMSO-d$_6$) δ 13.12 (s, 1H), 10.82 (s, 1H), 9.06 (dd, J=1.6, 1.0 Hz, 2H), 8.68 (dd, J=10.3, 1.6 Hz, 2H), 8.42 (dd, J=2.0, 0.7 Hz, 2H), 8.25 (dd, J=1.6, 0.8 Hz, 2H), 7.84 (t, J=1.7 Hz, 3H), 7.80 (dd, J=8.9, 1.9 Hz, 1H), 7.57 (dd, J=9.0, 0.7 Hz, 2H), 7.00 (dd, J=1.9, 0.9 Hz, 2H). MS-ESI (m/z) calc'd for C$_{15}$H$_{11}$FN$_5$O$_2$[M+H]$^+$: 348.1. Found 348.0.

Example 2: 2-Bromo-4-cyano-N-(3-(furan-3-yl)-1H-indazol-5-yl)benzamide

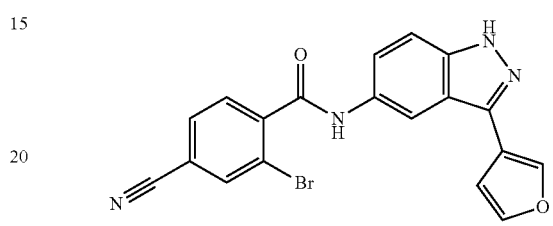

To a mixture of 2-bromo-4-cyanobenzoic acid (45.21 mg, 0.200 mmol), 3-(furan-3-yl)-1H-indazol-5-amine (Intermediate A-1, 39.84 mg, 0.200 mmol) and triethylamine (27.88 µL, 0.200 mmol) was added HATU (76.05 mg, 0.200 mmol) and the mixture was stirred at 25° C. for 15 h. Water was added and the solid that formed was filtered and purified by reverse phase column chromatography on a Biotage Isolera One apparatus (NH, 11 g) using a gradient of 0-5% MeOH in DCM for 10 CV to afford the title compound (22.3 mg, 0.055 mmol, 27.4% yield) as a beige solid. $^1$H NMR (400 MHz, DMSO-d$_6$) δ 13.11 (s, 1H), 10.66 (s, 1H), 8.38-8.33 (m, 2H), 8.18 (dd, J=1.5, 0.8 Hz, 1H), 8.02 (dd, J=7.9, 1.5 Hz, 1H), 7.85 (t, J=1.7 Hz, 1H), 7.80 (d, J=7.8 Hz, 1H), 7.61 (dd, J=8.9, 1.8 Hz, 1H), 7.57 (dd, J=8.9, 0.8 Hz, 1H), 6.98 (dd, J=1.8, 0.8 Hz, 1H). MS-ESI (m/z) calc'd for C$_{19}$H$_{12}$BrN$_4$O$_2$ [M+H]$^+$: 407.0, 409.0. Found 406.9, 408.9.

Example 3: 4-Cyano-2-fluoro-N-(3-(furan-3-yl)-1H-indazol-5-yl)benzamide

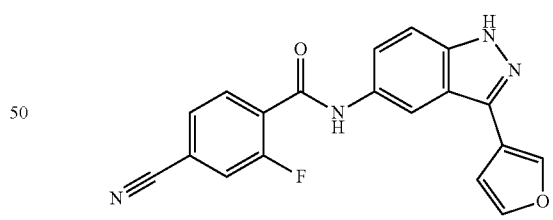

To a mixture of 4-cyano-2-fluorobenzoic acid (33.02 mg, 0.200 mmol), 3-(furan-3-yl)-1H-indazol-5-amine (Intermediate A-1, 39.84 mg, 0.200 mmol) and triethylamine (27.88 µL, 0.200 mmol) was added HATU (76.05 mg, 0.200 mmol) and the mixture was stirred at 25° C. for 15 h. Water was added and the solid that formed was filtered and purified by column chromatography on a Biotage Isolera One apparatus (SiO$_2$, 10 g) using a gradient of 0-5% MeOH in DCM for 10 CV to afford the title compound (15 mg, 0.043 mmol, 21.7% yield) as a yellow solid. $^1$H NMR (400 MHz, DMSO-d$_6$) δ 13.11 (s, 1H), 10.65 (s, 1H), 8.37 (d, J=1.8 Hz, 1H), 8.24-8.18 (m, 1H), 8.07 (dd, J=9.7, 1.4 Hz, 1H), 7.95-7.88

(m, 1H), 7.86 (dd, J=7.9, 1.4 Hz, 1H), 7.84 (t, J=1.7 Hz, 1H), 7.63 (dd, J=8.9, 1.8 Hz, 1H), 7.57 (d, J=8.9 Hz, 1H), 6.98 (dd, J=1.9, 0.8 Hz, 1H). MS-ESI (m/z) calc'd for $C_{19}H_{12}FN_4O_2[M+H]^+$: 347.1. Found 347.1.

Example 4: 4-Cyano-N-(3-(furan-3-yl)-1H-indazol-5-yl)-2-iodobenzamide

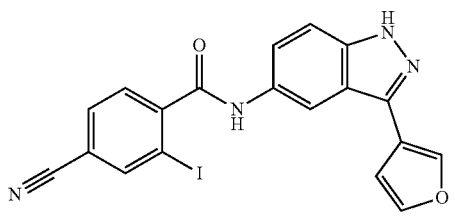 [SMILES: N#Cc1ccc(C(=O)Nc2ccc3[nH]nc(-c4ccoc4)c3c2)c(I)c1]

To a mixture of 4-cyano-2-iodobenzoic acid (54.61 mg, 0.200 mmol), 3-(furan-3-yl)-1H-indazol-5-amine (Intermediate A-1, 39.84 mg, 0.200 mmol) and triethylamine (27.88 µL, 0.200 mmol) was added HATU (76.05 mg, 0.200 mmol) and the mixture was stirred at 25° C. for 15 hrs. Water was added and the solid formed was filtered and purified by reverse phase column chromatography on a Biotage Isolera One apparatus (NH, 11 g) using a gradient of 0-5% MeOH in DCM for 10 CV to obtain the title compound (25.5 mg, 0.056 mmol, 28.1% yield) as an off-white solid. $^1$H NMR (400 MHz, DMSO-d$_6$) δ 13.12 (s, 1H), 10.59 (s, 1H), 8.48 (d, J=1.6 Hz, 1H), 8.35 (dd, J=1.8, 0.8 Hz, 1H), 8.18 (dd, J=1.5, 0.9 Hz, 1H), 8.02 (dd, J=7.9, 1.6 Hz, 1H), 7.86 (t, J=1.7 Hz, 1H), 7.71 (d, J=7.8 Hz, 1H), 7.63 (dd, J=8.9, 1.8 Hz, 1H), 7.58 (dd, J=8.9, 0.8 Hz, 1H), 6.99 (dd, J=1.9, 0.8 Hz, 1H). MS-ESI (m/z) calc'd for $C_{19}H_{12}IN_4O_2[M+H]^+$: 455.0. Found 455.0.

Example 5: 2-Chloro-4-cyano-N-(3-(furan-3-yl)-1H-indazol-5-yl)benzamide

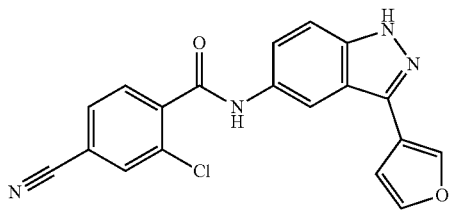 [SMILES: N#Cc1ccc(C(=O)Nc2ccc3[nH]nc(-c4ccoc4)c3c2)c(Cl)c1]

To a mixture of 2-chloro-4-cyanobenzoic acid (36.32 mg, 0.200 mmol), 3-(furan-3-yl)-1H-indazol-5-amine (Intermediate A-1, 39.84 mg, 0.200 mmol) and triethylamine (27.88 µL, 0.200 mmol) was added HATU (76.05 mg, 0.200 mmol) and the mixture was stirred at 25° C. for 15 h. Water was added and the solid that formed was filtered and purified by reverse phase column chromatography on a Biotage Isolera One apparatus (NH, 11 g) using a gradient of 0-5% MeOH in DCM for 10 CV to obtain the title compound (17.4 mg, 0.048 mmol, 24.0% yield) as a beige solid. $^1$H NMR (400 MHz, DMSO-d$_6$) δ 13.12 (s, 1H), 10.69 (s, 1H), 8.36 (dd, J=1.8, 0.8 Hz, 1H), 8.23 (d, J=1.5 Hz, 1H), 8.19 (dd, J=1.5, 0.8 Hz, 1H), 7.99 (dd, J=7.9, 1.5 Hz, 1H), 7.87-7.82 (m, 2H), 7.61 (dd, J=9.0, 1.8 Hz, 1H), 7.57 (dd, J=8.9, 0.8 Hz, 1H), 6.98 (dd, J=1.9, 0.8 Hz, 1H). MS-ESI (m/z) calc'd for $C_{19}H_{12}ClN_4O_2[M+H]^+$: 363.1, 365.1. Found 363.0, 365.0.

Example 6: 4-Cyano-N-(3-(furan-3-yl)-1H-indazol-5-yl)-2-(trifluoromethyl)benzamide

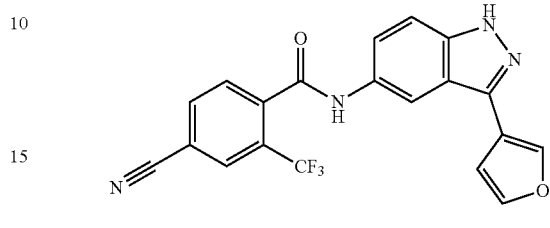

To a mixture of 4-cyano-2-(trifluoromethyl)benzoic acid (43.03 mg, 0.200 mmol), 3-(furan-3-yl)-1H-indazol-5-amine (Intermediate A-1, 39.84 mg, 0.200 mmol) and triethylamine (27.88 µL, 0.200 mmol) was added HATU (76.05 mg, 0.200 mmol) and the mixture was stirred at 25° C. for 15 h. Water was added and the solid that formed was filtered and purified by reverse phase column chromatography on a Biotage Isolera One apparatus (NH, 11 g) using a gradient of 0-5% MeOH in DCM for 10 CV to obtain the title compound (20.5 mg, 0.052 mmol, 25.9% yield) as a beige solid. $^1$H NMR (400 MHz, DMSO-d$_6$) δ 13.13 (s, 1H), 10.74 (s, 1H), 8.50-8.46 (m, 1H), 8.33 (dd, J=7.9, 1.6 Hz, 1H), 8.30 (t, J=1.3 Hz, 1H), 8.21-8.16 (m, 1H), 7.98 (d, J=7.9 Hz, 1H), 7.85 (t, J=1.7 Hz, 1H), 7.62-7.53 (m, 2H), 6.98 (dd, J=1.9, 0.8 Hz, 1H). MS-ESI (m/z) calc'd for $C_{20}H_{12}F_3N_4O_2[M+H]^+$: 397.1. Found 397.0.

Example 7: 4-Cyano-2,6-difluoro-N-(3-(furan-3-yl)-1H-indazol-5-yl)benzamide

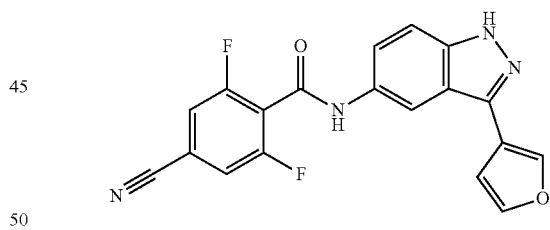

To a mixture of 4-cyano-2,6-difluorobenzoic acid (36.62 mg, 0.200 mmol), 3-(furan-3-yl)-1H-indazol-5-amine (Intermediate A-1, 39.84 mg, 0.200 mmol) and triethylamine (27.88 L, 0.200 mmol) was added HATU (76.05 mg, 0.200 mmol) and the mixture was stirred at 25° C. for 15 h. Water was added and the solid that formed was filtered to obtain the product (55 mg, 0.151 mmol, 75.5% yield) as a beige solid which was further purified by prep HPLC (Method A) to afford the title compound (26.1 mg, 0.072 mmol, 35.8% yield) as a yellow solid. $^1$H NMR (400 MHz, DMSO-d$_6$) δ 13.15 (s, 1H), 11.00 (s, 1H), 8.33 (t, J=1.3 Hz, 1H), 8.21 (dd, J=1.5, 0.8 Hz, 1H), 8.06-7.97 (m, 2H), 7.84 (t, J=1.7 Hz, 1H), 7.63-7.53 (m, 2H), 6.98 (dd, J=1.8, 0.8 Hz, 11H). MS-ESI (m/z) calc'd for $C_{19}H_{11}F_2N_4O_2[M+H]^+$: 365.1. Found 365.0.

Example 8: 6-Cyano-N-(3-(furan-3-yl)-1H-indazol-5-yl)-2-methylnicotinamide

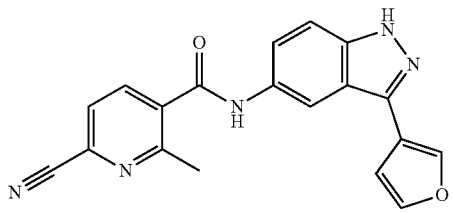 [SMILES: Cc1nc(C#N)ccc1C(=O)Nc1ccc2[nH]nc(-c3ccoc3)c2c1]

To a mixture of 6-cyano-2-methylpyridine-3-carboxylic acid (32.43 mg, 0.200 mmol), 3-(furan-3-yl)-1H-indazol-5-amine (Intermediate A-1, 39.84 mg, 0.200 mmol) and triethylamine (27.88 μL, 0.200 mmol) was added HATU (76.05 mg, 0.200 mmol) and the mixture was stirred at 25° C. for 15 h. Water was added and the solid that formed was filtered to obtain the product (60 mg, 0.175 mmol, 87.4% yield) as a beige solid which was further purified by prep HPLC (Method A) to afford the title compound (26.22 mg, 0.076 mmol, 38.2% yield) as a yellow solid. $^1$H NMR (400 MHz, DMSO-d$_6$) δ 13.12 (s, 1H), 10.65 (s, 1H), 8.37 (dd, J=1.8, 0.7 Hz, 1H), 8.21 (dd, J=1.5, 0.9 Hz, 1H), 8.18 (d, J=7.8 Hz, 1H), 8.06 (dd, J=7.8, 0.6 Hz, 1H), 7.85 (t, J=1.7 Hz, 1H), 7.62 (dd, J=8.9, 1.8 Hz, 1H), 7.57 (dd, J=8.9, 0.8 Hz, 1H), 6.99 (dd, J=1.9, 0.8 Hz, 1H), 2.65 (s, 3H). MS-ESI (m/z) calc'd for C$_{19}$H$_{14}$N$_5$O$_2$ [M+H]$^+$: 344.1. Found 344.0.

Example 9: 6-Cyano-N-(3-(furan-3-yl)-1H-indazol-5-yl)nicotinamide

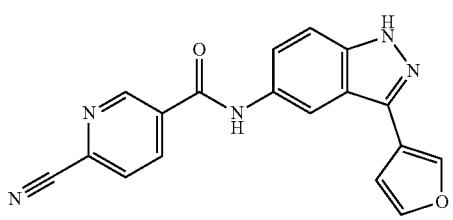 [SMILES: N#Cc1ccc(C(=O)Nc2ccc3[nH]nc(-c4ccoc4)c3c2)cn1]

To a mixture of 6-cyano-3-pyridinecarboxylic acid (29.62 mg, 0.200 mmol), 3-(furan-3-yl)-1H-indazol-5-amine (Intermediate A-1, 39.84 mg, 0.200 mmol) and triethylamine (27.88 μL, 0.200 mmol) was added HATU (76.05 mg, 0.200 mmol) and the mixture was stirred at 25° C. for 15 h. Water was added and the solid formed was filtered and purified by reverse phase column chromatography on a Biotage Isolera One apparatus (SiO$_2$, 10 g) using a gradient of 0-5% MeOH in DCM for 10 CV to obtain the product (24 mg, 0.073 mmol, 36.44% yield) as a yellow solid which was further purified by prep HPLC (Method A) to obtain the title compound (12 mg, 0.036 mmol, 18.2% yield) as a yellow solid. $^1$H NMR (400 MHz, DMSO-d$_6$) δ 13.14 (s, 1H), 10.73 (s, 1H), 9.28 (dd, J=2.2, 0.9 Hz, 1H), 8.57 (dd, J=8.1, 2.2 Hz, 1H), 8.43-8.36 (m, 1H), 8.26 (dd, J=8.1, 0.9 Hz, 1H), 8.24 (dd, J=1.5, 0.9 Hz, 1H), 7.85 (t, J=1.7 Hz, 1H), 7.71 (dd, J=8.9, 1.9 Hz, 1H), 7.59 (d, J=8.9 Hz, 1H), 7.00 (dd, J=1.9, 0.8 Hz, 1H). MS-ESI (m/z) calc'd for C$_{15}$H$_{12}$N$_5$O$_2$ [M+H]$^+$: 330.1. Found 330.3.

Example 10: 4-Cyano-N-(3-(furan-3-yl)-1H-indazol-5-yl)-2,6-dimethylbenzamide

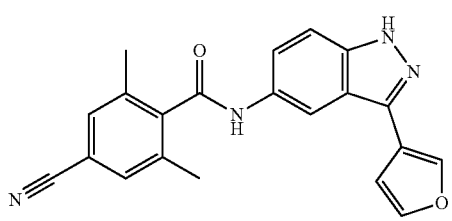 [SMILES: Cc1cc(C#N)cc(C)c1C(=O)Nc1ccc2[nH]nc(-c3ccoc3)c2c1]

To a mixture of 4-cyano-2,6-dimethylbenzoic acid (35.09 mg, 0.200 mmol), 3-(furan-3-yl)-1H-indazol-5-amine (Intermediate A-1, 39.84 mg, 0.200 mmol) and triethylamine (27.88 μL, 0.200 mmol) was added HATU (76.05 mg, 0.200 mmol) and the mixture was stirred at 25° C. for 15 h. Water was added and the solid formed was filtered to obtain the product (66 mg, 0.185 mmol, 92.5% yield) which was further purified by prep HPLC (Method B) to obtain the title compound (2.3 mg, 0.006 mmol, 3.22% yield) as a white solid. $^1$H NMR (400 MHz, DMSO-d$_4$) δ 13.11 (br. s, 1H), 10.55 (s, 1H), 8.37 (s, 1H), 8.21 (s, 1H), 7.86 (t, J=1.65 Hz, 1H), 7.52-7.70 (m, 4H), 6.99 (d, J=1.10 Hz, 1H), 2.37 (s, 6H). MS-ESI (m/z) calc'd for C$_{21}$H$_{17}$N$_4$O$_2$ [M+H]$^+$: 357.1. Found 357.1.

Example 11: 4-Cyano-N-(3-(furan-3-yl)-1H-indazol-5-yl)benzamide

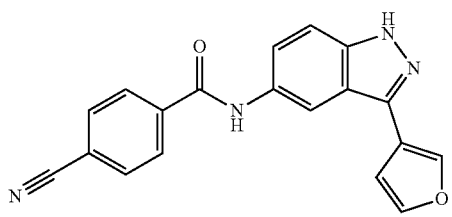 [SMILES: N#Cc1ccc(C(=O)Nc2ccc3[nH]nc(-c4ccoc4)c3c2)cc1]

To a mixture of 4-cyanobenzoic acid (29.54 mg, 0.200 mmol), 3-(furan-3-yl)-1H-indazol-5-amine (Intermediate A-1, 39.84 mg, 0.200 mmol) and triethylamine (27.88 μL, 0.200 mmol) was added HATU (76.05 mg, 0.200 mmol) and the mixture was stirred at 25° C. for 15 hrs. Water was added and the solid that formed was filtered to obtain the product (55 mg, 0.168 mmol, 83.4% yield) which was further purified by prep HPLC (Method C) to obtain the title compound (5.5 mg, 0.017 mmol, 8.34% yield) as a white solid. $^1$H NMR (400 MHz, DMSO-d$_6$) δ 13.12 (br. s., 1H), 10.54 (br. s., 1H), 8.39 (s, 1H), 8.25 (s, 1H), 8.02-8.19 (m, 4H), 7.86 (t, J=1.65 Hz, 1H), 7.73 (dd, J=8.91, 1.43 Hz, 1H), 7.58 (d, J=9.02 Hz, 1H), 7.01 (d, J=1.54 Hz, 1H). MS-ESI (m/z) calc'd for C$_{19}$H$_3$N$_4$O$_2$ [M+H]$^+$: 329.1. Found 329.1.

Example 12: 4-Cyano-2-methyl-N-(3-methyl-1H-indazol-5-yl)benzamide

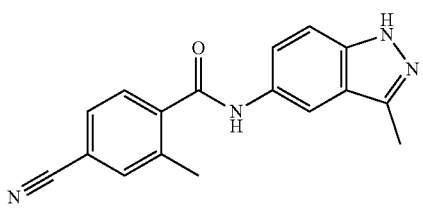 [SMILES: Cc1cc(C#N)ccc1C(=O)Nc1ccc2[nH]nc(C)c2c1]

To a mixture of 4-cyano-2-methylbenzoic acid (32.23 mg, 0.200 mmol), 3-methyl-1H-indazole (29.44 mg, 0.200 mmol) and triethylamine (27.88 uL, 0.200 mmol) was added HATU (76.05 mg, 0.200 mmol) and the mixture was stirred at 25° C. for 4 hrs. Water was added and the solid that formed was filtered and washed with Et$_2$O to obtain the title compound (20 mg, 0.069 mmol, 34.4% yield) as a white solid. $^1$H NMR (400 MHz, DMSO-d$_6$) δ 12.59 (s, 1H), 10.44 (s, 1H), 8.20 (d, J=1.8 Hz, 1H), 7.86-7.82 (m, 1H), 7.80 (dd, J=8.1, 1.4 Hz, 1H), 7.66 (d, J=7.9 Hz, 1H), 7.49 (dd, J=8.9, 1.9 Hz, 1H), 7.43 (d, J=8.8 Hz, 1H), 2.47 (s, 3H), 2.43 (s, 3H). MS-ESI (m/z) calc'd for C$_{17}$H$_{15}$N$_4$O [M+H]$^+$: 291.1. Found 291.1.

Example 13: 5-Cyano-N-(3-(furan-3-yl)-1H-indazol-5-yl)-6-methylpicolinamide

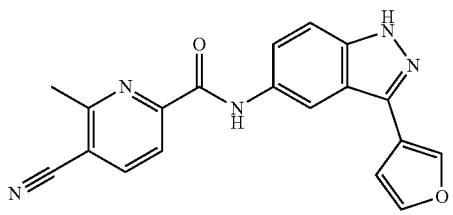 [SMILES: Cc1nc(C(=O)Nc2ccc3[nH]nc(-c4ccoc4)c3c2)ccc1C#N]

To a mixture of (32.43 mg, 0.200 mmol), 3-(furan-3-yl)-1H-indazol-5-amine (Intermediate A-1, 39.84 mg, 0.200 mmol) and triethylamine (27.88 μL, 0.200 mmol) was added HATU (76.05 mg, 0.200 mmol) and the mixture was stirred at 25° C. for 15 hrs. Water was added and the solid that formed was filtered and purified by column chromatography on a Biotage Isolera One apparatus (SiO$_2$, 10 g) using a gradient of 0-5% MeOH in DCM for 10 CV to obtain the title compound (60 mg, 0.175 mmol, 87.4% yield) as a yellow solid. $^1$H NMR (400 MHz, DMSO-d$_6$) δ 13.11 (s, 1H), 10.65 (s, 1H), 8.51 (d, J=8.1 Hz, 1H), 8.47-8.44 (m, 1H), 8.31 (dd, J=1.4, 0.8 Hz, 1H), 8.13 (d, J=8.0 Hz, 1H), 7.94 (dd, J=8.9, 1.9 Hz, 1H), 7.85 (t, J=1.7 Hz, 1H), 7.58 (d, J=8.9 Hz, 1H), 7.02 (dd, J=1.9, 0.8 Hz, 1H), 2.86 (s, 3H). MS-ESI (m/z) calc'd for C$_{19}$H$_{14}$N$_5$O$_2$ [M+H]$^+$: 344.1. Found 344.4.

Example 14: 5-Cyano-N-(3-(furan-3-yl)-1H-indazol-5-yl)-3-methylpicolinamide

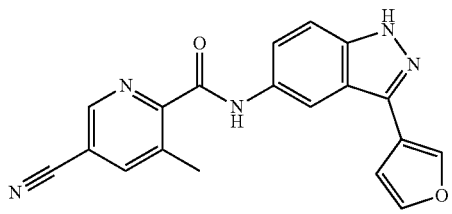 [SMILES: Cc1cc(C#N)cnc1C(=O)Nc1ccc2[nH]nc(-c3ccoc3)c2c1]

To a mixture of 5-cyano-3-methylpyridine-2-carboxylic acid (32.43 mg, 0.200 mmol), 3-(furan-3-yl)-1H-indazol-5-amine (Intermediate A-1, 39.84 mg, 0.200 mmol) and triethylamine (27.88 μL, 0.200 mmol) was added HATU (76.05 mg, 0.200 mmol) and the mixture was stirred at 25° C. for 4 h. Water was added and the solid that formed was filtered and purified by reverse phase column chromatography on a Biotage Isolera One apparatus (NH, 11 g) using a gradient of 0-5% MeOH in DCM for 15 CV to obtain the title compound (37 mg, 0.108 mmol, 53.9% yield) as a yellow solid. $^1$H NMR (400 MHz, DMSO-d$_6$) δ 13.09 (s, 1H), 10.70 (s, 1H), 9.00 (dd, J=2.0, 0.7 Hz, 1H), 8.45-8.39 (m, 2H), 8.26 (dd, J=1.5, 0.9 Hz, 1H), 7.84 (t, J=1.7 Hz, 1H), 7.82 (dd, J=9.0, 1.9 Hz, 1H), 7.61-7.53 (m, 1H), 7.00 (dd, J=1.8, 0.8 Hz, 1H), 2.61 (t, J=0.7 Hz, 3H). MS-ESI (m/z) calc'd for C$_{19}$H$_{14}$N$_5$O$_2$ [M+H]$^+$: 344.1. Found 344.1.

Example 15: 4-Cyano-N-(3-(furan-3-yl)-1H-indazol-5-yl)-2-methoxybenzamide

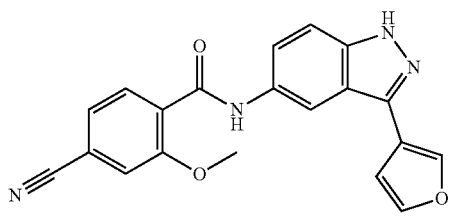 [SMILES: COc1cc(C#N)ccc1C(=O)Nc1ccc2[nH]nc(-c3ccoc3)c2c1]

To a mixture of 4-cyano-2-methoxybenzoic acid (35.43 mg, 0.200 mmol), 3-(furan-3-yl)-1H-indazol-5-amine (Intermediate A-1, 39.84 mg, 0.200 mmol) and triethylamine (27.88 μL, 0.200 mmol) was added HATU (76.05 mg, 0.200 mmol) and the mixture was stirred at 25° C. for 3 hrs. Water was added and the resulting solid was filtered and dried under vacuum to obtain the title compound (67 mg, 0.187 mmol, 93.5% yield) as a yellow solid. $^1$H NMR (400 MHz, DMSO-d$_6$) δ 12.27 (s, 1H), 9.51 (s, 1H), 7.60-7.53 (m, 1H), 7.40 (dd, J=1.5, 0.8 Hz, 1H), 7.03 (t, J=1.7 Hz, 1H), 6.95 (d, J=7.8 Hz, 1H), 6.89 (d, J=1.4 Hz, 1H), 6.83 (dd, J=9.0, 1.9 Hz, 1H), 6.77-6.71 (m, 2H), 6.17 (dd, J=1.9, 0.8 Hz, 11H), 3.14 (s, 3H). MS-ESI (m/z) calc'd for C$_{20}$H$_{15}$N$_4$O$_3$ [M+H]$^+$: 359.1. Found 359.1.

Example 16: 5-Cyano-N-(3-(furan-3-yl)-1H-indazol-5-yl)picolinamide

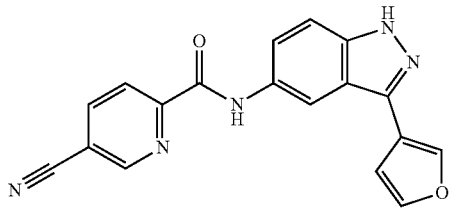 [SMILES: N#Cc1ccc(C(=O)Nc2ccc3[nH]nc(-c4ccoc4)c3c2)nc1]

To a mixture of 5-cyanopyridine-2-carboxylic acid (29.62 mg, 0.200 mmol), 3-(furan-3-yl)-1H-indazol-5-amine (Intermediate A-1, 39.84 mg, 0.200 mmol) and triethylamine (20.24 mg, 0.200 mmol) was added HATU (76.05 mg, 0.200 mmol) and the mixture was stirred at 25° C. for 3 hrs. Water was added and the resulting solid was filtered and dried under vacuum to obtain the title compound (58 mg, 0.176 mmol, 88.1% yield) as a yellow solid. $^1$H NMR (400 MHz, DMSO-$d_6$) δ 13.10 (s, 1H), 10.84 (s, 1H), 9.22 (dd, J=2.0, 0.9 Hz, 1H), 8.60 (dd, J=8.2, 2.1 Hz, 1H), 8.52 (d, J=1.9 Hz, 1H), 8.33 (dd, J=8.2, 0.9 Hz, 1H), 8.30 (t, J=1.1 Hz, 1H), 8.00 (dd, J=9.0, 1.9 Hz, 1H), 7.85 (t, J=1.7 Hz, 1H), 7.57 (d, J=8.9 Hz, 1H), 7.02 (dd, J=1.9, 0.8 Hz, 1H). MS-ESI (m/z) calc'd for $C_{15}H_{12}N_5O_2$ [M+H]$^+$: 330.1. Found 330.1.

Example 17: 5-Cyano-N-(3-(furan-3-yl)-1H-indazol-5-yl)-2-methylbenzamide

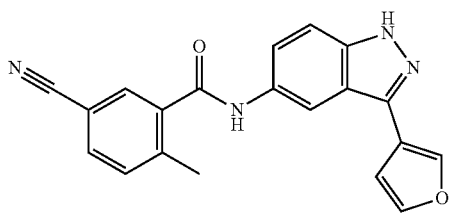 [SMILES: Cc1ccc(C#N)cc1C(=O)Nc1ccc2[nH]nc(-c3ccoc3)c2c1]

To a mixture of 5-cyano-2-methylbenzoic acid (40.29 mg, 0.250 mmol), 3-(furan-3-yl)-1H-indazol-5-amine (Intermediate A-1, 49.8 mg, 0.250 mmol) and triethylamine (34.85 μL, 0.250 mmol) was added HATU (95.06 mg, 0.250 mmol) and the mixture was stirred at 25° C. for 15 hrs. The solvent was evaporated, the residue was taken up in water and extracted with EtOAc (3×), the combined organic layers were passed through a phase separator and evaporated to obtain a residue which was taken up in DCM and stirred for 15 min. The solid that formed was filtered and purified by column chromatography on a Biotage Isolera One apparatus using a gradient of 0-100% EtOAc in cyclohexane for 10 CV to obtain the title compound (42 mg, 0.123 mmol, 49.1% yield) as a white solid. $^1$H NMR (400 MHz, DMSO-$d_6$) δ 13.05 (bs, 1H), 10.45 (s, 1H), 8.37 (d, J=1.9 Hz, 1H), 8.20 (q, J=1.0 Hz, 1H), 8.01 (d, J=1.8 Hz, 1H), 7.87 (dd, J=8.0, 1.9 Hz, 1H), 7.85 (t, J=1.7 Hz, 1H), 7.66 (dd, J=8.9, 1.9 Hz, 1H), 7.58-7.53 (m, 2H), 7.01-6.96 (m, 1H), 2.50 (s, 3H). MS-ESI (m/z) calc'd for $C_{20}H_{15}N_4O_2$ [M+H]$^+$: 343.1. Found 343.1.

Example 18: 4-Cyano-N-(3-(furan-3-yl)-1H-indazol-5-yl)-2-methylbenzamide

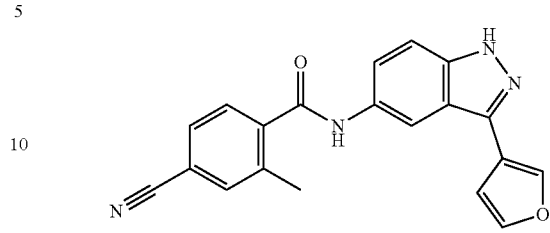

To a mixture of 4-cyano-2-methylbenzoic acid (40.29 mg, 0.250 mmol), 3-(furan-3-yl)-1H-indazol-5-amine (Intermediate A-1, 49.8 mg, 0.250 mmol), and triethylamine (0.03 mL, 0.250 mmol) was added HATU (95.06 mg, 0.250 mmol) and the mixture was stirred at 25° C. for 15 hrs. The solvent was evaporated, the residue was taken up in water and extracted with EtOAc (3×), the combined organic layers were passed through a phase separator and evaporated to obtain a residue which was taken up in DCM and stirred for 15 min. The solid that formed was filtered and purified by column chromatography on a Biotage Isolera One apparatus using a gradient of 0-100% EtOAc in cyclohexane for 10 CV to obtain the title compound (42 mg, 0.123 mmol, 49.1% yield) as a light pink solid. $^1$H NMR (400 MHz, DMSO-$d_6$) δ 13.09 (s, 1H), 10.49 (s, 1H), 8.38 (d, J=1.9 Hz, 1H), 8.20 (t, J=1.2 Hz, 1H), 7.85 (q, J=1.6 Hz, 2H), 7.81 (dd, J=7.9, 1.6 Hz, 1H), 7.69 (d, J=7.9 Hz, 1H), 7.64 (dd, J=9.0, 1.8 Hz, 1H), 7.55 (d, J=8.9 Hz, 1H), 6.98 (dd, J=1.8, 0.8 Hz, 1H), 2.45 (s, 3H). MS-ESI (m/z) calc'd for $C_{20}H_{15}N_4O_2$[M+H]$^+$: 343.1. Found 343.1.

Example 19: 3-Cyano-N-(3-(furan-3-yl)-1H-indazol-5-yl)-2-methylbenzamide

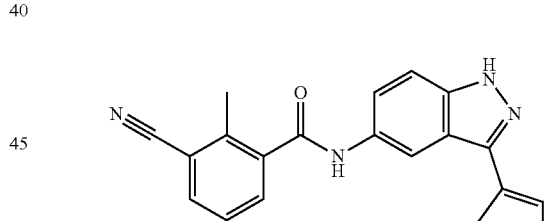

To a mixture of 3-cyano-2-methylbenzoic acid (32.23 mg, 0.200 mmol), 3-(furan-3-yl)-1H-indazol-5-amine (Intermediate A-1, 39.84 mg, 0.200 mmol) and triethylamine (27.88 μL, 0.200 mmol) was added HATU (76.05 mg, 0.200 mmol) and the mixture was stirred at 25° C. for 15 hrs. Water was added and the solid that formed was filtered and purified by reverse phase column chromatography on Biotage Isolera One apparatus (NH, 11 g) using a gradient of 0-5% MeOH in DCM for 10 CV to obtain the title compound (19.1 mg, 0.056 mmol, 27.9% yield) as a grey solid. $^1$H NMR (400 MHz, DMSO-$d_6$) δ 13.10 (s, 1H), 10.51 (s, 1H), 8.39 (d, J=1.5 Hz, 2H), 8.21 (dd, J=1.6, 0.8 Hz, 1H), 7.94 (dd, J=7.7, 1.3 Hz, 1H), 7.87-7.82 (m, 2H), 7.65 (dd, J=9.0, 1.9 Hz, 1H), 7.61-7.50 (m, 2H), 6.99 (dd, J=1.9, 0.8 Hz, 1H), 2.60 (s, 3H). MS-ESI (m/z) calc'd for $C_{20}H_{15}N_4O_2$ [M+H]$^+$: 343.1. Found 343.1.

Example 20: 2-Cyano-N-(3-(furan-3-yl)-1H-indazol-5-yl)thiazole-5-carboxamide

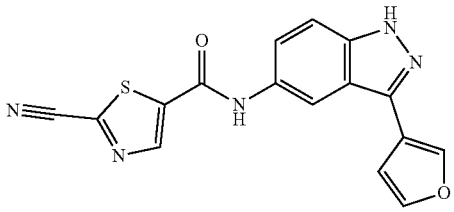 [SMILES: N#Cc1ncc(C(=O)Nc2ccc3[nH]nc(-c4ccoc4)c3c2)s1]

To a mixture of 2-cyano-1,3-thiazole-5-carboxylic acid (30.83 mg, 0.200 mmol), 3-(furan-3-yl)-1H-indazol-5-amine (Intermediate A-1, 39.84 mg, 0.200 mmol) and triethylamine (27.88 µL, 0.200 mmol) was added HATU (76.05 mg, 0.200 mmol) and the mixture was stirred at 25° C. for 15 hrs. Water was added and the solid that formed was filtered to obtain the product (55 mg, 0.164 mmol, 82.01% yield) which was further purified by prep HPLC (Method A) to afford the title compound (28.3 mg, 0.084 mmol, 42.2% yield) as a yellow solid. $^1$H NMR (400 MHz, DMSO-$d_6$) δ 13.16 (s, 1H), 10.85 (s, 1H), 8.90 (s, 1H), 8.31 (dd, J=1.8, 0.8 Hz, 1H), 8.26 (dd, J=1.5, 0.9 Hz, 1H), 7.84 (t, J=1.7 Hz, 1H), 7.65 (dd, J=9.0, 1.8 Hz, 1H), 7.60 (dd, J=8.9, 0.8 Hz, 1H), 7.00 (dd, J=1.8, 0.8 Hz, 1H). MS-ESI (m/z) calc'd for $C_{16}H_{10}N_5O_2S$ [M+H]$^+$: 336.1. Found 336.0.

Example 21: 3-Cyano-N-(3-(pyridin-4-yl)-1H-indazol-5-yl)benzamide

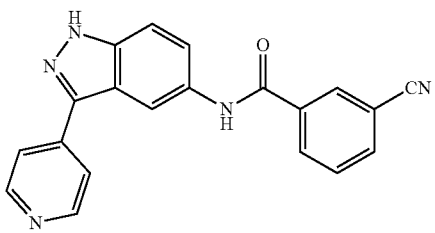 [SMILES: N#Cc1cccc(C(=O)Nc2ccc3[nH]nc(-c4ccncc4)c3c2)c1]

To a solution of 3-cyanobenzoic acid (50 mg, 339.83 µmol) in DCM (4 mL) was added T3P/EtOAc (324.39 mg, 509.75 µmol, 50% purity) and TEA (103.16 mg, 1.02 mmol) followed by 3-(pyridin-4-yl)-1H-indazol-5-amine (Intermediate A-2, 107.17 mg, 509.75 µmol). The mixture was stirred at 15° C. for 12 hrs. The reaction mixture was concentrated and purified by prep-HPLC (Method E) to afford the title compound (18.76 mg, 40.36 umol, 12% yield, 97% purity, TFA salt) as a pale yellow solid. $^1$H NMR (400 MHz, DMSO-$d_6$) δ 13.96 (br s, 1H) 10.63 (s, 1H) 8.86 (br d, J=5 Hz, 2H) 8.75 (s, 1H) 8.48 (s, 1H) 8.32 (d, J=8 Hz, 1H) 8.24 (br s, 2H) 8.11 (d, J=8 Hz, 1H) 7.72-7.85 (m, 3H). MS-ESI (m/z) calc'd for $C_{20}H_{14}N_5O$ [M+H]$^+$: 340.1. Found 340.1.

Example 22: 2-Cyano-N-(3-(pyridin-4-yl)-1H-indazol-5-yl)isonicotinamide

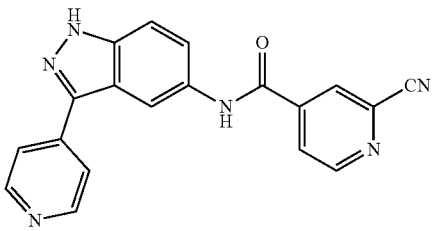 [SMILES: N#Cc1cc(C(=O)Nc2ccc3[nH]nc(-c4ccncc4)c3c2)ccn1]

This compound was prepared as described for 3-cyano-N-(3-(pyridin-4-yl)-1H-indazol-5-yl)benzamide (Example 20) using 2-cyanoisonicotinic acid in place of 3-cyanobenzoic acid. $^1$H NMR (400 MHz, DMSO-$d_6$) δ 13.67 (br s, 1H), 10.80 (s, 1H), 9.00 (d, J=5.0 Hz, 1H), 8.75-8.71 (m, 2H), 8.67 (s, 1H), 8.57 (s, 1H), 8.24 (dd, J=1.7, 5.1 Hz, 1H), 7.96-7.92 (m, 2H), 7.83-7.78 (m, 1H), 7.73-7.68 (m, 1H). MS-ESI (m/z) calc'd for $C_{19}H_{13}N_6O$ [M+H]$^+$: 341.1. Found 341.1.

Example 23: 4-Cyano-N-(3-(pyridin-4-yl)-1H-indazol-5-yl)picolinamide

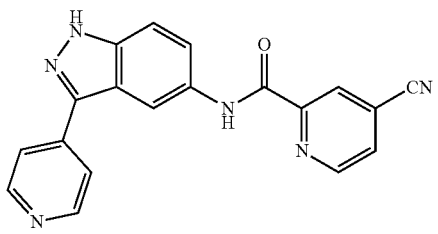

This compound was prepared as described for 3-cyano-N-(3-(pyridin-4-yl)-1H-indazol-5-yl)benzamide (Example 20) using 4-cyanopicolinic acid in place of 3-cyanobenzoic acid. $^1$H NMR (400 MHz, DMSO-$d_6$) δ 13.93 (br s, 1H), 10.96 (s, 1H), 9.00 (d, J=5.07 Hz, 1H), 8.75-8.89 (m, 3H), 8.50 (s, 1H), 8.25 (br s, 2H), 8.17 (dd, J=4.85, 1.54 Hz, 1H), 8.04 (dd, J=9.04, 1.76 Hz, 1H), 7.71 (d, J=9.04 Hz, 1H). MS-ESI (m/z) calc'd for $C_{19}H_{13}N_6O$ [M+H]$^+$: 341.1. Found 341.1.

Example 24: 5-Cyano-N-(3-(pyridin-4-yl)-1H-indazol-5-yl)nicotinamide


This compound was prepared as described for 3-cyano-N-(3-(pyridin-4-yl)-1H-indazol-5-yl)benzamide (Example 20) using 5-cyanonicotinic acid in place of 3-cyanobenzoic acid. $^1$H NMR (400 MHz, DMSO-$d_6$) δ 13.99 (br s, 1H), 10.79 (s, 1H), 9.38 (d, J=1.8 Hz, 1H), 9.24 (d, J=1.5 Hz, 1H), 8.86 (br s, 3H), 8.75 (s, 1H), 8.23 (br d, J=4.2 Hz, 2H), 7.83-7.72 (m, 2H). MS-ESI (m/z) calc'd for $C_{19}H_{13}N_6O$ [M+H]$^+$: 341.1. Found 341.1.

Example 25: 2-Cyano-N-(3-(pyridin-4-yl)-1H-indazol-5-yl)pyrimidine-5-carboxamide

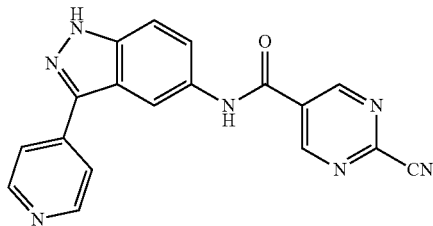 [SMILES: N#Cc1ncc(C(=O)Nc2ccc3[nH]nc(-c4ccncc4)c3c2)cn1]

This compound was prepared as described for 3-cyano-N-(3-(pyridin-4-yl)-1H-indazol-5-yl)benzamide (Example 20) using 2-cyanopyrimidine-5-carboxylic acid in place of 3-cyanobenzoic acid. $^1$H NMR (400 MHz, DMSO-$d_6$) δ 13.66 (br s, 1H), 10.91 (br s, 1H), 9.49 (s, 2H), 8.74-8.66 (m, 3H), 7.92 (d, J=4.9 Hz, 2H), 7.79-7.68 (m, 2H). MS-ESI (m/z) calc'd for $C_{19}H_{12}N_7O$ [M+H]$^+$: 342.1. Found 342.0.

Example 26: 5-Cyano-1,2-dimethyl-N-(3-phenyl-1H-indazol-5-yl)-1H-pyrrole-3-carboxamide

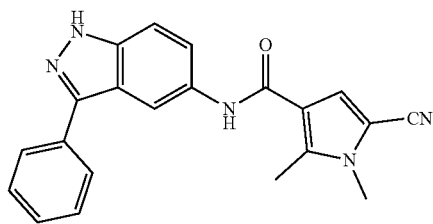 [SMILES: Cc1c(C(=O)Nc2ccc3[nH]nc(-c4ccccc4)c3c2)cc(C#N)n1C]

To a solution of 5-cyano-1,2-dimethyl-1H-pyrrole-3-carboxylic acid (Intermediate A-4, 85 mg, 517.78 μmol) and 3-phenyl-1H-indazol-5-amine (Intermediate A-3, 108.34 mg, 517 μmol) in DCM (4 mL) was added T$_3$P/EtOAc (428.35 mg, 673 umol, 400 μL, 50% purity) and TEA (209.58 mg, 2.07 mmol). The mixture was stirred at 15° C. for 3 hrs. The reaction mixture was concentrated under reduced pressure to remove solvent. The residue was purified by Prep-HPLC (column: Waters XBridge 150*25 mm, 5 μm; mobile phase: [water (10 mM NH$_4$HCO$_3$)-MeCN]; B %: 30%-50%, 10 min) to afford the title compound (24.73 mg, 69 μmol, 13% yield, 99% purity) as a pale purple solid. $^1$H NMR (400 MHz, DMSO-$d_6$) δ 13.19 (br s, 1H), 9.76 (s, 1H), 8.47 (s, 1H), 7.94 (br d, J=7.1 Hz, 2H), 7.72 (br dd, J=1.3, 8.8 Hz, 1H), 7.61 (s, 1H), 7.59-7.51 (m, 3H), 7.44-7.37 (m, 1H), 3.67 (s, 3H), 2.56 (s, 3H). MS-ESI (m/z) calc'd for $C_{21}H_{18}N_5O$ [M+H]$^+$: 356.1. Found 356.1.

Example 27: 5-Cyano-2-methyl-N-(3-phenyl-1H-indazol-5-yl)furan-3-carboxamide

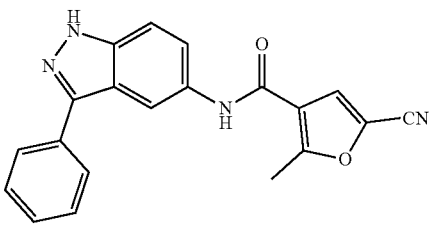 [SMILES: Cc1oc(C#N)cc1C(=O)Nc1ccc2[nH]nc(-c3ccccc3)c2c1]

To a stirred solution of methyl 5-cyano-2-methylfuran-3-carboxylate (Intermediate A-5, 200 mg, 1.21 mmol) in toluene (2 mL) was added 3-phenyl-1H-indazol-5-amine (Intermediate A-3, 253.41 mg, 1.21 mmol), followed by AlMe$_3$ (2 M, 1.21 mL) dropwise at 15° C. The mixture was then stirred at 15° C. for 12 hrs under N$_2$ and the reaction was monitored by TLC (petroleum ether:EtOAc=1/1, Rr (product)=0.06). The mixture was quenched by slow addition of sat. aq. NH$_4$Cl (5.0 mL) at 0° C. The mixture was filtered and the solid was washed with EtOAc (5.0 mL×3). The combined filtrates were separated and the aqueous layer was extracted with EtOAc (2.0 mL×2). The combined organic layers were dried over Na$_2$SO$_4$ and concentrated under vacuum. The residue was purified by Prep-HPLC (Method E) to afford the title compound (29.12 mg, 63 umol, 5% yield, 99% purity, TFA salt) as a pale yellow solid. $^1$H NMR (400 MHz, DMSO-$d_6$) δ 13.24 (br s, 1H) 10.09 (s, 1H) 8.45 (s, 1H) 8.11 (s, 1H) 7.94 (d, J=7.70 Hz, 2H) 7.67 (s, 1H) 7.50-7.63 (m, 3H) 7.42 (s, 1H) 2.66 (s, 3H). MS-ESI (m/z) calc'd for $C_{20}H_{15}N_4O_2$[M+H]$^+$: 343.1. Found 343.1.

Further compounds of the invention, which were prepared according to the methods described above, are provided in Table 1 below.

TABLE 1

| Ex. No. | Structure/Name | Data |
|---|---|---|
| 28 | ![structure] 5-cyano-N-(3-(3,4-dimethylphenyl)-1H-indazol-5-yl)-3-methylpicolinamide | $^1$H NMR (400 MHz, DMSO-$d_6$) δ 3.15 (s, 1H), 10.75 (s, 1H), 9.01 (dd, J = 2.0, 0.8 Hz, 1H), 8.62-8.51 (m, 1H), 8.41 (dd, J = 2.0, 0.9 Hz, 1H), 7.82 (dd, J = 8.9, 1.9 Hz, 1H), 7.74 (d, J = 1.5 Hz, 1H), 7.67 (dd, J = 7.7, 1.9 Hz, 1H), 7.58 (d, J = 9.2 Hz, 1H), 7.30 (d, J = 7.8 Hz, 1H), 2.59 (s, 3H), 2.34 (s, 3H), 2.30 (s, 3H). MS-ESI (m/z calc'd for $C_{23}H_{20}N_5O$ [M + H]$^+$: 382.2. Found 382.2. |

TABLE 1-continued

| Ex. No. | Structure/Name | Data |
|---|---|---|
| 29 | 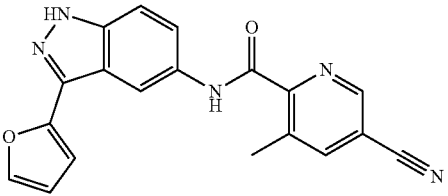 [SMILES: Cc1cc(C#N)cnc1C(=O)Nc1ccc2[nH]nc(-c3ccco3)c2c1]<br>5-cyano-N-(3-(furan-2-yl)-1H-indazol-5-yl-3-methylpicolinamide | $^1$H NMR (400 MHz, DMSO-d$_6$) δ 13.26 (s, 1H), 10.76 (s, 1H), 9.00 (d, J = 1.9 Hz, 1H), 8.69-8.57 (m, 1H), 8.41 (dd, J = 2.0, 0.9 Hz, 1H), 7.87 (dd, J = 1.8, 0.8 Hz, 1H), 7.76 (dd, J = 9.0, 1.9 Hz, 1H), 7.61-7.52 (m, 1H), 6.90 (dd, J = 3.4, 0.8 Hz, 1H), 6.69 (dd, J = 3.4, 1.8 Hz, 1H), 2.60 (s, 3H). MS-ESI (m/z) calc'd for C$_{19}$H$_{13}$N$_5$O$_2$ [M + H]$^+$: 344.1. Found 344.1. |
| 30 | 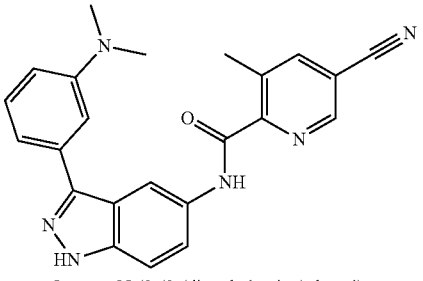<br>5-cyano-N-(3-(3-(dimethylamino)phenyl)-1H-indazol-5-yl)-3-methylpicolinamide | $^1$H NMR (400 MHz, DMSO-d$_6$) δ 13.14 (s, 1H), 10.76 (s, 1H), 9.00 (d, J = 1.9 Hz, 1H), 8.69 (d, J = 1.8 Hz, 1H), 8.41 (dd, J = 2.0, 0.9 Hz, 1H), 7.75 (dd, J = 9.0, 1.9 Hz, 1H), 7.58 (d, J = 8.9 Hz, 1H), 7.35 (t, J = 7.9 Hz, 1H), 7.29 (dd, J = 2.6, 1.4 Hz, 1H), 7.24 (dt, J = 7.6, 1.2 Hz, 1H), 6.80 (ddd, J = 8.4, 2.8, 1.0 Hz, 1H), 3.00 (s, 6H), 2.58 (s, 3H). MS-ESI (m/z) calc'd for C$_{23}$H$_{21}$N$_6$O [M + H]$^+$: 397.2. Found 397.2. |
| 31 | 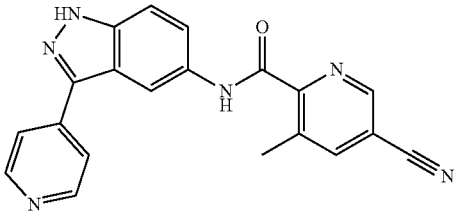 [SMILES: Cc1cc(C#N)cnc1C(=O)Nc1ccc2[nH]nc(-c3ccncc3)c2c1]<br>5-cyano-3-methyl-N-(3-(pyridin-4-yl)-1H-indazol-5-yl)picolinamide | $^1$H NMR (400 MHz, DMSO-d$_6$) δ 13.62 (s, 1H), 10.82 (s, 1H), 9.02 (d, J = 1.9 Hz, 1H), 8.76-8.69 (m, 3H), 8.43 (dd, J = 2.0, 0.9 Hz, 1H), 8.20 (s, 1H), 7.98-7.93 (m, 2H), 7.88 (dd, J = 9.0, 1.9 Hz, 1H), 7.67 (d, J = 9.0 Hz, 1H), 2.62 (s, 3H). MS-ESI (m/z) calc'd for C$_{20}$H$_{14}$N$_6$O [M + H]$^+$: 355.1. Found 355.2. |
| 32 | 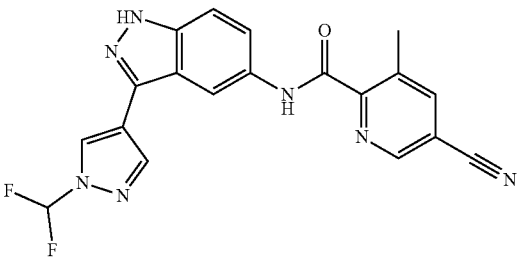 [SMILES: Cc1cc(C#N)cnc1C(=O)Nc1ccc2[nH]nc(-c3cnn(C(F)F)c3)c2c1]<br>5-Cyano-N-(3-(1-(difluoromethyl)-1H-pyrazol-4-yl)-1H-indazol-5-yl)-3-methylpicolinamide | $^1$H NMR (400 MHz, DMSO-d$_6$) δ 13.20 (s, 1H) 10.73 (s, 1H) 9.01 (d, J = 1.35 Hz, 1H) 8.74 (s, 1H) 8.43 (dd, J = 9.48, 1.28 Hz, 2H) 8.30 (s, 1H) 7.78-8.09 (m, 2H) 7.58 (d, J = 8.93 Hz, 1 H) 2.61 (s, 3H). MS-ESI (m/z) calc'd for C$_{19}$H$_{14}$F$_2$N$_7$O [M + H]$^+$: 394.1. Found 394.2. |
| 33 | 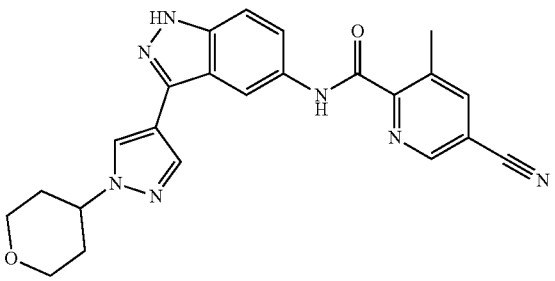 [SMILES: Cc1cc(C#N)cnc1C(=O)Nc1ccc2[nH]nc(-c3cnn(C4CCOCC4)c3)c2c1]<br>5-cyano-3-methyl-N-(3-(1-(tetrahydro-2H-pyran-4-yl)-1H-pyrazol-4-yl)-1H-indazol-5-yl)picolinamide | $^1$H NMR (400 MHz, DMSO-d$_6$) δ 12.97 (s, 1H) 10.69 (s, 1H) 9.01 (d, J = 1.47 Hz, 1H) 8.40-8.46 (m, 2H) 8.31 (s, 1H) 7.97 (s, 1H) 7.80-7.84 (m, 1H) 7.54 (d, J = 8.93 Hz, 1H) 4.49-4.58 (m, 1H) 3.98-4.03 (m, 2H) 3.47-3.54 (m, 2H) 2.61 (s, 3H) 2.02-2.08 (m, 4H). MS-ESI (m/z) calc'd for C$_{23}$H$_{22}$N$_7$O$_2$ [M + H]$^+$: 428.2. Found 428.1. |

TABLE 1-continued

| Ex. No. | Structure/Name | Data |
|---|---|---|
| 34 | 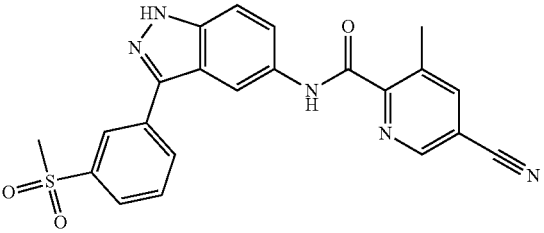 [SMILES: Cc1cc(C#N)cnc1C(=O)Nc1ccc2[nH]nc(-c3cccc(S(C)(=O)=O)c3)c2c1]<br>5-Cyano-3-methyl-N-(3-(3-(methylsulfonyl)phenyl)-1H-indazol-5-yl)picolinamide | $^1$H NMR (400 MHz, DMSO-$d_6$) δ 13.50 (s, 1H), 10.83 (s, 1H), 9.01 (d, J = 1.5 Hz, 1H), 8.60 (s, 1H), 8.46 (s, 1H), 8.41 (d, J = 1.2 Hz, 1H), 8.29 (d, J = 7.8 Hz, 1H), 7.97 (d, J = 8.1 Hz, 1H), 7.89-7.83 (m, 2H), 7.65 (d, J = 9.0 Hz, 1H), 3.31 (s, 3H), 2.59 (s, 3H). MS-ESI (m/z) calc'd for $C_{22}H_{18}N_5O_2S$ [M + H]$^+$: 432.1. Found 432.0. |
| 35 | 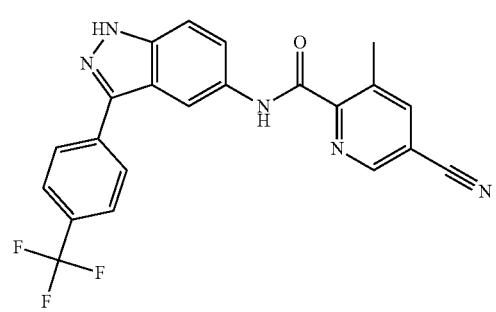 [SMILES: Cc1cc(C#N)cnc1C(=O)Nc1ccc2[nH]nc(-c3ccc(C(F)(F)F)cc3)c2c1]<br>5-Cyano-3-methyl-N-(3-(4-(trifluoromethyl)phenyl)-1H-indazol-5-yl)picolinamide | $^1$H NMR (400 MHz, DMSO-$d_6$) δ 13.50 (s, 1H), 10.81 (s, 1H), 9.01 (d, J = 1.6 Hz, 1H), 8.66 (s, 1H), 8.41 (d, J = 1.2 Hz, 1H), 8.18 (d, J = 8.1 Hz, 2H), 7.91 (d, J = 8.4 Hz, 2H), 7.84 (dd, J = 1.7, 9.0 Hz, 1H), 7.64 (d, J = 8.9 Hz, 1H), 2.60 (s, 3H). MS-ESI (m/z) calc'd for $C_{22}H_{15}F_3N_5O$ [M + H]$^+$: 422.1. Found 422.0. |
| 36 | 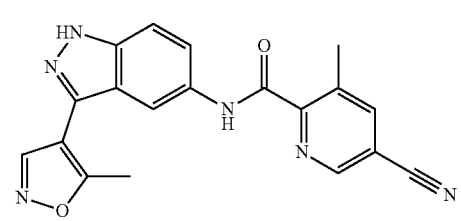 [SMILES: Cc1cc(C#N)cnc1C(=O)Nc1ccc2[nH]nc(-c3cnoc3C)c2c1]<br>5-Cyano-3-methyl-N-(3-(5-methylisoxazol-4-yl)-1H-indazol-5-yl)picolinamide | $^1$H NMR (400 MHz, DMSO-$d_6$) δ 13.32 (s, 1H) 10.75 (s, 1H) 9.00 (s, 2 H) 8.40 (dd, J = 11, 1 Hz, 2H) 7.85 (dd, J = 9, 2 Hz, 1H) 7.61 (d, J = 9 Hz, 1H) 2.71 (s, 3H) 2.60 (s, 3H). MS-ESI (m/z) calc'd for $C_{19}H_{15}N_6O_2$ [M + H]$^+$: 359.1. Found 359.0. |
| 37 | 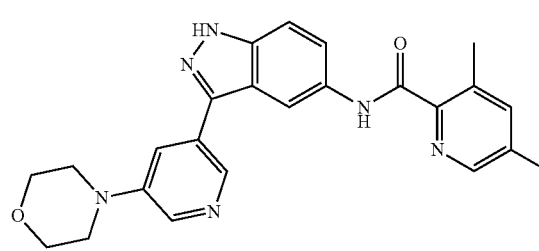<br>5-Cyano-3-methyl-N-(3-(5-morpholinopyridin-3-yl)-1H-indazol-5-yl)picolinamide | $^1$H NMR (400 MHz, DMSO-$d_6$) δ 13.39 (br s, 1H), 10.79 (s, 1H), 9.00 (d, J = 1.1 Hz, 1H), 8.66 (s, 1H), 8.61 (d, J = 1.1 Hz, 1H), 8.44-8.35 (m, 2H), 7.84 (dd, J = 1.2, 8.9 Hz, 1H), 7.75 (br s, 1H), 7.62 (d, J = 9.0 Hz, 1H), 3.83-3.76 (m, 4H), 3.31-3.23 (m, 4H), 2.59 (s, 3H). MS-ESI (m/z) calc'd for $C_{24}H_{22}N_7O_2$ [M + H]$^+$: 440.2. Found 440.1. |
| 38 | 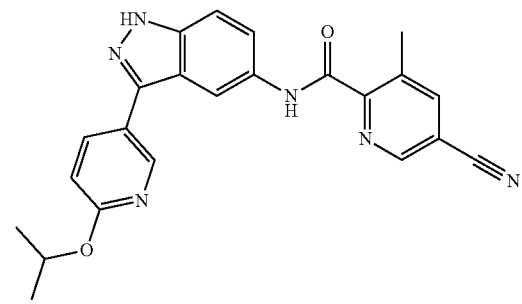 [SMILES: Cc1cc(C#N)cnc1C(=O)Nc1ccc2[nH]nc(-c3ccc(OC(C)C)nc3)c2c1]<br>5-Cyano-N-(3-(6-isopropoxypyridin-3-yl)-1H-indazol-5-yl)-3-methylpicolinamide | $^1$H NMR (400 MHz, DMSO-$d_6$) δ 13.26 (br s, 1H), 10.77 (s, 1H), 9.00 (d, J = 1.3 Hz, 1H), 8.72 (d, J = 2.4 Hz, 1H), 8.62 (s, 1H), 8.41 (d, J = 1.1 Hz, 1H), 8.20 (dd, J = 2.4, 8.6 Hz, 1H), 7.82 (dd, J = 1.87 9.0 Hz, 1H), 7.59 (d, J = 8.8 Hz, 1H), 6.93 (d, J = 8.6 Hz, 1H), 5.34 (quin, J = 6.2 Hz, 1H), 2.60 (s, 3H), 1.34 (d, J = 6.2 Hz, 6H). MS-ESI (m/z) calc'd for $C_{23}H_{21}N_6O_2$ [M + H]$^+$: 413.2. Found 413.0. |

TABLE 1-continued

| Ex. No. | Structure/Name | Data |
| --- | --- | --- |
| 39 | 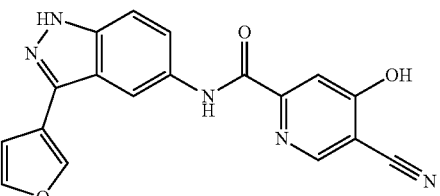<br>5-Cyano-N-(3-(furan-3-yl)-1H-indazol-5-yl)-4-hydroxypicolinamide | $^1$H NMR (400 MHz, DMSO-d$_6$) δ 13.09 (s, 1H), 10.61 (s, 1H), 8.48 (s, 1H) 8.43 (s, 1H) 8.30 (s, 1H) 7.90 (br d, J = 8.9 Hz, 1H), 7.84 (t, J = 1.7 Hz, 1H), 7.55 (d, J = 8.9 Hz, 1H), 7.26 (s, 1H), 7.01 (d, J = 1.1 Hz, 1H). MS-ESI (m/z) calc'd for C$_{11}$H$_{19}$N$_5$O$_3$ [M + H]$^+$: 345.1. Found 345.5. |
| 40 | 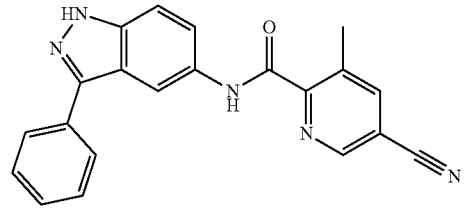 [SMILES: Cc1cc(C#N)cnc1C(=O)Nc1ccc2[nH]nc(-c3ccccc3)c2c1]<br>5-Cyano-3-methyl-N-(3-phenyl-1H-indazol-5-yl)picolinamide | $^1$H NMR (400 MHz, DMSO-d$_6$) δ 10.76 (br s, 1H), 8.99 (d, J = 1.4 Hz, 1H), 8.62 (d, J = 1.3 Hz, 1H), 8.41-8.38 (m, 1H), 7.99-7.93 (m, 2H), 7.80 (dd, J = 1.8, 8.9 Hz, 1H), 7.63-7.51 (m, 3H), 7.45-7.38 (m, 1H), 2.59 (s, 3H). MS-ESI (m/z) calc'd for C$_{21}$H$_{16}$N$_5$O [M + H]$^+$: 354.1. Found 354.1. |
| 41 | 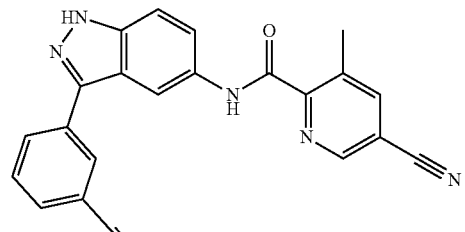<br>5-Cyano-N-(3-(3-cyanophenyl)-1H-indazol-5-yl)-3-methylpicolinamide | $^1$H NMR (400 MHz, DMSO-d$_6$) δ 13.49 (br s, 1H), 10.81 (s, 1H), 9.01 (s, 1H), 8.58 (s, 1H), 8.42 (s, 1H), 8.35-8.26 (m, 2H), 7.91 (br dd, J = 8.4, 17.3 Hz, 2H), 7.82-7.72 (m, 1H), 7.64 (br d, J = 8.9 Hz, 1H), 2.60 (s, 3H). MS-ESI (m/z) calc'd for C$_{22}$H$_{15}$N$_6$O [M + H]$^+$: 379.1. Found 379.1. |
| 42 | 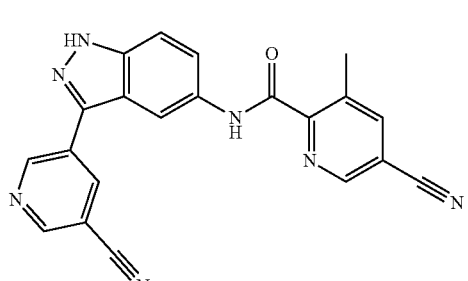<br>5-Cyano-N-(3-(5-cyanopyridin-3-yl)-1H-indazol-5-yl)-3-methylpicolinamide | $^1$H NMR (400 MHz, DMSO-d$_6$) δ 13.68 (s, 1H), 10.82 (s, 1H), 9.43 (d, J = 2.0 Hz, 1H), 9.06 (d, J = 1.8 Hz, 1H), 9.01 (d, J = 1.3 Hz, 1H), 8.75 (t, J = 2.0 Hz, 1H), 8.61 (s, 1H), 8.42 (s, 1H), 7.96 (dd, J = 1.5, 9.0 Hz, 1H), 7.67 (d, J = 9.0 Hz, 1H), 2.61 (s, 3H), MS-ESI (m/z) calc'd for C$_{21}$H$_{14}$N$_7$O [M + H]$^+$: 380.1. Found 380.1. |
| 43 | 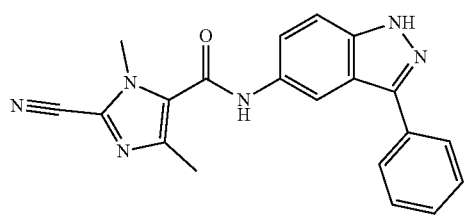 [SMILES: Cc1nc(C#N)n(C)c1C(=O)Nc1ccc2[nH]nc(-c3ccccc3)c2c1]<br>2-Cyano-1,4-dimethyl-N-(3-phenyl-1H-indazol-5-yl)-1H-imidazole-5-carboxamide | $^1$H NMR (400 MHz, DMSO-d$_6$) δ 13.28 (br s, 1H), 10.48 (s, 1H), 8.52 (s, 1H), 7.95-7.92 (m, 2H), 7.66-7.60 (m, 2H), 7.55 (t, J = 7.6 Hz, 2H), 7.44-7.40 (m, 1H), 3.91 (s, 3H), 2.38 (s, 3H). MS-ESI (m/z) calc'd for C$_{20}$H$_{17}$N$_6$O [M + H]$^+$: 357.1. Found 357.1. |

TABLE 1-continued

| Ex. No. | Structure/Name | Data |
|---|---|---|
| 44 | 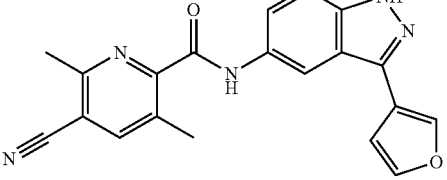<br>5-cyano-N-(3-(furan-3-yl)-1H-indazol-5-yl)-3,6-dimethylpicolinamide | $^1$H NMR (400 MHz, DMSO-d$_6$) δ 13.10 (s, 1H), 10.63 (s, 1H), 8.41-8.37 (m, 1H), 8.31 (s, 1H), 8.26 (dd, J = 1.6, 0.8 Hz, 1H), 7.85 (t, J = 1.7 Hz, 1H), 7.78 (dd, J = 9.0, 1.9 Hz, 1H), 7.56 (d, J = 9.1 Hz, 1H), 7.00 (dd, J = 1.9, 0.8 Hz, 1H), 2.76 (s, 3H), 2.54 (s, 3H), MS-ESI (m/z) calc'd for C$_{20}$H$_{16}$N$_5$O$_2$ [M + H]$^+$: 358.1. Found 358.1 |
| 45 | 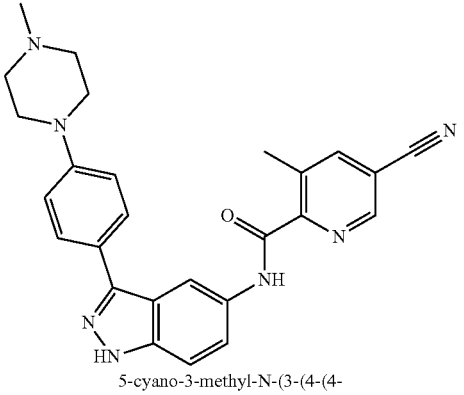<br>5-cyano-3-methyl-N-(3-(4-(4-methylpiperazin-1-yl)phenyl)-1H-indazol-5-yl)picolinamide | $^1$H NMR (400 MHz, DMSO-d$_6$) δ 13.02 (s, 1H), 10.73 (s, 1H), 9.00 (d, J = 2.0 Hz, 1H), 8.59 (d, J = 1.9 Hz, 1H), 8.40 (dd, J = 2.0, 0.9 Hz, 1H), 7.80 (d, J = 8.7 Hz, 2H), 7.75 (dd, J = 9.0, 1.9 Hz, 1H), 7.54 (d, J = 8.9 Hz, 1H), 7.10 (d, J = 8.9 Hz, 2H), 3.26-3.19 (m, 4H), 2.59 (s, 3H), 2.49-2.45 (m, 4H), 2.24 (s, 3H). MS-ESI: (m/z) calc'd for C$_{26}$H$_{26}$N$_7$O [M + H]$^+$: 452.2. Found 452.2. |
| 46 | 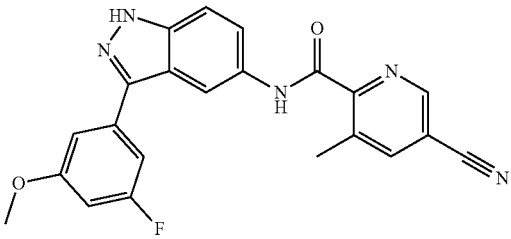 [SMILES: COc1cc(F)cc(-c2n[nH]c3ccc(NC(=O)c4ncc(C#N)cc4C)cc23)c1]<br>5-cyano-N-(3-(3-fluoro-5-methoxyphenyl)-1H-indazol-5-yl)-3-methylpicolinamide | $^1$H NMR (400 MHz, DMSO-d$_6$) δ 13.39 (br. s., 1H), 10.81 (s, 1H), 9.01 (d, J = 1.54 Hz, 1H), 8.62 (d, J = 1.32 Hz, 1H), 8.38-8.44 (m, 1H), 7.89 (dd, J = 9.02, 1.76 Hz, 1H), 7.63 (d, J = 9.02 Hz, 1H), 7.27-7.39 (m, 2H), 6.90 (dt, J = 11.11, 2.26 Hz, 1H), 3.89 (s, 3H), 2.60 (s, 3H). MS-ESI (m/z) calc'd for C$_{22}$H$_{17}$FN$_5$O$_2$ [M + H]$^+$: 402.1. Found 402.2. |
| 47 | 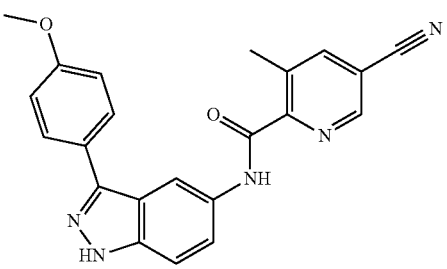 [SMILES: COc1ccc(-c2n[nH]c3ccc(NC(=O)c4ncc(C#N)cc4C)cc23)cc1]<br>5-cyano-N-(3-(4-methoxyphenyl)-1H-indazol-5-yl)-3-methylpicolinamide | $^1$H NMR (400 MHz, DMSO-d$_6$) δ 13.10 (s, 1H), 10.74 (s, 1H), 9.00 (dd, J = 2.0, 0.6 Hz, 1H), 8.59 (dd, J = 1.9, 0.7 Hz, 1H), 8.40 (dd, J = 2.0, 0.8 Hz, 1H), 7.88 (d, J = 8.8 Hz, 2H), 7.77 (dd, J = 8.9, 1.9 Hz, 1H), 7.56 (d, J = 9.0 Hz, 1H), 7.12 (d, J = 8.8 Hz, 2H), 3.83 (s, 3H), 2.59 (d, J = 0.7 Hz, 3H). MS-ESI (m/z) calc'd for C$_{22}$H$_{18}$N$_5$O$_2$ [M + H]$^+$: 384.1. Found 384.2. |
| 48 | 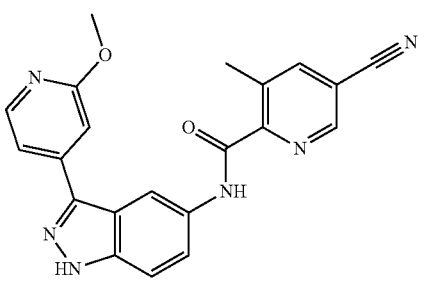<br>5-cyano-N-(3-(2-methoxypyridin-4-yl)-1H-indazol-5-yl)-3-methylpicolinamide | $^1$H NMR (400 MHz, DMSO-d$_6$) δ 13.58 (br. s., 1H) 10.83 (s, 1H) 9.02 (d, J = 1.54 Hz, 1H) 8.69 (d, J = 1.32 Hz, 1H) 8.42 (d, J = 1.10 Hz, 1H) 8.31 (d, J = 5.28 Hz, 1H) 7.91 (dd, J = 9.13, 1.87 Hz, 1H) 7.66 (d, J = 9.02 Hz, 1H) 7.59 (dd, J = 5.39, 1.43 Hz, 1H) 7.33 (s, 1H) 3.94 (s, 3H) 2.62 (s, 3H). MS-ESI (m/z) calc'd for C$_{21}$H$_{17}$N$_6$O$_2$ [M + H]$^+$: 485.1. Found 485.2. |

TABLE 1-continued

| Ex. No. | Structure/Name | Data |
| --- | --- | --- |
| 49 | 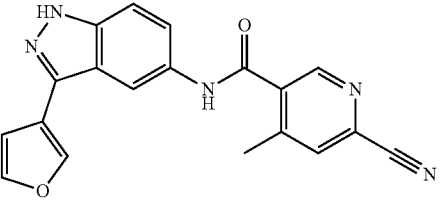 [SMILES: Cc1cc(C#N)ncc1C(=O)Nc1ccc2[nH]nc(-c3ccoc3)c2c1]<br>6-cyano-N-(3-(furan-3-yl)-1H-indazol-5-yl)-4-methylnicotinamide | $^1$H NMR (400 MHz, DMSO-d$_6$) δ 13.12 (s, 1H), 10.69 (s, 1H), 8.86 (s, 1H), 8.38 (dd, J = 1.7, 0.8 Hz, 1H), 8.21 (t, J = 1.2 Hz, 1H), 8.11 (d, J = 0.9 Hz, 1H), 7.85 (t, J = 1.7 Hz, 1H), 7.63 (dd, J = 8.9, 1.8 Hz, 1H), 7.57 (d, J = 8.9 Hz, 1H), 6.99 (dd, J = 1.8, 0.8 Hz, 1H), 2.51 (s, 3H). MS-ESI (m/z) calc'd for C$_{19}$H$_{14}$N$_5$O$_2$ [M + H]$^+$: 344.1. Found 344.1 |
| 50 | 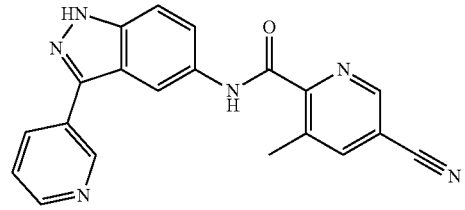 [SMILES: Cc1cc(C#N)cnc1C(=O)Nc1ccc2[nH]nc(-c3cccnc3)c2c1]<br>5-cyano-3-methyl-N-(3-(pyridin-3-yl)-1H-indazol-5-yl)picolinamide | $^1$H NMR (400 MHz, DMSO-d$_6$) δ 13.46 (s, 1H), 10.80 (s, 1H), 9.18 (d, J = 2.3, 0.9 Hz, 1H), 9.01 (d, J = 2.0 Hz, 1H), 8.67 (d, J = 1.8 Hz, 1H), 8.63 (dd, J = 4.8, 1.6 Hz, 1H), 8.42 (dd, J = 1.9, 0.9 Hz, 1H), 8.32 (dt, J = 8.0, 1.9 Hz, 1H), 7.86 (dd, J = 9.0, 1.9 Hz, 1H), 7.64 (d, J = 8.9 Hz, 1H), 7.59 (ddd, J = 7.9, 4.7, 0.9 Hz, 1H), 2.61 (s, 3H). MS-ESI (m/z) calc'd for C$_{20}$H$_{15}$N$_6$O [M + H]$^+$: 355.1. Found 355.1. |
| 51 | 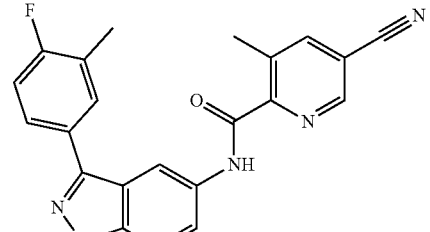<br>5-cyano-N-(3-(4-fluoro-3-methylphenyl)-1H-indazol-5-yl)-3-methylpicolinamide | $^1$H NMR (400 MHz, DMSO-d$_6$) δ 13.23 (s, 1H), 10.75 (s, 1H), 9.02-8.97 (m, 1H), 8.53 (d, J = 1.8 Hz, 1H), 8.41 (dd, J = 2.0, 0.9 Hz, 1H), 7.84 (td, J = 8.8, 2.1 Hz, 2H), 7.78 (ddd, J = 8.0, 5.1, 2.3 Hz, 1H), 7.59 (d, J = 9.0 Hz, 1H), 7.35-7.28 (m, 1H), 2.59 (s, 3H), 2.35 (d, J = 1.9 Hz, 3H). MS-ESI (m/z) calc'd for C$_{22}$H$_{17}$FN$_5$O [M + H]$^+$: 386.1. Found 386.2. |
| 52 | 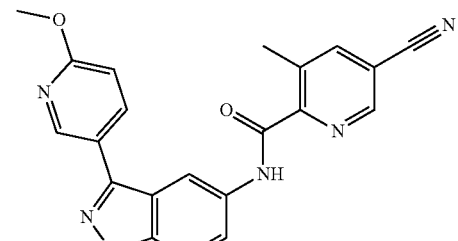<br>5-cyano-N-(3-(6-methoxypyridin-3-yl)-1H-indazol-5-yl)-3-methylpicolinamide | $^1$H NMR (400 MHz, DMSO-d$_6$) δ 13.28 (s, 1H), 10.77 (s, 1H), 9.01 (dd, J = 2.0, 0.8 Hz, 1H), 8.75 (dd, J = 2.4, 0.8 Hz, 1H), 8.64 (dd, J = 2.0, 0.7 Hz, 1H), 8.42 (dd, J = 2.0, 0.8 Hz, 1H), 8.24 (dd, J = 8.6, 2.4 Hz, 1H), 7.81 (dd, J = 9.0, 1.9 Hz, 1H), 7.61 (d, J = 9.0, 0.7 Hz, 1H), 7.02 (dd, J = 8.6, 0.8 Hz, 1H), 3.95 (s, 3H), 2.61 (d, J = 0.8 Hz, 3H). MS-ESI (m/z) calc'd for C$_{21}$H$_{17}$N$_6$O$_2$ [M + H]$^+$: 385.1. Found 385.1. |
| 53 | 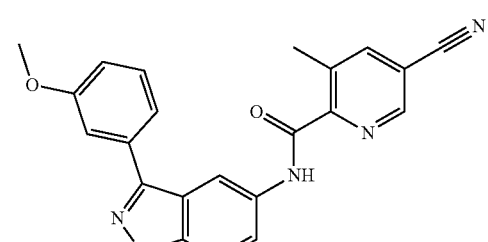<br>5-cyano-N-(3-(3-methoxyphenyl)-1H-indazol-5-yl)-3-methylpicolinamide | $^1$H NMR (400 MHz, DMSO-d$_6$) δ 13.25 (br. s, 1H), 10.75 (br. s, 1H), 9.01 (d, J = 1.32 Hz, 1H), 8.64 (d, J = 1.32 Hz, 1 H), 8.41 (d, J = 1.10 Hz, 1H), 7.83 (dd, J = 9.02, 1.76 Hz, 1H), 7.60 (d, J = 9.24 Hz, 1H), 7.52-7.57 (m, 1H), 7.44-7.51 (m, 2H), 6.94-7.03 (m, 1H), 3.87 (s, 3H), 2.60 (s, 3H). MS-ESI (m/z) calc'd for C$_{22}$H$_{18}$N$_5$O$_2$ [M + H]$^+$: 384.1. Found 384.2. |

TABLE 1-continued

| Ex. No. | Structure/Name | Data |
|---|---|---|
| 54 | 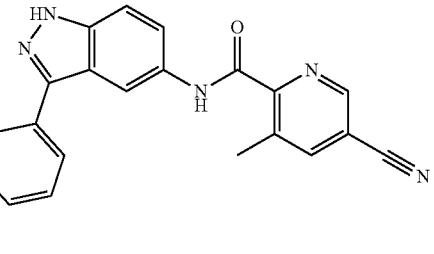<br>5-cyano-3-methyl-N-(3-(3-(trifluoromethoxy)phenyl)-1H-indazol-5-yl)picolinamide | $^1$H NMR (400 MHz, DMSO-$d_6$) δ 13.44 (s, 1H), 10.80 (s, 1H), 9.00 (d, J = 1.9 Hz, 1H), 8.62 (d, J = 1.8 Hz, 1H), 8.41 (dd, J = 2.0, 0.8 Hz, 1H), 8.04-7.96 (m, 1H), 7.90-7.81 (m, 2H), 7.70 (t, J = 8.0 Hz, 1H), 7.63 (d, J = 9.0 Hz, 1H), 7.41 (ddt, J = 8.2, 2.4, 1.0 Hz, 1H), 2.59 (s, 3H). MS-ESI (m/z) calc'd for $C_{22}H_{15}F_3N_5O_2$ [M + H]$^+$: 438.1. Found 438.1. |
| 55 | 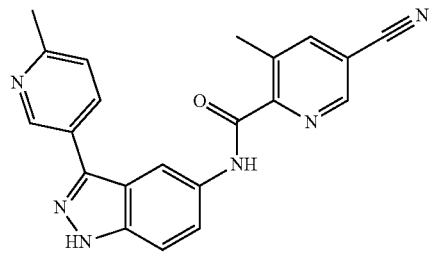 [SMILES: Cc1ccc(-c2n[nH]c3ccc(NC(=O)c4ncc(C#N)cc4C)cc23)cn1]<br>5-cyano-3-methyl-N-(3-(6-methylpyridin-3-yl)-1H-indazol-5-yl)picolinamide | $^1$H NMR (400 MHz, DMSO-$d_6$) δ 13.38 (s, 1H), 10.78 (s, 1H), 9.03 (d, J = 2.3 Hz, 1H), 9.00 (d, J = 1.9 Hz, 1H), 8.64 (d, J = 1.8 Hz, 1H), 8.41 (dd, J = 2.0, 0.9 Hz, 1H), 8.19 (dd, J = 8.0, 2.3 Hz, 1H), 7.82 (dd, J = 9.0, 1.9 Hz, 1H), 7.62 (d, J = 8.9 Hz, 1H), 7.44 (d, J = 8.1 Hz, 1H), 2.60 (s, 3H), 2.55 (s, 3H). MS-ESI (m/z) calc'd for $C_{21}H_{17}N_6O$ [M + H]$^+$: 369.2. Found 369.2. |
| 56 | 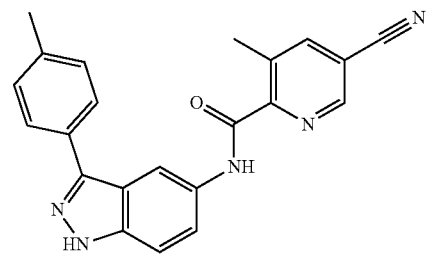 [SMILES: Cc1ccc(-c2n[nH]c3ccc(NC(=O)c4ncc(C#N)cc4C)cc23)cc1]<br>5-cyano-3-methyl-N-(3-(p-tolyl)-1H-indazol-5-yl)picolinamide | $^1$H NMR (400 MHz, DMSO-$d_6$) δ 13.20 (br. s., 1H), 10.76 (s, 1H), 9.01 (d, J = 1.54 Hz, 1H), 8.61 (s, 1H), 8.41 (d, J = 1.10 Hz, 1H), 7.85 (d, J = 8.14 Hz, 2H), 7.80 (dd, J = 8.91, 1.65 Hz, 1H), 7.59 (d, J = 9.02 Hz, 1H), 7.36 (d, J = 7.92 Hz, 2H), 2.60 (s, 3H), 2.39 (s, 3H). MS-ESI (m/z) calc'd for $C_{22}H_{18}N_5O$ [M + H]$^+$: 368.1. Found 368.2. |
| 57 | 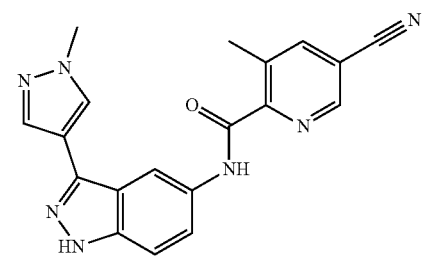 [SMILES: Cc1cc(C#N)cnc1C(=O)Nc1ccc2[nH]nc(-c3cnn(C)c3)c2c1]<br>5-cyano-3-methyl-N-(3-(1-methyl-1H-pyrazol-4-yl)-1H-indazol-5-yl)picolinamide | $^1$H NMR (400 MHz, DMSO-$d_6$) δ 12.95 (s, 1H) 10.70 (s, 1H) 9.01 (d, J = 1.32 Hz, 1H) 8.38-8.47 (m, 2H) 8.22 (s, 1H) 7.93 (s, 1H) 7.80 (dd, J = 9.02, 1.76 Hz, 1H) 7.54 (d, J = 8.80 Hz, 1H) 3.96 (s, 3H) 2.62 (s, 3H). MS-ESI (m/z) calc'd for $C_{19}H_{16}N_7O$ [M + H]$^+$: 358.1. Found 358.1. |
| 58 | 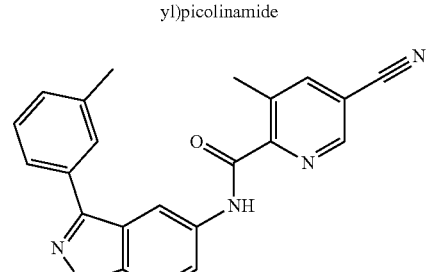<br>5-cyano-3-methyl-N-(3-(m-tolyl)-1H-indazol-5-yl)picolinamide | $^1$H NMR (400 MHz, DMSO-$d_6$) δ 13.22 (s, 1H), 10.75 (s, 1H), 9.00 (dd, J = 2.0, 0.7 Hz, 1H), 8.60-8.49 (m, 1H), 8.40 (dd, J = 2.0, 0.8 Hz, 1H), 7.83 (dd, J = 9.0, 1.9 Hz, 1H), 7.77 (s, 1.11), 7.74 (d, J = 7.8 Hz, 1H), 7.59 (d, J = 9.2 Hz, 1H), 7.43 (t, J = 7.6 Hz, 1H), 7.25-7.21 (m, 1H), 2.59 (d, J = 0.7 Hz, 3H), 2.42 (s, 3H). MS-ESI (m/z) calc'd for $C_{22}H_{18}N_5O$ [M + H]$^+$: 368.1. Found 368.2. |

TABLE 1-continued

| Ex. No. | Structure/Name | Data |
|---|---|---|
| 59 | 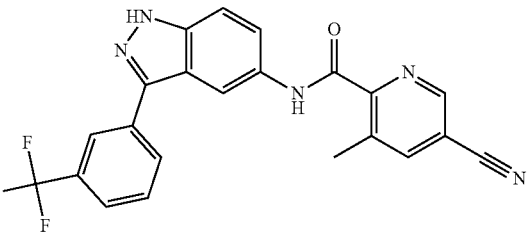<br>5-cyano-3-methyl-N-(3-(3-(trifluoromethyl)phenyl)-1H-indazol-5-yl)picolinamide | $^1$H NMR (400 MHz, DMSO-d$_6$) δ 13.47 (s, 1H), 10.81 (s, 1H), 9.00 (dd, J = 1.9, 0.7 Hz, 1H), 8.61 (d, J = 1.9 Hz, 1H), 8.41 (dd, J = 1.9, 0.9 Hz, 1H), 8.27 (d, J = 7.5 Hz, 1H), 8.23 (s, 1H), 7.87 (dd, J = 9.0, 1.9 Hz, 1H), 7.81 (t, J = 7.6 Hz, 1H), 7.78 (d, J = 7.9 Hz, 1H), 7.64 (d, J = 9.2 Hz, 1H), 2.59 (s, 3H). MS-ESI (m/z) calc'd for C$_{22}$H$_{15}$F$_3$N$_5$O [M + H]$^+$: 422.1. Found 422.1. |
| 60 | 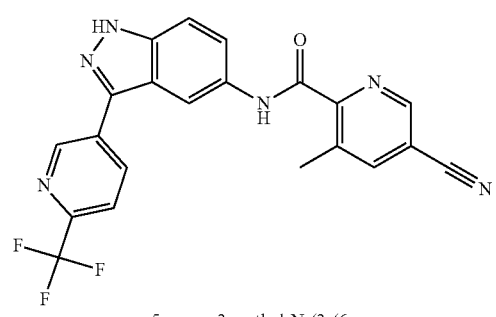<br>5-cyano-3-methyl-N-(3-(6-(trifluoromethyl)pyridin-3-yl)-1H-indazol-5-yl)picolinamide | $^1$H NMR (400 MHz, DMSO-d$_6$) δ 13.69 (br. s., 1H) 10.83 (s, 1H) 9.36 (d, J = 1.98 Hz, 1H) 9.02 (d, J = 1.32 Hz, 1H) 8.72 (d, J = 1.32 Hz, 1H) 8.60 (dd, J = 8.25, 1.65 Hz, 1H) 8.39-8.47 (m, 1H) 8.10 (d, J = 8.14 Hz, 1H) 7.88 (dd, J = 8.91, 1.87 Hz, 1H) 7.69 (d, J = 8.58 Hz, 1H) 2.62 (s, 3H). MS-ESI (m/z) calc'd for C$_{21}$H$_{14}$F$_3$N$_6$O [M + H]$^+$: 423.1. Found 423.1. |
| 61 | 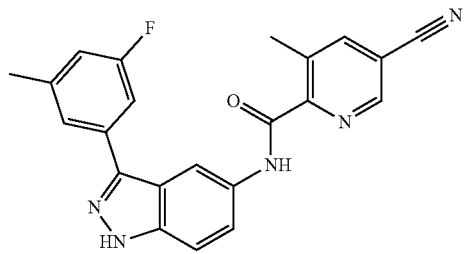 [SMILES: Cc1cc(F)cc(-c2n[nH]c3ccc(NC(=O)c4ncc(C#N)cc4C)cc23)c1]<br>5-cyano-N-(3-(3-fluoro-5-methylphenyl)-1H-indazol-5-yl)-3-methylpicolinamide | $^1$H NMR (400 MHz, DMSO-d$_6$) δ 13.36 (br. s., 1H) 10.79 (s, 1H) 9.01 (d, J = 1.32 Hz, 1H) 8.56 (d, J = 1.32 Hz, 1H) 8.42 (dd, J = 1.87, 0.77 Hz, 1H) 7.91 (dd, J = 9.02, 1.98 Hz, 1H) 7.57-7.69 (m, 2H) 7.51 (d, J = 10.12 Hz, 1 H) 7.09 (d, J = 9.68 Hz, 1H) 2.60 (s, 3 H) 2.45 (s, 3H). MS-ESI (m/z) calc'd for C$_{22}$H$_{17}$FN$_5$O [M + H]$^+$: 386.1. Found 386.2. |
| 62 | 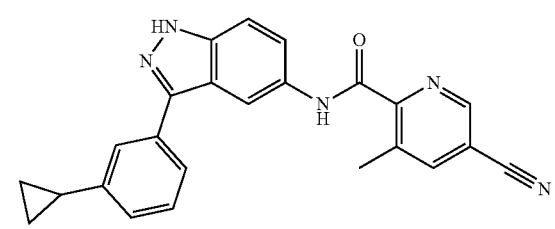 [SMILES: Cc1cc(C#N)cnc1C(=O)Nc1ccc2[nH]nc(-c3cccc(C4CC4)c3)c2c1]<br>5-cyano-N-(3-(3-cyclopropylphenyl)-1H-indazol-5-yl)-3-methylpicolinamide | $^1$H NMR (400 MHz, DMSO-d$_6$) δ 13.22 (br. s., 1H) 10.77 (s, 1H) 9.01 (d, J = 1.54 Hz, 1H) 8.61 (d, J = 1.32 Hz, 1H) 8.38-8.46 (m, 1H) 7.80 (dd, J = 9.02, 1.76 Hz, 1H) 7.71 (d, J = 7.70 Hz, 1H) 7.64 (s, 1H) 7.60 (d, J = 9.02 Hz, 1H) 7.42 (t, J = 7.70 Hz, 1H) 7.14 (d, J = 7.48 Hz, 1H) 2.59 (s, 3H) 2.00-2.10 (m, 1H) 0.99-1.06 (m, 2H) 0.75-0.82 (m, 2H). MS-ESI (m/z) calc'd for C$_{24}$H$_{20}$N$_5$O [M + H]$^+$: 394.2. Found 394.2. |
| 63 | 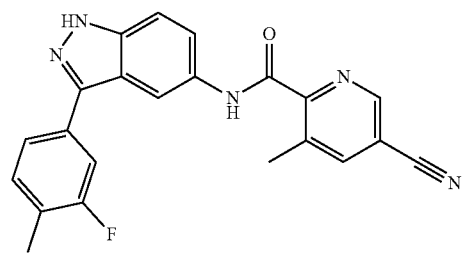 [SMILES: Cc1ccc(-c2n[nH]c3ccc(NC(=O)c4ncc(C#N)cc4C)cc23)cc1F]<br>5-cyano-N-(3-(3-fluoro-4-methylphenyl)-1H-indazol-5-yl)-3-methylpicolinamide | $^1$H NMR (400 MHz, DMSO-d$_6$) δ 13.32 (br. s., 1H) 10.79 (s, 1H) 9.01 (d, J = 1.32 Hz, 1H), 8.57-8.67 (m, 1 H), 8.42 (dd, J = 1.98, 0.66 Hz, 1H), 7.86 (dd, J = 8.91, 1.87 Hz, 1H), 7.59-7.75 (m, 3H), 7.47 (t, J = 8.25 Hz, 1H), 2.61 (s, 3H), 2.32 (d, J = 1.32 Hz, 3H). MS-ESI (m/z) calc'd for C$_{22}$H$_{17}$FN$_5$O [M + H]$^+$: 386.1. Found 386.2. |

TABLE 1-continued

| Ex. No. | Structure/Name | Data |
|---|---|---|
| 64 | 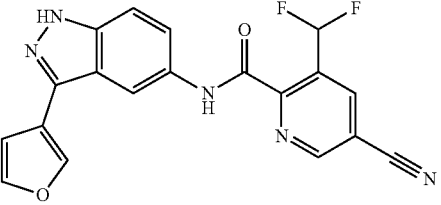 [SMILES: N#Cc1cnc(C(=O)Nc2ccc3[nH]nc(-c4ccoc4)c3c2)c(C(F)F)c1]<br>5-Cyano-3-(difluoromethyl)-N-(3-(furan-3-yl)-1H-indazol-5-yl)picolinamide | $^1$H NMR (400 MHz, DMSO-d$_6$) δ 13.15 (s, 1H) 11.00 (s, 1H) 9.36 (s, 1 H) 8.90 (s, 1H) 8.46 (s, 1H) 8.29 (s, H) 7.68-7.96 (m, 3H) 7.58 (d, J = 9 Hz, 1H) 7.02 (d, J = 1 Hz, 1H). MS-ESI (m/z) calc'd for C$_{19}$H$_{12}$F$_2$N$_5$O$_2$ [M + H]$^+$: 380.1. Found 380.1. |
| 65 | 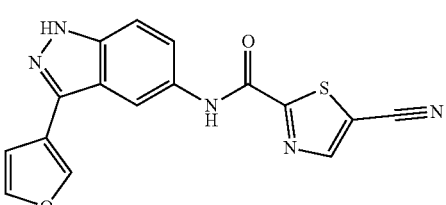<br>5-Cyano-N-(3-(furan-3-yl)-1H-indazol-5-yl)thiazole-2-carboxamide | $^1$H NMR (400 MHz, DMSO-d$_6$) δ 13.16 (br s, 1H) 11.11 (s, 1H) 8.95 (s, 1H) 8.46 (d, J = 1.47 Hz, 1H) 8.26 (s, 1H) 7.89 (dd, J = 9.05, 1.83 Hz, 1H) 7.85 (t, J = 1.65 Hz, 1H) 7.58 (d, J = 8.93 Hz, 1H) 6.98-7.03 (m, 1H). MS-ESI (m/z) calc'd for C$_{16}$H$_{10}$N$_5$O$_2$S [M + H]$^+$: 336.0. Found 336.0. |
| 66 | 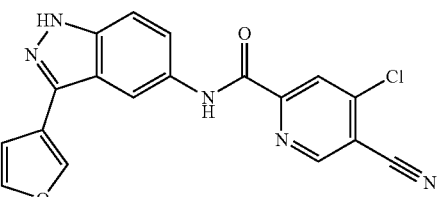<br>4-Chloro-5-cyano-N-(3-(furan-3-yl)-1H-indazol-5-yl)picolinamide | $^1$H NMR (400 MHz, DMSO-d$_6$) δ 13.13 (s, 1H), 10.91 (s, 1H), 9.29 (s, 1H), 8,51 (s, 1H), 8.44 (s, 1H), 8.29 (s, 1H), 7.99 (br d, J = 9.0 Hz, 1H), 7.85 (s, 1H), 7.57 (d, J = 9.0 Hz, 1H), 7.01 (s, 1H). MS-ESI (m/z) calc'd for C$_{18}$H$_{11}$ClN$_5$O$_2$ [M + H]$^+$: 364.0. Found 364.0. |
| 67 | 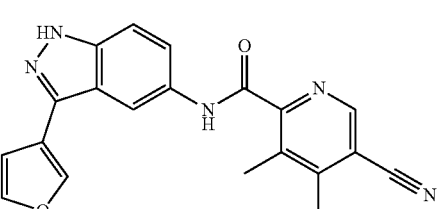<br>5-cyano-N-(3-(furan-3-yl)-1H-indazol-5-yl)-3,4-dimethylpicolinamide | $^1$H NMR (400 MHz, DMSO-d$_6$) δ 13.10 (s, 1H), 10.67 (s, 1H), 8.89 (s, 1H), 8.40 (d, J = 1.7 Hz, 1H), 8.23 (t, J =1.1 Hz, 1H), 7.84 (t, J = 1.7 Hz, 1H), 7.74 (dd, J = 8.9, 1.9 Hz, 1H), 7.56 (d, J = 9.0 Hz, 1H), 6.99 (dd, J = 1.9, 0.8 Hz, 1H), 2.56 (s, 3H), 2.47 (s, 3H). MS-ESI (m/z) calc'd for C$_{20}$H$_{16}$N$_5$O$_2$ [M + H]$^+$: 358.1. Found 358.1 |
| 68 | 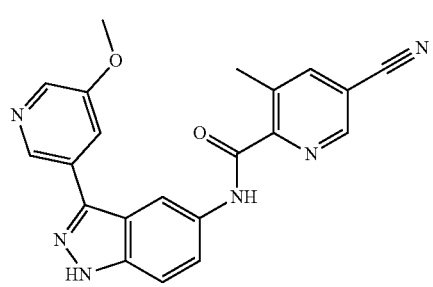 [SMILES: COc1cncc(-c2n[nH]c3ccc(NC(=O)c4ncc(C#N)cc4C)cc23)c1]<br>5-cyano-N-(3-(5-methoxypyridin-3-yl)-1H-indazol-5-yl)-3-methylpicolinamide | $^1$H NMR (400 MHz, DMSO-d$_6$) δ 13.49 (bs, 1H), 10.81 (s, 1H), 9.01 (d, J = 2.0 Hz, 1H), 8.79 (d, J = 1.7 Hz, 1H), 8.67 (d, J = 1.8 Hz, 1H), 8.42 (dd, J = 2.0, 0.9 Hz, 1H), 8.36 (d, J = 2.8 Hz, 1H), 7.88 (dd, J = 9.0, 1.9 Hz, 1H), 7.84 (dd, J = 2.9, 1.7 Hz, 1H), 7.65 (d, J = 9.0 Hz, 1H), 3.96 (s, 3H), 2.61 (s, 3H).<br>MS-ESI (m/z) calc'd for C$_{21}$H$_{17}$N$_6$O$_2$ [M + H]$^+$: 385.1. Found 385.2. |
| 69 | 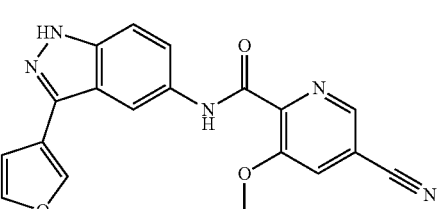<br>5-cyano-N-(3-(furan-3-yl)-1H-indazol-5-yl)-3-methoxypicolinamide | $^1$H NMR (400 MHz, DMSO-d$_6$) δ 13.10 (s, 1H), 10.60 (s, 1H), 8.70 (d, J = 1.5 Hz, 1H), 8.39 (d, J = 1.8 Hz, 1H), 8.24 (d, J = 1.6 Hz, 1H), 8.21 (d, J = 1.2 Hz, 1H), 7.85 (t, J = 1.7 Hz, 1H), 7.67 (dd, J = 8.9, 1.9 Hz, 1H), 7.56 (d, J = 8.9 Hz, 1H), 6.99 (d, J = 1.9 Hz, 1H), 3.94 (s, 3H). MS-ESI (m/z) calc'd for C$_{19}$H$_{14}$N$_5$O$_3$ [M + H]$^+$: 360.1. Found 360.2. |

TABLE 1-continued

| Ex. No. | Structure/Name | Data |
|---|---|---|
| 70 | 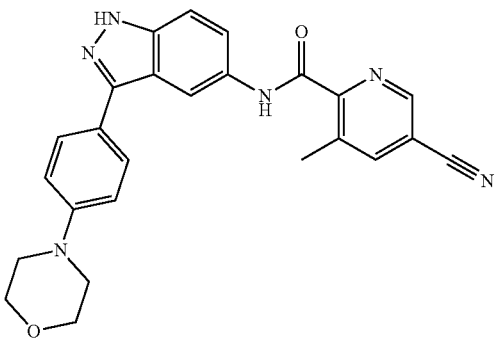 [SMILES: Cc1cc(C#N)cnc1C(=O)Nc1ccc2[nH]nc(-c3ccc(N4CCOCC4)cc3)c2c1]<br>5-cyano-3-methyl-N-(3-(4-morpholinophenyl)-1H-indazol-5-yl)picolinamide | ¹H NMR (400 MHz, Chloroform-d) δ 10.12 (s, 1H), 8.74 (d, J = 2.0 Hz, 1H), 8.49 (d, J = 2.0 Hz, 1H), 7.96 (d, J = 1.9 Hz, 1H), 7.91 (d, J = 8.7 Hz, 2H), 7.68 (dd, J = 8.9, 1.9 Hz, 1H), 7.51 (d, J = 8.9 Hz, 1H), 7.09-7.05 (m, 2H), 3.93-3.89 (m, 4H), 3.28-3.24 (m, 4H), 2.90 (s, 3H). MS-ESI (m/z) calc'd for $C_{25}H_{23}N_6O_2$ [M + H]⁺: 439.2. Found 439.1. |
| 71 | 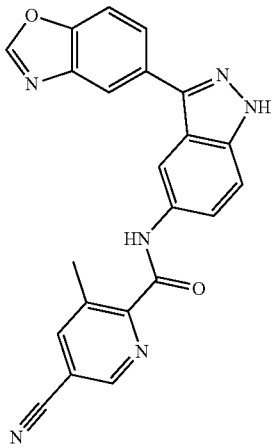 [SMILES: Cc1cc(C#N)cnc1C(=O)Nc1ccc2[nH]nc(-c3ccc4ocnc4c3)c2c1]<br>N-(3-(benzo[d]oxazol-5-yl)-1H-indazol-5-yl)-5-cyano-3-methylpicolinamide | ¹H NMR (400 MHz, DMSO-d₆) δ 13.30 (s, 1H), 10.81 (s, 1H), 9.01 (dd, J = 2.0, 0.8 Hz, 1H), 8.84 (s, 1H), 8.68 (d, 1H), 8.42 (dd, J = 2.0, 0.9 Hz, 1H), 8.30 (d, J = 1.6 Hz, 1H), 8.07 (dd, J = 8.5, 1.7 Hz, 1H), 7.96 (d, J = 8.5 Hz, 1H), 7.87 (dd, J = 9.0, 1.9 Hz, 1H), 7.63 (d, J = 9.0 Hz, 1H), 2.61 (s, 3H). MS-ESI (m/z) calc'd for $C_{22}H_{15}N_6O_2$ [M + H]⁺: 395.1. Found 395.1. |
| 72 | 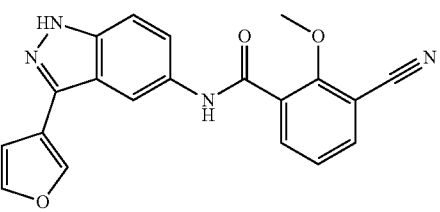 [SMILES: COc1c(C#N)cccc1C(=O)Nc1ccc2[nH]nc(-c3ccoc3)c2c1]<br>3-cyano-N-(3-(furan-3-yl)-1H-indazol-5-yl)-2-methoxybenzamide | ¹H NMR (400 MHz, DMSO-d₆) δ 13.10 (br. s., 1H), 10.51 (s, 1H), 8.38 (d, J = 1.1 Hz, 1H), 8.22 (dd, J = 0.8, 1.4 Hz, 1H), 7.96 (dd, J = 1.7, 7.8 Hz, 1H), 7.91 (dd, J = 1.5, 7.7 Hz, 1H), 7.86 (t, J = 1.7 Hz, 1H), 7.70-7.63 (m, 1H), 7.61-7.53 (m, 1H), 7.41 (t, J = 7.7 Hz, 1H), 7.00 (dd, J = 0.8, 1.9 Hz, 1H), 4.03 (s, 3H). MS-ESI (m/z) calc'd for $C_{20}H_{15}N_4O_3$ [M + H]⁺: 359.1. Found 359.2. |
| 73 | 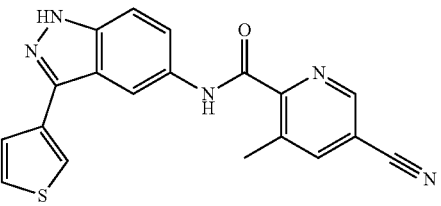 [SMILES: Cc1cc(C#N)cnc1C(=O)Nc1ccc2[nH]nc(-c3ccsc3)c2c1]<br>5-cyano-3-methyl-N-(3-(thiophen-3-yl)-1H-indazol-5-yl)picolinamide | ¹H NMR (400 MHz, DMSO-d₆) δ 13.13 (bs, 1H), 10.74 (s, 1H), 9.01 (d, J = 2.0 Hz, 1H), 8.60 (d, J = 1.8 Hz, 1H), 8.42 (dd, J = 2.0, 0.9 Hz, 1H), 7.96 (dd, J = 2.9, 1.3 Hz, 1H), 7.81 (dd, J = 9.0, 1.9 Hz, 1H), 7.74 (dd, J = 5.0, 2.8 Hz, 1H), 7.70 (dd, J = 5.0, 1.3 Hz, 1H), 7.58 (d, J = 8.9 Hz, 1H), 2.62 (s, 3H). MS-ESI (m/z) calc'd for $C_{19}H_{14}N_5OS$ [M + H]⁺: 360.1. Found 360.1. |

TABLE 1-continued

| Ex. No. | Structure/Name | Data |
|---|---|---|
| 74 | 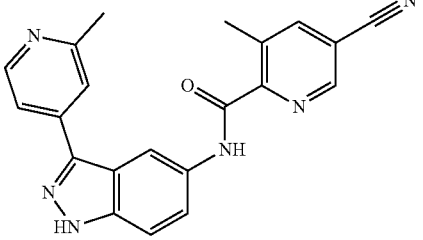<br>5-cyano-3-methyl-N-(3-(2-methylpyridin-4-yl)-1H-indazol-5-yl)picolinamide | $^1$H NMR (400 MHz, DMSO-d$_6$) δ 13.57 (bs, 1H), 10.80 (s, 1H), 9.02 (d, J = 1.9 Hz, 1H), 8.64 (d, J = 1.8 Hz, 1H), 8.58 (d, J = 5.1 Hz, 1H), 8.42 (dd, J = 1.8, 0.8 Hz, 1H), 7.91 (dd, J = 9.0, 1.9 Hz, 1H), 7.82 (d, J = 1.7 Hz, 1H), 7.74 (dd, J = 5.3, 1.7 Hz, 1H), 7.66 (d, J = 9.0 Hz, 1H), 2.61 (s, 3H), 2.59 (s, 3H). MS-ESI (m/z) calc'd for C$_{21}$H$_{16}$N$_6$O [M + H]$^+$: 369.1. Found 369.2. |
| 75 | 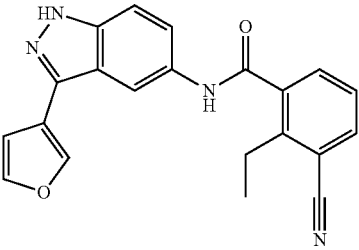<br>3-cyano-2-ethyl-N-(3-(furan-3-yl)-1H-indazol-5-yl)benzamide | $^1$H NMR (400 MHz, DMSO-d$_6$) δ 13.10 (s, 1H), 10.55 (s, 1H), 8.37 (d, J = 1.1 Hz, 1H), 8.21 (dd, J = 0.8, 1.4 Hz, 1H), 7.95 (dd, J = 1.3, 7.7 Hz, 1H), 7.89-7.81 (m, 2H), 7.71-7.63 (m, 1H), 7.61-7.52 (m, 2H), 6.99 (dd, J = 0.7, 1.8 Hz, 1H), 2.95 (q, J = 7.4 Hz, 2H), 1.27 (t, J = 7.5 Hz, 3H). MS-ESI (m/z) calc'd for C$_{21}$H$_{17}$N$_4$O$_2$ [M + H]$^+$: 357.1. Found 357.1. |
| 76 | 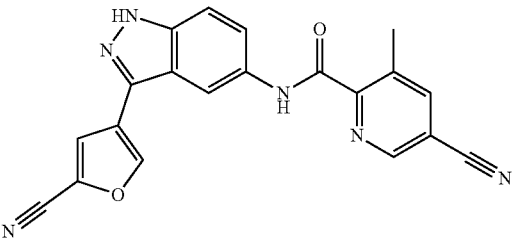 [SMILES: Cc1cc(C#N)cnc1C(=O)Nc1ccc2[nH]nc(-c3coc(C#N)c3)c2c1]<br>5-Cyano-N-(3-(5-cyanofuran-3-yl)-1H-indazol-5-yl)-3-methylpicolinamide | $^1$H NMR (400 MHz, DMSO-d$_6$) δ 13.38 (s, 1H) 10.73 (s, 1H) 9.01 (s, H) 8.69 (s, 1H) 8.42 (br d, J = 6 Hz, 2 H) 8.14 (s, 1H) 7.85 (br d, J = 8 Hz, H) 7.61 (d, J = 9 Hz, 1H) 2.62 (s, 3H). MS-ESI (m/z) calc'd for C$_{20}$H$_{13}$N$_6$O$_2$ [M + H]$^+$: 369.1. Found 369.0. |
| 77 | 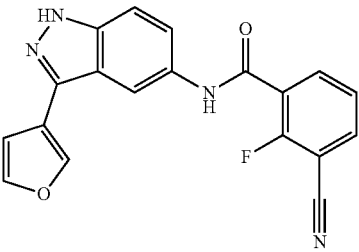 [SMILES: N#Cc1cccc(C(=O)Nc2ccc3[nH]nc(-c4ccoc4)c3c2)c1F]<br>3-cyano-2-fluoro-N-(3-(furan-3-yl)-1H-indazol-5-yl)benzamide | $^1$H NMR (400 MHz, DMSO-d$_6$) δ 13.13 (br. s., 1H), 10.64 (br. s., 1H), 8.37 (d, J = 0.9 Hz, 1H), 8.22 (dd, J = 0.8, 1.4 Hz, 1H), 8.18-8.03 (m, 2H), 7.86 (t, J = 1.7 Hz, 1H), 7.68-7.53 (m, 3H), 7.00 (dd, J = 0.8, 1.9 Hz, 1H). MS-ESI (m/z) calc'd for C$_{19}$H$_{12}$FN$_4$O$_2$ [M + H]$^+$: 347.1. Found 347.1. |
| 78 | 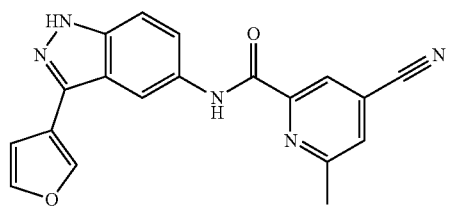 [SMILES: Cc1cc(C#N)cc(C(=O)Nc2ccc3[nH]nc(-c4ccoc4)c3c2)n1]<br>4-cyano-N-(3-(furan-3-yl)-1H-indazol-5-yl)-6-methylpicolinamide | $^1$H NMR (400 MHz, DMSO-d$_6$) δ 13.12 (s, 1H), 10.60 (s, 1H), 8.45 (d, J = 1.5 Hz, 1H), 8.37-8.27 (m, 2H), 8.07 (d, J = 0.9 Hz, 1H), 7.96 (dd, J = 1.9, 8.9 Hz, 1H), 7.86 (t, J = 1.7 Hz, 1H), 7.59 (d, J = 8.8 Hz, 1H), 7.03 (dd, J = 0.9, 1.8 Hz, 1H), 2.74 (s, 3H). MS-ESI (m/z) calc'd for C$_{19}$H$_{14}$N$_5$O$_2$ [M + H]$^+$: 344.1. Found 344.2. |

TABLE 1-continued

| Ex. No. | Structure/Name | Data |
|---|---|---|
| 79 | 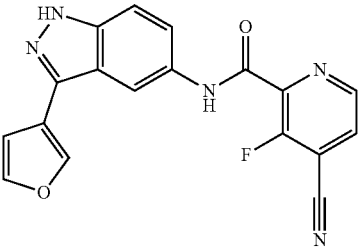<br>4-cyano-3-fluoro-N-(3-(furan-3-yl)-1H-indazol-5-yl)picolinamide | $^1$H NMR (400 MHz, DMSO-d$_6$) δ 13.12 (s, 1H), 10.77 (s, 1H), 8.82 (d, J = 4.8 Hz, 1H), 8.43 (s, 1H), 8.32-8.24 (m, 2H), 7.90-7.80 (m, 2H), 7.58 (d, J = 9.0 Hz, 1H), 7.01 (d, J = 0.9 Hz, 1H). MS-ESI (m/z) calc'd for C$_{18}$H$_{11}$FN$_5$O$_2$ [M + H]$^+$: 348.1. Found 348.1. |
| 80 | 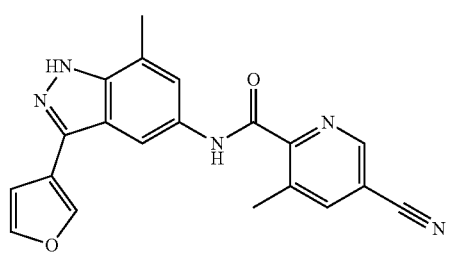 [SMILES: Cc1cc(C#N)cnc1C(=O)Nc1cc(C)c2[nH]nc(-c3ccoc3)c2c1]<br>5-cyano-N-(3-(furan-3-yl)-7-methyl-1H-indazol-5-yl)-3-methylpicolinamide | $^1$H NMR (400 MHz, DMSO-d$_6$) δ 13.17 (s, 1H), 10.61 (s, 1H), 9.04-8.97 (m, 1H), 8.41 (dd, J = 0.8, 1.9 Hz, 1H), 8.30-8.20 (m, 2H), 7.85 (t, J = 1.7 Hz, 1H), 7.64 (s, 1H), 7.01 (dd, J = 0.9, 1.8 Hz, 1H), 2.61 (s, 3H), 2.55 (s, 3H). MS-ESI (m/z) calc'd for C$_{24}$H$_{16}$N$_5$O$_2$ [M + H]$^+$: 358.1. Found 358.2. |
| 81 | 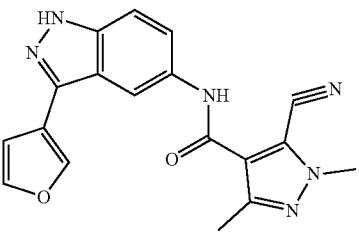 [SMILES: Cc1nn(C)c(C#N)c1C(=O)Nc1ccc2[nH]nc(-c3ccoc3)c2c1]<br>5-Cyano-N-(3-(furan-3-yl)-1H-indazol-5-yl)-1,3-dimethyl-1H-pyrazole-4-carboxamide | $^1$H NMR (400 MHz, DMSO-d$_6$) δ 13.11 (br s, 1H) 10.18 (s, 1H) 8.31 (s, 1H) 8.22 (s, 1H) 7.85 (t, J = 1.59 Hz, 1 H) 7.56 (s, 2H) 6.99 (d, J = 1.10 Hz, 1 H) 4.01 (s, 3H) 2.42 (s, 3H). MS-ESI (m/z) calc'd for C$_{18}$H$_{15}$N$_6$O$_2$ [M + H]$^+$: 347.1. Found 347.1. |
| 82 | 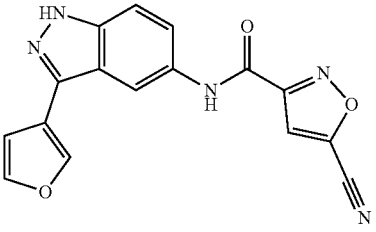 [SMILES: N#Cc1cc(C(=O)Nc2ccc3[nH]nc(-c4ccoc4)c3c2)no1]<br>5-Cyano-N-(3-(furan-3-yl)-1H-indazol-5-yl)isoxazole-3-carboxamide | $^1$H NMR (400 MHz, DMSO-d$_6$) δ 13.15 (s, 1H), 11.02 (s, 1H), 8.38 (s, 1H), 8.24 (s, 1H), 8.14 (s, 1H), 7.85 (s, 1H), 7.75 (d, J = 9.0 Hz, 1H), 7.58 (d, J = 8.9 Hz, 1H), 6.99 (s, 1H). MS-ESI (m/z) calc'd for C$_{16}$H$_{10}$N$_5$O$_3$ [M + H]$^+$: 320.1. Found 320.0. |
| 83 | 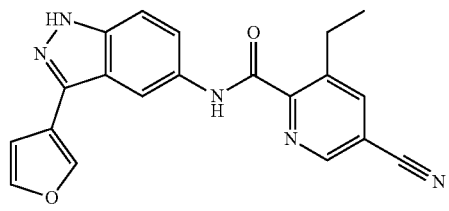 [SMILES: CCc1cc(C#N)cnc1C(=O)Nc1ccc2[nH]nc(-c3ccoc3)c2c1]<br>5-Cyano-3-ethyl-N-(3-(furan-3-yl)-1H-indazol-5-yl)picolinamide | $^1$H NMR (400 MHz, DMSO-d$_6$) δ 13.11 (br s, 1H) 10.71 (s, 1H) 9.00 (d, J = 1.10 Hz, 1H) 8.42 (d, J = 12.59 Hz, 2 H) 8.25 (s, 1H) 7.85 (s, 1H) 7.76-7.82 (m, 1H) 7.56 (d, J = 8.93 Hz, 1H) 7.00 (s, 1H) 2.97 (q, J = 7.34 Hz, 2H) 1.24 (t, J = 7.46 Hz, 3H). MS-ESI (m/z) calc'd for C$_{20}$H$_{16}$N$_5$O$_2$ [M + H]$^+$: 358.1. Found 358.1. |

TABLE 1-continued

| Ex. No. | Structure/Name | Data |
|---|---|---|
| 84 | 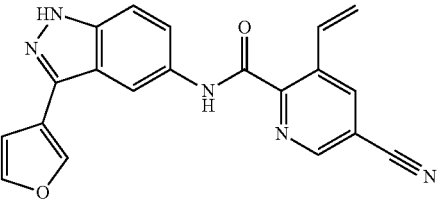 [SMILES: C=Cc1cc(C#N)cnc1C(=O)Nc1ccc2[nH]nc(-c3ccoc3)c2c1]<br>5-Cyano-N-(3-(furan-3-yl)-1H-indazol-5-yl)-3-vinylpicolinamide | $^1$H NMR (400 MHz, DMSO-d$_6$) δ 13.12 (br s, 1H) 10.79 (s, 1H) 9.06 (s, 1H) 8.82 (s, 1H) 8.43 (s, 1H) 8.26 (s, 1H) 7.73-7.88 (m, 2H) 7.56 (br d, J = 8.80 Hz, 1H) 7.35 (br dd, J = 17.42, 11.07 Hz, 1H) 7.00 (s, 1H) 6.14 (br d, J = 17.48 Hz, 1H) 5.61 (br d, J = 11.13 Hz, 1H). MS-ESI (m/z) calc'd for C$_{20}$H$_{14}$N$_5$O$_2$ [M + H]$^+$: 356.1. Found 356.0. |
| 85 | 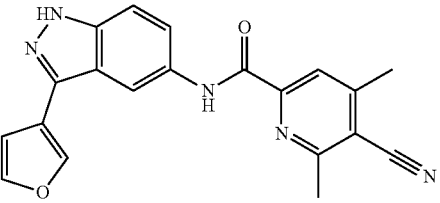 [SMILES: Cc1cc(C(=O)Nc2ccc3[nH]nc(-c4ccoc4)c3c2)nc(C)c1C#N]<br>5-cyano-N-(3-(furan-3-yl)-1H-indazol-5-yl)-4,6-dimethylpicolinamide | $^1$H NMR (400 MHz, DMSO-d$_6$) δ 13.11 (s, 1H), 10.62 (s, 1H), 8.45 (s, 1H), 8.33 (s, 1H), 8.09 (s, 1H), 7.97 (dd, J = 9.0, 1.9 Hz, 1H), 7.85 (t, J = 1.7 Hz, 1H), 7.59 (d, J = 9.0 Hz, 1H), 7.03 (d, J = 1.9 Hz, 1H), 2.84 (s, 3H), 2.63 (s, 3H). MS-ESI (m/z) calc'd for C$_{20}$H$_{16}$N$_5$O$_2$ [M + H]$^+$: 358.1. Found 358.2. |
| 86 | 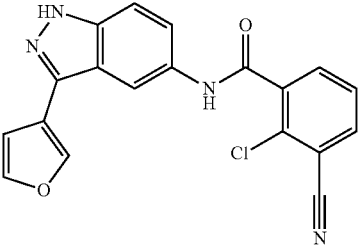 [SMILES: N#Cc1cccc(C(=O)Nc2ccc3[nH]nc(-c4ccoc4)c3c2)c1Cl]<br>2-chloro-3-cyano-N-(3-(furan-3-yl)-1H-indazol-5-yl)benzamide | $^1$H NMR (400 MHz, DMSO-d$_6$) δ 13.13 (br. s., 1H), 10.69 (br. s., 1H), 8.37 (s, 1H), 8.23-8.18 (m, 1H), 8.13 (dd, J = 1.7, 7.8 Hz. 1H), 8.00 (dd, J = 1.5, 7.7 Hz, 1H), 7.86 (t, J = 1.7 Hz, 1H), 7.71 (t, J = 7.7 Hz, 1H), 7.64-7.55 (m, 2H), 6.99 (dd, J = 0.8, 1.9 Hz, 1H). MS-ESI (m/z) calc'd for C$_{19}$H$_{12}$ClN$_4$O$_2$ [M + H]$^+$: 363.1. Found 363.1, 365.3. |
| 87 | 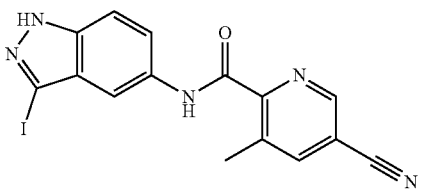 [SMILES: Cc1cc(C#N)cnc1C(=O)Nc1ccc2[nH]nc(I)c2c1]<br>5-cyano-N-(3-iodo-1H-indazol-5-yl)-3-methylpicolinamide | $^1$H NMR (400 MHz, DMSO-d$_6$) δ 13.50 (s, 1H), 10.80 (s, 1H), 9.00 (d, J = 1.9 Hz, 1H), 8.41 (d, J = 2.0 Hz, 1H), 8.14 (s, 1H), 7.72 (dd, J = 9.0, 1.9 Hz, 1H), 7.56 (d, J = 8.9 Hz, 1H), 2.59 (s, 3H). MS-ESI (m/z) calc'd for C$_{15}$H$_{11}$IN$_5$O [M + H]$^+$: 404.0. Found 404.1. |
| 88 | 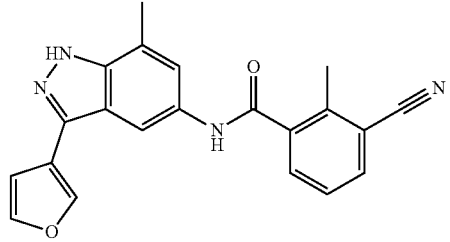<br>3-cyano-N-(3-(furan-3-yl)-7-methyl-1H-indazol-5-yl)-2-methylbenzamide | $^1$H NMR (400 MHz, DMSO-d$_6$) δ 13.12 (br. s., 1H), 10.65 (br. s., 1H), 8.37 (s, 1H), 8.23-8.16 (m, 1H), 8.08 (dd, J = 1.7, 7.8 Hz, 1H), 7.93 (dd, J = 1.7, 7.6 Hz, 1H), 7.86 (t, J = 1.7 Hz, 1H), 7.74 (t, J = 7 .7 Hz, 1H), 7.67-7.53 (m, 2H), 6.99 (dd, J = 0.8, 1.9 Hz, 1H). MS-ESI (m/z) calc'd for C$_{19}$H$_{12}$BrN$_4$O$_2$ [M + H]$^+$: 407.0. Found 407.0. |

TABLE 1-continued

| Ex. No. | Structure/Name | Data |
|---|---|---|
| 89 | 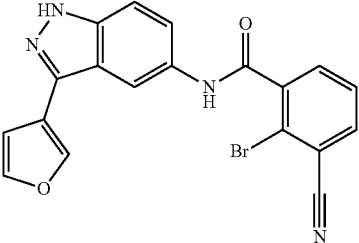 [SMILES: N#Cc1cccc(C(=O)Nc2ccc3[nH]nc(-c4ccoc4)c3c2)c1Br]<br>2-bromo-3-cyano-N-(3-(furan-3-yl)-1H-indazol-5-yl)benzamide | $^1$H NMR (400 MHz, DMSO-d$_6$) δ 13.16 (s, 1H), 10.42 (s, 1H), 8.19 (d, J = 6.6 Hz, 2H), 7.93 (d, J = 6.8 Hz, 1H), 7.87-7.78 (m, 2H), 7.54 (t, J = 7.7 Hz, 1H), 7.45 (s, 1H), 6.99 (s, 1H), 2.90 (s, 1H), 2.59 (s, 3H), 2.54 (s, 3H). MS-ESI (m/z) calc'd for C$_{21}$H$_{17}$N$_4$O$_2$ [M + H]$^+$: 357.1. Found 357.2. |
| 90 | 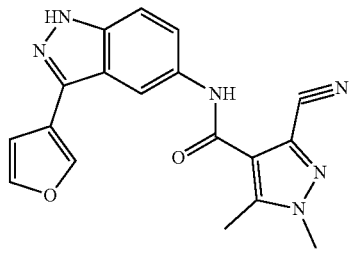 [SMILES: Cc1c(C(=O)Nc2ccc3[nH]nc(-c4ccoc4)c3c2)c(C#N)nn1C]<br>3-Cyano-N-(3-(furan-3-yl)-1H-indazol-5-yl)-1,5-dimethyl-1H-pyrazole-4-carboxamide | $^1$H NMR (400 MHz, DMSO-d$_6$) δ 13.10 (br s, 1H) 10.24 (s, 1H) 8.30 (s, 1H) 8.22 (s, 1H) 7.85 (t, J = 1.59 Hz, 1 H) 7.56 (s, 2H) 6.98 (d, J = 1.22 Hz, 1 H) 3.91 (s, 3H) 2.49 (br s, 3H). MS-ESI (m/z) calc'd for C$_{18}$H$_{15}$N$_6$O$_2$ [M + H]$^+$: 347.1. Found 347.1. |
| 91 | 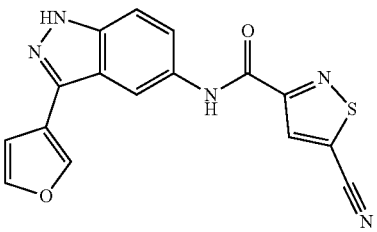 [SMILES: N#Cc1cc(C(=O)Nc2ccc3[nH]nc(-c4ccoc4)c3c2)ns1]<br>5-Cyano-N-(3-(furan-3-yl)-1H-indazol-5-yl)isothiazole-3-carboxamide | $^1$H NMR (400 MHz, DMSO-d$_6$) δ 8.67 (s, 1H), 8.49-8.39 (m, 1H), 8.25 (s, 1H), 7.93-7.81 (m, 2H), 7.57 (br d, J = 8.9 Hz, 1H), 7.04-6.98 (m, 1H). MS-ESI (m/z) calc'd for C$_{16}$H$_{10}$N$_5$O$_2$S [M + H]$^+$: 336.1. Found 336.1. |
| 92 | 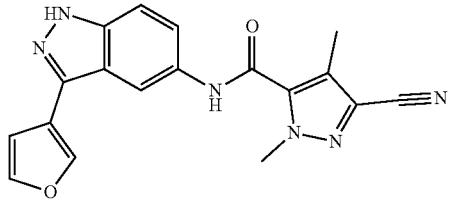 [SMILES: Cc1c(C#N)nn(C)c1C(=O)Nc1ccc2[nH]nc(-c3ccoc3)c2c1]<br>3-Cyano-N-(3-(furan-3-yl)-1H-indazol-5-yl)-1,4-dimethyl-1H-pyrazole-5-carboxamide | $^1$H NMR (400 MHz, DMSO-d$_6$) δ 13.15 (br s, 1H) 10.57 (br s, 1H) 8.36 (s, 1H) 8.25 (s, 1H) 7.86 (s, 1H) 7.55-7.68 (m, 2H) 7.00 (s, 1H) 4.06 (s, 3 H) 2.51 (br s, 3H). MS-ESI (m/z) calc'd for C$_{18}$H$_{15}$N$_6$O$_2$ [M + H]$^+$: 347.1. Found 347.1. |
| 93 | 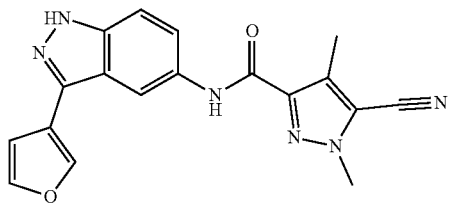 [SMILES: Cc1c(C(=O)Nc2ccc3[nH]nc(-c4ccoc4)c3c2)nn(C)c1C#N]<br>5-Cyano-N-(3-(furan-3-yl)-1H-indazol-5-yl)-1,4-dimethyl-1H-pyrazole-3-carboxamide | $^1$H NMR (400 MHz, DMSO-d$_6$) δ 13.04 (s, 1H), 10.23 (s, 1H) 8.37 (s, 1 H) 8.25 (s, 1H) 7.79-7.89 (m, 2H) 7.52 (d, J = 9.05 Hz, 1H) 7.00 (s, 1H) 4.10 (s, 3H) 2.42 (s, 3H). MS-ESI (m/z) calc'd for C$_{18}$H$_{15}$N$_6$O$_2$ [M + H]$^+$: 347.1. Found 347.1. |

TABLE 1-continued

| Ex. No. | Structure/Name | Data |
|---|---|---|
| 94 | 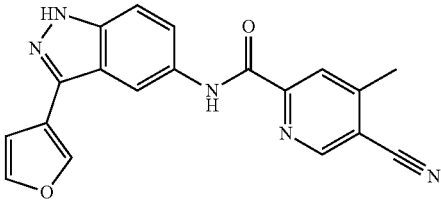 [SMILES: Cc1cc(C(=O)Nc2ccc3[nH]nc(-c4ccoc4)c3c2)ncc1C#N]<br>5-Cyano-N-(3-(furan-3-yl)-1H-indazol-5-yl)-4-methylpicolinamide | $^1$H NMR (400 MHz, DMSO-d$_6$) δ 13.10 (s, 1H), 10.81 (s, 1H), 9.11 (s, 1H), 8.50 (s, 1H), 8.29 (d, J = 9.7 Hz, 2H), 8.01 (br d, J = 8.9 Hz, 1H), 7.85 (s, 1H), 7.57 (d, J = 8.9 Hz, 1H), 7.02 (s, 1H), 2.65 (s, 3H). MS-ESI (m/z) calc'd for C$_{19}$H$_{14}$N$_5$O$_2$ [M + H]$^+$: 344.1. Found 344.2. |
| 95 | 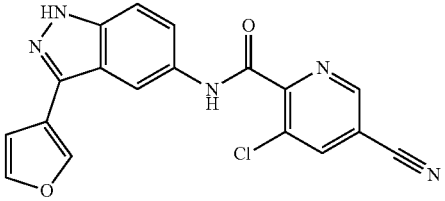 [SMILES: N#Cc1cnc(C(=O)Nc2ccc3[nH]nc(-c4ccoc4)c3c2)c(Cl)c1]<br>3-chloro-5-cyano-N-(3-(furan-3-yl)-1H-indazol-5-yl)picolinamide | $^1$H NMR (400 MHz, DMSO-d$_6$) δ 13.14 (s, 1H), 10.85 (s, 1H), 9.13 (d, J = 1.7 Hz, 1H), 8.82 (d, J = 1.7 Hz, 1H), 8.37 (dd, J = 1.9, 0.8 Hz, 1H), 8.22 (dd, J = 1.5, 0.8 Hz, 1H), 7.85 (t, J = 1.7 Hz, 1H), 7.67 (dd, J = 9.0, 1.9 Hz, 1H), 7.58 (dd, J = 8.9, 0.8 Hz, 1H), 6.99 (dd, J =1.8, 0.8 Hz, 1H). MS-ESI (m/z) calc'd for C$_{18}$H$_{11}$ClN$_5$O$_2$ [M + H]$^+$: 364.1. Found 364.0, 366.0. |
| 96 | 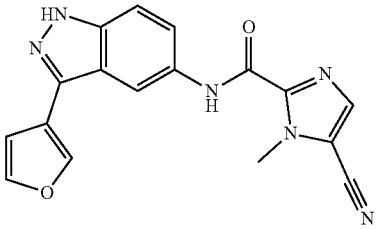 [SMILES: Cn1c(C#N)cnc1C(=O)Nc1ccc2[nH]nc(-c3ccoc3)c2c1]<br>5-Cyano-N-(3-(furan-3-yl)-1H-indazol-5-yl)-1-methyl-1H-imidazole-2-carboxamide | $^1$H NMR (400 MHz, DMSO-d$_6$) δ 13.08 (br s, 1H), 10.65 (br s, 1H), 8.41 (s, 1H), 8.26 (s, 1H), 8.04 (s, 1H), 7.88 (br d, J = 8.9 Hz, 1H), 7.84 (s, 1H), 7.55 (d, J = 9.0 Hz, 1H), 7.01 (s, 1H), 4.12 (s, 3H). MS-ESI (m/z) calc'd for C$_{17}$H$_{13}$N$_6$O$_2$ [M + H]$^+$: 333.1. Found 333.0. |
| 97 | 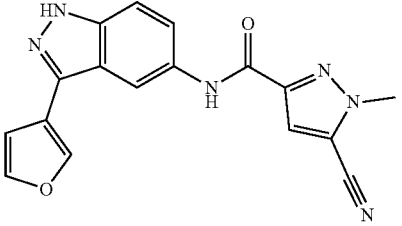 [SMILES: Cn1nc(C(=O)Nc2ccc3[nH]nc(-c4ccoc4)c3c2)cc1C#N]<br>5-Cyano-N-(3-(furan-3-yl)-1H-indazol-5-yl)-1-methyl-1H-pyrazole-3-carboxamide | $^1$H NMR (400 MHz, DMSO-d$_6$) δ 13.08 (s, 1H) 10.37 (s, 1H) 8.39 (s, 1 H) 8.25 (s, 1H) 7.80-7.88 (m, 2H) 7.65 (s, 1H) 7.53 (d, J = 9.04 Hz, 1H) 7.00 (s, 1H) 4.15 (s, 3H). MS-ESI (m/z calc'd for C$_{17}$H$_{13}$N$_6$O$_2$ [M + H]$^+$: 333.1. Found 333.0. |
| 98 | 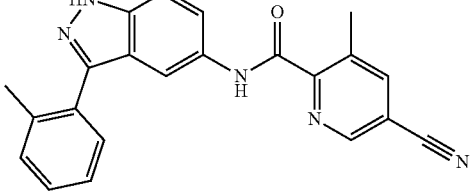<br>5-Cyano-3-methyl-N-(3-(o-tolyl)-1H-indazol-5-yl)picolinamide | $^1$H NMR (400 MHz, DMSO-d$_6$) δ 13.21 (br s, 1H), 10.72 (s, 1H), 8.97 (d, J = 1.1 Hz, 1H), 8.38 (s, 1H), 8.23 (s, 1H), 7.72 (dd, J = 1.5, 9.0 Hz, 1H), 7.59 (d, J = 9.0 Hz, 1H), 7.53-7.46 (m, 1H), 7.44-7.31 (m, 3H), 2.54 (s, 3H), 2.36 (s, 3H). MS-ESI (m/z) calc'd for C$_{22}$H$_{18}$N$_5$O [M + H]$^+$: 368.1. Found 368.1. |

TABLE 1-continued

| Ex. No. | Structure/Name | Data |
|---|---|---|
| 99 | 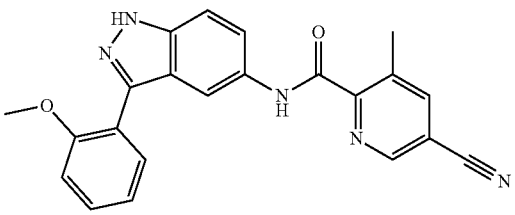 [SMILES: COc1ccccc1-c1n[nH]c2ccc(NC(=O)c3ncc(C#N)cc3C)cc12]

5-Cyano-N-(3-(2-methoxyphenyl)-1H-indazol-5-yl)-3-methylpicolinamide | $^1$H NMR (400 MHz, DMSO-d$_6$) δ 13.12 (br s, 1H) 10.65 (s, 1H) 8.97 (d, J = 0.98 Hz, 1H) 8.38 (s, 1H) 8.24 (s, 1H) 7.65 (dd, J = 8.93, 1.22 Hz, 1H) 7.53 (br d, J = 8.19 Hz, 2H) 7.41-7.47 (m, 1H) 7.20 (d, J = 8.31 Hz, 1H) 7.07 (t, J = 7.40 Hz, 1H) 3.82 (s, 3H) 2.54 (s, 3H). MS-ESI (m/z) calc'd for C$_{22}$H$_{18}$N$_5$O$_2$ [M + H]$^+$: 384.1. Found 384.1. |

Detailed methods for the preparation of Examples 28-99 are provided below:

Example 28: 5-Cyano-N-(3-(3,4-dimethylphenyl)-1H-indazol-5-yl)-3-methylpicolinamide

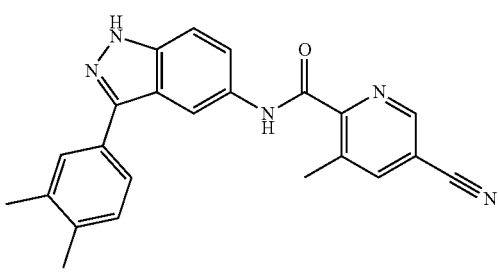 [SMILES: Cc1ccc(-c2n[nH]c3ccc(NC(=O)c4ncc(C#N)cc4C)cc23)cc1C]

5-Cyano-N-(3-iodo-1H-indazol-5-yl)-3-methylpicolinamide (70 mg, 0.170 mmol) was dissolved in 1,4-dioxane (3.53 mL). Then a solution of K$_3$PO$_4$ (110.56 mg, 0.52 mmol) and (3,4-dimethylphenyl)boronic acid (52.08 mg, 0.350 mmol) in water (0.882 mL) was added and the mixture was degassed with N$_2$ for 15 minutes. SPhos-Pd-G2 (12.51 mg, 0.020 mmol) was added and the mixture was stirred at 80° C., under N$_2$ atmosphere for 2 hrs. Then another portion of (3,4-dimethylphenyl)boronic acid (52.08 mg, 0.350 mmol) and SPhos-Pd-G2 (12.51 mg, 0.020 mmol) were added and stirring was continued at 80° C. for further 18 hrs. The mixture was diluted with water and then extracted with EtOAc. The phases were separated and the organic solvent was evaporated under reduced pressure. The residue (124 mg) was purified by semi-preparative HPLC (Method A) to afford the title compound (22.4 mg, 0.059 mmol, 34% yield) as a yellow solid. $^1$H NMR (400 MHz, DMSO-d$_6$) δ 13.15 (s, 1H), 10.75 (s, 1H), 9.01 (dd, J=2.0, 0.8 Hz, 1H), 8.62-8.51 (m, 1H), 8.41 (dd, J=2.0, 0.9 Hz, 1H), 7.82 (dd, J=8.9, 1.9 Hz, 1H), 7.74 (d, J=1.5 Hz, 1H), 7.67 (dd, J=7.7, 1.9 Hz, 1H), 7.58 (d, J=9.2 Hz, 1H), 7.30 (d, J=7.8 Hz, 1H), 2.59 (s, 3H), 2.34 (s, 3H), 2.30 (s, 3H). MS-ESI (m/z) calc'd for C$_{23}$H$_{20}$N$_3$O [M+H]$^+$: 382.2. Found 382.2.

Example 29: 5-Cyano-N-(3-(furan-2-yl)-1H-indazol-5-yl)-3-methylpicolinamide

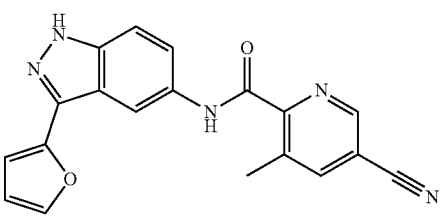 [SMILES: Cc1cc(C#N)cnc1C(=O)Nc1ccc2[nH]nc(-c3ccco3)c2c1]

5-Cyano-N-(3-iodo-1H-indazol-5-yl)-3-methylpicolinamide (70.0 mg, 0.170 mmol) was dissolved in 1,4-dioxane (3.53 mL). Then a solution of K$_3$PO$_4$ (110.56 mg, 0.520 mmol) and (furan-2-yl)boronic acid (38.85 mg, 0.350 mmol) in water (0.882 mL) was added and the mixture was degassed with N$_2$ for 15 minutes. SPhos-Pd-G2 (12.51 mg, 0.020 mmol) was added and the mixture was stirred at 80° C. under N$_2$ atmosphere for 3 hrs. Water was added and the mixture was extracted with EtOAc. The phases were separated and the organic solvent was evaporated under reduced pressure. The residue was purified by column chromatography (SiO$_2$, acetone in DCM [0%, 50%, 6 CV]). The appropriate fractions were collected and concentrated under reduced pressure. The residue was triturated with MeCN (1 mL) and then the solid was taken up in 1 mL of water and then concentrated and dried to obtain the product (37.1 mg, 0.108 mmol, 62.24% yield) as a yellow solid, which was further purified by reverse phase column chromatography (Cis-cartridge, MeCN in H$_2$O+0.1% HCOOH, [2%, 30%, 7 CV]) to afford the title compound (19.2 mg, 0.056 mmol, 32% yield) as a yellow solid. $^1$H NMR (400 MHz, DMSO-d$_6$) δ 13.26 (s, 1H), 10.76 (s, 1H), 9.00 (d, J=1.9 Hz, 1H), 8.69-8.57 (m, 1H), 8.41 (dd, J=2.0, 0.9 Hz, 1H), 7.87 (dd, J=1.8, 0.8 Hz, 1H), 7.76 (dd, J=9.0, 1.9 Hz, 1H), 7.61-7.52 (m, 1H), 6.90 (dd, J=3.4, 0.8 Hz, 1H), 6.69 (dd, J=3.4, 1.8 Hz, 1H), 2.60 (s, 3H). MS-ESI (m/z) calc'd for C$_{19}$H$_{14}$N$_5$O$_2$ [M+H]$^+$: 344.1. Found 344.1.

Example 30: 5-Cyano-N-(3-(3-(dimethylamino) phenyl)-1H-indazol-5-yl)-3-methylpicolinamide

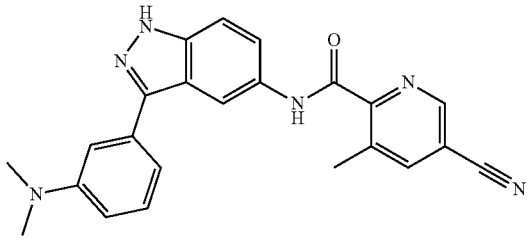 [SMILES: Cc1cc(C#N)cnc1C(=O)Nc1ccc2[nH]nc(-c3cccc(N(C)C)c3)c2c1]

5-Cyano-N-(3-iodo-1H-indazol-5-yl)-3-methylpicolinamide (70.0 mg, 0.170 mmol) was dissolved in 1,4-dioxane (3.529 mL). Then a solution of $K_3PO_4$ (110.56 mg, 0.520 mmol) and [3-(dimethylamino)phenyl]boronic acid (57.29 mg, 0.350 mmol) in water (0.882 mL) was added and the mixture was degassed with $N_2$ for 15 minutes. SPhos-Pd-G2 (12.51 mg, 0.020 mmol) was added and the mixture was stirred at 80° C., under $N_2$ atmosphere, for 18 hrs. Water was added and the mixture was extracted with EtOAc. The phases were separated and the organic solvent was evaporated under reduced pressure. The residue (130 mg) was purified by semi-preparative HPLC (Method B). The batch obtained (26.1 mg) was further purified by reverse phase column chromatography ($C_{18}$-cartridge, MeCN in $H_2O$+ 0.1% HCOOH, [2%, 100%, 7 CV]) to afford the title compound (14.1 mg, 0.036 mmol, 20% yield) as a yellow solid. $^1$H NMR (400 MHz, DMSO-$d_6$) δ 13.14 (s, 1H), 10.76 (s, 1H), 9.00 (d, J=1.9 Hz, 1H), 8.69 (d, J=1.8 Hz, 1H), 8.41 (dd, J=2.0, 0.9 Hz, 1H), 7.75 (dd, J=9.0, 1.9 Hz, 1H), 7.58 (d, J=8.9 Hz, 1H), 7.35 (t, J=7.9 Hz, 1H), 7.29 (dd, J=2.6, 1.4 Hz, 1H), 7.24 (dt, J=7.6, 1.2 Hz, 1H), 6.80 (ddd, J=8.4, 2.8, 1.0 Hz, 1H), 3.00 (s, 6H), 2.58 (s, 3H). MS-ESI (m/z) calc'd for $C_{23}H_{21}N_6O$ [M+H]$^+$: 397.2. Found 397.2.

Example 31: 5-Cyano-3-methyl-N-(3-(pyridin-4-yl)-1H-indazol-5-yl)picolinamide

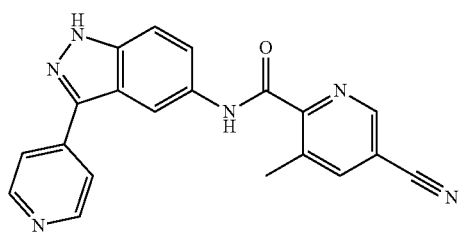 [SMILES: Cc1cc(C#N)cnc1C(=O)Nc1ccc2[nH]nc(-c3ccncc3)c2c1]

5-Cyano-N-(3-iodo-1H-indazol-5-yl)-3-methylpicolinamide (70.0 mg, 0.170 mmol) was dissolved in 1,4-dioxane (3.294 mL). Then a solution of $K_3PO_4$ (110.56 mg, 0.520 mmol) and pyridin-4-ylboronic acid (32.01 mg, 0.260 mmol) in water (0.824 mL) was added and the mixture was degassed with $N_2$ for 15 minutes. SPhos-Pd-G2 (12.51 mg, 0.020 mmol) was added and the mixture was stirred at 80° C., under $N_2$ atmosphere for 2 hrs. Then, additional pyridin-4-ylboronic acid (60 mg) and SPhos-Pd-G2 (12.51 mg, 0.020 mmol) were added and the reaction was left stirring under $N_2$ atmosphere at 80° C. for 18 hrs. Water was added and the mixture was extracted with EtOAc. The organic phase was separated, dried over $Na_2SO_4$, filtered and concentrated under reduced pressure. The residue (90 mg) was purified by semi-preparative HPLC (Method R) to afford the formic acid salt of the title compound (10.2 mg, 0.025 mmol, 15% yield) as a yellow solid. $^1$H NMR (400 MHz, DMSO-$d_6$) δ 13.62 (s, 1H), 10.82 (s, 1H), 9.02 (d, J=1.9 Hz, 1H), 8.76-8.69 (m, 3H), 8.43 (dd, J=2.0, 0.9 Hz, 1H), 8.20 (s, 1H), 7.98-7.93 (m, 2H), 7.88 (dd, J=9.0, 1.9 Hz, 1H), 7.67 (d, J=9.0 Hz, 1H), 2.62 (s, 3H). MS-ESI (m/z) calc'd for $C_{20}H_{15}N_6O$ [M+H]$^+$: 355.1. Found 355.2.

Example 32: 5-Cyano-N-(3-(1-(difluoromethyl)-1H-pyrazol-4-yl)-1H-indazol-5-yl)-3-methylpicolinamide

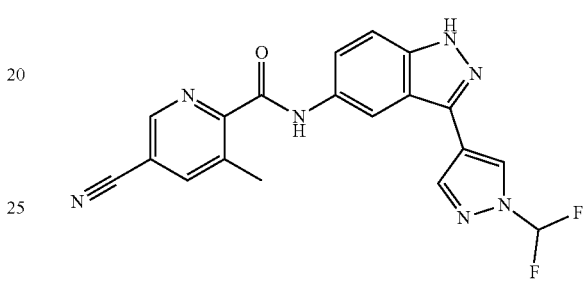

Prepared as described for 5-cyano-3-methyl-N-(3-(3-(methylsulfonyl)phenyl)-1H-indazol-5-yl)picolinamide using (1-(difluoromethyl)-1H-pyrazol-4-yl)boronic acid in place of 3-(methylsulfonyl)phenyl)boronic acid. $^1$H NMR (400 MHz, DMSO-$d_6$) δ 13.20 (s, 1H) 10.73 (s, 1H) 9.01 (d, J=1.35 Hz, 1H) 8.74 (s, 1H) 8.43 (dd, J=9.48, 1.28 Hz, 2H) 8.30 (s, 1H) 7.78-8.09 (m, 2H) 7.58 (d, J=8.93 Hz, 1H) 2.61 (s, 3H). MS-ESI (m/z) calc'd for $C_{19}H_{14}F_2N_7O$ [M+H]$^+$: 394.1. Found 394.2.

Example 33: 5-cyano-3-methyl-N-(3-(1-(tetrahydro-2H-pyran-4-yl)-1H-pyrazol-4-yl)-1H-indazol-5-yl)picolinamide

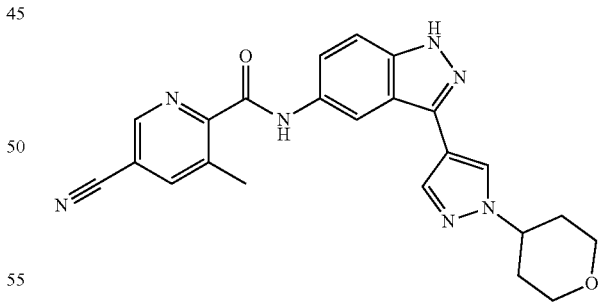

Prepared as described for 5-cyano-3-methyl-N-(3-(3-(methylsulfonyl)phenyl)-1H-indazol-5-yl)picolinamide using (1-(tetrahydro-2H-pyran-4-yl)-1H-pyrazol-4-yl)boronic acid in place of 3-(methylsulfonyl)phenyl)boronic acid. $^1$H NMR (400 MHz, DMSO-$d_6$) δ 12.97 (s, 1H) 10.69 (s, 1H) 9.01 (d, J=1.47 Hz, 1H) 8.40-8.46 (m, 2H) 8.31 (s, 1H) 7.97 (s, 1H) 7.80-7.84 (m, 1H) 7.54 (d, J=8.93 Hz, 1H) 4.49-4.58 (m, 1H) 3.98-4.03 (m, 2H) 3.47-3.54 (m, 2H) 2.61 (s, 3H) 2.02-2.08 (m, 4H). MS-ESI (m/z) calc'd for $C_{23}H_{22}N_7O_2$ [M+H]$^+$: 428.2. Found 428.1.

Example 34: 5-Cyano-3-methyl-N-(3-(3-(methylsulfonyl)phenyl)-1H-indazol-5-yl)picolinamide

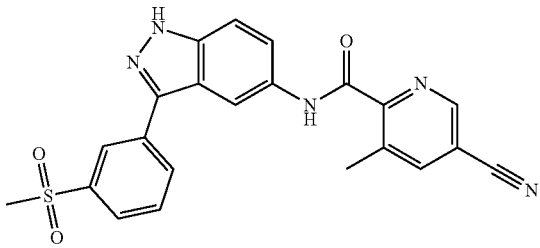 [SMILES: Cc1cc(C#N)cnc1C(=O)Nc1ccc2[nH]nc(-c3cccc(S(C)(=O)=O)c3)c2c1]

Step 1: N-(3-bromo-1H-indazol-5-yl)-5-cyano-3-methylpicolinamide

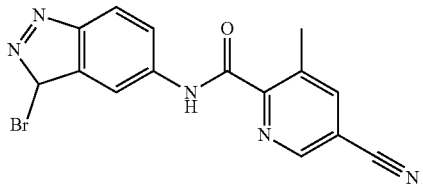 [SMILES: Cc1cc(C#N)cnc1C(=O)Nc1ccc2c(c1)C(Br)N=N2]

To a solution of 3-bromo-1H-indazol-5-amine (1.96 g, 9.25 mmol) and 5-cyano-3-methylpicolinic acid (1.5 g, 9.25 mmol) in pyridine (45 mL) was added EDCI (2.66 g, 13.88 mmol). The mixture was stirred at 25° C. for 12 hrs and monitored by TLC (petroleum ether:EtOAc=1:1, Rf=0.43). The reaction mixture was concentrated to give a residue. The residue was diluted with MeOH (300 mL) and filtered. The solid was washed with MeOH (200 mL) and dried to afford the title compound (2.5 g) as a white solid which was used without further purification.

Step 2: 5-Cyano-3-methyl-N-(3-(3-(methylsulfonyl)phenyl)-1H-indazol-5-yl)picolinamide

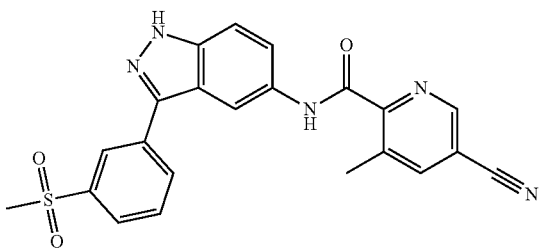 [SMILES: Cc1cc(C#N)cnc1C(=O)Nc1ccc2[nH]nc(-c3cccc(S(C)(=O)=O)c3)c2c1]

A mixture of N-(3-bromo-1H-indazol-5-yl)-5-cyano-3-methylpicolinamide (70 mg, 197 umol), (3-(methylsulfonyl)phenyl)boronic acid (47 mg, 236 umol), Pd(Amphos)Cl$_2$ (14 mg, 20 umol) and AcOK (58 mg, 590 umol) in EtOH (2 mL) and H$_2$O (0.5 mL) was degassed and purged with N$_2$ (3×). The mixture was then stirred at 100° C. for 12 hrs under N$_2$ atmosphere. The reaction mixture was concentrated under reduced pressure to remove solvent and the residue was purified by preparative HPLC (Method AH) to afford the title compound (49 mg, 88 umol, 45% yield, TFA salt) as a yellow solid. $^1$H NMR (400 MHz, DMSO-d$_6$) δ 13.50 (s, 1H), 10.83 (s, 1H), 9.01 (d, J=1.5 Hz, 1H), 8.60 (s, 1H), 8.46 (s, 1H), 8.41 (d, J=1.2 Hz, 1H), 8.29 (d, J=7.8 Hz, 1H), 7.97 (d, J=8.1 Hz, 1H), 7.89-7.83 (m, 2H), 7.65 (d, J=9.0 Hz, 1H), 3.31 (s, 3H), 2.59 (s, 3H). MS-ESI (m/z) calc'd for C$_{22}$H$_{15}$N$_5$O$_2$S [M+H]$^+$: 432.1. Found 432.0.

Example 35: 5-Cyano-3-methyl-N-(3-(4-(trifluoromethyl)phenyl)-1H-indazol-5-yl)picolinamide

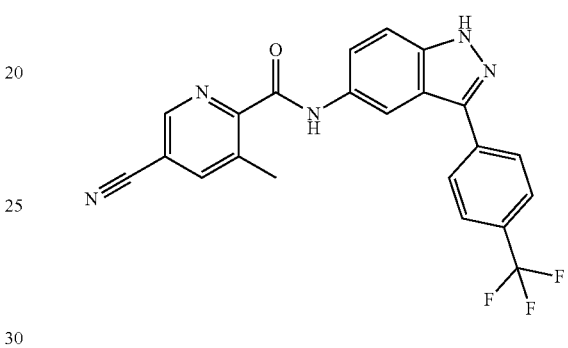

Prepared as described for 5-cyano-3-methyl-N-(3-(3-(methylsulfonyl)phenyl)-1H-indazol-5-yl)picolinamide using (4-(trifluoromethyl)phenyl)boronic acid in place of 3-(methylsulfonyl)phenyl)boronic acid. $^1$H NMR (400 MHz, DMSO-d$_6$) δ 13.50 (s, 1H), 10.81 (s, 1H), 9.01 (d, J=1.6 Hz, 1H), 8.66 (s, 1H), 8.41 (d, J=1.2 Hz, 1H), 8.18 (d, J=8.1 Hz, 2H), 7.91 (d, J=8.4 Hz, 2H), 7.84 (dd, J=1.7, 9.0 Hz, 1H), 7.64 (d, J=8.9 Hz, 1H), 2.60 (s, 3H). MS-ESI (m/z) calc'd for C$_{22}$H$_{15}$F$_3$N$_5$O [M+H]$^+$: 422.1. Found 422.0.

Example 36: 5-Cyano-3-methyl-N-(3-(5-methylisoxazol-4-yl)-1H-indazol-5-yl)picolinamide

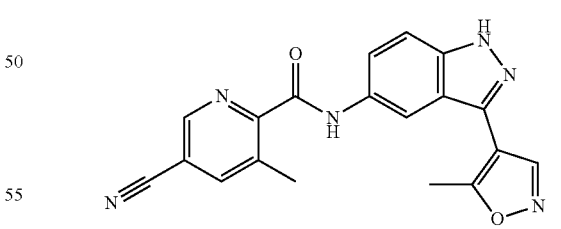

Prepared as described for 5-cyano-3-methyl-N-(3-(3-(methylsulfonyl)phenyl)-1H-indazol-5-yl)picolinamide using (5-methylisoxazol-4-yl)boronic acid in place of 3-(methylsulfonyl)phenyl)boronic acid. $^1$H NMR (400 MHz, DMSO-d$_6$) δ 13.32 (s, 1H) 10.75 (s, 1H) 9.00 (s, 2H) 8.40 (dd, J=11, 1 Hz, 2H) 7.85 (dd, J=9, 2 Hz, 1H) 7.61 (d, J=9 Hz, 1H) 2.71 (s, 3H) 2.60 (s, 3H). MS-ESI (m/z) calc'd for C$_{19}$H$_{11}$N$_6$O$_2$[M+H]$^+$: 359.1. Found 359.0.

Example 37: 5-Cyano-3-methyl-N-(3-(5-morpholinopyridin-3-yl)-1H-indazol-5-yl)picolinamide

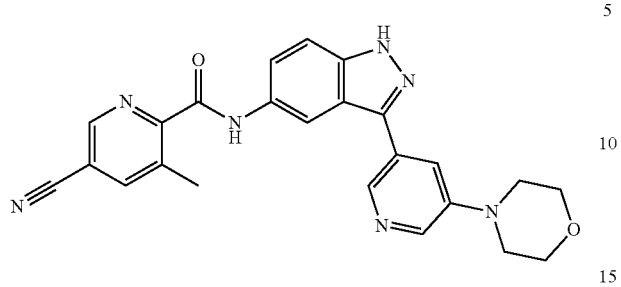

Prepared as described for 5-cyano-3-methyl-N-(3-(3-(methylsulfonyl)phenyl)-1H-indazol-5-yl)picolinamide using (5-morpholinopyridin-3-yl)boronic acid in place of 3-(methylsulfonyl)phenyl)boronic acid. $^1$H NMR (400 MHz, DMSO-$d_6$) δ 13.39 (br s, 1H), 10.79 (s, 1H), 9.00 (d, J=1.1 Hz, 1H), 8.66 (s, 1H), 8.61 (d, J=1.1 Hz, 1H), 8.44-8.35 (m, 2H), 7.84 (dd, J=1.2, 8.9 Hz, 1H), 7.75 (br s, 1H), 7.62 (d, J=9.0 Hz, 1H), 3.83-3.76 (m, 4H), 3.31-3.23 (m, 4H), 2.59 (s, 3H). MS-ESI (m/z) calc'd for $C_{24}H_{22}N_7O_2$ [M+H]$^+$: 440.2. Found 440.1.

Example 38: 5-Cyano-N-(3-(6-isopropoxypyridin-3-yl)-1H-indazol-5-yl)-3-methylpicolinamide

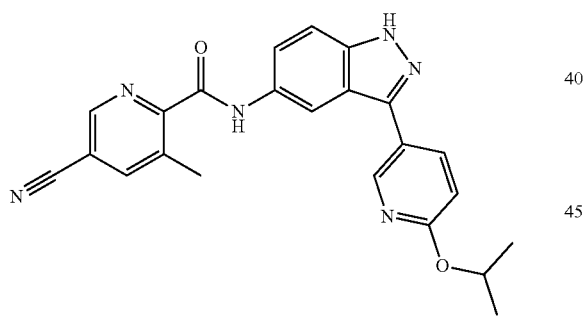

Prepared as described for 5-cyano-3-methyl-N-(3-(3-(methylsulfonyl)phenyl)-1H-indazol-5-yl)picolinamide using (6-isopropoxypyridin-3-yl)boronic acid in place of 3-(methylsulfonyl)phenyl)boronic acid. $^1$H NMR (400 MHz, DMSO-$d_6$) δ 13.26 (br s, 1H), 10.77 (s, 1H), 9.00 (d, J=1.3 Hz, 1H), 8.72 (d, J=2.4 Hz, 1H), 8.62 (s, 1H), 8.41 (d, J=1.1 Hz, 1H), 8.20 (dd, J=2.4, 8.6 Hz, 1H), 7.82 (dd, J=1.8, 9.0 Hz, 1H), 7.59 (d, J=8.8 Hz, 1H), 6.93 (d, J=8.6 Hz, 1H), 5.34 (quin, J=6.2 Hz, 1H), 2.60 (s, 3H), 1.34 (d, J=6.2 Hz, 6H). MS-ESI (m/z) calc'd for $C_{23}H_{21}N_6O_2$[M+H]$^+$: 413.2. Found 413.0.

Example 39: 5-Cyano-N-(3-(furan-3-yl)-1H-indazol-5-yl)-4-hydroxypicolinamide

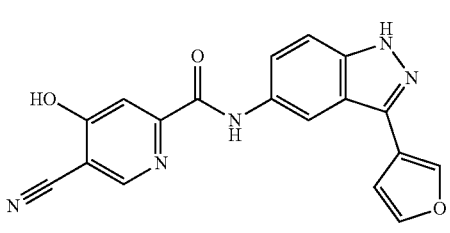 [SMILES: N#Cc1cnc(C(=O)Nc2ccc3[nH]nc(-c4ccoc4)c3c2)cc1O]

Step 1: 5-Bromo-4-chloro-N-(3-(furan-3-yl)-1H-indazol-5-yl)picolinamide

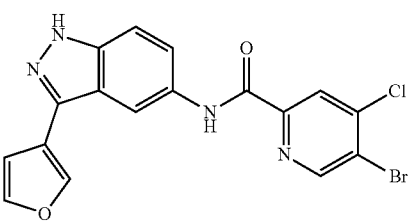 [SMILES: O=C(Nc1ccc2[nH]nc(-c3ccoc3)c2c1)c1cc(Cl)c(Br)cn1]

To a solution of 5-bromo-4-chloropicolinic acid (50 mg, 211.46 umol) and 3-(furan-3-yl)-1H-indazol-5-amine (42.12 mg, 211.46 umol) in pyridine (2 mL) was added EDCI (60.81 mg, 317.19 umol). The reaction mixture was stirred at 25° C. for 12 hrs. The reaction mixture was poured into water (5 mL) and extracted with dichloromethane (5 mL×3). The combined organic phases were washed with brine (5 mL×1), dried over anhydrous $Na_2SO_4$, filtered and concentrated. The residue was purified by column chromatography ($SiO_2$, petroleum ether/EtOAc=20/1 to 0/1) to afford the title compound (60 mg, 144 umol, 68% yield) as a green solid.

Step 2: 4-Chloro-5-cyano-N-(3-(furan-3-yl)-1H-indazol-5-yl))picolinamide

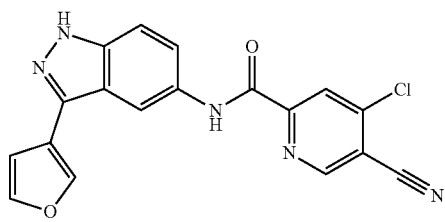 [SMILES: N#Cc1cnc(C(=O)Nc2ccc3[nH]nc(-c4ccoc4)c3c2)cc1Cl]

To a solution of 5-bromo-4-chloro-N-(3-(furan-3-yl)-1H-indazol-5-yl)picolinamide (60 mg, 143.66 umol) and $Zn(CN)_2$ (8.43 mg, 71.83 umol) in DMF (2 mL) was added Pd(PPh$_3$)$_4$ (16.60 mg, 14.37 umol). The reaction mixture was stirred at 150° C. for 1 hr under $N_2$. The reaction mixture was filtered and the filtrate was concentrated. The residue was purified by preparative HPLC under neutral conditions (Method U) and further purified by preparative HPLC under TFA conditions (Method V) to afford the title compound (8.37 mg, 17.48 umol, 12% yield, TFA salt) as a yellow solid.

Step 3: 5-Cyano-N-(3-(furan-3-yl)-1H-indazol-5-yl)-4-hydroxypicolinamide

To a solution of 4-chloro-5-cyano-N-(3-(furan-3-yl)-1H-indazol-5-yl)picolinamide (70 mg, 146 umol, TFA salt) in DMSO (3 mL) was added CsF (67 mg, 439 umol, 16 uL). The reaction mixture was stirred at 120° C. for 12 hrs. The reaction mixture was filtered and the filtrate was concentrated. The residue was purified by preparative HPLC (Method W) to afford the title compound (5.98 mg, 17 umol, 12% yield) as a yellow solid. $^1$H NMR (400 MHz, DMSO-$d_6$) δ 13.09 (s, 1H), 10.61 (s, 1H), 8.48 (s, 1H), 8.43 (s, 1H), 8.30 (s, 1H), 7.90 (br d, J=8.9 Hz, 1H), 7.84 (t, J=1.7 Hz, 1H), 7.55 (d, J=8.9 Hz, 1H), 7.26 (s, 1H), 7.01 (d, J=1.1 Hz, 1H). MS-ESI (m/z) calc'd for $C_{11}H_{19}N_5O_3$ [M+H]$^+$: 345.1. Found 345.5.

Example 40: 5-Cyano-3-methyl-N-(3-phenyl-1H-indazol-5-yl)picolinamide

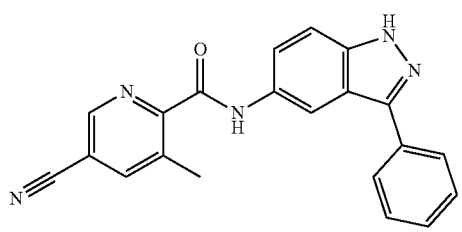 [SMILES: Cc1cc(C#N)cnc1C(=O)Nc1ccc2[nH]nc(-c3ccccc3)c2c1]

Prepared as described for 5-cyano-3-methyl-N-(3-(3-(methylsulfonyl)phenyl)-1H-indazol-5-yl)picolinamide using phenylboronic acid in place of 3-(methylsulfonyl)phenyl)boronic acid. $^1$H NMR (400 MHz, DMSO-$d_6$) δ 10.76 (br s, 1H), 8.99 (d, J=1.4 Hz, 1H), 8.62 (d, J=1.3 Hz, 1H), 8.41-8.38 (m, 1H), 7.99-7.93 (m, 2H), 7.80 (dd, J=1.8, 8.9 Hz, 1H), 7.63-7.51 (m, 3H), 7.45-7.38 (m, 1H), 2.59 (s, 3H). MS-ESI (m/z) calc'd for $C_{21}H_{16}N_5O$ [M+H]$^+$: 354.1. Found 354.1.

Example 41: 5-Cyano-N-(3-(3-cyanophenyl)-1H-indazol-5-yl)-3-methylpicolinamide

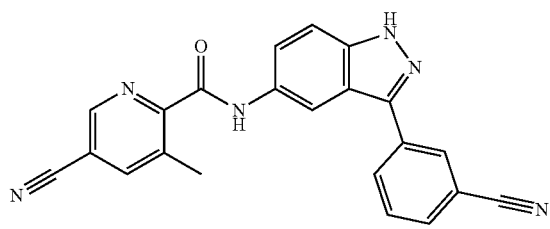 [SMILES: Cc1cc(C#N)cnc1C(=O)Nc1ccc2[nH]nc(-c3cccc(C#N)c3)c2c1]

Prepared as described for 5-cyano-3-methyl-N-(3-(3-(methylsulfonyl)phenyl)-1H-indazol-5-yl)picolinamide using (3-cyanophenyl)boronic acid in place of 3-(methylsulfonyl)phenyl)boronic acid. $^1$H NMR (400 MHz, DMSO-$d_6$) δ 13.49 (br s, 1H), 10.81 (s, 1H), 9.01 (s, 1H), 8.58 (s, 1H), 8.42 (s, 1H), 8.35-8.26 (m, 2H), 7.91 (br dd, J=8.4, 17.3 Hz, 2H), 7.82-7.72 (m, 1H), 7.64 (br d, J=8.9 Hz, 1H), 2.60 (s, 3H). MS-ESI (m/z) calc'd for $C_{22}H_{15}N_6O$ [M+H]$^+$: 379.1. Found 379.1.

Example 42: 5-Cyano-N-(3-(5-cyanopyridin-3-yl)-1H-indazol-5-yl)-3-methylpicolinamide

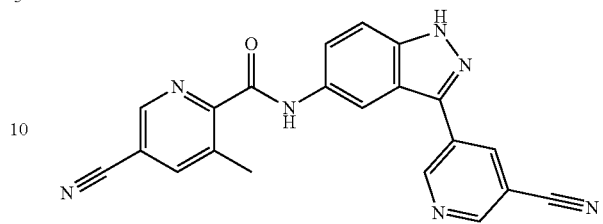

Prepared as described for 5-cyano-3-methyl-N-(3-(3-(methylsulfonyl)phenyl)-1H-indazol-5-yl)picolinamide using (5-cyanopyridin-3-yl)boronic acid in place of 3-(methylsulfonyl)phenyl)boronic acid. $^1$H NMR (400 MHz, DMSO-$d_6$) δ 13.68 (s, 1H), 10.82 (s, 1H), 9.43 (d, J=2.0 Hz, 1H), 9.06 (d, J=1.8 Hz, 1H), 9.01 (d, J=1.3 Hz, 1H), 8.75 (t, J=2.0 Hz, 1H), 8.61 (s, 1H), 8.42 (s, 1H), 7.96 (dd, J=1.5, 9.0 Hz, 1H), 7.67 (d, J=9.0 Hz, 1H), 2.61 (s, 3H). MS-ESI (m/z) calc'd for $C_{21}H_{14}N_7O$ [M+H]$^+$: 380.1. Found 380.1.

Example 43: 2-Cyano-1,4-dimethyl-N-(3-phenyl-1H-indazol-5-yl)-1H-imidazole-5-carboxamide

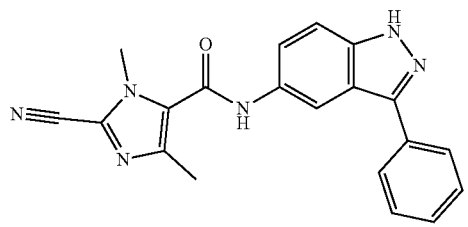 [SMILES: Cc1nc(C#N)n(C)c1C(=O)Nc1ccc2[nH]nc(-c3ccccc3)c2c1]

Step 1: Ethyl 1,4-dimethyl-1H-imidazole-5-carboxylate

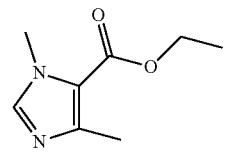

To a solution of NaH (778.38 mg, 19.46 mmol, 60% purity) in DMF (25 mL) was added ethyl 5-methyl-1H-imidazole-4-carboxylate (2 g, 12.97 mmol) at 0° C. The mixture was stirred at 0° C. for 1 hr; MeI (2.76 g, 19.46 mmol, 1.21 mL) was then added at 0° C. The mixture was stirred at 25° C. for 12 hrs and monitored by TLC (CHCl$_2$:MeOH=10:1). The reaction mixture was quenched by addition of 10 mL of H$_2$O at 20° C. The mixture was then concentrated under reduced pressure to remove solvent. Then the mixture diluted with H$_2$O (30 mL) and extracted with EtOAc (50 mL×8). The combined organic layers were dried over Na$_2$SO$_4$, filtered and concentrated under reduced pressure to give a residue. The residue was purified by column chromatography (SiO$_2$, petroleum ether/MeOH=1/0 to 0/1) to afford ethyl 1,5-dimethyl-1H-imidazole-4-carboxylate (1.8 g, 3.83 mmol, 30%/a yield) as an orange solid and the title compound (500 mg, 2.97 mmol, 23% yield) as a yellow oil.

Step 2: Ethyl 2-bromo-1,4-dimethyl-1H-imidazole-5-carboxylate

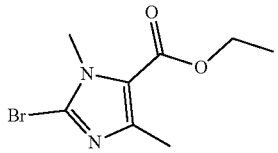

To a solution of ethyl 1,4-dimethyl-1H-imidazole-5-carboxylate (500 mg, 2.97 mmol) in CH$_3$CN (15 mL) was added NBS (635 mg, 3.57 mmol). The mixture was stirred at 20° C. for 12 hrs and monitored by TLC (petroleum ether:EtOAc=5:1, Rf=0.50). The reaction mixture was concentrated under reduced pressure to remove solvent and purified by column chromatography (SiO$_2$, petroleum ether/EtOAc=1/0 to 10/1) to afford the title compound (160 mg, 647 umol, 22% yield) as a yellow solid.

Step 3: Ethyl 2-cyano-1,4-dimethyl-1H-imidazole-5-carboxylate

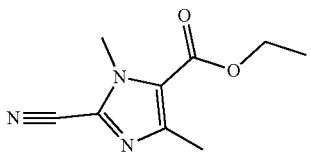

A mixture of ethyl 2-bromo-1,4-dimethyl-1H-imidazole-5-carboxylate (160 mg, 648 umol), Zn (5 mg, 78 umol), Zn(CN)$_2$ (46 mg, 388 umol), dppf (14.36 mg, 26 umol) and Pd$_2$(dba)$_3$ (11.86 mg, 13 umol) in DMA (4 mL) was degassed and purged with N$_2$ (3x). The reaction mixture was stirred at 120° C. for 3 hrs under N$_2$ atmosphere and monitored by TLC (petroleum ether:EtOAc=1:1, Rf=0.71). The reaction mixture was diluted with 20 mL H$_2$O and extracted with EtOAc (20 mL×3). The combined organic phases were dried with Na$_2$SO$_4$ and concentrated under reduced pressure to give a residue. The residue was purified by preparative TLC (SiO$_2$, petroleum ether:EtOAc=1:1, Rf=0.71) to afford the title compound (55 mg, 219 umol, 34% yield) as a yellow solid.

Step 4: 2-Ethynyl-1,4-dimethyl-1H-imidazole-5-carboxylic acid

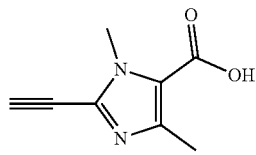

To solution of ethyl 2-cyano-1,4-dimethyl-1H-imidazole-5-carboxylate (50 mg, 259 umol) in THF (3 mL) was added a solution of LiOH.H$_2$O (21.72 mg, 518 umol) in H$_2$O (1 mL) at 0° C. The mixture was stirred at 0° C. for 1 hr and monitored by TLC (petroleum ether:EtOAc=1:1). Water (2 mL) was added and the reaction mixture was extracted with EtOAc (3 mL×4). The organic layer was discarded. The aqueous phase was then acidified with 1N HCl to pH=1 and extracted with EtOAc (3 mL×4). This organic layer was dried over anhydrous Na$_2$SO$_4$, filtered and the filtrate was concentrated under vacuum to afford the title compound (40 mg) as a white solid which was used without further purification.

Step 5: 2-Cyano-1,4-dimethyl-N-(3-phenyl-1H-indazol-5-y)-1H-imidazole-5-carboxamide To a solution of 2-ethynyl-1,4-dimethyl-1H-imidazole-5-carboxylic acid (40 mg, 242.21 umol) and 3-phenyl-1H-indazol-5-amine (50.68 mg, 242 umol) in DMF (2 mL) was added DIEA (93.91 mg, 726.62 umol), EDCI (55.72 mg, 290 umol) and HOBt (39.27 mg, 290 umol). The mixture was stirred at 20° C. for 12 hrs. The reaction mixture was concentrated under reduced pressure to remove solvent and purified by preparative HPLC (Method AH) to afford the title compound (23 mg, 49 umol, 20% yield, TFA salt) as a white solid. $^1$H NMR (400 MHz, DMSO-d$_6$) δ 13.28 (br s, 1H), 10.48 (s, 1H), 8.52 (s, 1H), 7.95-7.92 (m, 2H), 7.66-7.60 (m, 2H), 7.55 (t, J=7.6 Hz, 2H), 7.44-7.40 (m, 1H), 3.91 (s, 3H), 2.38 (s, 3H). MS-ESI (m/z) calc'd for C$_{20}$H$_{17}$N$_6$O [M+H]$^+$: 357.1. Found 357.1.

Example 44: 5-Cyano-N-(3-(furan-3-yl)-1H-indazol-5-yl)-3,6-dimethylpicolinamide

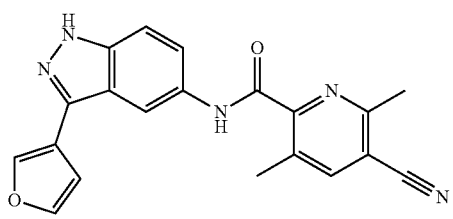 [SMILES: Cc1cc(C#N)c(C)nc1C(=O)Nc1ccc2[nH]nc(-c3ccoc3)c2c1]

Step 1: 3-Bromo-2,5-dimethyl-6-vinylpyridine

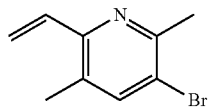

A solution of 2,5-dibromo-3,6-dimethylpyridine (1.32 g, 5 mmol) and tributyl(vinyl)tin (1.46 mL, 5 mmol) in toluene (25 mL) was sparged with N$_2$ for 10 minutes. Tetrakis(triphenylphosphine)palladium(0) (0.29 g, 0.250 mmol) was then added and the mixture was stirred at 100° C. under N$_2$ for 3 hrs. The solvent was evaporated and the residue was purified by column chromatography (SiO$_2$, 25 g, EtOAc in cyclohexane [0%, 10%, 10 CV]) to afford the title compound (1.06 g, 5 mmol, 100% yield) as a clear oil. $^1$H NMR (400 MHz, DMSO-d$_6$) δ 7.83 (s, 1H), 6.95 (dd, J=16.9, 10.6 Hz, 1H), 6.28 (dd, J=16.9, 2.5 Hz, 1H), 5.49 (dd, J=10.7, 2.5 Hz, 1H), 2.53 (s, 3H), 2.29 (d, J=1.1 Hz, 3H). MS-ESI (m/z) calc'd for $C_9H_{11}BrN$ [M+H]$^+$: 212.0, 214.0. Found 211.9, 213.9.

Step 2: 5-Bromo-3,6-dimethylpicolinic acid

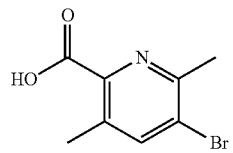

To a solution of 5-bromo-2-ethenyl-3,6-dimethylpyridine (1.06 g, 5 mmol) in acetone (25 mL) was added a solution of potassium permanganate (1.74 g, 11 mmol) in water (25 mL) and the mixture was stirred at 25° C. for 2 days. Excess permanganate was quenched by addition of formic acid and the solid was filtered and dried. The solid was taken up in water and extracted with EtOAc (3×). The combined organic layers were passed through a phase separator and evaporated to afford the title compound (900 mg, 3.912 mmol, 78% yield) as a white solid. $^1$H NMR (400 MHz, DMSO-d$_6$) δ 13.22 (s, 1H), 8.01 (s, 1H), 2.55 (s, 3H), 2.39 (s, 3H). MS-ESI (m/z) calc'd for $C_8H_9BrNO_2$ [M+H]$^+$: 230.0, 232.0. Found 229.9, 231.9.

Step 3: Methyl 5-bromo-3,6-dimethylpicolinate

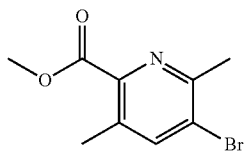

To a solution of 5-bromo-3,6-dimethylpicolinic acid (900.0 mg, 3.91 mmol) in DMF (6.52 mL) was added potassium carbonate (1.62 g, 11.74 mmol) and iodomethane (0.49 mL, 7.82 mmol). The mixture was stirred at 80° C. for 1 hr and then poured into water (150 mL) and stirred for 10 minutes. The solid formed was filtered and dried under vacuum to afford the title compound (833 mg, 3.413 mmol, 87% yield) as a brown solid. $^1$H NMR (400 MHz, DMSO-d$_6$) δ 8.08 (s, 1H), 3.85 (s, 3H), 2.56 (s, 3H), 2.40 (s, 3H). MS-ESI (m/z) calc'd for $C_9H_{11}BrNO_2$ [M+H]$^+$: 244.0, 246.0. Found 243.9, 245.9.

Step 4: Methyl 3,6-dimethyl-5-vinylpicolinate

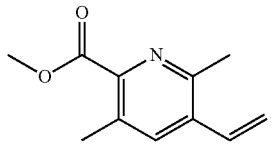

A solution of methyl 5-bromo-3,6-dimethylpicolinate (0.83 g, 3.41 mmol) and tributyl(vinyl)tin (1.99 mL, 6.83 mmol) in 1,4-dioxane (34.13 mL) was sparged with N$_2$ for 15 minutes. Bis(triphenylphosphine)palladium chloride (0.24 g, 0.340 mmol) was added and the mixture was stirred at 100° C. under N$_2$ for 2 hrs. The solvent was evaporated and the residue was purified by column chromatography (SiO$_2$, 50 g, EtOAc in cyclohexane [0%, 0%, 4 CV; 0%, 20%, 10 CV]) to afford the title compound (460 mg, 2.405 mmol, 70% yield) as a yellow solid. $^1$H NMR (400 MHz, DMSO-d$_6$) δ 7.88 (s, 1H), 6.94 (dd, J=17.5, 11.2 Hz, 1H), 5.92 (dd, J=17.4, 1.2 Hz, 1H), 5.52 (dd, J=11.0, 1.1 Hz, 1H), 3.84 (s, 3H), 2.49 (s, 3H), 2.42 (s, 3H). MS-ESI (m/z) calc'd for $C_{11}H_{14}NO_2$ [M+H]$^+$: 192.1. Found 192.0.

Step 5: Methyl 5-formyl-3,6-dimethylpicolinate

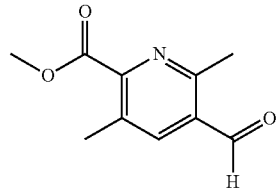

To a solution of methyl 3,6-dimethyl-5-vinylpicolinate (460.0 mg, 2.41 mmol) in 1,4-dioxane (12.03 mL) was added a solution of sodium periodate (1.03 g, 4.81 mmol) in water (12.03 mL) and the mixture was stirred at 25° C. for 5 minutes. Osmium tetroxide (4 wt % in water) (766.08 uL, 0.120 mmol) was added and the reaction mixture was stirred for 1 hr. The mixture was diluted with water and extracted with DCM (3×). The combined organic layers were passed through a phase separator and evaporated to afford the title compound (464.75 mg, 2.406 mmol, 100% yield) as a dark solid. $^1$H NMR (400 MHz, DMSO-d$_6$) δ 10.27 (s, 1H), 8.15 (s, 1H), 3.89 (s, 3H), 2.76 (s, 3H), 2.44 (t, J=0.7 Hz, 3H). MS-ESI (m/z) calc'd for $C_{10}H_{12}NO_3$ [M+H]$^+$: 194.1. Found 193.9.

Step 6: Methyl 5-cyano-3,6-dimethylpicolinate

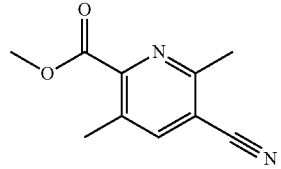

To a solution of methyl 5-formyl-3,6-dimethylpicolinate (464.75 mg, 2.41 mmol) in DMSO (2.406 mL) was added hydroxylamine hydrochloride (183.88 mg, 2.65 mmol) and the mixture was stirred at 90° C. for 4 hrs. Water was added and the mixture was extracted with EtOAc (3×).

The combined organic layers were washed with water (3×), passed through a phase separator and evaporated to afford the title compound (380 mg, 1.998 mmol, 83% yield) as a purple solid. $^1$H NMR (400 MHz, DMSO-d$_6$) δ 8.30 (s, 1H), 3.89 (s, 3H), 2.65 (s, 3H), 2.41 (s, 3H). MS-ESI (m/z) calc'd for $C_{10}H_{11}N_2O_2$[M+H]$^+$: 191.1. Found 191.0.

Step 7: 5-Cyano-3,6-dimethylpicolinic acid

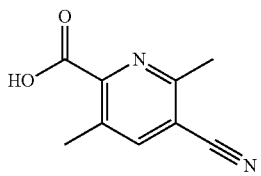

To a solution of methyl 5-cyano-3,6-dimethylpicolinate (380.0 mg, 2 mmol) in THF (10 mL) was added a solution of sodium hydroxide (81.93 mg, 2 mmol) in water (5 mL) and the mixture was stirred at 25° C. for 2 hrs. The THF was evaporated and the solution was extracted with Et$_2$O. The aqueous layer was acidified by addition of 1M HCl and extracted with EtOAc (6×). The combined organic layers were passed through a phase separator and evaporated to afford the title compound (260 mg, 1.476 mmol, 74% yield) as a grey-purple solid. $^1$H NMR (400 MHz, DMSO-d$_6$) δ 13.68 (s, 1H), 8.25 (s, 1H), 2.65 (s, 3H), 2.39 (s, 3H). MS-ESI (m/z) calc'd for C$_9$H$_9$N$_2$O$_2$[M+H]$^+$: 177.1. Found 177.0.

Step 8: 5-Cyano-N-(3-(furan-3-yl)-1H-indazol-5-yl)-3,6-dimethylpicolinamide

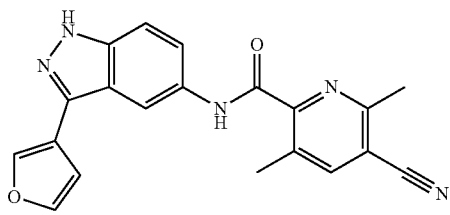 [SMILES: Cc1cc(C#N)c(C)nc1C(=O)Nc1ccc2[nH]nc(-c3ccoc3)c2c1]

To a solution of 5-cyano-3,6-dimethylpicolinic acid (35.23 mg, 0.200 mmol) and triethylamine (27.88 uL, 0.200 mmol) in MeCN (2 mL) was added HATU (76.05 mg, 0.200 mmol) and the mixture was stirred at 25° C. for 15 minutes. This solution was then added to a suspension of 3-(furan-3-yl)-1H-indazol-5-amine (39.84 mg, 0.200 mmol) in MeCN (2 mL) and the mixture was stirred at 25° C. for 30 minutes, then poured into water. The solid formed was filtered under vacuum. The residue was purified by column chromatography (NH, 11 g, MeOH in DCM [0%, 5%, 10 CV]) to afford the title compound (46 mg, 0.129 mmol, 64% yield) as a yellow solid. $^1$H NMR (400 MHz, DMSO-d$_6$) δ 13.10 (s, 1H), 10.63 (s, 1H), 8.41-8.37 (m, 1H), 8.31 (s, 1H), 8.26 (dd, J=1.6, 0.8 Hz, 1H), 7.85 (t, J=1.7 Hz, 1H), 7.78 (dd, J=9.0, 1.9 Hz, 1H), 7.56 (d, J=9.1 Hz, 1H), 7.00 (dd, J=1.9, 0.8 Hz, 1H), 2.76 (s, 3H), 2.54 (s, 3H). MS-ESI (m/z) calc'd for C$_{20}$H$_{16}$N$_5$O$_2$ [M+H]$^+$: 358.1. Found 358.1.

Example 45: 5-Cyano-3-methyl-N-(3-(4-(4-methylpiperazin-1-yl)phenyl)-1H-indazol-5-yl)picolinamide

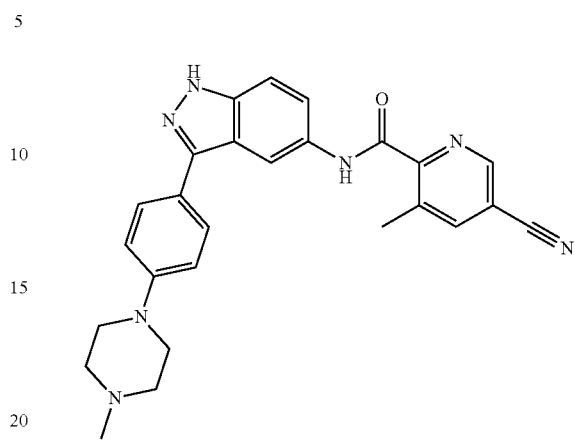

To a suspension of 5-cyano-N-(3-iodo-1H-indazol-5-yl)-3-methylpicolinamide (75.0 mg, 0.190 mmol) in 1,4-dioxane (3.72 mL) was added a solution of tripotassium phosphate (118.46 mg, 0.560 mmol) and (4-(4-methylpiperazin-1-yl)phenyl)boronic acid (53.22 mg, 0.240 mmol) in water (0.930 mL). The mixture was then degassed with N$_2$ for 15 minutes. SPhos-Pd-G2 (13.41 mg, 0.020 mmol) was added and the mixture was stirred at 80° C. under N$_2$ for 15 hrs. The solvent was evaporated and the residue was taken up in water and extracted with EtOAc (3×). The combined organic layers were passed through a phase separator and evaporated to afford a residue which was passed through a 2 g SCX ion exchange cartridge to obtain a dark yellow solid which was purified by column chromatography (NH, 11 g, acetone in DCM [0%, 10%, 10 CV]) to afford a yellow solid. This solid was further purified by prep HPLC (Method T) to afford the title compound (17 mg, 0.038 mmol, 20% yield) as a yellow solid. $^1$H NMR (400 MHz, DMSO-d$_6$) δ 13.02 (s, 1H), 10.73 (s, 1H), 9.00 (d, J=2.0 Hz, 1H), 8.59 (d, J=1.9 Hz, 1H), 8.40 (dd, J=2.0, 0.9 Hz, 1H), 7.80 (d, J=8.7 Hz, 2H), 7.75 (dd, J=9.0, 1.9 Hz, 1H), 7.54 (d, J=8.9 Hz, 1H), 7.10 (d, J=8.9 Hz, 2H), 3.26-3.19 (m, 4H), 2.59 (s, 3H), 2.49-2.45 (m, 4H), 2.24 (s, 3H). MS-ESI (m/z) calc'd for C$_{26}$H$_{26}$N$_7$O [M+H]$^+$: 452.2. Found 452.2.

Example 46: 5-Cyano-N-(3-(3-fluoro-5-methoxyphenyl)-1H-indazol-5-yl)-3-methylpicolinamide

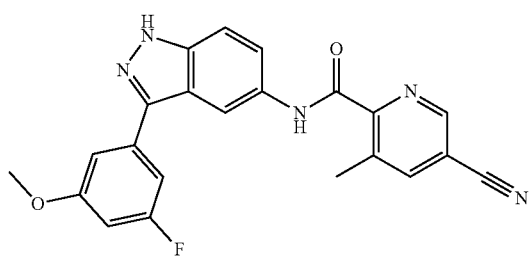 [SMILES: COc1cc(F)cc(-c2n[nH]c3ccc(NC(=O)c4ncc(C#N)cc4C)cc23)c1]

To a suspension of 5-cyano-N-(3-iodo-1H-indazol-5-yl)-3-methylpicolinamide (70.0 mg, 0.170 mmol) in 1,4-dioxane (3.48 mL) was added a solution of tripotassium phosphate (112.14 mg, 0.520 mmol) and 3-fluoro-5- methoxybenzeneboronic acid (38.36 mg, 0.230 mmol) in water (0.800 mL) and the mixture was degassed with $N_2$ for 15 minutes. SPhos-Pd-G2 (12.51 mg, 0.020 mmol) was added and the mixture was stirred at 80° C. under $N_2$ for 15 hrs. The solvent was evaporated and the residue was taken up in water and extracted with EtOAc (3×). The combined organic layers were passed through a phase separator and evaporated to obtain a residue that was purified by preparative HPLC (Method J) to afford the title compound (9.2 mg, 0.023 mmol, 13% yield) as a yellow solid. $^1$H NMR (400 MHz, DMSO-$d_6$) δ ppm 13.39 (br. s., 1H), 10.81 (s, 1H), 9.01 (d, J=1.54 Hz, 1H), 8.62 (d, J=1.32 Hz, 1H), 8.38-8.44 (m, 1H), 7.89 (dd, J=9.02, 1.76 Hz, 1H), 7.63 (d, J=9.02 Hz, 1H), 7.27-7.39 (m, 2H), 6.90 (dt, J=11.11, 2.26 Hz, 1H), 3.89 (s, 3H), 2.60 (s, 3H). MS-ESI (m/z) calc'd for $C_{22}H_{17}N_5O_2$ [M+H]$^+$: 402.1. Found 402.2.

Example 47: 5-Cyano-N-(3-(4-methoxyphenyl)-1H-indazol-5-yl)-3-methylpicolinamide

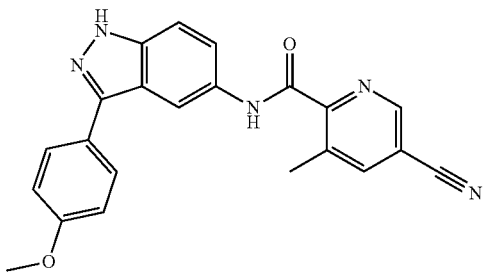

To a suspension of 5-cyano-N-(3-iodo-1H-indazol-5-yl)-3-methylpicolinamide (70.0 mg, 0.170 mmol) in 1,4-dioxane (3.472 mL) was added a solution of tripotassium phosphate (110.56 mg, 0.520 mmol) and (4-methoxyphenyl)boronic acid (34.3 mg, 0.230 mmol) in water (0.868 mL). The mixture was then degassed with $N_2$ for 15 minutes. SPhos-Pd-G2 (12.51 mg, 0.020 mmol) was added and the mixture was stirred at 80° C. under $N_2$ for 15 hrs. The solvent was evaporated and the residue was taken up in water and extracted with EtOAc (3×). The combined organic layers were passed through a phase separator and evaporated to obtain a residue which was purified by column chromatography (SiO$_2$, 10 g, acetone in DCM [0%, 10%, 15 CV]) to give a yellow solid which was further purified by prep HPLC (method I) to afford the title compound (17 mg, 0.044 mmol, 26% yield) as a yellow solid. $^1$H NMR (400 MHz, DMSO-$d_6$) δ 13.10 (s, 1H), 10.74 (s, 1H), 9.00 (dd, J=2.0, 0.6 Hz, 1H), 8.59 (dd, J=1.9, 0.7 Hz, 1H), 8.40 (dd, J=2.0, 0.8 Hz, 1H), 7.88 (d, J=8.8 Hz, 2H), 7.77 (dd, J=8.9, 1.9 Hz, 1H), 7.56 (d, J=9.0 Hz, 1H), 7.12 (d, J=8.8 Hz, 2H), 3.83 (s, 3H), 2.59 (d, J=0.7 Hz, 3H). MS-ESI (m/z) calc'd for $C_{22}H_{18}N_5O_2$ [M+H]$^+$: 384.1. Found 384.2.

Example 48: 5-Cyano-N-(3-(2-methoxypyridin-4-yl)-1H-indazol-5-yl)-3-methylpicolinamide

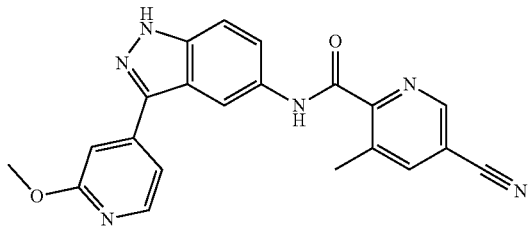 [SMILES: COc1cc(-c2n[nH]c3ccc(NC(=O)c4ncc(C#N)cc4C)cc23)ccn1]

To a suspension of 5-cyano-N-(3-iodo-1H-indazol-5-yl)-3-methylpicolinamide (75.0 mg, 0.190 mmol) and 2-methoxypyridine-4-boronic acid (36.99 mg, 0.240 mmol) in 1,4-dioxane (4 mL) was added a solution of tripotassium phosphate (118.46 mg, 0.560 mmol) in water (1 mL) and the mixture was degassed with $N_2$ for 5 minutes. SPhos-Pd-G2 (13.41 mg, 0.020 mmol) was added and the mixture was stirred at 80° C. under $N_2$ for 16 hrs. Another 37 mg of 2-methoxypyridine-4-boronic acid and 13.41 mg of SPhos-Pd-G2 were added under $N_2$ and the mixture was stirred at 80° C. for an additional 24 hrs. The reaction mixture was partitioned between water and EtOAc, the phases were separated, the aqueous layer was extracted with EtOAc (2×) and the combined organic phases were washed with brine (1×), dried over anhydrous Na$_2$SO$_4$ and evaporated to dryness. The material was purified by normal phase chromatography on a 25 g silica gel column using a 0-50% EtOAc/cyclohexane gradient eluent. The purest fractions were combined, evaporated to dryness and the residue purified again by reversed phase chromatography on a 12 g C18 cartridge using a 5-55% MeCN/H$_2$O (0.1% formic acid) gradient eluent to afford the title compound (16.5 mg, 23% yield) as a yellow solid. $^1$H NMR (400 MHz, DMSO-$d_6$) δ ppm 13.58 (br. s., 1H) 10.83 (s, 1H) 9.02 (d, J=1.54 Hz, 1H) 8.69 (d, J=1.32 Hz, 1H) 8.42 (d, J=1.10 Hz, 1H) 8.31 (d, J=5.28 Hz, 1H) 7.91 (dd, J=9.13, 1.87 Hz, 1H) 7.66 (d, J=9.02 Hz, 1H) 7.59 (dd, J=5.39, 1.43 Hz, 1H) 7.33 (s, 1H) 3.94 (s, 3H) 2.62 (s, 3H). MS-ESI (m/z) calc'd for $C_{21}H_{17}N_6O_2$[M+H]$^+$: 385.1. Found 385.2.

Example 49: 6-Cyano-N-(3-(furan-3-yl)-1H-indazol-5-yl)-4-methylnicotinamide

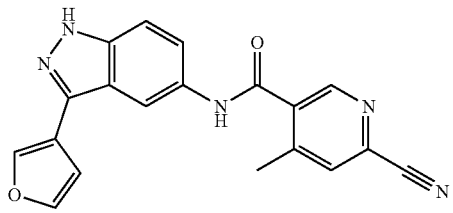 [SMILES: Cc1cc(C#N)ncc1C(=O)Nc1ccc2[nH]nc(-c3ccoc3)c2c1]

To a mixture of 6-cyano-4-methylpyridine-3-carboxylic acid (32.43 mg, 0.200 mmol), 3-(furan-3-yl)-1H-indazol-5-amine (39.84 mg, 0.200 mmol) and triethylamine (27.88 uL, 0.200 mmol) in MeCN (2 mL) was added HATU (76.05 mg, 0.200 mmol). The mixture was then stirred at 25° C. for 15 h. The reaction mixture was poured into 1M NaOH (10 mL) and extracted with EtOAc (3×). The combined organic layers were passed through a phase separator and evaporated to give a yellow residue which was purified by reversed phase column chromatography using a 0-5% MeOH/DCM gradient eluent over 10 CV to afford the title compound (20 mg, 29% yield) as a pale yellow solid. $^1$H NMR (400 MHz, DMSO-d$_4$) δ 13.12 (s, 1H), 10.69 (s, 1H), 8.86 (s, 1H), 8.38 (dd, J=1.7, 0.8 Hz, 1H), 8.21 (t, J=1.2 Hz, 1H), 8.11 (d, J=0.9 Hz, 1H), 7.85 (t, J=1.7 Hz, 1H), 7.63 (dd, J=8.9, 1.8 Hz, 1H), 7.57 (d, J=8.9 Hz, 1H), 6.99 (dd, J=1.8, 0.8 Hz, 1H), 2.51 (s, 3H). MS-ESI (m/z) calc'd for C$_{19}$H$_{14}$N$_5$O$_2$ [M+H]$^+$: 344.1. Found 344.1.

Example 50: 5-Cyano-3-methyl-N-(3-(pyridin-3-yl)-1H-indazol-5-yl)picolinamide

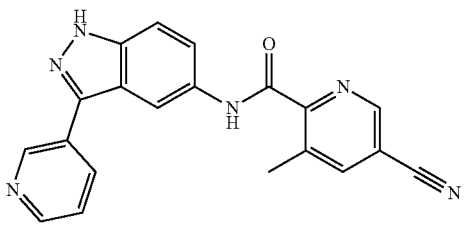 [SMILES: Cc1cc(C#N)cnc1C(=O)Nc1ccc2[nH]nc(-c3cccnc3)c2c1]

5-Cyano-N-(3-iodo-1H-indazol-5-yl)-3-methylpicolinamide (75.0 mg, 0.190 mmol) was dissolved in 1,4-dioxane (3.529 mL). Then a solution of K$_3$PO$_4$ (118.46 mg, 0.560 mmol) and pyridin-3-ylboronic acid (29.73 mg, 0.240 mmol) in water (0.882 mL) was added and the mixture was degassed with N$_2$ for 15 minutes. SPhos-Pd-G2 (13.41 mg, 0.020 mmol) was added and the mixture was stirred at 80° C. under N$_2$ atmosphere for 2 hrs. Then additional 3-pyridinylboronic acid (60 mg) and SPhos-Pd-G2 (13.41 mg, 0.020 mmol) were added and the reaction was stirred for 18 hrs. Water was added and the mixture was extracted with EtOAc (2×). The organic phases were collected, dried over Na$_2$SO$_4$, filtered and evaporated. The residue was purified by silica gel column chromatography using a 0-30% MeOH/DCM gradient eluent over 12 CV to obtain 49 mg of a yellow solid. To remove trace impurities the solid was triturated with 1 mL of MeCN and the solid was taken up in 1 mL of water and concentrated and dried to afford 23 mg of a solid which was further purified by reversed phase column chromatography using 2-100% MeCN/H$_2$O (0.1% HCOOH) gradient eluent over 7 CV to afford the title compound (15.5 mg, 24% yield) as a yellow solid. $^1$H NMR (400 MHz, DMSO-d$_6$) δ 13.46 (s, 1H), 10.80 (s, 1H), 9.18 (d, J=2.3, 0.9 Hz, 1H), 9.01 (d, J=2.0 Hz, 1H), 8.67 (d, J=1.8 Hz, 1H), 8.63 (dd, J=4.8, 1.6 Hz, 1H), 8.42 (dd, J=1.9, 0.9 Hz, 1H), 8.32 (dt, J=8.0, 1.9 Hz, 1H), 7.86 (dd, J=9.0, 1.9 Hz, 1H), 7.64 (d, J=8.9 Hz, 1H), 7.59 (ddd, J=7.9, 4.7, 0.9 Hz, 1H), 2.61 (s, 3H). MS-ESI (m/z) calc'd for C$_{20}$H$_{15}$N$_6$O [M+H]$^+$: 355.1. Found 355.2.

Example 51: 5-Cyano-N-(3-(4-fluoro-3-methylphenyl)-1H-indazol-5-yl)-3-methylpicolinamide

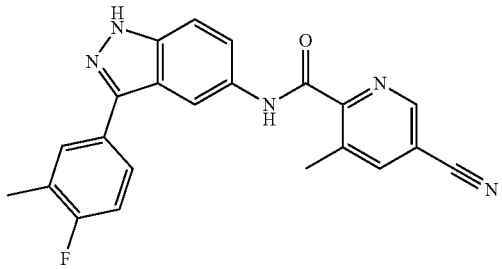 [SMILES: Cc1cc(-c2n[nH]c3ccc(NC(=O)c4ncc(C#N)cc4C)cc23)ccc1F]

To a suspension of 5-cyano-N-(3-iodo-1H-indazol-5-yl)-3-methylpicolinamide (70.0 mg, 0.170 mmol) in 1,4-dioxane (3.472 mL) was added a solution of tripotassium phosphate (110.56 mg, 0.520 mmol) and (4-fluoro-3-methylphenyl)boronic acid (34.75 mg, 0.230 mmol) in water (0.868 mL). The mixture was then degassed with N$_2$ for 15 minutes. SPhos-Pd-G2 (12.51 mg, 0.020 mmol) was added and the mixture was stirred at 80° C. under N$_2$ for 15 hrs. The solvent was evaporated, the residue was taken up in water and extracted with EtOAc (3×). The combined organic layers were passed through a phase separator and evaporated to obtain a residue which was purified by silica gel column chromatography using a 0-20% acetone/DCM gradient eluent over 15 CV to give a solid (60 mg) which was further purified by preparative HPLC (method H) to afford the title compound (21 mg, 31% yield) as a yellow solid. $^1$H NMR (400 MHz, DMSO-d$_6$) δ 13.23 (s, 1H), 10.75 (s, 1H), 9.02-8.97 (m, 1H), 8.53 (d, J=1.8 Hz, 1H), 8.41 (dd, J=2.0, 0.9 Hz, 1H), 7.84 (td, J=8.8, 2.1 Hz, 2H), 7.78 (ddd, =8.0, 5.1, 2.3 Hz, 1H), 7.59 (d, J=9.0 Hz, 1H), 7.35-7.28 (m, 1H), 2.59 (s, 3H), 2.35 (d, J=1.9 Hz, 3H). MS-ESI (m/z) calc'd for C$_{22}$H$_{17}$FN$_5$O [M+H]$^+$: 386.1. Found 386.2.

Example 52: 5-Cyano-N-(3-(6-methoxypyridin-3-yl)-1H-indazol-5-yl)-3-methylpicolinamide

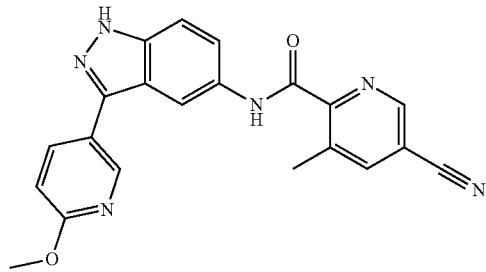

5-Cyano-N-(3-iodo-1H-indazol-5-yl)-3-methylpicolinamide (70.0 mg, 0.170 mmol) was dissolved in 1,4-dioxane (3.294 mL). Then a solution of K$_3$PO$_4$ (110.56 mg, 0.520 mmol) and (6-methoxypyridin-3-yl)boronic acid (39.83 mg, 0.260 mmol) in water (0.824 mL) was added and the mixture was degassed with N$_2$ for 15 minutes. SPhos-Pd-G2 (12.51 mg, 0.020 mmol) was added and the mixture was stirred at 80° C., under N$_2$ atmosphere, for 2 hrs. Then another portion of (6-methoxypyridin-3-yl)boronic acid (39.83 mg, 0.260 mmol) and SPhos-Pd-G2 (12.51 mg, 0.020 mmol) were added and the reaction was stirred for 18 hrs. Water was added and the mixture was extracted with EtOAc. The phases were separated and the organic solvent was evaporated. The residue was purified by silica gel column chromatography using a 0-50% acetone/DCM gradient eluent over 6 CV. Product-containing fractions were collected and concentrated under reduced pressure. The residue was triturated with 1 mL of MeCN and then the solid was taken up in 1 mL of water and concentrated and dried to afford the title compound (26.1 mg, 39% yield) as a yellow solid. $^1$H NMR (400 MHz, DMSO-d$_6$) δ 13.28 (s, 1H), 10.77 (s, 1H), 9.01 (dd, J=2.0, 0.8 Hz, 1H), 8.75 (dd, J=2.4, 0.8 Hz, 1H), 8.64 (dd, J=2.0, 0.7 Hz, 1H), 8.42 (dd, J=2.0, 0.8 Hz, 1H), 8.24 (dd, J=8.6, 2.4 Hz, 1H), 7.81 (dd, J=9.0, 1.9 Hz, 1H), 7.61 (d, J=9.0, 0.7 Hz, 1H), 7.02 (dd, J=8.6, 0.8 Hz, 1H), 3.95 (s, 3H), 2.61 (d, J=0.8 Hz, 3H). MS-ESI (m/z) calc'd for $C_{21}H_{17}N_6O_2[M+H]^+$: 385.1. Found 385.1.

Example 53: 5-Cyano-N-(3-(3-methoxyphenyl)-1H-indazol-5-yl)-3-methylpicolinamide

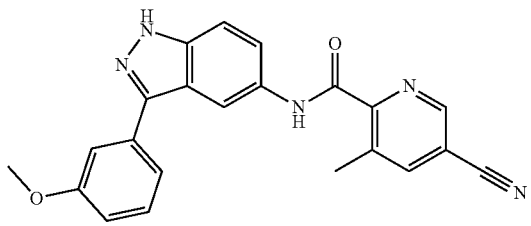 [SMILES: COc1cccc(-c2n[nH]c3ccc(NC(=O)c4ncc(C#N)cc4C)cc23)c1]

To a suspension of 5-cyano-N-(3-iodo-1H-indazol-5-yl)-3-methylpicolinamide (70.0 mg, 0.170 mmol) in 1,4-dioxane (3.5 mL) was added a solution of tripotassium phosphate (110.56 mg, 0.520 mmol) and (3-methoxyphenyl)boronic acid (34.3 mg, 0.230 mmol) in water (0.868 mL) and the mixture was degassed with N$_2$ for 15 minutes. SPhos-Pd-G2 (12.51 mg, 0.020 mmol) was added and the mixture was stirred at 80° C. under N$_2$ for 15 hrs. The solvent was evaporated and the residue was taken up in water and extracted with EtOAc (3×). The combined organic layers were passed through a phase separator and evaporated and the material was purified by preparative HPLC (Method L) to afford crude product (14.2 mg, 0.037 mmol, 21% yield) that was re-purified by chiral chromatography to afford the title compound (6.7 mg, 10% yield) as a yellow solid. $^1$H NMR (400 MHz, DMSO-d$_6$) δ ppm 13.25 (br. s, 1H), 10.75 (br. s, 1H), 9.01 (d, J=1.32 Hz, 1H), 8.64 (d, J=1.32 Hz, 1H), 8.41 (d, J=1.10 Hz, 1H), 7.83 (dd, J=9.02, 1.76 Hz, 1H), 7.60 (d, J=9.24 Hz, 1H), 7.52-7.57 (m, 1H), 7.44-7.51 (m, 2H), 6.94-7.03 (m, 1H), 3.87 (s, 3H), 2.60 (s, 3H). MS-ESI (m/z) calc'd for $C_{22}H_{18}N_5O_2$ [M+H]$^+$: 384.1. Found 384.2.

Example 54: 5-Cyano-3-methyl-N-(3-(3-(trifluoromethoxy)phenyl)-1H-indazol-5-yl)picolinamide

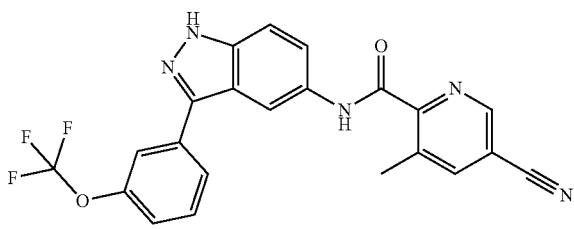 [SMILES: Cc1cc(C#N)cnc1C(=O)Nc1ccc2[nH]nc(-c3cccc(OC(F)(F)F)c3)c2c1]

To a suspension of 5-cyano-N-(3-iodo-1H-indazol-5-yl)-3-methylpicolinamide (70.0 mg, 0.170 mmol) in 1,4-dioxane (3.472 mL) was added a solution of tripotassium phosphate (110.56 mg, 0.520 mmol) and [3-(trifluoromethoxy)phenyl]boronic acid (46.48 mg, 0.230 mmol) in water (0.868 mL). The mixture was then degassed with N$_2$ for 15 minutes. SPhos-Pd-G2 (12.51 mg, 0.020 mmol) was added and the mixture was stirred at 80° C. under N$_2$ for 15 hrs. The solvent was evaporated and the residue was taken up in water and extracted with EtOAc (3×). The combined organic layers were passed through a phase separator and evaporated to obtain a residue which was purified by silica gel column chromatography using a 0-20% acetone/DCM gradient eluent over 15 CV to give a yellow solid (70 mg) which was further purified by preparative HPLC (method H) to obtain the title compound (35.3 mg, 46.49% yield) as a yellow solid. $^1$H NMR (400 MHz, DMSO-d$_4$) δ 13.44 (s, 1H), 10.80 (s, 1H), 9.00 (d, J=1.9 Hz, 1H), 8.62 (d, J=1.8 Hz, 1H), 8.41 (dd, J=2.0, 0.8 Hz, 1H), 8.04-7.96 (m, 1H), 7.90-7.81 (m, 2H), 7.70 (t, J=8.0 Hz, 1H), 7.63 (d, J=9.0 Hz, 1H), 7.41 (ddt, J=8.2, 2.4, 1.0 Hz, 1H), 2.59 (s, 3H). MS-ESI (m/z) calc'd for $C_{22}H_{15}F_3N_5O_2[M+H]^+$: 438.1. Found 438.1.

Example 55: 5-Cyano-3-methyl-N-(3-(6-methylpyridin-3-yl)-1H-indazol-5-yl)picolinamide

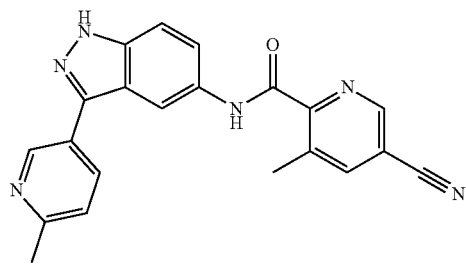 [SMILES: Cc1ccc(-c2n[nH]c3ccc(NC(=O)c4ncc(C#N)cc4C)cc23)cn1]

To a suspension of 5-cyano-N-(3-iodo-1H-indazol-5-yl)-3-methylpicolinamide (75.0 mg, 0.190 mmol) in 1,4-dioxane (3.72 mL) was added a solution of tripotassium phosphate (118.46 mg, 0.560 mmol) and (6-methylpyridin-3-yl)boronic acid (33.12 mg, 0.240 mmol) in water (0.930 mL). The mixture was then degassed with N$_2$ for 15 minutes. SPhos-Pd-G2 (13.41 mg, 0.020 mmol) was added and the mixture was stirred at 80° C. under N$_2$ for 15 h. The solvent was evaporated and the residue was taken up in water and extracted with EtOAc (3×). The combined organic layers were passed through a phase separator and evaporated to give crude material which was purified by preparative HPLC (method F) to afford the title compound (15 mg, 22% yield) as an orange solid. $^1$H NMR (400 MHz, DMSO-d$_6$) δ 13.38 (s, 1H), 10.78 (s, 1H), 9.03 (d, J=2.3 Hz, 1H), 9.00 (d, J=1.9 Hz, 1H), 8.64 (d, J=1.8 Hz, 1H), 8.41 (dd, J=2.0, 0.9 Hz, 1H), 8.19 (dd, J=8.0, 2.3 Hz, 1H), 7.82 (dd, J=9.0, 1.9 Hz, 1H), 7.62 (d, J=8.9 Hz, 1H), 7.44 (d, J=8.1 Hz, 1H), 2.60 (s, 3H), 2.55 (s, 3H). MS-ESI (m/z) calc'd for $C_{21}H_{17}N_6O$ [M+H]$^+$: 369.1. Found 369.2.

Example 56: 5-Cyano-3-methyl-N-(3-(p-tolyl)-1H-indazol-5-yl)picolinamide

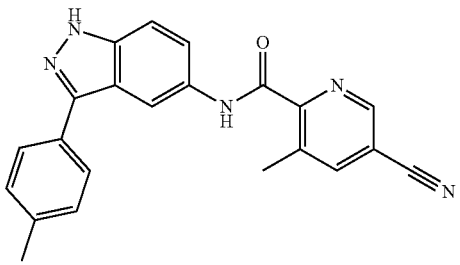 [SMILES: Cc1ccc(-c2n[nH]c3ccc(NC(=O)c4ncc(C#N)cc4C)cc23)cc1]

5-cyano-N-(3-iodo-1H-indazol-5-yl)-3-methylpyridine-2-carboxamide (70.0 mg, 0.170 mmol) was suspended in 1,4-dioxane (3.5 mL). A solution of tripotassium phosphate (110.56 mg, 0.520 mmol) and (4-methylphenyl)boronic acid (30.69 mg, 0.230) in water (0.8 ml) was added and the mixture was degassed with $N_2$ for 15 minutes. S-Phos-Pd-G2 (12.51 mg, 0.020 mmol) was added and the mixture was stirred at 80° C. under $N_2$ for 15 hrs. The solvent was evaporated; the residue was taken up in water and extracted with EtOAc (3×). The combined organic layers were passed through a phase separator and evaporated to obtain crude material that was purified by prep. HPLC (Method K) to afford the title compound (8.8 mg, 14% yield) as a yellow solid. $^1$H NMR (400 MHz, DMSO-$d_6$) δ ppm 13.20 (br. s., 1H), 10.76 (s, 1H), 9.01 (d, J=1.54 Hz, 1H), 8.61 (s, 1H), 8.41 (d, J=1.10 Hz, 1H), 7.85 (d, J=8.14 Hz, 2H), 7.80 (dd, J=8.91, 1.65 Hz, 1H), 7.59 (d, J=9.02 Hz, 1H), 7.36 (d, J=7.92 Hz, 2H), 2.60 (s, 3H), 2.39 (s, 3H). MS-ESI (m/z) calc'd for $C_{22}H_{15}N_5O$ [M+H]$^+$: 368.1. Found 368.2.

Example 57: 5-Cyano-3-methyl-N-(3-(1-methyl-1H-pyrazol-4-yl)-1H-indazol-5-yl)picolinamide

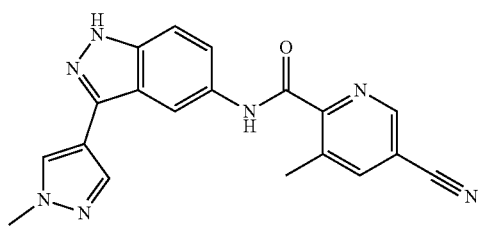 [SMILES: Cc1cc(C#N)cnc1C(=O)Nc1ccc2[nH]nc(-c3cnn(C)c3)c2c1]

To a suspension of 5-cyano-N-(3-iodo-1H-indazol-5-yl)-3-methylpicolinamide (75.0 mg, 0.190 mmol) and 1-methyl-1H-pyrazole-4-boronic acid (30.45 mg, 0.240 mmol) in 1,4-dioxane (4 mL) was added a solution of tripotassium phosphate (118.46 mg, 0.560 mmol) in water (1 mL) and the mixture was degassed with $N_2$ for 5 minutes. SPhos-Pd-G2 (13.41 mg, 0.020 mmol) was added and the mixture was stirred at 80° C. under $N_2$ for 16 hrs. The reaction mixture was partitioned between water and EtOAc, the phases were separated, the aqueous layer was extracted with EtOAc (2×) and the combined organic phases washed with brine (1×), dried over anhydrous $Na_2SO_4$ and evaporated to dryness. The crude material was purified by normal phase chromatography on a 25 g silica gel column using a 0-70% EtOAc/cyclohexane gradient eluent to afford the title compound (12.5 mg, 19% yield) as a yellow solid. $^1$H NMR (400 MHz, DMSO-$d_6$) δ ppm 12.95 (s, 1H) 10.70 (s, 1H) 9.01 (d, J=1.32 Hz, 1H) 8.38-8.47 (m, 2H) 8.22 (s, 1H) 7.93 (s, 1H) 7.80 (dd, J=9.02, 1.76 Hz, 1H) 7.54 (d, J=8.80 Hz, 1H) 3.96 (s, 3H) 2.62 (s, 3H). MS-ESI (m/z) calc'd for $C9H_{16}N_7O$ [M+H]$^+$: 358.1. Found 358.1.

Example 58: 5-Cyano-3-methyl-N-(3-(m-tolyl)-1H-indazol-5-yl)picolinamide

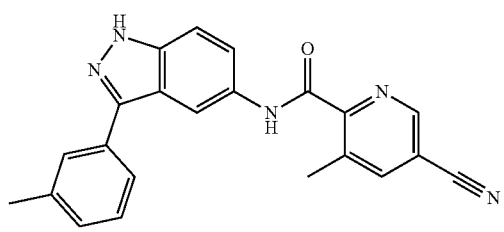 [SMILES: Cc1cccc(-c2n[nH]c3ccc(NC(=O)c4ncc(C#N)cc4C)cc23)c1]

To a suspension of 5-cyano-N-(3-iodo-1H-indazol-5-yl)-3-methylpicolinamide (70.0 mg, 0.170 mmol) in 1,4-dioxane (3.472 mL) was added a solution of tripotassium phosphate (110.56 mg, 0.520 mmol) and (3-methylphenyl)boronic acid (30.69 mg, 0.230 mmol) in water (0.868 mL). The mixture was then degassed with $N_2$ for 15 minutes. SPhos-Pd-G2 (12.51 mg, 0.020 mmol) was added and the mixture was stirred at 80° C. under $N_2$ for 15 hrs. The solvent was evaporated and the residue was taken up in water and extracted with EtOAc (3×). The combined organic layers were passed through a phase separator and evaporated to obtain a residue which was purified by silica gel column chromatography using a 0-10% acetone/DCM gradient eluent over 15 CV to give a yellow solid (60 mg) which was further purified by prep HPLC (method H) to afford the title compound (12 mg, 19% yield) as a yellow solid. $^1$H NMR (400 MHz, DMSO-$d_6$) δ 13.22 (s, 1H), 10.75 (s, 1H), 9.00 (dd, J=2.0, 0.7 Hz, 1H), 8.60-8.49 (m, 1H), 8.40 (dd, J=2.0, 0.8 Hz, 1H), 7.83 (dd, J=9.0, 1.9 Hz, 1H), 7.77 (s, 1H), 7.74 (d, J=7.8 Hz, 1H), 7.59 (d, J=9.2 Hz, 1H), 7.43 (t, J=7.6 Hz, 1H), 7.25-7.21 (m, 1H), 2.59 (d, J=0.7 Hz, 3H), 2.42 (s, 3H). MS-ESI (m/z) calc'd for $C_{22}H_{15}N_5O$ [M+H]$^+$: 368.1. Found 368.2.

Example 59: 5-Cyano-3-methyl-N-(3-(3-(trifluoromethyl)phenyl)-1H-indazol-5-yl)picolinamide

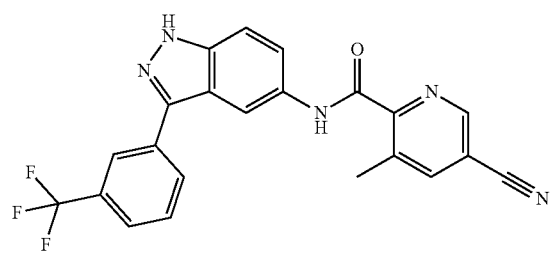 [SMILES: Cc1cc(C#N)cnc1C(=O)Nc1ccc2[nH]nc(-c3cccc(C(F)(F)F)c3)c2c1]

To a suspension of 5-cyano-N-(3-iodo-1H-indazol-5-yl)-3-methylpicolinamide (70.0 mg, 0.170 mmol) in 1,4-dioxane (3.472 mL) was added a solution of tripotassium phosphate (110.56 mg, 0.520 mmol) and [3-(trifluoromethyl)phenyl]boronic acid (42.87 mg, 0.230 mmol) in water (0.868 mL). The mixture was then degassed with $N_2$ for 15 minutes. SPhos-Pd-G2 (12.51 mg, 0.020 mmol) was added and the mixture was stirred at 80° C. under N₂ for 15 hrs. The solvent was evaporated and the residue was taken up in water and extracted with EtOAc (3×). The combined organic layers were passed through a phase separator and evaporated to give crude material which was further purified by prep HPLC (method G) to afford the title compound (24.3 mg, 33% yield) as a yellow solid. ¹H NMR (400 MHz, DMSO-d₆) δ 13.47 (s, 1H), 10.81 (s, 1H), 9.00 (dd, J=1.9, 0.7 Hz, 1H), 8.61 (d, J=1.9 Hz, 1H), 8.41 (dd, J=1.9, 0.9 Hz, 1H), 8.27 (d, J=7.5 Hz, 1H), 8.23 (s, 1H), 7.87 (dd, J=9.0, 1.9 Hz, 1H), 7.81 (t, J=7.6 Hz, 1H), 7.78 (d, J=7.9 Hz, 1H), 7.64 (d, J=9.2 Hz, 1H), 2.59 (s, 3H). MS-ESI (m/z) calc'd for C₂₂H₁₅F₃N₅O [M+H]⁺: 422.1. Found 422.1.

Example 60: 5-Cyano-3-methyl-N-(3-(6-(trifluoromethyl)pyridin-3-yl)-1H-indazol-5-yl)picolinamide

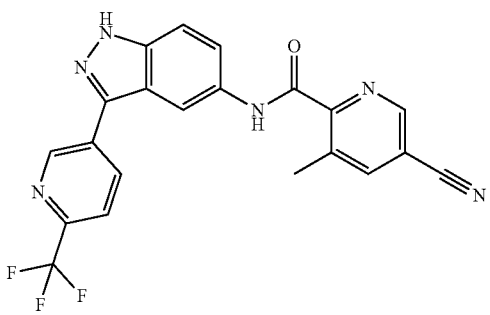 [SMILES: Cc1cc(C#N)cnc1C(=O)Nc1ccc2[nH]nc(-c3ccc(C(F)(F)F)nc3)c2c1]

To a suspension of 5-cyano-N-(3-iodo-1H-indazol-5-yl)-3-methylpicolinamide (75.0 mg, 0.190 mmol) and 2-(trifluoromethyl)pyridine-5-boronic acid (46.17 mg, 0.240 mmol) in 1,4-dioxane (4 mL) was added a solution of tripotassium phosphate (118.46 mg, 0.560 mmol) in water (1 mL) and the mixture was degassed with N₂ for 5 minutes. SPhos-Pd-G2 (13.41 mg, 0.020 mmol) was added and the mixture was stirred at 80° C. under N₂ for 16 hrs. The reaction mixture was partitioned between water and EtOAc, the phases were separated, the aqueous layer was extracted with EtOAc (2×) and the combined organic phases washed with water (1×), dried over anhydrous Na₂SO₄ and evaporated to dryness. The crude material was purified by normal phase chromatography on a 25 g silica gel column using a 0-50% EtOAc/cyclohexane gradient eluent. Pure fractions were combined and evaporated to dryness to afford the title compound (13 mg, 17% yield) as a yellow solid. ¹H NMR (400 MHz, DMSO-d₆) δ ppm 13.69 (br. s., 1H) 10.83 (s, 1H) 9.36 (d, J=1.98 Hz, 1H) 9.02 (d, J=1.32 Hz, 1H) 8.72 (d, J=1.32 Hz, 1H) 8.60 (dd, J=8.25, 1.65 Hz, 1H) 8.39-8.47 (m, 1H) 8.10 (d, J=8.14 Hz, 1H) 7.88 (dd, J=8.91, 1.87 Hz, 1H) 7.69 (d, J=8.58 Hz, 1H) 2.62 (s, 3H). MS-ESI (m/z) calc'd for C₂H₁₄F₃N₆O [M+H]⁺: 423.1. Found 423.1.

Example 61. 5-Cyano-N-(3-(3-fluoro-5-methylphenyl)-1H-indazol-5-yl)-3-methylpicolinamide

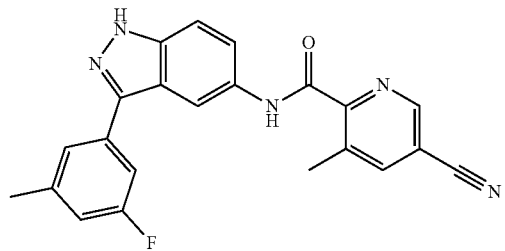 [SMILES: Cc1cc(F)cc(-c2n[nH]c3ccc(NC(=O)c4ncc(C#N)cc4C)cc23)c1]

To a suspension of 5-cyano-N-(3-iodo-1H-indazol-5-yl)-3-methylpicolinamide (75.0 mg, 0.190 mmol) and (3-fluoro-5-methylphenyl)boronic acid (37.23 mg, 0.240 mmol) in 1,4-dioxane (4 mL) was added a solution of tripotassium phosphate (118.46 mg, 0.560 mmol) in water (1 mL) and the mixture was degassed with N₂ for 5 minutes. SPhos-Pd-G2 (13.41 mg, 0.020 mmol) was added and the mixture was stirred at 80° C. under N₂ for 16 hrs. The reaction mixture was partitioned between water and EtOAc, the phases were separated, the aqueous layer was extracted with EtOAc (2×) and the combined organic phases washed with brine (1×), dried over anhydrous Na₂SO₄ and evaporated to dryness. The crude material was purified by normal phase chromatography on a 25 g silica gel column using a 0-50% EtOAc/cyclohexane gradient eluent. The purest fractions were combined and evaporated to dryness to obtain material of insufficient purity that was further purified by preparative HPLC (method A) to afford the title compound (30 mg, 42% yield) as a yellow solid. ¹H NMR (400 MHz, DMSO-d₆) δ ppm 13.36 (br. s., 1H) 10.79 (s, 1H) 9.01 (d, J=1.32 Hz, 1H) 8.56 (d, J=1.32 Hz, 1H) 8.42 (dd, J=1.87, 0.77 Hz, 1H) 7.91 (dd, J=9.02, 1.98 Hz, 1H) 7.57-7.69 (m, 2H) 7.51 (d, J=10.12 Hz, 1H) 7.09 (d, J=9.68 Hz, 1H) 2.60 (s, 3H) 2.45 (s, 3H). MS-ESI (m/z) calc'd for C₂₂H₁₇FN₅O [M+H]⁺: 386.1. Found 386.2.

Example 62: 5-cyano-N-(3-(3-cyclopropylphenyl)-1H-indazol-5-yl)-3-methylpicolinamide

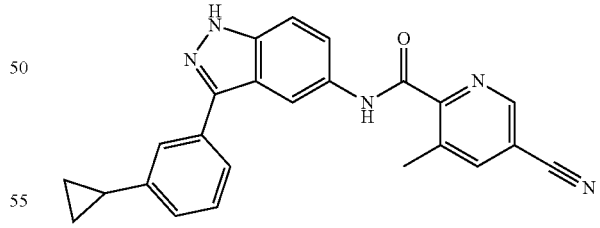

To a suspension of 5-cyano-N-(3-iodo-1H-indazol-5-yl)-3-methylpicolinamide (75.0 mg, 0.190 mmol) and (3-cyclopropylphenyl)boronic acid (39.17 mg, 0.240 mmol) in 1,4-dioxane (4 mL) was added a solution of tripotassium phosphate (118.46 mg, 0.560 mmol) in water (1 mL) and the mixture was degassed with N₂ for 5 minutes. SPhos-Pd-G2 (13.41 mg, 0.020 mmol) was added and the mixture was stirred at 80° C. under N₂ for 15 hrs. The reaction mixture was partitioned between water and EtOAc, the phases were separated, the aqueous layer was extracted with EtOAc (2×)

and the combined organic phases washed with water (1×), dried over anhydrous Na₂SO₄ and evaporated to dryness. The material was purified by normal phase chromatography on a 25 g silica gel column, using a 0-50% EtOAc/cyclohexane gradient eluent. The purest fractions were combined and evaporated to dryness to afford material of insufficient purity that was further purified by preparative HPLC (method M) to afford the title compound (22.7 mg, 31% yield) as a yellow solid. ¹H NMR (400 MHz, DMSO-d₆) δ ppm 13.22 (br. s., 1H) 10.77 (s, 1H) 9.01 (d, J=1.54 Hz, 1H) 8.61 (d, J=1.32 Hz, 1H) 8.38-8.46 (m, 1H) 7.80 (dd, J=9.02, 1.76 Hz, 1H) 7.71 (d, J=7.70 Hz, 1H) 7.64 (s, 1H) 7.60 (d, J=9.02 Hz, 1H) 7.42 (t, J=7.70 Hz, 1H) 7.14 (d, J=7.48 Hz, 1H) 2.59 (s, 3H) 2.00-2.10 (m, 1H) 0.99-1.06 (m, 2H) 0.75-0.82 (m, 2H). MS-ESI (m/z) calc'd for C₂₄H₂₀N₅O [M+H]⁺: 394.2. Found 394.2.

Example 63: 5-Cyano-N-(3-(3-fluoro-4-methylphenyl)-1H-indazol-5-yl)-3-methylpicolinamide

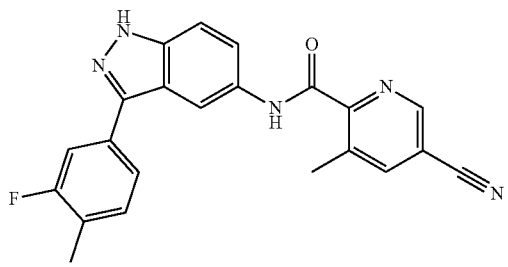 [SMILES: Cc1ccc(-c2n[nH]c3ccc(NC(=O)c4ncc(C#N)cc4C)cc23)cc1F]

To a suspension of 5-cyano-N-(3-iodo-1H-indazol-5-yl)-3-methylpicolinamide (70.0 mg, 0.170 mmol)) in 1,4-dioxane (3.48 mL) was added a solution of tripotassium phosphate (112.14 mg, 0.520 mmol) and (3-fluoro-4-methylphenyl)boronic acid (34.75 mg, 0.230 mmol) in water (0.870 mL) and the mixture was degassed with N₂ for 15 minutes. SPhos-Pd-G2 (12.51 mg, 0.020 mmol)) was added and the mixture was stirred at 80° C. under N₂ for 15 hrs. The solvent was evaporated and the residue was taken up in water and extracted with EtOAc (3×). The combined organic layers were passed through a phase separator and evaporated to obtain a residue (90 mg) which was purified by preparative HPLC (method Q) to afford the title compound (13 mg, 19% yield) as a yellow solid. ¹H NMR (400 MHz, DMSO-d₆) δ ppm 13.32 (br. s., 1H), 10.79 (s, 1H), 9.01 (d, J=1.32 Hz, 1H), 8.57-8.67 (m, 1H), 8.42 (dd, J=1.98, 0.66 Hz, 1H), 7.86 (dd, J=8.91, 1.87 Hz, 1H), 7.59-7.75 (m, 3H), 7.47 (t, J=8.25 Hz, 1H), 2.61 (s, 3H), 2.32 (d, J=1.32 Hz, 3H). MS-ESI (m/z) calc'd for C₂₂H₁₇FN₅O [M+H]⁺: 386.1. Found 386.2.

Example 64: 5-Cyano-3-(difluoromethyl)-N-(3-(furan-3-yl)-1H-indazol-5-yl)picolinamide

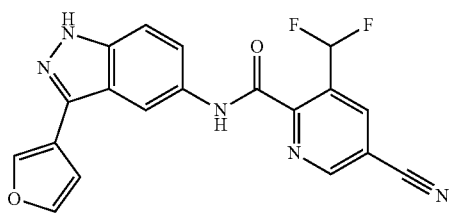 [SMILES: N#Cc1cnc(C(=O)Nc2ccc3[nH]nc(-c4ccoc4)c3c2)c(C(F)F)c1]

Step 1: 5-Bromo-3-formylpicolinic acid

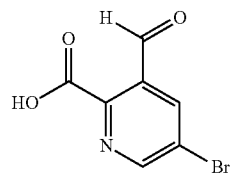

To a solution of n-BuLi (2.5 M, 15.66 mL) in THF (50 mL) was added 3,5-dibromopicolinic acid (5 g, 17.80 mmol) in THF (75 mL) at −70° C. After 1 hr, DMF (13.01 g, 178.00 mmol) was added to the mixture and stirring was continued at 0° C. for 2 hrs. The reaction mixture was quenched by addition of H₂O (100 mL) at 20° C. and extracted with EtOAc (90 mL×5). The aqueous phase was acidified with 1N HCl to pH=3 and extracted with EtOAc (90 mL×3). The organic layers were dried over anhydrous Na₂SO₄, filtered and concentrated under reduced pressure to afford the title compound (3.37 g) as a yellow oil which was used without further purification.

Step 2: Methyl 5-bromo-3-(dimethoxymethyl)picolinate

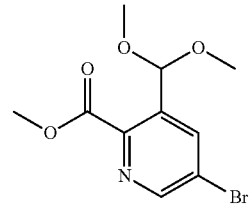 [SMILES: COC(=O)c1ncc(Br)cc1C(OC)OC]

A solution of 5-bromo-3-formylpicolinic acid (3.37 g, 14.65 mmol) in MeOH (40 mL) and H₂SO₄ (0 mL) (98% purity) was stirred at 70° C. for 1 hr. The reaction was concentrated to give a residue, which was diluted with H₂O (40 mL), basified with saturated aqueous NaHCO₃ to pH=8, and extracted with EtOAc (30 mL×3). The combined organic layers were dried over Na₂SO₄, filtered and concentrated to give a residue. The residue was purified by silica gel column chromatography using a 0-10% EtOAc/petroleum ether gradient eluent to afford the title compound (1.3 g, 31% yield) as a light yellow solid.

Step 3: Methyl 5-bromo-3-formylpicolinate

To a solution of methyl 5-bromo-3-(dimethoxymethyl) picolinate (1.3 g, 4.48 mmol) in dioxane (15 mL) and H₂O (15 mL) was added PTSA (231.49 mg, 1.34 mmol). The mixture was stirred at 50° C. for 16 hrs. The reaction mixture was basified with saturated aqueous NaHCO₃ to pH=8 and extracted with EtOAc (5 mL×4). The combined organic layers were dried over Na₂SO₄, filtered and concentrated to afford the title compound (750 mg) as a pale yellow solid which was used without further purification.

Step 4: Methyl 5-bromo-3-(difluoromethyl)picolinate

To a solution of methyl 5-bromo-3-formylpicolinate (500 mg, 2.05 mmol) in CH₂Cl₂ (15 mL) was added DAST (825.62 mg, 5.12 mmol). The mixture was stirred at 20° C. for 12 hrs. The reaction mixture was concentrated and purified by silica gel column chromatography using a 0-10% EtOAc/petroleum ether gradient eluent to afford the title compound (280 mg, 51% yield) as a white solid.

Step 5: Methyl 5-cyano-3-(difluoromethyl)picolinate

A mixture of methyl 5-bromo-3-(difluoromethyl)picolinate (280 mg, 1.05 mmol), Zn(CN)₂ (247.17 mg, 2.10 mmol), Pd(PPh₃)₄ (121.62 mg, 105.25 umol) in DMF (4 mL) was degassed and purged with N₂ (3×). The mixture was then stirred at 120° C. for 12 hrs under an N₂ atmosphere. The reaction mixture was concentrated and purified by silica gel column chromatography using a 0-10% EtOAc/petroleum ether gradient eluent to afford the title compound (40 mg, 18% yield) as a white solid.

Step 6: 5-Cyano-3-(difluoromethyl)picolinic acid

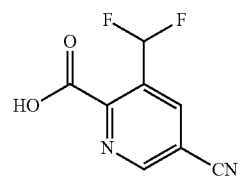 [SMILES: N#Cc1cnc(C(=O)O)c(C(F)F)c1]

To a solution of methyl 5-cyano-3-(difluoromethyl)picolinate (40 mg, 189 umol) in THF (2 mL) was added TMSOK (73 mg, 566 umol). The mixture was stirred at 20° C. for 10 min and monitored by TLC (petroleum ether:EtOAc=3:1). The reaction mixture was acidified with 1N HCl to pH=3 and then extracted with EtOAc (2 mL×3). The combined organic layers were dried over Na₂SO₄, filtered and concentrated to afford the title compound (25 mg) as a yellow solid which was used without further purification.

Step 7: 5-Cyano-3-(difluoromethyl)-N-(3-(furan-3-yl)-1H-indazol-5-yl)picolinamide

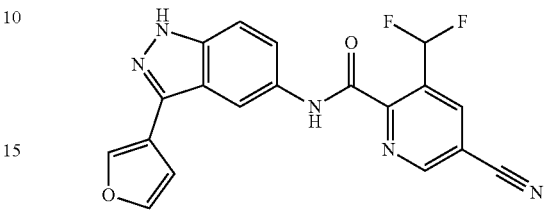

To a solution of 5-cyano-3-(difluoromethyl)picolinic acid (20 mg, 101 umol) in CH₂Cl₂ (2 mL) was added 3-(furan-3-yl)-1H-indazol-5-amine (40 mg, 202 umol) and T3P (50 wt. % in EtOAc, 96 mg, 151 umol). The mixture was stirred at 20° C. for 2.5 hrs. The reaction mixture was concentrated and purified by preparative HPLC (Method V) to afford the title compound (8.24 mg, 16% yield) as a yellow solid, TFA salt. ¹H NMR (400 MHz, DMSO-d₆) δ 13.15 (s, 1H) 11.00 (s, 1H) 9.36 (s, 1H) 8.90 (s, 1H) 8.46 (s, 1H) 8.29 (s, 1H) 7.68-7.96 (m, 3H) 7.58 (d, J=9 Hz, 1H) 7.02 (d, J=1 Hz, 1H). MS-ESI (m/z) calc'd for $C_{19}H_{12}F_2N_5O_2$ [M+H]⁺: 380.1. Found 380.1.

Example 65: 5-Cyano-N-(3-(furan-3-yl)-1H-indazol-5-yl)thiazole-2-carboxamide

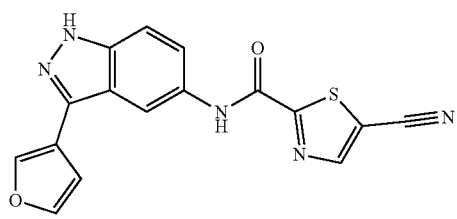 [SMILES: N#Cc1cnc(C(=O)Nc2ccc3[nH]nc(-c4ccoc4)c3c2)s1]

Step 1: Methyl 5-bromothiazole-2-carboxylate

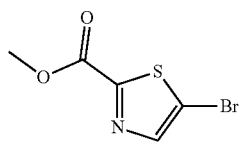

To a solution of 5-bromothiazole-2-carboxylic acid (400 mg, 1.92 mmol) in DCM (5 mL) was added (COCl)₂ (297.74 mg, 2.35 mmol) and DMF (28.11 mg, 384.55 umol). The mixture was stirred at 20° C. for 0.5 hr. MeOH (1 mL) was then added and the mixture was stirred at 20° C. for 1 hr and monitored by TLC (petroleum ether:EtOAc=3:1 Rf=0.63). The reaction mixture was concentrated under reduced pressure to remove solvent and purified by flash silica gel chromatography (ISCO; 4 g SepaFlash column) using a 0-7% EtOAc/petroleum ether gradient eluent to afford the title compound (380 mg, 89%) as a white solid.

Step 2: Methyl 5-cyanothiazole-2-carboxylate

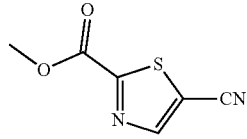

A mixture of methyl 5-bromothiazole-2-carboxylate (200 mg, 900.66 umol), Zn(CN)$_2$ (211.52 mg, 1.80 mmol), Pd$_2$(dba)$_3$ (24.74 mg, 27.02 umol), dppf (29.96 mg, 54.04 umol) and Zn (5.30 mg, 81.06 umol) in DMA (10 mL) was degassed and purged with N$_2$ (3×). The mixture was stirred at 110° C. for 2 hrs under N$_2$ atmosphere in a microwave reactor and monitored by TLC (petroleum ether:EtOAc=2:1, Rf=0.49). The reaction mixture was concentrated under reduced pressure to remove solvent and purified by flash silica gel chromatography (ISCO; 4 g SepaFlash column) using a 0-5% EtOAc/petroleum ether gradient eluent to afford the title compound (100 mg, 61%) as a white solid.

Step 3: 5-Cyano-N-(3-(furan-3-yl)-1H-indazol-5-yl)thiazole-2-carboxamide

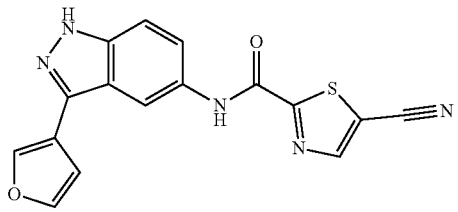 [SMILES: N#Cc1cnc(C(=O)Nc2ccc3[nH]nc(-c4ccoc4)c3c2)s1]

To a solution of methyl 5-cyanothiazole-2-carboxylate (10 mg, 59.46 umol) and 3-(furan-3-yl)-1H-indazol-5-amine (23.69 mg, 118.93 umol) in toluene (2 mL) was added AlMe$_3$ (2 M, 89.19 uL). The mixture was stirred at 0° C. for 1 hr. The reaction mixture was quenched by addition of MeOH (3 mL) at 0° C. and concentrated under reduced pressure to give a residue. The residue was purified by preparative HPLC (Method AH) to afford the title compound (7 mg, 25% yield) as a yellow solid, TFA salt. $^1$H NMR (400 MHz, DMSO-d$_6$) δ 13.16 (br s, 1H) 11.11 (s, 1H) 8.95 (s, 1H) 8.46 (d, J=1.47 Hz, 1H) 8.26 (s, 1H) 7.89 (dd, J=9.05, 1.83 Hz, 1H) 7.85 (t, J=1.65 Hz, 1H) 7.58 (d, J=8.93 Hz, 1H) 6.98-7.03 (m, 1H). MS-ESI (m/z) calc'd for C$_{16}$H$_{10}$N$_5$O$_2$S [M+H]$^+$: 336.0. Found 336.0.

Example 66: 4-Chloro-5-cyano-N-(3-(furan-3-yl)-1H-indazol-5-yl)picolinamide

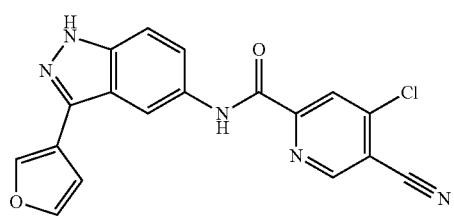 [SMILES: N#Cc1cnc(C(=O)Nc2ccc3[nH]nc(-c4ccoc4)c3c2)cc1Cl]

Step 1: 5-Bromo-4-chloro-N-(3-(furan-3-yl)-1H-indazol-5-yl)picolinamide

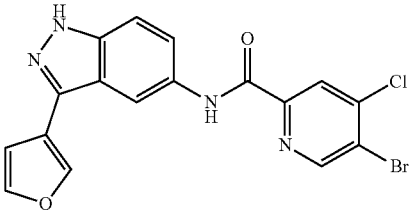 [SMILES: O=C(Nc1ccc2[nH]nc(-c3ccoc3)c2c1)c1cc(Cl)c(Br)cn1]

To a solution of 5-bromo-4-chloropicolinic acid (50 mg, 211.46 umol) and 3-(furan-3-yl)-1H-indazol-5-amine (42.12 mg, 211.46 umol) in pyridine (2 mL) was added EDCI (60.81 mg, 317.19 umol). The reaction mixture was stirred at 25° C. for 12 hrs and then poured into water (5 mL) and extracted with CH$_2$Cl$_2$ (5 mL×3). The combined organic phases were washed with brine (5 mL×1), dried over anhydrous Na$_2$SO$_4$, filtered and concentrated in vacuum. The residue was purified by silica gel column chromatography using a 5-100% EtOAc/petroleum ether gradient eluent to afford the title compound (60 mg, 68% yield) as a green solid.

Step 2: 4-Chloro-5-cyano-N-(3-(furan-3-yl)-1H-indazol-5-yl)picolinamide

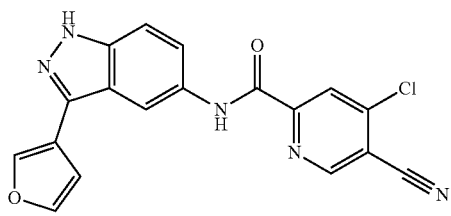 [SMILES: N#Cc1cnc(C(=O)Nc2ccc3[nH]nc(-c4ccoc4)c3c2)cc1Cl]

To a solution of 5-bromo-4-chloro-N-(3-(furan-3-yl)-1H-indazol-5-yl)picolinamide (60 mg, 143.66 umol) and Zn(CN)$_2$ (8.43 mg, 71.83 umol) in DMF (2 mL) was added Pd(PPh$_3$)$_4$ (16.60 mg, 14.37 umol). The reaction mixture was stirred at 150° C. for 1 hr under N$_2$. The reaction mixture was filtered and the filtrate was concentrated. The residue was purified by preparative HPLC (Method U) and further purified by preparative HPLC (Method V) to afford the title compound (8.37 mg, 12% yield) as a yellow solid, TFA salt. $^1$H NMR (400 MHz, DMSO-d$_6$) δ 13.13 (s, 1H), 10.91 (s, 1H), 9.29 (s, 1H), 8.51 (s, 1H), 8.44 (s, 1H), 8.29 (s, 1H), 7.99 (br d, J=9.0 Hz, 1H), 7.85 (s, 1H), 7.57 (d, J=9.0 Hz, 1H), 7.01 (s, 1H). MS-ESI (m/z) calc'd for C$_{18}$H$_{11}$ClN$_5$O$_2$ [M+H]$^+$: 364.0. Found 364.0.

Example 67: 5-Cyano-N-(3-(furan-3-yl)-1H-indazol-5-yl)-3,4-dimethylpicolinamide

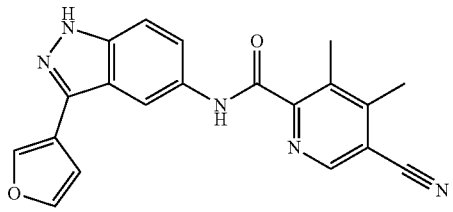 [SMILES: Cc1c(C#N)cnc(C(=O)Nc2ccc3[nH]nc(-c4ccoc4)c3c2)c1C]

Step 1: 5-Cyano-2,3,4-trimethylpyridine 1-oxide

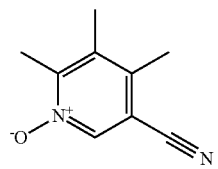

To a solution of 4,5,6-trimethylnicotinonitrile (500.0 mg, 3.42 mmol) in DCM (17.1 mL) was added meta-chloroperoxybenzoic acid (843.18 mg, 3.42 mmol) and the mixture was stirred at 25° C. for 5 hrs. The solution was washed with aqueous $K_2CO_3$ solution (3×) and the combined aqueous layers were extracted with DCM (3×). All the organic phases were combined, passed through a phase separator, and evaporated to dryness to afford the title compound (530 mg, 96% yield) as a yellow solid. $^1$H NMR (400 MHz, DMSO-$d_6$) δ 8.73 (s, 1H), 2.44 (s, 3H), 2.39 (s, 3H), 2.28 (s, 3H). MS-ESI (m/z) calc'd for $C_9H_{11}N_2O$ [M+H]$^+$: 162.1. Found 162.9.

Step 2: 6-(Hydroxymethyl)-4,5-dimethylnicotinonitrile

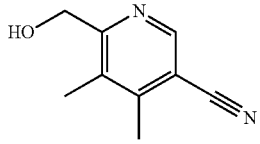

To a solution of 5-cyano-2,3,4-trimethylpyridine 1-oxide (530.0 mg, 3.27 mmol) in DCM (5 mL) was added a solution of 2,2,2-trifluoroacetic acid (2,2,2-trifluoro-1-oxoethyl) ester (1.36 mL, 9.8 mmol) in DCM (5 mL) dropwise and the mixture was stirred at 25° C. for 15 hrs. The solvent was evaporated to dryness to give a red oil which was dissolved in MeOH (20 mL). $K_2CO_3$ (1 g) was added and the suspension was stirred for 1 hr. The solvent was evaporated and the residue was taken up in water and extracted with DCM (3×). The combined organic layers were passed through a phase separator and evaporated to afford the title compound (510 mg, 96% yield) as a beige solid. $^1$H NMR (400 MHz, DMSO-$d_6$) δ 8.70 (s, 1H), 5.23 (t, J=5.6 Hz, 1H), 4.64 (d, J=5.6 Hz, 2H), 2.46 (s, 3H), 2.29 (s, 3H). MS-ESI (m/z) calc'd for $C_9H_{11}N_2O$ [M+H]$^+$: 162.1. Found 162.9.

Step 3: 5-Cyano-3,4-dimethylpicolinic acid

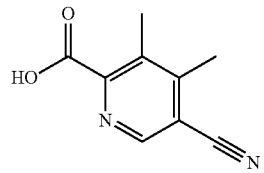

To a solution of 6-(hydroxymethyl)-4,5-dimethylnicotinonitrile (510.0 mg, 3.14 mmol) in acetone (10 mL) was added a solution of potassium permanganate (546.61 mg, 3.46 mmol) in water (5 mL) dropwise at 0° C. and the mixture was stirred for 30 minutes. The dark solid was filtered and washed with 1M aqueous $K_2CO_3$. The filtrate was concentrated to remove the organic solvent and the pH was adjusted to 4-5 by addition of conc. HCl. The solution was extracted with EtOAc (3×) and the combined organic layers were passed through a phase separator and evaporated to afford the title compound (500 mg, 90% yield) as a beige solid. $^1$H NMR (400 MHz, DMSO-$d_6$) δ 13.82 (s, 1H), 8.78 (s, 1H), 2.50 (s, 3H), 2.33 (s, 3H). MS-ESI (m/z) calc'd for $C_9H_9N_2O_2$ [M+H]$^+$: 177.1. Found 177.3.

Step 4: 5-Cyano-N-(3-(furan-3-yl)-1H-indazol-5-yl)-3,4-dimethylpicolinamide

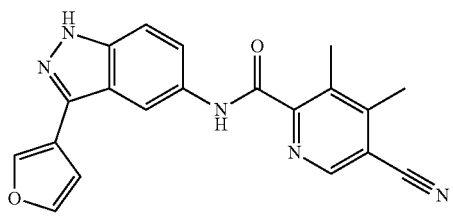 [SMILES: Cc1c(C#N)cnc(C(=O)Nc2ccc3[nH]nc(-c4ccoc4)c3c2)c1C]

To a solution of 5-cyano-3,4-dimethylpicolinic acid (35.23 mg, 0.200 mmol), triethylamine (27.88 uL, 0.200 mmol) and 3-(furan-3-yl)-1H-indazol-5-amine (0.05 mL, 0.200 mmol) was added HATU (76.05 mg, 0.200 mmol) and the mixture was stirred at 25° C. for 2 hrs. Water was added and the solid that formed was filtered under vacuum and purified by silica gel column chromatography using a 0-5% MeOH/DCM gradient eluent to afford the title compound (40 mg, 56% yield) as a yellow solid. $^1$H NMR (400 MHz, DMSO-$d_6$) δ 13.10 (s, 1H), 10.67 (s, 1H), 8.89 (s, 1H), 8.40 (d, J=1.7 Hz, 1H), 8.23 (t, J=1.1 Hz, 1H), 7.84 (t, J=1.7 Hz, 1H), 7.74 (dd, J=8.9, 1.9 Hz, 1H), 7.56 (d, J=9.0 Hz, 1H), 6.99 (dd, J=1.9, 0.8 Hz, 1H), 2.56 (s, 3H), 2.47 (s, 3H). MS-ESI (m/z) calc'd for $C_{20}H_{16}N_5O_2$ [M+H]$^+$: 358.1. Found 358.1.

Example 68: 5-Cyano-N-(3-(5-methoxypyridin-3-yl)-1H-indazol-5-yl)-3-methylpicolinamide

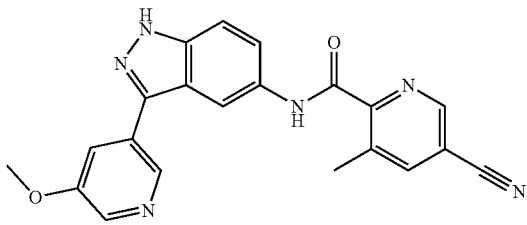 [SMILES: COc1cncc(-c2n[nH]c3ccc(NC(=O)c4ncc(C#N)cc4C)cc23)c1]

5-Cyano-N-(3-iodo-1H-indazol-5-yl)-3-methylpicolinamide (50.0 mg, 0.110 mmol) was dissolved in 1,4-dioxane (2 mL). Then a solution of $K_3PO_4$ (67.13 mg, 0.320 mmol) and (5-methoxypyridin-3-yl)boronic acid (20.96 mg, 0.140 mmol) in water (0.500 mL) was added and the mixture was degassed with $N_2$ for 15 minutes. SPhos-Pd-G2 (7.6 mg, 0.010 mmol) was added and the mixture was stirred at 80° C. under an $N_2$ atmosphere for 2 hrs. Water was added and the mixture was extracted with EtOAc (2×). The organic phases were separated, dried over $Na_2SO_4$, filtered and concentrated under reduced pressure. The residue was purified by semi-preparative HPLC (Method S) to afford the title compound (9.9 mg, 24% yield) as an orange solid. $^1$H NMR (400 MHz, DMSO-$d_6$) δ 13.49 (bs, 1H), 10.81 (s, 1H), 9.01 (d, J=2.0 Hz, 1H), 8.79 (d, J=1.7 Hz, 1H), 8.67 (d, J=1.8 Hz, 1H), 8.42 (dd, J=2.0, 0.9 Hz, 1H), 8.36 (d, J=2.8 Hz, 1H), 7.88 (dd, J=9.0, 1.9 Hz, 1H), 7.84 (dd, J=2.9, 1.7 Hz, 1H), 7.65 (d, J=9.0 Hz, 1H), 3.96 (s, 3H), 2.61 (s, 3H). MS-ESI (m/z) calc'd for $C_{21}H_{17}N_6O_2$ [M+H]$^+$: 385.1. Found 385.2.

Example 69: 5-Cyano-N-(3-(furan-3-yl)-1H-indazol-5-yl)-3-methoxypicolinamide

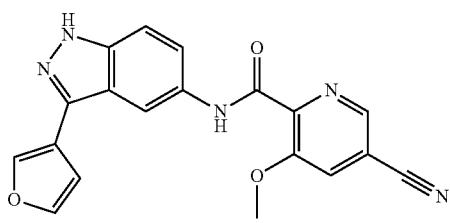 [SMILES: COc1cc(C#N)cnc1C(=O)Nc1ccc2[nH]nc(-c3ccoc3)c2c1]

Step 1: 5-Bromo-N-(3-(furan-3-yl)-1H-indazol-5-yl)-3-methoxypicolinamide

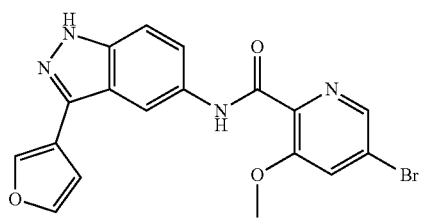 [SMILES: COc1cc(Br)cnc1C(=O)Nc1ccc2[nH]nc(-c3ccoc3)c2c1]

To a mixture of 5-bromo-3-methoxypyridine-2-carboxylic acid (100.0 mg, 0.430 mmol) in MeCN (3.814 mL) was added triethylamine (0.07 mL, 0.520 mmol) and HATU (163.87 mg, 0.430 mmol). The mixture was then stirred at 25° C. for 15 minutes. This solution was added dropwise to a solution of 3-(furan-3-yl)-1H-indazol-5-amine (85.86 mg, 0.430 mmol) in MeCN (3.814 mL) and the mixture was stirred at 25° C. for 18 hrs. The reaction was filtered and the solid was washed with MeCN. The solid was triturated with MeOH and then dried under vacuum to afford the title compound (160 mg, 90% yield) as a yellow solid. $^1$H NMR (400 MHz, DMSO-$d_6$) δ 13.08 (s, 1H), 10.44 (s, 1H), 8.40 (d, J=1.8 Hz, 1H), 8.37 (d, J=1.7 Hz, 1H), 8.21 (s, 1H), 7.98 (d, J=1.8 Hz, 1H), 7.85 (t, 1H), 7.70 (dd, J=9.0, 1.8 Hz, 1H), 7.54 (d, J=8.9 Hz, 1H), 6.99 (d, 1H), 3.92 (s, 3H). MS-ESI (m/z) calc'd for $C_{20}H_{16}N_5O_2$ [M+H]$^+$: 413.0, 415.0. Found 413.2, 415.1.

Step 2: 5-Cyano-N-(3-(furan-3-yl)-1H-indazol-5-yl)-3-methoxypicolinamide

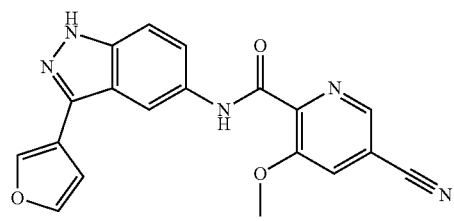 [SMILES: COc1cc(C#N)cnc1C(=O)Nc1ccc2[nH]nc(-c3ccoc3)c2c1]

To a microwave reaction vial (vial A) equipped with a magnetic stir bar was added a 0.1 N solution of potassium hexacyanoferrate (III) (0.69 mL, 0.070 mmol) in water. To a separate microwave reaction vial (vial B) equipped with a magnetic stir bar was added XPhos (9.21 mg, 0.020 mmol) and XPhos-Pd-G3 (16.36 mg, 0.020 mmol). The vials were sealed with a teflon-lined screw cap septum, evacuated and flushed with nitrogen (3×). 1,4-Dioxane (9.66 mL) was added to vial B via syringe and the solution was stirred until all solids dissolved. This solution was degassed with $N_2$ and then added via syringe to vial A. 5-Bromo-N-(3-(furan-3-yl)-1H-indazol-5-yl)-3-methoxypicolinamide (113.8 mg, 0.275 mmol) and a 0.2 M solution of KOAc in degassed water (0.692 mL) (13.51 mg, 0.5 equivalent of KOAc) was then added and the reaction was stirred at 100° C. for 4 hrs. Additional Xphos-Pd-G3 (9.32 mg, 0.010 mmol), XPhos (5.25 mg, 0.010 mmol) and 0.1 N potassium hexacyanoferrate (11) (0.69 mL, 0.070 mmol) were added and the reaction mixture was stirred at 100° C. for 18 hrs. Sat. aq. $NaHCO_3$ was added and the mixture was extracted with EtOAc (2×). The organic phases were combined, dried over $Na_2SO_4$, filtered and concentrated under reduced pressure. The residue (106 mg) was purified by semi-preparative HPLC (Method S) to afford the title compound (3.4 mg, 3% yield) as a yellow solid. $^1$H NMR (400 MHz, DMSO-$d_6$) δ 13.10 (s, 1H), 10.60 (s, 1H), 8.70 (d, J=1.5 Hz, 1H), 8.39 (d, J=1.8 Hz, 1H), 8.24 (d, J=1.6 Hz, 1H), 8.21 (d, J=1.2 Hz, 1H), 7.85 (t, J=1.7 Hz, 1H), 7.67 (dd, J=8.9, 1.9 Hz, 1H), 7.56 (d, J=8.9 Hz, 1H), 6.99 (d, J=1.9 Hz, 1H), 3.94 (s, 3H). MS-ESI (m/z) calc'd for $C19H_{14}N_5O_3$ [M+H]$^+$: 360.1. Found 360.2.

Example 70: 5-Cyano-3-methyl-N-(3-(4-morpholinophenyl)-1H-indazol-5-yl)picolinamide

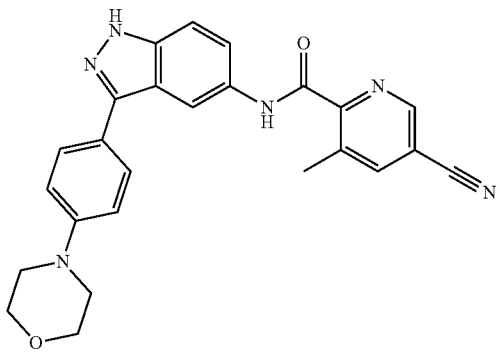 [SMILES: Cc1cc(C#N)cnc1C(=O)Nc1ccc2[nH]nc(-c3ccc(N4CCOCC4)cc3)c2c1]

To a suspension of 5-cyano-N-(3-iodo-1H-indazol-5-yl)-3-methylpicolinamide (47.43 mg, 0.100 mmol) in 1,4-dioxane (2 mL) was added a solution of tripotassium phosphate (63.68 mg, 0.300 mmol) and (4-morpholinophenyl)boronic acid (26.91 mg, 0.130 mmol) in water (0.500 mL). The mixture was degassed with $N_2$ for 15 minutes. SPhos-Pd-G2 (7.21 mg, 0.010 mmol) was added and the mixture was stirred at 80° C. under $N_2$ for 15 hrs. The solvent was evaporated and the residue was taken up in water and extracted with EtOAc (3×). The combined organic layers were passed through a phase separator and evaporated to obtain a residue which was purified by reversed phase column chromatography using a 0-10% MeOH/DCM gradient eluent to afford a solid (18 mg) which was passed through a 2 g SCX ion exchange cartridge to give a yellow solid which was further purified by reversed phase column chromatography using a 5-100% MeCN/$H_2O$ (0.1% formic acid) gradient eluent to afford the title compound (2.3 mg, 5% yield) as a yellow solid. $^1$H NMR (400 MHz, CDCl$_3$) δ 10.12 (s, 1H), 8.74 (d, J=2.0 Hz, 1H), 8.49 (d, J=2.0 Hz, 1H), 7.96 (d, J=1.9 Hz, 1H), 7.91 (d, J=8.7 Hz, 2H), 7.68 (dd, J=8.9, 1.9 Hz, 1H), 7.51 (d, J=8.9 Hz, 1H), 7.09-7.05 (m, 2H), 3.93-3.89 (m, 4H), 3.28-3.24 (m, 4H), 2.90 (s, 3H). MS-ESI (m/z) calc'd for $C_{25}H_{23}N_6O_2$ [M+H]$^+$: 439.2. Found 439.1.

Example 71: N-(3-(Benzo[d]oxazol-5-yl)-1H-indazol-5-yl)-5-cyano-3-methylpicolinamide

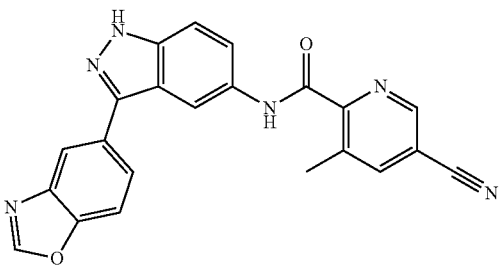 [SMILES: Cc1cc(C#N)cnc1C(=O)Nc1ccc2[nH]nc(-c3ccc4ocnc4c3)c2c1]

5-Cyano-N-(3-iodo-1H-indazol-5-yl)-3-methylpicolinamide (75.0 mg, 0.190 mmol) was dissolved in 1,4-dioxane (3.543 mL). Then a solution of $K_3PO_4$ (118.46 mg, 0.560 mmol) and 5-(4,4,5,5-tetramethyl-1,3,2-dioxaborolan-2-yl)-1,3-benzoxazole (59.27 mg, 0.240 mmol) in water (0.886 mL) was added and the mixture was degassed with $N_2$ for 15 minutes. SPhos-Pd-G2 (13.41 mg, 0.020 mmol) was added and the mixture was stirred at 80° C., under an $N_2$ atmosphere, for 2 hrs. Additional SPhos-Pd-G2 (13.41 mg, 0.020 mmol) and 5-(4,4,5,5-tetramethyl-1,3,2-dioxaborolan-2-yl)-1,3-benzoxazole (59.27 mg, 0.240 mmol) were added and the mixture was stirred for 2 hrs. Water was added and the mixture was extracted with EtOAc (2×). The organic phase was separated, dried over $Na_2SO_4$, filtered and concentrated under reduced pressure. The residue was then purified by silica gel column chromatography using a 0-100% acetone/DCM gradient eluent to obtain the title compound (31.1 mg, 42% yield) as a yellow solid. $^1$H NMR (400 MHz, DMSO-d$_6$) δ 13.30 (s, 1H), 10.81 (s, 1H), 9.01 (dd, J=2.0, 0.8 Hz, 1H), 8.84 (s, 1H), 8.68 (d, 1H), 8.42 (dd, J=2.0, 0.9 Hz, 1H), 8.30 (d, J=1.6 Hz, 1H), 8.07 (dd, J=8.5, 1.7 Hz, 1H), 7.96 (d, J=8.5 Hz, 1H), 7.87 (dd, J=9.0, 1.9 Hz, 1H), 7.63 (d, J=9.0 Hz, 1H), 2.61 (s, 3H). MS-ESI (m/z) calc'd for $C_{22}H_{15}N_6O_2$ [M+H]$^+$: 395.1. Found 395.1.

Example 72: 3-Cyano-N-(3-(furan-3-yl)-1H-indazol-5-yl)-2-methoxybenzamide

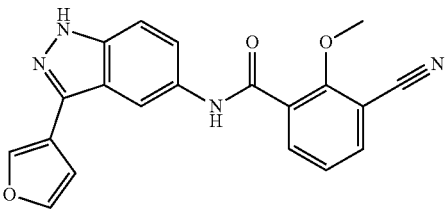 [SMILES: COc1c(C#N)cccc1C(=O)Nc1ccc2[nH]nc(-c3ccoc3)c2c1]

A mixture of 3-(furan-3-yl)-1H-indazol-5-amine (30.0 mg, 0.150 mmol) and methyl 3-cyano-2-methoxybenzoate (28.79 mg, 0.150 mmol) in toluene (1.5 mL) was flushed with nitrogen for 5 min. A 2 M solution of trimethylaluminum in toluene (0.23 mL, 0.450 mmol) was then added and the reaction mixture was stirred for 1 hr at 95° C. The reaction mixture was then cooled to rt, diluted with water and EtOAc, the phases were separated, the aqueous layer was extracted with EtOAc (2×), and the combined organic phases were washed with water (1×), dried over anhydrous $Na_2SO_4$ and evaporated to dryness. The material obtained was purified by normal phase chromatography on a 10 g silica gel column using a 0-70% EtOAc/cyclohexane gradient eluent. Product-containing fractions were combined and evaporated to dryness to afford impure product. This was further purified by reverse phase chromatography on a 12 g C18 column using a 5-55% $CH_3CN/H_2O$ (0.1% formic acid) gradient eluent to afford the title compound (29 mg, 54% yield) as an off-white solid. $^1$H NMR (400 MHz, DMSO-d$_6$) δ ppm 13.10 (br. s., 1H), 10.51 (s, 1H), 8.38 (d, J=1.1 Hz, 1H), 8.22 (dd, J=0.8, 1.4 Hz, 1H), 7.96 (dd, J=1.7, 7.8 Hz, 1H), 7.91 (dd, J=1.5, 7.7 Hz, 1H), 7.86 (t, J=1.7 Hz, 1H), 7.70-7.63 (m, 1H), 7.61-7.53 (m, 1H), 7.41 (t, J=7.7 Hz, 1H), 7.00 (dd, J=0.8, 1.9 Hz, 1H), 4.03 (s, 3H). MS-ESI (m/z) calc'd for $C_{20}H_{15}N_4O_3$ [M+H]$^+$: 359.1. Found 359.2.

Example 73: 5-Cyano-3-methyl-N-(3-(thiophen-3-yl)-1H-indazol-5-yl)picolinamide

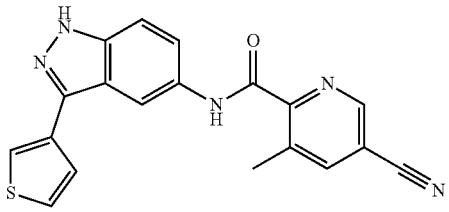 [SMILES: Cc1cc(C#N)cnc1C(=O)Nc1ccc2[nH]nc(-c3ccsc3)c2c1]

5-Cyano-N-(3-iodo-1H-indazol-5-yl)-3-methylpicolinamide (75 mg, 0.19 mmol) was dissolved in 1,4-dioxane (3.529 mL). A solution of K$_3$PO$_4$ (118.46 mg, 0.56 mmol) and 3-thiophenylboronic acid (30.94 mg, 0.24 mmol) in water (0.88 mL) was then added and the mixture was degassed with N$_2$ for 15 minutes. SPhos-Pd-G2 (13.41 mg, 0.02 mmol) was added and the mixture was stirred at 80° C. under N$_2$ atmosphere for 2 hrs. Water was added and the mixture was extracted with EtOAc (2×). The organic phases were separated, dried over Na$_2$SO$_4$, filtered and concentrated under reduced pressure. The residue was then purified by silica gel column chromatography using a 0-100% acetone/DCM gradient eluent to afford the title compound (50.4 mg, 75% yield) as a yellow solid. $^1$H NMR (400 MHz, DMSO-d$_6$) δ 13.13 (bs, 1H), 10.74 (s, 1H), 9.01 (d, J=2.0 Hz, 1H), 8.60 (d, J=1.8 Hz, 1H), 8.42 (dd, J=2.0, 0.9 Hz, 1H), 7.96 (dd, J=2.9, 1.3 Hz, 1H), 7.81 (dd, J=9.0, 1.9 Hz, 1H), 7.74 (dd, J=5.0, 2.8 Hz, 1H), 7.70 (dd, J=5.0, 1.3 Hz, 1H), 7.58 (d, J=8.9 Hz, 1H), 2.62 (s, 3H). MS-ESI (m/z) calc'd for C$_{19}$H$_{14}$N$_5$OS [M+H]$^+$: 360.1. Found 360.2.

Example 74: 5-Cyano-3-methyl-N-(3-(2-methylpyridin-4-yl)-1H-indazol-5-yl)picolinamide

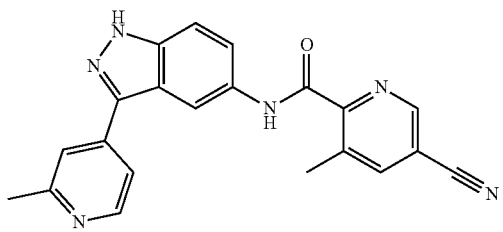 [SMILES: Cc1cc(-c2n[nH]c3ccc(NC(=O)c4ncc(C#N)cc4C)cc23)ccn1]

5-Cyano-N-(3-iodo-1H-indazol-5-yl)-3-methylpicolinamide (75 mg, 0.190 mmol) was dissolved in 1,4-dioxane (3.543 mL). Then a solution of K$_3$PO$_4$ (118.46 mg, 0.560 mmol) and (2-methylpyridin-4-yl)boronic acid (33.12 mg, 0.24 mmol) in water (0.886 mL) was added and the mixture was degassed with N$_2$ for 15 minutes. SPhos-Pd-G2 (13.41 mg, 0.02 mmol) was added and the mixture was stirred at 80° C. under N$_2$ atmosphere for 2 hrs. Additional SPhos-Pd-G2 (13.41 mg, 0.020 mmol) and 2-picoline-4-boronic acid (33.12 mg, 0.24 mmol) were then added and the mixture was stirred for 18 hrs. Water was added and the mixture was extracted with EtOAc (2×). The organic phases were separated, dried over Na$_2$SO$_4$, and concentrated under reduced pressure. The residue was purified by silica gel column chromatography using a 0-60% acetone/DCM gradient eluent. The product-containing fractions were collected and concentrated under reduced pressure to afford 40 mg of a yellow solid. The solid was then triturated with 1 mL of MeCN and taken up in 1 mL of water and concentrated to afford the title compound (15 mg, 22% yield) as a yellow solid. $^1$H NMR (400 MHz, DMSO-d$_6$) δ 13.57 (bs, 1H), 10.80 (s, 1H), 9.02 (d, J=1.9 Hz, 1H), 8.64 (d, J=1.8 Hz, 1H), 8.58 (d, J=5.1 Hz, 1H), 8.42 (dd, J=1.8, 0.8 Hz, 1H), 7.91 (dd, J=9.0, 1.9 Hz, 1H), 7.82 (d, J=1.7 Hz, 1H), 7.74 (dd, J=5.3, 1.7 Hz, 1H), 7.66 (d, J=9.0 Hz, 1H), 2.61 (s, 3H), 2.59 (s, 3H). MS-ESI (m/z) calc'd for C$_{21}$H$_{17}$N$_6$O [M+H]$^+$: 369.1. Found 369.2.

Example 75: 3-Cyano-2-ethyl-N-(3-(furan-3-yl)-1H-indazol-5-yl)benzamide

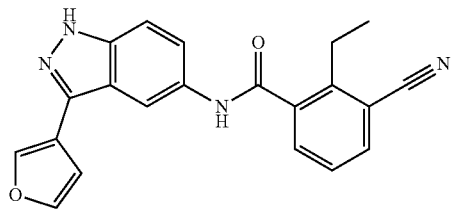 [SMILES: CCc1c(C#N)cccc1C(=O)Nc1ccc2[nH]nc(-c3ccoc3)c2c1]

2-Bromo-3-cyano-N-[3-(furan-3-yl)-1H-indazol-5-yl]benzamide (50.0 mg, 0.120 mmol) was dissolved in toluene (5 mL) and water (0.500 mL). The mixture was flushed with N$_2$ for 5 min. A 1M solution of triethylborane (0.12 mL, 0.120 mmol) in hexanes was added followed by tripotassium phosphate (52.13 mg, 0.250 mmol), (1E,4E)-1,5-diphenyl-3-penta-1,4-dienone palladium (22.49 mg, 0.020 mmol) and bis(1-adamantyl)-butylphosphine (4.4 mg, 0.010 mmol). The mixture was then stirred at 110° C. for 2 hrs. Another 60 µL of 1M triethylborane in hexanes and 11 mg of Pd$_2$(dba)$_3$ were added and the mixture was stirred at 110° C. for an additional 2 hrs. The reaction mixture was partitioned between water and EtOAc, the phases were separated, the aqueous layer was extracted with EtOAc (2×) and the combined organic phases washed with water (1×), dried over anhydrous Na$_2$SO$_4$ and evaporated to dryness. The material obtained was purified by preparative HPLC (method N) to afford the title compound (2.2 mg, 5% yield) as a white solid. $^1$H NMR (400 MHz, DMSO-de) δ ppm 13.10 (s, 1H), 10.55 (s, 1H), 8.37 (d, J=1.1 Hz, 1H), 8.21 (dd, J=0.8, 1.4 Hz, 1H), 7.95 (dd, J=1.3, 7.7 Hz, 1H), 7.89-7.81 (m, 2H), 7.71-7.63 (m, 1H), 7.61-7.52 (m, 2H), 6.99 (dd, J=0.7, 1.8 Hz, 1H), 2.95 (q, J=7.4 Hz, 2H), 1.27 (t, J=7.5 Hz, 3H). MS-ESI (m/z) calc'd for C$_{21}$H$_{17}$N$_4$O$_2$[M+H]$^+$: 357.1. Found 357.1.

Example 76: 5-Cyano-N-(3-(5-cyanofuran-3-yl)-1H-indazol-5-yl)-3-methylpicolinamide

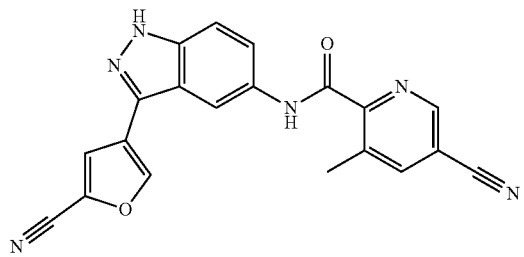 [SMILES: Cc1cc(C#N)cnc1C(=O)Nc1ccc2[nH]nc(-c3coc(C#N)c3)c2c1]

Step 1:
4-(5-Nitro-1H-indazol-3-yl)furan-2-carbaldehyde

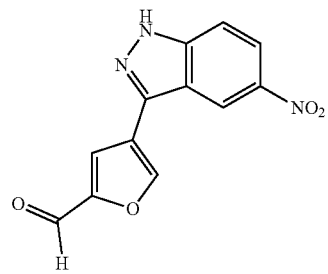 [SMILES: O=Cc1cc(-c2n[nH]c3ccc([N+](=O)[O-])cc23)co1]

A mixture of 3-bromo-5-nitro-1H-indazole (150 mg, 619.76 umol), (5-formyl-3-furyl)boronic acid (95.38 mg, 681.74 umolq), Pd(Amphos)Cl$_2$ (43.88 mg, 61.98 umol), KOAc (182.47 mg, 1.86 mmol) in EtOH (2 mL) and H$_2$O (0.5 mL) was degassed and purged with N$_2$ (3×). The mixture was then stirred at 90° C. for 12 hrs under an N$_2$ atmosphere. The reaction mixture was concentrated to give a residue. The residue was diluted with EtOAc (50 mL) and H$_2$O (30 mL). The mixture was filtered and the solid was collected, washed with H$_2$O (30 mL×2) and EtOAc (50 mL×3), and dried under vacuum. The procedure was repeated an additional 3× and the products were combined to afford the title compound (500 mg) as a yellow solid which was used without further purification.

Step 2:
4-(5-Nitro-1H-indazol-3-yl)furan-2-carbonitrile

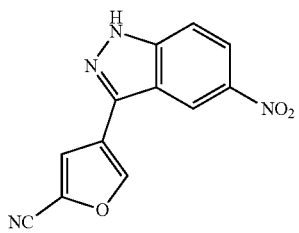 [SMILES: N#Cc1cc(-c2n[nH]c3ccc(N)cc23)co1]

To a solution of 4-(5-nitro-1H-indazol-3-yl)furan-2-carbaldehyde (500 mg, 1.94 mmol) in pyridine (50 mL) was added NH$_2$OH.HCl (500 mg, 7.20 mmol). The mixture was stirred at 100° C. for 30 min and then Ac$_2$O (10 mL) was added. The mixture was stirred at 100° C. for another 12 hrs and monitored by TLC (petroleum ether:EtOAc=3:1, Rf=0.53). The reaction mixture was concentrated and purified by silica gel column chromatography using a 0-30% EtOAc/petroleum ether gradient eluent to afford the title compound (400 mg, 57% yield) as a yellow solid.

Step 3:
4-(5-Amino-1H-indazol-3-yl)furan-2-carbonitrile

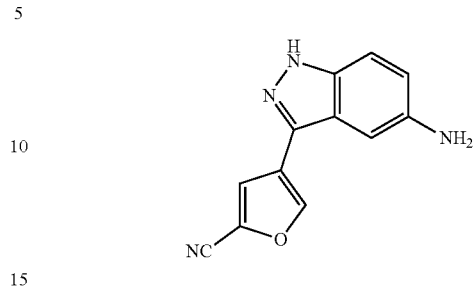

To a solution of 4-(5-nitro-1H-indazol-3-yl)furan-2-carbonitrile (380 mg, 1.05 mmol) in EtOH (20 mL) was added SnCl$_2$2H$_2$O (1.18 g, 5.23 mmol). The mixture was stirred at 80° C. for 1 hr and monitored by TLC (petroleum ether: EtOAc=1:1, Rf=0.24). The reaction mixture was concentrated to give a residue which was diluted with EtOAc (30 mL) and basified with saturated aqueous NaHCO$_3$ to pH=8. The mixture was filtered and the filtrate was extracted with EtOAc (30 mL×3), dried over Na$_2$SO$_4$, filtered and concentrated to afford the title compound (200 mg) as a yellow solid which was used without further purification.

Step 4: 5-Cyano-N-(3-(5-cyanofuran-3-yl)-1H-indazol-5-yl)-3-methylpicolinamide

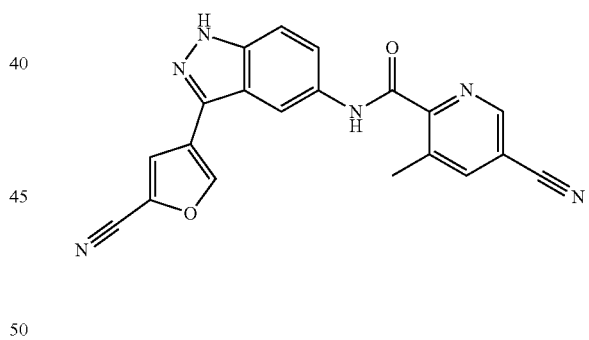

To a solution of 5-cyano-3-methylpicolinic acid (70 mg, 431.71 umol) in pyridine (5 mL) was added EDCI (124.14 mg, 647.57 umol) and 4-(5-amino-1H-indazol-3-yl)furan-2-carbonitrile (96.80 mg, 431.71 umol). The mixture was stirred at 20° C. for 12 hrs. The reaction mixture was concentrated and purified by preparative HPLC twice under basic conditions (Method X and Method Y) to afford the title compound (12 mg, 7% yield) as a yellow solid. $^1$H NMR (400 MHz, DMSO-d$_6$) δ 13.38 (s, 1H) 10.73 (s, 1H) 9.01 (s, 1H) 8.69 (s, 1H) 8.42 (br d, J=6 Hz, 2H) 8.14 (s, 1H) 7.85 (br d, J=8 Hz, 1H) 7.61 (d, J=9 Hz, 1H) 2.62 (s, 3H). MS-ESI (m/z) calc'd for C$_{20}$H$_{13}$N$_6$O$_2$ [M+H]$^+$: 369.1. Found 369.0.

Example 77: 3-Cyano-2-fluoro-N-(3-(furan-3-yl)-1H-indazol-5-yl)benzamide

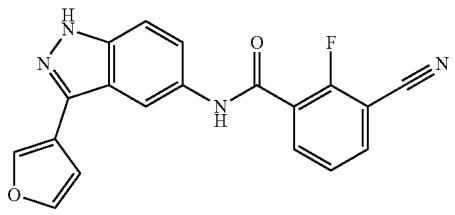 [SMILES: N#Cc1cccc(C(=O)Nc2ccc3[nH]nc(-c4ccoc4)c3c2)c1F]

To a mixture of 3-cyano-2-fluorobenzoic acid (24.87 mg, 0.150 mmol), 3-(furan-3-yl)-1H-indazol-5-amine (30.0 mg, 0.150 mmol) and triethylamine (20.99 uL, 0.150 mmol) was added HATU (57.26 mg, 0.150 mmol) and the mixture was stirred at room temperature over the weekend. The reaction mixture was partitioned between water and EtOAc, the phases were separated, the aqueous layer was extracted with EtOAc (2×) and the combined organic phases washed with brine (1×), dried over anhydrous $Na_2SO_4$ and evaporated to dryness. Crude material was purified by normal phase chromatography on a 25 g silica gel column using as a 0-100% EtOAc/cyclohexane gradient eluent. The purest fractions were combined and evaporated to dryness to afford the title compound (32 mg, 61% yield) as a white solid. $^1$H NMR (400 MHz, DMSO-$d_6$) δ ppm 13.13 (br. s., 1H), 10.64 (br. s., 1H), 8.37 (d, J=0.9 Hz, 1H), 8.22 (dd, J=0.8, 1.4 Hz, 1H), 8.18-8.03 (m, 2H), 7.86 (t, J=1.7 Hz, 1H), 7.68-7.53 (m, 3H), 7.00 (dd, J=0.8, 1.9 Hz, 1H). MS-ESI (m/z) calc'd for $C_{18}H_{12}FN_4O_2$ [M+H]$^+$: 347.1. Found 347.1.

Example 78: 4-Cyano-N-(3-(furan-3-yl)-1H-indazol-5-yl)-6-methylpicolinamide

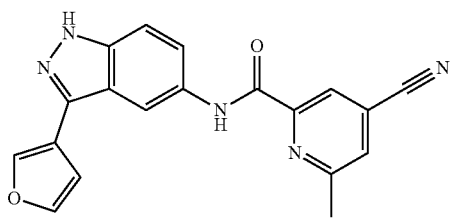 [SMILES: Cc1cc(C#N)cc(C(=O)Nc2ccc3[nH]nc(-c4ccoc4)c3c2)n1]

To a mixture of 4-cyano-6-methylpyridine-2-carboxylic acid (24.42 mg, 0.150 mmol), 3-(furan-3-yl)-1H-indazol-5-amine (30.0 mg, 0.150 mmol) and triethylamine (20.99 uL, 0.150 mmol) was added HATU (57.26 mg, 0.150 mmol) and the mixture was stirred at room temperature over the weekend. The reaction mixture was partitioned between water and EtOAc, the phases were separated, the aqueous layer was extracted with EtOAc (2×) and the combined organic phases washed with brine (1×), dried over anhydrous $Na_2SO_4$ and evaporated to dryness. The material obtained was purified by normal phase chromatography on a 25 g silica gel column using a 0-100% EtOAc/cyclohexane gradient eluent. Clean fractions were combined and evaporated to dryness to afford crude product which was further purified by preparative HPLC (method 0) to afford the title compound (20.7 mg, 40% yield) as a yellow solid. $^1$H NMR (400 MHz, DMSO-$d_6$) δ ppm 13.12 (s, 1H), 10.60 (s, 1H), 8.45 (d, J=1.5 Hz, 1H), 8.37-8.27 (m, 2H), 8.07 (d, J=0.9 Hz, 1H), 7.96 (dd, J=1.9, 8.9 Hz, 1H), 7.86 (t, J=1.7 Hz, 1H), 7.59 (d, J=8.8 Hz, 1H), 7.03 (dd, J=0.9, 1.8 Hz, 1H), 2.74 (s, 3H). MS-ESI (m/z) calc'd for $C_{19}H_{14}N_5O_2$ [M+H]$^+$: 344.1. Found 344.2.

Example 79: 4-Cyano-3-fluoro-N-(3-(furan-3-yl)-1H-indazol-5-yl)picolinamide

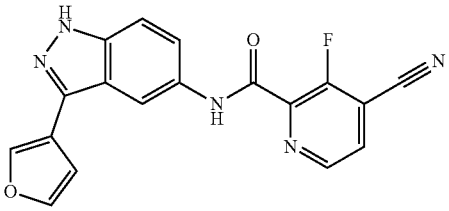 [SMILES: N#Cc1ccnc(C(=O)Nc2ccc3[nH]nc(-c4ccoc4)c3c2)c1F]

To a mixture of 4-cyano-3-fluoropyridine-2-carboxylic acid (25.02 mg, 0.150 mmol), 3-(furan-3-yl)-1H-indazol-5-amine (30.0 mg, 0.150 mmol) and triethylamine (20.99 uL, 0.150 mmol) was added HATU (57.26 mg, 0.150 mmol) and the mixture was stirred at room temperature over the weekend. The reaction mixture was partitioned between water and EtOAc, the phases were separated, the aqueous layer was extracted with EtOAc (2×) and the combined organic phases washed with brine (1×), dried over anhydrous $Na_2SO_4$ and evaporated to dryness. The material was purified by reversed phase chromatography using a 5-55% $CH_3CN/H_2O$ (0.1% formic acid) gradient eluent on a 12 g C18 column. Pure fractions were combined and evaporated to dryness to afford the title compound (24 mg, 46% yield) as a yellow solid. $^1$H NMR (400 MHz, DMSO-$d_6$) δ ppm 13.12 (s, 1H), 10.77 (s, 1H), 8.82 (d, J=4.8 Hz, 1H), 8.43 (s, 1H), 8.32-8.24 (m, 2H), 7.90-7.80 (m, 2H), 7.58 (d, J=9.0 Hz, 1H), 7.01 (d, J=0.9 Hz, 1H). MS-ESI (m/z) calc'd for $C_{15}H_{11}FN_5O_2$ [M+H]$^+$: 348.1. Found 348.1.

Example 80: 5-Cyano-N-(3-(furan-3-yl)-7-methyl-1H-indazol-5-yl)-3-methylpicolinamide

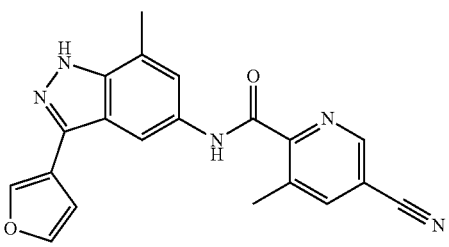 [SMILES: Cc1cc(C#N)cnc1C(=O)Nc1cc(C)c2[nH]nc(-c3ccoc3)c2c1]

Step 1: 3-Iodo-7-methyl-5-nitro-1H-indazole

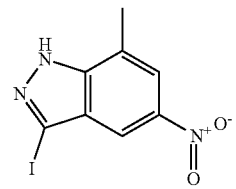

7-Methyl-5-nitro-1H-indazole (500.0 mg, 2.82 mmol) was dissolved in DCM (7 mL). The solution was cooled to 0° C. and 1-iodopyrrolidine-2,5-dione (698.46 mg, 3.1 mmol) was added in portions. The mixture was stirred at room temperature overnight. Then 1 additional equivalent of NIS was added and the mixture was stirred at 50° C. for 24 hrs. The mixture was quenched with water and extracted with DCM (2×). The combined organic layers were washed with water (1×), passed through a phase separator and evaporated to dryness. The residue was purified by column chromatography on a 100 g silica gel column using a 0-20% EtOAc/cyclohexane gradient eluent to afford the title compound (0.560 g, 65% yield) as a yellow solid. $^1$H NMR (400 MHz, DMSO-d$_6$) δ ppm 14.25 (br. s., 1H), 8.21-8.15 (m, 1H), 8.10 (dd, J=1.1, 2.0 Hz, 1H), 2.61 (s, 3H). MS-ESI (m/z) calc'd for C$_8$H$_7$IN$_3$O$_2$[M+H]$^+$: 304.0. Found 304.0.

Step 2: 3-Iodo-7-methyl-1H-indol-5-amine

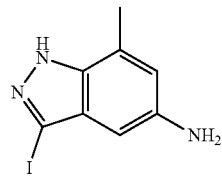

A mixture of 3-iodo-7-methyl-5-nitro-1H-indazole (560.0 mg, 1.79 mmol), ammonium chloride (0.11 g, 1.97 mmol) and iron powder (400.42 mg, 7.17 mmol) in ethanol (10 mL) and water (10 mL) was stirred at 80° C. for 2 hrs. The solids were removed by filtration through Celite and the solid was washed with EtOH. Volatiles were removed from the filtrate under vacuum and re-dissolved in EtOAc. Water was added and the two phases were separated, the aqueous layer was extracted with EtOAc (2×) and the combined organic layers were washed with water (1×), dried over anhydrous Na$_2$SO$_4$ and the solvent was removed under reduced pressure to afford the title compound (430 mg, 88% yield) as a yellow solid. $^1$H NMR (400 MHz, DMSO-d$_6$) δ ppm 13.24-12.97 (m, 1H), 6.64 (dd, J=1.0, 1.9 Hz, 1H), 6.26 (s, 1H), 4.88 (br. s., 2H), 2.38 (s, 3H). MS-ESI (m/z) calc'd for C$_8$H$_9$IN$_3$ [M+H]$^+$: 274.0. Found 274.0.

Step 3: 3-(Furan-3-yl)-7-methyl-1H-indazol-5-amine

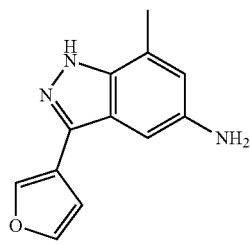 [SMILES: Cc1cc(N)cc2c(-c3ccoc3)n[nH]c12]

3-Furanylboronic acid (264.29 mg, 2.36 mmol), 3-iodo-7-methyl-1H-indazol-5-amine (430.0 mg, 1.57 mmol) and tripotassium phosphate (1002.78 mg, 4.72 mmol) were dissolved in a mixture of THF (9 mL) and water (3 mL). The reaction mixture was degassed with nitrogen for 15 min and then SPhos-Pd-G2 (170.21 mg, 0.240 mmol) was added.

The mixture was heated to 80° C. and stirred for 16 hrs. The reaction was cooled to rt and then diluted with water and EtOAc. The phases were separated, the aqueous layer was extracted with EtOAc (2×) and the combined organic layers washed with water (1×), dried over anhydrous Na$_2$SO$_4$ and then concentrated under reduced pressure. The material was purified by reversed phase column chromatography on a 30 g C$_{18}$ column using a 3-15% CH$_3$CN/H$_2$O (0.1% formic acid) gradient eluent to afford the title compound (60 mg, 18% yield) as a white solid. $^1$H NMR (400 MHz, DMSO-d$_6$) δ ppm 12.67 (br. s., 1H), 8.13 (dd, J=0.8, 1.4 Hz, 1H), 7.78 (t, J=1.7 Hz, 1H), 6.94 (dd, J=0.9, 1.8 Hz, 1H), 6.80 (d, J=1.3 Hz, 1H), 6.61 (dd, J=0.9, 1.8 Hz, 1H), 2.41 (s, 3H). MS-ESI (m/z) calc'd for C$_{12}$H$_{12}$N$_3$O [M+H]$^+$: 214.1. Found 214.1.

Step 4: 5-Cyano-N-(3-(furan-3-yl)-7-methyl-1H-indazol-5-yl)-3-methylpicolinamide

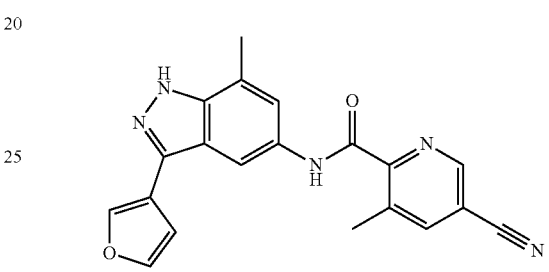

To a mixture of 5-cyano-3-methylpyridine-2-carboxylic acid (22.81 mg, 0.140 mmol), 3-(furan-3-yl)-7-methyl-1H-indazol-5-amine (30.0 mg, 0.140 mmol) and triethylamine (39.22 uL, 0.280 mmol) was added HATU (53.49 mg, 0.140 mmol) and the mixture was stirred at room temperature for 1 hr. The reaction mixture was partitioned between water and EtOAc, the phases were separated. The aqueous layer was extracted with EtOAc (2×) and the combined organic phases were washed with brine (1×), dried over anhydrous Na$_2$SO$_4$ and evaporated to dryness. The material was purified by silica gel chromatography on a 25 g column using a 0-100% EtOAc/cyclohexane gradient eluent. Product-containing fractions were combined, evaporated to dryness to afford impure material which was further purified by preparative HPLC (method P) to afford the title compound (16.5 mg, 33% yield) as a yellow solid. $^1$H NMR (400 MHz, DMSO-d$_6$) δ ppm 13.17 (s, 1H), 10.61 (s, 1H), 9.04-8.97 (m, 1H), 8.41 (dd, J=0.8, 1.9 Hz, 1H), 8.30-8.20 (m, 2H), 7.85 (t, J=1.7 Hz, 1H), 7.64 (s, 1H), 7.01 (dd, J=0.9, 1.8 Hz, 1H), 2.61 (s, 3H), 2.55 (s, 3H). MS-ESI (m/z) calc'd for C$_{20}$H$_{16}$N$_5$O$_2$ [M+H]$^+$: 358.1. Found 358.2.

Example 81: 5-Cyano-N-(3-(furan-3-yl)-1H-indazol-5-yl)-1,3-dimethyl-1H-pyrazole-4-carboxamide

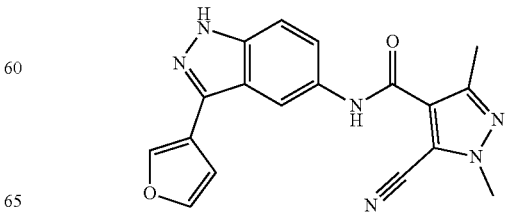

Prepared as described for 5-cyano-N-(3-(furan-3-yl)-1H-indazol-5-yl)-1,4-dimethyl-1H-pyrazole-3-carboxamide using ethyl 5-ethynyl-3-methyl-1H-pyrazole-4-carboxylate in place of ethyl 5-ethynyl-4-methyl-1H-pyrazole-3-carboxylate in step 2. $^1$H NMR (400 MHz, DMSO-$d_6$) δ 13.11 (br s, 1H) 10.18 (s, 1H) 8.31 (s, 1H) 8.22 (s, 1H) 7.85 (t, J=1.59 Hz, 1H) 7.56 (s, 2H) 6.99 (d, J=1.10 Hz, 1H) 4.01 (s, 3H) 2.42 (s, 3H). MS-ESI (m/z) calc'd for $C_{18}H_{15}N_6O_2$ [M+H]$^+$: 347.1. Found 347.1.

Example 82: 5-Cyano-N-(3-(furan-3-yl)-1H-indazol-5-yl)isoxazole-3-carboxamide

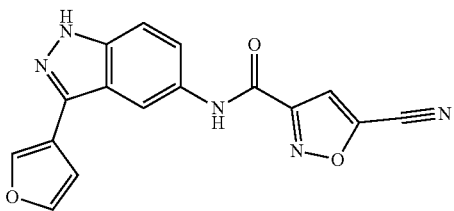 [SMILES: N#Cc1cc(C(=O)Nc2ccc3[nH]nc(-c4ccoc4)c3c2)no1]

To a solution of 5-ethynylisoxazole-3-carboxylic acid (40 mg, 289.69 umol) and 3-(furan-3-yl)-1H-indazol-5-amine (69.25 mg, 347.62 umol) in pyridine (2 mL) was added EDCI (111.07 mg, 579.37 umol). The mixture was stirred at 20° C. for 12 hrs. The reaction was combined with another 10 mg batch and the combined reaction mixtures were concentrated under reduced pressure to remove solvent. The residue was purified by preparative HPLC under neutral condition (Method Z) and then further purified by preparative HPLC under TFA conditions (Method AA) to afford the title compound (10.14 mg, TFA salt) as a white solid. $^1$H NMR (400 MHz, DMSO-$d_6$) δ 13.15 (s, 1H), 11.02 (s, 1H), 8.38 (s, 1H), 8.24 (s, 1H), 8.14 (s, 1H), 7.85 (s, 1H), 7.75 (d, J=9.0 Hz, 1H), 7.58 (d, J=8.9 Hz, 1H), 6.99 (s, 1H). MS-ESI (m/z) calc'd for $C_{16}H_{10}N_5O_3$[M+H]$^+$: 320.1. Found 320.0.

Example 83: 5-Cyano-3-ethyl-N-(3-(furan-3-yl)-1H-indazol-5-yl)picolinamide

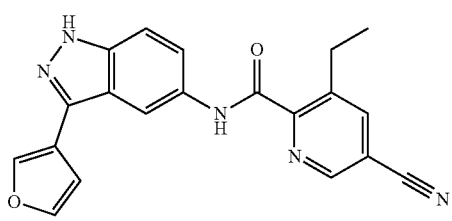 [SMILES: CCc1cc(C#N)cnc1C(=O)Nc1ccc2[nH]nc(-c3ccoc3)c2c1]

Step 1: 2-Chloro-5-ethynyl-3-vinylpyridine

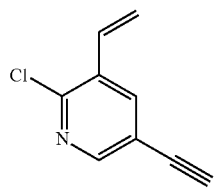

A mixture of 3-bromo-2-chloro-5-ethynylpyridine (2 g, 9.20 mmol), 4,4,5,5-tetramethyl-2-vinyl-1,3,2-dioxaborolane (1.42 g, 9.20 mmol, 1.56 mL), Pd(dppf)Cl$_2$.CH$_2$Cl$_2$ (751.10 mg, 919.75 umol), Na$_2$CO$_3$ (2 M, 13.80 mL) in dioxane (50 mL) was degassed and purged with N$_2$ (3×). The mixture was then stirred at 90° C. for 1.5 hrs under N$_2$ atmosphere and monitored by TLC (petroleum ether:EtOAc=10:1, Rf=0.48). The reaction mixture was concentrated under reduced pressure to remove solvent, diluted with H$_2$O (30 mL) and extracted with EtOAc (50 mL×4). The combined organic layers were dried over Na$_2$SO$_4$, filtered and concentrated under reduced pressure to give a residue. The residue was purified by flash silica gel chromatography (ISCO; 20 g SepaFlash column) using a 0-7% EtOAc/petroleum ether gradient eluent to afford the title compound (920 mg, 30% yield) as a yellow solid.

Step 2: Methyl 5-ethynyl-3-vinylpicolinate

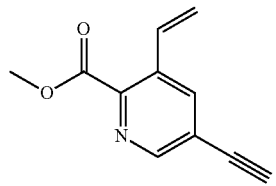

A mixture of 2-chloro-5-ethynyl-3-vinylpyridine (900 mg, 5.47 mmol), Pd(dppf)Cl$_2$ (400.10 mg, 547.00 umol), Et$_3$N (2.77 g, 27.35 mmol) in MeOH (10 mL) was degassed and purged with CO (3×), and then the mixture was stirred at 30° C. for 2 hrs under CO atmosphere (50 psi). The reaction mixture was concentrated under reduced pressure to remove solvent and purified by flash silica gel chromatography (ISCO; 20 g SepaFlash column) using a 0-8% EtOAc/petroleum ether gradient eluent to afford the title compound (240 mg, 23% yield) as a white solid.

Step 3: Methyl 3-ethyl-5-ethynylpicolinate

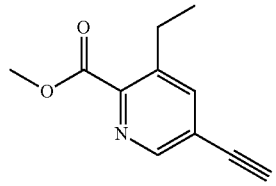

A mixture of methyl 5-ethynyl-3-vinylpicolinate (230 mg, 1.22 mmol) and 10% Pd/C (200 mg) in EtOH (10 mL) was degassed and purged with H$_2$ (3×). The mixture was then stirred at 20° C. for 2 hrs under H$_2$ atmosphere (15 psi). The mixture was filtered and the filtrate was concentrated under reduced pressure to afford the title compound (170 mg) as a yellow solid which was used without further purification.

Step 4: 3-Ethyl-5-ethynylpicolinic acid

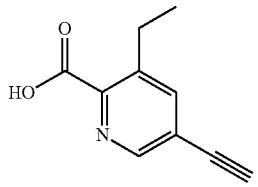

To a solution methyl 3-ethyl-5-ethynylpicolinate of (170 mg, 893.80 umol) in THF (5 mL) was added NaOH (71.50 mg, 1.79 mmol). The mixture was stirred at 20° C. for 2 hrs and monitored by TLC (petroleum ether:EtOAc=3:1, Rf=0.00). The reaction mixture was diluted with $H_2O$ (10 mL) and the mixture was adjusted to pH 3 with 1N HCl. Then it was extracted with EtOAc (20 mL×6). The combined organic layers were dried over $Na_2SO_4$, filtered and concentrated under reduced pressure to afford the title compound (110 mg) as a pale yellow solid that was used without further purification.

Step 4: 5-Cyano-3-ethyl-N-(3-(furan-3-yl)-1H-indazol-5-yl)picolinamide

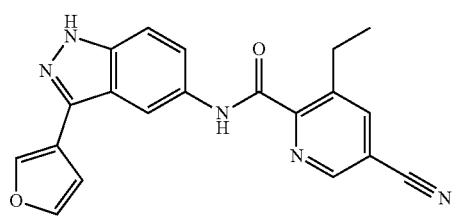 [SMILES: CCc1cc(C#N)cnc1C(=O)Nc1ccc2[nH]nc(-c3ccoc3)c2c1]

To a solution of 3-ethyl-5-ethynylpicolinic acid (110 mg, 624.39 umol) in pyridine (3 mL) was added EDCI (239.39 mg, 1.25 mmol) and 3-(furan-3-yl)-1H-indazol-5-amine (136.82 mg, 686.83 umol). The mixture was stirred at 20° C. for 12 hrs. The reaction mixture was concentrated and purified by preparative HPLC (Method AB) to afford the title compound (65.03 mg, 21% yield) as a yellow solid, TFA salt. $^1$H NMR (400 MHz, DMSO-d$_6$) δ 13.11 (br s, 1H) 10.71 (s, 1H) 9.00 (d, J=1.10 Hz, 1H) 8.42 (d, J=12.59 Hz, 2H) 8.25 (s, 1H) 7.85 (s, 1H) 7.76-7.82 (m, 1H) 7.56 (d, J=8.93 Hz, 1H) 7.00 (s, 1H) 2.97 (q, J=7.34 Hz, 2H) 1.24 (t, J=7.46 Hz, 3H). MS-ESI (m/z) calc'd for $C_{20}H_{16}N_5O_2$ [M+H]$^+$: 358.1. Found 358.1.

Example 84: 5-Cyano-N-(3-(furan-3-yl)-1H-indazol-5-yl)-3-vinylpicolinamide

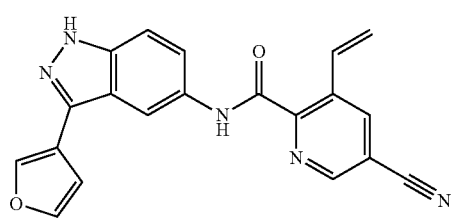 [SMILES: C=Cc1cc(C#N)cnc1C(=O)Nc1ccc2[nH]nc(-c3ccoc3)c2c1]

Prepared as described for 5-cyano-3-ethyl-N-(3-(furan-3-yl)-1H-indazol-5-yl)picolinamide using methyl 5-ethynyl-3-vinylpicolinate in place of methyl 3-ethyl-5-ethynylpicolinate in step 4. $^1$H NMR (400 MHz, DMSO-d$_6$) δ 13.12 (br s, 1H) 10.79 (s, 1H) 9.06 (s, 1H) 8.82 (s, 1H) 8.43 (s, 1H) 8.26 (s, 1H) 7.73-7.88 (m, 2H) 7.56 (br d, J=8.80 Hz, 1H) 7.35 (br dd, J=17.42, 11.07 Hz, 1H) 7.00 (s, 1H) 6.14 (br d, J=17.48 Hz, 1H) 5.61 (br d, J=11.13 Hz, 1H). MS-ESI (m/z) calc'd for $C_{20}H_{14}N_5O_2$ [M+H]$^+$: 358.1. Found 356.0.

Example 85: 5-Cyano-N-(3-(furan-3-yl)-1H-indazol-5-yl)-4,6-dimethylpicolinamide

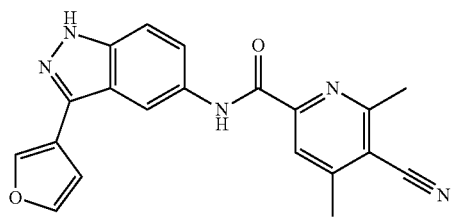 [SMILES: Cc1cc(C(=O)Nc2ccc3[nH]nc(-c4ccoc4)c3c2)nc(C)c1C#N]

Step 1: 2,4-Dimethyl-6-vinylnicotinonitrile

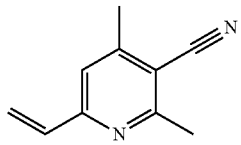

A mixture of 6-chloro-2,4-dimethylnicotinonitrile (70.0 mg, 0.420 mmol), tributyl(vinyl)tin (0.15 mL, 0.500 mmol) and tetrakis(triphenylphosphine)palladium(0) (24.28 mg, 0.020 mmol) in toluene (3.6 mL) was heated in a sealed tube at 100° C. for 1.5 hrs. After cooling to r.t., volatiles were evaporated at reduced pressure and the residue was partitioned between EtOAc and water. The organic phase was concentrated under reduced pressure and purified by reversed phase column chromatography using a 0-30% EtOAc/cyclohexane gradient eluent (C-18 Biotage) to afford the title compound (90 mg) as a pale yellow oil. $^1$H NMR (400 MHz, CDCl$_3$) δ 7.09 (s, 1H), 6.75 (dd, J=17.4, 10.7 Hz, 1H), 6.33 (dd, J=17.4, 1.2 Hz, 1H), 5.62 (dd, J=10.7, 1.2 Hz, 1H), 2.74 (s, 3H), 2.52 (s, 3H). MS-ESI (m/z) calc'd for $C_{10}H_{11}N_2$ [M+H]$^+$: 159.1. Found 159.0.

Step 2: 5-Cyano-4,6-dimethylpicolinic acid

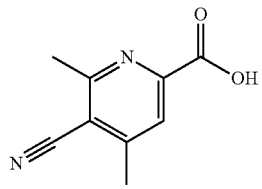

To a solution of 2,4-dimethyl-6-vinylnicotinonitrile (90.0 mg, 0.570 mmol) in acetone (3.3 mL) and water (3.3 mL)

was added potassium permanganate (89.9 mg, 0.570 mmol). The mixture was stirred at r.t. for 1 hr. The solution was then diluted with water and extracted with EtOAc. The organic phase was concentrated under reduced pressure to afford the title compound (60 mg, 60% yield) which was used directly without further purification. MS-ESI (m/z) calc'd for $C_9H_9N_2O_2[M+H]^+$: 177.1. Found 177.0.

Step 3: 5-(Cyano-N-(3-(furan-3-yl)-1H-indazol-5-yl)-4,6-dimethylpicolinamide

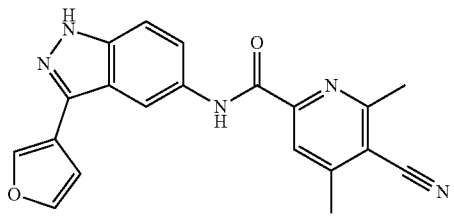 [SMILES: Cc1cc(C(=O)Nc2ccc3[nH]nc(-c4ccoc4)c3c2)nc(C)c1C#N]

5-Cyano-4,6-dimethylpicolinic acid (60.0 mg, 0.340 mmol) and 3-(furan-3-yl)-1H-indazol-5-amine (0.12 mL, 0.440 mmol) were dissolved in DMF (3.014 mL). Triethylamine (0.06 mL, 0.410 mmol) and HATU (129.5 mg, 0.340 mmol) were sequentially added and the mixture was stirred at r.t. for 18 hrs. Water was added and the mixture was extracted with EtOAc. The organic phase was dried over $Na_2SO_4$, filtered and concentrated under reduced pressure. The residue was purified by reverse phase column chromatography (Cis-cartridge, MeCN in $H_2O$+0.1% HCOOH, [2%, 100%, 7 CV] and then with 100% MeOH). The product-containing fractions were collected and concentrated under reduced pressure. The residue was triturated with MeCN and then the solid phase was filtered. To remove traces of solvent, the product was taken up in 1 mL of water and then concentrated and dried to afford the title compound (13.6 mg, 11% yield) as a beige solid. $^1$H NMR (400 MHz, DMSO-$d_6$) δ 13.11 (s, 1H), 10.62 (s, 1H), 8.45 (s, 1H), 8.33 (s, 1H), 8.09 (s, 1H), 7.97 (dd, J=9.0, 1.9 Hz, 1H), 7.85 (t, J=1.7 Hz, 1H), 7.59 (d, J=9.0 Hz, 1H), 7.03 (d, J=1.9 Hz, 1H), 2.84 (s, 3H), 2.63 (s, 3H). MS-ESI (m/z) calc'd for $C_{20}H_{16}N_5O_2$ $[M+H]^+$: 358.1. Found 358.2.

Example 86: 2-Chloro-3-cyano-N-(3-(furan-3-yl)-1H-indazol-5-yl)benzamide

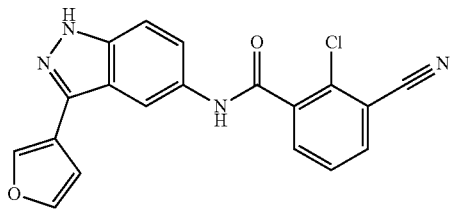

To a mixture of 2-chloro-3-cyanobenzoic acid (45.58 mg, 0.250 mmol), 3-(furan-3-yl)-1H-indazol-5-amine (50.0 mg, 0.250 mmol) and triethylamine (34.98 uL, 0.250 mmol) was added HATU (95.43 mg, 0.250 mmol) and the mixture was stirred at room temperature for 56 hrs. The reaction mixture was partitioned between water and EtOAc, the phases were separated, the aqueous layer was extracted with EtOAc (2×) and the combined organic phases were washed with water (1×), dried over anhydrous $Na_2SO_4$ and evaporated to dryness. The material was purified by silica gel chromatography on a 25 g column using a 0-80% EtOAc/cyclohexane gradient eluent to afford the title compound (73 mg, 80% yield) as an off-white solid. $^1$H NMR (400 MHz, DMSO-$d_4$) δ ppm 13.13 (br. s., 1H), 10.69 (br. s., 1H), 8.37 (s, 1H), 8.23-8.18 (m, 1H), 8.13 (dd, J=1.7, 7.8 Hz, 1H), 8.00 (dd, J=1.5, 7.7 Hz, 1H), 7.86 (t, J=1.7 Hz, 1H), 7.71 (t, J=7.7 Hz, 1H), 7.64-7.55 (m, 2H), 6.99 (dd, J=0.8, 1.9 Hz, 1H). MS-ESI (m/z) calc'd for $C_{19}H_{12}ClN_4O_2[M+H]^+$: 363.1. Found 363.1, 365.0.

Example 87: 5-Cyano-N-(3-iodo-1H-indazol-5-yl)-3-methylpicolinamide

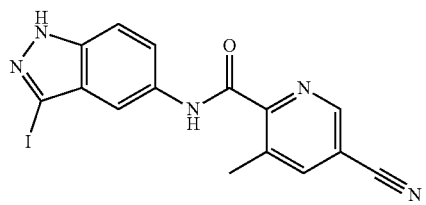 [SMILES: Cc1cc(C#N)cnc1C(=O)Nc1ccc2[nH]nc(I)c2c1]

To a mixture of 3-iodo-1H-indazol-5-amine (2.3 g, 8.88 mmol) and 5-cyano-3-methylpyridine-2-carboxylic acid (1.06 g, 6.51 mmol) in MeCN (57.58 mL) was added triethylamine (906.85 uL, 6.51 mmol) and HATU (2.47 g, 6.51 mmol). The mixture was stirred at r.t. for 45 minutes. The suspension was filtered and the residue was washed with MeCN and water. The solid was dried under reduced pressure at 50° C. for 18 hrs. To remove traces of impurities, the solid was triturated with MeOH and water and then filtered. The solid was washed with MeOH and then dried under reduced pressure to afford the title compound (2.49 g, 95% yield) as a beige solid. $^1$H NMR (400 MHz, DMSO-$d_6$) δ 13.50 (s, 1H), 10.80 (s, 1H), 9.00 (d, J=1.9 Hz, 1H), 8.41 (d, J=2.0 Hz, 1H), 8.14 (s, 1H), 7.72 (d, J=9.0, 1.9 Hz, 1H), 7.56 (d, J=8.9 Hz, 1H), 2.59 (s, 3H). MS-ESI (m/z) calc'd for $C_{15}H_{10}IN_5O$ $[M+H]^+$: 404.1. Found 404.1.

Example 88: 3-Cyano-N-(3-(furan-3-yl)-7-methyl-1H-indazol-5-yl)-2-methylbenzamide

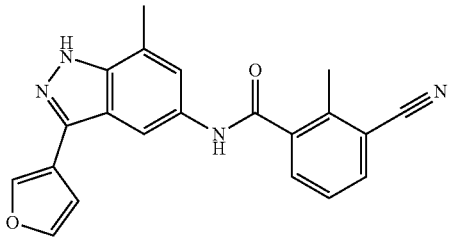 [SMILES: Cc1c(C#N)cccc1C(=O)Nc1cc(C)c2[nH]nc(-c3ccoc3)c2c1]

To a mixture of 3-cyano-2-methylbenzoic acid (22.67 mg, 0.140 mmol), 3-(furan-3-yl)-7-methyl-1H-indazol-5-amine (30.0 mg, 0.140 mmol) and triethylamine (39.22 uL, 0.280 mmol) was added HATU (53.49 mg, 0.140 mmol) and the mixture was stirred at room temperature overnight. The reaction mixture was partitioned between water and EtOAc and the phases were separated. The aqueous layer was extracted with EtOAc (2×) and the combined organic phases washed with brine (1×), dried over anhydrous Na$_2$SO$_4$ and evaporated to dryness. The material was dissolved in DMF and purified by silica gel chromatography on a 25 g column using a 0-80% EtOAc/cyclohexane gradient eluent to afford the title compound (18 mg, 36% yield) as a white solid. $^1$H NMR (400 MHz, DMSO-d$_6$) δ ppm 13.16 (s, 1H), 10.42 (s, 1H), 8.19 (d, J=6.6 Hz, 2H), 7.93 (d, J=6.8 Hz, 1H), 7.87-7.78 (m, 2H), 7.54 (t, J=7.7 Hz, 1H), 7.45 (s, 1H), 6.99 (s, 1H), 2.90 (s, 1H), 2.59 (s, 3H), 2.54 (s, 3H). MS-ESI (m/z) calc'd for C$_{21}$H$_{17}$N$_4$O$_2$ [M+H]$^+$: 357.1. Found 357.2.

Example 89: 2-Bromo-3-cyano-N-(3-(furan-3-yl)-1H-indazol-5-yl)benzamide

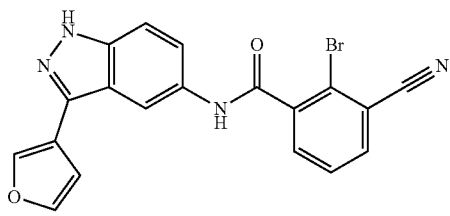

To a mixture of 2-bromo-3-cyanobenzoic acid (113.46 mg, 0.500 mmol), 3-(furan-3-yl)-1H-indazol-5-amine (100.0 mg, 0.500 mmol) and triethylamine (50.8 mg, 0.500 mmol) was added HATU (190.87 mg, 0.500 mmol) and the mixture was stirred at room temperature over the weekend. The reaction mixture was partitioned between water and EtOAc, the phases were separated, the aqueous layer was extracted with EtOAc (2×) and the combined organic phases washed with brine (1×), dried over anhydrous Na$_2$SO$_4$ and evaporated to dryness. The material was purified by silica gel chromatography on a 25 g column using a 0-100% EtOAc/cyclohexane gradient eluent. Pure fractions were combined and evaporated to dryness to afford the title compound (29 mg, 0.071 mmol) as a white solid. $^1$H NMR (400 MHz, DMSO-d$_6$) δ ppm 13.12 (br. s., 1H), 10.65 (br. s., 1H), 8.37 (s, 1H), 8.23-8.16 (m, 1H), 8.08 (dd, J=1.7, 7.8 Hz, 1H), 7.93 (dd, J=1.7, 7.6 Hz, 1H), 7.86 (t, J=1.7 Hz, 1H), 7.74 (t, J=7.7 Hz, 1H), 7.67-7.53 (m, 2H), 6.99 (dd, J=0.8, 1.9 Hz, 1H). MS-ESI (m/z) calc'd for C$_{19}$H$_{12}$BrN$_4$O$_2$ [M+H]$^+$: 407.0. Found 407.1, 409.1.

Example 90: 3-Cyano-N-(3-(furan-3-yl)-1H-indazol-5-yl)-1,5-dimethyl-1H-pyrazole-4-carboxamide

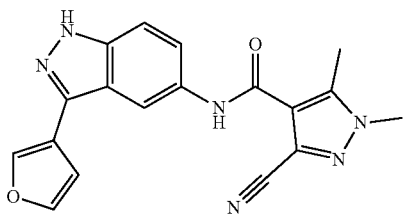 [SMILES: Cc1c(C(=O)Nc2ccc3[nH]nc(-c4ccoc4)c3c2)c(C#N)nn1C]

Prepared as described for 5-cyano-N-(3-(furan-3-yl)-1H-indazol-5-yl)-1,4-dimethyl-1H-pyrazole-3-carboxamide using 3-cyano-1,5-dimethyl-1H-pyrazole-4-carboxylic acid in place of 5-cyano-1,4-dimethyl-1H-pyrazole-3-carboxylic acid in step 4. $^1$H NMR (400 MHz, DMSO-d$_6$) δ 13.10 (br s, 1H) 10.24 (s, 1H) 8.30 (s, 1H) 8.22 (s, 1H) 7.85 (t, J=1.59 Hz, 1H) 7.56 (s, 2H) 6.98 (d, J=1.22 Hz, 1H) 3.91 (s, 3H) 2.49 (br s, 3H). MS-ESI (m/z) calc'd for C$_{18}$H$_{15}$N$_6$O$_2$ [M+H]$^+$: 347.1. Found 347.1.

Example 91: 5-Cyano-N-(3-(furan-3-yl)-1H-indazol-5-yl)isothiazole-3-carboxamide

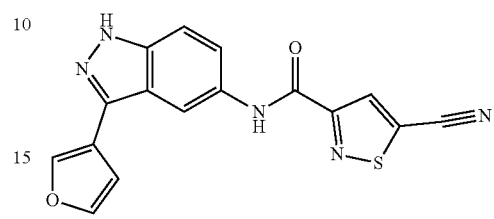

Step 1: 3-Azidothiophene-2-carbaldehyde

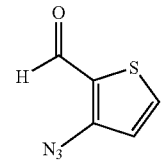

To a stirred solution of 3-bromothiophene-2-carbaldehyde (2 g, 10.47 mmol) in DMSO (15 mL) was added NaN$_3$ (2.72 g, 41.87 mmol). The reaction mixture was stirred at 80° C. for 4 hrs under N$_2$ and monitored by TLC (petroleum ether:EtOAc=5:1, R$_f$=0.40). After cooling to 20° C., the reaction mixture was poured into water (100 mL) and extracted with EtOAc (100 mL×2). The combined organic phases were dried over anhydrous Na$_2$SO$_4$, filtered and concentrated. The residue was purified by silica gel column chromatography using a 0-20% EtOAc/petroleum ether gradient eluent to afford the title compound (1 g, 62% yield) as a light yellow solid.

Step 2: Ethyl (Z)-2-azido-3-(3-azidothiophen-2-yl)acrylate

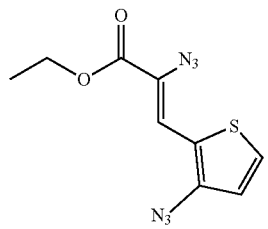 [SMILES: CCOC(=O)/C(=C/c1sccc1N=[N+]=[N-])N=[N+]=[N-]]

To a stirred solution of EtONa (3.17 g, 9.30 mmol, 20% purity) in EtOH (20 mL) at −15° C. was added a mixture of 3-azidothiophene-2-carbaldehyde (950 mg, 6.20 mmol) and ethyl 2-azidoacetate (800.86 mg, 6.20 mmol, 870.50 uL) in EtOH (10 mL) dropwise while keeping the temperature below −10° C. The reaction mixture was stirred at −15° C. for 2.5 hrs and monitored by TLC (petroleum ether:EtOAc=5:1, Rf=0.50). After warming to 0° C., the reaction mixture was poured into water (30 mL) and extracted with EtOAc (30 mL×3). The combined organic phases were dried over anhydrous Na₂SO₄, filtered and concentrated. The residue was purified by silica gel column chromatography using a 0-20% EtOAc/petroleum ether gradient eluent to afford the title compound (210 mg, 13% yield) as a light yellow solid.

Step 4: Ethyl 5-cyanoisothiazole-3-carboxylate

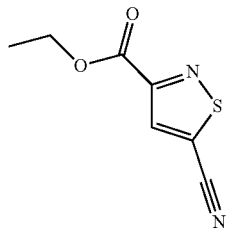

Ethyl (Z)-2-azido-3-(3-azidothiophen-2-yl)acrylate (210 mg, 794.66 umol) was dissolved in toluene (5 mL) and the reaction mixture was stirred at 110° C. for 0.5 hr under N₂ and monitored by TLC (petroleum ether:EtOAc=4:1, Rf=0.50). After cooling to 20° C., the reaction mixture was concentrated and the residue was purified by silica gel column chromatography using a 0-20% EtOAc/petroleum ether gradient eluent to afford the title compound (30 mg, 21% yield) as a yellow oil.

Step 5: 5-Cyano-N-(3-(furan-3-yl)-1H-indazol-5-yl) isothiazole-3-carboxamide

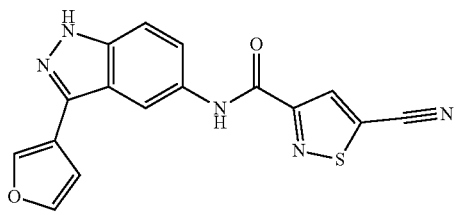

To a stirred solution of ethyl 5-cyanoisothiazole-3-carboxylate (20 mg, 109.77 umol) and 3-(furan-3-yl)-1H-indazol-5-amine (21.87 mg, 109.77 umol) in toluene (1 mL) was added AlMe₃ (2 M, 109.77 uL) and the reaction mixture was stirred at 20° C. for 12 hrs. The reaction mixture was poured into ice-water (3 mL) and extracted with EtOAc (3 mL×3). The combined organic phases were concentrated. The residue was purified by preparative HPLC (Method AC) to afford the title compound (6.31 mg, 17% yield) as a yellow solid. ¹H NMR (400 MHz, DMSO-d₆) δ 8.67 (s, 1H), 8.49-8.39 (m, 1H), 8.25 (s, 1H), 7.93-7.81 (m, 2H), 7.57 (br d, J=8.9 Hz, 1H), 7.04-6.98 (m, 1H). MS-ESI (m/z) calc'd for C₁₆H₁₀N₅O₂S [M+H]⁺: 336.1. Found 336.1.

Example 92: 3-Cyano-N-(3-(furan-3-yl)-1H-indazol-5-yl)-1,4-dimethyl-1H-pyrazole-5-carboxamide

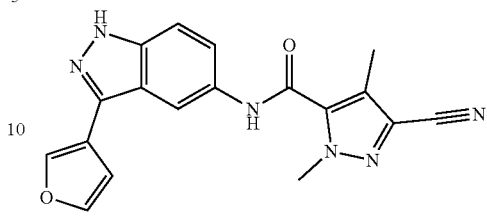

Prepared as described for 5-cyano-N-(3-(furan-3-yl)-1H-indazol-5-yl)-1,4-dimethyl-1H-pyrazole-3-carboxamide using ethyl 3-ethynyl-1,4-dimethyl-1H-pyrazole-5-carboxylate in place of ethyl 5-cyano-1,4-dimethyl-1H-pyrazole-3-carboxylate in step 2. ¹H NMR (400 MHz, DMSO-d₆) δ 13.15 (br s, 1H) 10.57 (br s, 1H) 8.36 (s, 1H) 8.25 (s, 1H) 7.86 (s, 1H) 7.55-7.68 (m, 2H) 7.00 (s, 1H) 4.06 (s, 3H) 2.51 (br s, 3H). MS-ESI (m/z) calc'd for C₁₅H₅N₆O₂ [M+H]⁺: 347.1. Found 347.1.

Example 93: 5-Cyano-N-(3-(furan-3-yl)-1H-indazol-5-yl)-1,4-dimethyl-1H-pyrazole-3-carboxamide

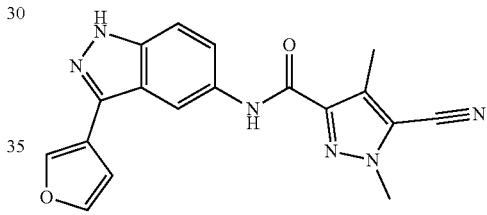

Step 1: Ethyl 5-cyano-4-methyl-1H-pyrazole-3-carboxylate

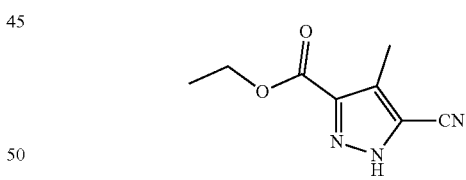

To a solution of ethyl but-2-ynoate (5 g, 44.59 mmol, 5.20 mL) and 2-aminoacetonitrile (7.43 g, 80.27 mmol, HCl) in CHCl₃ (120 mL) and H₂O (4 mL) was added NaNO₂ (9.23 g, 133.78 mmol). The mixture was stirred at 20° C. for 12 hrs and monitored by TLC (petroleum ether/EtOAc=5:1). The reaction mixture was diluted with H₂O (100 mL) and extracted with CHCl₃ (30 mL×3). The combined organic layers were washed with brine (50 mL×1), dried over Na₂SO₄, filtered and concentrated under reduced pressure to give a residue. The residue was purified by silica gel column chromatography using a 0-25% EtOAc/petroleum ether gradient eluent to afford the title compound (200 mg, 870.65 umol) as a yellow oil and ethyl 5-cyano-3-methyl-1H-pyrazole-4-carboxylate (140 mg, 687.59 umol) as a yellow solid.

Step 2: Ethyl 5-cyano-1,4-dimethyl-1H-pyrazole-3-carboxylate

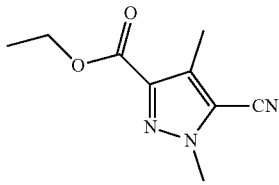

To a solution of ethyl 5-cyano-4-methyl-1H-pyrazole-3-carboxylate (150 mg, 837.17 umol) in DMF (2 mL) was added K₂CO₃ (347.11 mg, 2.51 mmol) and the mixture was stirred at 20° C. for 0.5 hr, then MeI (142.59 mg, 1.00 mmol) was added and the resulting mixture was stirred at 20° C. for 12 hrs and monitored by TLC (SiO₂, petroleum ether/EtOAc=3/1). The reaction mixture was concentrated under reduced pressure to remove solvent. The residue was purified by preparative TLC (SiO₂, petroleum ether/EtOAc=3:1) to afford the title compound (40 mg, 25%) as a light yellow solid and ethyl 3-cyano-1,4-dimethyl-1H-pyrazole-5-carboxylate (100 mg, 517.59 umol) as a white solid.

Step 3: 5-Cyano-1,4-dimethyl-1H-pyrazole-3-carboxylic acid

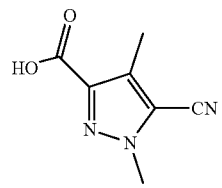

To a solution of ethyl 5-cyano-1,4-dimethyl-1H-pyrazole-3-carboxylate (15 mg, 77.64 umol) in THF (1 mL) and H₂O (0.5 mL) was added NaOH (6.21 mg, 155.28 umol) and the mixture was stirred at 20° C. for 1 hr. The reaction mixture was concentrated under reduced pressure to remove solvent. The residue was diluted with H₂O (10 mL) and adjusted pH to 3 with 1 N HCl. Then the aqueous phase was extracted with EtOAc (3 mL×3). The combined organic layers were dried over Na₂SO₄, filtered and concentrated under reduced pressure to afford the title compound (15 mg) as a white solid which was used without further purification.

Step 4: 5-Cyano-N-(3-(furan-3-yl)-1H-indazol-5-yl)-1,3-dimethyl-1H-pyrazole-4-carboxamide

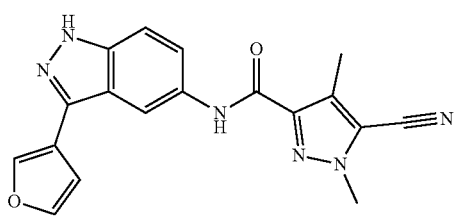 [SMILES: Cc1c(C(=O)Nc2ccc3[nH]nc(-c4ccoc4)c3c2)nn(C)c1C#N]

To a solution of 5-cyano-1,4-dimethyl-1H-pyrazole-3-carboxylic acid (15 mg, 90.83 umol) and 3-(furan-3-yl)-1H-indazol-5-amine (18.09 mg, 90.83 umol) in pyridine (1 mL) was added EDCI (34.82 mg, 181.65 umol) and the mixture was stirred at 20° C. for 12 hrs. The reaction was filtered and the filtrate was collected and purified by preparative HPLC (Method AD) to afford the title compound (13.37 mg, 42%) as a pale yellow solid. ¹H NMR (400 MHz, DMSO-d₆) δ 13.04 (s, 1H) 10.23 (s, 1H) 8.37 (s, 1H) 8.25 (s, 1H) 7.79-7.89 (m, 2H) 7.52 (d, J=9.05 Hz, 1H) 7.00 (s, 1H) 4.10 (s, 3H) 2.42 (s, 3H). MS-ESI (m/z) calc'd for C15H15N6O2 [M+H]⁺: 347.1. Found 347.1.

Example 94: 5-Cyano-N-(3-(furan-3-yl)-1H-indazol-5-yl)4-methylpicolinamide

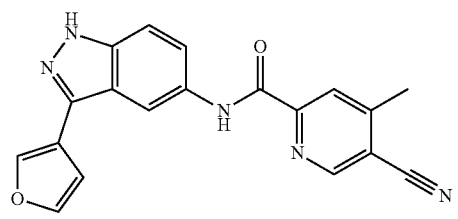 [SMILES: Cc1cc(C(=O)Nc2ccc3[nH]nc(-c4ccoc4)c3c2)ncc1C#N]

Step 1: Methyl 5-cyano-4-methylpicolinate

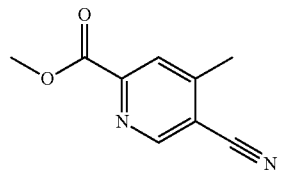

A mixture of 6-bromo-4-methylnicotinonitrile (350 mg, 1.78 mmol), TEA (359.50 mg, 3.55 mmol) and Pd(dppf)Cl₂ (259.95 mg, 355.27 umol) in MeOH (5 mL) and DMF (5 mL) was degassed and purged with CO (3×). The mixture was then stirred at 60° C. under a CO atmosphere (50 Psi) and monitored by TLC (petroleum ether:EtOAc=1:1, Rf=0.17). After 12 hrs, the temperature was raised to 70° C. and stirring under a CO atmosphere (50 Psi) was continued for 5 hrs. The reaction mixture was concentrated under reduced pressure to remove solvent and purified by silica gel column chromatography using a 0-30% EtOAc/petroleum ether gradient eluent to afford the title compound (360 mg, 81% yield) as a white solid.

Step 2: 5-Cyano-4-methylpicolinic acid

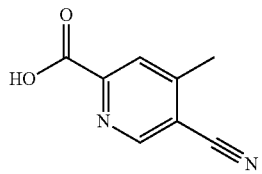

To a solution of methyl 5-cyano-4-methylpicolinate (200 mg, 1.14 mmol) in H₂O (3 mL) and THF (9 mL) was added LiOH.H₂O (95.28 mg, 2.27 mmol). The mixture was stirred at 20° C. for 4 hrs. The reaction mixture was added to H₂O (10 mL) and acidified with 1N HCl to pH=2, extracted with EtOAc (10 mL×4), the combined organic layers were dried over anhydrous Na₂SO₄, filtered and the filtrate was concentrated under vacuum to afford the title compound (150 mg) as a white solid which was used without further purification.

Step 3: 5-Cyano-N-(3-(furan-3-yl)-1H-indazol-5-yl)-4-methylpicolinamide

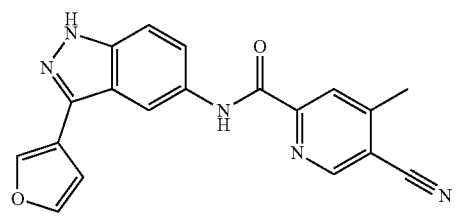 [SMILES: Cc1cc(C(=O)Nc2ccc3[nH]nc(-c4ccoc4)c3c2)ncc1C#N]

To a solution of 5-cyano-4-methylpicolinic acid (100 mg, 616.73 umol) and 3-(furan-3-yl)-1H-indazol-5-amine (245.72 mg, 1.23 mmol) in pyridine (4 mL) was added EDCI (236.46 mg, 1.23 mmol) and the mixture was stirred at 20° C. for 12 hrs. The reaction mixture was concentrated under reduced pressure to remove solvent. The residue was diluted with DMF (1 mL) and acidified with TFA to pH=1. The mixture was purified by preparative HPLC (Method AE) to afford the title compound (117.52 mg, 42% yield) as a gray solid, TFA salt. ¹H NMR (400 MHz, DMSO-d₆) δ 13.10 (s, 1H), 10.81 (s, 1H), 9.11 (s, 1H), 8.50 (s, 1H), 8.29 (d, J=9.7 Hz, 2H), 8.01 (br d, J=8.9 Hz, 1H), 7.85 (s, 1H), 7.57 (d, J=8.9 Hz, 1H), 7.02 (s, 1H), 2.65 (s, 3H). MS-ESI (m/z) calc'd for C19H14N5O2 [M+H]⁺: 344.1. Found 344.2.

Example 95: 3-Chloro-5-cyano-N-(3-(furan-3-yl)-1H-indazol-5-yl)picolinamide

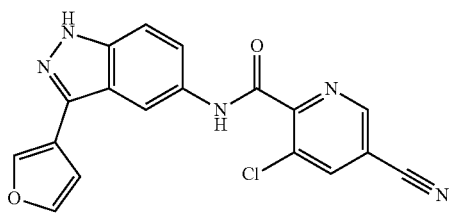

To a mixture of 3-chloro-5-cyanopicolinic acid (36.51 mg, 0.200 mmol) and triethylamine (27.88 uL, 0.200 mmol) in MeCN (2 mL) was added HATU (76.05 mg, 0.200 mmol). The mixture was stirred at 25° C. for 5 minutes and then 3-(furan-3-yl)-1H-indazol-5-amine (39.84 mg, 0.200 mmol) was added and the mixture was stirred at 25° C. for 15 minutes. The solvent was evaporated and the residue was taken up in water and extracted with EtAOc (3×). The combined organic layers were passed through a phase separator and evaporated to obtain a residue which was purified by silica gel column chromatography using a 0-5% MeOH/DCM gradient eluent to afford the title compound (31 mg, 43% yield) as a yellow solid. ¹H NMR (400 MHz, DMSO-d₆) δ 13.14 (s, 1H), 10.85 (s, 1H), 9.13 (d, J=1.7 Hz, 1H), 8.82 (d, J=1.7 Hz, 1H), 8.37 (dd, J=1.9, 0.8 Hz, 1H), 8.22 (dd, J=1.5, 0.8 Hz, 1H), 7.85 (t, J=1.7 Hz, 1H), 7.67 (dd, J=9.0, 1.9 Hz, 1H), 7.58 (dd, J=8.9, 0.8 Hz, 1H), 6.99 (dd, J=1.8, 0.8 Hz, 1H). MS-ESI (m/z) calc'd for C₁₅H₁₁ClN₅O₂ [M+H]⁺: 364.1, 366.1. Found 364.0, 366.0.

Example 96: 5-Cyano-N-(3-(furan-3-yl)-1H-indazol-5-yl)-1-methyl-1H-imidazole-2-carboxamide

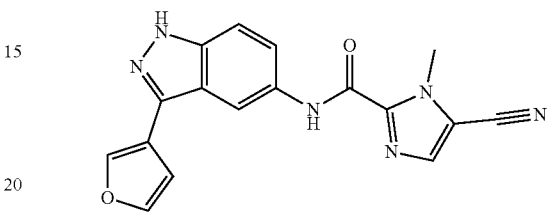

Step 1:
5-Cyano-1-methyl-1H-imidazole-2-carboxylic acid

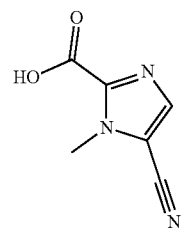

To a solution of 1-methyl-1H-imidazole-5-carbonitrile (100 mg, 933.59 umol) in THF (6 mL) was added LDA (2 M, 560.16 uL) at −78° C. and the reaction mixture was stirred at −78° C. for 0.5 hr. Then dry ice (410.87 mg, 9.34 mmol) was added and the reaction mixture was stirred at −78° C. for 1.5 hrs under N₂ (15 Psi). The reaction mixture was quenched with water (10 mL), basified to pH=9 with saturated aqueous Na₂CO₃, and extracted with EtOAc (15 mL×2). The aqueous phase was then acidified to pH=3 with 1N HCl solution and the mixture was filtered and dried to afford the title compound (60 mg, 43% yield) as a white solid, which was used without further purification.

Step 2: 5-Cyano-N-(3-(furan-3-yl)-1H-indazol-5-yl)-1-methyl-1H-imidazole-2-carboxamide

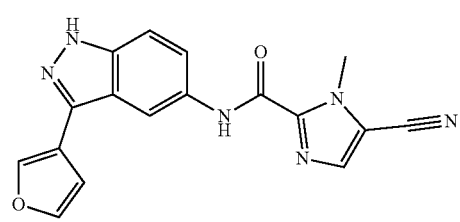 [SMILES: Cn1c(C#N)cnc1C(=O)Nc1ccc2[nH]nc(-c3ccoc3)c2c1]

To a solution of 5-cyano-1-methyl-1H-imidazole-2-carboxylic acid (40 mg, 264.69 umol) in pyridine (1 mL) was added EDCI (101.48 mg, 529.37 umol) and 3-(furan-3-yl)-1H-indazol-5-amine (52.73 mg, 264.69 umol) and the reaction mixture was stirred at 20° C. for 12 hrs. The reaction mixture was concentrated and purified by preparative HPLC (Method AF) to afford the title compound (38.95 mg, 44% yield) as a white solid. $^1$H NMR (400 MHz, DMSO-d$_6$) δ 13.08 (br s, 1H), 10.65 (br s, 1H), 8.41 (s, 1H), 8.26 (s, 1H), 8.04 (s, 1H), 7.88 (br d, J=8.9 Hz, 1H), 7.84 (s, 1H), 7.55 (d, J=9.0 Hz, 1H), 7.01 (s, 1H), 4.12 (s, 3H). MS-ESI (m/z) calc'd for C$_{17}$H$_{13}$N$_6$O$_2$ [M+H]$^+$: 333.1. Found 333.0.

Example 97: 5-Cyano-N-(3-(furan-3-yl)-1H-indazol-5-yl)-1-methyl-1H-pyrazole-3-carboxamide

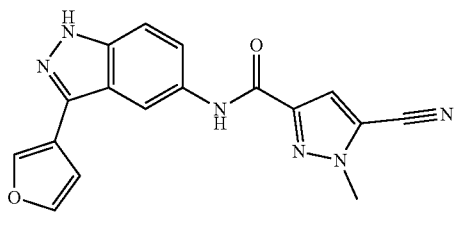 [SMILES: Cn1nc(C(=O)Nc2ccc3[nH]nc(-c4ccoc4)c3c2)cc1C#N]

Step 1: Methyl 5-cyano-1-methyl-1H-pyrazole-3-carboxylate

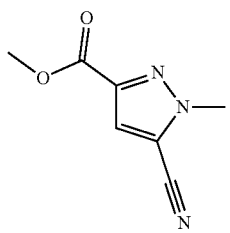

To a solution of methyl 5-bromo-1-methyl-1H-pyrazole-3-carboxylate (200 mg, 913.09 umol) in DMF (5 mL) was added CuCN (327.12 mg, 3.65 mmol). The mixture was stirred at 140° C. for 12 hrs in a sealed tube. The reaction mixture was concentrated and purified by silica gel column chromatography using a 0-30% EtOAc/petroleum ether gradient eluent to afford the title compound (60 mg, 40% yield) as a white solid and methyl 5-carbamoyl-1-methyl-1H-pyrazole-3-carboxylate (28 mg, 152.87 umol) as a pale yellow solid.

Step 2: 5-Cyano-N-(3-(furan-3-yl)-1H-indazol-5-yl)-1-methyl-1H-pyrazole-3-carboxamide

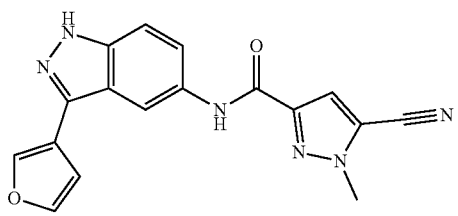 [SMILES: Cn1nc(C(=O)Nc2ccc3[nH]nc(-c4ccoc4)c3c2)cc1C#N]

To a solution of methyl 5-cyano-1-methyl-1H-pyrazole-3-carboxylate (50 mg, 302.76 umol) and methyl 5-carbamoyl-1-methyl-1H-pyrazole-3-carboxylate (90.47 mg, 454.14 umol) in toluene (2 mL) was added AlMe$_3$ (2 M, 454.14 uL). The mixture was stirred at 80° C. for 12 hrs. The reaction mixture was concentrated under reduced pressure and purified by preparative HPLC (Method AH) to afford the title compound (45.23 mg, 33% yield) as a brown solid, TFA salt. $^1$H NMR (400 MHz, DMSO-d$_4$) δ 13.08 (s, 1H) 10.37 (s, 1H) 8.39 (s, 1H) 8.25 (s, 1H) 7.80-7.88 (m, 2H) 7.65 (s, 1H) 7.53 (d, J=9.04 Hz, 1H) 7.00 (s, 1H) 4.15 (s, 3H). MS-ESI (m/z) calc'd for C$_{17}$H$_{13}$N$_6$O$_2$ [M+H]$^+$: 333.1. Found 333.0.

Example 98: 5-Cyano-3-methyl-N-(3-(o-tolyl)-1H-indazol-5-yl)picolinamide

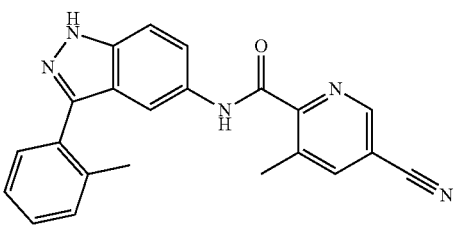 [SMILES: Cc1ccccc1-c1n[nH]c2ccc(NC(=O)c3ncc(C#N)cc3C)cc12]

Prepared as described for 5-cyano-N-(3-(2-methoxyphenyl)-1H-indazol-5-yl)-3-methylpicolinamide using o-tolylboronic acid in place of (2-methoxyphenyl)boronic acid in step 2. $^1$H NMR (400 MHz, DMSO-d$_6$) δ 13.21 (br s, 1H), 10.72 (s, 1H), 8.97 (d, J=1.1 Hz, 11H), 8.38 (s, 1H), 8.23 (s, 1H), 7.72 (dd, J=1.5, 9.0 Hz, 1H), 7.59 (d, J=9.0 Hz, 1H), 7.53-7.46 (m, 1H), 7.44-7.31 (m, 3H), 2.54 (s, 3H), 2.36 (s, 3H). MS-ESI (m/z) calc'd for C$_{22}$H$_{18}$N$_5$O [M+H]$^+$: 368.1. Found 368.1.

Example 99: 5-Cyano-N-(3-(2-methoxyphenyl)-1H-indazol-5-yl)-3-methylpicolinamide

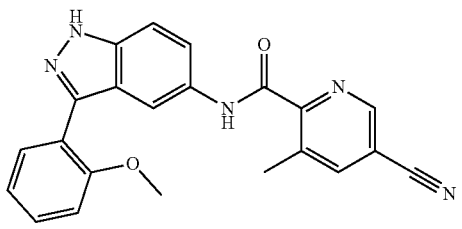 [SMILES: COc1ccccc1-c1n[nH]c2ccc(NC(=O)c3ncc(C#N)cc3C)cc12]

Step 1: 3-Bromo-1H-indazol-5-amine

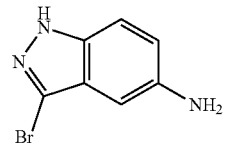 [SMILES: Nc1ccc2[nH]nc(Br)c2c1]

To a solution of 3-bromo-5-nitro-1H-indazole (1.42 g, 5.87 mmol) in EtOH (30 mL) was added SnCl$_2$.2H$_2$O (6.62 g, 29.34 mmol). The mixture was stirred at 90° C. for 12 hrs and monitored by TLC (petroleum ether:EtOAc=1:1, Rf=0.40). The reaction mixture was concentrated under reduced pressure to remove solvent and then diluted with 1 M NaOH (70 mL) and extracted with EtOAc (80 mL×4). The combined organic layers were dried over Na₂SO₄, filtered and concentrated under reduced pressure to afford the title compound (1.1 g) as a blue solid which was used without further purification.

Step 2: 3-(2-Methoxyphenyl)-1H-indazol-5-amine

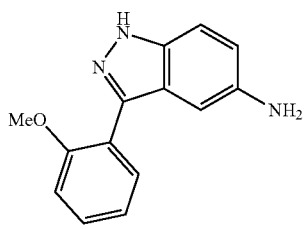 [SMILES: COc1ccccc1-c1n[nH]c2ccc(N)cc12]

To a solution of 3-bromo-1H-indazol-5-amine (600 mg, 2.83 mmol) in dioxane (8 mL) and H₂O (8 mL) was added (2-methoxyphenyl)boronic acid (644.95 mg, 4.24 mmol), Pd(dppf)Cl₂ (207.04 mg, 282.96 umol) and Na₂CO₃ (1.50 g, 14.15 mmol). The mixture was stirred at 120° C. for 3 hrs under N₂ atmosphere and monitored by TLC (petroleum ether:EtOAc=1:1, Rf=0.25). The reaction mixture was concentrated under reduced pressure to remove solvent and purified by flash silica gel chromatography (ISCO; 20 g SepaFlash column) using a 0-34% EtOAc/petroleum ether gradient to afford the title compound (400 mg, 59% yield) as a brown solid.

Step 3: 5-Cyano-N-(3-(2-methoxyphenyl)-1H-indazol-5-yl)-3-methylpicolinamide

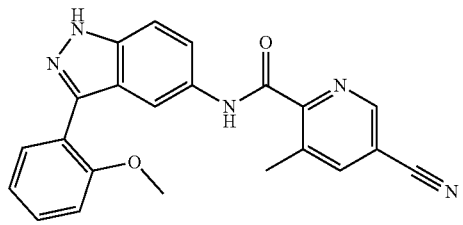 [SMILES: COc1ccccc1-c1n[nH]c2ccc(NC(=O)c3ncc(C#N)cc3C)cc12]

To a solution of 5-cyano-N-(3-(2-methoxyphenyl)-1H-indazol-5-yl)-3-methylpicolinamide (130 mg, 543.31 umol) in pyridine (3 mL) was added 5-cyano-3-methyl-pyridine-2-carboxylic acid (129.49 mg, 651.98 umol, HCl) and EDCI (208.31 mg, 1.09 mmol). The mixture was stirred at 20° C. for 12 hrs. The reaction mixture was concentrated and purified by preparative HPLC (Method AG) to afford the title compound (35.88 mg, 17% yield) as a pale yellow solid. ¹H NMR (400 MHz, DMSO-d₆) δ 13.12 (br s, 1H) 10.65 (s, 1H) 8.97 (d, J=0.98 Hz, 1H) 8.38 (s, 1H) 8.24 (s, 1H) 7.65 (dd, J=8.93, 1.22 Hz, 1H) 7.53 (br d, J=8.19 Hz, 2H) 7.41-7.47 (m, 1H) 7.20 (d, J=8.31 Hz, 1H) 7.07 (t, J=7.40 Hz, 1H) 3.82 (s, 3H) 2.54 (s, 3H). MS-ESI (m/z) calc'd for C₂₂H₁₈N₅O₂ [M+H]⁺: 384.1. Found 384.1.

Example 100: 5-Cyano-N-(3-(furan-3-yl)-1H-pyrazolo[4,3-b]pyridin-5-yl)-3-methylpicolinamide

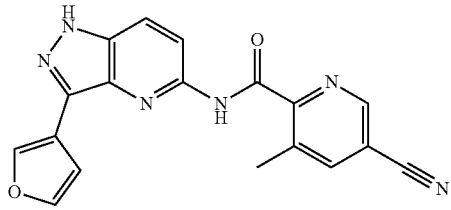 [SMILES: Cc1cc(C#N)cnc1C(=O)Nc1ccc2[nH]nc(-c3ccoc3)c2n1]

Step 1: Methyl 5-cyano-3-methylpicolinate

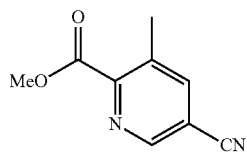

A mixture of methyl 5-bromo-3-methylpicolinate (1 g, 4.35 mmol), Zn(CN)₂ (612.49 mg, 5.22 mmoL), Pd(PPh₃)₄ (251.14 mg, 217.34 umol) in DMF (10 mL) was degassed and purged with N₂ for 3 times, and then the mixture was stirred at 120° C. for 2 hrs under N₂ atmosphere. The reaction mixture was concentrated to give a residue. The residue was purified by flash silica gel chromatography (ISCO; 4 g SepaFlash column) using a 0-10% EtOAc/petroleum ether gradient eluent to afford the title compound (640 mg, 84% yield) as a white solid.

Step 2: 5-Cyano-3-methylpicolinamide

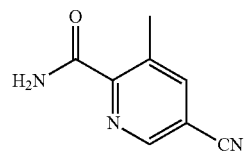

A stirred mixture of methyl 5-cyano-3-methylpicolinate (200 mg, 1.14 mmol) in NH₃·H₂O (18.20 g, 129.83 mmol, 20.00 mL, 25% purity) was stirred at 25° C. for 10 min. The mixture was extracted with EtOAc (6.0 mL×3). The combined organic layers were dried over Na₂SO₄ and concentrated under vacuum to afford the title compound (180 mg) as a white solid which was used without further purification.

Step 3: 5-Chloro-3-(furan-3-yl)-1H-pyrazolo[4,3-b]pyridine

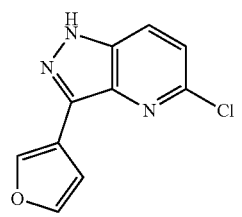 [SMILES: Clc1ccc2[nH]nc(-c3ccoc3)c2n1]

To a stirred solution of 5-chloro-3-iodo-1H-pyrazolo[4,3-b]pyridine (Intermediate A-6, 5.0 g, 17.89 mmol) in dioxane (100 mL) was added furan-3-ylboronic acid (2.40 g, 21.47 mmol), followed by adding Pd(dppf)Cl$_2$ (1.31 g, 1.79 mmol) and K$_2$CO$_3$ (4.95 g, 35.78 mmol) in one portion. Then the mixture was stirred at 90° C. for 24 hrs under N$_2$. The mixture was cooled to room temperature and filtered. The filtrate was concentrated under vacuum and purified by silica gel column chromatography using a 5:1, then 2:1, then 1:1 petroleum ether/EtOAc step gradient to afford the title compound (700 mg) as a brown solid.

Step 4: 5-(Chloro-3-(furan-3-yl)-1-(tetrahydro-2H-pyran-2-yl)-1H-pyrazolo[4,3-b]pyridine

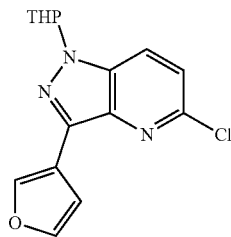

To a stirred solution of 5-chloro-3-(furan-3-yl)-1H-pyrazolo[4,3-b]pyridine (650 mg, 2.96 mmol) in DCM (20 mL) was added 3,4-dihydro-2H-pyran (373.42 mg, 4.44 mmol, 405.89 µL), followed by adding TsOH (50.96 mg, 295.96 µmol) in one portion. The mixture was then stirred at 25° C. for 12 hrs. The mixture was washed with 20% aq. sodium bicarbonate (5.0 mL 3), dried over Na$_2$SO$_4$ and concentrated under vacuum to afford the title compound (1.2 g) as a brown oil which was used without further purification.

Step 5: 5-Cyano-N-(3-(furan-3-yl)-1-(tetrahydro-2H-pyran-2-yl)-1H-pyrazolo[4,3-b]pyridin-5-yl)-3-methylpicolinamide

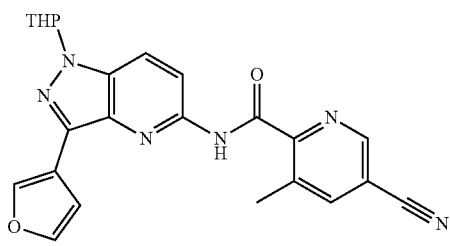

To a stirred solution of 5-chloro-3-(furan-3-yl)-1-(tetrahydro-2H-pyran-2-yl)-1H-pyrazolo[4,3-b]pyridine (200 mg, 658.45 µmol) in toluene (10 mL) was added 5-cyano-3-methylpicolinamide (116.73 mg, 724.30 µmol), followed by adding Pd$_2$(dba)$_3$ (30.15 mg, 32.92 µmol), XPhos (31.39 mg, 65.85 µmol) and Cs$_2$CO$_3$ (536.34 mg, 1.65 mmol). Then the mixture was degassed under vacuum and purged with N$_2$ (3×). Then the mixture was stirred at 110° C. for 12 hrs. The mixture was filtered. The filtrate was concentrated under vacuum and purified by Prep-TLC (petroleum ether: EtOAc=1/1, Rf=0.62) to afford the title compound (100 mg, 35% yield) as a yellow solid.

Step 6: 5-Cyano-N-(3-(furan-3-yl)-1H-pyrazolo[4,3-b]pyridin-5-yl)-3-methylpicolinamide

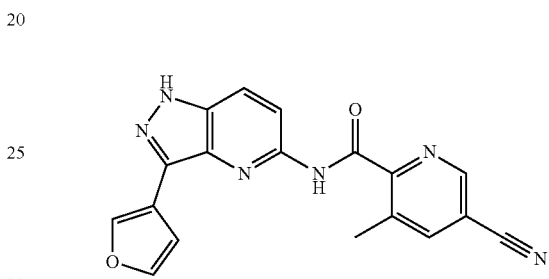

To a stirred solution of 5-cyano-N-(3-(furan-3-yl)-1-(tetrahydro-2H-pyran-2-yl)-1H-pyrazolo[4,3-b]pyridin-5-yl)-3-methylpicolinamide (90 mg, 210.06 umol) in DCM (3.0 mL) was added TFA (1.54 g, 13.51 mmol, 1 mL) dropwise at 0° C. Then the mixture was stirred at 25° C. for 1 hr. The mixture was concentrated under vacuum and purified by Prep-HPLC (Method E) to afford the TFA salt of the title compound (12.4 mg, 12% yield) as a pale yellow solid. $^1$H NMR (400 MHz, DMSO-d$_6$) δ 13.26-13.38 (m, 1H) 10.85-10.98 (m, 1H) 8.96-9.09 (m, 1H) 8.50-8.61 (m, 1H) 8.40-8.46 (m, 1H) 8.28-8.40 (m, 1H) 8.06-8.19 (m, 1H) 7.77-7.88 (m, 1H) 7.01-7.18 (m, 1H) 2.62 (br s, 3H). MS-ESI (m/z) calc'd for C$_{18}$H$_{13}$N$_6$O$_2$[M+H]$^+$: 345.1. Found 345.1.

Further compounds of the invention, which were prepared according to the methods described above, are provided in Table 2 below.

TABLE 2

| Ex. No | Structure | Name | m/z |
| --- | --- | --- | --- |
| 101 | 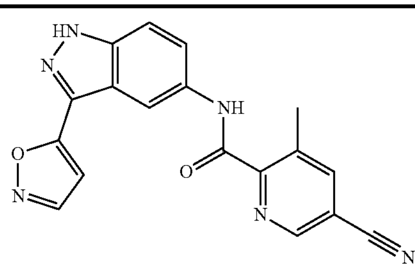 | 5-cyano-N-(3-(isoxazol-5-yl)-1H-indazol-5-yl)-3-methylpicolinamide | 345.23 |

TABLE 2-continued

| Ex. No | Structure | Name | m/z |
|---|---|---|---|
| 102 | 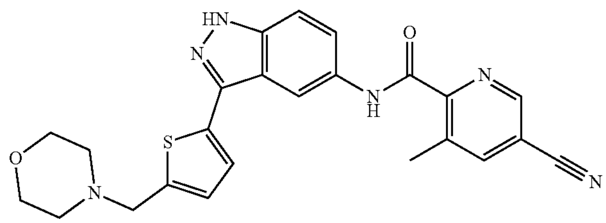 [SMILES: Cc1cc(C#N)cnc1C(=O)Nc1ccc2[nH]nc(-c3ccc(CN4CCOCC4)s3)c2c1] | 5-cyano-3-methyl-N-(3-(5-(morpholinomethyl)thiophen-2-yl)-1H-indazol-5-yl)picolinamide | 459.16 |
| 103 | 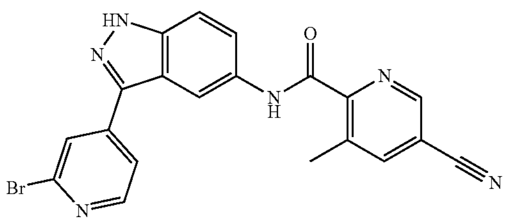 [SMILES: Cc1cc(C#N)cnc1C(=O)Nc1ccc2[nH]nc(-c3ccnc(Br)c3)c2c1] | N-(3-(2-bromopyridin-4-yl)-1H-indazol-5-yl)-5-cyano-3-methylpicolinamide | 433.15, 435.19 |
| 104 | 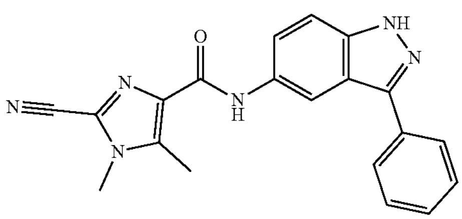 [SMILES: Cc1c(C(=O)Nc2ccc3[nH]nc(-c4ccccc4)c3c2)nc(C#N)n1C] | 2-cyano-1,5-dimethyl-N-(3-phenyl-1H-indazol-5-yl)-1H-imidazole-4-carboxamide | 357.0 |
| 105 | 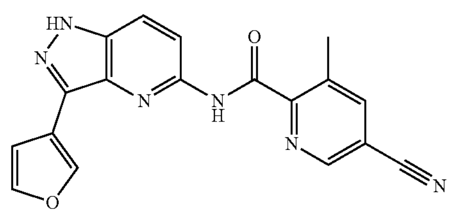 [SMILES: Cc1cc(C#N)cnc1C(=O)Nc1ccc2[nH]nc(-c3ccoc3)c2n1] | 5-cyano-N-(3-(furan-3-yl)-1H-pyrazolo[4,3-b]pyridin-5-yl)-3-methylpicolinamide | 345.1 |
| 106 | 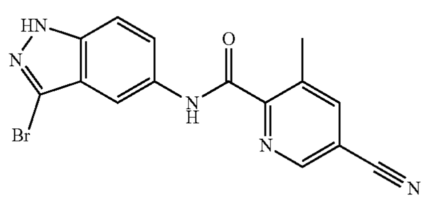 [SMILES: Cc1cc(C#N)cnc1C(=O)Nc1ccc2[nH]nc(Br)c2c1] | N-(3-bromo-1H-indazol-5-yl)-5-cyano-3-methylpicolinamide | 355.9/ 357.9 |
| 107 | 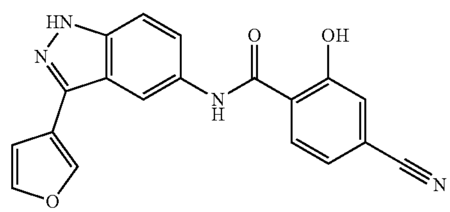 [SMILES: N#Cc1ccc(C(=O)Nc2ccc3[nH]nc(-c4ccoc4)c3c2)c(O)c1] | 4-cyano-N-(3-(furan-3-yl)-1H-indazol-5-yl)-2-hydroxybenzamide | 345.0 |

TABLE 2-continued

| Ex. No | Structure | Name | m/z |
|---|---|---|---|
| 108 | 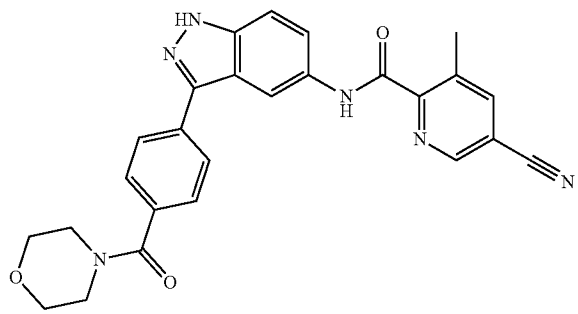 [SMILES: Cc1cc(C#N)cnc1C(=O)Nc1ccc2[nH]nc(-c3ccc(C(=O)N4CCOCC4)cc3)c2c1] | 5-cyano-3-methyl-N-(3-(4-(morpholine-4-carbonyl)phenyl)-1H-indazol-5-yl)picolinamide | 467.1 |
| 109 | 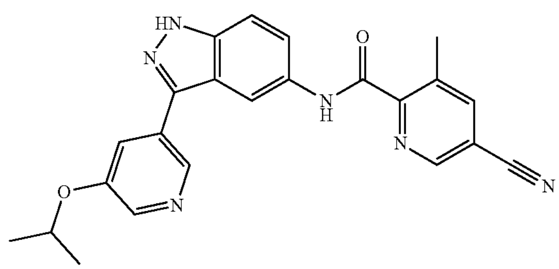 [SMILES: Cc1cc(C#N)cnc1C(=O)Nc1ccc2[nH]nc(-c3cncc(OC(C)C)c3)c2c1] | 5-cyano-N-(3-(5-isopropoxypyridin-3-yl)-1H-indazol-5-yl)-3-methylpicolinamide | 413.1 |
| 110 | 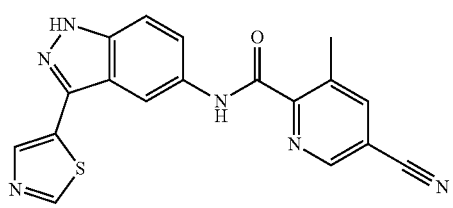 [SMILES: Cc1cc(C#N)cnc1C(=O)Nc1ccc2[nH]nc(-c3cnco3)c2c1] | 5-cyano-3-methyl-N-(3-(thiazol-5-yl)-1H-indazol-5-yl)picolinamide | 361.1 |
| 111 | 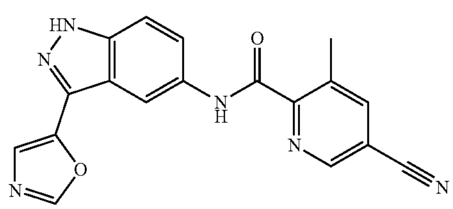 | 5-cyano-3-methyl-N-(3-(oxazol-5-yl)-1H-indazol-5-yl)picolinamide | 345.2 |
| 112 | 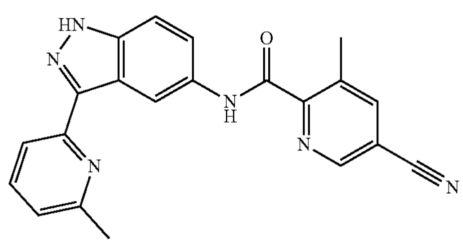 [SMILES: Cc1cccc(-c2n[nH]c3ccc(NC(=O)c4ncc(C#N)cc4C)cc23)n1] | 5-cyano-3-methyl-N-(3-(6-methylpyridin-2-yl)-1H-indazol-5-yl)picolinamide | 369.0 |
| 113 | 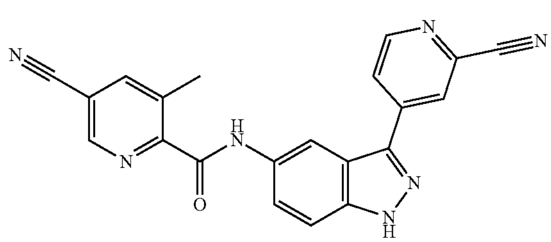 [SMILES: Cc1cc(C#N)cnc1C(=O)Nc1ccc2[nH]nc(-c3ccnc(C#N)c3)c2c1] | 5-cyano-N-(3-(2-cyanopyridin-4-yl)-1H-indazol-5-yl)-3-methylpicolinamide | 380.0 |

TABLE 2-continued

| Ex. No | Structure | Name | m/z |
|---|---|---|---|
| 114 | 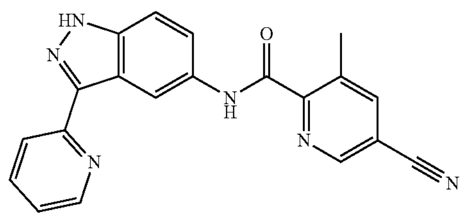 [SMILES: Cc1cc(C#N)cnc1C(=O)Nc1ccc2[nH]nc(-c3ccccn3)c2c1] | 5-cyano-3-methyl-N-(3-(pyridin-2-yl)-1H-indazol-5-yl)picolinamide | 355.0 |
| 115 | 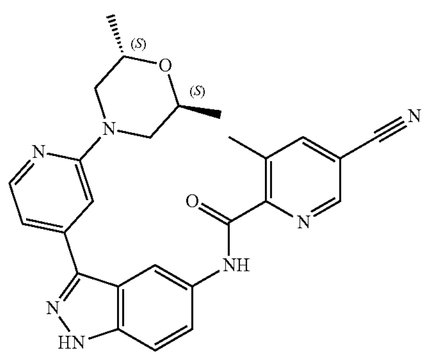 | 5-cyano-N-(3-(2-((2S,6S)-2,6-dimethylmorpholino)pyridin-4-yl)-1H-indazol-5-yl)-3-methylpicolinamide | 468.39 |
| 116 | 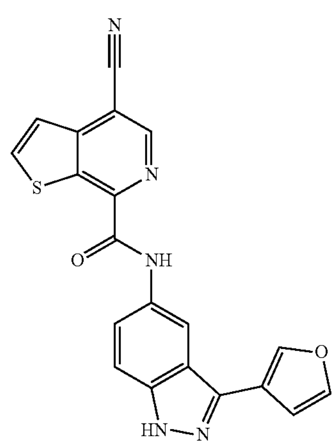 [SMILES: N#Cc1cnc(C(=O)Nc2ccc3[nH]nc(-c4ccoc4)c3c2)c2sccc12] | 4-cyano-N-(3-(furan-3-yl)-1H-indazol-5-yl)thieno[2,3-c]pyridine-7-carboxamide | 386.2 |
| 117 | 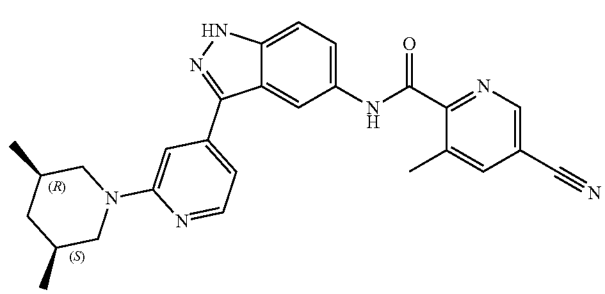 | 5-cyano-N-(3-(2-(3R,5S)-3,5-dimethylpiperidin-1-yl)pyridin-4-yl)-1H-indazol-5-yl)-3-methylpicolinamide | 466.42 |

TABLE 2-continued

| Ex. No | Structure | Name | m/z |
|---|---|---|---|
| 118 | 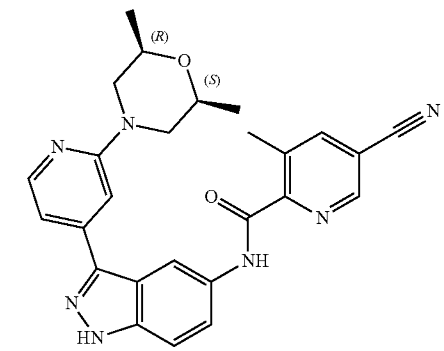 | 5-cyano-N-(3-(2-((2S,6R)-2,6-dimethylmorpholino)pyridin-4-yl)-1H-indazol-5-yl)-3-methylpicolinamide | 468.41 |
| 119 | 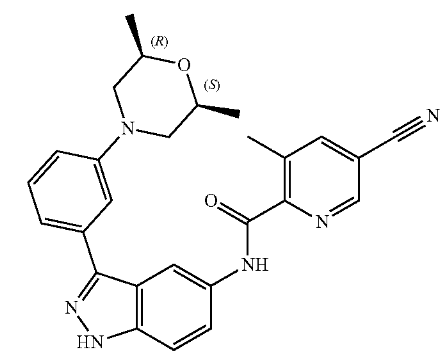 | 5-cyano-N-(3-(3-((2S,6R)-2,6-dimethylmorpholino)phenyl)-1H-indazol-5-yl)-3-methylpicolinamide | 467.39 |
| 120 | 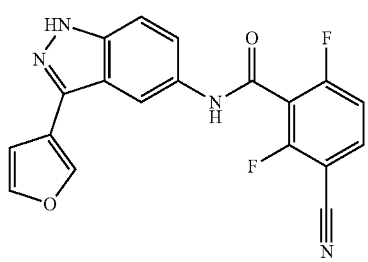 | 3-cyano-2,6-difluoro-N-(3-(furan-3-yl)-1H-indazol-5-yl)benzamide | 365.21 |
| 121 | 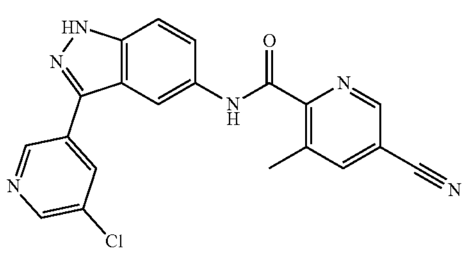 [SMILES: Cc1cc(C#N)cnc1C(=O)Nc1ccc2[nH]nc(-c3cncc(Cl)c3)c2c1] | N-(3-(5-chloropyridin-3-yl)-1H-indazol-5-yl)-5-cyano-3-methylpicolinamide | 389.1 |
| 122 | 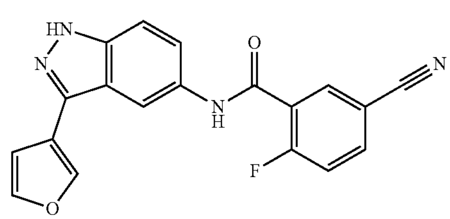 [SMILES: N#Cc1ccc(F)c(C(=O)Nc2ccc3[nH]nc(-c4ccoc4)c3c2)c1] | 5-cyano-2-fluoro-N-(3-(furan-3-yl)-1H-indazol-5-yl)benzamide | 347.1 |

TABLE 2-continued

| Ex. No | Structure | Name | m/z |
|---|---|---|---|
| 123 | 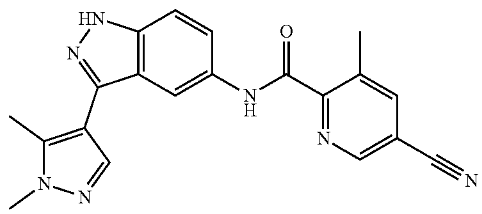 [SMILES: Cc1cc(C#N)cnc1C(=O)Nc1ccc2[nH]nc(-c3cnn(C)c3C)c2c1] | 5-cyano-N-(3-(1,5-dimethyl-1H-pyrazol-4-yl)-1H-indazol-5-yl)-3-methylpicolinamide | 372.1 |
| 124 | 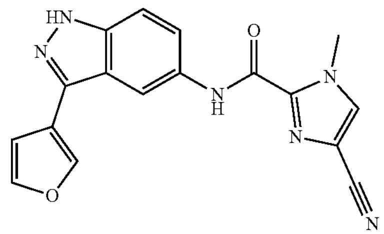 [SMILES: Cn1cc(C#N)nc1C(=O)Nc1ccc2[nH]nc(-c3ccoc3)c2c1] | 4-cyano-N-(3-(furan-3-yl)-1H-indazol-5-yl)-1-methyl-1H-imidazole-2-carboxamide | 333.0 |
| 125 | 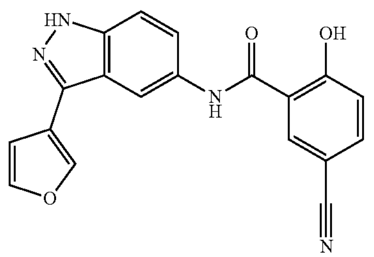 [SMILES: N#Cc1ccc(O)c(C(=O)Nc2ccc3[nH]nc(-c4ccoc4)c3c2)c1] | 5-cyano-N-(3-(furan-3-yl)-1H-indazol-5-yl)-2-hydroxybenzamide | 345.0 |
| 126 | 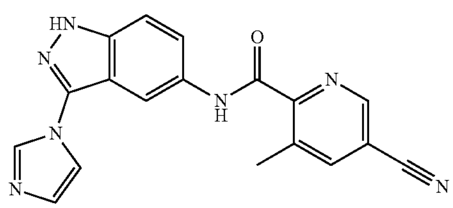 [SMILES: Cc1cc(C#N)cnc1C(=O)Nc1ccc2[nH]nc(-n3ccnc3)c2c1] | N-(3-(1H-imidazol-1-yl)-1H-indazol-5-yl)-5-cyano-3-methylpicolinamide | 344.2 |
| 127 | 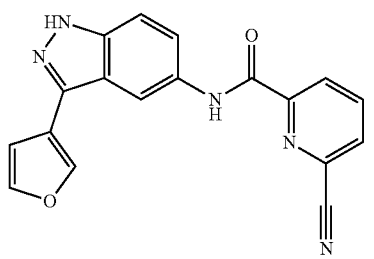 [SMILES: N#Cc1cccc(C(=O)Nc2ccc3[nH]nc(-c4ccoc4)c3c2)n1] | 6-cyano-N-(3-(furan-3-yl)-1H-indazol-5-yl)picolinamide | 330.1 |
| 128 | 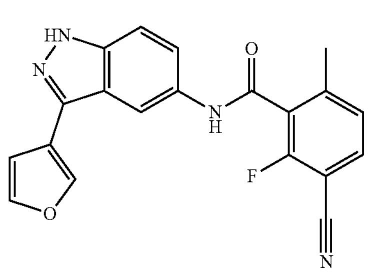 [SMILES: Cc1ccc(C#N)c(F)c1C(=O)Nc1ccc2[nH]nc(-c3ccoc3)c2c1] | 3-cyano-2-fluoro-N-(3-(furan-3-yl)-1H-indazol-5-yl)-6-methylbenzamide | 361.0 |

TABLE 2-continued

| Ex. No | Structure | Name | m/z |
|---|---|---|---|
| 129 | 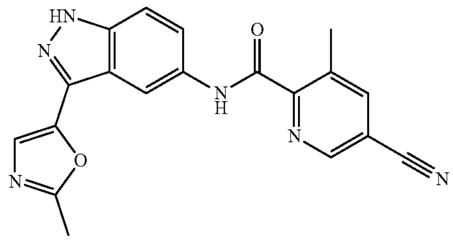 [SMILES: Cc1ncc(-c2n[nH]c3ccc(NC(=O)c4ncc(C#N)cc4C)cc23)o1] | 5-cyano-3-methyl-N-(3-(2-methyloxazol-5-yl)-1H-indazol-5-yl)picolinamide | 359.2 |
| 130 | 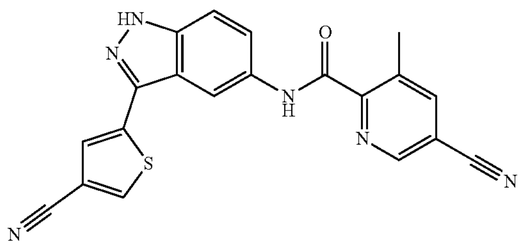 [SMILES: Cc1cc(C#N)cnc1C(=O)Nc1ccc2[nH]nc(-c3cc(C#N)cs3)c2c1] | 5-cyano-N-(3-(4-cyanothiophen-2-yl)-1H-indazol-5-yl)-3-methylpicolinamide | 385.0 |
| 131 | 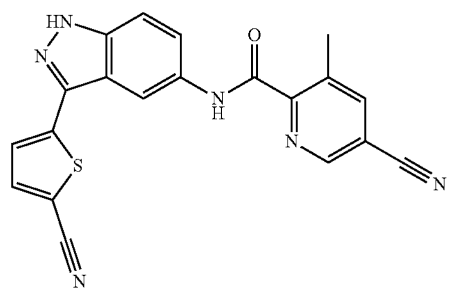 [SMILES: Cc1cc(C#N)cnc1C(=O)Nc1ccc2[nH]nc(-c3ccc(C#N)s3)c2c1] | 5-cyano-N-(3-(5-cyanothiophen-2-yl)-1H-indazol-5-yl)-3-methylpicolinamide | 384.9 |
| 132 | 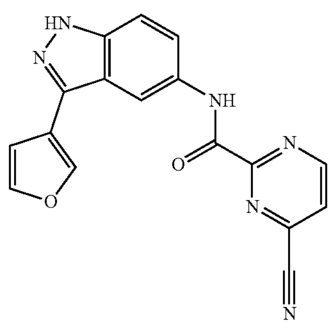 [SMILES: N#Cc1ccnc(C(=O)Nc2ccc3[nH]nc(-c4ccoc4)c3c2)n1] | 4-cyano-N-(3-(furan-3-yl)-1H-indazol-5-yl)pyrimidine-2-carboxamide | 331.19 |
| 133 | 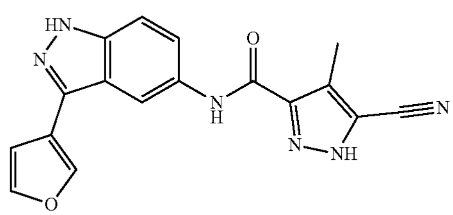 [SMILES: Cc1c(C(=O)Nc2ccc3[nH]nc(-c4ccoc4)c3c2)n[nH]c1C#N] | 5-cyano-N-(3-(furan-3-yl)-1H-indazol-5-yl)-4-methyl-1H-pyrazole-3-carboxamide | 333.0 |
| 134 | 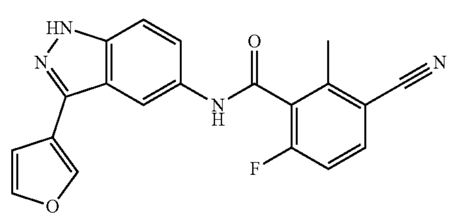 [SMILES: Cc1c(C#N)ccc(F)c1C(=O)Nc1ccc2[nH]nc(-c3ccoc3)c2c1] | 3-cyano-6-fluoro-N-(3-(furan-3-yl)-1H-indazol-5-yl)-2-methylbenzamide | 361.1 |

TABLE 2-continued

| Ex. No | Structure | Name | m/z |
|---|---|---|---|
| 135 | 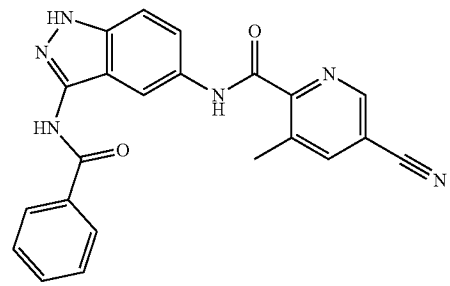 [SMILES: Cc1cc(C#N)cnc1C(=O)Nc1ccc2[nH]nc(NC(=O)c3ccccc3)c2c1] | N-(3-benzamido-1H-indazol-5-yl)-5-cyano-3-methylpicolinamide | 397.2 |
| 136 | 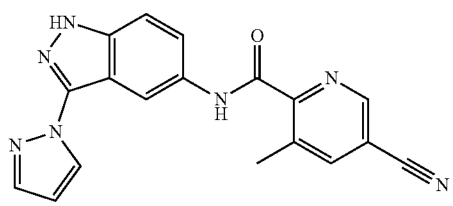 [SMILES: Cc1cc(C#N)cnc1C(=O)Nc1ccc2[nH]nc(-n3cccn3)c2c1] | N-(3-(1H-pyrazol-1-yl)-1H-indazol-5-yl)-5-cyano-3-methylpicolinamide | 344.0 |
| 137 | 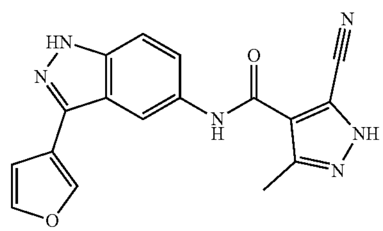 [SMILES: Cc1n[nH]c(C#N)c1C(=O)Nc1ccc2[nH]nc(-c3ccoc3)c2c1] | 5-cyano-N-(3-(furan-3-yl)-1H-indazol-5-yl)-3-methyl-1H-pyrazole-4-carboxamide | 333 |
| 138 | 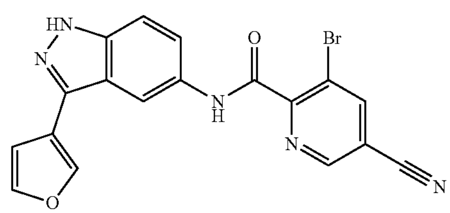 [SMILES: N#Cc1cnc(C(=O)Nc2ccc3[nH]nc(-c4ccoc4)c3c2)c(Br)c1] | 3-bromo-5-cyano-N-(3-(furan-3-yl)-1H-indazol-5-yl)picolinamide | 407.9/ 409.9 |
| 139 | 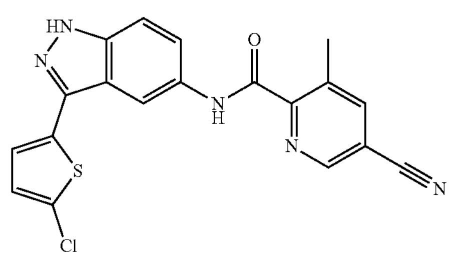 [SMILES: Cc1cc(C#N)cnc1C(=O)Nc1ccc2[nH]nc(-c3ccc(Cl)s3)c2c1] | N-(3-(5-chlorothiophen-2-yl)-1H-indazol-5-yl)-5-cyano-3-methylpicolinamide | 393.9/ 395.9 |
| 140 | 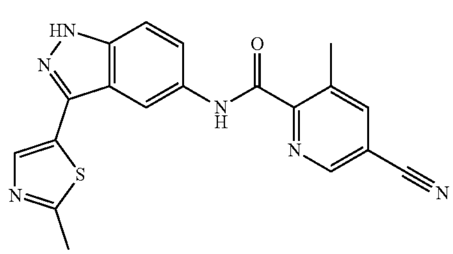 [SMILES: Cc1ncc(-c2n[nH]c3ccc(NC(=O)c4ncc(C#N)cc4C)cc23)s1] | 5-cyano-3-methyl-N-(3-(2-methylthiazol-5-yl)-1H-indazol-5-yl)picolinamide | 375.1 |

TABLE 2-continued

| Ex. No | Structure | Name | m/z |
|---|---|---|---|
| 141 | 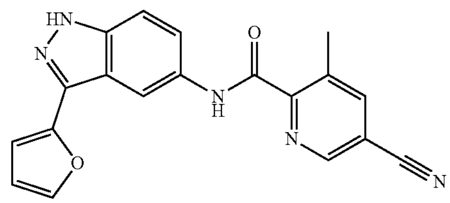 [SMILES: Cc1cc(C#N)cnc1C(=O)Nc1ccc2[nH]nc(-c3ccco3)c2c1] | 5-cyano-3-methyl-N-(3-(5-methylfuran-2-yl)-1H-indazol-5-yl)picolinamide | 358.2 |
| 142 | 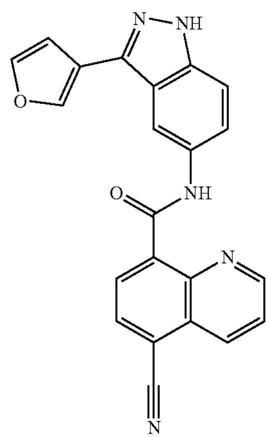 [SMILES: N#Cc1ccc(C(=O)Nc2ccc3[nH]nc(-c4ccoc4)c3c2)c2ncccc12] | 5-cyano-N-(3-(furan-3-yl)-1H-indazol-5-yl)quinoline-8-carboxamide | 380.13 |
| 143 | 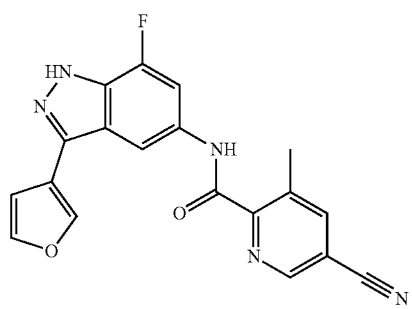 [SMILES: Cc1cc(C#N)cnc1C(=O)Nc1cc(F)c2[nH]nc(-c3ccoc3)c2c1] | 5-cyano-N-(7-fluoro-3-(furan-3-yl)-1H-indazol-5-yl)-3-methylpicolinamide | 362.07 |
| 144 | 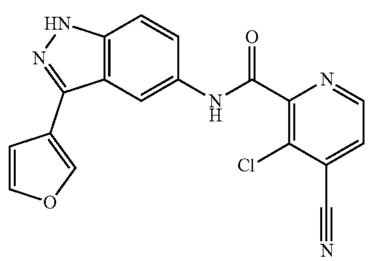 [SMILES: N#Cc1ccnc(C(=O)Nc2ccc3[nH]nc(-c4ccoc4)c3c2)c1Cl] | 3-chloro-4-cyano-N-(3-(furan-3-yl)-1H-indazol-5-yl)picolinamide | 364.17 |
| 145 | 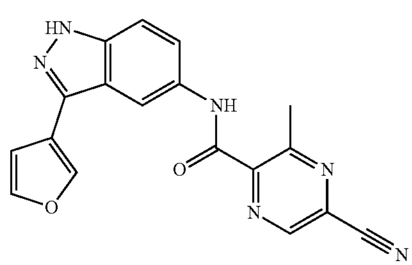 [SMILES: Cc1nc(C#N)cnc1C(=O)Nc1ccc2[nH]nc(-c3ccoc3)c2c1] | 5-cyano-N-(3-(furan-3-yl)-1H-indazol-5-yl)-3-methylpyrazine-2-carboxamide | 345.16 |

TABLE 2-continued

| Ex. No | Structure | Name | m/z |
|---|---|---|---|
| 146 | 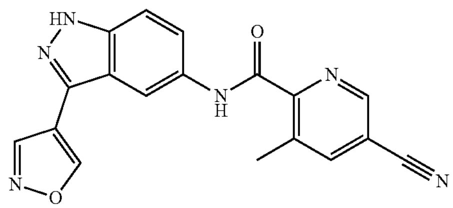 [SMILES: Cc1cc(C#N)cnc1C(=O)Nc1ccc2[nH]nc(-c3cnoc3)c2c1] | 5-cyano-N-(3-(isoxazol-4-yl)-1H-indazol-5-yl)-3-methylpicolinamide | 345.73 |
| 147 | 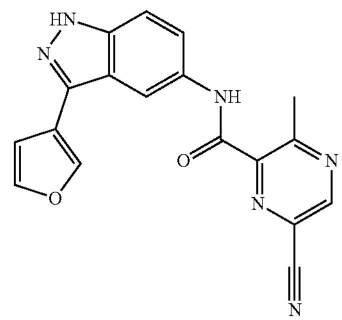 [SMILES: Cc1ncc(C#N)nc1C(=O)Nc1ccc2[nH]nc(-c3ccoc3)c2c1] | 6-cyano-N-(3-(furan-3-yl)-1H-indazol-5-yl)-3-methylpyrazine-2-carboxamide | 345.16 |
| 148 | 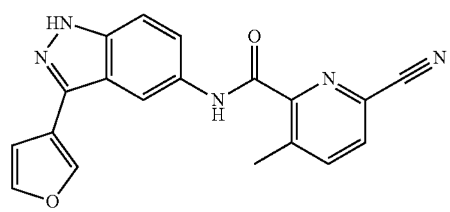 [SMILES: Cc1ccc(C#N)nc1C(=O)Nc1ccc2[nH]nc(-c3ccoc3)c2c1] | 6-cyano-N-(3-(furan-3-yl)-1H-indazol-5-yl)-3-methylpicolinamide | 344.19 |
| 149 | 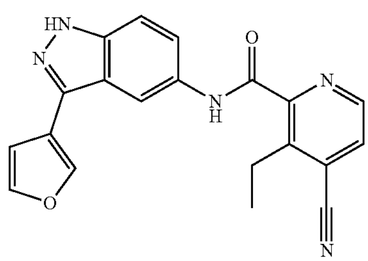 [SMILES: CCc1c(C#N)ccnc1C(=O)Nc1ccc2[nH]nc(-c3ccoc3)c2c1] | 4-cyano-3-ethyl-N-(3-(furan-3-yl)-1H-indazol-5-yl)picolinamide | 358.14 |
| 150 | 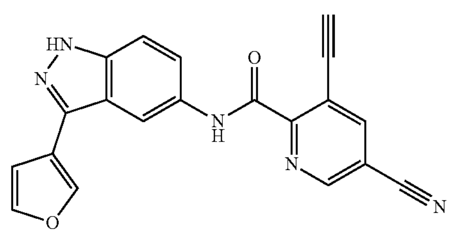 [SMILES: C#Cc1cc(C#N)cnc1C(=O)Nc1ccc2[nH]nc(-c3ccoc3)c2c1] | 5-cyano-3-ethynyl-N-(3-(furan-3-yl)-1H-indazol-5-yl)picolinamide | 354.0 |
| 151 | 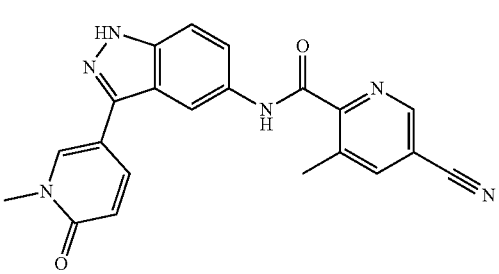 [SMILES: Cc1cc(C#N)cnc1C(=O)Nc1ccc2[nH]nc(-c3ccc(=O)n(C)c3)c2c1] | 5-cyano-3-methyl-N-(3-(1-methyl-6-oxo-1,6-dihydropyridin-3-yl)-1H-indazol-5-yl)picolinamide | 385.0 |

TABLE 2-continued

| Ex. No | Structure | Name | m/z |
|---|---|---|---|
| 152 | 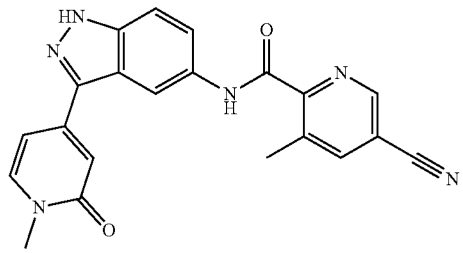 [SMILES: Cc1cc(C#N)cnc1C(=O)Nc1ccc2[nH]nc(-c3ccn(C)c(=O)c3)c2c1] | 5-cyano-3-methyl-N-(3-(1-methyl-2-oxo-1,2-dihydropyridin-4-yl)-1H-indazol-5-yl)picolinamide | 385.0 |
| 153 | 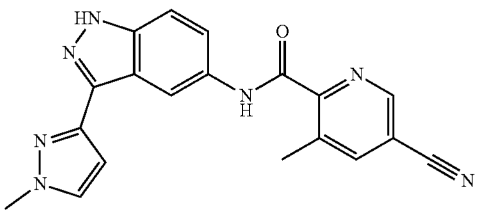 [SMILES: Cc1cc(C#N)cnc1C(=O)Nc1ccc2[nH]nc(-c3ccn(C)n3)c2c1] | 5-cyano-3-methyl-N-(3-(1-methyl-1H-pyrazol-3-yl)-1H-indazol-5-yl)picolinamide | 358.0 |
| 154 | 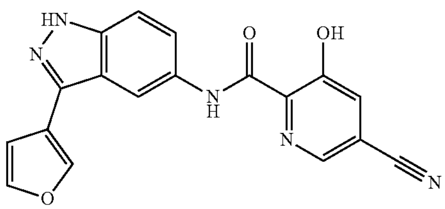 [SMILES: N#Cc1cnc(C(=O)Nc2ccc3[nH]nc(-c4ccoc4)c3c2)c(O)c1] | 5-cyano-N-(3-(furan-3-yl)-1H-indazol-5-yl)-3-hydroxypicolinamide | 346.0 |
| 155 | 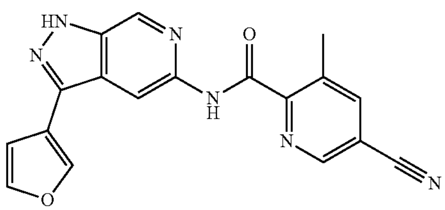 [SMILES: Cc1cc(C#N)cnc1C(=O)Nc1cc2c(-c3ccoc3)n[nH]c2cn1] | 5-cyano-N-(3-(furan-3-yl)-1H-pyrazolo[3,4-c]pyridin-5-yl)-3-methylpicolinamide | 345.0 |
| 156 | 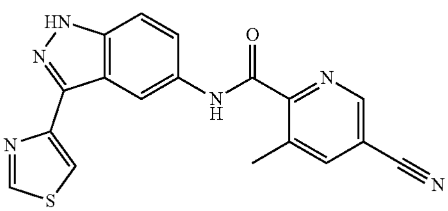 [SMILES: Cc1cc(C#N)cnc1C(=O)Nc1ccc2[nH]nc(-c3cscn3)c2c1] | 5-cyano-3-methyl-N-(3-(thiazol-4-yl)-1H-indazol-5-yl)picolinamide | 361.1 |
| 157 | 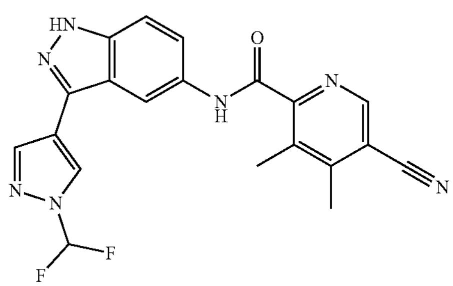 [SMILES: Cc1c(C#N)cnc(C(=O)Nc2ccc3[nH]nc(-c4cnn(C(F)F)c4)c3c2)c1C] | 5-cyano-N-(3-(1-(difluoromethyl)-1H-pyrazol-4-yl)-1H-indazol-5-yl)-3,4-dimethylpicolinamide | 408.18 |

TABLE 2-continued

| Ex. No | Structure | Name | m/z |
|---|---|---|---|
| 158 | 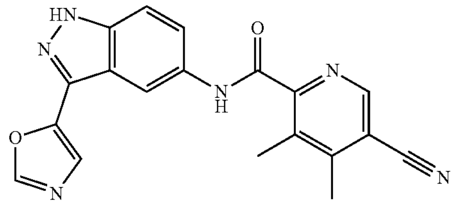 | 5-cyano-3,4-dimethyl-N-(3-(oxazol-5-yl)-1H-indazol-5-yl)picolinamide | 359.21 |
| 159 | 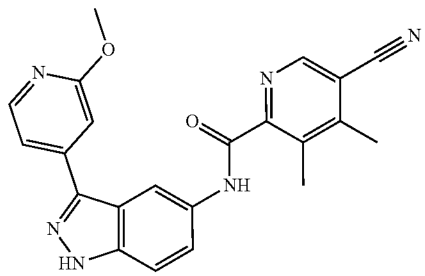 [SMILES: COc1cc(-c2n[nH]c3ccc(NC(=O)c4ncc(C#N)c(C)c4C)cc23)ccn1] | 5-cyano-N-(3-(2-methoxypyridin-4-yl)-1H-indazol-5-yl)-3,4-dimethylpicolinamide | 399.21 |
| 160 | 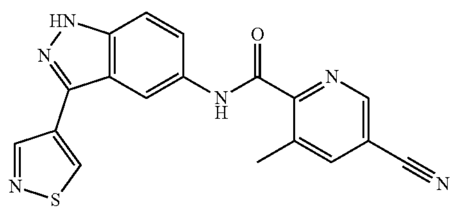 [SMILES: Cc1cc(C#N)cnc1C(=O)Nc1ccc2[nH]nc(-c3cnsc3)c2c1] | 5-cyano-N-(3-(isothiazol-4-yl)-1H-indazol-5-yl)-3-methylpicolinamide | 361.0 |
| 161 | 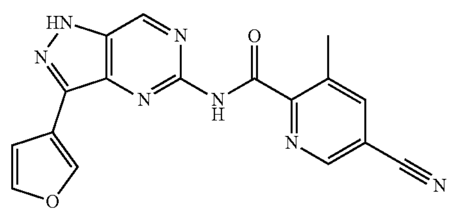 [SMILES: Cc1cc(C#N)cnc1C(=O)Nc1ncc2[nH]nc(-c3ccoc3)c2n1] | 5-cyano-N-(3-(furan-3-yl)-1H-pyrazolo[4,3-d]pyrimidin-5-yl)-3-methylpicolinamide | 346.0 |
| 162 | 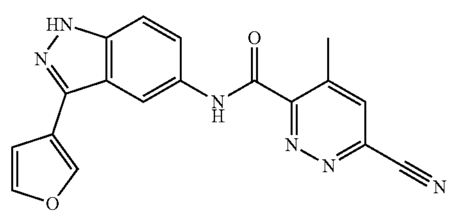 [SMILES: Cc1cc(C#N)nnc1C(=O)Nc1ccc2[nH]nc(-c3ccoc3)c2c1] | 6-cyano-N-(3-(furan-3-yl)-1H-indazol-5-yl)-4-methylpyridazine-3-carboxamide | 345.1 |
| 163 | 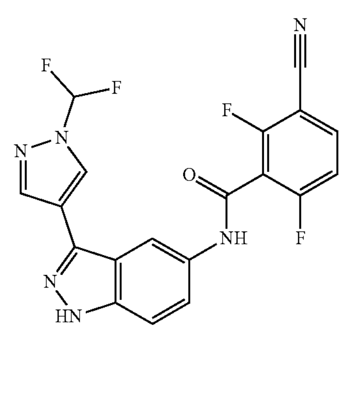 [SMILES: N#Cc1ccc(F)c(C(=O)Nc2ccc3[nH]nc(-c4cnn(C(F)F)c4)c3c2)c1F] | 3-cyano-N-(3-(1-(difluoromethyl)-1H-pyrazol-4-yl)-1H-indazol-5-yl)-2,6-difluorobenzamide | 415.21 |

TABLE 2-continued

| Ex. No | Structure | Name | m/z |
|---|---|---|---|
| 164 | 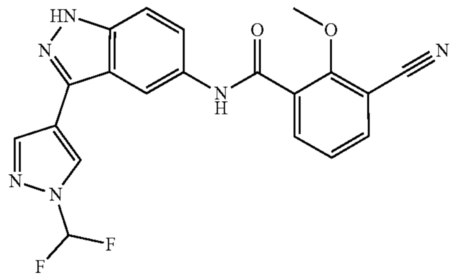 [SMILES: COc1c(C#N)cccc1C(=O)Nc1ccc2[nH]nc(-c3cnn(C(F)F)c3)c2c1] | 3-cyano-N-(3-(1-(difluoromethyl)-1H-pyrazol-4-yl)-1H-indazol-5-yl)-2-methoxybenzamide | 409.23 |
| 165 | 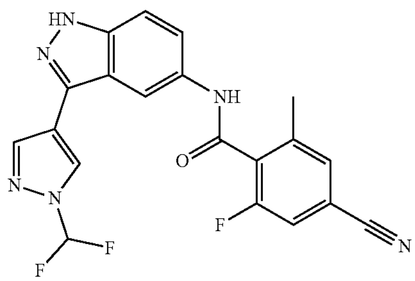 [SMILES: Cc1cc(C#N)cc(F)c1C(=O)Nc1ccc2[nH]nc(-c3cnn(C(F)F)c3)c2c1] | 4-cyano-N-(3-(1-(difluoromethyl)-1H-pyrazol-4-yl)-1H-indazol-5-yl)-2-fluoro-6-methylbenzamide | 411.31 |
| 166 | 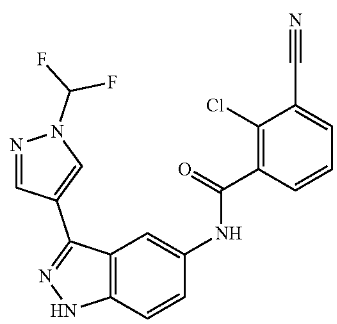 [SMILES: N#Cc1cccc(C(=O)Nc2ccc3[nH]nc(-c4cnn(C(F)F)c4)c3c2)c1Cl] | 2-chloro-3-cyano-N-(3-(1-(difluoromethyl)-1H-pyrazol-4-yl)-1H-indazol-5-yl)benzamide | 413.2-415.2 |
| 167 | 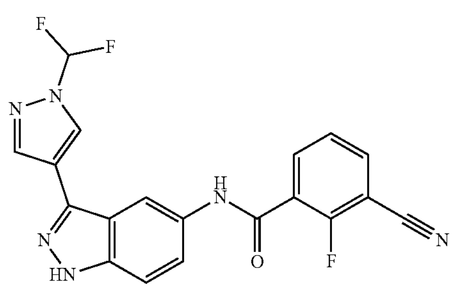 [SMILES: N#Cc1cccc(C(=O)Nc2ccc3[nH]nc(-c4cnn(C(F)F)c4)c3c2)c1F] | 3-cyano-N-(3-(1-(difluoromethyl)-1H-pyrazol-4-yl)-1H-indazol-5-yl)-2-fluorobenzamide | 397.24 |
| 168 | 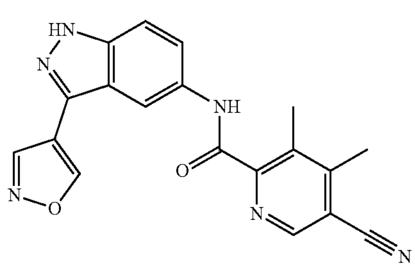 [SMILES: Cc1c(C#N)cnc(C(=O)Nc2ccc3[nH]nc(-c4cnoc4)c3c2)c1C] | 5-cyano-N-(3-(isoxazol-4-yl)-1H-indazol-5-yl)-3,4-dimethylpicolinamide | 359.24 |

TABLE 2-continued

| Ex. No | Structure | Name | m/z |
|---|---|---|---|
| 169 | 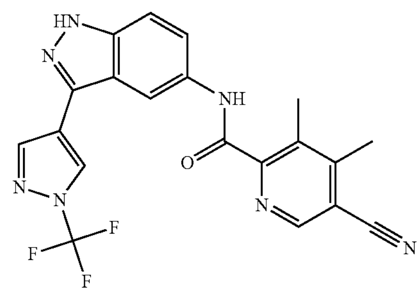 [SMILES: Cc1c(C#N)cnc(C(=O)Nc2ccc3[nH]nc(-c4cnn(C(F)(F)F)c4)c3c2)c1C] | 5-cyano-3,4-dimethyl-N-(3-(1-(trifluoromethyl)-1H-pyrazol-4-yl)-1H-indazol-5-yl)picolinamide | 426.31 |
| 170 | 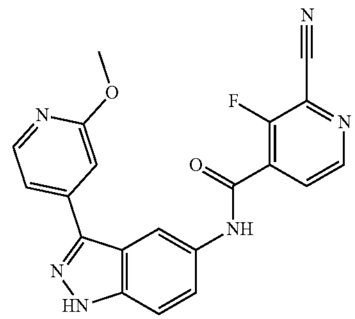 [SMILES: COc1cc(-c2n[nH]c3ccc(NC(=O)c4ccnc(C#N)c4F)cc23)ccn1] | 2-cyano-3-fluoro-N-(3-(2-methoxypyridin-4-yl)-1H-indazol-5-yl)isonicotinamide | 389.26 |
| 171 | 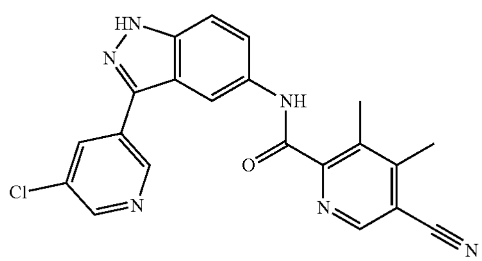 [SMILES: Cc1c(C#N)cnc(C(=O)Nc2ccc3[nH]nc(-c4cncc(Cl)c4)c3c2)c1C] | N-(3-(5-chloropyridin-3-yl)-1H-indazol-5-yl)-5-cyano-3,4-dimethylpicolinamide | 403.27, 405.22 |
| 172 | 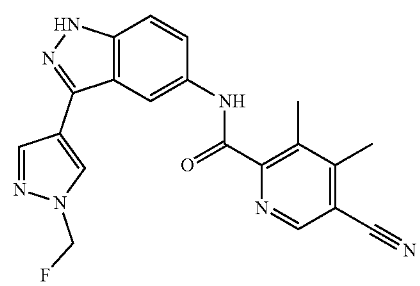 [SMILES: Cc1c(C#N)cnc(C(=O)Nc2ccc3[nH]nc(-c4cnn(CF)c4)c3c2)c1C] | 5-cyano-N-(3-(1-(fluoromethyl)-1H-pyrazol-4-yl)-1H-indazol-5-yl)-3,4-dimethylpicolinamide | 390.31 |
| 173 | 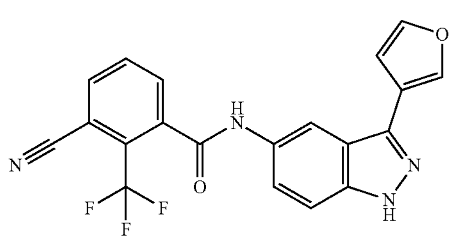 [SMILES: N#Cc1cccc(C(=O)Nc2ccc3[nH]nc(-c4ccoc4)c3c2)c1C(F)(F)F] | 3-cyano-N-(3-(furan-3-yl)-1H-indazol-5-yl)-2-(trifluoromethyl)benzamide | 397.23 |

TABLE 2-continued

| Ex. No | Structure | Name | m/z |
|---|---|---|---|
| 174 | 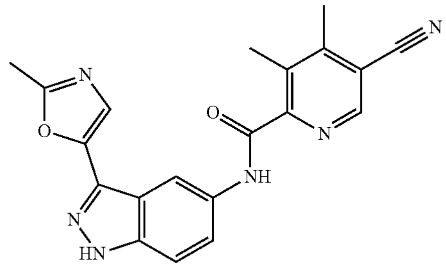 [SMILES: Cc1ncc(-c2n[nH]c3ccc(NC(=O)c4ncc(C#N)c(C)c4C)cc23)o1] | 5-cyano-3,4-dimethyl-N-(3-(2-methyloxazol-5-yl)-1H-indazol-5-yl)picolinamide | 373.29 |
| 175 | 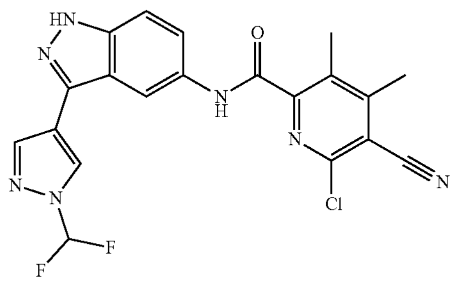 [SMILES: Cc1c(C(=O)Nc2ccc3[nH]nc(-c4cnn(C(F)F)c4)c3c2)nc(Cl)c(C#N)c1C] | 6-chloro-5-cyano-N-(3-(1-(difluoromethyl)-1H-pyrazol-4-yl)-1H-indazol-5-yl)-3,4-dimethylpicolinamide | 442.22; 444.23 |
| 176 | 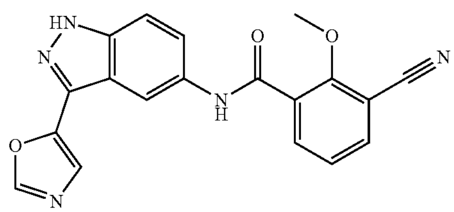 [SMILES: COc1c(C#N)cccc1C(=O)Nc1ccc2[nH]nc(-c3cnco3)c2c1] | 3-cyano-2-methoxy-N-(3-(oxazol-5-yl)-1H-indazol-5-yl)benzamide | 360.2 |
| 177 | 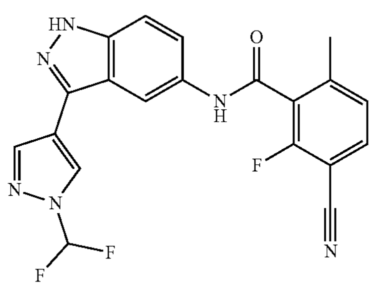 [SMILES: Cc1ccc(C#N)c(F)c1C(=O)Nc1ccc2[nH]nc(-c3cnn(C(F)F)c3)c2c1] | 3-cyano-N-(3-(1-(difluoromethyl)-1H-pyrazol-4-yl)-1H-indazol-5-yl)-2-fluoro-6-methylbenzamide | 411.0 |
| 178 | 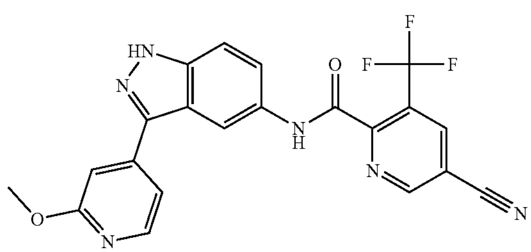 [SMILES: COc1cc(-c2n[nH]c3ccc(NC(=O)c4ncc(C#N)cc4C(F)(F)F)cc23)ccn1] | 5-cyano-N-3-(2-methoxypyrimidin-4-yl)-1H-indazol-5-yl)-3-(trifluoromethyl)picolinamide | 439.2 |
| 179 | 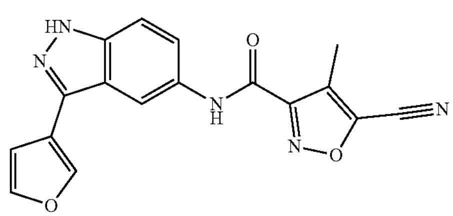 [SMILES: Cc1c(C(=O)Nc2ccc3[nH]nc(-c4ccoc4)c3c2)noc1C#N] | 5-cyano-N-(3-(furan-3-yl)-1H-indazol-5-yl)-4-methylisoxazole-3-carboxamide | 334.0 |

TABLE 2-continued

| Ex. No | Structure | Name | m/z |
|---|---|---|---|
| 180 | 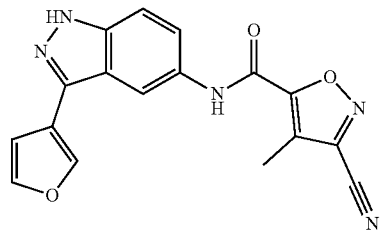 [SMILES: Cc1c(C#N)noc1C(=O)Nc1ccc2[nH]nc(-c3ccoc3)c2c1] | 3-cyano-N-(3-(furan-3-yl)-1H-indazol-5-yl)-4-methylisoxazole-5-carboxamide | 334.0 |
| 181 | 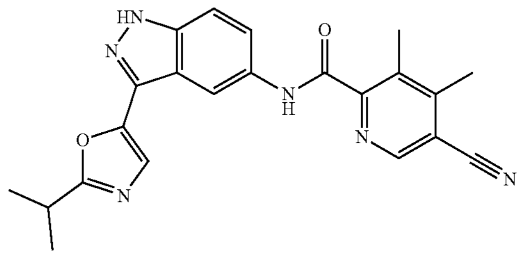 [SMILES: Cc1c(C#N)cnc(C(=O)Nc2ccc3[nH]nc(-c4cnc(C(C)C)o4)c3c2)c1C] | 5-cyano-N-(3-(2-isopropyloxazol-5-yl)-1H-indazol-5-yl)-3,4-dimethylpicolinamide | 401.0 |
| 182 | 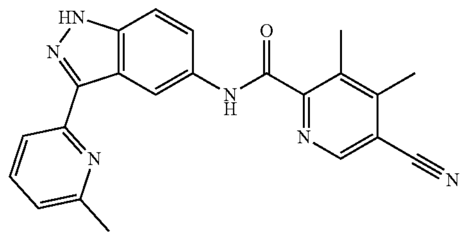 [SMILES: Cc1cccc(-c2n[nH]c3ccc(NC(=O)c4ncc(C#N)c(C)c4C)cc23)n1] | 5-cyano-3,4-dimethyl-N-(3-(6-methylpyridin-2-yl)-1H-indazol-5-yl)picolinamide | 383.2 |
| 183 | 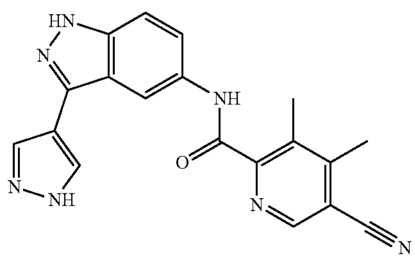 [SMILES: Cc1c(C#N)cnc(C(=O)Nc2ccc3[nH]nc(-c4cn[nH]c4)c3c2)c1C] | N-(3-(1H-pyrazol-4-yl)-1H-indazol-5-yl)-5-cyano-3,4-dimethylpicolinamide | 358.28 |
| 184 | 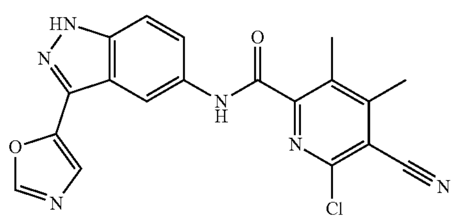 [SMILES: Cc1c(C(=O)Nc2ccc3[nH]nc(-c4cnco4)c3c2)nc(Cl)c(C#N)c1C] | 6-chloro-5-cyano-3,4-dimethyl-N-(3-(oxazol-5-yl)-1H-indazol-5-yl)picolinamide | 393.14; 395.13 |
| 185 | 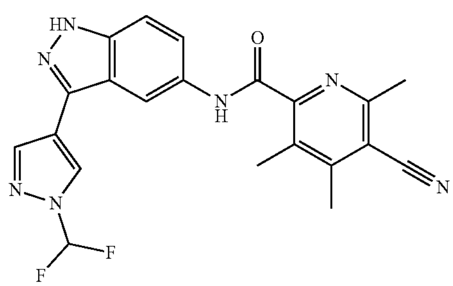 [SMILES: Cc1nc(C(=O)Nc2ccc3[nH]nc(-c4cnn(C(F)F)c4)c3c2)c(C)c(C)c1C#N] | 5-cyano-N-(3-(1-(difluoromethyl)-1H-pyrazol-4-yl)-1H-indazol-5-yl)-3,4,6-trimethylpicolinamide | 422.21 |

TABLE 2-continued

| Ex. No | Structure | Name | m/z |
|---|---|---|---|
| 186 | 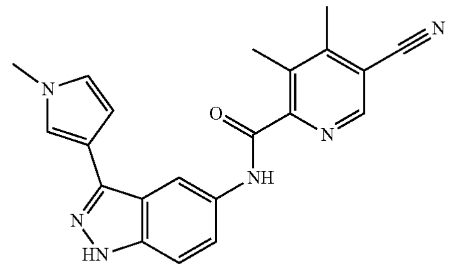 [SMILES: Cc1c(C#N)cnc(C(=O)Nc2ccc3[nH]nc(-c4ccn(C)c4)c3c2)c1C] | 5-cyano-3,4-dimethyl-N-(3-(1-methyl-1H-pyrrol-3-yl)-1H-indazol-5-yl)picolinamide | 371.22 |
| 187 | 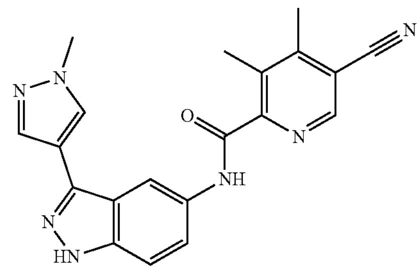 [SMILES: Cc1c(C#N)cnc(C(=O)Nc2ccc3[nH]nc(-c4cnn(C)c4)c3c2)c1C] | 5-cyano-3,4-dimethyl-N-(3-(1-methyl-1H-pyrazol-4-yl)-1H-indazol-5-yl)picolinamide | 372.31 |
| 188 | 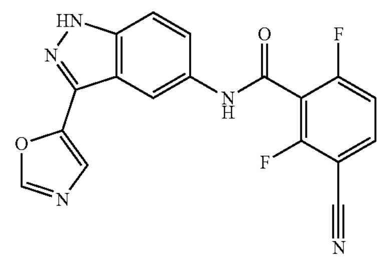 [SMILES: N#Cc1ccc(F)c(C(=O)Nc2ccc3[nH]nc(-c4cnco4)c3c2)c1F] | 3-cyano-2,6-difluoro-N-(3-(oxazol-5-yl)-1H-indazol-5-yl)benzamide | 366.11 |
| 189 | 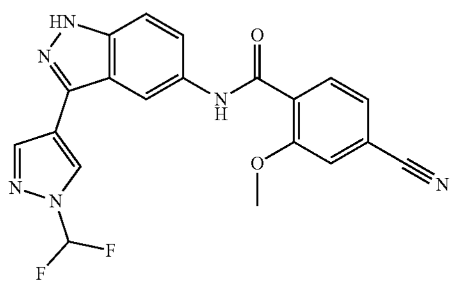 [SMILES: COc1cc(C#N)ccc1C(=O)Nc1ccc2[nH]nc(-c3cnn(C(F)F)c3)c2c1] | 4-cyano-N-(3-(1-(difluoromethyl)-1H-pyrazol-4-yl)-1H-indazol-5-yl)-2-methoxybenzamide | 409.26 |
| 190 | 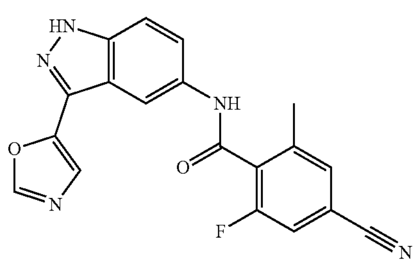 [SMILES: Cc1cc(C#N)cc(F)c1C(=O)Nc1ccc2[nH]nc(-c3cnco3)c2c1] | 4-cyano-2-fluoro-6-methyl-N-(3-(oxazol-5-yl)-1H-indazol-5-yl)benzamide | 362.2 |
| 191 | 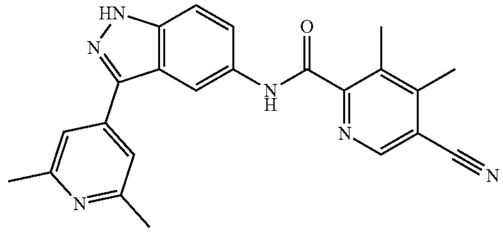 [SMILES: Cc1cc(-c2n[nH]c3ccc(NC(=O)c4ncc(C#N)c(C)c4C)cc23)cc(C)n1] | 5-cyano-N-(3-(2,6-dimethylpyridin-4-yl)-1H-indazol-5-yl)-3,4-dimethylpicolinamide | 397.3 |

TABLE 2-continued

| Ex. No | Structure | Name | m/z |
|---|---|---|---|
| 192 | 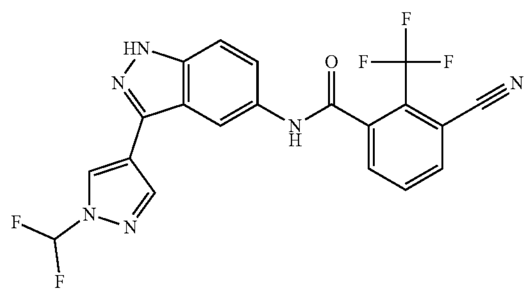 [SMILES: N#Cc1cccc(C(=O)Nc2ccc3[nH]nc(-c4cnn(C(F)F)c4)c3c2)c1C(F)(F)F] | 3-cyano-N-(3-(1-(difluoromethyl)-1H-pyrazol-4-yl)-1H-indazol-5-yl)-2-(trifluoromethyl)benzamide | 447.1 |
| 193 | 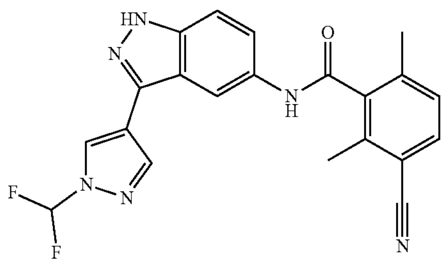 [SMILES: Cc1ccc(C#N)c(C)c1C(=O)Nc1ccc2[nH]nc(-c3cnn(C(F)F)c3)c2c1] | 3-cyano-N-(3-(1-(difluoromethyl)-1H-pyrazol-4-yl)-1H-indazol-5-yl)-2,6-dimethylbenzamide | 407.2 |
| 194 | 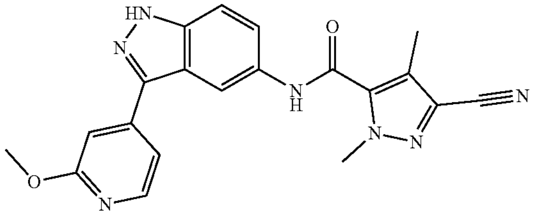 [SMILES: COc1cc(-c2n[nH]c3ccc(NC(=O)c4c(C)c(C#N)nn4C)cc23)ccn1] | 3-cyano-N-(3-(2-methoxypyridin-4-yl)-1H-indazol-5-yl)-1,4-dimethyl-1H-pyrazole-5-carboxamide | 388.2 |
| 195 | 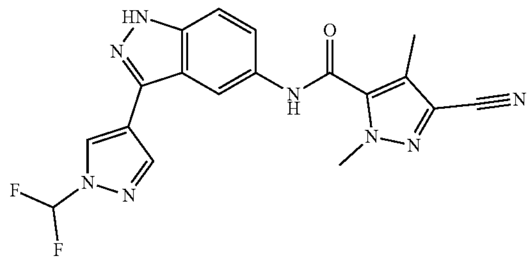 [SMILES: Cc1c(C#N)nn(C)c1C(=O)Nc1ccc2[nH]nc(-c3cnn(C(F)F)c3)c2c1] | 3-cyano-N-(3-(1-(difluoromethyl)-1H-pyrazol-4-yl)-1H-indazol-5-yl)-1,4-dimethyl-1H-pyrazole-5-carboxamide | 397.2 |
| 196 | 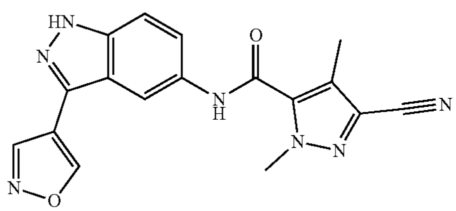 [SMILES: Cc1c(C#N)nn(C)c1C(=O)Nc1ccc2[nH]nc(-c3cnoc3)c2c1] | 3-cyano-N-(3-(isoxazol-4-yl)-1H-indazol-5-yl)-1,4-dimethyl-1H-pyrazole-5-carboxamide | 348.0 |
| 197 | 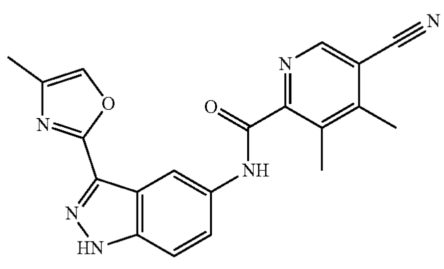 [SMILES: Cc1coc(-c2n[nH]c3ccc(NC(=O)c4ncc(C#N)c(C)c4C)cc23)n1] | 5-cyano-3,4-dimethyl-N-(3-(4-methyloxazol-2-yl)-1H-indazol-5-yl)picolinamide | 373.29 |

TABLE 2-continued

| Ex. No | Structure | Name | m/z |
|---|---|---|---|
| 198 | 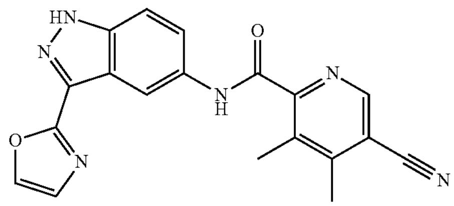 [SMILES: Cc1c(C#N)cnc(C(=O)Nc2ccc3[nH]nc(-c4ncco4)c3c2)c1C] | 5-cyano-3,4-dimethyl-N-(3-(oxazol-2-yl)-1H-indazol-5-yl)picolinamide | 359.23 |
| 199 | 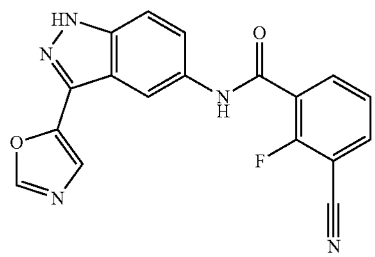 [SMILES: N#Cc1cccc(C(=O)Nc2ccc3[nH]nc(-c4cnco4)c3c2)c1F] | 3-cyano-2-fluoro-N-(3-(oxazol-5-yl)-1H-indazol-5-yl)benzamide | 348.15 |
| 200 | 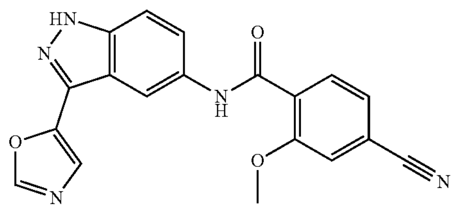 [SMILES: COc1cc(C#N)ccc1C(=O)Nc1ccc2[nH]nc(-c3cnco3)c2c1] | 4-cyano-2-methoxy-N-(3-(oxazol-5-yl)-1H-indazol-5-yl)benzamide | 360.26 |
| 201 | 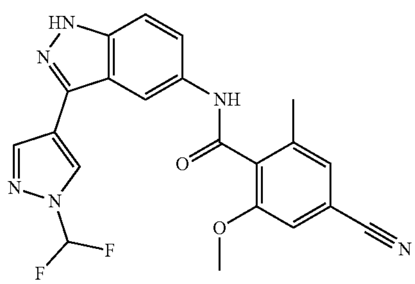 [SMILES: COc1cc(C#N)cc(C)c1C(=O)Nc1ccc2[nH]nc(-c3cnn(C(F)F)c3)c2c1] | 4-cyano-N-(3-(1-(difluoromethyl)-1H-pyrazol-4-yl)-1H-indazol-5-yl)-2-methoxy-6-methylbenzamide | 423.3 |
| 202 | 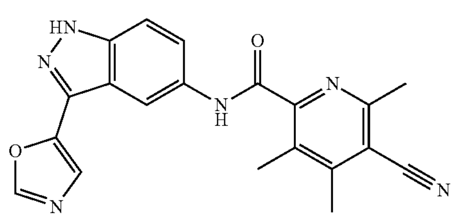 [SMILES: Cc1nc(C(=O)Nc2ccc3[nH]nc(-c4cnco4)c3c2)c(C)c(C)c1C#N] | 5-cyano-3,4,6-trimethyl-N-(3-(oxazol-5-yl)-1H-indazol-5-yl)picolinamide | 373.3 |
| 203 | 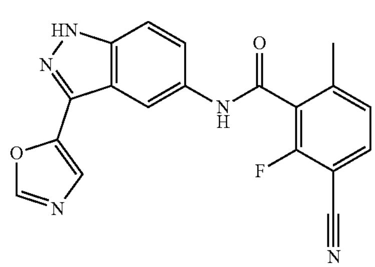 [SMILES: Cc1ccc(C#N)c(F)c1C(=O)Nc1ccc2[nH]nc(-c3cnco3)c2c1] | 3-cyano-2-fluoro-6-methyl-N-(3-(oxazol-5-yl)-1H-indazol-5-yl)benzamide | 362.0 |

TABLE 2-continued

| Ex. No | Structure | Name | m/z |
|---|---|---|---|
| 204 | 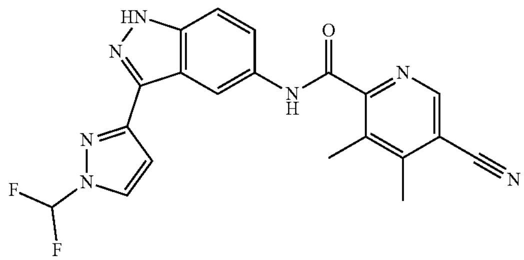 [SMILES: Cc1c(C#N)cnc(C(=O)Nc2ccc3[nH]nc(-c4ccn(C(F)F)n4)c3c2)c1C] | 5-cyano-N-(3-(1-(difluoromethyl)-1H-pyrazol-3-yl)-1H-indazol-5-yl)-3,4-dimethylpicolinamide | 408.0 |
| 205 | 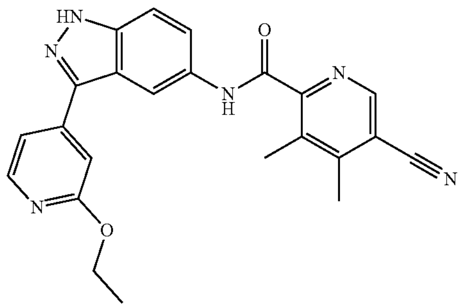 [SMILES: CCOc1cc(-c2n[nH]c3ccc(NC(=O)c4ncc(C#N)c(C)c4C)cc23)ccn1] | 5-cyano-N-(3-(2-ethoxypyridin-4-yl)-1H-indazol-5-yl)-3,4-dimethylpicolinamide | 413.0 |
| 206 | 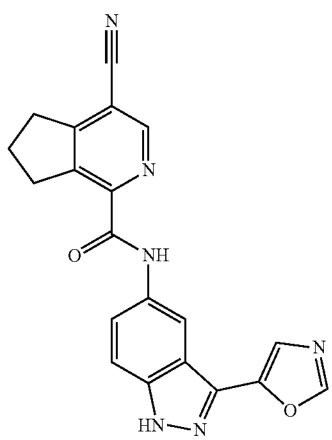 [SMILES: N#Cc1cnc(C(=O)Nc2ccc3[nH]nc(-c4cnco4)c3c2)c2c1CCC2] | 4-cyano-N-(3-(oxazol-5-yl)-1H-indazol-5-yl)-6,7-dihydro-5H-cyclopenta[c]pyridine-1-carboxamide | 371.19 |
| 207 | 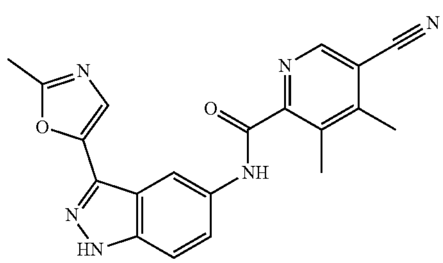 [SMILES: Cc1ncc(-c2n[nH]c3ccc(NC(=O)c4ncc(C#N)c(C)c4C)cc23)o1] | 5-cyano-3,4-dimethyl-N-(3-(5-methyloxazol-2-yl)-1H-indazol-5-yl)picolinamide | 373.26 |
| 208 | 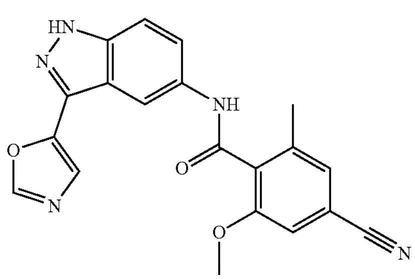 [SMILES: COc1cc(C#N)cc(C)c1C(=O)Nc1ccc2[nH]nc(-c3cnco3)c2c1] | 4-cyano-2-methoxy-6-methyl-N-(3-(oxazol-5-yl)-1H-indazol-5-yl)benzamide | 374.25 |

TABLE 2-continued

| Ex. No | Structure | Name | m/z |
|---|---|---|---|
| 209 | 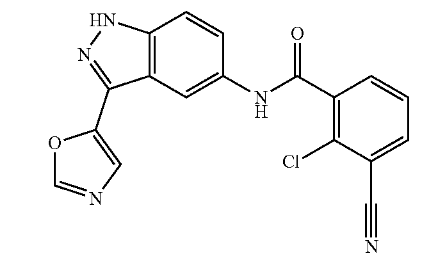 [SMILES: N#Cc1cccc(C(=O)Nc2ccc3[nH]nc(-c4cnco4)c3c2)c1Cl] | 2-chloro-3-cyano-N-(3-(oxazol-5-yl)-1H-indazol-5-yl)benzamide | 364.16-366.15 |
| 210 | 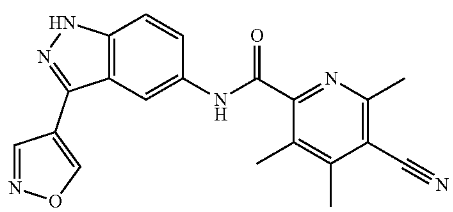 [SMILES: Cc1nc(C(=O)Nc2ccc3[nH]nc(-c4cnoc4)c3c2)c(C)c(C)c1C#N] | 5-cyano-N-(3-(isoxazol-4-yl)-1H-indazol-5-yl)-3,4,6-trimethylpicolinamide | 373.26 |
| 211 | 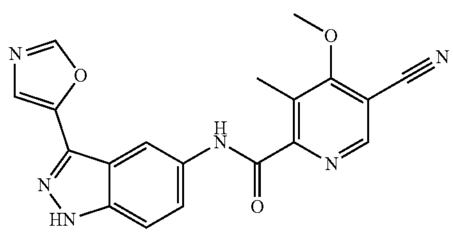 [SMILES: COc1c(C#N)cnc(C(=O)Nc2ccc3[nH]nc(-c4cnco4)c3c2)c1C] | 5-cyano-4-methoxy-3-methyl-N-(3-(oxazol-5-yl)-1H-indazol-5-yl)picolinamide | 375.2 |
| 212 | 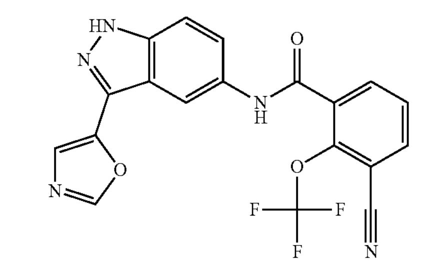 [SMILES: N#Cc1cccc(C(=O)Nc2ccc3[nH]nc(-c4cnco4)c3c2)c1OC(F)(F)F] | 3-cyano-N-(3-(oxazol-5-yl)-1H-indazol-5-yl)-2-(trifluoromethoxy)benzamide | 413.9 |
| 213 | 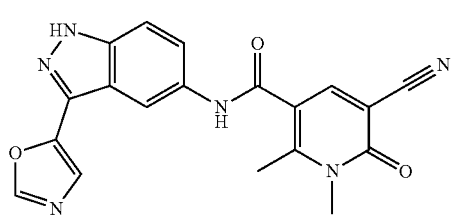 [SMILES: Cc1c(C(=O)Nc2ccc3[nH]nc(-c4cnco4)c3c2)cc(C#N)c(=O)n1C] | 5-cyano-1,2-dimethyl-N-(3-(oxazol-5-yl)-1H-indazol-5-yl)-6-oxo-1,6-dihydropyridine-3-carboxamide | 375.1 |
| 214 | 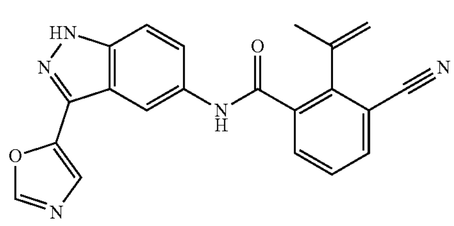 [SMILES: C=C(C)c1c(C#N)cccc1C(=O)Nc1ccc2[nH]nc(-c3cnco3)c2c1] | 3-cyano-N-(3-(oxazol-5-yl)-1H-indazol-5-yl)-2-(prop-1-en-2-yl)benzamide | 370.2 |

TABLE 2-continued

| Ex. No | Structure | Name | m/z |
|---|---|---|---|
| 215 | 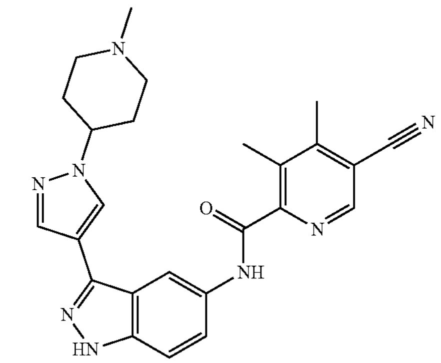 [SMILES: Cc1c(C#N)cnc(C(=O)Nc2ccc3[nH]nc(-c4cnn(C5CCN(C)CC5)c4)c3c2)c1C] | 5-cyano-3,4-dimethyl-N-(3-(1-(1-methylpiperidin-4-yl)-1H-pyrazol-4-yl)-1H-indazol-5-yl)picolinamide | 455.42 |
| 216 | 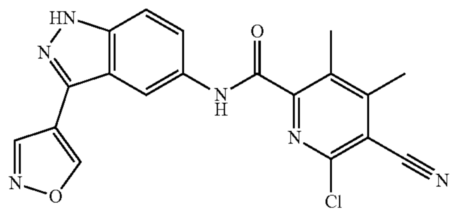 [SMILES: Cc1c(C(=O)Nc2ccc3[nH]nc(-c4cnoc4)c3c2)nc(Cl)c(C#N)c1C] | 6-chloro-5-cyano-N-(3-(isoxazol-4-yl)-1H-indazol-5-yl)-3,4-dimethylpicolinamide | 393.16 |
| 217 | 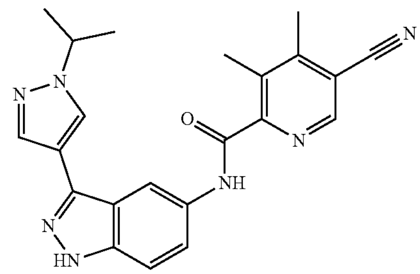 [SMILES: Cc1c(C#N)cnc(C(=O)Nc2ccc3[nH]nc(-c4cnn(C(C)C)c4)c3c2)c1C] | 5-cyano-N-(3-(1-isopropyl-1H-pyrazol-4-yl)-1H-indazol-5-yl)-3,4-dimethylpicolinamide | 400.32 |
| 218 | 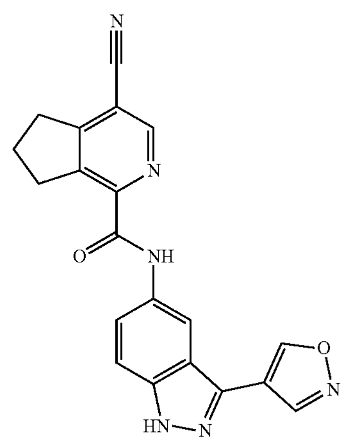 [SMILES: N#Cc1cnc(C(=O)Nc2ccc3[nH]nc(-c4cnoc4)c3c2)c2c1CCC2] | 4-cyano-N-(3-(isoxazol-4-yl)-1H-indazol-5-yl)-6,7-dihydro-5H-cyclopenta[c]pyridine-1-carboxamide | 371.22 |
| 219 | 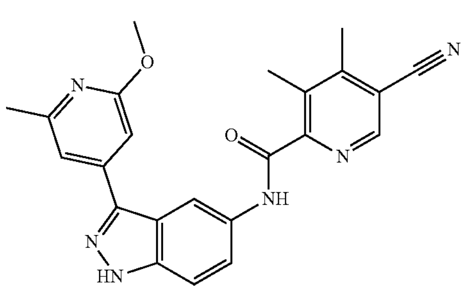 [SMILES: COc1cc(-c2n[nH]c3ccc(NC(=O)c4ncc(C#N)c(C)c4C)cc23)cc(C)n1] | 5-cyano-N-(3-(2-methoxy-6-methylpyridin-4-yl)-1H-indazol-5-yl)-3,4-dimethylpicolinamide | 413.32 |

TABLE 2-continued

| Ex. No | Structure | Name | m/z |
|---|---|---|---|
| 220 | 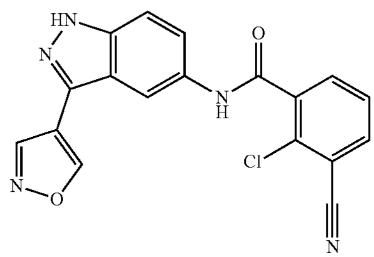 [SMILES: N#Cc1cccc(C(=O)Nc2ccc3[nH]nc(-c4cnoc4)c3c2)c1Cl] | 2-chloro-3-cyano-N-(3-(isoxazol-4-yl)-1H-indazol-5-yl)benzamide | 364.14, 366.16 |
| 221 | 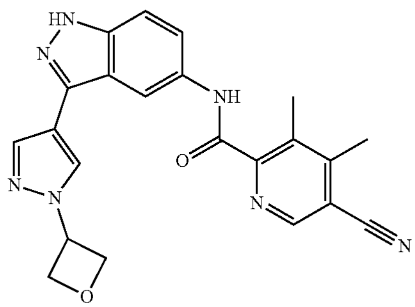 [SMILES: Cc1c(C#N)cnc(C(=O)Nc2ccc3[nH]nc(-c4cnn(C5COC5)c4)c3c2)c1C] | 5-cyano-3,4-dimethyl-N-(3-(1-(oxetan-3-yl)-1H-pyrazol-4-yl)-1H-indazol-5-yl)picolinamide | 414.25 |
| 222 | 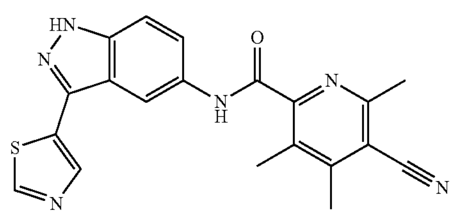 [SMILES: Cc1nc(C(=O)Nc2ccc3[nH]nc(-c4cncs4)c3c2)c(C)c(C)c1C#N] | 5-cyano-3,4,6-trimethyl-N-(3-(thiazol-5-yl)-1H-indazol-5-yl)picolinamide | 389.23 |
| 223 | 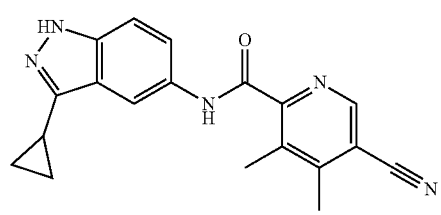 [SMILES: Cc1c(C#N)cnc(C(=O)Nc2ccc3[nH]nc(C4CC4)c3c2)c1C] | 5-cyano-N-(3-cyclopropyl-1H-indazol-5-yl)-3,4-dimethylpicolinamide | 332.1 |
| 224 | 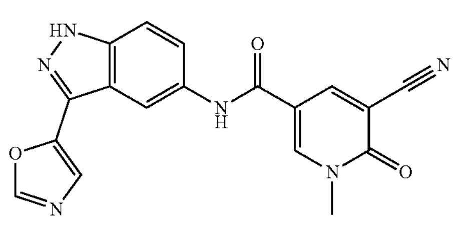 [SMILES: Cn1cc(C(=O)Nc2ccc3[nH]nc(-c4cnco4)c3c2)cc(C#N)c1=O] | 5-cyano-1-methyl-N-(3-(oxazol-5-yl)-1H-indazol-5-yl)-6-oxo-1,6-dihydropyridine-3-carboxamide | 361.1 |
| 225 | 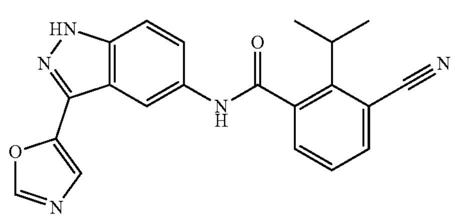 [SMILES: CC(C)c1c(C#N)cccc1C(=O)Nc1ccc2[nH]nc(-c3cnco3)c2c1] | 3-cyano-2-isopropyl-N-(3-(oxazol-5-yl)-1H-indazol-5-yl)benzamide | 372.2 |

TABLE 2-continued

| Ex. No | Structure | Name | m/z |
|---|---|---|---|
| 226 | 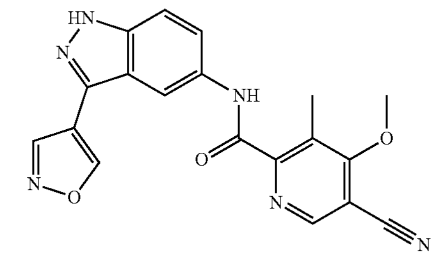 | 5-cyano-N-(3-(isoxazol-4-yl)-1H-indazol-5-yl)-4-methoxy-3-methylpicolinamide | |
| 227 | 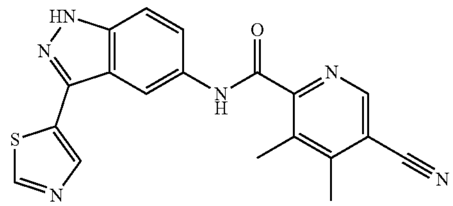 [SMILES: Cc1c(C#N)cnc(C(=O)Nc2ccc3[nH]nc(-c4cncs4)c3c2)c1C] | 5-cyano-3,4-dimethyl-N-(3-(thiazol-5-yl)-1H-indazol-5-yl)picolinamide | 375.2 |
| 228 | 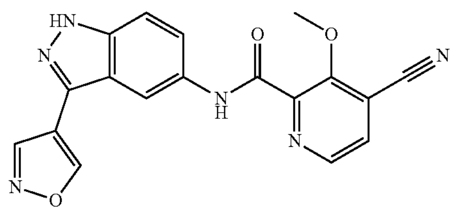 [SMILES: COc1c(C#N)ccnc1C(=O)Nc1ccc2[nH]nc(-c3cnoc3)c2c1] | 4-cyano-N-(3-(isoxazol-4-yl)-1H-indazol-5-yl)-3-methoxypicolinamide | 361.19 |
| 229 | 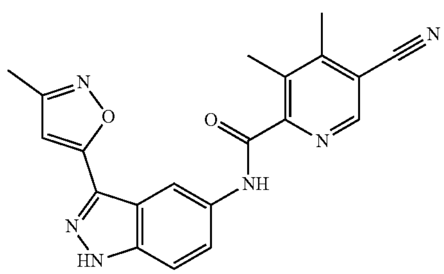 [SMILES: Cc1cc(-c2n[nH]c3ccc(NC(=O)c4ncc(C#N)c(C)c4C)cc23)on1] | 5-cyano-3,4-dimethyl-N-(3-(3-methylisoxazol-5-yl)-1H-indazol-5-yl)picolinamide | 373.18 |
| 230 | 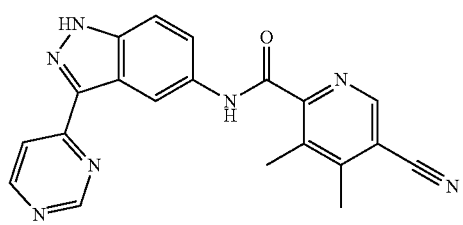 [SMILES: Cc1c(C#N)cnc(C(=O)Nc2ccc3[nH]nc(-c4ccncn4)c3c2)c1C] | 5-cyano-3,4-dimethyl-N-(3-(pyrimidin-4-yl)-1H-indazol-5-yl)picolinamide | 370.2 |
| 231 | 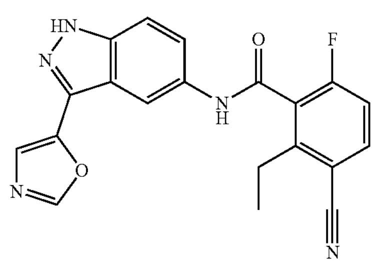 [SMILES: CCc1c(C#N)ccc(F)c1C(=O)Nc1ccc2[nH]nc(-c3cnco3)c2c1] | 3-cyano-2-ethyl-6-fluoro-N-(3-(oxazol-5-yl)-1H-indazol-5-yl)benzamide | 376.1 |

TABLE 2-continued

| Ex. No | Structure | Name | m/z |
|---|---|---|---|
| 232 | 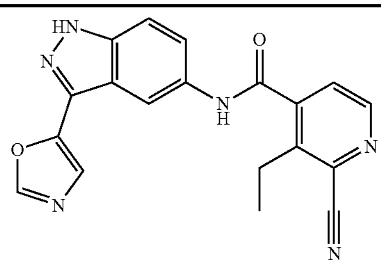 | 2-cyano-3-ethyl-N-(3-(oxazol-5-yl)-1H-indazol-5-yl)isonicotinamide | 359.1 |
| 233 | 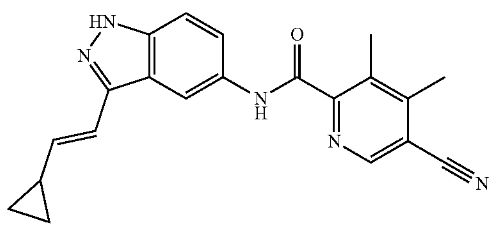 [SMILES: Cc1c(C#N)cnc(C(=O)Nc2ccc3[nH]nc(/C=C/C4CC4)c3c2)c1C] | (E)-5-cyano-N-(3-(2-cyclopropylvinyl)-1H-indazol-5-yl)-3,4-dimethylpicolinamide | 358.1 |
| 234 | 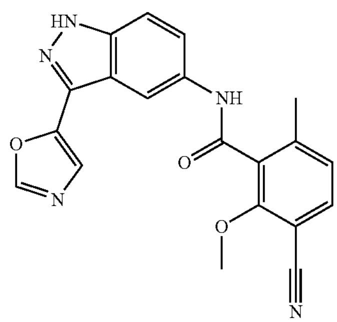 [SMILES: COc1c(C#N)ccc(C)c1C(=O)Nc1ccc2[nH]nc(-c3cnco3)c2c1] | 3-cyano-2-methoxy-6-methyl-N-(3-(oxazol-5-yl)-1H-indazol-5-yl)benzamide | 374.27 |
| 235 | 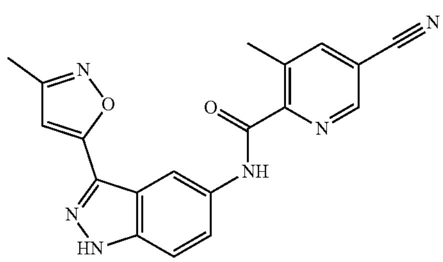 [SMILES: Cc1cc(-c2n[nH]c3ccc(NC(=O)c4ncc(C#N)cc4C)cc23)on1] | 5-cyano-3-methyl-N-(3-(3-methylisoxazol-5-yl)-1H-indazol-5-yl)picolinamide | 359.19 |
| 236 | 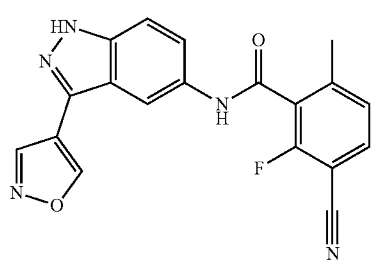 [SMILES: Cc1ccc(C#N)c(F)c1C(=O)Nc1ccc2[nH]nc(-c3cnoc3)c2c1] | 3-cyano-2-fluoro-N-(3-(isoxazol-4-yl)-1H-indazol-5-yl)-6-methylbenzamide | 362.22 |
| 237 | 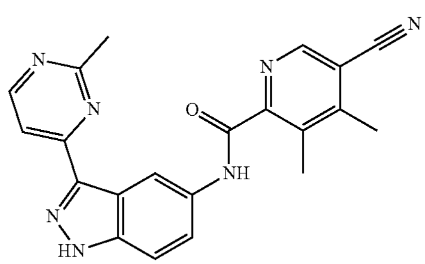 [SMILES: Cc1nccc(-c2n[nH]c3ccc(NC(=O)c4ncc(C#N)c(C)c4C)cc23)n1] | 5-cyano-3,4-dimethyl-N-(3-(2-methylpyrimidin-4-yl)-1H-indazol-5-yl)picolinamide | 384.3 |

TABLE 2-continued

| Ex. No | Structure | Name | m/z |
|---|---|---|---|
| 238 | 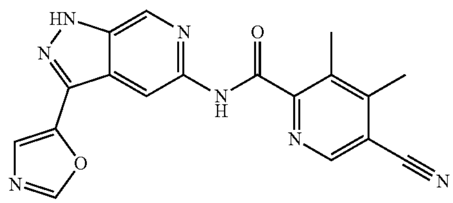 [SMILES: Cc1c(C#N)cnc(C(=O)Nc2cc3c(-c4cnco4)n[nH]c3cn2)c1C] | 5-cyano-3,4-dimethyl-N-(3-(oxazol-5-yl)-1H-pyrazolo[3,4-c]pyridin-5-yl)picolinamide | 360.1 |
| 239 | 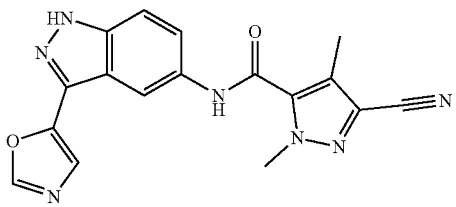 [SMILES: Cc1c(C#N)nn(C)c1C(=O)Nc1ccc2[nH]nc(-c3cnco3)c2c1] | 3-cyano-1,4-dimethyl-N-(3-(oxazol-5-yl)-1H-indazol-5-yl)-1H-pyrazole-5-carboxamide | 348.1 |

Detailed methods for the preparation of Examples 101-239 are provided below:

Example 101: 5-Cyano-N-(3-(isoxazol-5-yl)-1H-indazol-5-yl)-3-methylpicolinamide

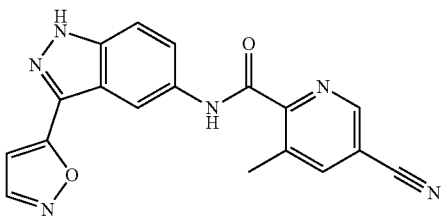 [SMILES: Cc1cc(C#N)cnc1C(=O)Nc1ccc2[nH]nc(-c3ccno3)c2c1]

Prepared as described for 5-cyano-N-(7-fluoro-3-(furan-3-yl)-1H-indazol-5-yl)-3-methylpicolinamide using 5-cyano-3-methylpicolinic acid in place of 5-cyano-3-methylpicolinic acid and using 3-(isoxazol-5-yl)-1H-indazol-5-amine in place of 7-fluoro-3-(furan-3-yl)-1H-indazol-5-amine to afford the title compound (1.7 mg, 4%) as a yellow solid. $^1$H NMR (400 MHz, DMSO-d$_6$) δ 13.79 (br. s., 1H) 10.85 (s, 1H) 9.01 (d, J=1.54 Hz, 1H) 8.75 (d, J=1.76 Hz, 2H) 8.42 (s, 1H) 7.79-7.89 (m, 1H) 7.68 (d, J=9.02 Hz, 1H) 6.95 (d, J=1.98 Hz, 1H) 2.61 (s, 3H). MS-ESI (m/z) calc'd for C$_{15}$H$_{13}$N$_6$O$_2$ [M+H]$^+$: 345.1. Found 345.2.

Example 102: 5-Cyano-3-methyl-N-(3-(5-(morpholinomethyl)thiophen-2-yl)-1H-indazol-5-yl)picolinamide

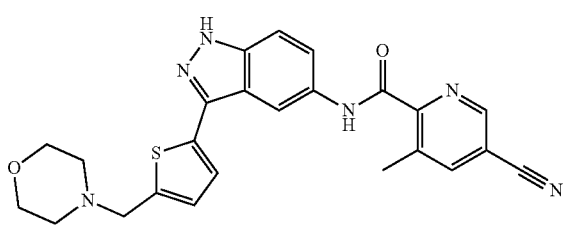 [SMILES: Cc1cc(C#N)cnc1C(=O)Nc1ccc2[nH]nc(-c3ccc(CN4CCOCC4)s3)c2c1]

Prepared as described for 5-cyano-N-(3-(isoxazol-4-yl)-1H-indazol-5-yl)-3-methylpicolinamide using (5-(morpholinomethyl)thiophen-2-yl)boronic acid in place of isoxazole-4-boronic acid to afford the title compound (60.7 mg, 65%) as a yellow solid. $^1$H NMR (400 MHz, DMSO-d$_6$) δ 13.18 (s, 1H), 10.78 (s, 1H), 9.00 (d, J=1.9 Hz, 1H), 8.63 (d, J=1.8 Hz, 1H), 8.41 (d, J=2.3 Hz, 1H), 8.18 (s, 1H), 7.81 (dd, J=9.0, 1.9 Hz, 1H), 7.57 (d, J=9.0 Hz, 1H), 7.46 (d, J=3.6 Hz, 1H), 7.07 (d, J=3.6 Hz, 1H), 3.72 (s, 2H), 3.60 (t, J=4.6 Hz, 4H), 2.60 (s, 3H), 2.46 (d, J=4.6 Hz, 4H). MS-ESI (m/z) calc'd for C$_{24}$H$_{23}$N$_6$O$_2$S [M+H]$^+$: 459.2. Found 459.2.

Example 103: N-(3-(2-Bromopyridin-4-yl)-1H-indazol-5-yl)-5-cyano-3-methylpicolinamide

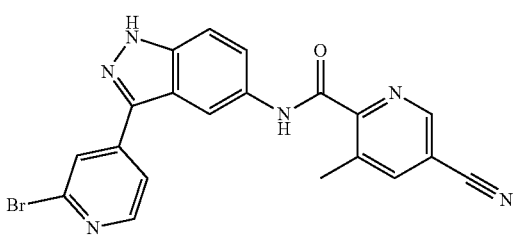 [SMILES: Cc1cc(C#N)cnc1C(=O)Nc1ccc2[nH]nc(-c3ccnc(Br)c3)c2c1]

Prepared as described for 5-cyano-N-(3-(isoxazol-4-yl)-1H-indazol-5-yl)-3-methylpicolinamide using (2-bromopyridin-4-yl)boronic acid in place of isoxazole-4-boronic acid to afford the title compound (6 mg, 7%) as a yellow solid. $^1$H NMR (400 MHz, DMSO-d$_6$) δ 13.73 (br. s., 1H) 10.86 (s, 1H) 9.02 (d, J=1.76 Hz, 1H) 8.64 (s, 1H) 8.54 (d, J=5.06 Hz, 1H) 8.43 (d, J=1.32 Hz, 1H) 8.11 (s, 1H) 8.01 (dd, J=5.17, 1.43 Hz, 1H) 7.95 (dd, J=9.13, 1.65 Hz, 1H) 7.69 (d, J=9.02 Hz, 1H) 2.62 (s, 3H). MS-ESI (m/z) calc'd for C$_{20}$H$_{14}$BrN$_6$O [M+H]$^+$: 433.0/435.0. Found 433.2/435.2.

Example 104: 2-Cyano-1,5-dimethyl-N-(3-phenyl-1H-indazol-5-yl)-1H-imidazole-4-carboxamide

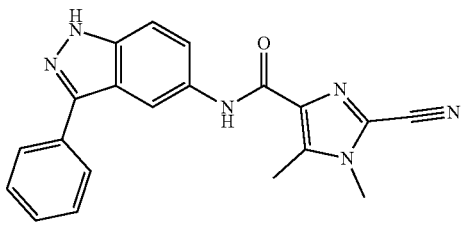 [SMILES: Cc1c(C(=O)Nc2ccc3[nH]nc(-c4ccccc4)c3c2)nc(C#N)n1C]

Step 1: Ethyl 1,5-dimethyl-1H-imidazole-4-carboxylate

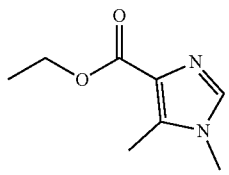

To a solution of NaH (155.66 mg, 3.89 mmol, 60% purity) in DMF (10 mL) was added ethyl 5-methyl-1H-imidazole-4-carboxylate (500 mg, 3.24 mmol) at 0° C. and the mixture was stirred for 15 min. Then MeI (552.41 mg, 3.89 mmol) was added and the mixture was stirred at 25° C. for 12 hrs. The reaction mixture was quenched by addition of $H_2O$ (10 mL) at 20° C., concentrated, and then diluted with $H_2O$ (20 mL) and extracted with EtOAc (50 mL×4). The combined organic layers were dried over $Na_2SO_4$, filtered and concentrated under reduced pressure to give a residue. The residue was purified by flash silica gel chromatography (ISCO; 20 g SepaFlash column) using a 0-54% EtOAc/petroleum ether gradient eluent to afford the title compound (140 mg, 26%) as a yellow solid. MS-ESI (m/z) calcd for $C_8H_{13}N_2O_2$ $[M+H]^+$: 169.1. Found 169.1.

Step 2: Ethyl 2-bromo-1,5-dimethyl-1H-imidazole-4-carboxylate

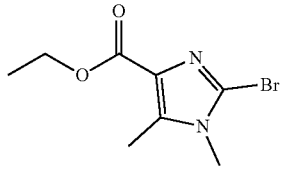

To a solution of ethyl 1,5-dimethyl-1H-imidazole-4-carboxylate (760 mg, 4.52 mmol) in MeCN (23 mL) was added NBS (965.09 mg, 5.42 mmol) and the mixture was stirred at 20° C. for 12 hrs. The reaction mixture was concentrated and then diluted with $H_2O$ (25 mL) and extracted with EtOAc (50 mL×3). The combined organic layers were dried over $Na_2SO_4$, filtered and concentrated under reduced pressure to give a residue. The residue was purified by flash silica gel chromatography (ISCO; 20 g SepaFlash column) using a 0-60% EtOAc/petroleum ether gradient eluent to afford the tite compound (880 mg, 79%) as a yellow oil. MS-ESI (m/z) calcd for $C_8H_{12}BrN_2O_2$ $[M+H]^+$: 247.0/249.0. Found 247.0/249.0.

Step 3: 2-Bromo-1,5-dimethyl-1H-imidazole-4-carboxylic acid

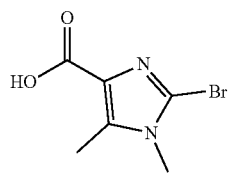

To a solution of ethyl 2-bromo-1,5-dimethyl-1H-imidazole-4-carboxylate (90 mg, 364.24 umol) in $H_2O$ (1 mL) and THF (3 mL) was added NaOH (43.71 mg, 1.09 mmol). The mixture was stirred at 20° C. for 5 hrs and then acidified with 1 N HCl to pH=3. The mixture was extracted with EtOAc (15 mL×5) and the combined organic layers were dried over $Na_2SO_4$, filtered and concentrated to afford the title compound (60 mg) as an orange solid which was used without further purification. MS-ESI (m/z) calcd for $C_6H_8BrN_2O_2$ $[M+H]^+$: 219.0/221.0. Found 218.9/220.9.

Step 4: 2-Bromo-1,5-dimethyl-N-(3-phenyl-1H-indazol-5-yl)-1H-imidazole-4-carboxamide

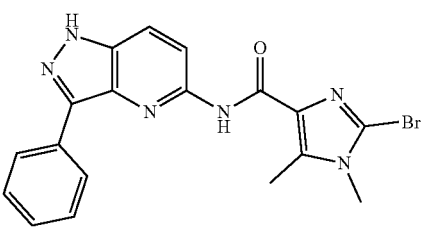 [SMILES: Cc1c(C(=O)Nc2ccc3[nH]nc(-c4ccccc4)c3n2)nc(Br)n1C]

To a solution of 2-bromo-1,5-dimethyl-1H-imidazole-4-carboxylic acid (110 mg, 502.20 umol) in pyridine (3 mL) was added 3-phenyl-1H-indazol-5-amine (126.10 mg, 602.64 umol) and EDCI (192.55 mg, 1.00 mmol). The mixture was stirred at 20° C. for 12 hrs and then concentrated. The material was purified by flash silica gel chromatography (ISCO; 12 g SepaFlash column) using a 0-30% (EtOAc/MeOH=20/1)/petroleum ether gradient eluent to afford the title compound (50 mg, 12%) as a yellow solid. MS-ESI (m/z) calcd for $C_{19}H_{17}BrN_5O$ $[M+H]^+$: 410.1/412.1. Found 410.0/412.0.

Step 5: 2-Cyano-1,5-dimethyl-N-(3-phenyl-1H-indazol-5-yl)-1H-imidazole-4-carboxamide

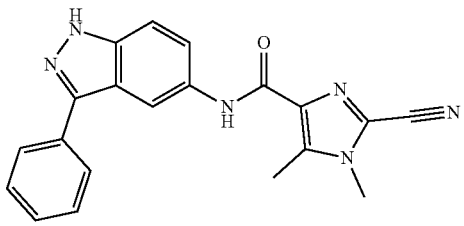 [SMILES: Cc1c(C(=O)Nc2ccc3[nH]nc(-c4ccccc4)c3c2)nc(C#N)n1C]

To a solution of 2-bromo-1,5-dimethyl-N-(3-phenyl-1H-indazol-5-yl)-1H-imidazole-4-carboxamide (50 mg, 121.87 umol) in DMA (2 mL) was added Zn (956.30 ug, 14.62 umol), Zn(CN)$_2$ (14.31 mg, 121.87 umol), Pd$_2$(dba)$_3$ (2.23 mg, 2.44 umol), and DPPF (2.70 mg, 4.87 umol). The mixture was stirred at 120° C. for 3 hrs under an N$_2$ atmosphere and then concentrated under reduced pressure to remove solvent to afford a residue. The residue was diluted with H$_2$O (2 mL) and extracted with EtOAc (8 mL×4). The combined organic layers were dried over Na$_2$SO$_4$, filtered and concentrated under reduced pressure. The material was purified by preparative HPLC using Method BE to afford the title compound (9.58 mg, 17%) as an off-white solid TFA salt. $^1$H NMR (400 MHz, DMSO-d$_6$) δ 10.18 (s, 1H) 8.62 (d, J=1.22 Hz, 1H) 7.93-7.99 (m, 2H) 7.89 (dd, J=8.99, 1.77 Hz, 1H) 7.51-7.57 (m, 3H) 7.38-7.44 (m, 1H) 3.76 (s, 3H) 2.61 (s, 3H). MS-ESI (m/z) calc'd for C$_{20}$H$_{17}$N$_6$O [M+H]$^+$: 357.1 Found 357.0.

Example 105: 5-Cyano-N-(3-(furan-3-yl)-1H-pyrazolo[4,3-b]pyridin-5-yl)-3-methylpicolinamide

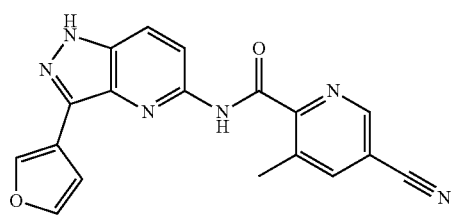 [SMILES: Cc1cc(C#N)cnc1C(=O)Nc1ccc2[nH]nc(-c3ccoc3)c2n1]

Step 1: 5-Chloro-3-iodo-1H-pyrazolo[4,3-b]pyridine

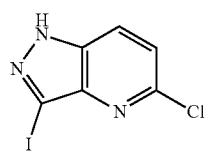 [SMILES: Clc1ccc2[nH]nc(I)c2n1]

To a stirred solution of 5-chloro-1H-pyrazolo[4,3-b]pyridine (4.0 g, 26.05 mmol) in DMF (100 mL) was added I$_2$ (26.44 g, 104.19 mmol) followed by addition of KOH (7.31 g, 130.23 mmol) in portions at 0° C. and the mixture was stirred at 25° C. for 12 hrs. The mixture was diluted with EtOAc (300 mL), washed with saturated aqueous Na$_2$SO$_3$ (150 mL×3), dried over Na$_2$SO$_4$ and concentrated to afford the title compound (4.0 g) as a yellow solid, which was used without further purification. MS-ESI (m/z) calcd for C$_6$H$_4$ClIN$_3$ [M+H]$^+$: 279.9/281.9. Found 279.9/281.9.

Step 2: 5-Chloro-3-(furan-3-yl)-1H-pyrazolo[4,3-b]pyridine

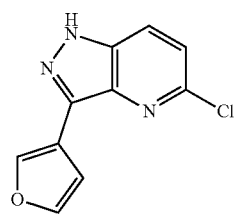 [SMILES: Clc1ccc2[nH]nc(-c3ccoc3)c2n1]

To a stirred solution of 5-chloro-3-iodo-1H-pyrazolo[4,3-b]pyridine (5.0 g, 17.89 mmol) in dioxane (100 mL) was added furan-3-ylboronic acid (2.40 g, 21.47 mmol) followed by addition of Pd(dppf)Cl$_2$ (1.31 g, 1.79 mmol) and K$_2$CO$_3$ (4.95 g, 35.78 mmol) in one portion. The mixture was then stirred at 90° C. for 24 hrs under N$_2$. The mixture was cooled to room temperature, filtered and the filtrate was concentrated to afford a residue. The residue was purified by silica gel column chromatography using a 20-50% EtOAc/petroleum ether gradient eluent to afford the title compound (700 mg, 18%) as a brown solid. MS-ESI (m/z) calcd for C$_{10}$H$_7$ClN$_3$O [M+H]$^+$: 220.0/222.0. Found 220.0/222.0.

Step 3: 5-Chloro-3-(furan-3-yl)-1-(tetrahydro-2H-pyran-2-yl)-1H-pyrazolo[4,3-b]pyridine

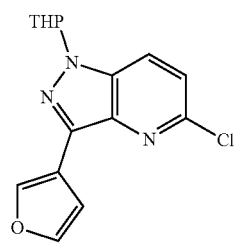

To a stirred solution of 5-chloro-3-(furan-3-yl)-1H-pyrazolo[4,3-b]pyridine (650 mg, 2.96 mmol) in DCM (20 mL) was added 3,4-dihydro-2H-pyran (373.42 mg, 4.44 mmol, 405.89 uL), followed by addition of TsOH (50.96 mg, 295.96 umol) in one portion and the mixture was then stirred at 25° C. for 12 hrs. The mixture was washed with 20% aqueous NaHCO$_3$ (5.0 mL×3), dried over Na$_2$SO$_4$ and concentrated to afford the title compound (1.2 g) as a brown oil which was used without further purification. MS-ESI (m/z) calcd for C$_{15}$H$_{15}$ClN$_3$O$_2$[M+H]$^+$: 304.1/306.1. Found 304.0/306.0.

Step 4: 5-Cyano-N-(3-(furan-3-yl)-1-(tetrahydro-2H-pyran-2-yl)-1H-pyrazolo[3,4-c]pyridin-5-yl)-3-methylpicolinamide

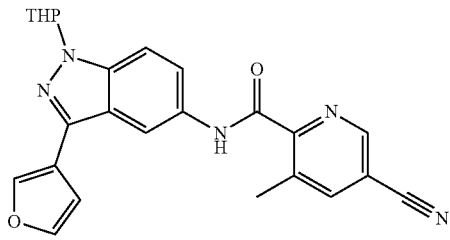

To a stirred solution of 5-chloro-3-(furan-3-yl)-1-(tetrahydro-2H-pyran-2-yl)-1H-pyrazolo[4,3-b]pyridine (200 mg, 658.45 umol) in toluene (10 mL) was added 5-cyano-3-methylpicolinamide (116.73 mg, 724.30 umol) followed by addition of Pd$_2$(dba)$_3$ (30.15 mg, 32.92 umol), XPhos (31.39 mg, 65.85 umol) and Cs$_2$CO$_3$ (536.34 mg, 1.65 mmol). Then the mixture was degassed under vacuum and purged with N$_2$ (3×) after which it was stirred at 110° C. for 12 hrs. The mixture was then filtered and the filtrate was concentrated and purified by preparative TLC (SiO$_2$, 1:1 petroleum ether/EtOAc, R$_f$=0.62) to afford the title compound (100 mg, 35%) as a yellow solid. MS-ESI (m/z) calcd for C$_{23}$H$_{21}$N$_6$O$_3$[M+H]$^+$: 429.2. Found 429.1.

Step 5: 5-Cyano-N-(3-(furan-3-yl)-1H-pyrazolo[4,3-b]pyridin-5-yl)-3-methylpicolinamide

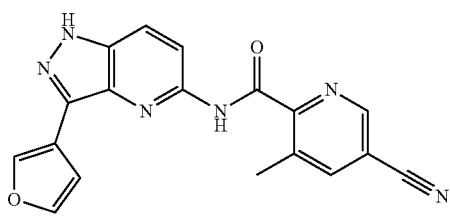 [SMILES: Cc1cc(C#N)cnc1C(=O)Nc1ccc2[nH]nc(-c3ccoc3)c2n1]

To a stirred solution of 5-cyano-N-(3-(furan-3-yl)-1-(tetrahydro-2H-pyran-2-yl)-1H-pyrazolo[3,4-c]pyridin-5-yl)-3-methylpicolinamide (90 mg, 210.06 umol) in DCM (3.0 mL) was added TFA (1.54 g, 13.51 mmol, 1 mL) dropwise at 0° C. and the mixture was stirred at 25° C. for 1 hr. The mixture was then concentrated to afford a residue which was purified by preparative HPLC using Method BG to afford the title compound (12.40 mg, 12%) as a pale yellow solid, TFA salt. $^1$H NMR (400 MHz, DMSO-de) δ 13.30 (s, 1H), 10.93 (s, 1H), 9.03 (s, 1H), 8.54 (s, 1H), 8.45 (s, 1H), 8.28-8.40 (m, 1H), 8.12-8.14 (m, 1H), 7.82 (s, 1H), 7.12 (s, 1H), 2.62 (br s, 3H). MS-ESI (m/z) calc'd for C$_{18}$H$_{13}$N$_6$O$_2$ [M+H]$^+$: 345.1 Found 345.0.

Example 106: N-(3-Bromo-1H-indazol-5-yl)-5-cyano-3-methylpicolinamide

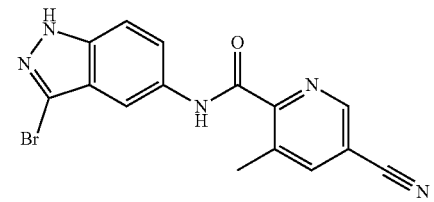 [SMILES: Cc1cc(C#N)cnc1C(=O)Nc1ccc2[nH]nc(Br)c2c1]

Step 1: Methyl 5-ethynyl-3-methylpicolinate

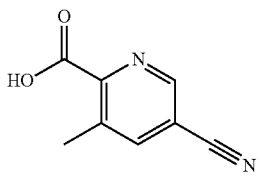

A mixture of methyl 5-bromo-3-methylpicolinate (1 g, 4.35 mmol), Zn(CN)$_2$ (612.49 mg, 5.22 mmol) and Pd(PPh$_3$)$_4$ (251.14 mg, 217.34 umol) in DMF (10 mL) was degassed and purged with N$_2$ (3×) and the mixture was stirred at 120° C. for 2 hrs under an N$_2$ atmosphere. The reaction mixture was concentrated and the residue obtained was purified by flash silica gel chromatography (ISCO; 4 g SepaFlash column) using a 0-10% EtOAc/petroleum ether gradient eluent to afford the title compound (640 mg, 84%) as a white solid.

Step 2: 5-Ethynyl-3-methylpicolinic acid

To a solution of methyl 5-ethynyl-3-methylpicolinate (640 mg, 3.63 mmol) in THF (15 mL) was added NaOH (290.60 mg, 7.27 mmol) and the mixture was stirred at 20° C. for 5 hrs. To the reaction mixture was then added H$_2$O (20 mL) and the aqueous phase was acidified with 1 N HCl to pH=3. The reaction was filtered, the solid was washed with H$_2$O (10 mL) and concentrated to give a residue. The phase that was recovered after separating the solid was extracted with EtOAc (30 mL×4), the organic layer was dried over anhydrous Na$_2$SO$_4$, filtered and the filtrate was concentrated to give a residue. This residue was combined with the separated solid to afford the title compound (580 mg) as a white solid, which was used without further purification. MS-ESI (m/z) calcd for C$_8$H$_7$N$_2$O$_2$ [M+H]$^+$: 163.0. Found 163.0.

Step 3: N-(3-Bromo-1H-indazol-5-yl)-5-cyano-3-methylpicolinamide

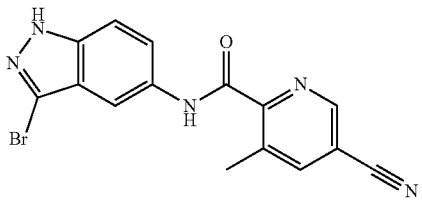 [SMILES: Cc1cc(C#N)cnc1C(=O)Nc1ccc2[nH]nc(Br)c2c1]

To a solution of 3-bromo-1H-indazol-5-amine (1.96 g, 9.25 mmol) and 5-ethynyl-3-methylpicolinic acid (1.5 g, 9.25 mmol) in pyridine (45 mL) was added EDCI (2.66 g, 13.88 mmol) and the mixture was stirred at 25° C. for 12 hrs. The reaction mixture was then concentrated to give a residue. The residue was diluted with MeOH (300 mL) and filtered. The solid was washed with MeOH (200 mL), filtered and dried to afford a residue (2.4 g) as a white solid. 100 mg of this material was purified by preparative HPLC using Method V to afford the title compound (6.2 mg, 5%) as a white solid TFA salt. $^1$H NMR (400 MHz, DMSO-$d_6$) δ 13.42 (br s, 1H), 10.83 (s, 1H), 8.99 (s, 1H), 8.41 (s, 1H), 8.26 (s, 1H), 7.72 (br d, J=9.2 Hz, 1H), 7.58 (d, J=9.0 Hz, 1H), 2.58 (s, 3H). MS-ESI (m/z) calc'd for $C_{15}H_{11}BrN_5O$ [M+H]$^+$: 356.0/358.0. Found 355.9/357.9.

Example 107: 4-Cyano-N-(3-(furan-3-yl)-1H-indazol-5-yl)-2-hydroxybenzamide

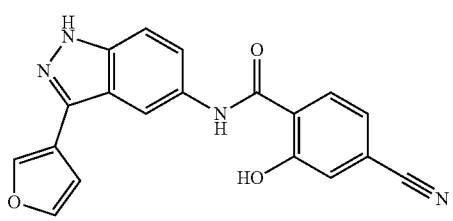 [SMILES: N#Cc1ccc(C(=O)Nc2ccc3[nH]nc(-c4ccoc4)c3c2)c(O)c1]

Step 1: Methyl 4-cyano-2-hydroxybenzoate

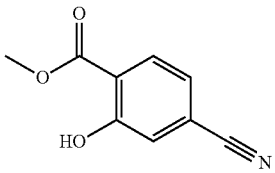

Methyl 2-hydroxy-4-iodobenzoate (1 g, 3.60 mmol) was dissolved in DMF (9 mL) and CuCN (773.33 mg, 8.63 mmol, 1.89 mL) was added. The reaction was heated to reflux at 140° C. for 2 hrs. The reaction was cooled to r.t. and dissolved in neat H$_2$O (50 mL). The resulting mixture was diluted with EtOAc (80 mL) and saturated aqueous NaHCO$_3$ (20 mL). The organic phase was separated, washed with H$_2$O (30 mL), dried over Na$_2$SO$_4$, filtered and concentrated under reduced pressure to afford the title compound (420 mg) as a yellow solid which was used without further purification. $^1$H NMR (400 MHz, DMSO-$d_6$) δ 10.75 (s, 1H), 7.84 (d, J=8 Hz, 1H), 7.41 (s, 1H), 7.33 (d, J=8 Hz, 1H), 3.88 (s, 3H).

Step 2: 4-Cyano-N-(3-(furan-3-yl)-1H-indazol-5-yl)-2-hydroxybenzamide

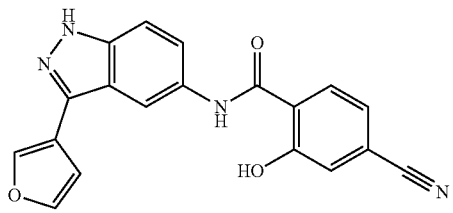 [SMILES: N#Cc1ccc(C(=O)Nc2ccc3[nH]nc(-c4ccoc4)c3c2)c(O)c1]

To a solution of methyl 4-cyano-2-hydroxybenzoate (70 mg, 395.13 umol) and 3-(furan-3-yl)-1H-indazol-5-amine (78.71 mg, 395.13 umol) in toluene (3 mL) was added AlMe$_3$ (2 M, 592.69 uL) and the mixture was stirred at 80° C. for 2 hrs. The reaction mixture was quenched by addition H$_2$O (10 mL) at 0° C., and concentrated under reduced pressure to remove solvent and give a residue. The residue was purified by preparative HPLC using Method BM to afford the title compound (12.25 mg, 9%) as a pale yellow solid. $^1$H NMR (400 MHz, DMSO-$d_6$) δ 13.11 (s, 1H), 11.21 (br s, 1H), 8.36 (s, 1H), 8.27 (s, 1H), 8.03 (d, J=7.9 Hz, 1H), 7.84 (s, 1H), 7.67-7.60 (m, 1H), 7.58-7.53 (m, 1H), 7.35-7.26 (m, 2H), 7.00 (s, 1H). MS-ESI (m/z) calc'd for $C_{19}H_{13}N_4O_3$ [M+H]$^+$: 345.1. Found 345.0.

Example 108: 5-Cyano-3-methyl-N-(3-(4-(morpholine-4-carbonyl)phenyl)-1H-indazol-5-yl)picolinamide

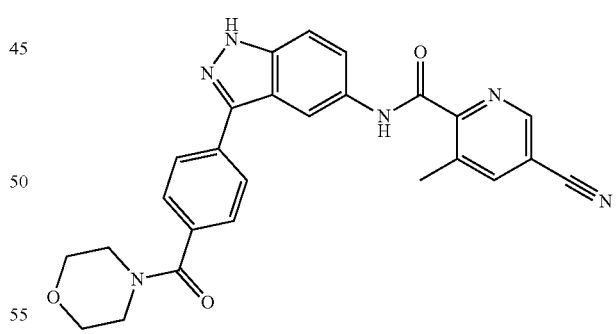

Prepared as described for 5-cyano-N-(3-(1,5-dimethyl-1H-pyrazol-4-yl)-1H-indazol-5-yl)-3-methylpicolinamide using (4-(morpholine-4-carbonyl)phenyl)boronic acid in place of (1,5-dimethyl-1H-pyrazol-4-yl)boronic acid to afford the title compound (10.94 mg, 17%) as a pale yellow solid. $^1$H NMR (400 MHz, DMSO-$d_6$) δ 10.79 (br s, 1H) 9.01 (s, 1H) 8.64 (s, 1H) 8.42 (s, 1H) 8.03 (d, J=8.19 Hz, 2H) 7.77-7.85 (m, 1H) 7.57-7.66 (m, 3H) 3.63 (br s, 8H) 2.60 (s, 3H). MS-ESI (m/z) calc'd for $C_{26}H_{23}N_6O_3$ [M+H]$^+$: 467.2. Found 467.1.

Example 109: 5-Cyano-N-(3-(5-isopropoxypyridin-3-yl)-1H-indazol-5-yl)-3-methylpicolinamide

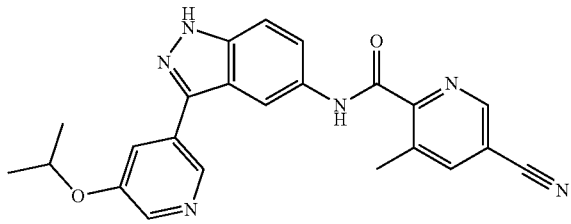 [SMILES: Cc1cc(C#N)cnc1C(=O)Nc1ccc2[nH]nc(-c3cncc(OC(C)C)c3)c2c1]

Prepared as described for 5-cyano-N-(3-(1,5-dimethyl-1H-pyrazol-4-yl)-1H-indazol-5-yl)-3-methylpicolinamide using (5-isopropoxypyridin-3-yl)boronic acid in place of (1,5-dimethyl-1H-pyrazol-4-yl)boronic acid to afford the title compound (10.29 mg, 17%) as a pale yellow solid. $^1$H NMR (400 MHz, DMSO-$d_6$) δ 13.53 (br s, 1H) 10.83 (s, 1H) 9.00 (d, J=1.59 Hz, 1H) 8.78 (d, J=1.22 Hz, 1H) 8.67 (d, J=1.10 Hz, 1H) 8.40 (dd, J=9.72, 1.90 Hz, 2H) 7.93 (s, 1H) 7.85 (dd, J=9.05, 1.59 Hz, 1H) 7.65 (d, J=8.93 Hz, 1H) 4.87 (spt, J=5.89 Hz, 1H) 2.59 (s, 3H) 1.37 (d, J=5.99 Hz, 6H). MS-ESI (m/z) calc'd for $C_{23}H_{21}N_6O_2[M+H]^+$: 413.2. Found 413.1.

Example 110: 5-Cyano-3-methyl-N-(3-(thiazol-5-yl)-1H-indazol-5-yl)picolinamide

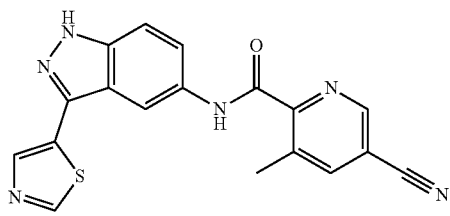 [SMILES: Cc1cc(C#N)cnc1C(=O)Nc1ccc2[nH]nc(-c3cncs3)c2c1]

A mixture of N-(3-bromo-1H-indazol-5-yl)-5-cyano-3-methylpicolinamide (50 mg, 140.38 umol), 5-(tributylstannyl)thiazole (52.53 mg, 140.38 umol), and Pd(PPh$_3$)$_2$Cl$_2$ (9.85 mg, 14.04 umol) in dioxane (3 mL) was degassed and purged with N$_2$ (3×), and then the mixture was stirred at 110° C. for 12 hrs under an N$_2$ atmosphere. The reaction mixture was then filtered and the filtrate was concentrated to give a residue which was purified by preparative HPLC using Method BI to afford the title compound (13.67 mg, 26%) as a yellow solid. $^1$H NMR (400 MHz, DMSO-$d_6$) δ 13.39 (br s, 1H), 10.80 (br s, 1H), 9.15 (s, 1H), 9.01 (br s, 1H), 8.64 (br s, 1H), 8.42 (br s, 2H), 7.87 (br d, J=8.9 Hz, 1H), 7.62 (br d, J=9.0 Hz, 1H), 2.61 (s, 3H). MS-ESI (m/z) calc'd for $C_{18}H_{13}N_6OS[M+H]^+$: 361.1 Found 361.1.

Example 111: 5-Cyano-3-methyl-N-(3-(oxazol-5-yl)-1H-indazol-5-yl)picolinamide

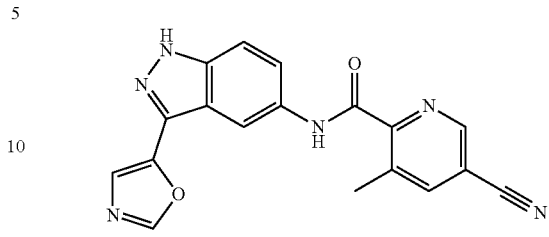

Prepared as described for 5-cyano-N-(3-(1,5-dimethyl-1H-pyrazol-4-yl)-1H-indazol-5-yl)-3-methylpicolinamide using oxazol-5-ylboronic acid in place of (1,5-dimethyl-1H-pyrazol-4-yl)boronic acid to afford the title compound (3.69 mg, 4%) as a pale yellow solid. $^1$H NMR (400 MHz, DMSO-$d_6$) δ 10.79 (br s, 1H), 9.00 (d, J=1.4 Hz, 1H), 8.61 (d, J=1.3 Hz, 1H), 8.58 (s, 1H), 8.41 (d, J=1.1 Hz, 1H), 7.80 (dd, J=1.9, 9.0 Hz, 1H), 7.65 (s, 11H), 7.62 (d, J=9.0 Hz, 1H), 2.60 (s, 3H). MS-ESI (m/z) calc'd for $C_{18}H_{13}N_6O_2[M+H]^+$: 345.1. Found 345.2.

Example 112: 5-Cyano-3-methyl-N-(3-(6-methylpyridin-2-yl)-1H-indazol-5-yl)picolinamide

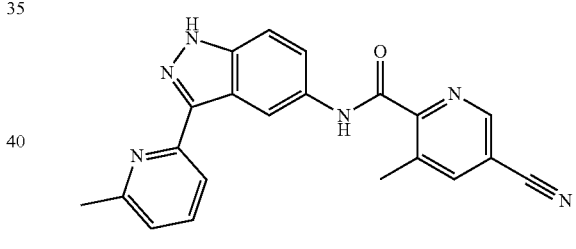

A mixture of N-(3-bromo-1H-indazol-5-yl)-5-cyano-3-methylpicolinamide (70 mg, 196.53 umol), 2-methyl-6-(tributylstannyl)pyridine (90.13 mg, 235.84 umol) and Pd(PPh$_3$)$_2$Cl$_2$ (13.79 mg, 19.65 umol) in dioxane (2.5 mL) was degassed and purged with N$_2$ (3×). The mixture was then stirred at 150° C. for 3 hrs under N$_2$ atmosphere in a microwave reactor. The reaction mixture was concentrated and purified by preparative HPLC using Method BK to afford the title compound (18.61 mg, 20%) as a pale yellow solid, TFA salt. $^1$H NMR (400 MHz, DMSO-$d_6$) δ 13.48 (br s, 1H) 10.76 (s, 1H) 8.94-9.14 (m, 2H) 8.41 (d, J=1.10 Hz, 1H) 8.01 (br d, J=7.70 Hz, 1H) 7.91 (br s, 1H) 7.81 (dd, J=9.05, 1.83 Hz, 1H) 7.61 (d, J=8.93 Hz, 1H) 7.33 (br d, J=7.09 Hz, 1H) 2.65 (s, 3H) 2.57 (s, 3H). MS-ESI (m/z) calc'd for $C_{21}H_{17}N_6O[M+H]^+$: 369.1. Found 369.0.

Example 113: 5-Cyano-N-(3-(2-cyanopyridin-4-yl)-1H-indazol-5-yl)-3-methylpicolinamide

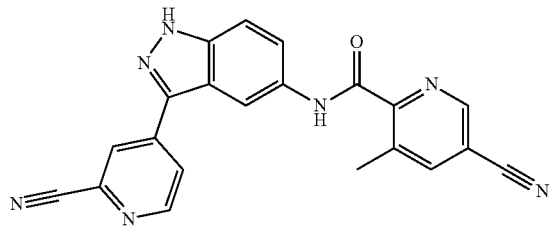 [SMILES: Cc1cc(C#N)cnc1C(=O)Nc1ccc2[nH]nc(-c3ccnc(C#N)c3)c2c1]

Prepared as described for 5-cyano-N-(3-(1,5-dimethyl-1H-pyrazol-4-yl)-1H-indazol-5-yl)-3-methylpicolinamide using (2-cyanopyridin-4-yl)boronic acid in place of (1,5-dimethyl-1H-pyrazol-4-yl)boronic acid to afford the title compound (5.23 mg, 8%) as a yellow solid. $^1$H NMR (400 MHz, DMSO-d$_6$) δ 13.87 (s, 1H) 10.85 (s, 1H) 9.02 (d, J=1.47 Hz, 1H) 8.88 (d, J=5.14 Hz, 1H) 8.66 (s, 1H) 8.49 (s, 1H) 8.43 (d, J=0.98 Hz, 1H) 8.26 (dd, J=5.20, 1.65 Hz, 1H) 7.98 (dd, J=8.99, 1.53 Hz, 1H) 7.70 (d, J=9.05 Hz, 1H) 2.62 (s, 3H). MS-ESI (m/z) calc'd for C$_{21}$H$_{14}$N$_7$O [M+H]$^+$: 380.1. Found 380.0.

Example 114: 5-Cyano-3-methyl-N-(3-(pyridin-2-yl)-1H-indazol-5-yl)picolinamide

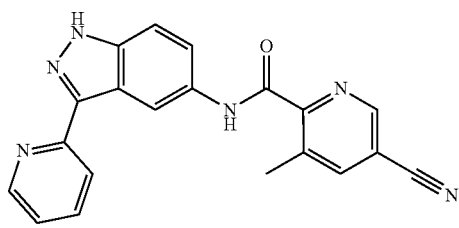 [SMILES: Cc1cc(C#N)cnc1C(=O)Nc1ccc2[nH]nc(-c3ccccn3)c2c1]

Prepared as described for 5-cyano-N-(3-(1,5-dimethyl-1H-pyrazol-4-yl)-1H-indazol-5-yl)-3-methylpicolinamide using pyridin-2-ylboronic acid in place of (1,5-dimethyl-1H-pyrazol-4-yl)boronic acid to afford the title compound (6.76 mg, 10%) as a yellow solid. $^1$H NMR (400 MHz, DMSO-d$_6$) δ 13.46 (br s, 1H), 10.75 (s, 1H), 8.99 (s, 2H), 8.73 (br d, J=4.5 Hz, 1H), 8.40 (s, 1H), 8.19 (d, J=7.9 Hz, 1H), 7.96 (br t, J=7.0 Hz, 1H), 7.79 (dd, J=1.7, 8.9 Hz, 1H), 7.61 (d, J=8.9 Hz, 1H), 7.40 (br t, J=5.7 Hz, 1H), 2.58 (s, 3H). MS-ESI (m/z) calc'd for C$_{20}$H$_{15}$N$_6$O [M+H]$^+$: 355.1. Found 355.0.

Example 115: 5-Cyano-N-(3-(2-((2S,6S)-2,6-dimethylmorpholino)pyridin-4-yl)-1H-indazol-5-yl)-3-methylpicolinamide

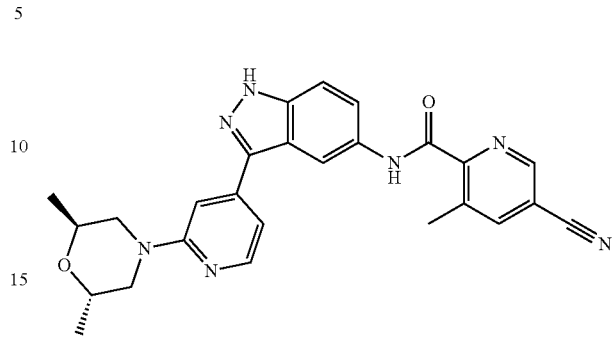

Prepared as described for 5-cyano-N-(7-fluoro-3-(furan-3-yl)-1H-indazol-5-yl)-3-methylpicolinamide using 5-cyano-3-methylpicolinic acid in place of 5-cyano-3-methylpicolinic acid and using 3-(2-((2S,6S)-2,6-dimethylmorpholino)pyridin-4-yl)-1H-indazol-5-amine in place of 7-fluoro-3-(furan-3-yl)-1H-indazol-5-amine to afford the title compound (69.8 mg, 40%) as a white solid. $^1$H NMR (400 MHz, acetone-d$_6$) δ 12.58 (s, 1H), 10.49 (s, 1H), 9.04 (q, J=1.7 Hz, 1H), 8.97-8.86 (m, 1H), 8.31 (dd, J=2.0, 0.9 Hz, 1H), 8.28 (dd, J=5.2, 0.7 Hz, 1H), 7.83 (dd, J=8.8, 1.9 Hz, 1H), 7.70 (d, J=8.9 Hz, 1H), 7.42 (t, J=1.1 Hz, 1H), 7.32 (dd, J=5.2, 1.3 Hz, 1H), 4.15 (qd, J=6.4, 3.4 Hz, 2H), 3.79 (dd, J=12.7, 3.4 Hz, 2H), 3.41 (dd, J=12.6, 6.3 Hz, 2H), 2.85 (s, 3H), 1.30 (d, J=6.4 Hz, 6H). MS-ESI (m/z) calc'd for C$_{26}$H$_{26}$N$_7$O$_2$ [M+H]$^+$: 468.2. Found 468.4.

Example 116: 4-Cyano-N-(3-(furan-3-yl)-1H-indazol-5-yl)thieno[2,3-c]pyridine-7-carboxamide

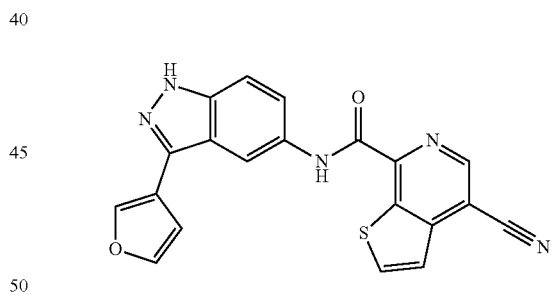

Prepared as described for 5-cyano-N-(7-fluoro-3-(furan-3-yl)-1H-indazol-5-yl)-3-methylpicolinamide using 4-cyanothieno[2,3-c]pyridine-7-carboxylic acid in place of 5-cyano-3-methylpicolinic acid and using 3-(furan-3-yl)-1H-indazol-5-amine in place of 7-fluoro-3-(furan-3-yl)-1H-indazol-5-amine to afford the title compound (4.3 mg, 15%) as a yellow solid. $^1$H NMR (400 MHz, DMSO-d$_6$) δ 13.13 (br. s., 1H) 11.14 (s, 1H) 9.19 (s, 1H) 8.64 (d, J=5.50 Hz, 1H) 8.55 (d, J=1.32 Hz, 1H) 8.34 (dd, J=1.54, 0.88 Hz, 1H) 8.08 (dd, J=9.02, 1.98 Hz, 1H) 7.87 (t, J=1.65 Hz, 1H) 7.80 (d, J=5.50 Hz, 1H) 7.60 (d, J=8.80 Hz, 1H) 7.04 (dd, J=1.76, 0.88 Hz, 1H). MS-ESI (m/z) calc'd for C$_{20}$H$_2$N$_5$O$_2$S [M+H]$^+$: 386.1. Found 386.2.

Example 117: 5-Cyano-N-(3-(2-((3R,5S)-3,5-dimethylpiperidin-1-yl)pyridin-4-yl)-1H-indazol-5-yl)-3-methylpicolinamide

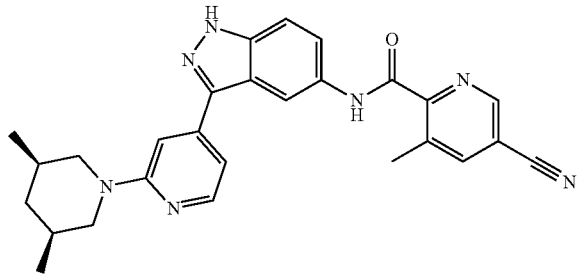 [SMILES: Cc1cc(C#N)cnc1C(=O)Nc1ccc2[nH]nc(-c3ccnc(N4C[C@H](C)C[C@H](C)C4)c3)c2c1]

Prepared as described for 5-cyano-N-(7-fluoro-3-(furan-3-yl)-1H-indazol-5-yl)-3-methylpicolinamide using 5-cyano-3-methylpicolinic acid in place of 5-cyano-3-methylpicolinic acid and using 3-(2-((3R,5S)-3,5-dimethylpiperidin-1-yl)pyridin-4-yl)-1H-indazol-5-amine in place of 7-fluoro-3-(furan-3-yl)-1H-indazol-5-amine to afford the title compound (47.4 mg, 61%) as a white solid. $^1$H NMR (400 MHz, DMSO-$d_6$) δ 13.45 (s, 1H), 10.80 (s, 1H), 9.01 (d, J=2.0 Hz, 1H), 8.82 (d, J=1.8 Hz, 1H), 8.41 (dd, J=2.0, 0.9 Hz, 1H), 8.23 (d, J=5.2 Hz, 1H), 7.74 (dd, J=9.0, 1.8 Hz, 1H), 7.63 (d, J=9.0 Hz, 1H), 7.30 (s, 1H), 7.15 (dd, J=5.2, 1.2 Hz, 1H), 4.39 (d, J=12.7 Hz, 2H), 2.60 (s, 3H), 2.37 (t, J=12.9, 11.3 Hz, 2H), 1.86-1.76 (m, 1H), 1.72-1.58 (m, 2H), 0.95 (d, J=6.5 Hz, 6H), 0.83 (q, J=12.1 Hz, 1H). MS-ESI (m/z) calc'd for $C_{27}H_{28}N_7O$ [M+H]$^+$: 466.2. Found 466.4.

Example 118: 5-Cyano-N-(3-(2-((2S,6R)-2,6-dimethylmorpholino)pyridin-4-yl)-1H-indazol-5-yl)-3-methylpicolinamide

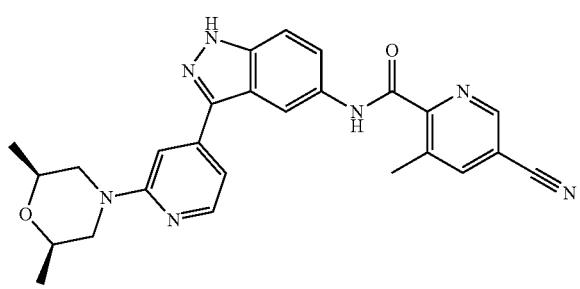 [SMILES: Cc1cc(C#N)cnc1C(=O)Nc1ccc2[nH]nc(-c3ccnc(N4C[C@@H](C)O[C@@H](C)C4)c3)c2c1]

Prepared as described for 5-cyano-N-(7-fluoro-3-(furan-3-yl)-1H-indazol-5-yl)-3-methylpicolinamide using 5-cyano-3-methylpicolinic acid in place of 5-cyano-3-methylpicolinic acid and using 3-(2-((2S,6R)-2,6-dimethylmorpholino)pyridin-4-yl)-1H-indazol-5-amine in place of 7-fluoro-3-(furan-3-yl)-1H-indazol-5-amine to afford the title compound (91.1 mg, 53%) as a yellow solid. $^1$H NMR (400 MHz, acetone-$d_6$) δ 12.58 (s, 1H), 10.49 (s, 1H), 9.02 (d, J=2.1 Hz, 1H), 8.91 (d, J=2.0 Hz, 1H), 8.36-8.24 (m, 2H), 7.84 (dd, J=9.0, 1.9 Hz, 1H), 7.71 (d, J=8.9 Hz, 1H), 7.44 (s, 1H), 7.35 (dd, J=5.1, 1.3 Hz, 1H), 4.41-4.28 (m, 2H), 3.75 (ddd, J=10.5, 6.3, 2.5 Hz, 2H), 2.85 (s, 3H), 2.55 (dd, J=12.7, 10.5 Hz, 2H), 1.27 (d, J=6.2 Hz, 6H). MS-ESI (m/z) calc'd for $C_{26}H_{26}N_7O_2$ [M+H]$^+$: 468.2. Found 468.4.

Example 119: 5-Cyano-N-(3-(3-((2S,6R)-2,6-dimethylmorpholino)phenyl)-1H-indazol-5-yl)-3-methylpicolinamide

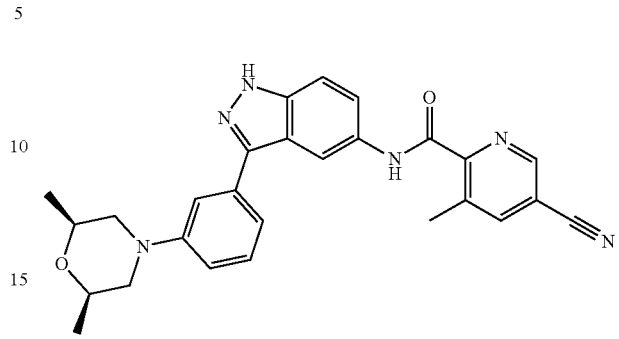

Prepared as described for 5-cyano-N-(7-fluoro-3-(furan-3-yl)-1H-indazol-5-yl)-3-methylpicolinamide using 5-cyano-3-methylpicolinic acid in place of 5-cyano-3-methylpicolinic acid and using 3-(3-((2S,6R)-2,6-dimethylmorpholino)phenyl)-1H-indazol-5-amine in place of 7-fluoro-3-(furan-3-yl)-1H-indazol-5-amine to afford the title compound (135.9 mg, 78%) as a yellow solid. $^1$H NMR (400 MHz, acetone-$d_6$) δ 12.31 (s, 1H), 10.44 (s, 1H), 8.98-8.94 (m, 1H), 8.92-8.88 (m, 1H), 8.30 (dd, J=1.9, 0.8 Hz, 1H), 7.79 (dd, J=8.9, 1.9 Hz, 1H), 7.70-7.62 (m, 2H), 7.53 (dt, J=7.7, 1.2 Hz, 1H), 7.41 (t, J=7.9 Hz, 1H), 7.09-7.01 (m, 1H), 3.82 (dtt, J=12.5, 6.2, 3.1 Hz, 2H), 3.75 (dt, J=10.8, 2.0 Hz, 2H), 2.84 (d, J=0.7 Hz, 3H), 2.46 (dd, J=11.9, 10.3 Hz, 2H), 1.26 (d, J=6.3 Hz, 6H). MS-ESI (m/z) calc'd for $C_{27}H_{27}N_6O_2$ [M+H]$^+$: 467.2. Found 467.4.

Example 120: 3-Cyano-2,6-difluoro-N-(3-(furan-3-yl)-1H-indazol-5-yl)benzamide

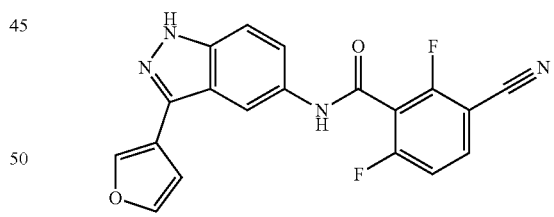

Prepared as described for 5-cyano-N-(7-fluoro-3-(furan-3-yl)-1H-indazol-5-yl)-3-methylpicolinamide using 3-cyano-2,6-difluorobenzoic acid in place of 5-cyano-3-methylpicolinic acid and using 3-(furan-3-yl)-1H-indazol-5-amine in place of 7-fluoro-3-(furan-3-yl)-1H-indazol-5-amine to afford the title compound (29.4 mg, 40%) as a white solid. $^1$H NMR (400 MHz, DMSO-$d_6$) δ 13.16 (br. s., 1H) 10.97 (s, 1H) 8.34 (s, 1H) 8.18-8.28 (m, 2H) 7.85 (t, J=1.65 Hz, 1H) 7.53-7.64 (m, 3H) 6.99 (dd, J=1.87, 0.77 Hz, 1H). MS-ESI (m/z) calc'd for $C_{19}H_{11}F_2N_4O_2$ [M+H]$^+$: 365.1. Found 365.2.

Example 121: N-(3-(5-Chloropyridin-3-yl)-1H-indazol-5-yl)-5-cyano-3-methylpicolinamide

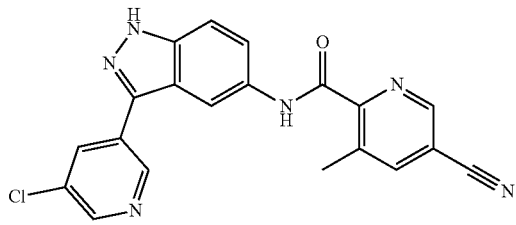 [SMILES: Cc1cc(C#N)cnc1C(=O)Nc1ccc2[nH]nc(-c3cncc(Cl)c3)c2c1]

Prepared as described for 5-cyano-N-(3-(isoxazol-4-yl)-1H-indazol-5-yl)-3-methylpicolinamide using (5-chloropyridin-3-yl)boronic acid in place of isoxazole-4-boronic acid to afford the title compound (2 mg, 3%) as a yellow solid. $^1$H NMR (400 MHz, DMSO-$d_6$) δ 13.64 (br. s., 1H) 10.83 (s, 1H) 9.14 (s, 1H) 9.02 (s, 1H) 8.59-8.75 (m, 2H) 8.40 (d, J=18.27 Hz, 2H) 7.94 (d, J=8.80 Hz, 1H) 7.67 (d, J=9.02 Hz, 1H) 2.61 (s, 3H). MS-ESI (m/z) calc'd for $C_{20}H_{14}ClN_6O$ [M+H]$^+$: 389.1/391.1. Found 389.1/391.1.

Example 122: 5-Cyano-2-fluoro-N-(3-(furan-3-yl)-1H-indazol-5-yl)benzamide

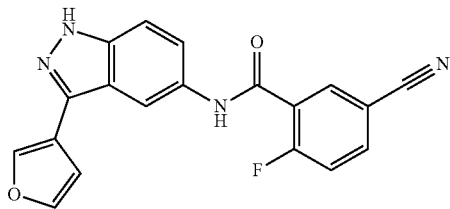 [SMILES: N#Cc1ccc(F)c(C(=O)Nc2ccc3[nH]nc(-c4ccoc4)c3c2)c1]

To a solution of 5-cyano-2-fluorobenzoic acid (100 mg, 605.62 umol) and 3-(furan-3-yl)-1H-indazol-5-amine (120.64 mg, 605.62 umol) in pyridine (3 mL) was added EDCI (197.37 mg, 1.03 mmol) and the reaction mixture was stirred at 40° C. for 2 hrs. The reaction mixture was concentrated to give a residue which was purified by preparative HPLC using Method BQ to afford the title compound (38.70 mg, 18%) as an off-white solid. $^1$H NMR (400 MHz, DMSO-$d_6$) δ 13.13 (s, 1H), 10.62 (s, 1H), 8.37 (s, 1H), 8.28 (dd, J=2.2, 6.4 Hz, 1H), 8.21 (s, 1H), 8.12 (ddd, J=2.1, 4.7, 8.6 Hz, 1H), 7.85 (t, J=1.7 Hz, 1H), 7.67-7.63 (m, 1H), 7.63-7.61 (m, 1H), 7.59-7.55 (m, 1H), 6.99-6.95 (m, 1H). MS-ESI (m/z) calc'd for $C_{19}H_{12}FN_4O_2$[M+H]$^+$: 347.1. Found 347.1.

Example 123: 5-Cyano-N-(3-(1,5-dimethyl-1H-pyrazol-4-yl)-1H-indazol-5-yl)-3-methylpicolinamide

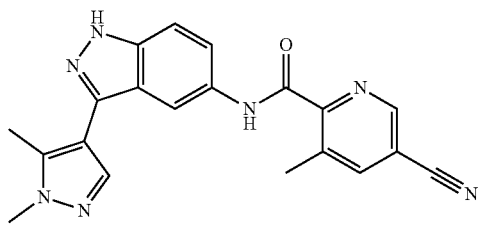 [SMILES: Cc1cc(C#N)cnc1C(=O)Nc1ccc2[nH]nc(-c3cnn(C)c3C)c2c1]

A mixture of N-(3-bromo-1H-indazol-5-yl)-5-cyano-3-methylpicolinamide (70 mg, 196.53 umol), (1,5-dimethyl-1H-pyrazol-4-yl)boronic acid (33.01 mg, 235.84 umol), Pd(Amphos)Cl$_2$ (13.92 mg, 19.65 umol) and AcOK (57.86 mg, 589.60 umol) in EtOH (2 mL) and H$_2$O (0.5 mL) was degassed and purged with N$_2$ (3×). The mixture was then stirred at 100° C. for 12 hrs under an N$_2$ atmosphere. The reaction mixture was then concentrated and purified by preparative HPLC using Method BJ to afford the title compound (18.45 mg, 18%) as a yellow solid, TFA salt. $^1$H NMR (400 MHz, DMSO-$d_6$) δ 12.96 (br s, 1H), 10.70 (s, 1H), 8.99 (d, J=1.5 Hz, 1H), 8.41 (dd, J=1.2, 6.9 Hz, 2H), 7.80 (s, 1H), 7.77 (dd, J=1.9, 8.9 Hz, 1H), 7.53 (d, J=9.0 Hz, 1H), 3.84 (s, 3H), 2.59 (s, 3H), 2.53 (s, 3H). MS-ESI (m/z) calc'd for $C_{20}H_{18}N_7O$ [M+H]$^+$: 372.2. Found 372.1.

Example 124: 4-Cyano-N-(3-(furan-3-yl)-1H-indazol-5-yl)-1-methyl-1H-imidazole-2-carboxamide

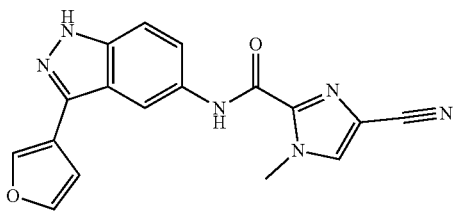 [SMILES: Cn1cc(C#N)nc1C(=O)Nc1ccc2[nH]nc(-c3ccoc3)c2c1]

Step 1: Methyl 4-cyano-1-methyl-1H-imidazole-2-carboxylate

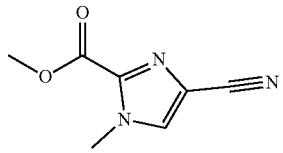

A mixture of methyl 4-bromo-1-methyl-1H-imidazole-2-carboxylate (300 mg, 1.37 mmol), Zn(CN)$_2$ (160.83 mg, 1.37 mmol), Zn (10.75 mg, 164.36 umol), DPPF (30.37 mg, 54.79 umol) and Pd$_2$(dba)$_3$ (250.84 mg, 273.93 umol) in DMA (5 mL) was degassed and purged with N$_2$ (3×), and then the mixture was stirred at 120° C. for 4 hrs under an N$_2$ atmosphere. The reaction mixture was concentrated and purified by flash silica gel chromatography using a 0-30% EtOAc/petroleum ether gradient eluent to afford the title compound (78 mg, 34%) as a yellow oil.

Step 2: 4-Cyano-N-(3-(furan-3-yl)-1H-indazol-5-yl)-1-methyl-1H-imidazole-2-carboxamide

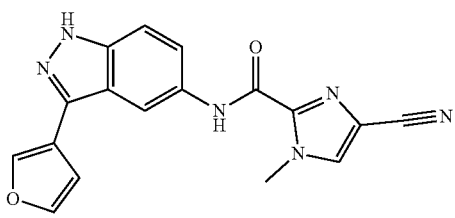

To a solution of methyl 4-cyano-1-methyl-1H-imidazole-2-carboxylate (40 mg, 242.21 umol) and 3-(furan-3-yl)-1H-indazol-5-amine (48.25 mg, 242.21 umol) in toluene (2 mL) was added Al(CH$_3$)$_3$ (2 M in toluene, 363.31 uL) and the mixture was stirred at 90° C. for 24 hrs. The reaction mixture was concentrated and purified by preparative HPLC using Method CB to afford the title compound (10.45 mg, 100%) as a brown solid, TFA salt. $^1$H NMR (400 MHz, DMSO-dt) δ 13.50-12.76 (m, 1H), 10.64 (s, 1H), 8.40 (br d, J=15.0 Hz, 2H), 8.25 (s, 1H), 7.90-7.82 (m, 2H), 7.54 (d, J=8.9 Hz, 1H), 7.00 (s, 1H), 4.05 (s, 3H). MS-ESI (m/z) calc'd for C$_{17}$H$_{13}$N$_6$O$_2$ [M+H]$^+$: 333.1. Found 333.0.

Example 125: 5-Cyano-N-(3-(furan-3-yl)-1H-indazol-5-yl)-2-hydroxybenzamide

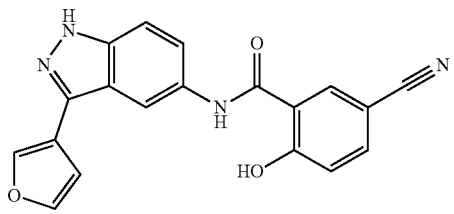 [SMILES: N#Cc1ccc(O)c(C(=O)Nc2ccc3[nH]nc(-c4ccoc4)c3c2)c1]

Step 1: 5-Cyano-2-hydroxybenzoic acid

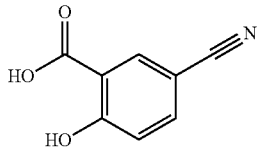 [SMILES: N#Cc1ccc(O)c(C(=O)O)c1]

To a solution of methyl 5-cyano-2-hydroxybenzoate (200 mg, 861.95 umol) in THF (1 mL) and MeOH (1 mL) and H$_2$O (0.5 mL) was added LiOH.H$_2$O (142.12 mg, 3.39 mmol) and the mixture was stirred at 20° C. for 20 hrs. The reaction was adjusted to pH=4 with 1 N HCl. The mixture was filtered and the filtrate was concentrated to afford the title compound (140 mg) as a white solid which was used without further purification. MS-ESI (m/z) calcd for C$_8$H$_4$NO$_3$ [M−H]$^−$: 162.0. Found 161.9.

Step 2: 5-Cyano-N-(3-(furan-3-v)-1H-indazol-5-yl)-2-hydroxybenzamide

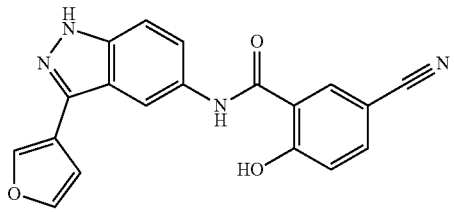 [SMILES: N#Cc1ccc(O)c(C(=O)Nc2ccc3[nH]nc(-c4ccoc4)c3c2)c1]

To a solution of 5-cyano-2-hydroxybenzoic acid (70 mg, 429.11 umol) in DMF (2 mL) was added 3-(furan-3-yl)-1H-indazol-5-amine (85.48 mg, 429.11 umol), EDCI (98.71 mg, 514.93 umol), HOBt (69.58 mg, 514.93 umol), and DIEA (83.19 mg, 643.66 umol). The mixture was stirred at 20° C. for 12 hrs and concentrated. The residue was purified by preparative HPLC using Method BN to afford the title compound (19.78 mg, 13%) as an off-white solid, TFA salt. $^1$H NMR (400 MHz, DMSO-d$_6$) δ 13.14 (s, 1H) 12.72 (br s, 1H) 10.56 (s, 1H) 8.42 (d, J=2.08 Hz, 1H) 8.30 (d, J=9.29 Hz, 2H) 7.83-7.91 (m, 2H) 7.64-7.67 (m, 1H) 7.56-7.60 (d, 1H) 7.15 (d, J=8.56 Hz, 1H) 7.01 (d, J=1.10 Hz, 1H). MS-ESI (m/z) calc'd for C$_{19}$H$_{13}$N$_4$O$_3$ [M+H]$^+$: 345.1. Found 345.0.

Example 126: N-(3-(1H-Imidazol-1-yl)-1H-indazol-5-yl)-5-cyano-3-methylpicolinamide

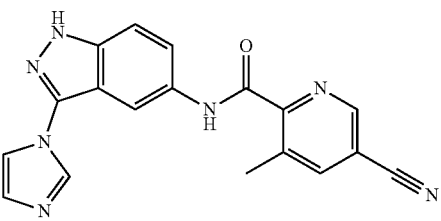 [SMILES: Cc1cc(C#N)cnc1C(=O)Nc1ccc2[nH]nc(-n3ccnc3)c2c1]

Step 1: 2,5-Dinitro-2H-indazole

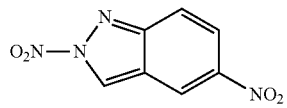 [SMILES: O=[N+]([O-])c1ccc2nn([N+](=O)[O-])cc2c1]

To a solution of 5-nitro-1H-indazole (1 g, 6.13 mmol) in AcOH (9 mL) was added HNO$_3$ (2.42 g, 37.58 mmol, 98% purity) and Ac$_2$O (4.38 g, 42.91 mmol) at −5° C. for 2 min. The mixture was then poured onto ice and stirred at 0° C. for 30 min. The mixture was filtered and the solid was dried under vacuum to afford the title compound (1.28 g) as an orange solid which was used without further purification.

Step 2: 3-(1H-Imidazol-1-yl)-5-nitro-1H-indazole

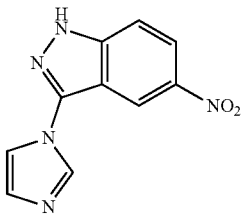 [SMILES: O=[N+]([O-])c1ccc2[nH]nc(-n3ccnc3)c2c1]

To a solution of 2,5-dinitro-2H-indazole (1.2 g, 4.80 mmol) in THF (27 mL) and H$_2$O (36 mL) was added 1H-imidazole (654.18 mg, 9.61 mmol). The mixture was stirred at 20° C. for 12 hrs. The reaction mixture was extracted with EtOAc (30 mL 10). The combined organic layers were dried over Na$_2$SO$_4$, filtered and concentrated under reduced pressure to afford the title compound (1 g) as a yellow solid which was used without further purification. MS-(ESI) (m/z) calcd for $C_{10}H_8N_5O_2$ (M+H)$^+$: 230.1. Found 230.0.

Step 3: 3-(1H-Imidazol-1-yl)-1H-indazol-5-amine

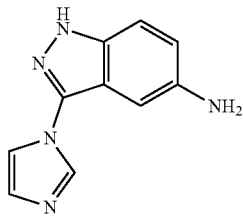 [SMILES: Nc1ccc2[nH]nc(-n3ccnc3)c2c1]

To a solution of 3-(1H-imidazol-1-yl)-5-nitro-1H-indazole (300 mg, 1.31 mmol) in EtOH (5 mL) and H$_2$O (5 mL) was added Fe (365.49 mg, 6.54 mmol) and NH$_4$Cl (350.08 mg, 6.54 mmol) and the mixture was stirred at 80° C. for 1 hr. The reaction mixture was filtered and the filtrate was concentrated under reduced pressure. Then the reaction mixture was diluted with H$_2$O (15 mL) and extracted with EtOAc (30 mL×4). The combined organic layers were washed with saturated aqueous NaHCO$_3$ (30 mL×3), dried over Na$_2$SO$_4$, filtered and concentrated under reduced pressure to afford the title compound (120 mg, 46%) as a yellow solid which was used without further purification. MS-(ESI) (m/z) calcd for $C_{10}H_{10}N_5$ (M+H)$^+$: 200.1. Found 200.1.

Step 4: N-(3-(1H-Imidazol-1-yl)-1H-indazol-5-yl)-5-cyano-3-methylpicolinamide

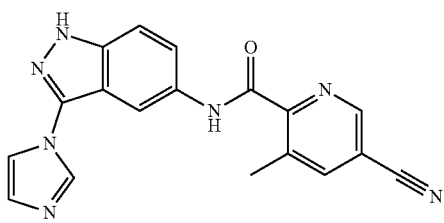 [SMILES: Cc1cc(C#N)cnc1C(=O)Nc1ccc2[nH]nc(-n3ccnc3)c2c1]

To a solution of 3-(1H-imidazol-1-yl)-1H-indazol-5-amine (100 mg, 501.98 umol) in pyridine (3 mL) was added EDCI (192.46 mg, 1.00 mmol) and 5-cyano-3-methylpicolinic acid (122.09 mg, 752.97 umol) and the mixture was stirred at 20° C. for 3 hrs. The reaction mixture was then concentrated and purified by preparative HPLC using Method BS to afford the title compound (45.59 mg, 26%) as a yellow solid. $^1$H NMR (400 MHz, DMSO-d$_6$) δ 13.15 (br s, 1H) 10.82 (s, 1H) 9.00 (d, J=1.34 Hz, 1H) 8.39-8.44 (m, 2H) 8.25 (s, 1H) 7.84 (dd, J=9.05, 1.83 Hz, 1H) 7.76 (t, J=1.16 Hz, 1H) 7.62 (d, J=8.93 Hz, 1H) 7.22 (s, 1H) 2.58 (s, 3H). MS-ESI (m/z) calc'd for $C_{18}H_{14}N_7O$ [M+H]$^+$: 344.1. Found 344.2.

Example 127: 6-Cyano-N-(3-(furan-3-yl)-1H-indazol-5-yl)picolinamide

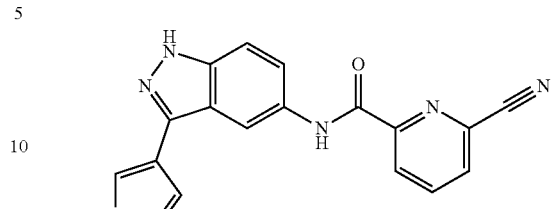

Step 1: 6-Bromo-N-(3-(furan-3-yl)-1H-indazol-5-yl)picolinamide

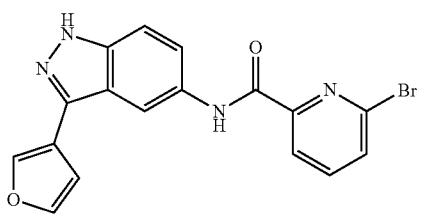 [SMILES: O=C(Nc1ccc2[nH]nc(-c3ccoc3)c2c1)c1cccc(Br)n1]

To a solution of 6-bromopicolinic acid (500 mg, 2.48 mmol) and 3-(furan-3-yl)-1H-indazol-5-amine (493.08 mg, 2.48 mmol) in pyridine (2 mL) was added EDCI (711.75 mg, 3.71 mmol) and the reaction mixture was stirred at 25° C. for 12 hrs. The reaction mixture was concentrated and the residue obtained was purified by silica gel column chromatography using a 5-100% EtOAc/petroleum ether gradient eluent to afford the title compound (800 mg, 84%) as a yellow solid. MS-(ESI) (m/z) calcd for $C_{17}H_{12}BrN_4O_2$ (M+H)$^+$: 383.0/385.0. Found 383.0/385.0.

Step 2: 6-Cyano-N-(3-(furan-3-yl)-1H-indazol-5-yl)picolinamide

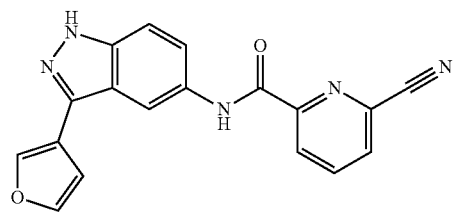 [SMILES: N#Cc1cccc(C(=O)Nc2ccc3[nH]nc(-c4ccoc4)c3c2)n1]

A mixture of 6-bromo-N-(3-(furan-3-yl)-1H-indazol-5-yl)picolinamide (300 mg, 782.88 umol), Zn(CN)$_2$ (45.97 mg, 391.44 umol) and Pd(PPh$_3$)$_4$ (90.47 mg, 78.29 umol) was placed in a microwave reactor tube in DMF (5 mL) under N$_2$. The sealed tube was heated at 150° C. for 1 hr in a microwave reactor. The reaction mixture was concentrated to give a residue which was poured into water (15 mL). The aqueous phase was extracted with EtOAc (15 mL×3). The combined organic phases were washed with brine (15 mL×1), dried over anhydrous Na$_2$SO$_4$, filtered and concentrated under reduced pressure. The residue was purified by preparative HPLC using Method BP to afford the title compound (109.5 mg, 31%) as a pale yellow solid, TFA salt. ¹H NMR (400 MHz, DMSO-$d_6$) δ 13.11 (br s, 1H), 10.68 (s, 1H), 8.47-8.42 (m, 2H), 8.37-8.32 (m, 1H), 8.31 (dd, J=1.7, 2.4 Hz, 2H), 7.95 (dd, J=1.8, 9.0 Hz, 1H), 7.85 (t, J=1.6 Hz, 1H), 7.57 (d, J=8.9 Hz, 1H), 7.02 (d, J=1.2 Hz, 1H). MS-ESI (m/z) calc'd for $C_{18}H_{12}N_5O_2$ [M+H]⁺: 330.1. Found 330.1.

Example 128: 3-Cyano-2-fluoro-N-(3-(furan-3-yl)-1H-indazol-5-yl)-6-methylbenzamide

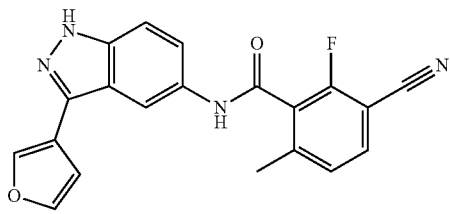 [SMILES: Cc1ccc(C#N)c(F)c1C(=O)Nc1ccc2[nH]nc(-c3ccoc3)c2c1]

Step 1: 3-Bromo-2-fluoro-6-methylbenzoic acid

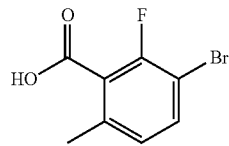

To a solution of 1-bromo-2-fluoro-4-methylbenzene (5 g, 26.45 mmol) in THF (50 mL) was added LDA (2 M, 15.87 mL) dropwise at −70° C. The mixture was stirred at −70° C. for 1 hr, and then dry ice (CO₂ solid, more than 10 eq) was added to the mixture. Stirring was continued at −70° C. for 1 hr. The mixture was diluted with H₂O (10 mL) and extracted with EtOAc (10 mL×2). The organic phase was discarded. The reaction was acidified with 1N HCl to adjust to pH=1. The reaction was filtered, the filtrate was collected and dried to afford the title compound (2.3 g, 37%) as a white solid.

Step 2: 3-Bromo-2-fluoro-N-(3-(furan-3-yl)-1H-indazol-5-yl)-6-methylbenzamide

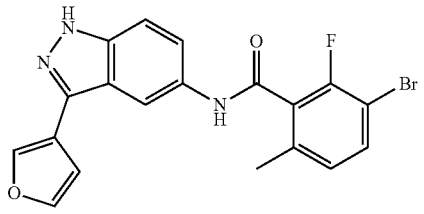 [SMILES: Cc1ccc(Br)c(F)c1C(=O)Nc1ccc2[nH]nc(-c3ccoc3)c2c1]

To a solution of 3-bromo-2-fluoro-6-methylbenzoic acid (200 mg, 858.24 umol) in pyridine (2 mL) was added EDCI (246.79 mg, 1.29 mmol) and 3-(furan-3-yl)-1H-indazol-5-amine (170.97 mg, 858.24 umol) and the mixture was stirred at 30° C. for 12 hrs. The reaction mixture was then concentrated under reduced pressure to remove solvent. The residue obtained was diluted with H₂O (20 mL), filtered and the solid was collected and dried to afford the title compound (300 mg) as a black solid which was used without further purification. MS-ESI (m/z) calcd for $C_{19}H_{14}BrFN_3O_2$ [M+H]⁺: 414.0/416.0. Found 414.0/416.0.

Step 3: 3-(Cyano-2-fluoro-N-(3-(furan-3-yl)-1H-indazol-5-yl)-6-methylbenzamide

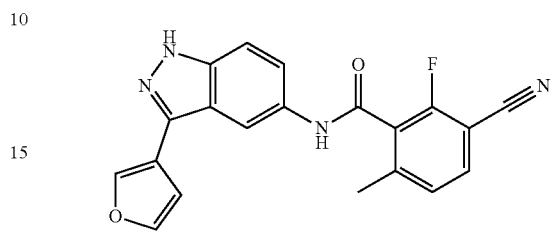

A mixture of 3-bromo-2-fluoro-N-(3-(furan-3-yl)-1H-indazol-5-yl)-6-methylbenzamide (100 mg, 241.41 umol), Zn(CN)₂ (56.70 mg, 482.83 umol), Zn (1.42 mg, 21.73 umol), dppf (4.02 mg, 7.24 umol), Pd₂(dba)₃ (13.26 mg, 14.48 umol) in DMF (1 mL) was degassed and purged with N₂ (3×). The mixture was stirred at 120° C. for 5 hrs under a N₂ atmosphere in a microwave reactor. The reaction mixture was concentrated and purified by preparative HPLC using Method BO to afford the title compound (7.15 mg, 6%) as a white solid, TFA salt. ¹H NMR (400 MHz, DMSO-$d_6$) δ 13.12 (s, 1H) 10.54 (s, 1H) 8.35 (s, 1H) 8.22 (s, 1H) 7.96 (t, J=7.76 Hz, 1H) 7.85 (s, 1H) 7.54-7.66 (m, 2H) 7.47 (d, J=8.07 Hz, 1H) 6.99 (s, 1H) 2.59 (s, 3H). MS-ESI (m/z) calc'd for $C_{20}H_{14}FN_4O_2$[M+H]⁺: 361.1. Found 361.0.

Example 129: 5-Cyano-3-methyl-N-(3-(2-methyl-oxazol-5-yl)-1H-indazol-5-yl)picolinamide

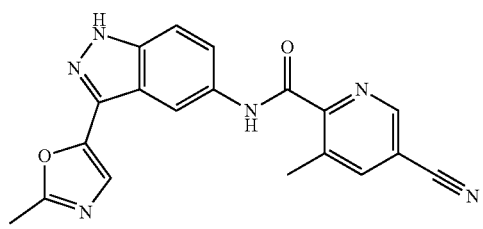

Prepared as described for 5-cyano-N-(3-(isoxazol-4-yl)-1H-indazol-5-yl)-3-methylpicolinamide using (2-methyl-oxazol-5-yl)boronic acid in place of isoxazole-4-boronic acid to afford the title compound (10.3 mg, 12%) as a yellow solid. ¹H NMR (400 MHz, DMSO-$d_6$) δ 13.47 (s, 1H), 10.78 (s, 1H), 9.01 (d, J=1.9 Hz, 1H), 8.48 (d, J=1.9 Hz, 1H), 8.42 (d, J=2.0 Hz, 1H), 7.86 (dd, J=9.0, 1.9 Hz, 1H), 7.61 (d, J=9.0 Hz, 1H), 7.49 (s, 1H), 2.60 (s, 3H), 2.56 (s, 3H). MS-ESI (m/z) calc'd for $C_{19}H_5N_6O_2$ [M+H]⁺: 359.1. Found 359.2.

Example 130: 5-Cyano-N-(3-(4-cyanothiophen-2-yl)-1H-indazol-5-yl)-3-methylpicolinamide

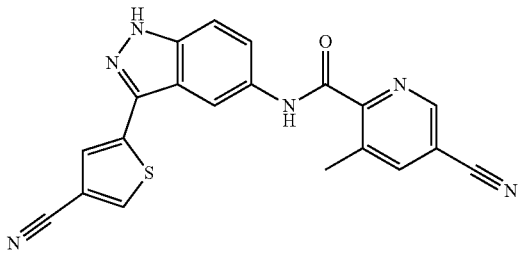 [SMILES: Cc1cc(C#N)cnc1C(=O)Nc1ccc2[nH]nc(-c3cc(C#N)cs3)c2c1]

Prepared as described for 5-cyano-N-(3-(5-cyanothiophen-2-yl)-1H-indazol-5-yl)-3-methylpicolinamide using (4-cyanothiophen-2-yl)boronic acid in place of (5-cyanothiophen-2-yl)boronic acid to afford the title compound (6.13 mg, 9%) as a yellow solid. $^1$H NMR (400 MHz, DMSO-d$_6$) δ 13.48 (s, 1H) 10.81 (s, 1H) 9.02 (s, 1H) 8.61 (s, 2H) 8.44 (s, 1H) 7.91-7.98 (m, 2H) 7.64 (d, J=9 Hz, 1H) 2.63 (s, 3H). MS-ESI (m/z) calc'd for C$_{19}$H$_{13}$N$_6$OS [M+H]$^+$: 385.1. Found 385.0.

Example 131: 5-Cyano-N-(3-(5-cyanothiophen-2-yl)-1H-indazol-5-yl)-3-methylpicolinamide

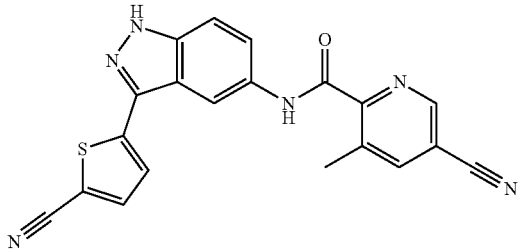 [SMILES: Cc1cc(C#N)cnc1C(=O)Nc1ccc2[nH]nc(-c3ccc(C#N)s3)c2c1]

To a solution of N-(3-bromo-1H-indazol-5-yl)-5-cyano-3-methylpicolinamide (50 mg, 140.38 umol) and (5-cyanothiophen-2-yl)boronic acid (25.77 mg, 168.46 umol) in THF (3 mL) was added XPhos-Pd-G2 (11.05 mg, 14.04 umol) and an aqueous solution of K$_3$PO$_4$ (0.4 M, 701.90 uL) and the mixture was stirred at 80° C. for 15 hrs under an N$_2$ atmosphere. The reaction mixture was concentrated and purified by preparative HPLC using Method V twice to afford the title compound (3.38 mg, 5%) as a yellow solid, TFA salt. $^1$H NMR (400 MHz, DMSO-d$_6$) δ 13.64 (s, 1H) 10.86 (s, 1H) 9.02 (s, 1H) 8.70 (s, 1H) 8.44 (s, 1H) 8.11 (d, J=4 Hz, 1H) 7.88 (br d, J=9 Hz, 1H) 7.74 (d, J=4 Hz, 1H) 7.67 (d, J=9 Hz, 1H) 2.62 (s, 3H). MS-ESI (m/z) calc'd for C$_{20}$H$_{13}$N$_6$O S [M+H]$^+$: 385.1.1 Found 384.9.

Example 132: 4-Cyano-N-(3-(furan-3-yl)-1H-indazol-5-yl)pyrimidine-2-carboxamide

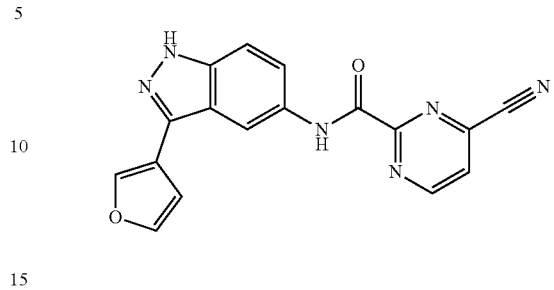

Step 1: 2-Vinylpyrimidine-4-carbonitrile

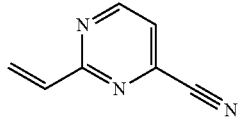

A mixture of 2-chloro-4-pyridinecarbonitrile (183.0 mg, 1.31 mmol), tributyl(ethenyl)stannane (0.42 mL, 1.44 mmol), and tetrakis(triphenylphosphine)palladium(0) (106.08 mg, 0.090 mmol) in toluene (6.6 mL) was refluxed under an atmosphere of N$_2$ for 2 hrs and then cooled to r.t. The organic phase was separated, dried over Na$_2$SO$_4$, filtered and concentrated to give a residue. The residue was purified by NH-silica gel column chromatography using a 0-30% EtOAc/cyclohexane gradient eluent to afford the title compound (247 mg, 100%). MS-ESI (m/z) calc'd for C$_7$H$_6$N$_3$ [M+H]$^+$: 132.1. Found 132.1.

Step 2: 4-Cyanopyrimidine-2-carboxylic acid

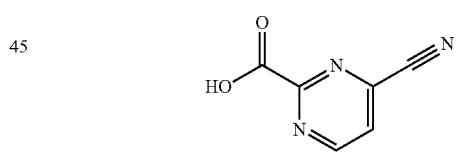

To a solution of 2-ethenylpyrimidine-4-carbonitrile (247.0 mg, 1.47 mmol) in acetone (8.606 mL) and H$_2$O (8.606 mL) was added KMnO$_4$ (348.27 mg, 2.2 mmol). The mixture was stirred at r.t. for 1 hr. and another portion of KMnO$_4$ (348.27 mg, 2.2 mmol) was added and stirring was continued for 6 hrs. A saturated aqueous solution of NaHCO$_3$ was added and then the solution was extracted with EtOAc. The aqueous phase was acidified with 2 M HCl to lower the pH to 3 and extracted with EtOAc (2×). The organic phases were collected and concentrated under reduced pressure to afford the title compound (40 mg, 18%) as a white solid. NMR (400 MHz, MeOH-d$_4$) δ 9.00 (d, J=4.9 Hz, 1H), 7.72 (d, J=4.9 Hz, 1H), 6.90 (dd, J=17.3, 10.5 Hz, 1H), 6.79-6.66 (m, 1H), 5.89 (dd, J=10.5, 1.7 Hz, 1H). MS-ESI (m/z) calc'd for C$_6$H$_2$N$_3$O$_2$ [M–H]$^+$: 148.0. Found 148.0.

Step 3: 4-Cyano-N-(3-(furan-3-yl)-1H-indazol-5-yl)pyrimidine-2-carboxamide

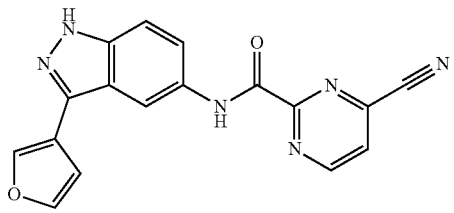 [SMILES: N#Cc1ccnc(C(=O)Nc2ccc3[nH]nc(-c4ccoc4)c3c2)n1]

Prepared as described for 5-cyano-N-(7-fluoro-3-(furan-3-yl)-1H-indazol-5-yl)-3-methylpicolinamide using 4-cyanopyrimidine-2-carboxylic acid in place of 5-cyano-3-methylpicolinic acid and using 3-(furan-3-yl)-1H-indazol-5-amine in place of 7-fluoro-3-(furan-3-yl)-1H-indazol-5-amine to afford the title compound (1.4 mg, 2%) as a yellow solid. $^1$H NMR (400 MHz, DMSO-$d_6$) δ 13.13 (s, 1H), 10.89 (s, 1H), 9.38 (d, J=4.9 Hz, 1H), 8.46 (d, J=1.9 Hz, 1H), 8.38 (d, J=4.9 Hz, 1H), 8.32-8.25 (m, 1H), 7.93 (dd, J=8.9, 1.9 Hz, 1H), 7.85 (t, J=1.7 Hz, 1H), 7.58 (d, J=9.0 Hz, 1H), 7.02 (d, J=1.8 Hz, 1H). MS-ESI (m/z) calc'd for $C_7H_{11}N_6O_2$ [M+H]$^+$: 331.1. Found 331.2.

Example 133: 5-Cyano-N-(3-(furan-3-yl)-1H-indazol-5-yl)-4-methyl-1H-pyrazole-3-carboxamide

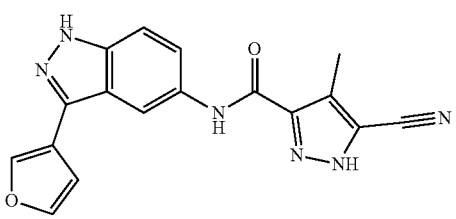 [SMILES: Cc1c(C(=O)Nc2ccc3[nH]nc(-c4ccoc4)c3c2)n[nH]c1C#N]

Step 1: Ethyl 5-cyano-4-methyl-1H-pyrazole-3-carboxylate

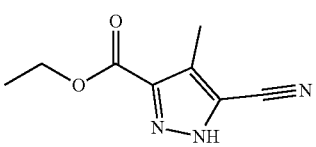

To a solution of ethyl but-2-ynoate (5 g, 44.59 mmol) and 2-aminoacetonitrile (7.43 g, 80.27 mmol, HCl salt) in CHCl$_3$ (120 mL) and H$_2$O (4 mL) was added NaNO$_2$ (9.23 g, 133.78 mmol) and the mixture was stirred at 60° C. for 12 hrs. The reaction mixture was then diluted with H$_2$O (100 mL) and extracted with EtOAc (30 mL×3). The combined organic layers were washed with brine (30 mL×2), dried over Na$_2$SO$_4$, filtered and concentrated to give a residue. The residue was purified by silica gel column chromatography using a 0-10% EtOAc/petroleum ether gradient eluent to afford the title compound (0.2 g, 3%) as a yellow oil. MS-(ESI) (m/z) calcd for $C_8H_{10}N_3O_2$ (M+H)$^+$: 180.1. Found 180.0.

Step 2: 5-Cyano-N-(3-(fura-3-yl)-1H-indazol-5-yl)-4-methyl-1H-pyrazole-3-carboxamide


To a solution of ethyl 5-cyano-4-methyl-1H-pyrazole-3-carboxylate (80 mg, 446.49 umol) and 3-(furan-3-yl)-1H-indazol-5-amine (106.73 mg, 535.79 umol) in toluene (3 mL) was added AlMe$_3$ (2 M in toluene, 892.98 uL) and the mixture was stirred at 90° C. for 12 hrs. The reaction mixture was then quenched with MeOH (10 mL). A solid formed and the mixture was filtered. The filtrate was concentrated and purified by preparative HPLC using Method BT to afford the title compound (20.71 mg, 10%) as a gray solid, TFA salt. $^1$H NMR (400 MHz, DMSO-$d_6$) δ 14.27 (br s, 1H) 12.89 (br s, 1H) 9.99 (s, 1H) 8.30 (br s, 1H) 8.19 (s, 1H) 7.80 (t, J=2 Hz, 1H) 7.69 (br s, 1H) 7.56 (br d, J=8 Hz, 1H) 7.00 (d, J=1 Hz, 1H) 2.42 (s, 3H). MS-ESI (m/z) calc'd for $C_{17}H_{13}N_6O_2$ [M+H]$^+$: 333.1. Found 333.0.

Example 134: 3-Cyano-6-fluoro-N-(3-(furan-3-yl)-1H-indazol-5-yl)-2-methylbenzamide

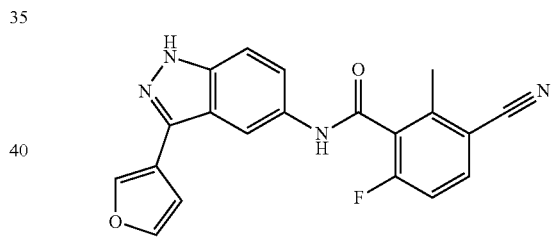

Step 1: 3-Bromo-6-fluoro-2-methylbenzoic acid

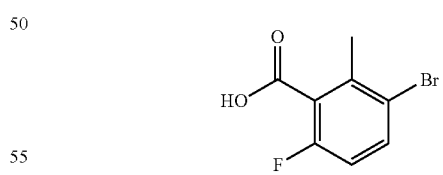

To a solution of 2-fluoro-6-methylbenzoic acid (700 mg, 4.54 mmol) in H$_2$SO$_4$ (20 mL) (purity: 98%) was added NBS (848.71 mg, 4.77 mmol) at 0° C. and the mixture was stirred at 0° C. for 3 hrs. The reaction mixture was then poured into ice water (100 mL), and extracted with EtOAc (2×100 mL). The organic layers were combined, dried over Na$_2$SO$_4$, and concentrated under vacuum to afford the title compound (1.2 g) as a gray solid which was used without further purification. $^1$H NMR (400 MHz, CDCl$_3$) δ 10.89 (s, 1H), 7.63-7.60 (m, 1H), 6.90 (t, J=8.8 Hz, 1H), 2.51 (s, 3H).

Step 2: 3-Bromo-6-fluoro-N-(3-(furan-3-yl)-1H-indazol-5-yl)-2-methylbenzamide

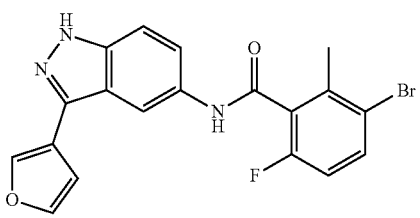 [SMILES: Cc1c(Br)ccc(F)c1C(=O)Nc1ccc2[nH]nc(-c3ccoc3)c2c1]

To a solution of 3-bromo-6-fluoro-2-methylbenzoic acid (300 mg, 1.29 mmol) and 3-(furan-3-yl)-1H-indazol-5-amine (256.45 mg, 1.29 mmol) in pyridine (8 mL) was added EDCI (493.58 mg, 2.57 mmol) and the mixture was stirred at 25° C. for 12 hrs. The reaction mixture was concentrated and purified by flash silica gel chromatography (ISCO; 20 g SepaFlash column) using a 0-30% EtOAc/petroleum ether gradient eluent to afford the title compound (90 mg, 17%) as a redish brown solid. MS-(ESI) (m/z) calcd for $C_{19}H_{14}BrFN_3O_2$ (M+H)~: 414.0/416.0. Found 414.0/416.0.

Step 3: 3-(Cyano-6-fluoro-N-(3-(furan-3-yl)-1H-indazol-5-yl)-2-methylbenzamide

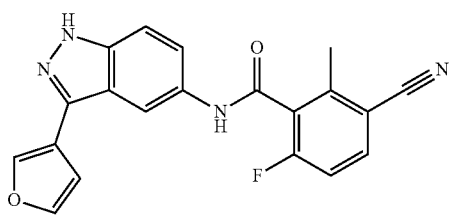 [SMILES: Cc1c(C#N)ccc(F)c1C(=O)Nc1ccc2[nH]nc(-c3ccoc3)c2c1]

A mixture of 3-bromo-6-fluoro-N-(3-(furan-3-yl)-1H-indazol-5-yl)-2-methylbenzamide (90 mg, 217.27 umol), $Zn(CN)_2$ (51.03 mg, 434.54 umol), Zn (1.28 mg, 19.55 umol), $Pd_2(dba)_3$ (11.94 mg, 13.04 umol) and DPPF (3.61 mg, 6.52 umol) in DMF (1 mL) in a sealed microwave tube was heated at 120° C. for 5 hrs under microwave irradiation. The reaction mixture was concentrated and purified by preparative HPLC using Method V to afford the title compound (33.02 mg, 32%) as a white solid, TFA salt. $^1$H NMR (400 MHz, DMSO-$d_6$) δ 13.14 (br s, 1H), 10.79 (s, 1H), 8.37 (s, 1H), 8.22 (d, J=0.9 Hz, 1H), 8.03 (dd, J=5.5, 8.8 Hz, 1H), 7.85 (t, J=1.5 Hz, 1H), 7.62-7.54 (m, 2H), 7.47 (t, J=8.7 Hz, 1H), 7.01-6.96 (m, 1H), 2.54 (s, 3H). MS-ESI (m/z) calc'd for $C_{20}H_{14}FN_4O_2[M+H]^+$: 361.1. Found 361.1.

Example 135: N-(3-Benzamido-1H-indazol-5-yl)-5-cyano-3-methylpicolinamide

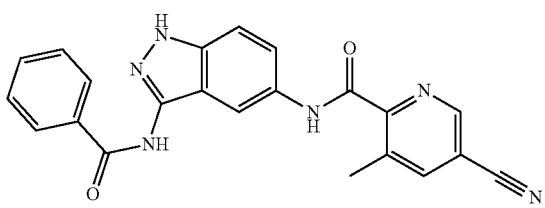 [SMILES: Cc1cc(C#N)cnc1C(=O)Nc1ccc2[nH]nc(NC(=O)c3ccccc3)c2c1]

Step 1: N-(5-Nitro-1H-indazol-3-yl)benzamide

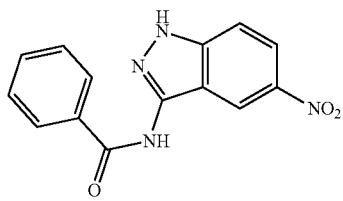

To a solution of 5-nitro-1H-indazol-3-amine (500 mg, 2.81 mmol) in pyridine (7.5 mL) was added a solution of benzoyl chloride (414.25 mg, 2.95 mmol) in MeCN (2.5 mL) at 0° C. The mixture was stirred at 0° C. for 2 hrs and then concentrated under reduced pressure to remove solvent. The residue obtained was washed with MeOH (10 mL), filtered, and the solid was dried under vacuum to afford the title compound (620 mg, 78%) as a yellow solid which was used without further purification. MS (ESI+) calcd for $C_{14}H_{11}N_4O_3$ (M+H)$^+$: 283.1. Found 283.0.

Step 2: N-(5-amino-1H-indazol-3-yl)benzamide

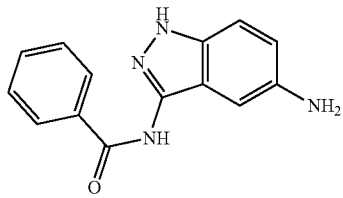 [SMILES: O=C(Nc1n[nH]c2ccc([N+](=O)[O-])cc12)c1ccccc1]

To a solution of N-(5-nitro-1H-indazol-3-yl)benzamide (620 mg, 2.20 mmol) in EtOH (12 mL) and $H_2O$ (3 mL) was added Fe (613.35 mg, 10.98 mmol) and $NH_4Cl$ (587.50 mg, 10.98 mmol). The mixture was stirred at 80° C. for 2 hrs and then filtered. The filtrate was concentrated under reduced pressure, diluted with $H_2O$ (15 mL) and extracted with EtOAc (30 mL×4). The combined organic layers were dried over $Na_2SO_4$, filtered and concentrated under reduced pressure to afford the title compound (350 mg, 63%) as a brown gum which was used without further purification. MS (ESI+) calcd for $C_{14}H_{13}N_4O$ (M+H)$^+$: 253.1. Found 253.1

Step 3: N-(3-Benzamido-1H-indazol-5-yl)-5-cyano-3-methylpicolinamide

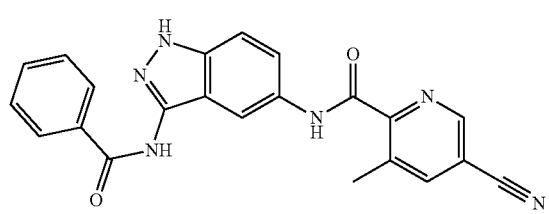 [SMILES: Cc1cc(C#N)cnc1C(=O)Nc1ccc2[nH]nc(NC(=O)c3ccccc3)c2c1]

To a solution of N-(5-amino-1H-indazol-3-yl)benzamide (100 mg, 396.40 umol) in DCM (4 mL) was added 5-cyano-3-methylpicolinic acid (38.56 mg, 237.84 umol), T3P (50 wt. % in EtOAc, 756.76 mg, 1.19 mmol), and $Et_3N$ (160.45 mg, 1.59 mmol). The mixture was stirred at 25° C. for 12 hrs and then concentrated. The material was purified by preparative HPLC using Method BU to afford the title compound (43.85 mg, 28%) as a yellow solid. ¹H NMR (400 MHz, DMSO-d₆) δ 12.82 (s, 1H) 10.76 (s, 1H) 10.68 (s, 1H) 8.97 (d, J=1.34 Hz, 1H) 8.36-8.39 (m, 1H) 8.21 (s, 1H) 8.08 (d, J=7.34 Hz, 2H) 7.70 (dd, J=9.05, 1.83 Hz, 1H) 7.60-7.65 (m, 1H) 7.53-7.59 (m, 2H) 7.50 (d, J=9.05 Hz, 1H) 2.54 (s, 3H). MS-ESI (m/z) calc'd for $C_{22}H_{17}N_6O_2$ [M+H]⁺: 397.1. Found 397.2.

Example 136: N-(3-(1H-Pyrazol-1-yl)-1H-indazol-5-yl)-5-cyano-3-methylpicolinamide

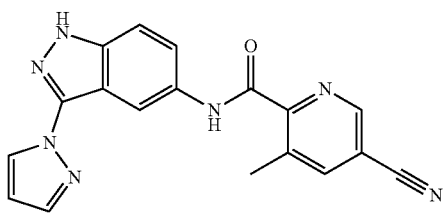 [SMILES: Cc1cc(C#N)cnc1C(=O)Nc1ccc2[nH]nc(-n3cccn3)c2c1]

Step 1: 5-Nitro-3-(1H-pyrazol-1-yl)-1-(tetrahydro-2H-pyran-2-yl)-1H-indazole

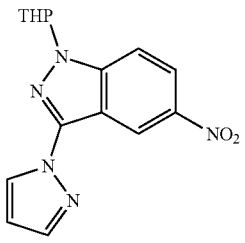

To a solution of 3-iodo-5-nitro-1-(tetrahydro-2H-pyran-2-yl)-1H-indazole (1 g, 2.68 mmol) and 1H-pyrazole (182.44 mg, 2.68 mmol) in DMF (12 mL) was added CuI (102.08 mg, 535.98 umol) and Cs₂CO₃ (1.31 g, 4.02 mmol) under N₂ and the mixture was stirred at 20° C. for 0.5 hr followed by stirring at 120° C. for 24 hrs under N₂. The reaction mixture was concentrated and purified by flash silica gel chromatography (ISCO; 20 g SepaFlash column) using a 0-24% EtOAc/petroleum ether gradient eluent to afford the title compound (190 mg, 23%) as a yellow solid. MS-(ESI) (m/z) calcd for $C_{15}H_{16}N_5O_3$ (M+H)⁺: 314.1. Found 314.1.

Step 2: 3-(1H-Pyrazol-1-yl)-1-(tetrahydro-2H-pyran-2-yl)-1H-indazol-5-amine

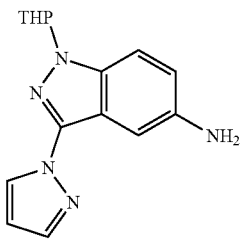

To a solution of 5-nitro-3-(1H-pyrazol-1-yl)-1-(tetrahydro-2H-pyran-2-yl)-1H-indazole (190 mg, 606.43 umol) in EtOH (2.5 mL) and H₂O (2.5 mL) was added Fe (169.33 mg, 3.03 mmol) and NH₄Cl (162.19 mg, 3.03 mmol) and the mixture was stirred at 80° C. for 1 hr. The reaction mixture was then filtered and the filtrate was concentrated under reduced pressure to give a residue which was taken up in H₂O (10 mL) and extracted with EtOAc (30 mL×4). The combined organic layers were dried over Na₂SO₄, filtered and concentrated under reduced pressure to afford the title compound (170 mg) as a brown gum which was used without further purification.

Step 3: N-(3-(1H-Pyrazol-1-yl)-1-(tetrahydro-2H-pyran-2-yl)-1H-indazol-5-yl)-5-cyano-3-methylpicolinamide

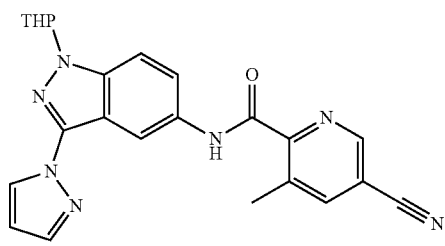

To a solution of 3-(1H-pyrazol-1-yl)-1-(tetrahydro-2H-pyran-2-yl)-1H-indazol-5-amine (160 mg, 564.72 umol) in pyridine (5 mL) was added EDCI (216.51 mg, 1.13 mmol) and 5-cyano-3-methylpicolinic acid (91.57 mg, 564.72 umol) and the mixture was stirred at 20° C. for 12 hrs. The reaction mixture was then concentrated under reduced pressure to remove solvent, diluted with H₂O (5 mL) and extracted with EtOAc (15 mL×6). The combined organic layers were dried over Na₂SO₄, filtered and concentrated under reduced pressure to afford the title compound (240 mg) as a brown solid which was used without further purification. MS-(ESI) (m/z) calcd for $C_2H_{22}N_7O_2$ (M+H)⁺: 428.2. Found 428.2.

Step 4: N-(3-(1H-Pyrazol-1-yl)-1H-indazol-5-yl)-5-cyano-3-methylpicolinamide

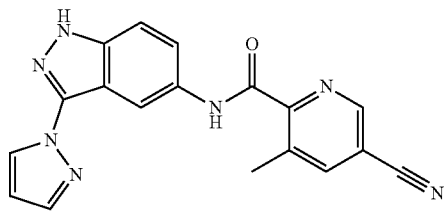 [SMILES: Cc1cc(C#N)cnc1C(=O)Nc1ccc2[nH]nc(-n3cccn3)c2c1]

To a solution of N-(3-(1H-pyrazol-1-yl)-1-(tetrahydro-2H-pyran-2-yl)-1H-indazol-5-yl)-5-cyano-3-methylpicolinamide (240 mg, 561.46 umol) in DCM (4 mL) was added TFA (6.16 g, 54.02 mmol) and the mixture was stirred at 20° C. for 12 hrs. The reaction mixture was then concentrated and purified by preparative HPLC using Method BO to afford the title compound (48.62 mg, 19%) as a yellow solid TFA salt. ¹H NMR (400 MHz, DMSO-d₆) δ 13.06 (s, 1H) 10.77 (s, 1H) 8.99 (d, J=1.34 Hz, 1H) 8.79 (d, J=1.83

Hz, 1H) 8.38-8.43 (m, 2H) 7.89 (d, J=1.34 Hz, 1H) 7.75 (dd, J=9.05, 1.96 Hz, 1H) 7.56 (d, J=8.93 Hz, 1H) 6.57-6.61 (m, 1H) 2.58 (s, 3H). MS-ESI (m/z) calc'd for $C_{18}H_{14}N_7O$ [M+H]$^+$: 344.1. Found 344.0.

Example 137: 5-Cyano-N-(3-(furan-3-yl)-1H-indazol-5-yl)-3-methyl-1H-pyrazole-4-carboxamide

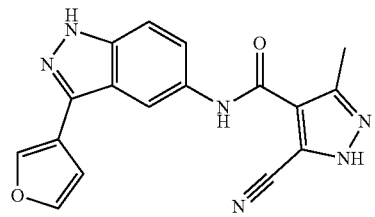 [SMILES: Cc1n[nH]c(C#N)c1C(=O)Nc1ccc2[nH]nc(-c3ccoc3)c2c1]

Step 1: Ethyl 5-cyano-3-methyl-1H-pyrazole-4-carboxylate

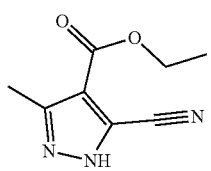

To a solution of ethyl but-2-ynoate (2.5 g, 22.30 mmol) in CHCl$_3$ (60 mL) and H$_2$O (2 mL) was added 2-aminoacetonitrile (3.71 g, 40.13 mmol, HCl salt) and NaNO$_2$ (4.61 g, 66.89 mmol). The mixture was stirred at 30° C. for 12 hrs and then warmed to 60° C. and stirred for an additional 12 hrs. The reaction mixture was quenched by addition of H$_2$O (20 mL) at 25° C. to give a biphasic mixture. The organic layer was separated and washed with H$_2$O (20 mL×1), dried over Na$_2$SO$_4$, filtered and concentrated under reduced pressure to give a residue. The residue was purified by flash silica gel chromatography (ISCO; 20 g SepaFlash column) using a 0-30% EtOAc/petroleum ether gradient eluent to afford the title compound (100 mg, 3%) as a pale yellow solid.

Step 2: 5-Cyano-N-(3-(furan-3-yl)-1H-indazol-5-yl)-3-methyl-1H-pyrazole-4-carboxamide

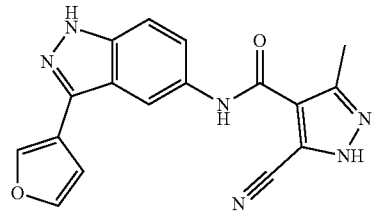 [SMILES: Cc1n[nH]c(C#N)c1C(=O)Nc1ccc2[nH]nc(-c3ccoc3)c2c1]

To a solution of ethyl 5-cyano-3-methyl-1H-pyrazole-4-carboxylate (50 mg, 279.06 umol), 3-(furan-3-yl)-1H-indazol-5-amine (66.71 mg, 334.87 umol) in toluene (2 mL) was added AlMe$_3$ (2 M in toluene, 558.11 uL) and the mixture was stirred at 90° C. for 12 hrs. The reaction mixture was quenched by addition of MeOH (2 mL) at 30° C. The reaction mixture was concentrated and purified by preparative HPLC using Method BO to afford the title compound (10.9 mg, 8%) as a white solid, TFA salt. $^1$H NMR (400 MHz, DMSO-d$_6$) δ 14.03 (br s, 1H) 13.10 (s, 1H) 10.11 (s, 1H) 8.18-8.35 (m, 2H) 7.85 (t, J=1.65 Hz, 1H) 7.50-7.61 (m, 2H) 6.99 (dd, J=1.76, 0.66 Hz, 1H). MS-ESI (m/z) calc'd for $C_{17}H_{13}N_6O_2$[M+H]$^+$: 333.1. Found 333.0.

Example 138: 3-Bromo-5-cyano-N-(3-(furan-3-yl)-1H-indazol-5-yl)picolinamide

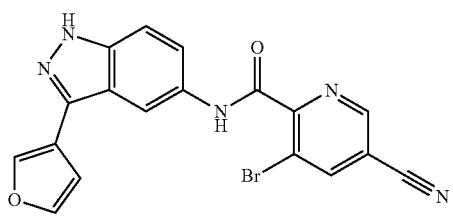 [SMILES: N#Cc1cnc(C(=O)Nc2ccc3[nH]nc(-c4ccoc4)c3c2)c(Br)c1]

Step 1: 3-Bromo-5-cyanopicolinic acid

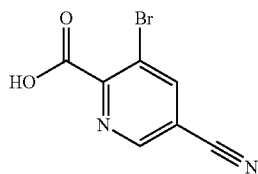 [SMILES: N#Cc1cnc(C(=O)O)c(Br)c1]

To a solution of methyl 3-bromo-5-cyanopicolinate (160 mg, 663.79 umol) in THF (3 mL) was added NaOH (53.10 mg, 1.33 mmol) and the mixture was stirred at 30° C. for 1 hr. The reaction mixture was quenched by addition of H$_2$O (2 mL) at 30° C., and then diluted with 1 N HCl to pH=2 and extracted with EtOAc (8 mL×2). The combined organic layers were dried over Na$_2$SO$_4$, filtered and concentrated under reduced pressure to afford the title compound (150 mg) as a pale yellow solid which was used without further purification. MS-ESI (m/z) calcd for $C_7H_2BrN_2O_2$ [M−H]$^-$: 224.9/226.9. Found 224.8/226.8.

Step 2: 3-Bromo-5-cyano-N-(3-(furan-3-yl)-1H-indazol-5-yl)picolinamide

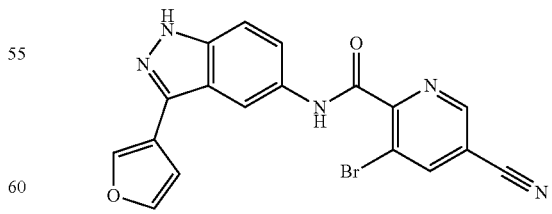

To a solution of 3-bromo-5-cyanopicolinic acid (150 mg, 660.75 umol) in pyridine (3 mL) was added EDCI (190.00 mg, 991.12 umol) and 3-(furan-3-yl)-1H-indazol-5-amine (157.95 mg, 792.90 umol) and the mixture was stirred at 30° C. for 12 hrs. The reaction mixture was concentrated to afford a residue. The residue was washed with H$_2$O (20 mL) and dried to afford 250 mg crude product, 100 mg was further purified by preparative HPLC using Method BD to afford the title compound (32.98 mg, 26%) as a yellow solid TFA salt. $^1$H NMR (400 MHz, DMSO-d$_6$) δ 13.14 (s, 1H) 10.84 (s, 1H) 9.15 (s, 1H) 8.93 (s, 1H) 8.36 (s, 1H) 8.22 (s, 1H) 7.85 (s, 1H) 7.62-7.69 (m, 1H) 7.53-7.61 (m, 1H) 6.99 (s, 1H). MS-ESI (m/z) calc'd for C$_{18}$H$_{11}$BrN$_5$O$_2$ [M+H]$^+$: 408.0/410.0. Found 407.9/409.9.

Example 139: N-(3-(5-Chlorothiophen-2-yl)-1H-indazol-5-yl)-5-cyano-3-methylpicolinamide

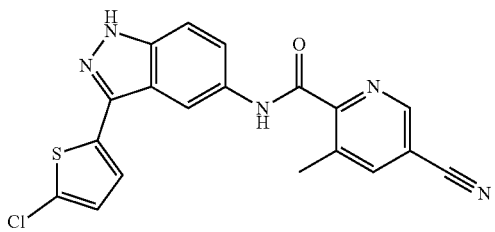 [SMILES: Cc1cc(C#N)cnc1C(=O)Nc1ccc2[nH]nc(-c3ccc(Cl)s3)c2c1]

Prepared as described for 5-cyano-N-(3-(5-cyanothiophen-2-yl)-1H-indazol-5-yl)-3-methylpicolinamide using (5-chlorothiophen-2-yl)boronic acid in place of (5-cyanothiophen-2-yl)boronic acid to afford the title compound (9.74 mg, 14%) as a yellow solid. $^1$H NMR (400 MHz, DMSO-d$_6$) δ 13.33 (s, 1H) 10.81 (s, 1H) 9.01 (s, 1H) 8.64 (s, 1H) 8.43 (s, 1H) 7.83 (br d, J=9 Hz, 1H) 7.61 (br d, J=9 Hz, 1H) 7.48 (br d, J=4 Hz, 1H) 7.27 (d, J=4 Hz, 1H) 2.61 (s, 3H). MS-ESI (m/z) calc'd for C$_{19}$H$_{13}$ClN$_5$OS [M+H]$^+$: 394.1. Found 393.9.

Example 140: 5-Cyano-3-methyl-N-(3-(2-methylthiazol-5-yl)-1H-indazol-5-yl)picolinamide

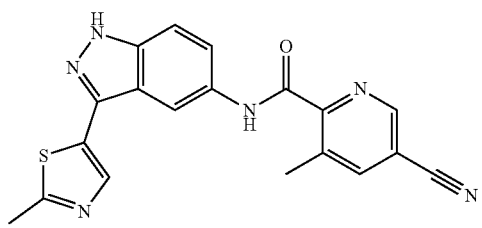 [SMILES: Cc1ncc(-c2n[nH]c3ccc(NC(=O)c4ncc(C#N)cc4C)cc23)s1]

Prepared as described for 5-cyano-N-(3-(5-cyanothiophen-2-yl)-1H-indazol-5-yl)-3-methylpicolinamide using (2-methylthiazol-5-yl)boronic acid in place of (5-cyanothiophen-2-yl)boronic acid to afford the title compound (1.98 mg, 2%) as a yellow solid. $^1$H NMR (400 MHz, DMSO-d$_6$) δ 13.34 (s, 1H), 10.80 (s, 1H), 9.01 (d, J=1.1 Hz, 1H), 8.59 (s, 1H), 8.42 (s, 1H), 8.13 (s, 1H), 7.86 (dd, J=1.7, 8.9 Hz, 1H), 7.60 (d, J=8.8 Hz, 1H), 2.72 (s, 3H), 2.61 (s, 3H). MS-ESI (m/z) calc'd for C$_{19}$H$_{18}$N$_6$OS [M+H]$^+$: 375.1. Found 375.1.

Example 141: 5-Cyano-3-methyl-N-(3-(5-methylfuran-2-yl)-1H-indazol-5-yl)picolinamide

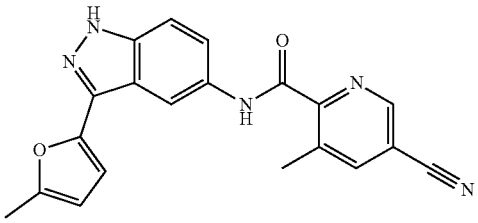 [SMILES: Cc1ccc(-c2n[nH]c3ccc(NC(=O)c4ncc(C#N)cc4C)cc23)o1]

Prepared as described for 5-cyano-N-(3-(1,5-dimethyl-1H-pyrazol-4-yl)-1H-indazol-5-yl)-3-methylpicolinamide using (5-methylfuran-2-yl)boronic acid in place of (1,5-dimethyl-1H-pyrazol-4-yl)boronic acid to afford the title compound (36.81 mg, 52%) as a yellow solid. $^1$H NMR (400 MHz, DMSO-d$_6$) δ 13.17 (s, 1H), 10.75 (s, 1H), 9.00 (d, J=1.5 Hz, 1H), 8.54 (d, J=1.3 Hz, 1H), 8.40 (d, J=1.1 Hz, 1H), 7.80 (dd, J=1.7, 8.9 Hz, 1H), 7.55 (d, J=9.0 Hz, 1H), 6.78 (d, J=3.1 Hz, 1H), 6.32-6.25 (m, 1H), 2.59 (s, 3H), 2.41 (s, 3H). MS-ESI (m/z) calc'd for C$_{20}$H$_{16}$N$_5$O$_2$ [M+H]$^+$: 358.1. Found 358.2.

Example 142: 5-Cyano-N-(3-(furan-3-yl)-1H-indazol-5-yl)quinoline-8-carboxamide

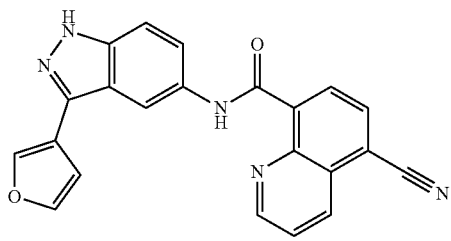 [SMILES: N#Cc1ccc(C(=O)Nc2ccc3[nH]nc(-c4ccoc4)c3c2)c2ncccc12]

Step 1: Methyl 5-vinylquinoline-8-carboxylate

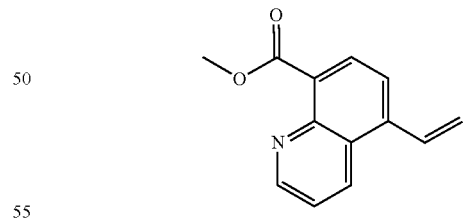

To a solution of methyl 5-bromoquinoline-8-carboxylate (1.33 g, 5 mmol) in 1,4-dioxane (50 mL) was added tributyl (ethenyl)stannane (1.75 mL, 6 mmol) and the mixture was degassed with N$_2$ for 10 minutes. Bis(triphenylphosphine) palladium(II) dichloride (175.98 mg, 0.250 mmol) was added and the reaction was stirred at 100° C. for 8 hrs. The solvent was evaporated and the residue was purified by silica gel column chromatography using 0-100% EtOAc/cyclohexane gradient eluent to afford the title compound (678 mg, 64%) as an orange oil. $^1$H NMR (400 MHz, DMSO-d$_6$) δ 8.98 (dd, J=4.2, 1.7 Hz, 1H), 8.72 (dd, J=8.7, 1.7 Hz, 1H), 7.92 (d, J=7.5 Hz, 1H), 7.86 (d, J=7.5 Hz, 1H), 7.67-7.55 (m, 2H), 6.02 (dd, J=17.3, 1.3 Hz, 1H), 5.63 (dd, J=11.0, 1.3 Hz, 1H), 3.91 (s, 3H). MS-ESI (m/z) calc'd for $C_{13}H_{12}NO_2$ [M+H]$^+$: 214.1. Found 214.1.

Step 2: Methyl 5-formylquinoline-8-carboxylate

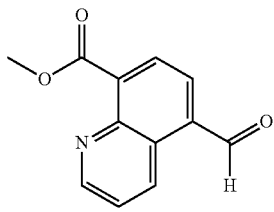 [SMILES: COC(=O)c1ccc(C=O)c2cccnc12]

To a solution of methyl 5-ethenylquinoline-8-carboxylate (678.0 mg, 3.18 mmol) in 1,4-dioxane (15.9 mL) was added a solution of NaIO$_4$ (1.36 g, 6.36 mmol) in H$_2$O (15.9 mL) and the mixture was stirred at 25° C. for 1 hr. The mixture was diluted with H$_2$O and extracted with DCM (3×). The combined organic layers were passed through a phase separator and evaporated to afford the title compound (684 mg, 99%) as a dark green oil. $^1$H NMR (400 MHz, DMSO-d$_6$) δ 10.46 (s, 1H), 9.49 (dd, J=8.7, 1.8 Hz, 1H), 9.06 (dd, J=4.2, 1.7 Hz, 1H), 8.34 (d, J=7.3 Hz, 1H), 8.13 (d, J=7.3 Hz, 1H), 7.81 (dd, J=8.7, 4.2 Hz, 1H), 3.57 (s, 3H). MS-ESI (m/z) calc'd for $C_{12}H_{10}NO_3$ [M+H]$^+$: 216.1. Found 216.0.

Step 3: Methyl 5-cyanoquinoline-8-carboxylate

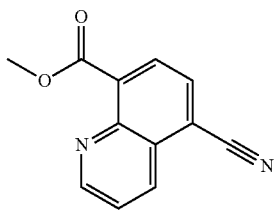 [SMILES: COC(=O)c1ccc(C#N)c2cccnc12]

To a solution of methyl 5-formylquinoline-8-carboxylate (684.0 mg, 3.18 mmol) in DMSO (4 mL) was added hydroxylamine hydrochloride (220.87 mg, 3.18 mmol) and the mixture was stirred at 90° C. for 1 hr. Water was added and a solid formed and the mixture was filtered. The filtrate was extracted with EtOAc (3×) and the combined organic layers were washed with H$_2$O, passed through a phase separator and evaporated to afford the title compound (327 mg, 48%) as a yellow solid. $^1$H NMR (400 MHz, DMSO-d$_6$) δ 9.24 (dd, J=4.4, 1.6 Hz, 1H), 8.74 (dd, J=8.5, 1.6 Hz, 1H), 8.44 (d, J=1.0 Hz, 2H), 8.00 (dd, J=8.5, 4.4 Hz, 1H), 3.96 (s, 3H). MS-ESI (m/z) calc'd for $C_{12}H_8N_2O_2$[M+H]$^+$: 213.1. Found 213.0.

Step 4: 5-Cyanoquinoline-8-carboxylic acid

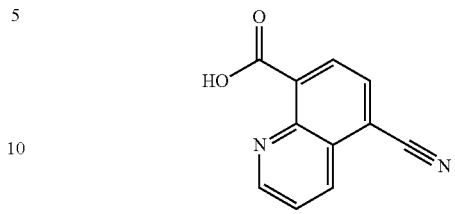

To a solution of methyl 5-cyanoquinoline-8-carboxylate (327.0 mg, 1.54 mmol) in THF (7.705 mL) was added a solution of NaOH (126.39 mg, 3.08 mmol) in H$_2$O (7.705 mL) and the mixture was stirred at 25° C. for 1 hr. The solvent was evaporated to dryness and the residue was taken up in POCl$_3$ (10 mL) and stirred at 100° C. for 1 hr. Excess POCl$_3$ was removed under vacuum and the solid that remained was extracted with H$_2$O and EtOAc (3×). The combined organic layers were passed through a phase separator and evaporated to afford the title compound (279 mg, 91%) as a beige solid. $^1$H NMR (400 MHz, DMSO-d$_6$) δ 15.26 (s, 1H), 9.24 (dd, J=4.4, 1.6 Hz, 1H), 8.74 (dd, J=8.5, 1.6 Hz, 1H), 8.49-8.37 (m, 2H), 8.00 (dd, J=8.5, 4.4 Hz, 1H). MS-ESI (m/z) calc'd for $C_{11}H_5N_2O_2$[M−H]$^-$: 197.0. Found 197.1.

Step 5: 5-Cyano-N-(3-(furan-3-yl)-1H-indazol-5-yl) quinoline-8-carboxamide

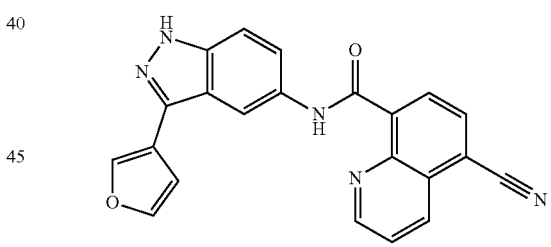

Prepared as described for 5-cyano-N-(7-fluoro-3-(furan-3-yl)-1H-indazol-5-yl)-3-methylpicolinamide using 5-cyanoquinoline-8-carboxylic acid in place of 5-cyano-3-methylpicolinic acid and using 3-(furan-3-yl)-1H-indazol-5-amine in place of 7-fluoro-3-(furan-3-yl)-1H-indazol-5-amine to afford the title compound (8 mg, 11%) as a orange solid. $^1$H NMR (400 MHz, DMSO-d$_6$) δ 13.13 (s, 1H), 12.41 (s, 1H), 9.33 (dd, J=4.3, 1.7 Hz, 1H), 8.72 (dd, J=8.5, 1.7 Hz, 1H), 8.56 (d, J=7.6 Hz, 1H), 8.52-8.51 (m, 1H), 8.46 (d, J=7.6 Hz, 1H), 8.30 (dd, J=1.5, 0.8 Hz, 1H), 7.98 (dd, J=8.5, 4.3 Hz, 1H), 7.85 (t, J=1.7 Hz, 1H), 7.80 (dd, J=9.0, 1.9 Hz, 1H), 7.60 (d, J=8.8 Hz, 1H), 7.02 (dd, J=1.8, 0.8 Hz, 1H). MS-ESI (m/z) calc'd for $C_{22}H_{14}N_5O_2$ [M+H]$^+$: 380.1. Found 380.1.

Example 143: 5-Cyano-N-(7-fluoro-3-(furan-3-yl)-1H-indazol-5-yl)-3-methylpicolinamide

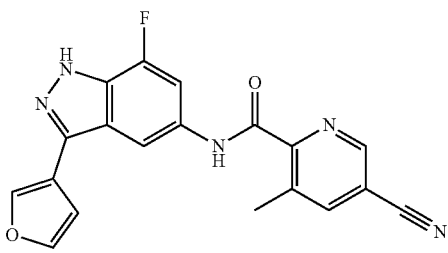 [SMILES: Cc1cc(C#N)cnc1C(=O)Nc1cc(F)c2[nH]nc(-c3ccoc3)c2c1]

Step 1: 7-Fluoro-3-iodo-5-nitro-1H-indazole

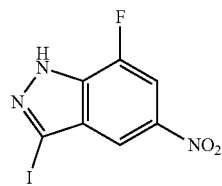 [SMILES: O=[N+]([O-])c1cc(F)c2[nH]nc(I)c2c1]

To a solution of 7-fluoro-5-nitro-1H-indazole (1.0 g, 5.52 mmol) in DMF (20 mL) was added KOH (1.17 g, 20.43 mmol)) and I$_2$ (2.8 g, 11.04 mmol) and the mixture was stirred for 1 hr. The mixture was then poured into saturated aqueous sodium metabisulfite (200 mL) and the solid formed was collected by filtration, washed with H$_2$O and dried to give the title compound (1.3 g, 77%) as a light brown solid which was used without further purification. MS-ESI (m/z) calc'd for C$_7$H$_4$FIN$_3$O$_2$[M+H]$^+$: 308.0. Found 307.8.

Step 2: 7-Fluoro-3-iodo-1H-indazol-5-amine

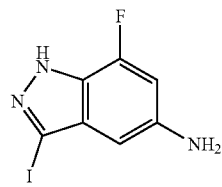

A mixture of 7-fluoro-3-iodo-5-nitro-1H-indazole (1.3 g, 4.23 mmol), NH$_4$Cl (249.14 mg, 4.66 mmol) and iron powder (945.93 mg, 16.94 mmol) in EtOH (13.43 mL) and water (13.43 mL) was stirred 80° C. for 1 hr. The solids were removed by filtration through Celite and the solid was washed with EtOH. The filtrate was evaporated, the residue was taken up in water and extracted with EtOAc (3×), the combined organic layers were passed through a phase separator and evaporated to afford the title compound (228 mg, 19%) as a yellow solid. MS-ESI (m/z) calc'd for C$_7$H$_6$FIN$_3$ [M+H]$^+$: 278.0. Found 278.1.

Step 3: 7-Fluoro-3-(furan-3-yl)-1H-indazol-5-amine

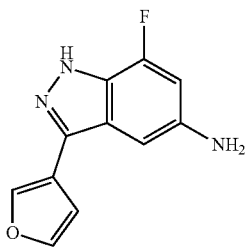 [SMILES: Nc1cc(F)c2[nH]nc(-c3ccoc3)c2c1]

A microwave vial was charged with 7-fluoro-3-iodo-1H-indazol-5-amine (55.0 mg, 0.200 mmol), 3-furanylboronic acid (44.43 mg, 0.400 mmol), KOAc (35.43 mg, 0.360 mmol) and Pd(amphos)Cl$_2$ (14.1 mg, 0.020 mmol). The vial was flushed with Ar, then 1,4-dioxane (0.375 ml) and H$_2$O (0.125 ml) were added in sequence. The vial was sealed and stirred at 100° C. in a microwave reactor for 30 minutes. The reaction was diluted with EtOAc and washed with H$_2$O. The aqueous layer was extracted with EtOAc and the combined organic layers were washed with brine, dried with Na$_2$SO$_4$, filtered and concentrated. The material was purified by silica gel column chromatography (Redi-Sep Gold (Teledyne Isco)) using a 0-100% EtOAc/cyclohexane gradient eluent to afford the title compound (20 mg, 46%). MS-ESI (m/z) calc'd for C$_{11}$H$_9$FN$_3$O [M+H]$^+$: 218.1. Found 218.0.

Step 4: 5-Cyano-N-(7-fluoro-3-(furan-3-yl)-1H-indazol-5-yl)-3-methylpicolinamide

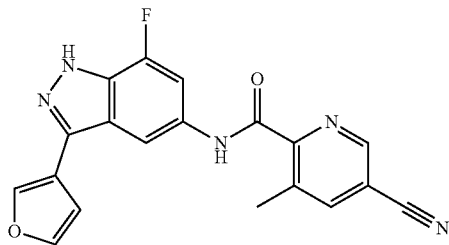 [SMILES: Cc1cc(C#N)cnc1C(=O)Nc1cc(F)c2[nH]nc(-c3ccoc3)c2c1]

To a solution of 5-cyano-3-methylpicolinic acid (15.0 mg, 0.090 mmol), triethylamine (0.01 mL, 0.090 mmol) and 7-fluoro-3-(furan-3-yl)-1H-indazol-5-amine (20.09 mg, 0.090 mmol) was added HATU (35.17 mg, 0.090 mmol) and the mixture was stirred at r.t. for 1 hr. Water and EtOAc were added and the organic phase was separated and washed with brine to afford a residue that was purified by preparative HPLC using Method CV to afford the title compound (2.2 mg, 7%) as a yellow solid. $^1$H NMR (400 MHz, DMSO-d$_6$) δ 2.57-2.70 (m, 3H) 7.02 (dd, J=1.87, 0.77 Hz, 1H) 7.81-7.97 (m, 2H) 8.22-8.34 (m, 2H) 8.38-8.57 (m, 1H) 9.02 (dd, J=1.98, 0.66 Hz, 1H) 10.85 (s, 1H) 13.68 (br. s., 1H). MS-ESI (m/z) calc'd for C$_{19}$H$_{13}$FN$_5$O$_2$ [M+H]$^+$: 362.1. Found 362.1.

Example 144: 3-Chloro-4-cyano-N-(3-(furan-3-yl)-1H-indazol-5-yl)picolinamide

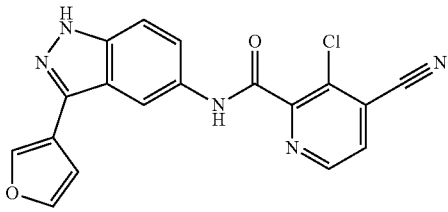

Prepared as described for 5-cyano-N-(7-fluoro-3-(furan-3-yl)-1H-indazol-5-yl)-3-methylpicolinamide using 3-chloro-4-cyanopicolinic acid in place of 5-cyano-3-methylpicolinic acid and using 3-(furan-3-yl)-1H-indazol-5-amine in place of 7-fluoro-3-(furan-3-yl)-1H-indazol-5-amine to afford the title compound (10.4 mg, 15%) as a yellow solid. $^1$H NMR (400 MHz, DMSO-$d_6$) δ 13.14 (br. s., 1H) 10.82 (s, 1H) 8.90 (d, J=4.84 Hz, 1H) 8.38 (d, J=1.10 Hz, 1H) 8.17-8.28 (m, 2H) 7.86 (t, J=1.65 Hz, 1H) 7.70 (dd, J=8.91, 1.87 Hz, 1H) 7.59 (d, J=9.46 Hz, 1H) 7.00 (dd, J=1.76, 0.88 Hz, 1H). MS-ESI (m/z) calc'd for $C_{18}H_{11}ClN_5O_2$ [M+H]$^+$: 364.1/366.1. Found 364.2/366.0.

Example 145: 5-Cyano-N-(3-(furan-3-yl)-1H-indazol-5-yl)-3-methylpyrazine-2-carboxamide

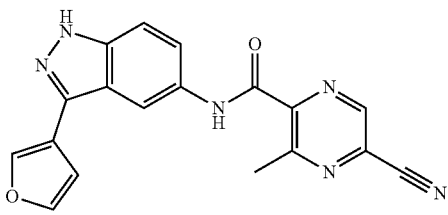 [SMILES: Cc1nc(C#N)cnc1C(=O)Nc1ccc2[nH]nc(-c3ccoc3)c2c1]

Prepared as described for 5-cyano-N-(7-fluoro-3-(furan-3-yl)-1H-indazol-5-yl)-3-methylpicolinamide using 5-cyano-3-methylpyrazine-2-carboxylic acid in place of 5-cyano-3-methylpicolinic acid and using 3-(furan-3-yl)-1H-indazol-5-amine in place of 7-fluoro-3-(furan-3-yl)-1H-indazol-5-amine to afford the title compound (16.1 mg, 13%) as a yellow solid. $^1$H NMR (400 MHz, DMSO-$d_6$) δ 13.14 (s, 1H), 10.78 (s, 1H), 9.30 (s, 1H), 8.44-8.37 (m, 1H), 8.27 (dd, J=1.5, 0.9 Hz, 1H), 7.86 (t, J=1.7 Hz, 1H), 7.79 (dd, J=9.0, 1.9 Hz, 1H), 7.59 (dd, J=9.0, 0.8 Hz, 1H), 7.01 (dd, J=1.8, 0.8 Hz, 1H), 2.88 (s, 3H). MS-ESI (m/z) calc'd for $C_{18}H_{13}N_6O_2$ [M+H]$^+$: 345.1. Found 345.2.

Example 146: 5-Cyano-N-(3-(isoxazol-4-yl)-1H-indazol-5-yl)-3-methylpicolinamide

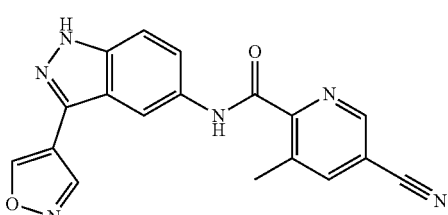

A microwave vial was charged with 5-cyano-N-(3-iodo-1H-indazol-5-yl)-3-methylpyridine-2-carboxamide (50.0 mg, 0.120 mmol), isoxazole-4-boronic acid (28.0 mg, 0.250 mmol), KOAc (22.13 mg, 0.220 mmol) and Pd(amphos)Cl$_2$ (8.81 mg, 0.010 mmol). The vial was flushed with N$_2$, then 1,4-dioxane (0.800 mL) and H$_2$O (0.125 mL) were added in sequence. The vial was sealed and irradiated in a microwave reactor at 100° C. for 30 minutes. The reaction was diluted with EtOAc and washed with water. The aqueous layer was extracted with EtOAc and the combined organic layers were washed with brine, dried with Na$_2$SO$_4$, filtered and concentrated. The residue was purified by preparative HPLC using Method CW to afford the title compound (23.5 mg, 55%) as a yellow solid. $^1$H NMR (400 MHz, DMSO-$d_6$) δ 13.35 (br. s., 1H) 10.71 (s, 1H) 9.57 (s, 1H) 9.15 (s, 1H) 9.01 (d, J=1.32 Hz, 1H) 8.51-8.35 (m, 2H) 7.85 (dd, J=9.02, 1.76 Hz, 1H) 7.61 (d, J=8.36 Hz, 1H) 3.33-3.33 (m, 1H) 2.67 (s, 1H) 2.72-2.56 (m, 3H). MS-ESI (m/z) calc'd for $C_{19}H_{13}N_6O_2$ [M+H]$^+$: 345.1. Found 345.2.

Example 147: 6-Cyano-N-(3-(furan-3-yl)-1H-indazol-5-yl)-3-methylpyrazine-2-carboxamide

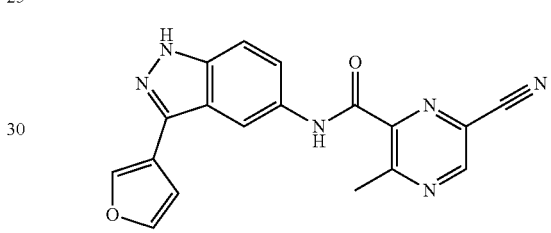

Prepared as described for 5-cyano-N-(7-fluoro-3-(furan-3-yl)-1H-indazol-5-yl)-3-methylpicolinamide using 6-cyano-3-methylpyrazine-2-carboxylic acid in place of 5-cyano-3-methylpicolinic acid and using 3-(furan-3-yl)-1H-indazol-5-amine in place of 7-fluoro-3-(furan-3-yl)-1H-indazol-5-amine to afford the title compound (12.5 mg, 10%) as an orange solid. $^1$H NMR (400 MHz, DMSO-$d_6$) δ 13.13 (s, 1H), 10.85 (s, 1H), 9.22 (q, J=0.7 Hz, 1H), 8.42 (dd, J=1.9, 0.8 Hz, 1H), 8.26 (dd, J=1.5, 0.9 Hz, 1H), 7.85 (t, J=1.7 Hz, 1H), 7.81 (dd, J=9.0, 1.9 Hz, 1H), 7.58 (dd, J=9.0, 0.7 Hz, 1H), 7.00 (dd, J=1.9, 0.8 Hz, 1H), 2.84 (d, J=0.7 Hz, 3H). MS-ESI (m/z) calc'd for $C_{15}H_{13}N_6O_2$ [M+H]$^+$: 345.1. Found 345.2.

Example 148: 6-Cyano-N-(3-(furan-3-yl)-1H-indazol-5-yl)-3-methylpicolinamide

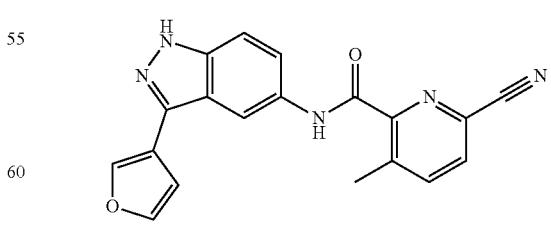

A mixture of 3-(furan-3-yl)-1H-indazol-5-amine (40.0 mg, 0.200 mmol) and methyl 6-cyano-3-methylpyridine-2-carboxylate (35.37 mg, 0.200 mmol) in toluene (2 mL) was flushed with N$_2$ for 5 min. Then a 2 M solution of trimethylaluminum in toluene (0.3 mL, 0.600 mmol) was added and the reaction mixture was stirred for 1 hr at 95° C. The reaction mixture was then cooled to r.t., diluted with H₂O and EtOAc, the phases were separated, the aqueous layer was extracted with EtOAc (2×) and the combined organic phases were washed with H₂O (1×), dried over Na₂SO₄ and evaporated to dryness. The material was purified by preparative HPLC using Method CZ to afford the title compound (9.2 mg, 13%) as a white solid. ¹H NMR (400 MHz, DMSO-d₆) δ 13.12 (s, 1H) 10.63 (s, 1H) 8.40 (d, J=1.54 Hz, 1H) 8.26 (d, J=0.88 Hz, 1H) 8.13-8.19 (m, 1H) 8.07-8.12 (m, 1H) 7.85 (t, J=1.65 Hz, 1H) 7.79 (dd, J=9.02, 1.76 Hz, 1H) 7.57 (d, J=8.80 Hz, 1H) 6.98-7.05 (m, 1H) 2.63 (s, 3H). MS-ESI (m/z) calc'd for C₁₉H₁₄N₅O₂ [M+H]⁺: 344.1. Found 344.2.

Example 149: 4-Cyano-3-ethyl-N-(3-(furan-3-yl)-1H-indazol-5-yl)picolinamide

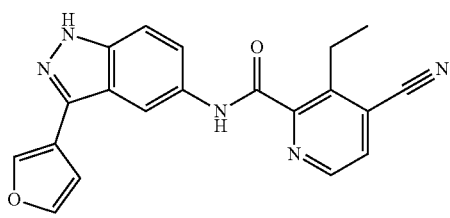 [SMILES: CCc1c(C#N)ccnc1C(=O)Nc1ccc2[nH]nc(-c3ccoc3)c2c1]

Step 1: Ethyl 4-cyano-3-vinylpicolinate

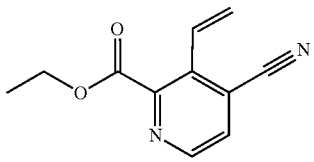

Ethyl 3-chloro-4-cyanopyridine-2-carboxylate (80.0 mg, 0.380 mmol) and 2-ethenyl-4,4,5,5-tetramethyl-1,3,2-dioxaborolane (0.1 mL, 0.570 mmol) were suspended in 1,4-dioxane (4 mL) and a solution of potassium carbonate (157.49 mg, 1.14 mmol) in H₂O (1 mL) was added. The mixture was degassed with N₂ for 5 minutes and tetrakis(triphenylphosphine)palladium(0) (43.89 mg, 0.040 mmol) was added and the mixture was stirred at 110° C. under N₂ for 2 hrs. The reaction mixture was partitioned between H₂O and EtOAc, the phases were separated, the aqueous layer was extracted with EtOAc (2×) and the combined organic phases were washed with water (1×), dried over anhydrous Na₂SO₄ and evaporated to dryness. The material was purified by silica gel column chromatography using a 0-50% EtOAc/cyclohexane gradient eluent to afford the title compound (60 mg, 78%) as a yellow solid. ¹H NMR (400 MHz, DMSO-d₆) δ 8.79 (d, J=5.28 Hz, 1H) 8.11 (d, J=5.06 Hz, 1H) 7.02 (dd, J=17.72, 11.55 Hz, 1H) 5.78-5.93 (m, 2H) 4.36 (q, J=7.04 Hz, 2H) 1.31 (t, J=7.15 Hz, 3H). MS-ESI (m/z) calc'd for C₁₁H₁N₂O₂[M+H]⁺: 203.1. Found 203.1.

Step 2: Ethyl 4-cyano-3-ethylpicolinate

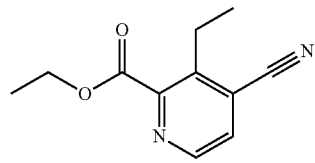

Ethyl 4-cyano-3-ethenylpyridine-2-carboxylate (60.0 mg, 0.140 mmol) was dissolved in EtOH (5 mL) and 10% Pd/C (15.16 mg) was added. The mixture was stirred at r.t. under H₂ atmosphere for 1 hr. The Pd/C was filtered off, washing with EtOH. The filtrate was collected and evaporated to dryness under reduced pressure to afford the title compound (40 mg) as a white solid which was used without further purification. ¹H NMR (400 MHz, MeOH-d₄) δ 8.68 (d, J=4.84 Hz, 1H) 7.87 (d, J=5.06 Hz, 1H) 4.47 (q, J=7.26 Hz, 2H) 3.09 (q, J=7.56 Hz, 2H) 1.43 (t, J=7.15 Hz, 3H) 1.34 (t, J=7.59 Hz, 3H). MS-ESI (m/z) calc'd for C₁₁H₁₃N₂O₂ [M+H]⁺: 205.1. Found 205.1.

Step 3: 4-Cyano-3-ethylpicolinic acid

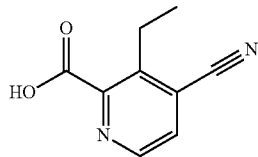

To a solution of ethyl 4-cyano-3-ethylpyridine-2-carboxylate (40.0 mg, 0.080 mmol) in THF (1.5 mL) was added a solution of NaOH (3.13 mg, 0.080 mmol) in H₂O (0.750 mL) and the mixture was stirred at r.t. for 2 hrs. The reaction was concentrated to afford the title compound (45 mg) as a white solid which was used without further purification. ¹H NMR (400 MHz, DMSO-d₆) δ ppm 8.37 (d, J=5.06 Hz, 1H) 7.47 (d, J=4.84 Hz, 1H) 2.80 (q, J=7.48 Hz, 2H) 1.19 (t, J=7.48 Hz, 3H). MS-ESI (m/z) calc'd for C₉H₇N₂O₂ [M−H]⁻: 175.1. Found 175.0.

Step 4: 4-Cyano-3-ethyl-N-(3-(furan-3-yl)-1H-indazol-5-yl)picolinamide

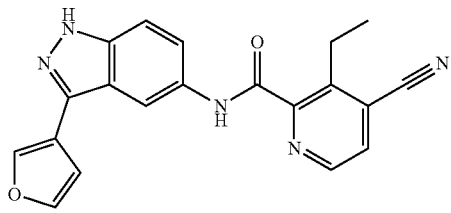 [SMILES: CCc1c(C#N)ccnc1C(=O)Nc1ccc2[nH]nc(-c3ccoc3)c2c1]

Prepared as described for 5-cyano-N-(7-fluoro-3-(furan-3-yl)-1H-indazol-5-yl)-3-methylpicolinamide using 4-cyano-3-ethylpicolinic acid in place of 5-cyano-3-methylpicolinic acid and using 3-(furan-3-yl)-1H-indazol-5-amine in place of 7-fluoro-3-(furan-3-yl)-1H-indazol-5-amine to afford the title compound (9.1 mg, 34%) as a yellow solid. $^1$H NMR (400 MHz, DMSO-d$_6$) δ 13.10 (s, 1H) 10.71 (s, 1H) 8.80 (d, J=5.06 Hz, 1H) 8.40 (d, J=1.54 Hz, 1H) 8.26 (dd, J=1.54, 0.88 Hz, 1H) 8.07 (d, J=4.84 Hz, 1H) 7.85 (t, J=1.65 Hz, 1H) 7.81 (dd, J=9.02, 1.98 Hz, 1H) 7.57 (d, J=8.80 Hz, 1H) 7.01 (dd, J=1.87, 0.77 Hz, 1H) 3.14 (q, J=7.41 Hz, 2H) 1.31 (t, J=7.48 Hz, 3H). MS-ESI (m/z) calc'd for C$_{20}$H$_{16}$N$_5$O$_2$ [M+H]$^+$: 358.1. Found 358.1.

Example 150: 5-Cyano-N-(3-(1-methoxyethyl)-1H-indazol-5-yl)-3,4-dimethylpicolinamide

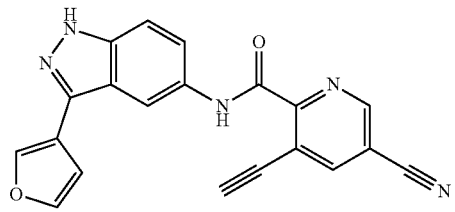

Step 1: 5-Bromo-6-iodonicotinonitrile

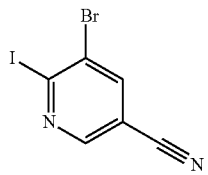

To a solution of 5-bromo-6-chloronicotinonitrile (2.26 g, 10.39 mmol) in MeCN (40 mL) was added NaI (4.52 g, 30.14 mmol) and TMSI (2.29 g, 11.43 mmol). The mixture was stirred at 25° C. for 1 hr. The mixture was quenched by addition of saturated aqueous NaHCO$_3$ (20 mL) and extracted with EtOAc (40 mL×2). The combined organic layers were dried over Na$_2$SO$_4$ and concentrated under reduced pressure to give a residue. The residue was purified by flash silica gel chromatography (ISCO; 20 g SepaFlash column) using a 0-3% EtOAc/petroleum ether gradient eluent to afford the title compound (3.1 g, 97%) as a yellow solid. MS-ESI (m/z) calcd for C$_6$H$_3$BrIN$_2$ [M+H]$^+$: 308.8/310.8. Found 308.8/310.8.

Step 2: Methyl 3-bromo-5-cyanopicolinate

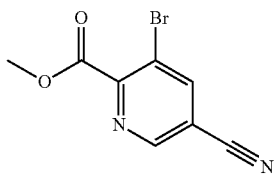

To a solution of 5-bromo-6-iodonicotinonitrile (1 g, 3.24 mmol) in MeCN (20 mL) and MeOH (6 mL) was added Pd(PPh$_3$)$_2$Cl$_2$ (113.61 mg, 161.86 umol) and Et$_3$N (982.74 mg, 9.71 mmol) under an N$_2$ atmosphere. The suspension was degassed and purged with CO (3×). The mixture was then stirred under CO (3 Mpa) at 50° C. for 7 hrs. The reaction mixture was concentrated and purified by flash silica gel chromatography (ISCO; 12 g SepaFlash column) using a 0-11% EtOAc/petroleum ether gradient eluent to afford the title compound (700 mg, 90%) as a pale yellow solid. MS-ESI (m/z) calcd for C$_8$H$_6$BrN$_2$O$_2$ [M+H]$^+$: 241.0/243.0. Found 241.1/243.1.

Step 3: 5-Cyano-3-((trimethylsilyl)ethynyl)picolinic acid

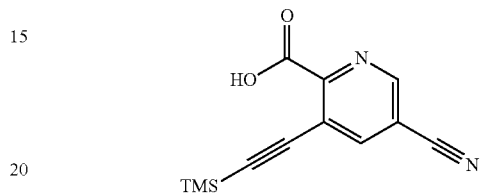

A mixture of methyl 3-bromo-5-cyanopicolinate (400 mg, 1.66 mmol), ethynyl(trimethyl)silane (488.97 mg, 4.98 mmol, 689.66 uL), CuI (15.80 mg, 82.97 umol), Pd(PPh$_3$)$_4$ (191.76 mg, 165.95 umol) and Et$_3$N (671.69 mg, 6.64 mmol, 923.91 uL) in THF (3.5 mL) was degassed and purged with N$_2$ (3×), and then the mixture was stirred at 80° C. for 12 hrs under an N$_2$ atmosphere. The reaction mixture was concentrated to afford a residue. The residue was purified by flash silica gel chromatography (ISCO; 12 g SepaFlash column) using a 0-8% EtOAc/petroleum ether gradient eluent to afford the title compound (210 mg, 39%) as a pale yellow solid. MS-ESI (m/z) calcd for C$_{13}$H$_{15}$N$_2$O$_2$Si [M+H]$^+$: 259.1. Found 259.0.

Step 4: 5-Cyano-3-ethynylpicolinic acid

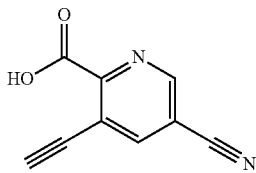

To a solution of 5-cyano-3-((trimethylsilyl)ethynyl)picolinic acid (110 mg, 425.78 umol) in THF (1.5 mL) was added NaOH (34.06 mg, 851.57 umol) and the mixture was stirred at 30° C. for 2 hrs. The mixture was diluted with H$_2$O (3 mL and extracted with EtOAc (5 mL×2). The EtOAc layer was discarded. The aqueous layer was then adjusted to pH=1 by addition of 1 N HCl, and the mixture was extracted with EtOAc (5 mL 2). The combined organic layers were dried over Na$_2$SO$_4$, filtered and concentrated under reduced pressure to afford the title compound (68 mg) as a pale yellow solid which was used without further purification. MS-ESI (m/z) calcd for C$_9$H$_5$N$_2$O$_2$ [M+H]$^+$: 173.0. Found 173.0.

287
Step 5: 5-Cyano-N-(3-(1-methoxyethyl)-1H-indazol-5-yl)-3,4-dimethylpicolinamide

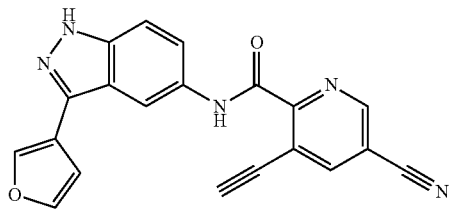 [SMILES: C#Cc1cc(C#N)cnc1C(=O)Nc1ccc2[nH]nc(-c3ccoc3)c2c1]

To a solution of 5-cyano-3-vinylpicolinic acid (20 mg, 116.18 umol) in DMF (1 mL) was added HOBt (23.55 mg, 174.28 umol), Et$_3$N (35.27 mg, 348.55 umol, 48.51 uL), EDCI (33.41 mg, 174.28 umol) and 3-(furan-3-yl)-1H-indazol-5-amine (23.14 mg, 116.18 umol). The reaction mixture was stirred at 30° C. for 12 hrs and then concentrated to afford a residue. The residue was purified by preparative HPLC using Method BC to afford the title compound (1.4 mg, 3%) as a yellow solid TFA salt. $^1$H NMR (400 MHz, DMSO-d$_6$) δ 13.38 (s, 1H), 9.32 (d, J=1.76 Hz, 1H), 9.24 (d, J=1.76 Hz, 1H), 8.46 (s, 1H), 8.17 (s, 1H), 7.82 (t, J=1.65 Hz, 1H), 7.75 (d, J=8.60 Hz, 1H), 7.42 (dd, J=1.87, 8.71 Hz, 1H), 7.05 (d, J=1.10 Hz, 1H), 5.77 (d, J=2.43 Hz, 1H), 4.95 (d, J=2.43 Hz, 1H). MS-ESI (m/z) calc'd for C$_{20}$H$_{12}$N$_5$O$_2$ [M+H]$^+$: 354.1. Found 354.0.

Example 151: 5-Cyano-3-methyl-N-(3-(1-methyl-6-oxo-1,6-dihydropyridin-3-yl)-1H-indazol-5-yl)picolinamide

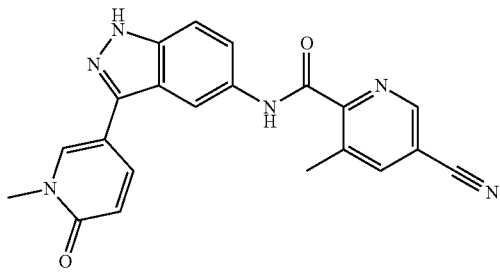 [SMILES: Cc1cc(C#N)cnc1C(=O)Nc1ccc2[nH]nc(-c3ccc(=O)n(C)c3)c2c1]

Prepared as described for 5-cyano-N-(3-(1,5-dimethyl-1H-pyrazol-4-yl)-1H-indazol-5-yl)-3-methylpicolinamide using (1-methyl-6-oxo-1,6-dihydropyridin-3-yl)boronic acid in place of (1,5-dimethyl-1H-pyrazol-4-yl)boronic acid to afford the title compound (22.18 mg, 27%) as a yellow solid. $^1$H NMR (400 MHz, DMSO-d$_6$) δ 13.18 (s, 1H), 10.71 (s, 1H), 9.00 (s, 1H), 8.40 (br d, J=13.8 Hz, 2H), 8.24 (d, J=2.1 Hz, 1H), 7.99 (dd, J=2.3, 9.3 Hz, 1H), 7.86 (br d, J=8.1 Hz, 1H), 7.57 (d, J=9.0 Hz, 1H), 6.58 (d, J=9.4 Hz, 1H), 3.57 (s, 3H), 2.60 (s, 3H). MS-ESI (m/z) calc'd for C$_{21}$H$_{17}$N$_6$O$_2$ [M+H]$^+$: 385.1. Found 385.0.

288
Example 152: 5-cyano-3-methyl-N-(3-(1-methyl-2-oxo-1,2-dihydropyridin-4-yl)-1H-indazol-5-yl)picolinamide

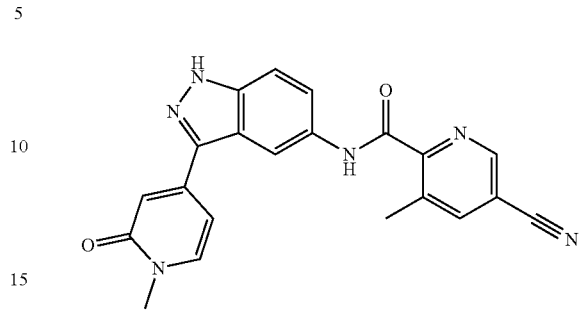

Prepared as described for 5-cyano-N-(3-(1,5-dimethyl-1H-pyrazol-4-yl)-1H-indazol-5-yl)-3-methylpicolinamide using (1-methyl-2-oxo-1,2-dihydropyridin-4-yl)boronic acid in place of (1,5-dimethyl-1H-pyrazol-4-yl)boronic acid to afford the title compound (7.75 mg, 8%) as a yellow solid. $^1$H NMR (400 MHz, DMSO-d$_6$) δ 13.62 (s, 1H), 10.87 (s, 1H), 9.01 (d, J=1.3 Hz, 1H), 8.68 (s, 1H), 8.42 (d, J=1.1 Hz, 1H), 7.92 (dd, J=9.2, 1.7 Hz, 1H), 7.80 (d, J=7.3 Hz, 1H), 7.65 (d, J=9.0 Hz, 1H), 6.95 (d, J=1.8 Hz, 1H), 6.87 (dd, J=7.1, 1.8 Hz, 1H), 6.85-6.90 (m, 1H), 6.85-6.90 (m, 1H), 3.48 (s, 3H), 2.61 ppm (s, 3H). MS-ESI (m/z) calc'd for C$_{21}$H$_{17}$N$_6$O$_2$[M+H]$^+$: 385.1. Found 385.0.

Example 153: 5-Cyano-3-methyl-N-(3-(1-methyl-1H-pyrazol-3-yl)-1H-indazol-5-yl)picolinamide

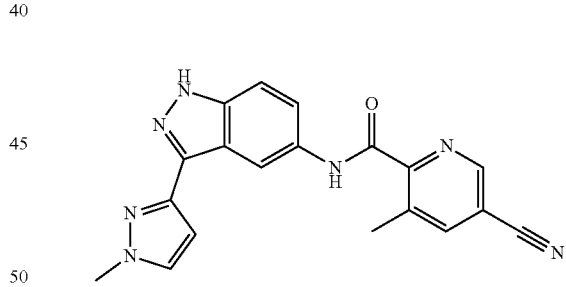

Prepared as described for 5-cyano-N-(3-(1,5-dimethyl-1H-pyrazol-4-yl)-1H-indazol-5-yl)-3-methylpicolinamide using (1-methyl-1H-pyrazol-3-yl)boronic acid in place of (1,5-dimethyl-1H-pyrazol-4-yl)boronic acid to afford the title compound (30.42 mg, 32%) as a yellow solid. $^1$H NMR (400 MHz, DMSO-d$_6$) δ 13.03 (br s, 1H), 10.71 (s, 1H), 8.99 (d, J=1.5 Hz, 1H), 8.67 (d, J=1.3 Hz, 1H), 8.40 (d, J=1.0 Hz, 1H), 7.79 (d, J=2.1 Hz, 1H), 7.74 (dd, J=2.0, 8.9 Hz, 1H), 7.53 (d, J=8.9 Hz, 1H), 6.69 (d, J=2.2 Hz, 1H), 3.96 (s, 3H), 2.57 (s, 3H). MS-ESI (m/z) calc'd for C$_{19}$H$_{16}$N$_7$O [M+H]$^+$: 358.1. Found 358.0.

Example 154: 5-Cyano-N-(3-(furan-3-yl)-1H-indazol-5-yl)-3-hydroxypicolinamide

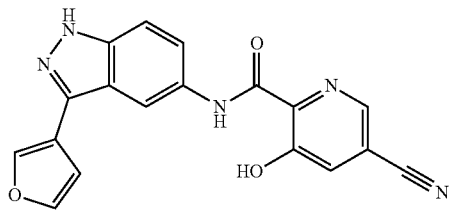 [SMILES: N#Cc1cnc(C(=O)Nc2ccc3[nH]nc(-c4ccoc4)c3c2)c(O)c1]

Step 1: 5-Bromo-3-hydroxypicolinic acid

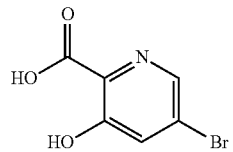 [SMILES: O=C(O)c1ncc(Br)cc1O]

To a solution of methyl 5-bromo-3-hydroxypicolinate (200 mg, 861.95 umol) in MeOH (4 mL) was added 6 M aqueous NaOH (0.8 mL) and the mixture was stirred at 20° C. for 3 hrs. The reaction mixture was then concentrated under reduced pressure and diluted with H$_2$O (3 mL). The mixture was adjusted to pH=4 with 1 N HCl, and then extracted with EtOAc (10 mL×5). The combined organic layers were dried over Na$_2$SO$_4$, filtered and concentrated under reduced pressure to afford the title compound (170 mg) as a white solid which was used without further purification. MS-ESI (m/z) calcd for C$_6$H$_5$BrNO$_3$ [M+H]$^+$: 217.9/219.9. Found 217.9/219.9.

Step 2: 5-Bromo-N-(3-(furan-3-yl)-1H-indazol-5-yl)-3-hydroxypicolinamide

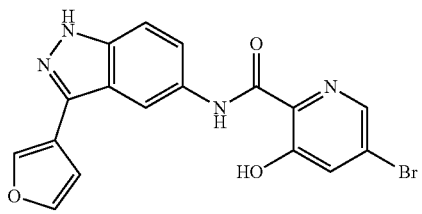 [SMILES: O=C(Nc1ccc2[nH]nc(-c3ccoc3)c2c1)c1ncc(Br)cc1O]

To a solution of 5-bromo-3-hydroxypicolinic acid (150 mg, 688.06 umol) in pyridine (5 mL) was added EDCI (263.80 mg, 1.38 mmol) and 3-(furan-3-yl)-1H-indazol-5-amine (150.77 mg, 756.86 umol) and the mixture was stirred at 20° C. for 3 hrs. The reaction mixture was concentrated under reduced pressure, then diluted with H$_2$O (8 mL) and MeOH (8 mL). The reaction mixture was concentrated under reduced pressure. The reaction was diluted with H$_2$O (20 mL) and filtered, the solid was dried under vacuum to afford the title compound (210 mg, 77%) as a brown solid which was used without further purification. MS-ESI (m/z) calcd for C$_{17}$H$_{12}$BrN$_4$O$_3$ [M+H]$^+$: 399.0/401.0. Found 399.0/401.0.

Step 3: 5-Cyano-N-(3-(furan-3-yl)-1H-indazol-5-yl)-3-hydroxypicolinamide

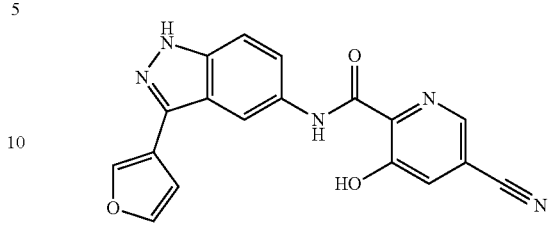

To a solution of 5-bromo-N-(3-(furan-3-yl)-1H-indazol-5-yl)-3-hydroxypicolinamide (210 mg, 526.06 umol) in DMF (5 mL) was added Zn(CN)$_2$ (74.13 mg, 631.27 umol) and Pd(PPh$_3$)$_4$ (60.79 mg, 52.61 umol) and the mixture was stirred at 100° C. for 5 hrs. The reaction mixture was then concentrated under reduced pressure and then diluted with H$_2$O (5 mL) and extracted with EtOAc (15 mL×6). The combined organic layers were dried over Na$_2$SO$_4$, filtered and concentrated under reduced pressure to give a residue. The residue was purified by preparative HPLC using Method BX to afford the title compound (12.42 mg, 5%) as a yellow solid, TFA salt. $^1$H NMR (400 MHz, DMSO-d$_6$) δ 13.16 (s, 1H) 12.53 (s, 1H) 11.11 (s, 1H) 8.67 (d, J=1.59 Hz, 1H) 8.43 (s, 1H) 8.32 (s, 1H) 8.13 (d, J=1.59 Hz, 1H) 7.83-7.91 (m, 2H) 7.59 (d, J=9.05 Hz, 1H) 7.02 (d, J=1.34 Hz, 1H). MS-ESI (m/z) calc'd for C$_{19}$H$_{12}$N$_5$O$_3$ [M+H]$^+$: 346.1. Found 346.0.

Example 155: 5-Cyano-N-(3-(1-methoxyethyl)-1H-indazol-5-yl)-3,4-dimethylpicolinamide

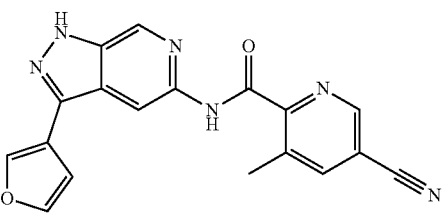 [SMILES: Cc1cc(C#N)cnc1C(=O)Nc1cc2c(-c3ccoc3)n[nH]c2cn1]

Step 1: 5-Chloro-3-iodo-1H-pyrazolo[3,4-c]pyridine

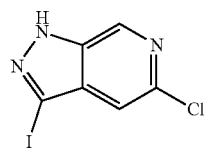 [SMILES: Clc1cc2c(I)n[nH]c2cn1]

To a solution of 5-chloro-1H-pyrazolo[3,4-c]pyridine (1 g, 6.51 mmol) in DMF (15 mL) was added KOH (548.02 mg, 9.77 mmol) and I$_2$ (2.48 g, 9.77 mmol) and the reaction mixture was stirred at 25° C. for 2 hrs. The reaction mixture was poured into saturated aqueous NaHCO$_3$ solution (30 mL). The aqueous phase was extracted with EtOAc (30 mL×3). The combined organic phases were washed with brine (30 mL×1), dried over Na$_2$SO$_4$, filtered and concentrated to afford the title compound (2.1 g) as an orange gum, which was used without further purification. MS-ESI (m/z) calcd for $C_6H_4ClIN_3$ [M+H]$^+$: 279.9/281.9. Found 279.9/281.9.

Step 2: 5-Chloro-3-iodo-1-(tetrahydro-2H-pyran-2-yl)-1H-pyrazolo[3,4-c]pyridine

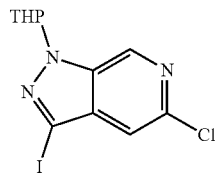

To a solution of 5-chloro-3-iodo-1H-pyrazolo[3,4-c]pyridine (1.3 g, 4.65 mmol) in DCM (15 mL) was added 3,4-dihydro-2H-pyran (586.93 mg, 6.98 mmol, 637.97 uL) and TsOH (160.21 mg, 930.35 umol) and the reaction mixture was stirred at 40° C. for 5 hr. The reaction mixture was poured into saturated aqueous NaHCO$_3$ solution (30 mL) and extracted with dichloromethane (30 mL×3). The combined organic phases were washed with brine (30 mL×1), dried over Na$_2$SO$_4$, filtered and concentrated to afford a residue. The residue was purified by flash silica gel chromatography using a 0-5% EtOAc/petroleum ether gradient eluent to afford the title compound (1.6 g, 95%) as a white solid. MS-ESI (m/z) calcd for $C_{11}H_{12}ClIN_3O$ [M+H]$^+$: 364.0/366.0. Found 363.9/365.9.

Step 3: 5-Chloro-3-(furan-3-yl)-1-(tetrahydro-2H-pyran-2-yl)-1H-pyrazolo[3,4-c]pyridine

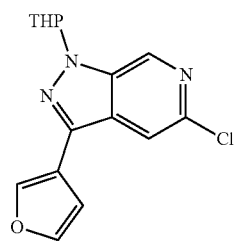

To a solution of 5-chloro-3-iodo-1-(tetrahydro-2H-pyran-2-yl)-1H-pyrazolo[3,4-c]pyridine (0.7 g, 1.93 mmol) and furan-3-ylboronic acid (129.25 mg, 1.16 mmol) in dioxane (12 mL) and H$_2$O (4 mL) was added Pd(dppf)Cl$_2$ (140.87 mg, 192.53 umol) and K$_2$CO$_3$ (798.26 mg, 5.78 mmol) under N$_2$. Then the reaction mixture was then stirred at 90° C. for 3 hrs under N$_2$. The reaction mixture was concentrated under reduced pressure at 40° C. and then poured into H$_2$O (20 mL). The aqueous phase was extracted with EtOAc (20 mL×3) and the combined organic phases were washed with brine (20 mL×1), dried over anhydrous Na$_2$SO$_4$, filtered and concentrated to afford a residue. The residue was purified by flash silica gel chromatography using a 0-5% EtOAc/petroleum ether gradient eluent to afford the title compound (400 mg, 68%) as a red solid. MS-ESI (m/z) calcd for $C_{15}H_{15}ClN_3O_2$[M+H]$^+$: 304.1/306.1. Found 304.1/306.1.

Step 4: N-(3-(Furan-3-yl)-1-(tetrahydro-2H-pyran-2-yl)-1H-pyrazolo[3,4-c]pyridin-5-yl)-1,1-diphenyl-methanimine

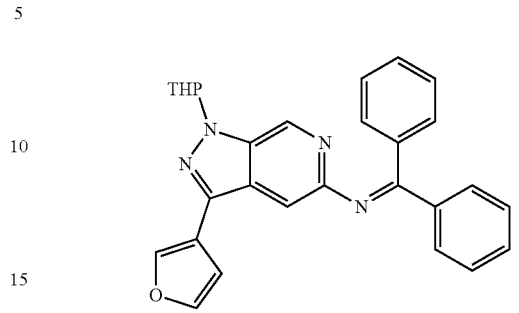

A mixture of 5-chloro-3-(furan-3-yl)-1-(tetrahydro-2H-pyran-2-yl)-1H-pyrazolo[3,4-c]pyridine (250 mg, 823.06 umol), diphenylmethanimine (179.00 mg, 987.68 umol, 165.74 uL), Pd$_2$(dba)$_3$ (75.37 mg, 82.31 umol), BINAP (51.25 mg, 82.31 umol) and t-BuONa (102.83 mg, 1.07 mmol) in toluene (3 mL) was degassed and purged with N$_2$ (3×). The mixture was stirred at 110° C. for 12 hrs under an N$_2$ atmosphere. The reaction mixture was filtered and the filtrate was concentrated. The residue was purified by flash silica gel chromatography using a 0-13% EtOAc/petroleum ether gradient eluent to afford the title compound (190 mg, 51%) as a yellow oil. MS-ESI (m/z) calcd for $C_{28}H_{25}N_4O_2$ [M+H]$^+$: 449.2. Found 449.2.

Step 5: 3-(Furan-3-yl)-1-(tetrahydro-2H-pyran-2-yl)-1H-pyrazolo[3,4-c]pyridin-5-amine

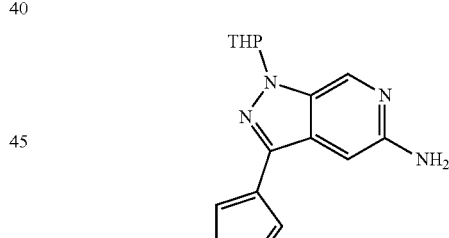

To a solution of N-(3-(furan-3-yl)-1-(tetrahydro-2H-pyran-2-yl)-1H-pyrazolo[3,4-c]pyridin-5-yl)-1,1-diphenyl-methanimine (160 mg, 356.73 umol) in THF (2 mL) was added HCl (4 M, 500.00 uL). Then the reaction mixture was stirred at 25° C. for 0.1 hr and then poured into H$_2$O (10 mL) and washed with EtOAc (10 mL×1). Then the aqueous phase was adjusted to pH 8 with saturated aqueous NaHCO$_3$ solution and extracted with EtOAc (10 mL×3). The combined organic phases were washed with brine (10 mL×1), dried over Na$_2$SO$_4$, filtered and concentrated to afford the title compound (101 mg) as a yellow oil, which was used without further purification. MS-ESI (m/z) calcd for $C_{15}H_{17}N_4O_2$ [M+H]$^+$: 285.1. Found 285.1.

Step 6: 5-Cyano-N-(3-(furan-3-yl)-1-(tetrahydro-2H-pyran-2-yl)-1H-pyrazolo[3,4-c]pyridin-5-yl)-3-methylpicolinamide

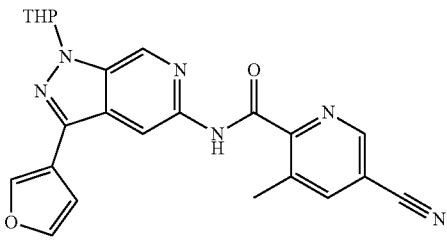

To a solution of 3-(furan-3-yl)-1-(tetrahydro-2H-pyran-2-yl)-1H-pyrazolo[3,4-c]pyridin-5-amine (85 mg, 298.97 umol) and 5-cyano-3-methylpicolinic acid (48.48 mg, 298.97 umol) in pyridine (2 mL) was added EDCI (171.94 mg, 896.90 umol) and the reaction mixture was stirred at 25° C. for 2 hrs. The mixture was then concentrated under reduced pressure at 40° C. The residue was poured into $H_2O$ (2 mL) and extracted with EtOAc (2 mL×3). The combined organic phases were washed with brine (2 mL×1), dried over $Na_2SO_4$, filtered and concentrated to afford the title compound (140 mg) as a yellow oil, which was used without further purification. MS-ESI (m/z) calcd for $C_{23}H_{21}N_6O_3$ [M+H]$^+$: 429.2. Found 429.1.

Step 7: 5-Cyano-N-(3-(1-methoxyethyl)-1H-indazol-5-yl)-3,4-dimethylpicolinamide

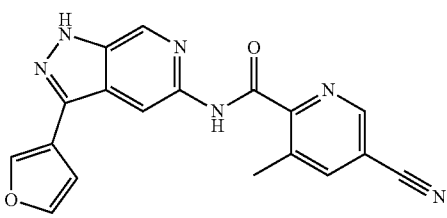 [SMILES: Cc1cc(C#N)cnc1C(=O)Nc1cc2c(-c3ccoc3)n[nH]c2cn1]

To a solution of 5-cyano-N-(3-(furan-3-yl)-1-(tetrahydro-2H-pyran-2-yl)-1H-pyrazolo[3,4-c]pyridin-5-yl)-3-methylpicolinamide (70 mg, 163.38 umol) in DCM (1 mL) was added TFA (770.00 mg, 6.75 mmol, 0.5 mL) and the reaction mixture was stirred at 25° C. for 12 hrs. The mixture was then directly purified by preparative HPLC using Method BF to afford the title compound (4.01 mg, 6%) as a yellow solid, HCl salt. $^1$H NMR (400 MHz, DMSO-d$_6$) δ 10.83 (s, 1H), 9.00 (s, 1H), 8.92 (s, 1H), 8.65 (s, 1H), 8.43 (s, 1H), 8.31 (s, 1H), 7.90 (t, J=1.6 Hz, 1H), 7.03 (d, J=1.0 Hz, 1H), 2.66 (s, 3H). MS-ESI (m/z) calc'd for $C_{18}H_3N_6O_2$[M+H]$^+$: 345.1 Found 345.0.

Example 156: 5-Cyano-3-methyl-N-(3-(thiazol-4-yl)-1H-indazol-5-yl)picolinamide

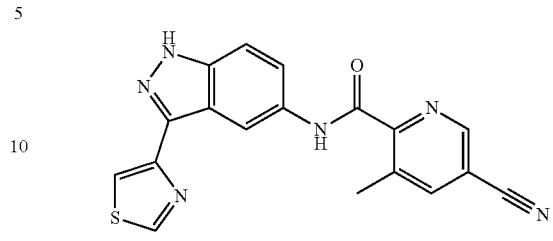

A mixture of N-(3-bromo-1H-indazol-5-yl)-5-cyano-3-methylpicolinamide (40 mg, 112.30 umol), 4-(tributylstannyl)thiazole (42.02 mg, 112.30 umol) and Pd(t-Bu$_3$P)$_2$ (5.74 mg, 11.23 umol) were taken up into a microwave tube in DMF (2 mL) under $N_2$. The sealed tube was heated at 150° C. for 1 hr under microwave irradiation. The reaction mixture was filtered and the filtrate was concentrated to give a residue. The residue was purified by preparative HPLC using Method BY to afford the title compound (11.93 mg, 29%) as a yellow solid. $^1$H NMR (400 MHz, DMSO-d$_6$) δ 13.28 (br s, 1H), 10.74 (br s, 1H), 9.33 (d, J=2.0 Hz, 1H), 9.00 (d, J=1.3 Hz, 1H), 8.87 (s, 1H), 8.41 (d, J=1.1 Hz, 1H), 8.12 (d, J=2.0 Hz, 1H), 7.72 (dd, J=1.9, 8.9 Hz, 1H), 7.58 (d, J=9.0 Hz, 1H), 2.58 (s, 3H). MS-ESI (m/z) calc'd for C18H$_{13}$N$_6$OS [M+H]$^+$: 361.1. Found 361.1.

Example 157: 5-Cyano-N-(3-(1-(difluoromethyl)-1H-pyrazol-4-yl)-1H-indazol-5-yl)-3,4-dimethylpicolinamide

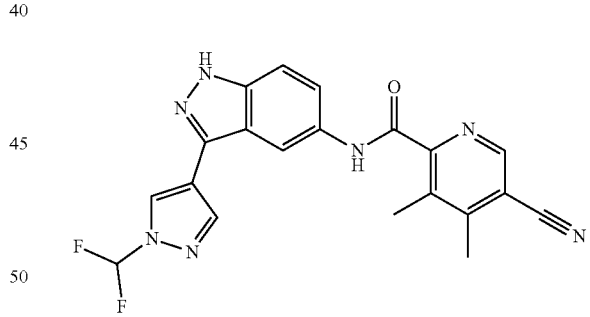

Prepared as described for 5-cyano-N-(7-fluoro-3-(furan-3-yl)-1H-indazol-5-yl)-3-methylpicolinamide using 5-cyano-3,4-dimethylpicolinic acid in place of 5-cyano-3-methylpicolinic acid and using 3-(1-(difluoromethyl)-1H-pyrazol-4-yl)-1H-indazol-5-amine in place of 7-fluoro-3-(furan-3-yl)-1H-indazol-5-amine to afford the title compound (77 mg, 95%) as a pale yellow solid. $^1$H NMR (400 MHz, DMSO-d$_6$) δ 13.20 (s, 1H), 10.68 (s, 1H), 8.90 (s, 1H), 8.72 (s, 1H), 8.46-8.38 (m, 1H), 8.29 (s, 1H), 7.93 (t, J=59.0 Hz, 1H), 7.77 (dd, J=9.0, 1.9 Hz, 1H), 7.62-7.54 (m, 1H), 2.56 (s, 3H), 2.48 (s, 3H). MS-ESI (m/z) calc'd for $C_{20}H_{16}F_2N_7O$ [M+H]$^+$: 408.1. Found 408.2.

Example 158: 5-Cyano-3,4-dimethyl-N-(3-(oxazol-5-yl)-1H-indazol-5-yl)picolinamide

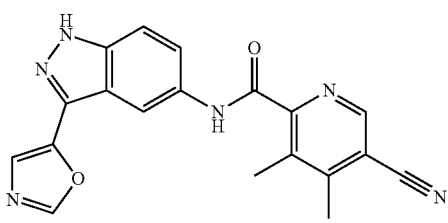

Step 1: (Z)-4-Amino-3-methylpent-3-en-2-one

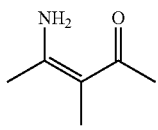

3-Methylpentane-2,4-dione (27.78 mL, 219.03 mmol) and NH₄OH (75.0 mL, 1925.8 mmol) were combined and stirred at 25° C. for 2 hrs. A white solid formed and the mixture was extracted with Et₂O. The combined organic layers were evaporated to give a yellow residue that was triturated with cyclohexane and then filtered and concentrated to afford the title compound (18.2 g, 73%) as a pale yellow solid. $^1$H NMR (400 MHz, DMSO-$d_6$) δ 10.20 (bs, 1H), 7.15 (bs, 1H), 1.99 (s, 3H), 1.89 (s, 3H), 1.74 (s, 3H). MS-ESI (m/z) calc'd for $C_6H_{12}NO$ [M+H]⁺: 114.1. Found 114.0.

Step 2: 4,5,6-Trimethyl-2-oxo-1,2-dihydropyridine-3-carbonitrile

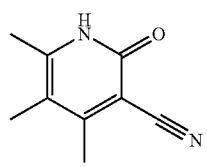

To a solution of (Z)-4-amino-3-methylpent-3-en-2-one (18.2 g, 160.83 mmol) in THF (120 mL) was added dropwise a solution of malononitrile (10.62 g, 160.83 mmol) in THF (40 mL) and the mixture was stirred at 25° C. for 15 hrs. The solid that formed was collected by filtration and washed with EtOAc to afford the title compound (17.89 g, 69%) as a white solid. $^1$H NMR (400 MHz, DMSO-$d_6$) δ 12.17 (s, 1H), 2.32 (s, 3H), 2.25 (s, 3H), 1.93 (s, 3H). MS-ESI (m/z) calc'd for $C_9H_{11}N_2O$ [M+H]⁺: 163.1. Found 163.0.

Step 3: 2-Chloro-4,5,6-trimethylnicotinonitrile

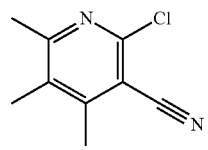

A suspension of 4,5,6-trimethyl-2-oxo-1,2-dihydropyridine-3-carbonitrile (17.89 g, 110.3 mmol) in POCl₃ (70.0 mL, 748.71 mmol) was heated at 100° C. for 15 hrs. The solution was concentrated and then poured into H₂O (1 L) and the pH was adjusted to 7 by addition of Na₂CO₃. The solid that formed was collected by filtration and concentrated to afford the title compound (18.59 g, 93%) as a yellow solid. $^1$H NMR (400 MHz, DMSO-$d_6$) δ 2.51 (s, 3H), 2.47 (s, 3H), 2.22 (s, 3H). MS-ESI (m/z) calc'd for $C_9H_{10}ClN_2$ [M+H]⁺: 163.1. Found 181.0.

Step 4: 4,5,6-Trimethylnicotinonitrile

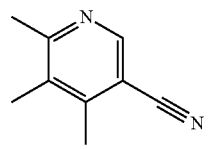

To a solution of 2-chloro-4,5,6-trimethylnicotinonitrile (1.81 g, 10 mmol) in MeOH (50 mL) was added 10% Pd/C (1.06 g, 1 mmol) followed by ammonium formate (630.6 mg, 10 mmol) and the mixture was stirred at 60° C. for 1 hr. The reaction mixture was filtered through Celite and the filtrate was evaporated to dryness. The residue was taken up in water and extracted with DCM (3×). The combined organic layers were passed through a phase separator and concentrated to afford the title compound (1.19 g, 81%) as a yellow solid. $^1$H NMR (400 MHz, DMSO-$d_6$) δ 8.61 (s, 1H), 2.53 (s, 3H), 2.44 (s, 3H), 2.23 (s, 3H). MS-ESI (m/z) calc'd for $C_9H_{10}N_2$ [M+H]⁺: 147.1. Found 146.9.

Step 5: 5-Cyano-2,3,4-trimethylpyridine 1-oxide

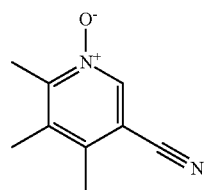

To a solution of 4,5,6-trimethylnicotinonitrile (1.19 g, 8.14 mmol) in DCM (40.7 mL) was added MCPBA (2.01 g, 8.14 mmol) and the mixture was stirred at 25° C. for 5 hrs. The solution was washed with K₂CO₃ solution (3×) and the aqueous layer was extracted with DCM (3×). The organic phases were combined, passed through a phase separator and concentrated to afford the title compound (1.19 g, 90%) as a yellow solid. $^1$H NMR (400 MHz, DMSO-$d_6$) δ 8.73 (s, 1H), 2.44 (s, 3H), 2.39 (s, 3H), 2.28 (s, 3H). MS-ESI (m/z) calc'd for $C_9H_{11}N_2O$ [M+H]$^+$: 163.1. Found 163.0.

Step 6:
6-(Hydroxymethyl)-4,5-dimethylnicotinonitrile

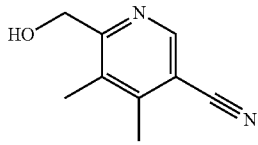

To a solution of 5-cyano-2,3,4-trimethylpyridine 1-oxide (4.15 g, 25.59 mmol) in DCM (39.15 mL) was added dropwise 2,2,2-trifluoroacetic anhydride (10.67 mL, 76.76 mmol) in DCM (39.15 mL) at 0° C. and the mixture was stirred at 25° C. for 15 hrs. The solvent was evaporated to give a red oil that was dissolved in MeOH (50 mL). $K_2CO_3$ (3 g) was added and the suspension was stirred for 15 min. The solvent was evaporated, the residue was taken up in $H_2O$ and extracted with DCM (3×). The combined organic layers were passed through a phase separator and concentrated to afford the title compound (3.65 g, 88%) as a dark orange solid. $^1$H NMR (400 MHz, DMSO-$d_6$) δ 8.70 (s, 1H), 5.22 (t, J=5.6 Hz, 1H), 4.63 (d, J=5.4 Hz, 2H), 2.45 (s, 3H), 2.29 (s, 3H). MS-ESI (m/z) calc'd for $C_9H_{11}N_2O$ [M+H]$^+$: 163.1. Found 163.0.

Step 7: 5-Cyano-3,4-dimethylpicolinic acid

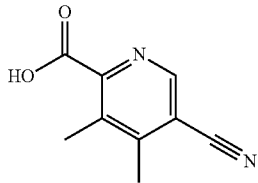

To a solution of 6-(hydroxymethyl)-4,5-dimethylnicotinonitrile (3.65 g, 22.5 mmol) in acetone (62.98 mL) was added dropwise (over 15 min) a solution of $KMnO_4$ (3.91 g, 24.75 mmol) in $H_2O$ (31.49 mL) at 25° C. and the mixture was stirred for 30 minutes. The dark mixture was filtered and the solid was washed with 1 M aqueous $K_2CO_3$. The filtrate was concentrated to remove the organic solvent. The pH was adjusted to 4-5 by addition of 6 M HCl and the solution was extracted with EtOAc (3×). Then another portion of 6 M HCl was added until pH 1 and the aqueous phase was further extracted with EtOAc (3×). The combined organic layers were passed through a phase separator and concentrated to afford the title compound (1.75 g, 44%) as a beige solid. $^1$H NMR (400 MHz, DMSO-$d_6$) δ 13.81 (s, 1H), 8.78 (s, 1H), 2.50 (s, 3H), 2.33 (s, 3H). MS-ESI (m/z) calc'd for $C_9H_9N_2O_2$ [M+H]$^+$: 177.1. Found 177.1.

Step 8: 5-(5-Nitro-1H-indazol-3-yl)oxazole

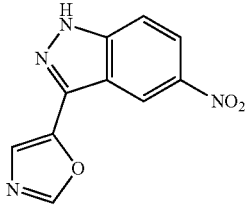 [SMILES: O=[N+]([O-])c1ccc2[nH]nc(-c3cnco3)c2c1]

To a suspension of 5-nitro-1H-indazole-3-carbaldehyde (1.91 g, 10 mmol) and 1-(isocyanomethylsulfonyl)-4-methylbenzene (2.15 g, 11 mmol) in MeOH (50 mL) was added $K_2CO_3$ (2.76 g, 20 mmol) and the mixture was stirred at 65° C. for 15 minutes. The mixture was poured into water and the solid that formed was collected by vacuum filtration and dried. The material was purified by silica gel column chromatography using a 0-100% EtOAc/cyclohexane gradient eluent to afford the title compound (653 mg, 28%) as a yellow solid. $^1$H NMR (400 MHz, DMSO-$d_6$) δ 14.13 (s, 1H), 8.96 (dd, J=2.1, 0.7 Hz, 1H), 8.64 (s, 1H), 8.28 (dd, J=9.2, 2.1 Hz, 1H), 7.96 (s, 1H), 7.82 (dd, J=9.2, 0.7 Hz, 1H). MS-ESI (m/z) calc'd for $C_{10}H_7N_4O_3$ [M+H]$^+$: 231.0. Found 231.1.

Step 9: 3-(Oxazol-5-yl)-1H-indazol-5-amine

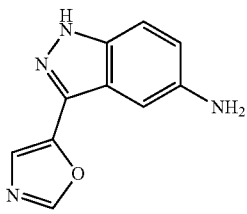

A mixture of 5-(5-nitro-1H-indazol-3-yl)oxazole (653.0 mg, 2.84 mmol) in MeOH (56.74 mL) was hydrogenated in the presence of 10% Pd/C (0.3 g, 0.280 mmol) at 25° C. for 2 hrs. The catalyst was removed by filtration through Celite and the solvent was concentrated to afford the title compound (516 mg, 91%) as a yellow solid. $^1$H NMR (400 MHz, DMSO-$d_6$) δ 12.99 (s, 1H), 8.48 (s, 1H), 7.51 (s, 1H), 7.31 (dd, J=8.8, 0.7 Hz, 1H), 7.03 (dd, J=2.0, 0.8 Hz, 1H), 6.86 (dd, J=8.8, 2.0 Hz, 1H), 4.98 (s, 2H). MS-ESI (m/z) calc'd for $C_{10}H_9N_4O$ [M+H]$^+$: 201.1. Found 201.1.

Step 10: 5-Cyano-3,4-dimethyl-N-(3-(oxazol-5-yl)-1H-indazol-5-yl)picolinamide

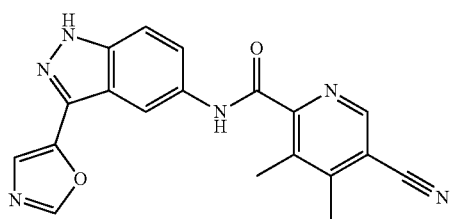

To a mixture of 5-cyano-3,4-dimethylpicolinic acid (330.0 mg, 1.84 mmol), 3-(oxazol-5-yl)-1H-indazol-5-amine (404.26 mg, 2.02 mmol) and Et$_3$N (255.86 uL, 1.84 mmol) in MeCN (18.36 mL) was added HATU (698.0 mg, 1.84 mmol) and the reaction was stirred at 25° C. for 2 hrs. Water was added and a solid precipitated which was collected by vacuum filtration, washed with H$_2$O and dried to afford the title compound (626 mg, 95%) as a yellow solid. $^1$H NMR (600 MHz, DMSO-d$_6$) δ 13.51 (s, 1H), 10.76 (s, 1H), 8.89 (s, 1H), 8.59 (s, 2H), 7.74 (dd, J=8.9, 1.5 Hz, 1H), 7.64 (s, 1H), 7.63 (d, J=8.9 Hz, 1H), 2.55 (s, 3H), 2.46 (s, 3H). MS-ESI (m/z) calc'd for C$_{19}$H$_{15}$N$_6$O$_2$[M+H]$^+$: 359.1. Found 359.2.

Example 159: 5-Cyano-N-(3-(2-methoxypyridin-4-yl)-1H-indazol-5-yl)-3,4-dimethylpicolinamide

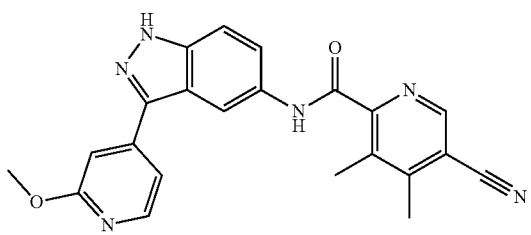 [SMILES: COc1cc(-c2n[nH]c3ccc(NC(=O)c4ncc(C#N)c(C)c4C)cc23)ccn1]

Prepared as described for 5-cyano-N-(7-fluoro-3-(furan-3-yl)-1H-indazol-5-yl)-3-methylpicolinamide using 5-cyano-3,4-dimethylpicolinic acid in place of 5-cyano-3-methylpicolinic acid and using 3-(2-methoxypyridin-4-yl)-1H-indazol-5-amine in place of 7-fluoro-3-(furan-3-yl)-1H-indazol-5-amine to afford the title compound (70 mg, 88%) as a yellow solid. $^1$H NMR (400 MHz, DMSO-d$_6$) δ 13.58 (s, 1H), 10.78 (s, 1H), 8.90 (s, 1H), 8.65 (d, J=1.8 Hz, 1H), 8.30 (d, J=5.5 Hz, 1H), 7.83 (dd, J=8.9, 1.5 Hz, 1H), 7.65 (d, J=9.0 Hz, 1H), 7.57 (dd, J=5.4, 1.4 Hz, 18H), 7.30 (t, J=1.0 Hz, 1H), 3.93 (s, 3H), 2.56 (s, 3H), 2.47 (s, 3H). MS-ESI (m/z) calc'd for C$_{22}$H$_{19}$N$_6$O$_2$ [M+H]$^+$: 399.2. Found 399.2.

Example 160: 5-Cyano-N-(3-(isothiazol-4-yl)-1H-indazol-5-yl)-3-methylpicolinamide

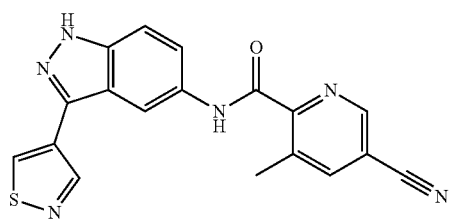

Prepared as described for 5-cyano-N-(3-(1,5-dimethyl-1H-pyrazol-4-yl)-1H-indazol-5-yl)-3-methylpicolinamide using isothiazol-4-ylboronic acid in place of (1,5-dimethyl-1H-pyrazol-4-yl)boronic acid to afford the title compound (27.23 mg, 34%) as a yellow solid. $^1$H NMR (400 MHz, DMSO-d$_6$) δ 13.32 (br s, 1H), 10.75 (s, 1H), 9.41 (s, 1H), 9.11 (s, 1H), 8.98 (d, J=1.54 Hz, 1H), 8.56 (d, J=1.10 Hz, 1H), 8.39 (d, J=10 Hz, 1H), 7.80 (dd, J=9.04, 1.54 Hz, 1H), 7.60 (d, J=9.04 Hz, 1H), 2.59 (s, 3H). MS-ESI (m/z) calc'd for C$_{18}$H$_{13}$N$_6$OS [M+H]$^+$: 361.1. Found 361.0.

Example 161: 5-Cyano-N-(3-(furan-3-yl)-1H-pyrazolo[4,3-d]pyrimidin-5-yl)-3-methylpicolinamide

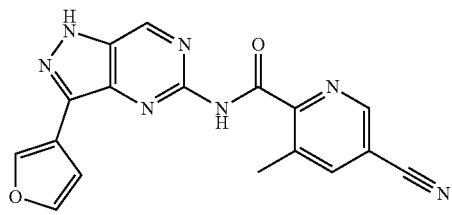 [SMILES: Cc1cc(C#N)cnc1C(=O)Nc1ncc2[nH]nc(-c3ccoc3)c2n1]

Step 1: 5-Chloro-3-iodo-1H-pyrazolo[4,3-d]pyrimidine

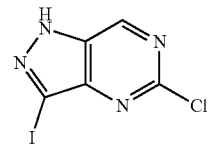

To a solution of 5-chloro-1H-pyrazolo[4,3-d]pyrimidine (400 mg, 2.59 mmol) in DMF (5 mL) was added N-iodosuccinimide (698.72 mg, 3.11 mmol) and the mixture was stirred at 30° C. for 12 hrs. The reaction mixture was then concentrated under reduced pressure to give a residue. The residue was diluted with H$_2$O (10 mL) and a pale yellow solid precipitated. The solid was collected by filtration, washed with H$_2$O (20 mL), and dried to afford the title compound (470 mg, 65%) as a pale yellow solid which was used without further purification. MS-(ESI) (m/z) calcd for C$_5$H$_3$ClIN$_4$ (M+H)$^+$: 280.9/282.9. Found 280.8/282.8.

Step 2: 5-Chloro-3-iodo-1-(tetrahydro-2H-pyran-2-yl)-1H-pyrazolo[4,3-d]pyrimidine

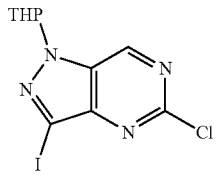

To a solution of 5-chloro-3-iodo-1H-pyrazolo[4,3-d]pyrimidine (470 mg, 1.51 mmol) in CHCl$_3$ (8 mL) was added MsOH (14.50 mg, 150.83 umol) and 3,4-dihydro-2H-pyran (380.61 mg, 4.52 mmol) and the mixture was stirred at 70° C. for 3 hrs. The reaction mixture was concentrated and purified by flash silica gel chromatography (ISCO; 4 g SepaFlash column) using a 0-9% EtOAc/petroleum ether gradient eluent to afford the title compound (470 mg, 50%) as a pale yellow solid. MS-(ESI) (m/z) calcd for C$_{10}$H$_{11}$ClIN$_4$O (M+H)$^+$: 365.0/367.0. Found 364.9/366.9.

Step 3: 5-Chloro-3-(furan-3-yl)-1-(tetrahydro-2H-pyran-2-yl)-1H-pyrazolo[4,3-d]pyrimidine

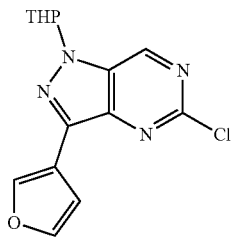

A mixture of 5-chloro-3-iodo-1-(tetrahydro-2H-pyran-2-yl)-1H-pyrazolo[4,3-d]pyrimidine (470 mg, 1.29 mmol), furan-3-ylboronic acid (158.67 mg, 1.42 mmol), Pd(Amphos)Cl$_2$ (91.28 mg, 128.92 umol), AcOK (379.57 mg, 3.87 mmol) in EtOH (4 mL) and H$_2$O (1 mL) was degassed and purged with N$_2$ (3×). The mixture was stirred at 90° C. for 3 hrs under an N$_2$ atmosphere. The reaction mixture was then concentrated and purified by flash silica gel chromatography (ISCO; 20 g SepaFlash column) using a 0-10% EtOAc/petroleum ether gradient eluent to afford the title compound (250 mg, 64%) as a purple solid. MS-(ESI) (m/z) calcd for C$_{14}$H$_{14}$ClN$_4$O$_2$(M+H)$^+$: 305.1/307.1. Found 305.0/307.0.

Step 4: 5-Cyano-N-(3-(furan-3-yl)-1-(tetrahydro-2H-pyran-2-yl)-1H-pyrazolo[4,3-d]pyrimidin-5-yl)-3-methylpicolinamide

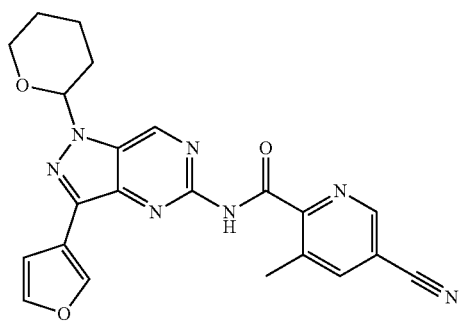 [SMILES: Cc1cc(C#N)cnc1C(=O)Nc1ncc2c(n1)c(-c1ccoc1)nn2C1CCCCO1]

A mixture of 5-chloro-3-(furan-3-yl)-1-(tetrahydro-2H-pyran-2-yl)-1H-pyrazolo[4,3-d]pyrimidine (250 mg, 820.40 umol), 5-cyano-3-methylpicolinamide (158.66 mg, 984.47 umol), Pd$_2$(dba)$_3$ (75.13 mg, 82.04 umol), Xantphos (47.47 mg, 82.04 umol) and Cs$_2$CO$_3$ (374.22 mg, 1.15 mmol) in dioxane (3 mL) was degassed and purged with N$_2$ (3×), and then the mixture was stirred at 100° C. for 12 hrs under an N$_2$ atmosphere. The reaction mixture was concentrated and purified by flash silica gel chromatography (ISCO; 20 g SepaFlash column) using a 0-30% EtOAc/petroleum ether gradient eluent to afford the title compound (240 mg, 68%) as a yellow solid. MS-(ESI) (m/z) calcd for C$_{22}$H$_{20}$N$_7$O$_3$ (M+H)$^+$: 430.2. Found 430.1.

Step 5: 5-Cyano-N-(3-(furan-3-yl)-1H-pyrazolo[4,3-d]pyrimidin-5-yl)-3-methylpicolinamide

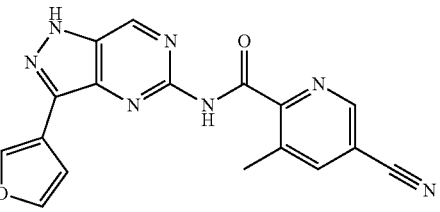

To a solution of 5-cyano-N-(3-(furan-3-yl)-1-(tetrahydro-2H-pyran-2-yl)-1H-pyrazolo[4,3-d]pyrimidin-5-yl)-3-methylpicolinamide (100 mg, 232.87 umol) in MeOH (2 mL) and H$_2$O (0.4 mL) was added 4-toluenesulfonic acid (120.30 mg, 698.60 umol) and the mixture was stirred at 70° C. for 2 hrs. The reaction mixture was concentrated and purified by preparative HPLC using Method BV to afford the title compound (6.66 mg, 6%) as a white solid, TFA salt. $^1$H NMR (400 MHz, DMSO-d$_6$) δ 12.94 (br s, 1H), 10.46 (br s, 1H), 8.36 (br s, 1H), 8.01 (br s, 1H), 7.56 (s, 1H), 7.05-7.49 (m, 1H), 6.98-7.01 (m, 1H), 6.09-6.20 ppm (m, 1H). MS-ESI (m/z) calc'd for C$_{17}$H$_{12}$N$_7$O$_2$ [M+H]$^+$: 346.1. Found 346.0.

Example 162: 6-Cyano-N-(3-(furan-3-yl)-1H-indazol-5-yl)-4-methylpyridazine-3-carboxamide

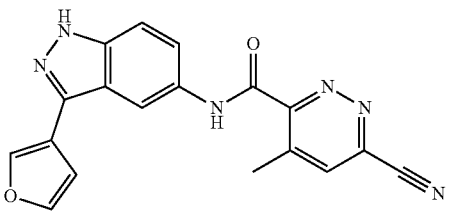 [SMILES: Cc1cc(C#N)nnc1C(=O)Nc1ccc2[nH]nc(-c3ccoc3)c2c1]

Step 1: 6-Hydroxy-5-methylpyridazine-3-carbonitrile

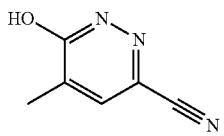

A stirred mixture of 6-chloro-4-methylpyridazin-3-ol (2.5 g, 17.29 mmol), Zn(CN)$_2$ (2.64 g, 22.48 mmol, 1.43 mL), Pd$_2$(dba)$_3$ (791.82 mg, 864.70 umol) and DPPF (766.99 mg, 1.38 mmol) in DMF (18 mL) was degassed and then heated to 120° C. for 3 hrs under N$_2$. After cooling to 25° C., the reaction mixture was concentrated to afford a residue which was diluted with dichloromethane (50 mL) and saturated aqueous NaHCO$_3$ (50 mL). The aqueous layer was separated and extracted with dichloromethane (50 mL×3) and DCM/i-PrOH (4/1) (50 mL×3). The combined organic layers were dried over Na$_2$SO$_4$, filtered and concentrated to give a residue. The residue was triturated with a mixture of petroleum ether/EtOAc (3:1) (40 mL) and filtered. The solid obtained was washed with petroleum ether (30 mL) and dried to afford the title compound (2 g) as a brown solid, which was used without further purification. MS-ESI (m/z) calcd for $C_6H_6N_3O$ [M+H]$^+$: 136.0. Found 136.1.

Step 2: 6-Chloro-5-methylpyridazine-3-carbonitrile

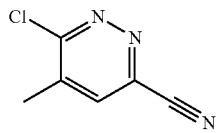

To a stirred solution of 6-hydroxy-5-methylpyridazine-3-carbonitrile (2 g, 14.80 mmol) in MeCN (15 mL) was added $POCl_3$ (6.81 g, 44.40 mmol, 4.13 mL) and the reaction mixture was stirred at 80° C. for 3 hrs. After cooling to 20° C., the mixture was concentrated to give a residue which was diluted with EtOAc (20 mL) and poured into ice-water (w/w=1/1) (50 mL). The aqueous phase was extracted with EtOAc (20 mL×3). The combined organic phases were washed with brine (20 mL×1), dried over $Na_2SO_4$, filtered and concentrated. The residue obtained was purified by silica gel column chromatography using 0-20% EtOAc/petroleum ether gradient eluent to afford the title compound (1.5 g, 66%) as a pale brown solid. MS-ESI (m/z) calcd for $C_6H_5ClN_3$ [M+H]$^+$: 154.0/156.0. Found 153.9/155.9.

Step 3: 6-(1-Ethoxyvinyl)-5-methylpyridazine-3-carbonitrile

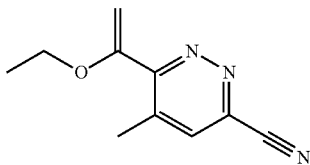

A stirred mixture of 6-chloro-5-methylpyridazine-3-carbonitrile (800 mg, 5.21 mmol), tributyl(1-ethoxyvinyl)stannane (3.76 g, 10.42 mmol, 3.52 mL) and $Pd(PPh_3)_2Cl_2$ (182.82 mg, 260.47 umol) in dioxane (20 mL) was degassed and then heated to 80° C. for 12 hrs under $N_2$. After cooling to 25° C., the reaction mixture was concentrated to give a residue. The residue was purified by silica gel column chromatography using 0-20% EtOAc/petroleum ether gradient eluent to afford the title compound (800 mg, 81%) as a light yellow oil. MS-ESI (m/z) calcd for $C_{10}H_{12}N_3O$ [M+H]$^+$: 190.1. Found 190.1.

Step 4: Ethyl 6-cyano-4-methylpyridazine-3-carboxylate

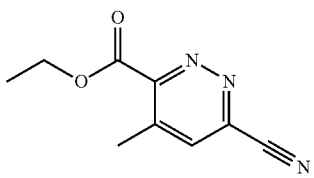

To a stirred solution of 6-(1-ethoxyvinyl)-5-methylpyridazine-3-carbonitrile (800 mg, 4.23 mmol) in dioxane (30 mL) was added a solution of $NaIO_4$ (1.81 g, 8.46 mmol, 468.57 uL) in $H_2O$ (15 mL), followed by $KMnO_4$ (133.63 mg, 845.61 umol) and the reaction mixture was stirred at 25° C. for 12 hrs. The reaction mixture was then filtered and washed with EtOAc (20 mL). The filtrate was diluted with $H_2O$ (20 mL) and extracted with EtOAc (20 mL×3). The combined organic phases were concentrated and purified by silica gel column chromatography using a 0-20% EtOAc/petroleum ether gradient eluent to afford the title compound (410 mg, 51%) as a light yellow oil. MS-ESI (m/z) calcd for $C_9H_{10}N_3O_2$[M+H]$^+$: 192.1 Found 192.1.

Step 5: 6-Cyano-4-methylpyridazine-3-carboxylic acid

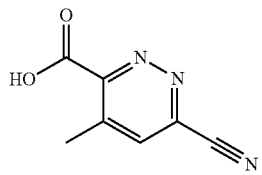

To a stirred solution of ethyl 6-cyano-4-methylpyridazine-3-carboxylate (30 mg, 156.92 umol) in THF (2 mL) was added NaOH (8.16 mg, 203.99 umol) at 0° C. and the reaction mixture was warmed to 25° C. and stirred for 12 hrs. The reaction mixture was adjusted to pH=3 with 1 N aqueous citric acid and extracted with EtOAc (5 mL×3). The combined organic phases were washed with brine (5 mL×1), dried over $Na_2SO_4$, filtered and concentrated to afford the title compound (60 mg) as a brown solid, which was used without further purification. MS-ESI (m/z) calcd for $C_7H_6N_3O_2$ [M+H]$^+$: 164.0 Found 164.0.

Step 6: 6-Cyano-N-(3-(furan-3-yl)-1H-indazol-5-yl)-4-methylpyridazine-3-carboxamide

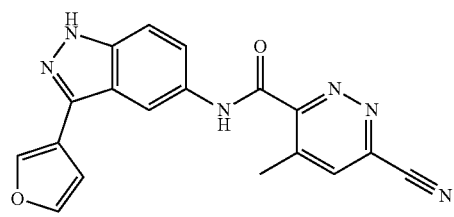 [SMILES: Cc1cc(C#N)nnc1C(=O)Nc1ccc2[nH]nc(-c3ccoc3)c2c1]

To a stirred solution of 6-cyano-4-methylpyridazine-3-carboxylic acid (60 mg, 367.80 umol) and 3-(furan-3-yl)-1H-indazol-5-amine (36.63 mg, 183.90 umol) in pyridine (2 mL) was added EDCI (105.76 mg, 551.70 umol) and the reaction mixture was stirred at 25° C. for 3 hrs.

The reaction mixture was then concentrated to give a residue which was purified by preparative HPLC using Method BH to afford the title compound (14.99 mg, 11%) as a yellow solid. $^1$H NMR (400 MHz, DMSO-d$_6$) δ 13.14 (br s, 1H), 11.05 (s, 1H), 8.49 (s, 1H), 8.46 (s, 1H), 8.26 (s, 1H), 7.85 (d, J=1.4 Hz, 1H), 7.83-7.80 (m, 1H), 7.59 (d, J=8.9 Hz, 1H), 7.02-7.00 (m, 1H), 2.62 (s, 3H). MS-ESI (m/z) calc'd for $C_{18}H_{13}N_6O_2$ [M+H]$^+$: 345.1 Found 345.0.

Example 163: 3-Cyano-N-(3-(1-(difluoromethyl)-1H-pyrazol-4-yl)-1H-indazol-5-yl)-2,6-difluorobenzamide

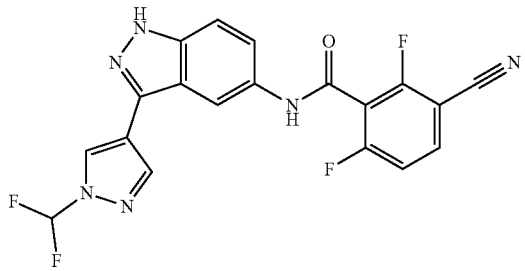

Prepared as described for 5-cyano-N-(7-fluoro-3-(furan-3-yl)-1H-indazol-5-yl)-3-methylpicolinamide using 3-cyano-2,6-difluorobenzoic acid in place of 5-cyano-3-methylpicolinic acid and using 3-(1-(difluoromethyl)-1H-pyrazol-4-yl)-1H-indazol-5-amine in place of 7-fluoro-3-(furan-3-yl)-1H-indazol-5-amine to afford the title compound (37.4 mg, 41%) as a white solid. $^1$H NMR (400 MHz, DMSO-$d_6$) δ 13.25 (br. s., 1H) 10.98 (s, 1H) 8.73 (d, J=0.66 Hz, 1H) 8.36 (d, J=1.54 Hz, 1H) 8.29 (s, 1H) 8.23 (ddd, J=8.86, 7.65, 5.94 Hz, 1H) 7.77-8.12 (m, 1H) 7.53-7.67 (m, 3H). MS-ESI (m/z) calc'd for $C_{19}H_{11}F_4N_6O$ [M+H]$^+$: 415.1. Found 415.2.

Example 164: 3-Cyano-N-(3-(1-(difluoromethyl)-1H-pyrazol-4-yl)-1H-indazol-5-yl)-2-methoxybenzamide

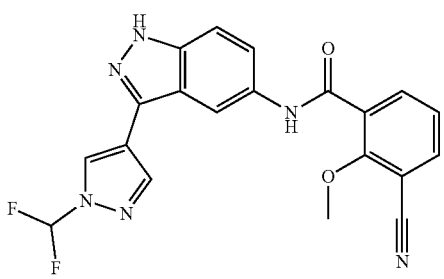 [SMILES: COc1c(C#N)cccc1C(=O)Nc1ccc2[nH]nc(-c3cnn(C(F)F)c3)c2c1]

Prepared as described for 5-cyano-N-(7-fluoro-3-(furan-3-yl)-1H-indazol-5-yl)-3-methylpicolinamide using 3-cyano-2-methoxybenzoic acid in place of 5-cyano-3-methylpicolinic acid and using 3-(1-(difluoromethyl)-1H-pyrazol-4-yl)-1H-indazol-5-amine in place of 5-cyano-3-methylpicolinic acid to afford the title compound (34.7 mg, 32%) as a white solid. $^1$H NMR (400 MHz, DMSO-$d_6$) δ 13.21 (s, 1H), 10.53 (s, 1H), 8.70 (d, J=0.7 Hz, 1H), 8.40 (dd, J=1.9, 0.8 Hz, 1H), 8.29 (d, J=0.7 Hz, 1H), 8.13-7.77 (m, 3H), 7.68 (dd, J=9.0, 1.9 Hz, 1H), 7.59 (dd, J=8.9, 0.7 Hz, 1H), 7.42 (t, J=7.7 Hz, 1H), 4.03 (s, 3H). MS-ESI (m/z) calc'd for $C_{20}H_{15}F_2N_6O_2$[M+H]$^+$: 409.1. Found 409.2.

Example 165: 4-Cyano-N-(3-(1-(difluoromethyl)-1H-pyrazol-3-yl)-1H-indazol-5-yl)-2-fluoro-6-methylbenzamide

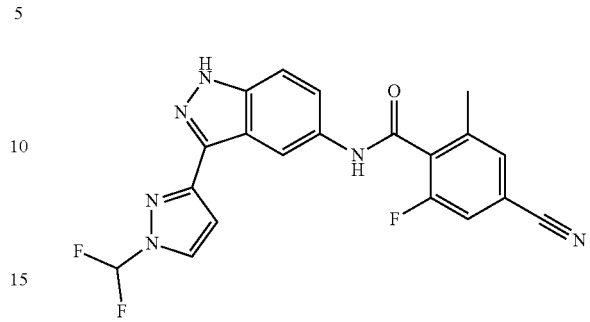

Prepared as described for 5-cyano-N-(7-fluoro-3-(furan-3-yl)-1H-indazol-5-yl)-3-methylpicolinamide using 4-cyano-2-fluoro-6-methylbenzoic acid in place of 5-cyano-3-methylpicolinic acid and using 3-(1-(difluoromethyl)-1H-pyrazol-4-yl)-1H-indazol-5-amine in place of 7-fluoro-3-(furan-3-yl)-1H-indazol-5-amine to afford the title compound (30 mg, 26%) as a white solid. $^1$H NMR (400 MHz, DMSO-$d_6$) δ 13.21 (s, 1H), 10.79 (s, 1H), 8.70 (s, 1H), 8.38 (t, J=1.3 Hz, 1H), 8.27 (s, 1H), 8.11-7.77 (m, 2H), 7.75 (s, 1H), 7.65-7.55 (m, 2H), 2.41 (s, 3H). MS-ESI (m/z) calc'd for $C_{20}H_{14}F_3N_6O$ [M+H]$^+$: 411.1. Found 411.3.

Example 166: 2-Chloro-3-cyano-N-(3-(1-(difluoromethyl)-1H-pyrazol-3-yl)-1H-indazol-5-yl)benzamide

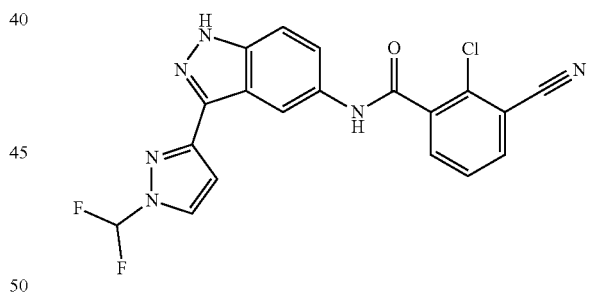

Prepared as described for 5-cyano-N-(7-fluoro-3-(furan-3-yl)-1H-indazol-5-yl)-3-methylpicolinamide using 2-chloro-3-cyanobenzoic acid in place of 5-cyano-3-methylpyridine-2-carboxylic acid and using 3-(1-(difluoromethyl)-1H-pyrazol-4-yl)-1H-indazol-5-amine in place of 7-fluoro-3-(furan-3-yl)-1H-indazol-5-amine to afford the title compound (10 mg, 9%) as a white solid. $^1$H NMR (400 MHz, DMSO-$d_6$) δ 13.22 (s, 1H), 10.70 (s, 1H), 8.69 (d, J=0.7 Hz, 1H), 8.39 (dd, J=1.8, 0.9 Hz, 1H), 8.27 (d, J=0.7 Hz, 1H), 8.19-7.89 (m, 3H), 7.83-7.67 (m, 1H), 7.65-7.56 (m, 2H). MS-ESI (m/z) calc'd for $C_{19}H_{12}ClF_2N_6O$ [M+H]$^+$: 413.1. Found 413.2.

Example 167: 3-Cyano-N-(3-(1-(difluoromethyl)-1H-pyrazol-4-yl)-1H-indazol-5-yl)-2-fluorobenzamide

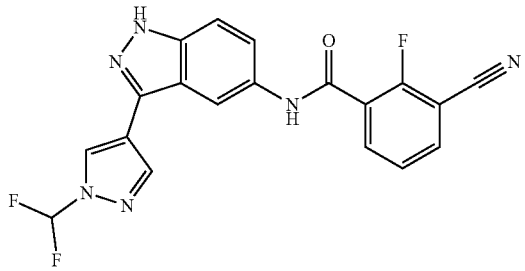 [SMILES: N#Cc1cccc(C(=O)Nc2ccc3[nH]nc(-c4cnn(C(F)F)c4)c3c2)c1F]

Prepared as described for 5-cyano-N-(7-fluoro-3-(furan-3-yl)-1H-indazol-5-yl)-3-methylpicolinamide using 3-cyano-2-fluorobenzoic acid in place of 5-cyano-3-methylpicolinic acid acid and using 3-(1-(difluoromethyl)-1H-pyrazol-4-yl)-1H-indazol-5-amine in place of 7-fluoro-3-(furan-3-yl)-1H-indazol-5-amine to afford the title compound (41.5 mg, 49%) as a yellow solid. $^1$H NMR (400 MHz, DMSO-d$_6$) δ 13.23 (s, 1H), 10.66 (s, 1H), 8.72 (d, J=0.7 Hz, 1H), 8.39 (dd, J=1.9, 0.8 Hz, 1H), 8.29 (d, J=0.6 Hz, 1H), 8.18-7.74 (m, 3H), 7.69-7.53 (m, 3H). MS-ESI (m/z) calc'd for C$_{19}$H$_{12}$F$_3$N$_6$O [M+H]$^+$: 397.1. Found 397.2.

Example 168: 5-Cyano-N-(3-(isoxazol-4-yl)-1H-indazol-5-yl)-3,4-dimethylpicolinamide

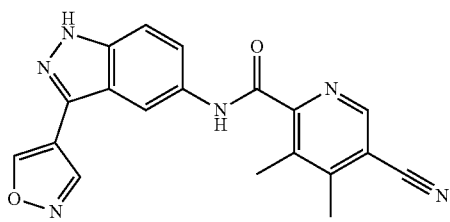 [SMILES: Cc1c(C#N)cnc(C(=O)Nc2ccc3[nH]nc(-c4cnoc4)c3c2)c1C]

Prepared as described for 5-cyano-N-(7-fluoro-3-(furan-3-yl)-1H-indazol-5-yl)-3-methylpicolinamide using 5-cyano-3,4-dimethylpicolinic acid in place of 5-cyano-3-methylpicolinic and using 3-(isoxazol-4-yl)-1H-indazol-5-amine in place of 7-fluoro-3-(furan-3-yl)-1H-indazol-5-amine to afford the title compound (207.9 mg, 64%) as a yellow solid. $^1$H NMR (400 MHz, DMSO-d$_6$) δ 13.35 (s, 1H), 10.69 (s, 1H), 9.56 (s, 1H), 9.15 (s, 1H), 8.90 (s, 1H), 8.39 (d, J=1.8 Hz, 1H), 7.76 (dd, J=8.9, 1.9 Hz, 1H), 7.61 (d, J=9.0 Hz, 1H), 2.57 (s, 3H), 2.49 (s, 3H). MS-ESI (m/z) calc'd for C$_{19}$H$_5$N$_6$O$_2$[M+H]$^+$: 359.1. Found 359.2.

Example 169: 5-Cyano-3,4-dimethyl-N-(3-(1-(trifluoromethyl)-1H-pyrazol-4-yl)-1H-indazol-5-yl)picolinamide

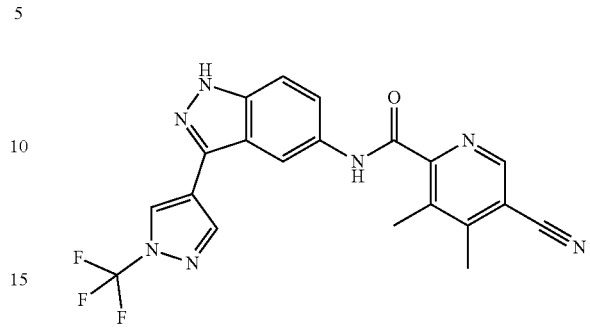

Prepared as described for 5-cyano-N-(3-(isoxazol-4-yl)-1H-indazol-5-yl)-3-methylpicolinamide using (1-(trifluoromethyl)-1H-pyrazol-4-yl)boronic acid in place of isoxazole-4-boronic acid and 5-cyano-N-(3-iodo-1H-indazol-5-yl)-3,4-dimethylpicolinamide in place of 5-cyano-N-(3-iodo-1H-indazol-5-yl)-3-methylpyridine-2-carboxamide to afford the title compound (13.2 mg, 33%) as a yellow solid. $^1$H NMR (400 MHz, DMSO-d$_6$) δ 13.31 (br. s, 1H) 10.67 (s, 1H) 8.97 (s, 1H) 8.90 (s, 1H) 8.46 (s, 1H) 8.40 (d, J=1.32 Hz, 1H) 7.83 (dd, J=9.02, 1.76 Hz, 1H) 7.61 (d, J=9.02 Hz, 1H) 2.57 (s, 3H) 2.49 (s, 3H). MS-ESI (m/z) calc'd for C$_{20}$H$_{15}$F$_3$N$_7$O [M+H]$^+$: 426.1. Found 426.3.

Example 170: 2-Cyano-3-fluoro-N-(3-(2-methoxypyridin-4-yl)-1H-indazol-5-yl)isonicotinamide

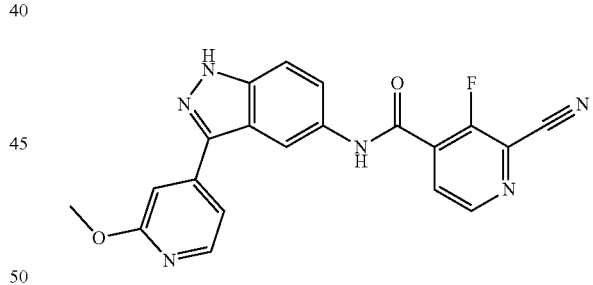

Prepared as described for 4-cyano-N-(3-(isoxazol-4-yl)-1H-indazol-5-yl)-3-methoxypicolinamide using 2-chloro-3-fluoro-N-(3-(2-methoxypyridin-4-yl)-1H-indazol-5-yl)isonicotinamide in place of 4-chloro-3-methoxy-N-[3-(1,2-oxazol-4-yl)-1H-indazol-5-yl]pyridine-2-carboxamide to afford the title compound (21.5 mg, 22%) as a yellow solid. $^1$H NMR (400 MHz, DMSO-d$_6$) δ 13.64 (s, 1H), 10.94 (s, 1H), 8.81 (dd, J=4.7, 0.8 Hz, 1H), 8.58 (t, J=1.3 Hz, 1H), 8.31 (dd, J=5.4, 0.7 Hz, 1H), 8.17 (dd, J=5.6, 4.7 Hz, 1H), 7.74-7.68 (m, 2H), 7.56 (dd, J=5.3, 1.4 Hz, 1H), 7.29 (dd, J=1.4, 0.7 Hz, 1H), 3.94 (s, 3H). MS-ESI (m/z) calc'd for C$_{20}$H$_{14}$FN$_6$O$_2$[M+H]$^+$: 389.1. Found 389.3.

Example 171: N-(3-(5-Chloropyridin-3-yl)-1H-indazol-5-yl)-5-cyano-3,4-dimethylpicolinamide

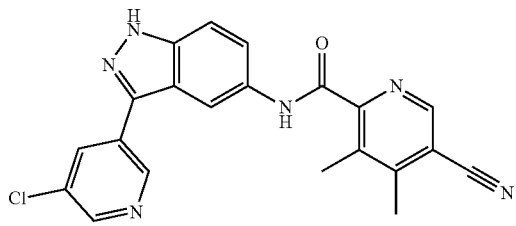

Prepared as described for 5-cyano-N-(3-(isoxazol-4-yl)-1H-indazol-5-yl)-3-methylpicolinamide using (5-chloropyridin-3-yl)boronic acid in place of isoxazole-4-boronic acid and 5-cyano-N-(3-iodo-1H-indazol-5-yl)-3,4-dimethylpicolinamide in place of 5-cyano-N-(3-iodo-1H-indazol-5-yl)-3-methylpyridine-2-carboxamide to afford the title compound (2.6 mg, 9%) as a yellow solid. $^1$H NMR (400 MHz, DMSO-$d_6$) δ 13.62 (br. s., 1H) 10.78 (s, 1H) 9.13 (d, J=1.98 Hz, 1H) 8.91 (s, 1H) 8.68 (d, J=2.42 Hz, 1H) 8.60 (d, J=1.32 Hz, 1H) 8.32-8.40 (m, 1H) 7.86 (dd, J=9.02, 1.76 Hz, 1H) 7.67 (d, J=9.02 Hz, 1H) 2.57 (s, 3H) 2.47 (s, 3H). MS-ESI (m/z) calc'd for $C_{12}H_{16}ClN_6O$ [M+H]$^+$: 403.1/405.1. Found 403.3/405.2.

Example 172: 5-Cyano-N-(3-(1-(fluoromethyl)-1H-pyrazol-4-yl)-1H-indazol-5-yl)-3,4-dimethylpicolinamide

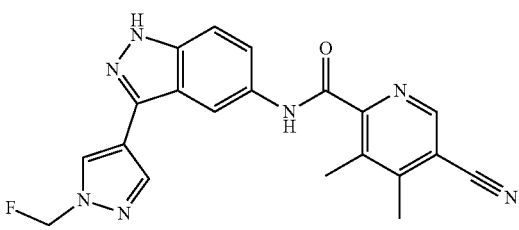 [SMILES: Cc1c(C#N)cnc(C(=O)Nc2ccc3[nH]nc(-c4cnn(CF)c4)c3c2)c1C]

Prepared as described for 5-cyano-N-(3-(isoxazol-4-yl)-1H-indazol-5-yl)-3-methylpicolinamide using (1-(fluoromethyl)-1H-pyrazol-4-yl)boronic acid in place of isoxazole-4-boronic acid and 5-cyano-N-(3-iodo-1H-indazol-5-yl)-3,4-dimethylpicolinamide in place of 5-cyano-N-(3-iodo-1H-indazol-5-yl)-3-methylpyridine-2-carboxamide to afford the title compound (24.8 mg, 66%) as a yellow solid. $^1$H NMR (400 MHz, DMSO-$d_6$) δ 13.12 (br. s., 1H) 10.48-10.81 (m, 1H) 8.90 (s, 1H) 8.61 (s, 1H) 8.44 (d, J=1.10 Hz, 1H) 8.17 (s, 1H) 7.72 (dd, J=9.02, 1.76 Hz, 1H) 7.57 (d, J=8.80 Hz, 1H) 6.15-6.40 (m, 2H) 2.57 (s, 3H) 2.48 (s, 3H). MS-ESI (m/z) calc'd for $C_{20}H_{17}FN_7O$ [M+H]$^+$: 390.1. Found 390.3.

Example 173: 3-Cyano-N-(3-(furan-3-yl)-1H-indazol-5-yl)-2-(trifluoromethyl)benzamide

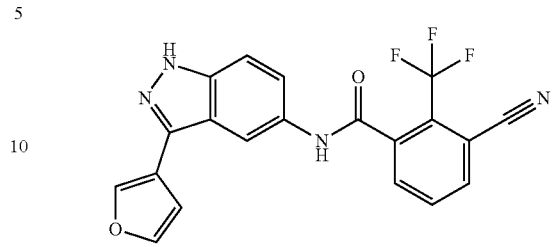

Prepared as described for 4-cyano-N-(3-(isoxazol-4-yl)-1H-indazol-5-yl)-3-methoxypicolinamide using 3-chloro-N-(3-(furan-3-yl)-1H-indazol-5-yl)-2-(trifluoromethyl)benzamide in place of 4-chloro-3-methoxy-N-[3-(1,2-oxazol-4-yl)-1H-indazol-5-yl]pyridine-2-carboxamide to afford the title compound (5.7 mg, 26%) as a white solid. $^1$H NMR (400 MHz, DMSO-$d_6$) δ 13.16 (br. s., 1H) 10.77 (s, 1H) 8.26-8.37 (m, 2H) 8.19 (dd, J=1.54, 0.88 Hz, 1H) 8.00-8.12 (m, 2H) 7.86 (t, J=1.65 Hz, 1H) 7.58 (s, 2H) 6.98 (dd, J=1.76, 0.88 Hz, 1H). MS-ESI (m/z) calc'd for $C_{20}H_{12}F_3N_4O_2$[M+H]$^+$: 397.1. Found 397.2.

Example 174: 5-Cyano-3,4-dimethyl-N-(3-(2-methyloxazol-5-yl)-1H-indazol-5-yl)picolinamide

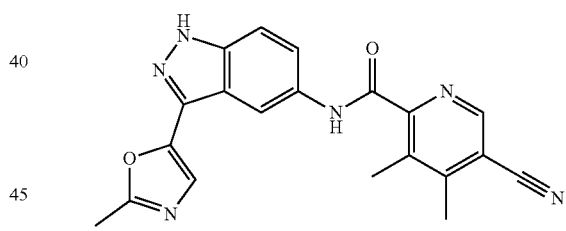

Prepared as described for 5-cyano-N-(3-(isoxazol-4-yl)-1H-indazol-5-yl)-3-methylpicolinamide using (2-methyloxazol-5-yl)boronic acid in place of isoxazole-4-boronic acid and 5-cyano-N-(3-iodo-1H-indazol-5-yl)-3,4-dimethylpicolinamide in place of 5-cyano-N-(3-iodo-1H-indazol-5-yl)-3-methylpyridine-2-carboxamide to afford the title compound (19.8 mg, 57%) as a white solid. $^1$H NMR (400 MHz, DMSO-$d_6$) δ 13.45 (br. s., 1H) 10.75 (s, 1H) 8.90 (s, 1H) 8.45-8.50 (m, 1H) 7.80 (dd, J=9.02, 1.98 Hz, 1H) 7.58-7.65 (m, 1H) 7.48 (s, 1H) 2.56 (s, 3H) 2.55 (s, 3H) 2.47 (s, 3H). MS-ESI (m/z) calc'd for $C_{20}H_{17}N_6O_2$ [M+H]$^+$: 373.1. Found 373.3.

Example 175: 6-Chloro-5-cyano-N-(3-(1-(difluoromethyl)-1H-pyrazol-4-yl)-1H-indazol-5-yl)-3,4-dimethylpicolinamide

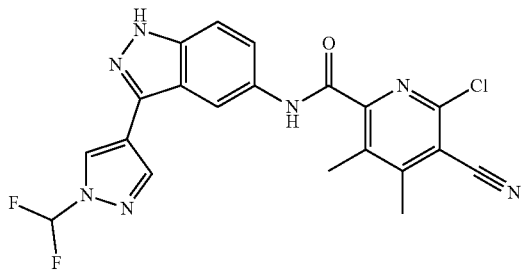

Prepared as described for 5-cyano-N-(7-fluoro-3-(furan-3-yl)-1H-indazol-5-yl)-3-methylpicolinamide using 6-chloro-5-cyano-3,4-dimethylpicolinic acid in place of 5-cyano-3-methylpicolinic acid and using 3-(1-(difluoromethyl)-1H-pyrazol-4-yl)-1H-indazol-5-amine in place of 7-fluoro-3-(furan-3-yl)-1H-indazol-5-amine to afford the title compound (54.2 mg, 70%) as a yellow solid. $^1$H NMR (400 MHz, DMSO-$d_6$) δ 13.24 (s, 1H), 10.75 (s, 1H), 8.74 (s, 1H), 8.38 (d, J=1.7 Hz, 1H), 8.30 (s, 1H), 7.94 (t, J=59.0 Hz, 1H), 7.71 (dd, J=9.0, 1.8 Hz, 1H), 7.60 (d, J=9.1 Hz, 1H), 2.61 (s, 3H), 2.42 (s, 3H). MS-ESI (m/z) calc'd for $C_{20}H_{15}ClF_2N_7O$ [M+H]$^+$: 442.1/444.1. Found 442.2/444.2.

Example 176: 3-Cyano-2-methoxy-N-(3-(oxazol-5-yl)-1H-indazol-5-yl)benzamide

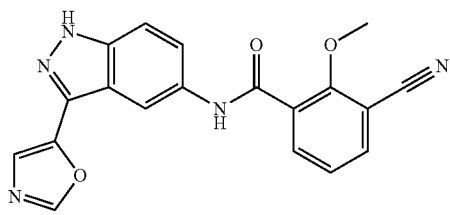 [SMILES: COc1c(C#N)cccc1C(=O)Nc1ccc2[nH]nc(-c3cnco3)c2c1]

Prepared as described for 5-cyano-N-(7-fluoro-3-(furan-3-yl)-1H-indazol-5-yl)-3-methylpicolinamide using 3-cyano-2-methoxybenzoic acid in place of 5-cyano-3-methylpicolinic acid and using 3-(oxazol-5-yl)-1H-indazol-5-amine in place of 7-fluoro-3-(furan-3-yl)-1H-indazol-5-amine to afford the title compound (17 mg, 17%) as an off-white solid. $^1$H NMR (400 MHz, DMSO-$d_6$) δ 13.52 (s, 1H), 10.60 (s, 1H), 8.64-8.38 (m, 2H), 7.93 (ddd, J=21.0, 7.7, 1.7 Hz, 2H), 7.73-7.56 (m, 3H), 7.40 (t, J=7.7 Hz, 1H), 4.01 (s, 3H). MS-ESI (m/z) calc'd for $C_{19}H_{14}N_5O_3$ [M+H]$^+$: 360.1. Found 360.2.

Example 177: 3-Cyano-N-(3-(1-(difluoromethyl)-1H-pyrazol-4-yl)-1H-indazol-5-yl)-2-fluoro-6-methylbenzamide

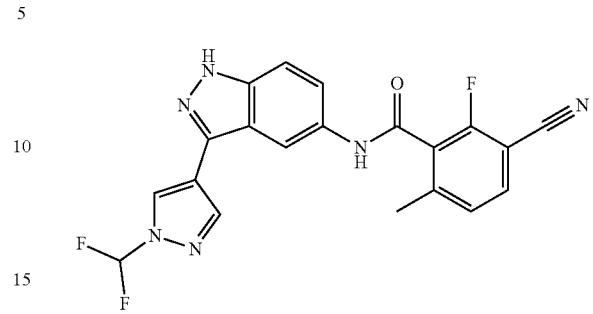

Step 1: 3-(1-(Difluoromethyl)-1H-pyrazol-4-yl)-5-nitro-1H-indazole

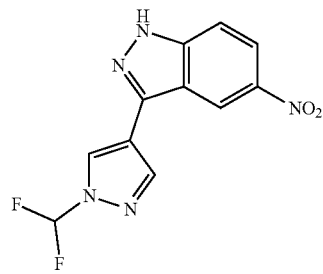 [SMILES: O=[N+]([O-])c1ccc2[nH]nc(-c3cnn(C(F)F)c3)c2c1]

A mixture of 3-bromo-5-nitro-1H-indazole (400 mg, 1.65 mmol), 1-(difluoromethyl)-4-(4,4,5,5-tetramethyl-1,3,2-dioxaborolan-2-yl)-1H-pyrazole (321.09 mg, 1.98 mmol), Pd(Amphos)Cl$_2$ (117.02 mg, 165.27 umol), KOAc (486.60 mg, 4.96 mmol) in EtOH (4 mL) and H$_2$O (0.8 mL) was degassed and purged with N$_2$ (3×), and then the mixture was stirred at 90° C. for 4 hrs under an N$_2$ atmosphere. The reaction mixture was concentrated and purified by flash silica gel chromatography (ISCO; 12 g SepaFlash column) using a 0-14% EtOAc/petroleum ether gradient eluent to afford the title compound (220 mg, 48%) as a yellow solid. MS-ESI (m/z) calcd for $C_{11}H_8F_2N_5O_2$ [M+H]$^+$: 280.1/282.1. Found 280.0/282.1.

Step 2: 3-(1-(Difluoromethyl)-1H-pyrazol-4-yl)-1H-indazol-5-amine

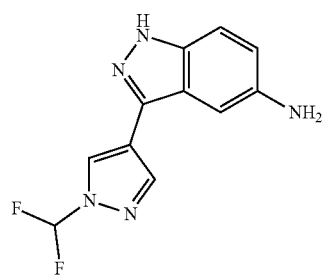

To a solution of 3-(1-(difluoromethyl)-1H-pyrazol-4-yl)-5-nitro-1H-indazole (100 mg, 358.16 umol) in EtOH (3 mL)

was added SnCl$_2$.2H$_2$O (242.46 mg, 1.07 mmol) and the mixture was stirred at 90° C. for 3 hrs. The reaction mixture was then concentrated under reduced pressure to give a residue. The residue was diluted with 1 M NaOH (5 mL) and EtOAc (5 mL). The suspension was filtered through a pad of Celite and the pad was washed with EtOAc (30 mL). The aqueous layers were extracted with EtOAc (10 mL×3). The combined organic layers were dried over Na$_2$SO$_4$, filtered and concentrated under reduced pressure to afford the title compound (60 mg, 67%) as a blue oil which was used without further purification. MS-ESI (m/z) calcd for C$_{11}$H$_{10}$F$_2$N$_5$ [M+H]$^+$: 250.1. Found 250.0.

Step 3: 3-Bromo-N-(3-(1-(difluoromethyl)-1H-pyrazol-4-yl)-1H-indazol-5-yl)-2-fluoro-6-methylbenzamide

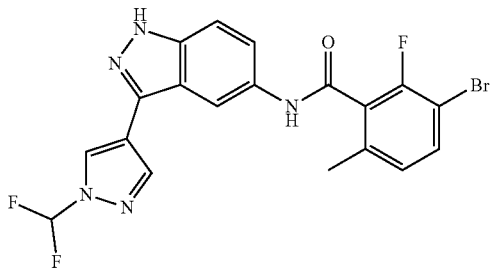

To a solution of 3-(1-(difluoromethyl)-1H-pyrazol-4-yl)-1H-indazol-5-amine (120 mg, 481.50 umol), 3-bromo-2-fluoro-6-methylbenzoic acid (134.65 mg, 577.80 umol) in pyridine (3 mL) was added EDCI (138.46 mg, 722.26 umol) and the mixture was stirred at 30° C. for 12 hrs. The reaction mixture was concentrated under reduced pressure to give a residue. The residue was diluted with H$_2$O (15 mL) and extracted with EtOAc (5 mL×3). The combined organic layers were dried over Na$_2$SO$_4$, filtered and concentrated under reduced pressure to give a residue which was purified by flash silica gel chromatography (ISCO; 4 g SepaFlash column) using a 0-15% EtOAc/petroleum ether gradient eluent to afford the title compound (100 mg, 45%) as a brown solid. MS-ESI (m/z) calcd for C$_{19}$H$_{14}$BrF$_3$N$_5$O [M+H]$^+$: 464.0/466.0. Found 464.0/466.0.

Step 4: 3-Cyano-N-(3-(1-(difluoromethyl)-1H-pyrazol-4-yl)-1H-indazol-5-yl)-2-fluoro-6-methylbenzamide

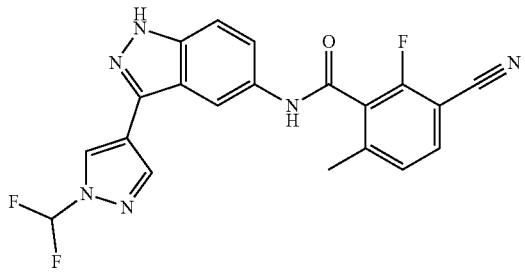

A mixture of 3-bromo-N-(3-(1-(difluoromethyl)-1H-pyrazol-4-yl)-1H-indazol-5-yl)-2-fluoro-6-methylbenzamide (100 mg, 215.41 umol), Zn(CN)$_2$ (50.59 mg, 430.81 umol), Zn (2.82 mg, 43.08 umol), Pd$_2$(dba)$_3$ (19.73 mg, 21.54 umol) and dppf (11.94 mg, 21.54 umol) in DMA (2 mL) was degassed and purged with N$_2$ (3×), and then the mixture was stirred at 120° C. for 5 hrs under an N$_2$ atmosphere in a microwave reactor. The reaction mixture was concentrated and purified by preparative HPLC using Method CE to afford the title compound (11.31 mg, 10%) as a white solid, TFA salt. $^1$H NMR (400 MHz, DMSO-d$_6$) δ 13.21 (s, 1H), 10.56 (s, 1H), 8.72 (s, 1H), 8.39 (s, 1H), 8.29 (s, 1H), 7.78-8.10 (m, 2H), 7.63-7.67 (m, 1H), 7.57-7.61 (m, 1H), 7.48 (d, J=8.1 Hz, 1H), 2.59 ppm (s, 3H). MS-ESI (m/z) calc'd for C$_{20}$H$_{14}$F$_3$N$_6$O [M+H]$^+$: 411.1. Found 411.0.

Example 178: 5-Cyano-N-(3-(2-methoxypyridin-4-yl)-1H-indazol-5-yl)-3-(trifluoromethyl)picolinamide

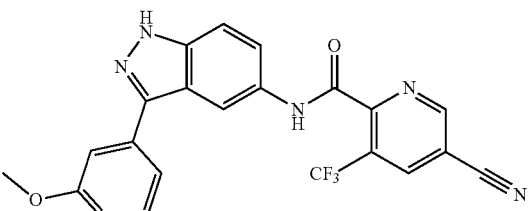

Step 1: (2-Methoxypyridin-4-yl)boronic acid

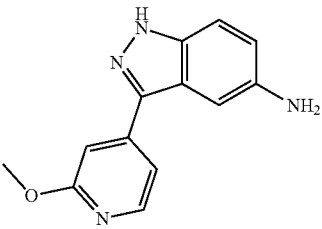 [SMILES: COc1cc(-c2n[nH]c3ccc(N)cc23)ccn1]

A mixture of 3-bromo-1H-indazol-5-amine (300 mg, 1.41 mmol), 3-(2-methoxypyridin-4-yl)-1H-indazol-5-amine (259.66 mg, 1.70 mmol), Pd(Amphos)Cl$_2$ (100.18 mg, 141.48 umol, 100.18 uL) and AcOK (416.54 mg, 4.24 mmol) in EtOH (6 mL) and H$_2$O (1.5 mL) was degassed and purged with N$_2$ (3×), and then the mixture was stirred at 100° C. for 12 hrs under an N$_2$ atmosphere. The reaction mixture was concentrated to give a residue which was diluted with 30 mL of H$_2$O and extracted with EtOAc (10 mL×3). The combined organic phases were dried over Na$_2$SO$_4$ and concentrated under reduced pressure to afford the title compound (333 mg) as a brown oil which was used without purification. MS-ESI (m/z) calcd for C$_3$H$_{13}$N$_4$O [M+H]$^+$: 241.1. Found 241.1.

Step 2: 5-Bromo-3-(trifluoromethyl)picolinic acid

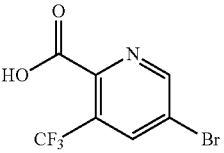

To a solution of methyl 5-bromo-3-(trifluoromethyl)picolinate (200 mg, 699.19 umol) in THF (8 mL) and H$_2$O (4 mL) was added NaOH (55.94 mg, 1.40 mmol) and the mixture was stirred at 25° C. for 2 hrs. The reaction mixture was diluted with 1M HCl to pH=4. The aqueous layers were extracted with EtOAc (15 mL×3). The combined organic layers were dried over Na$_2$SO$_4$, filtered and concentrated under reduced pressure to afford the title compound (187 mg) as a white solid which was used without purification. MS-ESI (m/z) calcd for C$_7$H$_4$BrF$_3$NO$_2$ [M+H]$^+$: 269.9/271.9. Found 269.9/271.9.

Step 3: 5-Bromo-N-(3-(2-methoxypyridin-4-yl)-1H-indazol-5-yl)-3-(trifluoromethyl)picolinamide

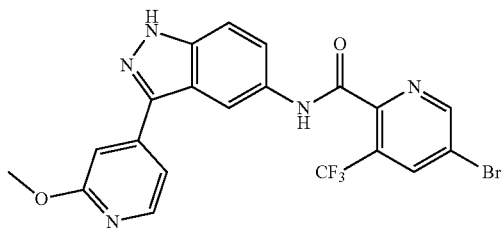

To a solution of 5-bromo-3-(trifluoromethyl)picolinic acid (260 mg, 962.95 umol) in pyridine (10 mL) was added EDCI (276.90 mg, 1.44 mmol) and (2-methoxypyridin-4-yl)boronic acid (347.04 mg, 1.44 mmol) and the mixture was stirred at 25° C. for 12 hrs. The mixture was concentrated and purified by flash silica gel chromatography (ISCO; 4 g SepaFlash column) using a 0-20% EtOAc/petroleum ether gradient eluent to afford the title compound (270 mg, 57%) as a yellow solid which was used without further purification. MS-ESI (m/z) calcd for C$_{20}$H$_{14}$BrF$_3$N$_5$O$_2$ [M+H]$^+$: 492.0/494.0. Found 492.0/494.0.

Step 4: 5-Cyano-N-(3-(2-methoxypyridin-4-yl)-1H-indazol-5-yl)-3-(trifluoromethyl)picolinamide

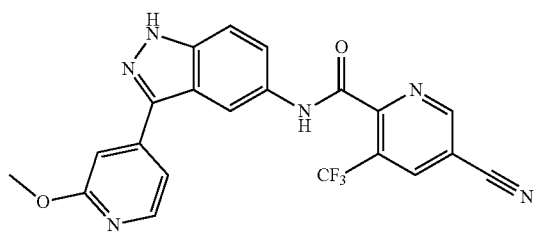 [SMILES: COc1cc(-c2n[nH]c3ccc(NC(=O)c4ncc(C#N)cc4C(F)(F)F)cc23)ccn1]

A mixture of 5-bromo-N-(3-(2-methoxypyridin-4-yl)-1H-indazol-5-yl)-3-(trifluoromethyl)picolinamide (100 mg, 203.15 umol), Zn(CN)$_2$ (23.85 mg, 203.15 umol), Pd$_2$(dba)$_3$ (18.60 mg, 20.31 umol), Zn (2.66 mg, 40.63 umol) and DPPF (33.79 mg, 60.94 umol) in DMA (10 mL) was degassed and purged with N$_2$ (3×), and then the mixture was stirred at 120° C. for 2 hrs under an N$_2$ atmosphere. The reaction was filtered and the filtrate was purified by preparative HPLC using Method CD to afford the title compound (22.14 mg, 25%) as a yellow solid. $^1$H NMR (400 MHz, DMSO-d$_6$) δ 11.00 (br s, 1H), 9.43 (d, J=1.54 Hz, 1H), 9.06 (d, J=1.32 Hz, 1H), 8.53 (s, 1H), 8.28 (d, J=5.29 Hz, 1H), 7.71-7.76 (m, 1H), 7.64-7.68 (m, 1H), 7.53 (dd, J=5.29, 1.32 Hz, 1H), 7.26 (s, 1H), 3.90 (s, 3H). MS-ESI (m/z) calc'd for C$_{21}$H$_{14}$F$_3$N$_6$O$_2$[M+H]$^+$: 439.1. Found 439.2.

Example 179: 5-Cyano-N-(3-(furan-3-yl)-1H-indazol-5-yl)-4-methylisoxazole-3-carboxamide

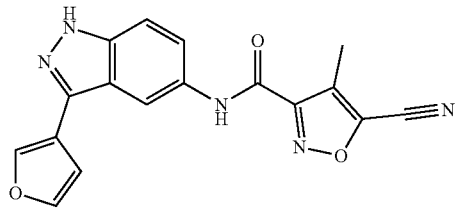 [SMILES: Cc1c(C(=O)Nc2ccc3[nH]nc(-c4ccoc4)c3c2)noc1C#N]

Step 1: Ethyl 4-methyl-5-oxo-2,5-dihydroisoxazole-3-carboxylate

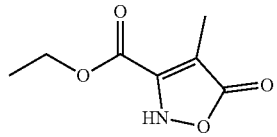

To a solution of diethyl 2-methylmalonate (10 g, 49.46 mmol, 9.17 mL) in EtOH (100 mL) was added NH$_2$OH.HCl (6.12 g, 88.03 mmol) and the mixture was stirred at 78° C. for 12 hrs. The reaction mixture was concentrated under reduced pressure to give a residue. The residue was diluted with H$_2$O (20 mL) and extracted with EtOAc (25 mL×2). The combined organic layers were dried over Na$_2$SO$_4$, filtered and concentrated under reduced pressure to afford the title compound (6.6 g, 52%) as a white solid which was used without further purification. MS-(ESI) (m/z) calcd for C$_7$H$_{10}$NO$_4$ (M+H)$^+$:172.1. Found 172.1.

Step 2: Ethyl 5-bromo-4-methylisoxazole-3-carboxylate

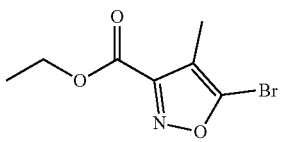

To a solution of ethyl 4-methyl-5-oxo-2,5-dihydroisoxazole-3-carboxylate (3.5 g, 20.45 mmol) in POBr$_3$ (23.45 g, 81.80 mmol) was added Et$_3$N (2.07 g, 20.45 mmol) and the mixture was stirred at 80° C. for 2 hrs. The reaction mixture was quenched by addition of ice water (20 mL), and then the mixture was extracted with EtOAc (20 mL×2). The combined organic layers were dried over Na$_2$SO$_4$, filtered and concentrated under reduced pressure to give a residue. The residue was purified by flash silica gel chromatography (ISCO; 12 g SepaFlash column), using petroleum ether as eluent to afford the title compound (3.5 g, 73%) as a colorless oil. MS-(ESI) (m/z) calcd for C$_7$H$_9$BrNO$_3$ (M+H)$^+$: 234.0/236.0. Found 233.9/235.9.

Step 3: Ethyl 4-methyl-5-vinylisoxazole-3-carboxylate

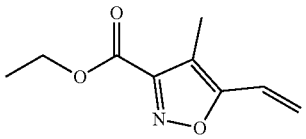

A mixture of ethyl 5-bromo-4-methylisoxazole-3-carboxylate (3.5 g, 14.95 mmol), tributyl(vinyl)stannane (5.69 g, 17.95 mmol), and Pd(PPh$_3$)$_4$ (1.73 g, 1.50 mmol) in dioxane (24 mL) was degassed and purged with N$_2$ (3×), and then the mixture was stirred at 100° C. for 3 hrs under an N$_2$ atmosphere. The reaction mixture was concentrated and purified by flash silica gel chromatography (ISCO; 12 g SepaFlash column) using a 0-5% EtOAc/petroleum ether gradient eluent to afford the title compound (1.7 g, 63%) as a pale yellow liquid. MS-(ESI) (m/z) calcd for C$_9$H$_{12}$NO$_3$ (M+H)$^+$: 182.1. Found 182.0.

Step 4: Ethyl 5-formyl-4-methylisoxazole-3-carboxylate

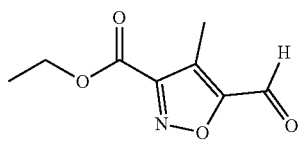

To a solution of ethyl 4-methyl-5-vinylisoxazole-3-carboxylate (1.7 g, 9.38 mmol) in THF (30 mL) and H$_2$O (15 mL) was added NaIO$_4$ (6.02 g, 28.15 mmol) and OsO$_4$ (477.06 mg, 1.88 mmol) and the mixture was stirred at 30° C. for 12 hrs. The mixture was then filtered through Celite washing with EtOAc. The filtrate was diluted with H$_2$O (15 mL) and extracted with EtOAc (15 mL×3). The combined organic layers were dried over Na$_2$SO$_4$, filtered and concentrated under reduced pressure to afford the title compound (1 g, 58%) as a pale yellow oil which was used without further purification. $^1$H NMR (400 MHz, DMSO-d$_6$) δ 4.49 (q, 2H, J=7.1 Hz), 2.43 (s, 3H), 1.45 (t, 3H, J=7.1 Hz). MS-(ESI) (m/z) calcd for C$_8$H$_{10}$NO$_4$ (M+H)~: 184.1. Found 184.

Step 5: Ethyl 5-cyano-4-methylisoxazole-3-carboxylate

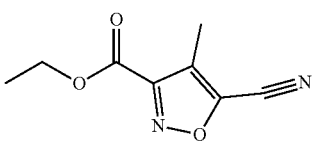

To a solution of ethyl 5-formyl-4-methylisoxazole-3-carboxylate (900 mg, 4.91 mmol) in pyridine (8 mL) was added NH$_2$OH.HCl (341.46 mg, 4.91 mmol) and the mixture was stirred at 90° C. for 0.5 hr. Ac$_2$O (5 mL) was then added and stirring was continued at 90° C. for another 1 hr. The reaction mixture was concentrated and purified by flash silica gel chromatography (ISCO; 4 g SepaFlash column) using a 0-3% EtOAc/petroleum ether gradient eluent to afford the title compound (600 mg, 68%) as a pale yellow oil.

Step 6: 5-Cyano-4-methylisoxazole-3-carboxylic acid

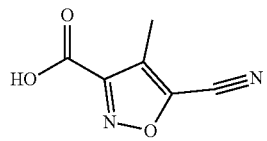

To a solution of ethyl 5-cyano-4-methylisoxazole-3-carboxylate (60 mg, 333.04 umol) in THF (3 mL) and H$_2$O (3 mL) was added LiOH.H$_2$O (27.95 mg, 666.07 umol) and the mixture was stirred at 0° C. for 0.25 hr. The mixture was acidified to pH=2 by addition of 1N HCl, and then the mixture was diluted with H$_2$O (3 mL) and extracted with EtOAc (5 mL×3). The combined organic layers were dried over Na$_2$SO$_4$, filtered and concentrated under reduced pressure to afford the title compound (40 mg, 79%) as a white solid which was used without further purification.

Step 7: 5-Cyano-N-(3-(furan-3-yl)-1H-indazol-5-yl)-4-methylisoxazole-3-carboxamide

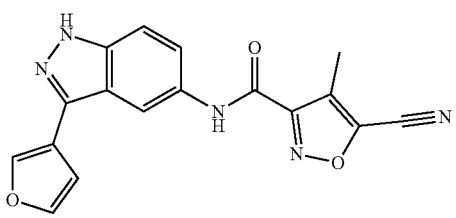 [SMILES: Cc1c(C(=O)Nc2ccc3[nH]nc(-c4ccoc4)c3c2)noc1C#N]

To a solution of 5-cyano-4-methylisoxazole-3-carboxylic acid (40 mg, 262.97 umol) and 3-(furan-3-yl)-1H-indazol-5-amine (62.86 mg, 315.57 umol) in pyridine (2 mL) was added EDCI (75.62 mg, 394.46 umol) and the mixture was stirred at 30° C. for 3 hrs. The reaction mixture was concentrated and purified by preparative HPLC using Method BW to afford the title compound (8.87 mg, 8%) as a white solid, TFA salt. $^1$H NMR (400 MHz, DMSO-d$_6$) δ 13.14 (s, 1H), 10.99 (s, 1H), 8.39 (s, 1H), 8.24 (s, 1H), 7.85 (s, 1H), 7.75 (dd, J=1.54, 9.04 Hz, 1H), 7.57 (d, J=9.04 Hz, 1H), 6.99 (s, 1H), 2.38 (s, 3H). MS-ESI (m/z) calc'd for C$_{17}$H$_{12}$N$_5$O$_3$ [M+H]$^+$: 334.1. Found 334.0.

Example 180: 3-Cyano-N-(3-(furan-3-yl)-1H-indazol-5-yl)-4-methylisoxazole-5-carboxamide

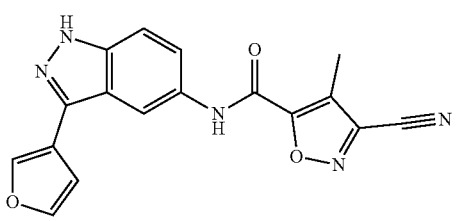

Step 1: 5-(1-Ethoxyvinyl)-4-methylisoxazole-3-carboxamide

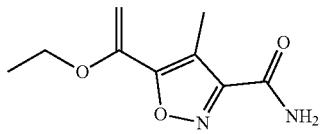

A mixture of 5-bromo-4-methylisoxazole-3-carboxamide (840 mg, 4.10 mmol), tributyl(1-ethoxyvinyl)stannane (1.78 g, 4.92 mmol), Pd(PPh$_3$)$_2$Cl$_2$ (143.80 mg, 204.87 umol) in dioxane (20 mL) was degassed and purged with N$_2$ (3×), and then the mixture was stirred at 90° C. for 3 hrs under an N$_2$ atmosphere. The reaction mixture was concentrated and purified by flash silica gel chromatography (ISCO; 20 g SepaFlash column) using a 0-20% EtOAc/petroleum ether gradient eluent to afford the title compound (690 mg, 86% yield) as a light yellow solid. MS-ESI (m/z) calcd for C$_9$H$_{13}$N$_2$O$_3$[M+H]$^+$: 197.1. Found 197.0.

Step 2: Ethyl 3-carbamoyl-4-methylisoxazole-5-carboxylate

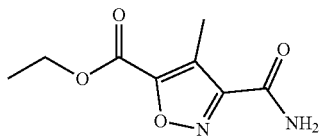

To a solution of 5-(1-ethoxyvinyl)-4-methylisoxazole-3-carboxamide (690 mg, 3.52 mmol) in dioxane (20 mL) was added NaIO$_4$ (1.50 g, 7.03 mmol) in H$_2$O (10 mL), followed by KMnO$_4$ (111.15 mg, 703.35 umol). The mixture was then stirred at 25° C. for 12 hrs. The reaction mixture was filtered and the filtrate was concentrated to give a residue which was diluted with H$_2$O (30 mL) and extracted with EtOAc (15 mL×3). The combined organic layers were dried over Na$_2$SO$_4$, filtered and concentrated to give a residue. The residue was purified by flash silica gel chromatography (ISCO; 20 g SepaFlash column) using a 0-19% EtOAc/petroleum ether gradient eluent to afford the title compound (360 mg, 52%) as a white solid. MS-ESI (m/z) calcd for C$_8$H$_{11}$N$_2$O$_4$ [M+H]$^+$: 199.1. Found 199.0.

Step 3: 3-Carbamoyl-4-methylisoxazole-5-carboxylic acid

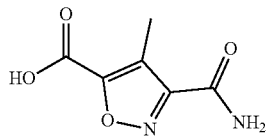

To a solution of ethyl 3-carbamoyl-4-methylisoxazole-5-carboxylate (100 mg, 504.60 umol) in THF (4 mL) and H$_2$O (2 mL) was added NaOH (40.37 mg, 1.01 mmol). The mixture was stirred at 25° C. for 1 hr. The reaction mixture was acidified with 1 N HCl to pH=3 and extracted with EtOAc (4 mL×4). The combined organic layers were dried over Na$_2$SO$_4$, filtered and concentrated to afford the title compound (65 mg, 38%) as a white solid which was used without further purification. MS-ESI (m/z) calcd for C$_6$H$_7$N$_2$O$_4$[M+H]$^+$: 171.0. Found 171.0.

Step 4: N-(3-(Furan-3-yl)-1H-indazol-5-yl)-4-methylisoxazole-3,5-dicarboxamide

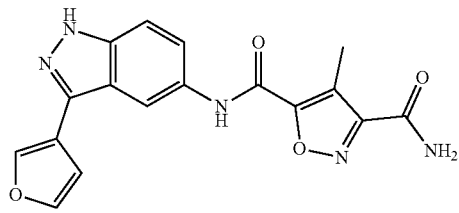 [SMILES: Cc1c(C(N)=O)noc1C(=O)Nc1ccc2[nH]nc(-c3ccoc3)c2c1]

To a solution of 3-carbamoyl-4-methylisoxazole-5-carboxylic acid (65 mg, 382.08 umol) in pyridine (4 mL) was added EDCI (87.89 mg, 458.49 umol) and 3-(furan-3-yl)-1H-indazol-5-amine (76.11 mg, 382.08 umol) and the mixture was stirred at 25° C. for 2 hrs. The reaction mixture was then concentrated and purified by preparative TLC (SiO$_2$, 1:3 petroleum ether/EtOAc, R$_f$=0.34) to afford the title compound (80 mg, 60%) as a yellow solid. MS-ESI (m/z) calcd for C$_7$H$_{14}$N$_5$O$_4$ [M+H]$^+$: 352.1. Found 352.2.

Step 5: 3-Cyano-N-(3-(furan-3-yl)-1H-indazol-5-yl)-4-methylisoxazole-5-carboxamide

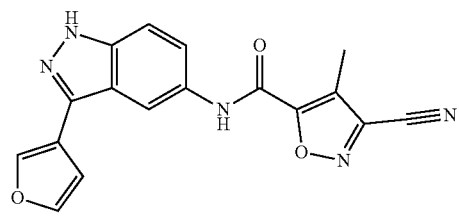

To a solution of N$^5$-(3-(furan-3-yl)-1H-indazol-5-yl)-4-methylisoxazole-3,5-dicarboxamide (80 mg, 227.72 umol) in THF (2 mL) was added TFAA (239.14 mg, 1.14 mmol) and Et$_3$N (46.08 mg, 455.43 umol) at 0° C. and the mixture was stirred at 20° C. for 10 hrs. The reaction mixture was then concentrated to give a residue. The process was repeated to give another 30 mgs of residue which was combined and purified by preparative HPLC using Method BL twice to afford the title compound (9.96 mg, 13%) as a yellow solid, TFA salt. $^1$H NMR (400 MHz, DMSO-d$_6$) δ 13.16 (s, 1H) 11.00 (s, 1H) 8.37 (s, 1H) 8.25 (s, 1H) 7.86 (d, J=1 Hz, 1H) 7.76 (br d, J=9 Hz, 1H) 7.58 (d, J=9 Hz, 1H) 7.00 (s, 1H) 2.42 (s, 3H). MS-ESI (m/z) calc'd for C$_{17}$H$_{12}$N$_5$O$_3$ [M+H]$^+$: 334.1. Found 334.0.

Example 181: 5-Cyano-N-(3-(2-isopropyloxazol-5-yl)-1H-indazol-5-yl)-3,4-dimethylpicolinamide

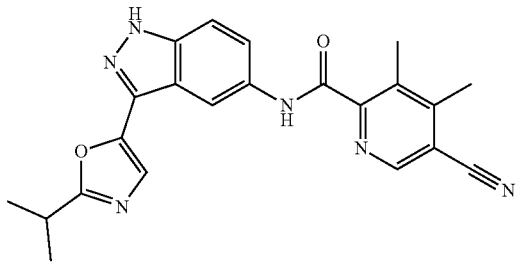 [SMILES: Cc1c(C#N)cnc(C(=O)Nc2ccc3[nH]nc(-c4cnc(C(C)C)o4)c3c2)c1C]

Step 1: 2-Isopropyl-5-(5-nitro-1-((2-(trimethylsilyl)ethoxy)methyl)-1H-indazol-3-yl)oxazole

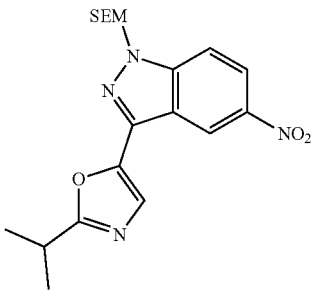 [SMILES: CC(C)c1ncc(-c2nn(COCC[Si](C)(C)C)c3ccc([N+](=O)[O-])cc23)o1]

A mixture of 5-nitro-3-(prop-1-en-2-yl)-1-((2-(trimethylsilyl)ethoxy)methyl)-1H-indazole (500 mg, 1.49 mmol), valine (523.86 mg, 4.47 mmol), oxone (2.75 g, 4.47 mmol), and $I_2$ (75.67 mg, 298.13 umol) in DMSO (10 mL) was degassed and purged with $N_2$ (3×), and then the mixture was stirred at 100° C. for 12 hrs under an $N_2$ atmosphere. The reaction mixture was quenched with saturated aqueous $NaHCO_3$ (20 mL) and extracted with EtOAc (15 mL×3). The combined organic layers were dried over $Na_2SO_4$, filtered and concentrated to give a residue. The residue was purified by flash silica gel chromatography (ISCO; 12 g SepaFlash column) using a 0-7% EtOAc/petroleum ether gradient eluent to afford the title compound (120 mg, 20%) as a yellow solid. MS-(ESI) (m/z) calcd for $C_{19}H_{27}N_4O_4Si$ (M+H)$^+$: 403.2. Found 403.1.

Step 2: 2-Isopropyl-5-(5-nitro-1H-indazol-3-yl)oxazole

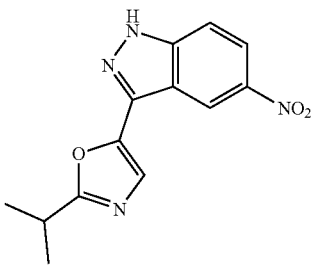 [SMILES: CC(C)c1ncc(-c2n[nH]c3ccc([N+](=O)[O-])cc23)o1]

To a solution of 2-isopropyl-5-(5-nitro-1-((2-(trimethylsilyl)ethoxy)methyl)-1H-indazol-3-yl)oxazole (110 mg, 273.28 umol) in THF (6 mL) was added TBAF (1 M, 2.73 mL) and ethane-1,2-diamine (164.24 mg, 2.73 mmol) and the mixture was stirred at 70° C. for 12 hrs. The reaction mixture was then concentrated, diluted with EtOAc (10 mL) and washed with $H_2O$ (5 mL×2). The organic layer was dried over $Na_2SO_4$, filtered and concentrated to afford the title compound (74 mg) as a yellow solid which was used without further purification. MS-(ESI) (m/z) calcd for $C_{13}H_{13}N_4O_3$ (M+H)$^+$: 273.1. Found 273.0.

Step 3: 3-(2-Isopropyloxazol-5-yl)-1H-indazol-5-amine

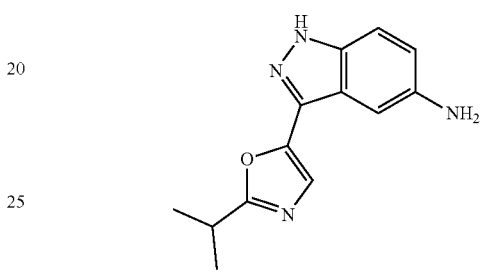

To a solution of 2-isopropyl-5-(5-nitro-1H-indazol-3-yl)oxazole (100 mg, 367.30 umol) in EtOH (2 mL) was added $SnCl_2.2H_2O$ (414.40 mg, 1.84 mmol) and the mixture was stirred at 80° C. for 1 hr. The reaction mixture was then concentrated under reduced pressure, diluted with EtOAc (10 mL), and basified with saturated aqueous $Na_2CO_3$ to pH=8. The organic layer was separated and the aqueous phase was extracted with EtOAc (5 mL×3). The combined organic layers were dried over $Na_2SO_4$, filtered and concentrated to give a residue. The residue was purified by preparative TLC (SiO$_2$, 0:1 petroleum ether/EtOAc, $R_f$=0.28) to afford the title compound (39 mg, 44%) as a brown solid. MS-(ESI) (m/z) calcd for $C_{13}H_{15}N_4O$ (M+H)$^+$: 243.1. Found 243.1.

Step 4: 5-Cyano-N-(3-(2-isopropyloxazol-5-yl)-1H-indazol-5-yl)-3,4-dimethylpicolinamide

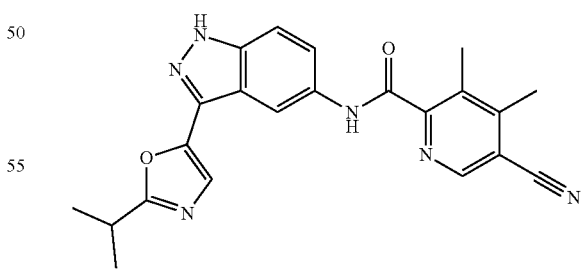

To a solution of 5-cyano-3,4-dimethylpicolinic acid (25 mg, 141.91 umol) in pyridine (2 mL) was added EDCI (40.81 mg, 212.86 umol) and 3-(2-isopropyloxazol-5-yl)-1H-indazol-5-amine (34.38 mg, 141.91 umol) and the mixture was stirred at 20° C. for 12 hrs. The reaction mixture was concentrated and purified by preparative HPLC using Method CC to afford the title compound (4.44 mg, 6%) as a pale yellow solid, TFA salt. $^1$H NMR (400 MHz, DMSO-d$_6$) δ 13.44 (s, 1H) 10.78 (s, 1H) 8.90 (s, 1H) 8.56 (s, 1H) 7.77 (dd, J=9, 2 Hz, 1H) 7.61 (d, J=9 Hz, 1H) 7.48 (s, 1H) 3.17-3.26 (m, 1H) 2.56 (s, 3H) 2.45 (s, 3H) 1.39 (d, J=7 Hz, 6H). MS-ESI (m/z) calc'd for C$_{22}$H$_{21}$N$_6$O$_2$ [M+H]$^+$: 401.2. Found 401.0.

Example 182: 5-Cyano-3,4-dimethyl-N-(3-(6-methylpyridin-2-yl)-1H-indazol-5-yl)picolinamide

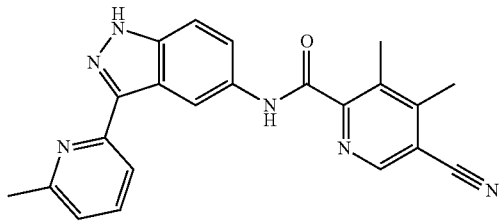 [SMILES: Cc1cccc(-c2n[nH]c3ccc(NC(=O)c4ncc(C#N)c(C)c4C)cc23)n1]

A mixture of N-(3-bromo-1H-indazol-5-yl)-5-cyano-3,4-dimethylpicolinamide (80 mg, 216.10 umol), 2-methyl-6-(tributylstannyl)pyridine (99.10 mg, 259.32 umol), Pd(PPh$_3$)$_2$Cl$_2$ (15.17 mg, 21.61 umol) in dioxane (3 mL) was degassed and purged with N$_2$ (3×), and then the mixture was stirred at 150° C. for 3 hrs under an N$_2$ atmosphere in a microwave reactor. The reaction mixture was concentrated and purified by preparative HPLC using Method BZ to afford the title compound (3.29 mg, 4%) as a pale yellow solid. $^1$H NMR (400 MHz, DMSO-d$_6$) δ 13.30 (s, 1H), 10.70 (s, 1H), 9.04 (s, 1H), 8.89 (s, 1H), 7.94 (d, J=7.72 Hz, 1H), 7.70-7.82 (m, 2H), 7.57 (d, J=9.04 Hz, 1H), 7.21 (d, J=7.50 Hz, 1H), 2.61 (s, 3H), 2.55 (s, 3H), 2.44 (s, 3H). MS-ESI (m/z) calc'd for C$_{22}$H$_{19}$N$_6$O [M+H]$^+$: 383.2. Found 383.2.

Example 183: N-(3-(1H-Pyrazol-4-yl)-1H-indazol-5-yl)-5-cyano-3,4-dimethylpicolinamide

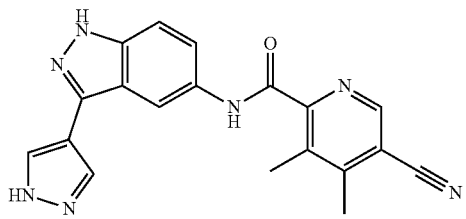 [SMILES: Cc1c(C#N)cnc(C(=O)Nc2ccc3[nH]nc(-c4cn[nH]c4)c3c2)c1C]

Prepared as described for 5-cyano-N-(3-(isoxazol-4-yl)-1H-indazol-5-yl)-3-methylpicolinamide using (1H-pyrazol-4-yl)boronic acid in place of isoxazole-4-boronic acid and 5-cyano-N-(3-iodo-1H-indazol-5-yl)-3,4-dimethylpicolinamide in place of 5-cyano-N-(3-iodo-1H-indazol-5-yl)-3-methylpyridine-2-carboxamide to afford the title compound (9.4 mg, 27%) as a yellow solid. $^1$H NMR (400 MHz, DMSO-d$_6$) δ 13.12 (br. s., 1H) 12.94 (s, 1H) 10.66 (s, 1H) 8.90 (s, 1H) 8.45 (d, J=1.32 Hz, 1H) 8.22 (br. s., 1H) 7.99 (br. s., 1H) 7.64-7.80 (m, 1H) 7.54 (d, J=8.80 Hz, 1H) 2.56 (s, 3H) 2.48 (s, 3H). MS-ESI (m/z) calc'd for C$_{19}$H$_{16}$N$_7$O [M+H]$^+$: 358.1. Found 358.3.

Example 184: 6-Chloro-5-cyano-3,4-dimethyl-N-(3-(oxazol-5-yl)-1H-indazol-5-yl)picolinamide

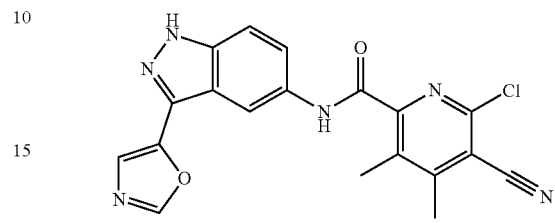

Prepared as described for 5-cyano-N-(7-fluoro-3-(furan-3-yl)-1H-indazol-5-yl)-3-methylpicolinamide using 6-chloro-5-cyano-3,4-dimethylpicolinic acid in place of 5-cyano-3-methylpicolinic acid and using 3-(oxazol-5-yl)-1H-indazol-5-amine in place of 7-fluoro-3-(furan-3-yl)-1H-indazol-5-amine to afford the title compound (6.5 mg, 9%) as a yellow solid. $^1$H NMR (400 MHz, DMSO-d$_6$) δ 13.59 (s, 1H), 10.84 (s, 1H), 8.59 (s, 1H), 8.54 (d, J=2.1 Hz, 1H), 7.72 (dd, J=9.0, 1.9 Hz, 1H), 7.67-7.62 (m, 2H), 2.61 (s, 3H), 2.41 (s, 3H). MS-ESI (m/z) calc'd for C$_{19}$H$_{14}$ClN$_6$O$_2$ [M+H]$^+$: 393.1/395.1. Found 393.1/395.1.

Example 185: 5-Cyano-N-(3-(1-(difluoromethyl)-1H-pyrazol-4-yl)-1H-indazol-5-yl)-3,4,6-trimethylpicolinamide

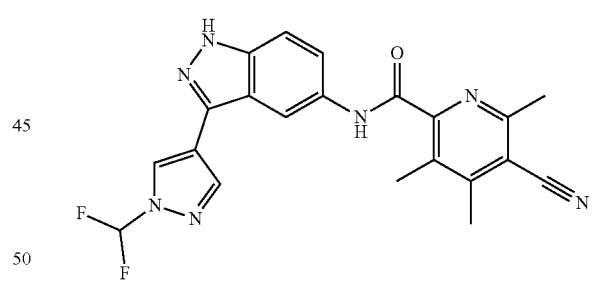

Prepared as described for 5-cyano-N-(7-fluoro-3-(furan-3-yl)-1H-indazol-5-yl)-3-methylpicolinamide using 5-cyano-3,4,6-trimethylpicolinic acid in place of 5-cyano-3-methylpicolinic acid and using 3-(1-(difluoromethyl)-1H-pyrazol-4-yl)-1H-indazol-5-amine in place of 7-fluoro-3-(furan-3-yl)-1H-indazol-5-amine to afford the title compound (40.2 mg, 44%) as a yellow solid. $^1$H NMR (400 MHz, DMSO-d$_4$) δ 13.20 (s, 1H), 10.63 (s, 1H), 8.73 (s, 1H), 8.41 (d, J=1.8 Hz, 1H), 8.30 (s, 1H), 7.94 (t, J=59.0 Hz, 1H), 7.74 (dd, J=8.9, 1.9 Hz, 1H), 7.59 (d, J=9.0 Hz, 1H), 2.72 (s, 3H), 2.55 (s, 3H), 2.42 (s, 3H). MS-ESI (m/z) calc'd for C$_{21}$H$_{18}$F$_2$N$_7$O [M+H]$^+$: 422.2. Found 422.2.

Example 187: 5-Cyano-3,4-dimethyl-N-(3-(1-methyl-1H-pyrazol-4-yl)-1H-indazol-5-yl)picolinamide

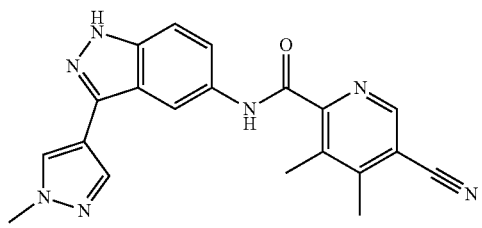 [SMILES: Cc1c(C#N)cnc(C(=O)Nc2ccc3[nH]nc(-c4cnn(C)c4)c3c2)c1C]

Prepared as described for 5-cyano-N-(3-(isoxazol-4-yl)-1H-indazol-5-yl)-3-methylpicolinamide using (1-methyl-1H-pyrazol-4-yl)boronic acid in place of isoxazole-4-boronic acid and 5-cyano-N-(3-iodo-1H-indazol-5-yl)-3,4-dimethylpicolinamide in place of 5-cyano-N-(3-iodo-1H-indazol-5-yl)-3-methylpyridine-2-carboxamide to afford the title compound (16.7 mg, 47%) as a yellow solid. $^1$H NMR (400 MHz, DMSO-$d_6$) δ 12.96 (s, 1H) 10.66 (s, 1H) 8.90 (s, 1H) 8.41 (d, J=1.54 Hz, 1H) 8.21 (s, 1H) 7.91 (d, J=0.66 Hz, 1H) 7.72 (dd, J=8.80, 1.76 Hz, 1H) 7.54 (d, J=9.02 Hz, 1H) 3.96 (s, 3H) 2.57 (s, 3H) 2.48 (s, 3H). MS-ESI (m/z) calc'd for $C_{20}H_{18}N_7O$ [M+H]$^+$: 372.2. Found 372.3.

Example 188: 3-Cyano-2,6-difluoro-N-(3-(oxazol-5-yl)-1H-indazol-5-yl)benzamide

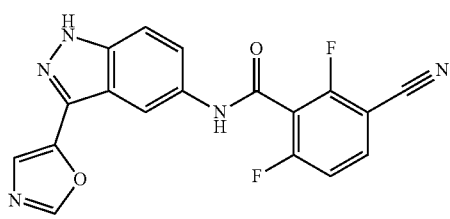

Prepared as described for 5-cyano-N-(7-fluoro-3-(furan-3-yl)-1H-indazol-5-yl)-3-methylpicolinamide using 3-cyano-2,6-difluorobenzoic acid in place of 5-cyano-3-methylpicolinic acid and using 3-(oxazol-5-yl)-1H-indazol-5-amine in place of 7-fluoro-3-(furan-3-yl)-1H-indazol-5-amine to afford the title compound (2.1 mg, 4%) as a white solid. $^1$H NMR (400 MHz, DMSO-$d_6$) δ 13.57 (s, 1H), 11.06 (s, 1H), 8.59 (s, 1H), 8.50 (dd, J=1.9, 0.8 Hz, 1H), 8.23 (ddd, J=8.8, 7.5, 5.9 Hz, 1H), 7.67 (dd, J=8.9, 0.8 Hz, 1H), 7.65 (s, 1H), 7.64-7.60 (m, 1H), 7.57 (dd, J=8.8, 1.1 Hz, 1H). MS-ESI (m/z) calc'd for $C_{15}H_{10}F_2N_5O_2$ [M+H]$^+$: 366.1. Found 366.1.

Example 189: 4-Cyano-N-(3-(1-(difluoromethyl)-1H-pyrazol-4-yl)-1H-indazol-5-yl)-2-methoxybenzamide

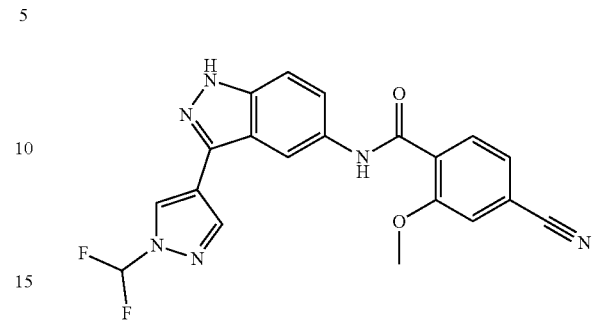

Prepared as described for 5-cyano-N-(7-fluoro-3-(furan-3-yl)-1H-indazol-5-yl)-3-methylpicolinamide using 4-cyano-2-methoxybenzoic acid in place of 5-cyano-3-methylpicolinic acid and using 3-(1-(difluoromethyl)-1H-pyrazol-4-yl)-1H-indazol-5-amine in place of 7-fluoro-3-(furan-3-yl)-1H-indazol-5-amine to afford the title compound (9.9 mg, 29%) as a white solid. $^1$H NMR (400 MHz, DMSO-$d_6$) δ 13.18 (br. s., 1H) 10.34 (s, 1H) 8.70 (s, 1H) 8.42 (d, J=1.32 Hz, 1H) 8.28 (s, 1H) 7.79-8.10 (m, 1H) 7.77 (d, J=7.70 Hz, 1H) 7.72 (d, J=1.32 Hz, 1H) 7.63-7.68 (m, 1H) 7.54-7.59 (m, 2H) 3.96 (s, 3H). MS-ESI (m/z) calc'd for $C_{20}H_{15}F_2N_6O_2$[M+H]$^+$: 409.1. Found 409.3.

Example 190: 4-Cyano-2-fluoro-6-methyl-N-(3-(oxazol-5-yl)-1H-indazol-5-yl)benzamide

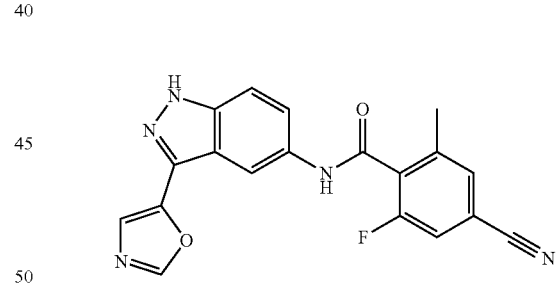

Prepared as described for 5-cyano-N-(7-fluoro-3-(furan-3-yl)-1H-indazol-5-yl)-3-methylpicolinamide using 4-cyano-2-fluoro-6-methylbenzoic acid in place of 5-cyano-3-methylpicolinic acid and using 3-(oxazol-5-yl)-1H-indazol-5-amine in place of 7-fluoro-3-(furan-3-yl)-1H-indazol-5-amine to afford the title compound (2.7 mg, 5%) as a white solid. $^1$H NMR (400 MHz, DMSO-$d_6$) δ 10.91 (s, 1H), 8.59 (s, 1H), 8.54 (dd, J=2.7, 1.1 Hz, 1H), 7.88 (dd, J=8.9, 1.4 Hz, 1H), 7.76 (d, J=1.3 Hz, 1H), 7.65-7.62 (m, 3H), 2.42 (s, 3H). MS-ESI (m/z) calc'd for $C_{19}H_{13}FN_5O_2$ [M+H]$^+$: 362.1. Found 362.2.

Example 191: 5-Cyano-N-(3-(2,6-dimethylpyridin-4-yl)-1H-indazol-5-yl)-3,4-dimethylpicolinamide

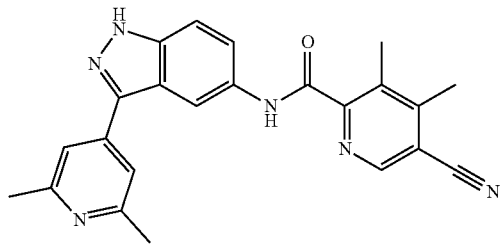 [SMILES: Cc1cc(-c2n[nH]c3ccc(NC(=O)c4ncc(C#N)c(C)c4C)cc23)cc(C)n1]

Step 1: 3-(2,6-Dimethylpyridin-4-yl)-1H-indazol-5-amine

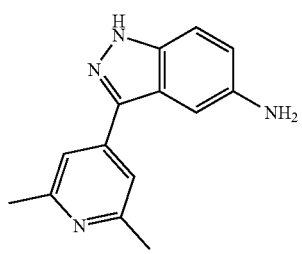 [SMILES: Cc1cc(-c2n[nH]c3ccc(N)cc23)cc(C)n1]

A mixture of 3-bromo-1H-indazol-5-amine (300 mg, 1.41 mmol), (2,6-dimethylpyridin-4-yl)boronic acid (256.31 mg, 1.70 mmol), K$_2$CO$_3$ (586.60 mg, 4.24 mmol) and Pd(dppf)Cl$_2$ (103.52 mg, 141.48 umol) in dioxane (5 mL) and H$_2$O (0.5 mL) was degassed and purged with N$_2$ (3×), and then the mixture was stirred at 100° C. for 12 hrs under an N$_2$ atmosphere The reaction mixture was poured into water (20 mL) and extracted with EtOAc (20 mL×3). The combined organic phases were washed with brine (20 mL×1), dried over Na$_2$SO$_4$, filtered and concentrated to give a residue. The residue was purified by preparative HPLC using Method CA to afford the title compound (80 mg, 24%) as a yellow solid. MS-(ESI) (m/z) calcd for C$_{14}$H$_{15}$N$_4$ (M+H)$^+$: 239.1. Found 239.2.

Step 2: 5-Cyano-N-(3-(2,6-dimethylpyridin-4-yl)-1H-indazol-5-vi)-3,4-dimethylpicolinamide

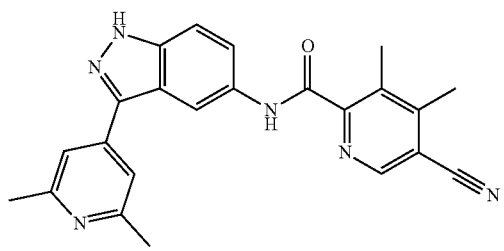 [SMILES: Cc1cc(-c2n[nH]c3ccc(NC(=O)c4ncc(C#N)c(C)c4C)cc23)cc(C)n1]

To a solution of 5-cyano-3,4-dimethylpicolinic acid (50 mg, 283.81 umol) in pyridine (2 mL) was added EDCI (81.61 mg, 425.72 umol) and 3-(2,6-dimethylpyridin-4-yl)-1H-indazol-5-amine (67.63 mg, 283.81 umol) and the mixture was stirred at 25° C. for 12 hrs. The reaction mixture was then concentrated to give a residue. The residue was purified by preparative HPLC using Method CB to afford the title compound (32.94 mg, 29%) as a pale yellow solid. $^1$H NMR (400 MHz, DMSO-d$_6$) δ 13.53 (br s, 1H), 10.76 (s, 1H), 8.91 (s, 1H), 8.55 (s, 1H), 7.88 (dd, J=1.6, 9.0 Hz, 1H), 7.65 (d, J=8.9 Hz, 1H), 7.60 (s, 2H), 2.56 (s, 3H), 2.53 (s, 6H), 2.47 (s, 3H). MS-ESI (m/z) calc'd for C$_{23}$H$_{21}$N$_6$O [M+H]$^+$: 397.2. Found 397.3.

Example 192: 3-Cyano-N-(3-(1-(difluoromethyl)-1H-pyrazol-4-yl)-1H-indazol-5-yl)-2-(trifluoromethyl)benzamide

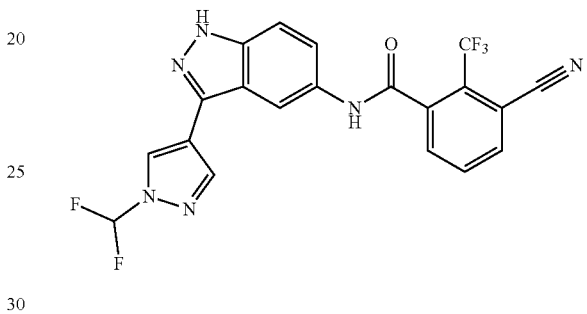

Step 1: N-(3-(1-(Difluoromethyl)-1H-pyrazol-4-yl)-1H-indazol-5-yl)-3-fluoro-2-(trifluoromethyl)benzamide

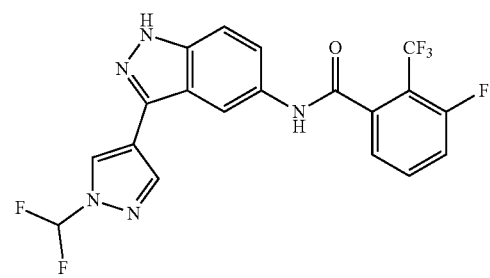 [SMILES: O=C(Nc1ccc2[nH]nc(-c3cnn(C(F)F)c3)c2c1)c1cccc(F)c1C(F)(F)F]

To a stirred solution of 3-fluoro-2-(trifluoromethyl)benzoic acid (100 mg, 480.52 umol) and 3-(1-(difluoromethyl)-1H-pyrazol-4-yl)-1H-indazol-5-amine (119.75 mg, 480.52 umol) in pyridine (3 mL) was added EDCI (119.75 mg, 624.67 umol) and the reaction mixture was stirred at 25° C. for 12 hrs. The reaction mixture was concentrated to give a residue which was poured into water (5 mL) and extracted with EtOAc (5 mL×3). The combined organic phases were washed with brine (5 mL×1), dried over Na$_2$SO$_4$, filtered and concentrated. The material was purified by silica gel column chromatography using a 0-50% EtOAc/petroleum ether gradient eluent to afford the title compound (120 mg, 57%) as an off-white solid which was used without further purification. MS-ESI (m/z) calcd for C$_{19}$H$_{12}$F$_6$N$_5$O [M+H]$^+$: 440.1. Found 440.1

Step 2: 3-Cyano-N-(3-(1-(difluoromethyl)-1H-pyrazol-4-yl)-1H-indazol-5-yl)-2-(trifluoromethyl)benzamide

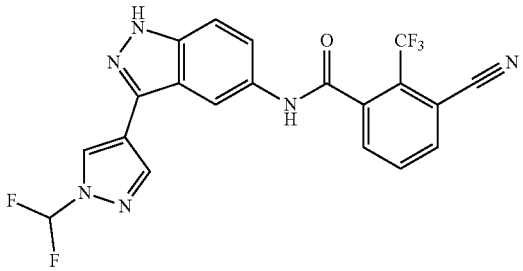 [SMILES: N#Cc1cccc(C(=O)Nc2ccc3[nH]nc(-c4cnn(C(F)F)c4)c3c2)c1C(F)(F)F]

N-(3-(1-(Difluoromethyl)-1H-pyrazol-4-yl)-1H-indazol-5-yl)-3-fluoro-2-(trifluoromethyl)benzamide (50 mg, 113.81 umol) and KCN (22.23 mg, 341.44 umol) were taken up in a microwave tube in DMF (2 mL). The sealed tube was heated at 150° C. for 2 hrs under microwave irradiation. After cooling to 25° C., the reaction mixture was adjusted to pH=8 with saturated aqueous NaHCO$_3$ and extracted with EtOAc (5 mL 3). The combined organic phases were washed with brine (5 mL×1), dried over Na$_2$SO$_4$, filtered and concentrated to give a residue. The residue was purified by preparative HPLC using Method CI to afford the title compound (17.96 mg, 17%) as a yellow solid. $^1$H NMR (400 MHz, DMSO-d$_6$) δ 13.23 (br s, 1H), 10.76 (s, 1H), 8.68 (s, 1H), 8.38-8.23 (m, 3H), 8.09-8.00 (m, 2H), 7.97-7.77 (m, 1H), 7.59 (s, 2H).) MS-ESI (m/z) calc'd for C$_{20}$H$_{12}$F$_5$N$_6$O [M+H]$^+$: 447.1. Found 447.1.

Example 193: 3-Cyano-N-(3-(1-(difluoromethyl)-1H-pyrazol-4-yl)-1H-indazol-5-yl)-2,6-dimethylbenzamide

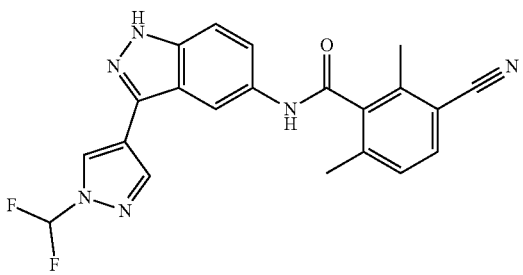 [SMILES: Cc1ccc(C#N)c(C)c1C(=O)Nc1ccc2[nH]nc(-c3cnn(C(F)F)c3)c2c1]

Step 1: 3-(1-(Difluoromethyl)-1H-pyrazol-4-yl)-1H-indazol-5-amine

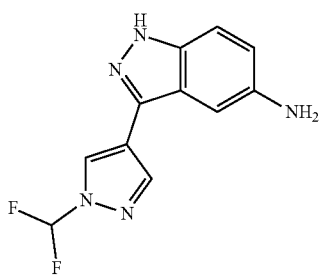

A mixture of 3-bromo-1H-indazol-5-amine (500 mg, 2.36 mmol), (1-(difluoromethyl)-1H-pyrazol-4-yl)boronic acid (572.64 mg, 3.54 mmol), Pd(Amphos)Cl$_2$ (166.96 mg, 235.80 umol) and AcOK (694.23 mg, 7.07 mmol) in EtOH (10 mL) and H$_2$O (2 mL) was degassed and purged with N$_2$ (3×), and then the mixture was stirred at 80° C. for 12 hrs under an N$_2$ atmosphere. After cooling to 25° C., the reaction mixture was filtered and the filtrate was concentrated. The residue was poured into water (10 mL) and extracted with EtOAc (10 mL×3). The combined organic phases were washed with brine (10 mL×1), dried over Na$_2$SO$_4$, filtered and concentrated to give a residue. The residue was purified by silica gel column chromatography using a 0-50% EtOAc/petroleum ether gradient eluent to afford the title compound (300 mg, 51%) as a brown solid. MS-ESI (m/z) calc'd for C$_{11}$H$_{10}$F$_2$N$_5$[M+H]$^+$: 250.1. Found 250.1.

Step 2: 3-Bromo-2,6-dimethylbenzoic acid

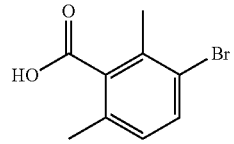

To a solution of methyl 3-bromo-2,6-dimethylbenzoate (300 mg, 1.23 mmol) in H$_2$O (3 mL) and MeOH (3 mL) was added NaOH (493.59 mg, 12.34 mmol) and the reaction mixture was stirred at 80° C. for 12 hrs. The reaction mixture was then concentrated and adjusted to pH=3 with 1 N aqueous HCl. The reaction mixture was filtered and the solid was dried to afford the title compound (250 mg, 88%) as a white solid, which was used without further purification. MS-ESI (m/z) calcd for C$_9$H$_{10}$BrO$_2$ [M−H]$^-$: 227.0/229.0. Found 226.9/228.9

Step 3: 3-Bromo-2,6-dimethylbenzoyl chloride

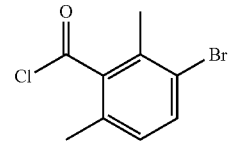

3-Bromo-2,6-dimethylbenzoic acid (160 mg, 698.48 umol) was dissolved into SOCl$_2$ (5 mL) and the reaction mixture was stirred at 80° C. for 12 hrs. The reaction mixture was then concentrated to afford the title compound (100 mg, 58%) as a yellow oil, which was used without further purification.

Step 4: 3-Bromo-N-(3-(f-(difluoromethyl)-1H-pyrazol-4-yl)-1H-indazol-5-yl)-2,6-dimethylbenzamide

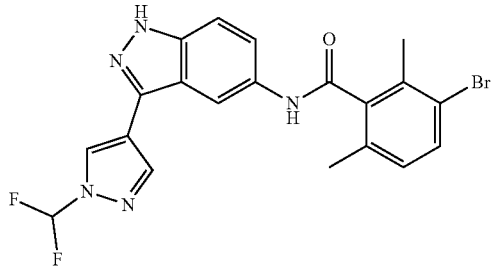

To a solution of 3-bromo-2,6-dimethylbenzoyl chloride (100 mg, 404.01 umol) in dioxane (5 mL) was added 3-(1-(difluoromethyl)-1H-pyrazol-4-yl)-1H-indazol-5-amine (70.48 mg, 282.81 umol) and Et$_3$N (122.65 mg, 1.21 mmol, 168.70 uL) and the mixture was stirred at 25° C. for 12 hrs. The reaction mixture was then concentrated to give a residue. The residue was purified by silica gel column chromatography using a 0-50% EtOAc/petroleum ether gradient eluent to afford the title compound (101 mg, 54%) as a yellow solid. MS-ESI (m/z) calcd for $C_{20}H_{17}BrF_2N_5O$ [M+H]$^+$: 460.1/462.1. Found 460.1/462.0.

Step 5: 3-Cyano-N-(3-(1-(difluoromethyl)-1H-pyrazol-4-yl)-1H-indazol-5-yl)-2,6-dimethylbenzamide

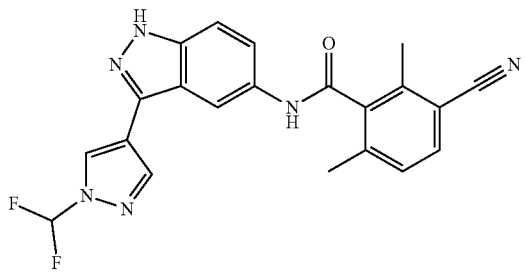 [SMILES: Cc1ccc(C#N)c(C)c1C(=O)Nc1ccc2[nH]nc(-c3cnn(C(F)F)c3)c2c1]

3-Bromo-N-(3-(1-(difluoromethyl)-1H-pyrazol-4-yl)-1H-indazol-5-yl)-2,6-dimethylbenzamide (80 mg, 173.81 umol), Zn(CN)$_2$ (20.41 mg, 173.81 umol, 11.03 uL), dppf (9.64 mg, 17.38 umol), Zn (1.14 mg, 17.38 umol) and Pd$_2$(dba)$_3$ (15.92 mg, 17.38 umol) were taken up in a microwave tube in DMA (2 mL) under N$_2$. The sealed tube was heated at 150° C. for 1 hr under microwave irradiation. The reaction mixture was poured into saturated aqueous NaHCO$_3$ (15 mL) and extracted with EtOAc (15 mL×3). The combined organic phases were washed with brine (15 mL×1), dried over Na$_2$SO$_4$, filtered and concentrated to give a residue. The residue was purified by preparative HPLC using Method BJ to afford the title compound (19.52 mg, 28%) as a white solid. $^1$H NMR (400 MHz, DMSO-d$_6$) δ 13.19 (br s, 1H), 10.57 (s, 1H), 8.69 (s, 1H), 8.41 (s, 1H), 8.28 (s, 1H), 8.14-7.90 (m, 1H), 7.78 (d, J=8.1 Hz, 1H), 7.70-7.52 (m, 2H), 7.38 (d, J=8.0 Hz, 1H), 2.49 (m, 3H), 2.40 (s, 3H). MS-ESI (m/z) calc'd for $C_{21}H_{17}F_2N_6O$ [M+H]$^+$: 407.1. Found 407.2.

Example 194: 3-Cyano-N-(3-(2-methoxypyridin-4-yl)-1H-indazol-5-yl)-1,4-dimethyl-1H-pyrazole-5-carboxamide

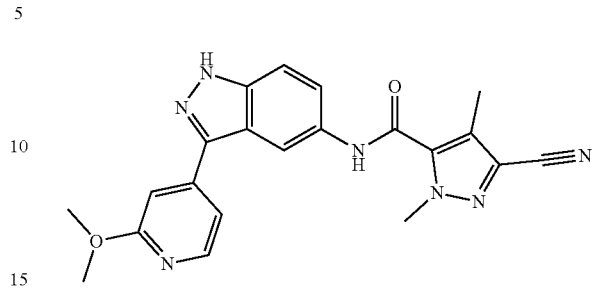

Prepared as described for 3-cyano-N-(3-(1-(difluoromethyl)-1H-pyrazol-4-yl)-1H-indazol-5-yl)-1,4-dimethyl-1H-pyrazole-5-carboxamide using 3-(2-methoxypyridin-4-yl)-1H-indazol-5-amine in place of 3-(1-(difluoromethyl)-1H-pyrazol-4-yl)-1H-indazol-5-amine to afford the title compound (24.46 mg, 28%) as a white solid. $^1$H NMR (400 MHz, DMSO-d$_6$) δ 8.59 (s, 1H), 8.30 (d, J=5.51 Hz, 1H), 7.61-7.73 (m, 2H), 7.55 (d, J=5.29 Hz, 1H), 7.29 (s, 1H), 4.03-4.07 (s, 3H), 3.93 (s, 3H), 2.31 (s, 3H). MS-ESI (m/z) calc'd for $C_{20}H_{18}N_7O_2$ [M+H]$^+$: 388.1. Found 388.2.

Example 195: 3-Cyano-N-(3-(1-(difluoromethyl)-1H-pyrazol-4-yl)-1H-indazol-5-yl)-1,4-dimethyl-1H-pyrazole-5-carboxamide

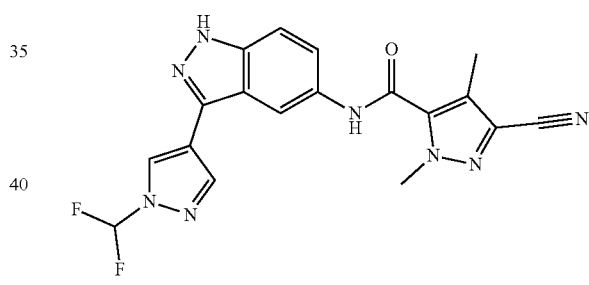

Step 1: Ethyl 3-cyano-4-methyl-1H-pyrazole-5-carboxylate

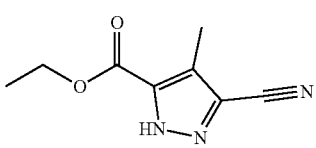

To a solution of ethyl but-2-ynoate (2.5 g, 22.30 mmol) in CHCl$_3$ (60 mL) and H$_2$O (2 mL) was added 2-aminoacetonitrile (3.71 g, 40.13 mmol, HCl salt) and NaNO$_2$ (4.61 g, 66.89 mmol). The mixture was stirred at 30° C. for 12 hrs, then warmed to 60° C. for another 12 hrs. The reaction mixture was quenched by addition of H$_2$O (20 mL) at 25° C. and the layers were separated. The organic layers were washed with H$_2$O (20 mL×1), dried over Na$_2$SO$_4$, filtered and concentrated under reduced pressure to give a residue. The residue was purified by flash silica gel chromatography (ISCO; 20 g SepaFlash column) using a 0-30% EtOAc/petroleum ether gradient eluent to afford the title compound (170 mg, 4%) as a yellow oil. MS-ESI (m/z) calcd for $C_8H_{10}N_3O_2[M+H]^+$: 180.1 Found 180.0.

Step 2: Ethyl 3-cyano-1,4-dimethyl-1H-pyrazole-5-carboxylate

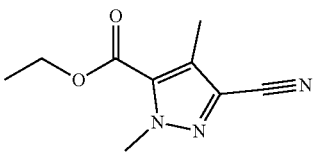

To a solution of ethyl 3-cyano-4-methyl-1H-pyrazole-5-carboxylate (100 mg, 558.11 umol) in DMF (1 mL) was added $K_2CO_3$ (231.40 mg, 1.67 mmol). The mixture was stirred at 25° C. for 0.5 hr. Then MeI (95.06 mg, 669.73 umol) was added and the mixture was stirred at 25° C. for 11.5 hrs. The reaction mixture was concentrated under reduced pressure to give a residue which was diluted with $H_2O$ (10 mL) and extracted with EtOAc (5 mL×3). The combined organic layers were dried over $Na_2SO_4$, filtered and concentrated under reduced pressure to give a residue. The residue was purified by preparative TLC ($SiO_2$, 5:1 petroleum ether/EtOAc, $R_f$=0.40) to afford the title compound (60 mg, 56%) as a white solid. MS-ESI (m/z) calcd for $C_9H_{12}N_3O_2$ $[M+H]^+$: 194.1. Found 194.1.

Step 3: 3-Cyano-1,4-dimethyl-1H-pyrazole-5-carboxylic acid

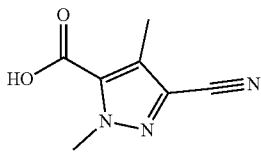

To a solution of ethyl 3-cyano-1,4-dimethyl-1H-pyrazole-5-carboxylate (60 mg, 310.56 umol) in THF (1 mL) and $H_2O$ (1 mL) was added NaOH (24.84 mg, 621.11 umol) and the mixture was stirred at 30° C. for 2 hrs. To the reaction mixture was added 1 N HCl to adjust to pH=2. The mixture was then diluted with $H_2O$ (2 mL) and extracted with EtOAc (5 mL×3). The combined organic layers were dried over $Na_2SO_4$, filtered and concentrated under reduced pressure to afford the title compound (40 mg, 78%) as a white solid, which was used without further purification.

Step 4: 3-Cyano-N-(3-(1-(difluoromethyl)-1H-pyrazol-4-yl)-1H-indazol-5-yl)-1,4-dimethyl-1H-pyrazole-5-carboxamide

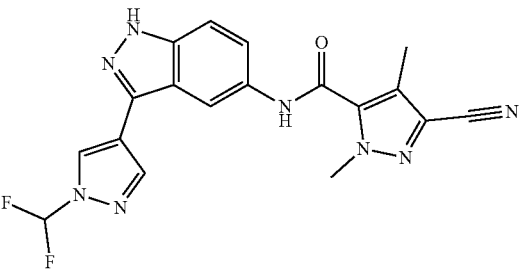 [SMILES: Cc1c(C#N)nn(C)c1C(=O)Nc1ccc2[nH]nc(-c3cnn(C(F)F)c3)c2c1]

To a solution of 3-cyano-1,4-dimethyl-1H-pyrazole-5-carboxylic acid (35 mg, 211.93 umol), 3-(1-(difluoromethyl)-1H-pyrazol-4-yl)-1H-indazol-5-amine (63.38 mg, 254.32 umol) in pyridine (1 mL) was added EDCI (60.94 mg, 317.89 umol) and the mixture was stirred at 30° C. for 2 hrs. The reaction mixture was concentrated and purified by preparative HPLC using Method BU to afford the title compound (14.73 mg, 18%) as a white solid. $^1$H NMR (400 MHz, DMSO-$d_6$) δ 13.24 (br s, 1H), 10.58 (s, 1H), 8.72 (s, 1H), 8.37 (s, 1H), 8.29 (s, 1H), 7.75-8.12 (m, 1H), 7.61 (s, 2H), 4.04 (s, 3H), 2.32 (s, 3H). MS-ESI (m/z) calc'd for $C_{18}H_{15}F_2N_5O$ $[M+H]^+$: 397.1. Found 397.2.

Example 196: 3-Cyano-N-(3-(isoxazol-4-yl)-1H-indazol-5-yl)-1,4-dimethyl-1H-pyrazole-5-carboxamide

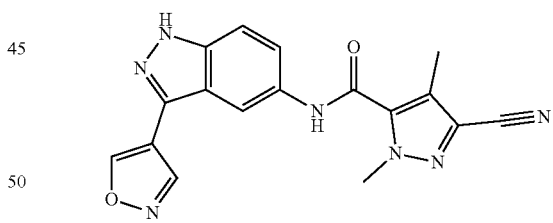

Prepared as described for 3-cyano-N-(3-(1-(difluoromethyl)-1H-pyrazol-4-yl)-1H-indazol-5-yl)-1,4-dimethyl-1H-pyrazole-5-carboxamide using 3-(isoxazol-4-yl)-1H-indazol-5-amine in place of 3-(1-(difluoromethyl)-1H-pyrazol-4-yl)-1H-indazol-5-amine to afford the title compound (100 mg, 29%) as a pale pink solid. $^1$H NMR (400 MHz, DMSO-$d_6$) δ 13.36 (s, 1H), 10.57 (s, 1H), 9.54 (s, 1H), 9.13 (s, 1H), 8.31 (s, 1H), 7.61 (s, 2H), 4.04 (s, 3H), 2.31 (s, 3H). MS-ESI (m/z) calc'd for $C_{17}H_{14}N_7O_2$ $[M+H]^+$: 348.1. Found 348.1.

Example 197: 5-Cyano-3,4-dimethyl-N-(3-(4-methyloxazol-2-yl)-1H-indazol-5-yl)picolinamide

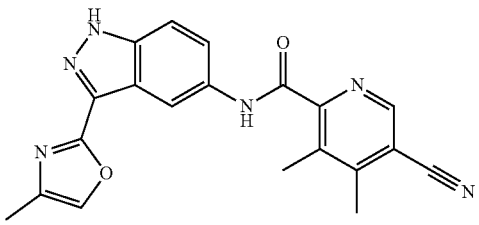 [SMILES: Cc1coc(-c2n[nH]c3ccc(NC(=O)c4ncc(C#N)c(C)c4C)cc23)n1]

Prepared as described for 5-cyano-3,4-dimethyl-N-(3-(2-methylpyrimidin-4-yl)-1H-indazol-5-yl)picolinamide using 4-methyl-2-(trimethylstannyl)oxazole in place of trimethyl-(2-methylpyrimidin-4-yl)stannane to afford the title compound (4 mg, 23%) as a pale yellow solid. $^1$H NMR (400 MHz, DMSO-d$_6$) δ 13.64 (s, 1H), 10.80 (s, 1H), 8.90 (s, 1H), 8.77-8.70 (m, 1H), 7.95 (q, J=1.1 Hz, 1H), 7.78 (dd, J=9.0, 2.0 Hz, 1H), 7.65 (dd, J=9.0, 0.8 Hz, 1H), 2.56 (s, 3H), 2.45 (s, 3H), 2.24 (d, J=1.3 Hz, 3H). MS-ESI (m/z) calc'd for $C_{20}H_{17}N_6O_2$[M+H]$^+$: 373.1. Found 373.3.

Example 198: 5-Cyano-3,4-dimethyl-N-(3-(oxazol-2-yl)-1H-indazol-5-yl)picolinamide

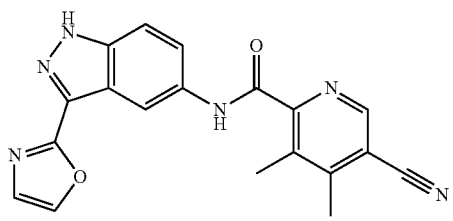 [SMILES: Cc1c(C#N)cnc(C(=O)Nc2ccc3[nH]nc(-c4ncco4)c3c2)c1C]

Prepared as described for 5-cyano-3,4-dimethyl-N-(3-(2-methylpyrimidin-4-yl)-1H-indazol-5-yl)picolinamide using 2-(trimethylstannyl)oxazole in place of trimethyl-(2-methylpyrimidin-4-yl)stannane to afford the title compound (12.2 mg, 9%) as a white solid. $^1$H NMR (400 MHz, DMSO-d$_6$) δ 13.67 (s, 1H), 10.79 (s, 1H), 8.90 (s, 1H), 8.89-8.86 (m, 1H), 8.27 (d, J=0.8 Hz, 1H), 7.72 (dd, J=9.0, 1.9 Hz, 1H), 7.65 (dd, J=9.0, 0.8 Hz, 1H), 7.50 (d, J=0.8 Hz, 1H), 2.56 (s, 3H), 2.46 (s, 3H). MS-ESI (m/z) calc'd for $C_{19}H_{15}N_6O_2$ [M+H]$^+$: 359.1. Found 359.2.

Example 199: 3-Cyano-2-fluoro-N-(3-(oxazol-5-yl)-1H-indazol-5-yl)benzamide

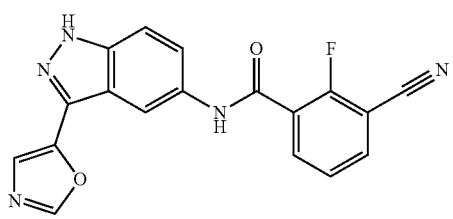 [SMILES: N#Cc1cccc(C(=O)Nc2ccc3[nH]nc(-c4cnco4)c3c2)c1F]

Prepared as described for 5-cyano-N-(7-fluoro-3-(furan-3-yl)-1H-indazol-5-yl)-3-methylpicolinamide using 3-cyano-2-fluorobenzoic acid in place of 5-cyano-3-methylpicolinic acid and using 3-(oxazol-5-yl)-1H-indazol-5-amine in place of 7-fluoro-3-(furan-3-yl)-1H-indazol-5-amine to afford the title compound (1.75 mg, 3%) as a white solid. $^1$H NMR (400 MHz, DMSO-d$_6$) δ 10.11 (dd, J=1.9, 0.8 Hz, 1H), 9.95 (s, 1H), 9.64 (ddd, J=8.4, 7.0, 1.8 Hz, 1H), 9.52 (ddd, J=7.8, 6.1, 1.8 Hz, 1H), 9.30-8.99 (m, 4H). MS-ESI (m/z) calc'd for $C_{18}H_{11}FN_5O_2$ [M+H]$^+$: 348.1. Found 348.1.

Example 200: 4-Cyano-2-methoxy-N-(3-(oxazol-5-yl)-1H-indazol-5-yl)benzamide

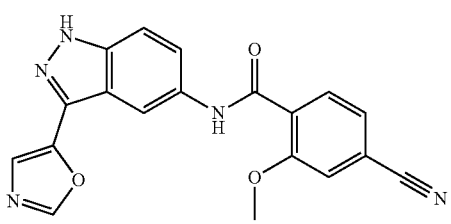 [SMILES: COc1cc(C#N)ccc1C(=O)Nc1ccc2[nH]nc(-c3cnco3)c2c1]

Prepared as described for 5-cyano-N-(7-fluoro-3-(furan-3-yl)-1H-indazol-5-yl)-3-methylpicolinamide using 4-cyano-2-methoxybenzoic acid in place of 5-cyano-3-methylpicolinic acid and using 3-(oxazol-5-yl)-1H-indazol-5-amine in place of 7-fluoro-3-(furan-3-yl)-1H-indazol-5-amine to afford the title compound (18.4 mg, 45%) as a yellow solid. $^1$H NMR (400 MHz, DMSO-d$_6$) δ 13.49 (br. s., 1H) 10.41 (s, 1H) 8.57-8.59 (m, 1H) 8.55 (d, J=0.88 Hz, 1H) 7.76 (d, J=7.70 Hz, 1H) 7.71 (d, J=1.32 Hz, 1H) 7.59-7.67 (m, 3H) 7.56 (dd, J=7.70, 1.32 Hz, 1H) 3.95 (s, 3H). MS-ESI (m/z) calc'd for $C_{19}H_{14}N_5O_3$ [M+H]$^+$: 360.1. Found 360.3.

Example 201: 4-Cyano-N-(3-(1-(difluoromethyl)-1H-pyrazol-4-yl)-1H-indazol-5-yl)-2-methoxy-6-methylbenzamide

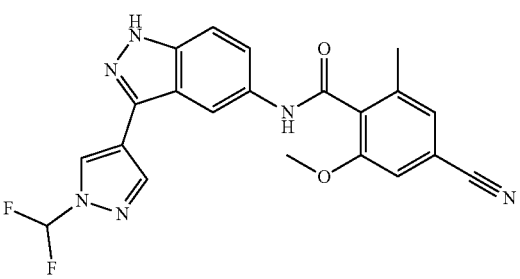 [SMILES: COc1cc(C#N)cc(C)c1C(=O)Nc1ccc2[nH]nc(-c3cnn(C(F)F)c3)c2c1]

Prepared as described for 4-cyano-N-(3-(isoxazol-4-yl)-1H-indazol-5-yl)-3-methoxypicolinamide using 4-chloro-2-methoxy-6-methyl-N-(3-(oxazol-5-yl)-1H-indazol-5-yl) benzamide in place of 4-chloro-3-methoxy-N-[3-(1,2-oxazol-4-yl)-1H-indazol-5-yl]pyridine-2-carboxamide to afford the title compound (29.4 mg, 47%) as a white solid. $^1$H NMR (400 MHz, DMSO-d$_6$) δ 13.18 (br. s., 1H) 10.49 (s, 1H) 8.67 (s, 1H) 8.43 (d, J=1.10 Hz, 1H) 8.27 (s, 1H) 7.77-8.12 (m, 1H) 7.61-7.66 (m, 1H) 7.54-7.59 (m, 1H) 7.49 (s, 1H) 7.44 (s, 1H) 3.85 (s, 3H) 2.33 (s, 3H). MS-ESI (m/z) calc'd for $C_{21}H_{17}F_2N_6O_2$ [M+H]$^+$: 423.1. Found 432.3.

Example 202: 5-Cyano-3,4,6-trimethyl-N-(3-(oxazol-5-yl)-1H-indazol-5-yl)picolinamide

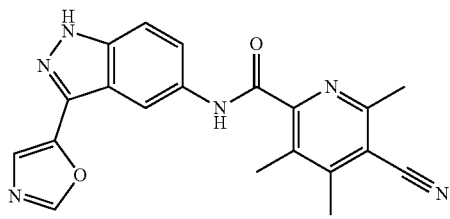 [SMILES: Cc1nc(C(=O)Nc2ccc3[nH]nc(-c4cnco4)c3c2)c(C)c(C)c1C#N]

Prepared as described for 5-cyano-N-(7-fluoro-3-(furan-3-yl)-1H-indazol-5-yl)-3-methylpicolinamide using 5-cyano-3,4,6-trimethylpicolinic acid in place of 5-cyano-3-methylpicolinic acid and using 3-(oxazol-5-yl)-1H-indazol-5-amine in place of 7-fluoro-3-(furan-3-yl)-1H-indazol-5-amine to afford the title compound (20.5 mg, 35%) as a yellow solid. $^1$H NMR (400 MHz, DMSO-d$_6$) δ 13.54 (s, 1H), 10.72 (s, 1H), 8.59 (s, 1H), 8.57 (d, J=1.6 Hz, 1H), 7.73 (dd, J=9.0, 1.9 Hz, 1H), 7.63 (m, 2H), 2.72 (s, 3H), 2.54 (s, 3H), 2.41 (s, 3H). MS-ESI (m/z) calc'd for $C_{20}H_{17}N_6O_2$ [M+H]$^+$: 373.3. Found 373.3.

Example 203: 3-Cyano-2-fluoro-6-methyl-N-(3-(oxazol-5-yl)-1H-indazol-5-yl)benzamide

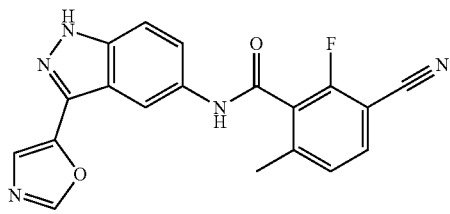 [SMILES: Cc1ccc(C#N)c(F)c1C(=O)Nc1ccc2[nH]nc(-c3cnco3)c2c1]

Step 1: 3-Bromo-2-fluoro-6-methyl-N-(3-(oxazol-5-yl)-1H-indazol-5-yl)benzamide

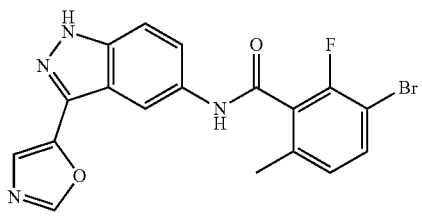

To a solution of 3-(oxazol-5-yl)-1H-indazol-5-amine (100 mg, 499.51 umol) and 3-bromo-2-fluoro-6-methylbenzoic acid (139.68 mg, 599.41 umol) in pyridine (2 mL) was added EDCI (143.64 mg, 749.27 umol) and the mixture was stirred at 25° C. for 12 hrs. The reaction mixture was concentrated under reduced pressure to remove solvent and then diluted with H$_2$O (5 mL) and filtered. The solid was washed with H$_2$O (10 mL) and dried in vacuum to afford the title compound (142 mg) as a red solid which was used without further purification. MS-ESI (m/z) calcd for $C_{15}H_{13}BrFN_4O_2$ [M+H]$^+$: 415.0/417.0. Found 415.0/417.0.

Step 2: 3-Cyano-2-fluoro-6-methyl-N-(3-(oxazol-5-yl)-1H-indazol-5-yl)benzamide

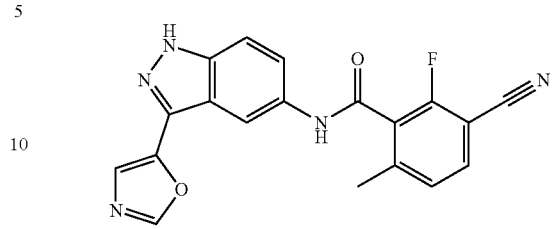

A mixture of 3-bromo-2-fluoro-6-methyl-N-(3-(oxazol-5-yl)-1H-indazol-5-yl)benzamide (70 mg, 168.59 umol), Zn(CN)$_2$ (39.59 mg, 337.17 umol), Zn (992.15 ug, 15.17 umol), dppf (2.80 mg, 5.06 umol) and Pd$_2$(dba)$_3$ (9.26 mg, 10.12 umol) in DMA (1 mL) was degassed and purged with N$_2$ (3×), and then the mixture was stirred at 120° C. for 5 hrs under an N$_2$ atmosphere in a microwave reactor. The reaction mixture was concentrated and purified by preparative HPLC using Method CJ to afford the title compound (8.54 mg, 11%) as a white solid, TFA salt. $^1$H NMR (400 MHz, DMSO-d$_6$) δ 13.54 (s, 1H), 10.65 (s, 1H), 8.59 (s, 1H), 8.52 (s, 1H), 7.97 (t, J=7.72 Hz, 11H), 7.60-7.71 (m, 3H), 7.47 (d, J=8.16 Hz, 11H), 2.58 (s, 3H). MS-ESI (m/z) calc'd for $C_{19}H_{13}FN_5O_2$ [M+H]$^+$: 362.1. Found 362.0.

Example 204: 5-Cyano-N-(3-(1-(difluoromethyl)-1H-pyrazol-3-yl)-1H-indazol-5-yl)-3,4-dimethylpicolinamide

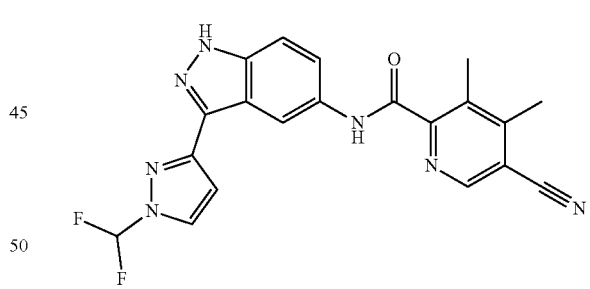

Prepared as described for 5-cyano-3,4-dimethyl-N-(3-(2-methylprop-1-en-1-yl)-1H-indazol-5-yl)picolinamide using 1-(difluoromethyl)-3-(4,4,5,5-tetramethyl-1,3,2-dioxaborolan-2-yl)-1H-pyrazole in place of 4,4,5,5-tetramethyl-2-(2-methylprop-1-en-1-yl)-1,3,2-dioxaborolane to afford the title compound (4.47 mg, 6%) as a white solid. $^1$H NMR (400 MHz, DMSO-d$_6$) δ 13.33 (br s, 1H) 10.74 (s, 1H) 8.88 (s, 1H) 8.63 (s, 1H) 8.34 (d, J=2.57 Hz, 1H) 7.74-8.06 (m, 2H) 7.59 (d, J=8.80 Hz, 1H) 6.98 (d, J=2.57 Hz, 1H) 2.55 (s, 3H) 2.44 (s, 3H). MS-ESI (m/z) calc'd for $C_{20}H_{16}F_2N_7O$ [M+H]$^+$: 408.1 Found 408.0.

Example 205: 5-Cyano-N-(3-(2-ethoxypyridin-4-yl)-1H-indazol-5-yl)-3,4-dimethylpicolinamide

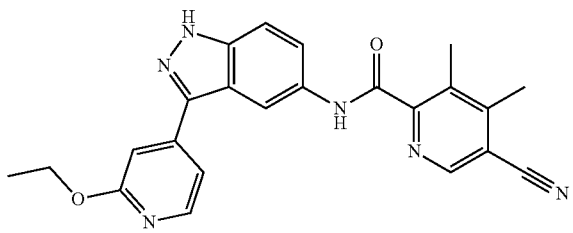 [SMILES: CCOc1cc(-c2n[nH]c3ccc(NC(=O)c4ncc(C#N)c(C)c4C)cc23)ccn1]

Prepared as described for 5-cyano-3,4-dimethyl-N-(3-(2-methylprop-1-en-1-yl)-1H-indazol-5-yl)picolinamide using 2-ethoxy-4-(4,4,5,5-tetramethyl-1,3,2-dioxaborolan-2-yl) pyridine in place of 4,4,5,5-tetramethyl-2-(2-methylprop-1-en-1-yl)-1,3,2-dioxaborolane to afford the title compound (45.33 mg, 15%) as a yellow solid. $^1$H NMR (400 MHz, DMSO-$d_6$) δ 13.59 (s, 1H) 10.81 (s, 1H) 8.90 (s, 1H) 8.62 (s, 1H) 8.28 (d, J=5.26 Hz, 1H) 7.86 (dd, J=8.99, 1.41 Hz, 1H) 7.65 (d, J=9.05 Hz, 1H) 7.55 (d, J=5.38 Hz, 1H) 7.27 (s, 1H) 4.38 (q, J=7.05 Hz, 2H) 2.56 (s, 3H) 2.46 (s, 3H) 1.36 (t, J=7.03 Hz, 3H). MS-ESI (m/z) calc'd for $C_{23}H_{21}N_6O_2$ [M+H]$^+$: 413.2 Found 413.0.

Example 206: 4-Cyano-N-(3-(oxazol-5-yl)-1H-indazol-5-yl)-6,7-dihydro-5H-cyclopenta[c]pyridine-1-carboxamide

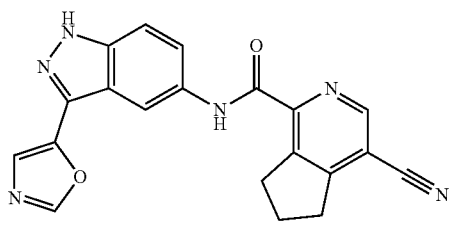 [SMILES: N#Cc1cnc(C(=O)Nc2ccc3[nH]nc(-c4cnco4)c3c2)c2c1CCC2]

Prepared as described for 5-cyano-N-(7-fluoro-3-(furan-3-yl)-1H-indazol-5-yl)-3-methylpicolinamide using 4-cyano-6,7-dihydro-5H-cyclopenta[c]pyridine-1-carboxylic acid in place of 5-cyano-3-methylpicolinic acid and using 3-(oxazol-5-yl)-1H-indazol-5-amine in place of 7-fluoro-3-(furan-3-yl)-1H-indazol-5-amine to afford the title compound (6 mg, 8.1%) as a yellow solid. $^1$H NMR (400 MHz, DMSO-$d_6$) δ 13.51 (s, 1H), 10.82 (s, 1H), 8.95 (s, 1H), 8.65 (d, J=1.9 Hz, 1H), 8.59 (s, 1H), 7.93 (dd, J=9.1, 1.9 Hz, 1H), 7.67 (s, 1H), 7.61 (d, J=9.0 Hz, 1H), 3.43 (t, J=7.6 Hz, 2H), 3.16 (t, J=7.7 Hz, 2H), 2.16 (p, J=7.7 Hz, 2H). MS-ESI (m/z) calc'd for $C_{20}H_{15}N_6O_2$ [M+H]$^+$: 371.1. Found 371.2.

Example 207: 5-Cyano-3,4-dimethyl-N-(3-(5-methyloxazol-2-yl)-1H-indazol-5-yl)picolinamide

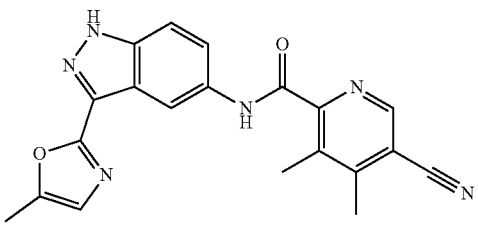

Prepared as described for 5-cyano-3,4-dimethyl-N-(3-(2-methylpyrimidin-4-yl)-1H-indazol-5-yl)picolinamide using 5-methyl-2-(trimethylstannyl)oxazole in place of trimethyl-(2-methylpyrimidin-4-yl)stannane to afford the title compound (9.5 mg, 26%) as a white solid. $^1$H NMR (400 MHz, DMSO-$d_6$) δ 13.63 (s, 1H), 10.75 (s, 1H), 8.88 (s, 1H), 8.80 (d, J=1.9 Hz, 1H), 7.69 (dd, J=9.0, 2.0 Hz, 1H), 7.62 (d, J=8.9 Hz, 1H), 7.08 (d, J=1.3 Hz, 1H), 2.55 (s, 3H), 2.44 (s, 3H), 2.43 (d, J=1.2 Hz, 3H). MS-ESI (m/z) calc'd for $C_{20}H_{17}N_6O_2$[M+H]$^+$: 373.1. Found 373.3.

Example 208: 4-Cyano-2-methoxy-6-methyl-N-(3-(oxazol-5-yl)-1H-indazol-5-yl)benzamide

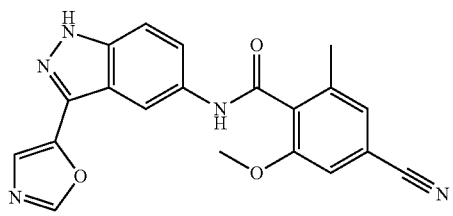 [SMILES: COc1cc(C#N)cc(C)c1C(=O)Nc1ccc2[nH]nc(-c3cnco3)c2c1]

Prepared as described for 4-cyano-N-(3-(isoxazol-4-yl)-1H-indazol-5-yl)-3-methoxypicolinamide using 4-chloro-2-methoxy-6-methyl-N-(3-(oxazol-5-yl)-1H-indazol-5-yl) benzamide in place of 4-chloro-3-methoxy-N-[3-(1,2-oxazol-4-yl)-1H-indazol-5-yl]pyridine-2-carboxamide to afford the title compound (9.6 mg, 18%) as an off-white solid. $^1$H NMR (400 MHz, DMSO-$d_6$) δ 13.52 (br. s., 1H) 10.56 (s, 1H) 8.53-8.62 (m, 2H) 7.58-7.65 (m, 3H) 7.49 (s, 1H) 7.44 (s, 1H) 3.86 (s, 3H) 2.32 (s, 3H). MS-ESI (m/z) calc'd for $C_{20}H_{16}N_5O_3$ [M+H]$^+$: 374.1. Found 374.3.

Example 210: 5-Cyano-N-(3-(isoxazol-4-yl)-1H-indazol-5-yl)-3,4,6-trimethylpicolinamide

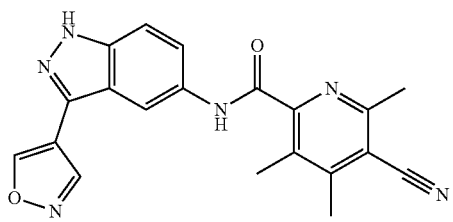 [SMILES: Cc1nc(C(=O)Nc2ccc3[nH]nc(-c4cnoc4)c3c2)c(C)c(C)c1C#N]

Prepared as described for 5-cyano-N-(7-fluoro-3-(furan-3-yl)-1H-indazol-5-yl)-3-methylpicolinamide using 5-cyano-3,4,6-trimethylpicolinic acid in place of 5-cyano-3-methylpicolinic acid and using 3-(isoxazol-4-yl)-1H-indazol-5-amine in place of 7-fluoro-3-(furan-3-yl)-1H-indazol-5-amine to afford the title compound (7.1 mg, 12%) as a yellow solid. $^1$H NMR (400 MHz, DMSO-d$_6$) δ 13.37 (s, 1H), 10.65 (s, 1H), 9.56 (s, 1H), 9.15 (s, 1H), 8.37 (dd, J=1.9, 0.8 Hz, 1H), 7.74 (dd, J=9.0, 1.9 Hz, 1H), 7.61 (dd, J=9.0, 0.8 Hz, 1H), 2.72 (s, 3H), 2.55 (s, 3H), 2.42 (s, 3H). MS-ESI (m/z) calc'd for C$_{20}$H$_{17}$N$_6$O$_2$[M+H]$^+$: 373.3. Found 373.3.

Example 211: 5-Cyano-4-methoxy-3-methyl-N-(3-(oxazol-5-yl)-1H-indazol-5-yl)picolinamide

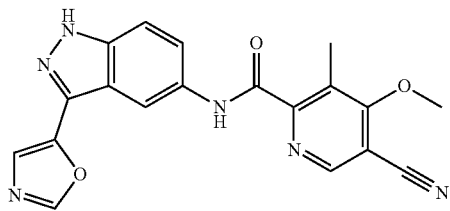 [SMILES: COc1c(C#N)cnc(C(=O)Nc2ccc3[nH]nc(-c4cnco4)c3c2)c1C]

Prepared as described for 5-cyano-N-(7-fluoro-3-(furan-3-yl)-1H-indazol-5-yl)-3-methylpicolinamide using 5-cyano-4-methoxy-3-methylpicolinic acid in place of 5-cyano-3-methylpicolinic acid and using 3-(oxazol-5-yl)-1H-indazol-5-amine in place of 7-fluoro-3-(furan-3-yl)-1H-indazol-5-amine to afford the title compound (12.7 mg, 17%) as a yellow solid. $^1$H NMR (400 MHz, DMSO-d$_6$) δ 13.53 (s, 1H), 10.75 (s, 1H), 8.85 (d, J=0.7 Hz, 1H), 8.58 (s, 2H), 7.76 (dd, J=9.0, 1.9 Hz, 1H), 7.64 (s, 1H), 7.62 (dd, J=9.0, 0.8 Hz, 1H), 4.27 (s, 3H), 2.39 (s, 3H). MS-ESI (m/z) calc'd for C$_{19}$H$_{15}$N$_6$O$_3$[M+H]$^+$: 375.1. Found 375.2.

Example 212: 3-Cyano-N-(3-(oxazol-5-yl)-1H-indazol-5-yl)-2-(trifluoromethoxy)benzamide

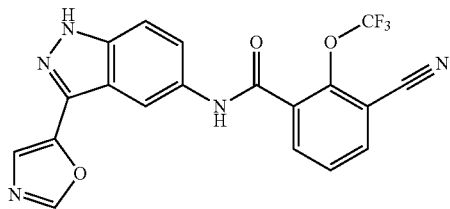 [SMILES: N#Cc1cccc(C(=O)Nc2ccc3[nH]nc(-c4cnco4)c3c2)c1OC(F)(F)F]

Step 1: 3-Bromo-2-(trifluoromethoxy)benzoic acid

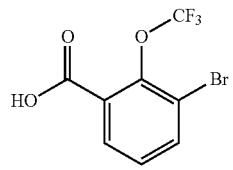 [SMILES: O=C(O)c1cccc(Br)c1OC(F)(F)F]

To a solution of 1-bromo-2-(trifluoromethoxy)benzene (500 mg, 2.07 mmol) in THF (3 mL) was added LDA (2 M in THF, 1.14 mL, 2.28 mmol). The mixture was stirred at −65° C. for 2 hrs and then dry ice (CO$_2$ solid, more than 10 eq) was added and the mixture was stirred at 25° C. for 10 hrs. The reaction mixture was diluted with 2 M NaOH to pH=12 and extracted with EtOAc (15 mL 3). The organic layers were discarded. To the aqueous layer was added 6 M HCl to pH=4 and the aqueous layers were extracted with EtOAc (15 mL×3). The combined organic layers were dried over Na$_2$SO$_4$, filtered and concentrated under reduced pressure to give a residue. The residue was purified by preparative HPLC using Method CK to afford the title compound (75 mg, 13%) as a colorless oil. MS-ESI (m/z) calcd for C$_8$H$_5$BrF$_3$O$_3$ [M−H]$^-$: 282.9/284.9. Found 282.8/284.8.

Step 2: 3-Bromo-N-(3-(oxazol-5-yl)-1H-indazol-5-yl)-2-(trifluoromethoxy)benzamide

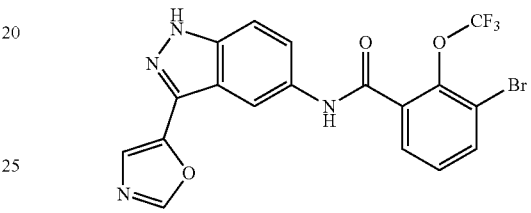

To a solution of 3-bromo-2-(trifluoromethoxy)benzoic acid (65 mg, 228.06 umol) in pyridine (5 mL) was added EDCI (87.44 mg, 456.12 umol) and 3-(oxazol-5-yl)-1H-indazol-5-amine (54.79 mg, 273.67 umol) and the mixture was stirred at 25° C. for 2 hrs. The mixture was then concentrated to give a residue which was diluted with water (5 mL). A red solid formed that was collected by filtration, washed with H$_2$O (3 mL×3), and dried under vacuum to afford the title compound (111 mg) as a red solid which was used without further purification. MS-ESI (m/z) calcd for C$_{15}$H$_{11}$BrF$_3$N$_4$O$_3$ [M−H]$^+$: 467.0/469.0. Found 467.1/469.1.

Step 3: 3-Cyano-N-(3-(oxazol-5-yl)-1H-indazol-5-yl)-2-(trifluoromethoxy)benzamide

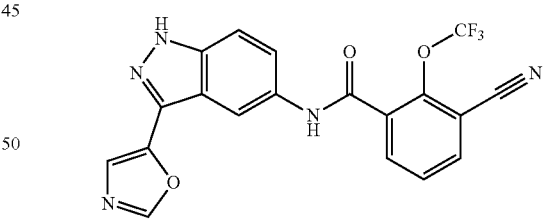

A mixture of 3-bromo-N-(3-(oxazol-5-yl)-1H-indazol-5-yl)-2-(trifluoromethoxy)benzamide (100 mg, 214.04 umol), Zn(CN)$_2$ (25.13 mg, 214.04 umol) and Pd(PPh$_3$)$_4$ (24.73 mg, 21.40 umol) in DMF (5 mL) was degassed and purged with N$_2$ (3×), and then the mixture was stirred at 100° C. for 2 hrs under an N$_2$ atmosphere. The reaction was filtered and the filtrate was concentrated to give a residue. The residue was purified by preparative HPLC using Method CL to afford the title compound (6.32 mg, 5%) as a pale yellow solid, TFA salt. $^1$H NMR (400 MHz, DMSO-d$_6$) δ 13.48 (br s, 1H), 10.74 (s, 1H), 8.52 (s, 1H), 8.40 (s, 1H), 8.03-8.21 (m, 2H), 7.74 (t, J=7.83 Hz, 1H), 7.46-7.59 (m, 3H). MS-ESI (m/z) calc'd for C$_{19}$H$_{11}$F$_3$N$_5$O$_3$ [M+H]$^+$: 414.1. Found 413.9.

Example 213: 5-Cyano-1,2-dimethyl-N-(3-(oxazol-5-yl)-1H-indazol-5-yl)-6-oxo-1,6-dihydropyridine-3-carboxamide

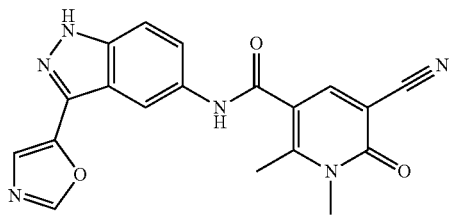 [SMILES: Cc1c(C(=O)Nc2ccc3[nH]nc(-c4cnco4)c3c2)cc(C#N)c(=O)n1C]

Step 1: Ethyl 2-((dimethylamino)methylene)-3-oxobutanoate

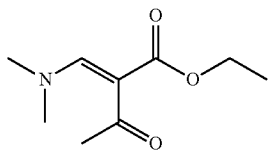

To a solution of ethyl 3-oxobutanoate (10 g, 76.84 mmol) in EtOH (50 mL) was added DMF-DMA (9.61 g, 80.68 mmol) and the mixture was stirred at 60° C. for 2 hrs. The reaction mixture was concentrated to afford the title compound (13.14 g, 100%) as a red oil which was used without further purification.

Step 2: Ethyl 5-cyano-2-methyl-6-oxo-1,6-dihydropyridine-3-carboxylate

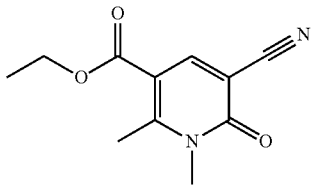 [SMILES: CCOC(=O)c1cc(C#N)c(=O)n(C)c1C]

A solution of NaOEt was prepared by adding Na (902.35 mg, 39.25 mmol) to EtOH (15 mL) at 25° C. and stirring for 0.5 hr. This was then added to another solution of 2-cyanoacetamide (3 g, 35.68 mmol) in EtOH (30 mL) slowly at 25° C. After addition, a solution of ethyl 2-((dimethylamino)methylene)-3-oxobutanoate (7.27 g, 39.25 mmol) in EtOH (10 mL) was added to the mixture and stirring was continued at 20° C. for 12 hrs. The mixture was acidified by addition of AcOH (5 g) to pH=5 and concentrated under vacuum at 45° C. 1 N HCl (50 mL) was added and the precipitated product was filtered, washed with $H_2O$ (20 mL×2) and dried under vacuum to afford the title compound (4 g, 58%) as a pink solid which was used without further purification. MS-(ESI) (m/z) calcd for $C_{10}H_{11}N_2O_3$ (M+H)$^+$: 207.1. Found 207.0

Step 3: Ethyl 5-cyano-1,2-dimethyl-6-oxo-1,6-dihydropyridine-3-carboxylate

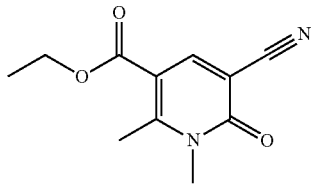 [SMILES: CCOC(=O)c1cc(C#N)c(=O)n(C)c1C]

To a solution of ethyl 5-cyano-2-methyl-6-oxo-1,6-dihydropyridine-3-carboxylate (500 mg, 2.42 mmol) in DMF (12 mL) was added $K_2CO_3$ (402.16 mg, 2.91 mmol) and MeI (344.18 mg, 2.42 mmol) and the mixture was stirred at 20° C. for 2 hrs. The reaction mixture was then diluted with $H_2O$ (30 mL) and extracted with EtOAc (15 mL×5). The combined organic layers were dried over $Na_2SO_4$, filtered and concentrated to give a residue which was purified by flash silica gel chromatography (ISCO; 12 g SepaFlash column) using a 0-30% EtOAc/petroleum ether gradient eluent to afford the title compound (370 mg, 69%) as a yellow solid. MS-(ESI) (m/z) calcd for $C_{11}H_{13}N_2O_3$ (M+H)$^+$: 221.1. Found 221.0.

Step 4: 5-Cyano-1,2-dimethyl-6-oxo-1,6-dihydropyridine-3-carboxylic acid

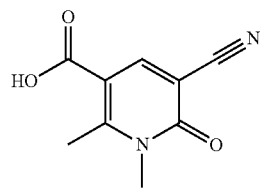

To a solution of ethyl 5-cyano-1,2-dimethyl-6-oxo-1,6-dihydropyridine-3-carboxylate (150 mg, 681.12 umol) in THF (4 mL) and MeOH (1 mL) was added a 1 M aqueous LiOH solution (2.04 mL, 0.002 mol) and the mixture was stirred at 20° C. for 1 hr. The reaction mixture was acidified with 1 N HCl to pH=2 and extracted with EtOAc (10 mL×3). The combined organic layers were dried over $Na_2SO_4$, filtered and concentrated to afford the title compound (100 mg, 76%) as a light yellow solid which was used without further purification. MS-(ESI) (m/z) calcd for $C_9H_9N_2O_3$ (M+H)$^+$: 193.1. Found 193.0.

Step 5: 5-Cyano-1,2-dimethyl-N-(3-(oxazol-5-yl)-1H-indazol-5-yl)-6-oxo-1,6-dihydropyridine-3-carboxamide

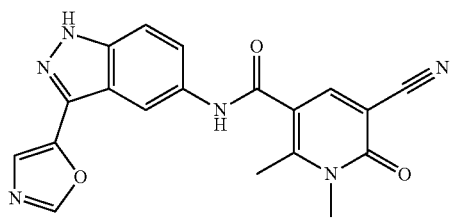 [SMILES: Cc1c(C(=O)Nc2ccc3[nH]nc(-c4cnco4)c3c2)cc(C#N)c(=O)n1C]

To a solution of 5-cyano-1,2-dimethyl-6-oxo-1,6-dihydropyridine-3-carboxylic acid (50 mg, 260.18 umol) in pyridine (2 mL) was added EDCI (74.82 mg, 390.28 umol) and 3-(oxazol-5-yl)-1H-indazol-5-amine (52.09 mg, 260.18 umol) and the mixture was stirred at 25° C. for 2 hrs. The reaction mixture was concentrated to give a residue which was diluted with MeOH (2 mL). A solid formed that was collected by filtration and washed with MeOH (2 mL×3). The solid was dried under vacuum and purified by preparative HPLC using Method CN to afford the title compound (35.56 mg, 28%) as a yellow solid, TFA salt. $^1$H NMR (400 MHz, DMSO-$d_6$) δ 13.51 (s, 1H) 10.47 (s, 1H) 8.59 (s, 1H) 8.48 (s, 1H) 8.40 (s, 1H) 7.60-7.69 (m, 3H) 3.60 (s, 3H) 2.65 (s, 3H). MS-ESI (m/z) calc'd for $C_{19}H_{15}N_6O_3$ [M+H]$^+$: 375.1. Found 375.1.

Example 214: 3-Cyano-N-(3-(oxazol-5-yl)-1H-indazol-5-yl)-2-(prop-1-en-2-yl)benzamide

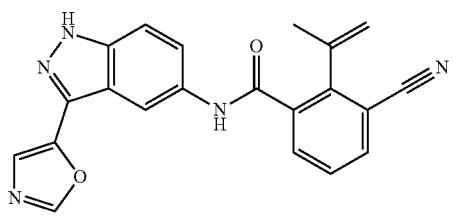 [SMILES: C=C(C)c1c(C#N)cccc1C(=O)Nc1ccc2[nH]nc(-c3cnco3)c2c1]

Step 1: Ethyl 3-cyano-2-iodobenzoate

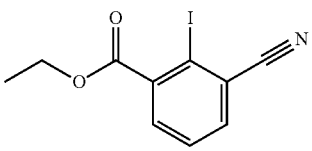

To a solution of ethyl 3-cyanobenzoate (500 mg, 2.85 mmol) in THF (6 mL) was added TMPMgCl.LiCl (1 M in THF/toluene, 4.28 mL, 4.28 mmol) and the mixture was stirred at 25° C. for 1 hr. Then a solution of I$_2$ (869.29 mg, 3.42 mmol, 689.91 uL) in THF (5 mL) was added and the reaction mixture was stirred at 25° C. for an additional 1 hr. The reaction mixture was poured into water (10 mL) and extracted with EtOAc (10 mL 3). The combined organic phases were washed with brine (10 mL×1), dried over Na$_2$SO$_4$, filtered and concentrated to give a residue. The residue was purified by silica gel column chromatography using a 0-20% EtOAc/petroleum ether gradient eluent to afford the title compound (450 mg, 52%) as a yellow solid. $^1$H NMR (400 MHz, DMSO-$d_6$) δ 7.86 (d, J=8.0 Hz, 1H), 7.68 (d, J=7.6 Hz, 1H), 7.53 (t, J=8.0 Hz, 1H), 4.43 (q, J=7.2 Hz, 2H), 1.43 (t, J=7.2 Hz, 3H).

Step 2: Ethyl 3-cyano-2-vinylbenzoate

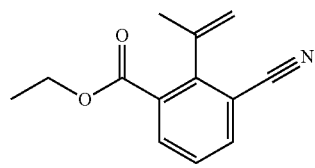 [SMILES: C=C(C)c1c(C#N)cccc1C(=O)OCC]

A mixture of ethyl 3-cyano-2-iodobenzoate (210 mg, 697.49 umol), 4,4,5,5-tetramethyl-2-(prop-1-en-2-yl)-1,3,2-dioxaborolane (175.81 mg, 1.05 mmol), Pd(Amphos)Cl$_2$ (49.39 mg, 69.75 umol) and KOAc (205.35 mg, 2.09 mmol) in EtOH (2 mL) and H$_2$O (0.2 mL) was degassed and purged with N$_2$ (3×), and then the mixture was stirred at 50° C. for 12 hrs under an N$_2$ atmosphere. The reaction mixture was concentrated to give a residue. The residue was purified by silica gel column chromatography using a 0-20% EtOAc/petroleum ether gradient eluent to afford the title compound (120 mg, 80%) as a white solid. $^1$H NMR (400 MHz, DMSO-$d_6$) δ 8.03 (d, J=8.0 Hz, 1H), 7.79 (d, J=6 Hz, 1H), 7.45 (t, J=8.0 Hz, 1H), 5.36 (s, 1H) 4.95 (s, 1H), 4.35 (q, J=7.2 Hz, 2H), 2.20 (s, 3H), 1.37 (t, J=7.2 Hz, 3H).

Step 3: 3-Cyano-2-vinylbenzoic acid

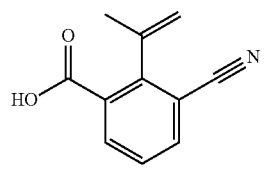

To a solution of ethyl 3-cyano-2-vinylbenzoate (210 mg, 975.62 umol) in THF (2 mL) and H$_2$O (2 mL) was added LiOH.H$_2$O (81.87 mg, 1.95 mmol) and the mixture was stirred at 25° C. for 12 hrs. The reaction mixture was adjusted to pH=7 with 1 N HCl. The aqueous phase was extracted with dichloromethane (15 mL×3) and the combined organic phases were washed with brine (15 mL×1), dried over Na$_2$SO$_4$, filtered and concentrated to afford the title compound (158 mg, 93%) as a brown solid which was used without further purification. MS-ESI (m/z) calcd for $C_{11}H_{10}NO_2$ [M−H]$^-$: 186.1. Found 186.0

Step 4: 3-Cyano-N-(3-(oxazol-5-yl)-1H-indazol-5-yl)-2-(prop-1-en-2-yl)benzamide

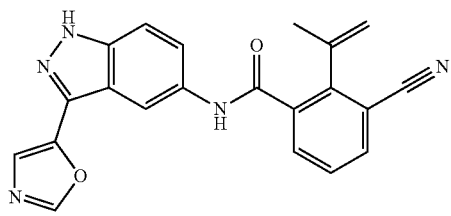 [SMILES: C=C(C)c1c(C#N)cccc1C(=O)Nc1ccc2[nH]nc(-c3cnco3)c2c1]

To a solution of 3-cyano-2-vinylbenzoic acid (50 mg, 267.10 umol) in DMF (2 mL) was added HOBt (43.31 mg, 320.52 umol), EDCI (61.44 mg, 320.52 umol) and Et$_3$N (81.08 mg, 801.31 umol, 111.53 uL) and the mixture was stirred at 25° C. for 0.5 hr. Then 3-(oxazol-5-yl)-1H-indazol-5-amine (53.47 mg, 267.10 umol) was added and the reaction mixture was stirred at 25° C. for 12 hrs. The reaction mixture was poured into water (5 mL) and extracted with EtOAc (5 mL×3). The combined organic phases were washed with brine (5 mL×1), dried over $Na_2SO_4$, filtered and concentrated to give a residue. The residue was purified by preparative HPLC using Method CG to afford the title compound (60 mg, 60%) as a white solid. $^1$H NMR (400 MHz, DMSO-$d_6$) δ 13.49 (br s, 1H), 10.51 (s, 1H), 8.58 (s, 1H), 8.48 (s, 1H), 7.99 (dd, J=1.1, 7.7 Hz, 1H), 7.89 (dd, J=1.2, 7.7 Hz, 1H), 7.67-7.62 (m, 1H), 7.60 (d, J=2.7 Hz, 3H), 5.36 (s, 1H), 5.05 (s, 1H), 2.13 (s, 3H). MS-ESI (m/z) calc'd for $C_{21}H_{16}NO_2$ $[M+H]^+$: 370.1. Found 370.2.

Example 215: 5-Cyano-3,4-dimethyl-N-(3-(1-(1-methylpiperidin-4-yl)-1H-pyrazol-4-yl)-1H-indazol-5-yl)picolinamide

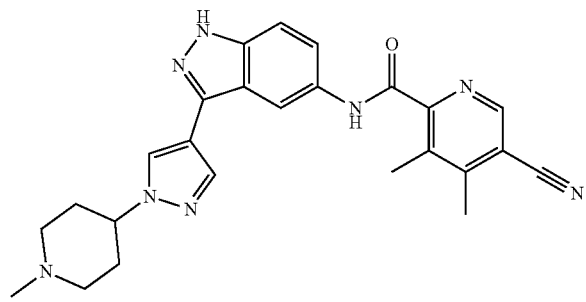 [SMILES: Cc1c(C#N)cnc(C(=O)Nc2ccc3[nH]nc(-c4cnn(C5CCN(C)CC5)c4)c3c2)c1C]

Prepared as described for 5-cyano-N-(3-(isoxazol-4-yl)-1H-indazol-5-yl)-3-methylpicolinamide using (1-(1-methylpiperidin-4-yl)-1H-pyrazol-4-yl)boronic acid in place of isoxazole-4-boronic acid and 5-cyano-N-(3-iodo-1H-indazol-5-yl)-3,4-dimethylpicolinamide in place of 5-cyano-N-(3-iodo-1H-indazol-5-yl)-3-methylpyridine-2-carboxamide to afford the title compound (22 mg, 46%) as a yellow solid. $^1$H NMR (400 MHz, DMSO-$d_6$) δ 12.95 (br. s., 1H) 10.64 (s, 1H) 8.90 (s, 1H) 8.39 (d, J=1.32 Hz, 1H) 8.26 (s, 1H) 8.18 (s, 1H) 7.94 (s, 1H) 7.75 (dd, J=9.02, 1.76 Hz, 1H) 7.53 (d, J=8.80 Hz, 1H) 4.20-4.32 (m, 1H) 2.85-2.95 (m, 2H) 2.56 (s, 3H) 2.48 (s, 3H) 2.24 (s, 3H) 2.01-2.15 (m, 6H). MS-ESI (m/z) calc'd for $C_{25}H_{27}N_5O$ $[M+H]^+$: 455.2. Found 455.2.

Example 216: 6-Chloro-5-cyano-N-(3-(isoxazol-4-yl)-1H-indazol-5-yl)-3,4-dimethylpicolinamide

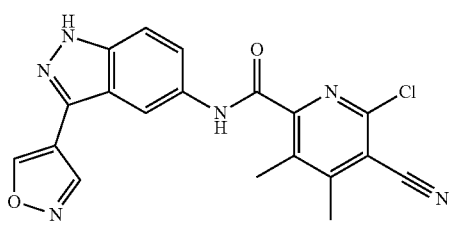 [SMILES: Cc1c(C(=O)Nc2ccc3[nH]nc(-c4cnoc4)c3c2)nc(Cl)c(C#N)c1C]

Prepared as described for 5-cyano-N-(7-fluoro-3-(furan-3-yl)-1H-indazol-5-yl)-3-methylpicolinamide using 6-chloro-5-cyano-3,4-dimethylpicolinic acid in place of 5-cyano-3-methylpicolinic acid and using 3-(isoxazol-4-yl)-1H-indazol-5-amine in place of 7-fluoro-3-(furan-3-yl)-1H-indazol-5-amine to afford the title compound (7.3 mg, 16%) as a yellow solid. $^1$H NMR (400 MHz, DMSO-$d_6$) δ 13.37 (br. s., 1H) 10.74 (br. s., 1H) 9.57 (s, 1H) 9.15 (s, 1H) 8.34 (d, J=1.10 Hz, 1H) 7.67-7.73 (m, 1H) 7.58-7.66 (m, 1H) 2.61 (s, 3H) 2.42 (s, 3H). MS-ESI (m/z) calc'd for $C_{19}H_{14}ClN_6O_2[M+H]^+$: 393.1/395.1. Found 393.2/395.3.

Example 217: 5-Cyano-N-(3-(1-isopropyl-1H-pyrazol-4-yl)-1H-indazol-5-yl)-3,4-dimethylpicolinamide

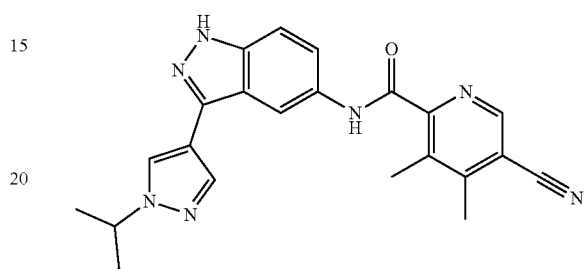

Prepared as described for 5-cyano-N-(3-(isoxazol-4-yl)-1H-indazol-5-yl)-3-methylpicolinamide using (1-isopropyl-1H-pyrazol-4-yl)boronic acid in place of isoxazole-4-boronic acid and 5-cyano-N-(3-iodo-1H-indazol-5-yl)-3,4-dimethylpicolinamide in place of 5-cyano-N-(3-iodo-1H-indazol-5-yl)-3-methylpyridine-2-carboxamide to afford the title compound (15.5 mg, 40%) as a yellow solid. $^1$H NMR (400 MHz, DMSO-$d_6$) δ 12.95 (s, 1H) 10.65 (s, 1H) 8.90 (s, 1H) 8.38 (d, J=1.32 Hz, 1H) 8.24 (s, 1H) 7.93 (s, 1H) 7.75 (dd, J=9.13, 1.65 Hz, 1H) 7.53 (d, J=9.02 Hz, 1H) 4.56-4.69 (m, 1H) 2.56 (s, 3H) 2.47 (s, 3H) 1.50 (d, J=6.60 Hz, 6H). MS-ESI (m/z) calc'd for $C_{22}H_{22}N_7O$ $[M+H]^+$: 400.2. Found 400.3.

Example 219: 5-Cyano-N-(3-(2-methoxy-6-methylpyridin-4-yl)-1H-indazol-5-yl)-3,4-dimethylpicolinamide

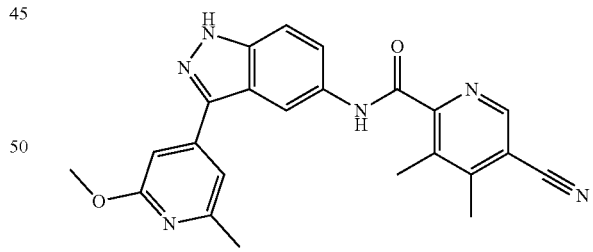

Prepared as described for 5-cyano-N-(3-(isoxazol-4-yl)-1H-indazol-5-yl)-3-methylpicolinamide using (2-methoxy-6-methylpyridin-4-yl)boronic acid in place of isoxazole-4-boronic acid and 3-cyano-2-fluoro-N-(3-iodo-1H-indazol-5-yl)benzamide in place of 5-cyano-N-(3-iodo-1H-indazol-5-yl)-3-methylpyridine-2-carboxamide to afford the title compound (2.1 mg, 4%) as a yellow solid. $^1$H NMR (400 MHz, DMSO-$d_6$) δ 13.54 (s, 1H), 10.77 (s, 1H), 8.90 (s, 1H), 8.59 (d, J=1.8 Hz, 1H), 7.86 (dd, J=9.0, 1.9 Hz, 1H), 7.64 (d, J=9.0 Hz, 1H), 7.43 (d, J=1.2 Hz, 11H), 7.10 (s, 1H), 3.91 (s, 3H), 3.28 (s, 3H), 2.56 (s, 3H), 2.46 (s, 3H). MS-ESI (m/z) calc'd for $C_{23}H_2N_6O_2[M+H]^+$: 413.2. Found 413.3.

Example 220: 2-Chloro-3-cyano-N-(3-(isoxazol-4-yl)-1H-indazol-5-yl)benzamide

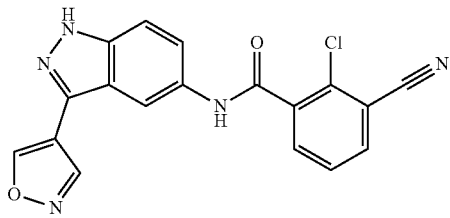 [SMILES: N#Cc1cccc(C(=O)Nc2ccc3[nH]nc(-c4cnoc4)c3c2)c1Cl]

Prepared as described for 5-cyano-N-(7-fluoro-3-(furan-3-yl)-1H-indazol-5-yl)-3-methylpicolinamide using 2-chloro-3-cyanobenzoic acid in place of 5-cyano-3-methylpicolinic acid acid and using 3-(isoxazol-4-yl)-1H-indazol-5-amine in place of 7-fluoro-3-(furan-3-yl)-1H-indazol-5-amine to afford the title compound (9 mg, 13%) as a light brown solid. $^1$H NMR (400 MHz, DMSO-$d_6$) δ 13.36 (s, 1H) 10.72 (s, 1H) 9.52 (s, 1H) 9.13 (s, 1H) 8.35 (s, 1H) 8.13 (dd, J=7.92, 1.54 Hz, 1H) 7.98 (dd, J=7.70, 1.76 Hz, 1H) 7.71 (t, J=7.70 Hz, 1H) 7.63 (s, 2H). MS-ESI (m/z) calc'd for $C_{15}H_{11}ClN_5O_2$ [M+H]$^+$: 364.1/366.1. Found 364.1/366.2.

Example 221: 5-Cyano-3,4-dimethyl-N-(3-(1-(oxetan-3-yl)-1H-pyrazol-4-yl)-1H-indazol-5-yl)picolinamide

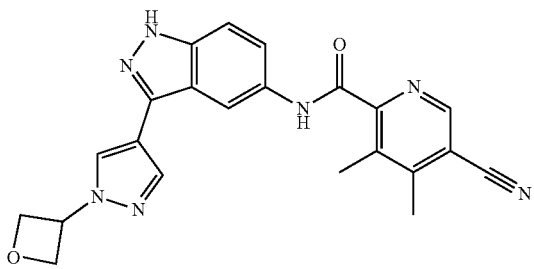 [SMILES: Cc1c(C#N)cnc(C(=O)Nc2ccc3[nH]nc(-c4cnn(C5COC5)c4)c3c2)c1C]

Prepared as described for 5-cyano-N-(3-(isoxazol-4-yl)-1H-indazol-5-yl)-3-methylpicolinamide using (1-(oxetan-3-yl)-1H-pyrazol-4-yl)boronic acid in place of isoxazole-4-boronic acid and 5-cyano-N-(3-iodo-1H-indazol-5-yl)-3,4-dimethylpicolinamide in place of 5-cyano-N-(3-iodo-1H-indazol-5-yl)-3-methylpyridine-2-carboxamide to afford the title compound (22.1 mg, 56%) as a yellow solid. $^1$H NMR (400 MHz, DMSO-$d_6$) δ 13.01 (s, 1H) 10.66 (s, 1H) 8.90 (s, 1H) 8.35-8.47 (m, 2H) 8.09 (s, 1H) 7.73 (dd, J=9.02, 1.54 Hz, 1H) 7.55 (d, J=8.80 Hz, 1H) 5.67-5.78 (m, 1H) 4.91-5.03 (m, 4H) 2.57 (s, 3H) 2.48 (s, 3H). MS-ESI (m/z) calc'd for $C_{22}H_{20}N_7O_2$ [M+H]$^+$: 414.2. Found 414.3.

Example 222: 5-Cyano-3,4,6-trimethyl-N-(3-(thiazol-5-yl)-1H-indazol-5-yl)picolinamide

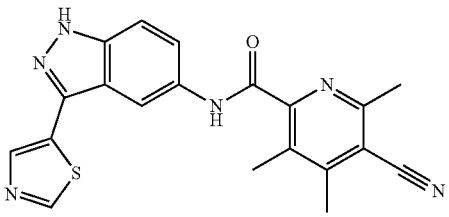

Prepared as described for 5-cyano-N-(7-fluoro-3-(furan-3-yl)-1H-indazol-5-yl)-3-methylpicolinamide using 5-cyano-3,4,6-trimethylpicolinic acid in place of 5-cyano-3-methylpicolinic acid and using 3-(thiazol-5-yl)-1H-indazol-5-amine in place of 7-fluoro-3-(furan-3-yl)-1H-indazol-5-amine to afford the title compound (12.3 mg, 17%) as a white solid. $^1$H NMR (400 MHz, DMSO-$d_6$) δ 13.42 (s, 1H), 10.71 (s, 1H), 9.15 (s, 1H), 8.59 (d, J=1.8 Hz, 1H), 8.40 (s, 1H), 7.77 (dd, J=9.0, 1.9 Hz, 1H), 7.63 (d, J=9.0 Hz, 1H), 2.41 (s, 3H), 2.72 (s, 3H), 2.54 (s, 3H). MS-ESI (m/z) calc'd for $C_{20}H_{17}N_6OS$ [M+H]$^+$: 389.1. Found 389.2.

Example 223: 5-Cyano-N-(3-cyclopropyl-1H-indazol-5-yl)-3,4-dimethylpicolinamide

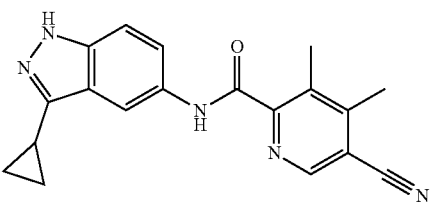 [SMILES: Cc1c(C#N)cnc(C(=O)Nc2ccc3[nH]nc(C4CC4)c3c2)c1C]

Step 1: 3-Cyclopropyl-5-nitro-1-(tetrahydro-2H-pyran-2-yl)-1H-indazole

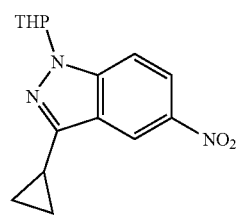

To a solution of 3-iodo-5-nitro-1-(tetrahydro-2H-pyran-2-yl)-1H-indazole (300 mg, 803.98 umol) and cyclopropylboronic acid (103.59 mg, 1.21 mmol) in toluene (6 mL) and $H_2O$ (0.4 mL) was added $K_3PO_4$ (682.63 mg, 3.22 mmol) and Pd(PPh$_3$)$_4$ (92.90 mg, 80.40 umol) and the mixture was stirred at 90° C. for 12 hrs under $N_2$. The reaction was concentrated and purified by flash silica gel chromatography (ISCO; 4 g SepaFlash column) using a 0-15% EtOAc/petroleum ether gradient eluent to afford the title compound (183 mg, 70%) as a yellow liquid. MS-ESI (m/z) calcd for $C_{15}H_{18}N_3O_3$ [M+H]$^+$: 288.1. Found 288.1.

Step 2: 3-Cyclopropyl-1-(tetrahydro-2H-pyran-2-yl)-1H-indazol-5-amine

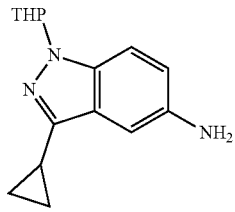

To a solution of 3-cyclopropyl-5-nitro-1-(tetrahydro-2H-pyran-2-yl)-1H-indazole (183 mg, 636.94 umol) in EtOH (4 mL) and H$_2$O (1 mL) was added Fe (177.85 mg, 3.18 mmol) and NH$_4$Cl (170.35 mg, 3.18 mmol) and the mixture was stirred at 80° C. for 2 hrs. The reaction was then filtered and the filtrate was concentrated to give residue. The residue was extracted with EtOAc (5 mL×3) and saturated aqueous NaHCO$_3$ (5 mL). The organic layers were dried over anhydrous Na$_2$SO$_4$, filtered and the filtrate was concentrated under vacuum to afford the title compound (153 mg, 93%) as a brown liquid which was used without further purification. MS-ESI (m/z) calcd for C$_{15}$H$_{20}$N$_3$O [M+H]$^+$: 258.2. Found 258.1.

Step 3: 5-Cyano-N-(3-cyclopropyl-1-(tetrahydro-2H-pyran-2-yl)-1H-indazol-5-yl)-3,4-dimethylpicolinamide

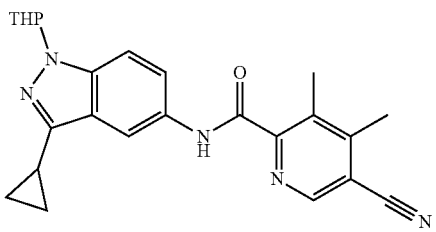

To a solution of 5-cyano-3,4-dimethylpicolinic acid (91.05 mg, 516.85 umol) in DMF (3 mL) was added HATU (294.78 mg, 775.27 umol), Et$_3$N (156.90 mg, 1.55 mmol) and 3-cyclopropyl-1-(tetrahydro-2H-pyran-2-yl)-1H-indazol-5-amine (133 mg, 516.85 umol) and the mixture was stirred at 25° C. for 12 hrs. The reaction was concentrated to give a residue which was purified by preparative TLC (SiO$_2$, 3:1 petroleum ether/EtOAc, R$_f$=0.23) to afford the title compound (57 mg, 27%) as a yellow solid. MS-ESI (m/z) calcd for C$_{24}$H$_{26}$N$_5$O$_2$ [M+H]$^+$: 416.2. Found 416.1.

Step 4: 5-Cyano-N-(3-cyclopropyl-1H-indazol-5-yl)-3,4-dimethylpicolinamide

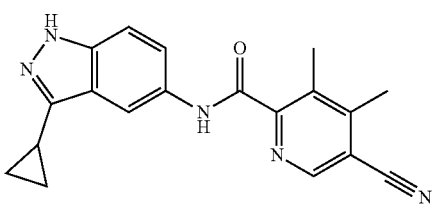

To a solution of 5-cyano-N-(3-cyclopropyl-1-(tetrahydro-2H-pyran-2-yl)-1H-indazol-5-yl)-3,4-dimethylpicolinamide (57 mg, 137.19 umol) in MeOH (2 mL) and H$_2$O (0.4 mL) was added PTSA (118.12 mg, 685.94 umol) and the mixture was stirred at 70° C. for 1.5 hrs. The reaction was filtered and the solid obtained was dried under vacuum to afford the title compound (12.86 mg, 28%) as a pale yellow solid. $^1$H NMR (400 MHz, DMSO-d$_6$) δ 12.53 (br s, 1H) 10.61 (s, 1H) 8.88 (s, 1H) 8.29 (s, 1H) 7.55 (br d, J=8.82 Hz, 1H) 7.43 (d, J=9.04 Hz, 1H) 2.55 (s, 3H) 2.44 (s, 3H) 2.18-2.23 (m, 1H) 0.96-1.02 (m, 2H) 0.90-0.95 (m, 2H). MS-ESI (m/z) calc'd for C$_{19}$H$_{18}$N$_5$O$_2$ [M+H]$^+$: 332.1. Found 332.1.

Example 224: 5-cyano-1-methyl-N-(3-(oxazol-5-yl)-1H-indazol-5-yl)-6-oxo-1,6-dihydropyridine-3-carboxamide

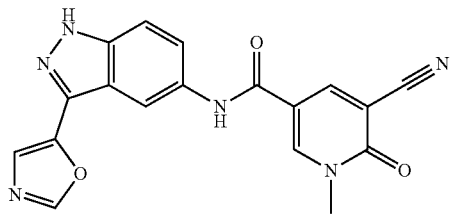 [SMILES: Cn1cc(C(=O)Nc2ccc3[nH]nc(-c4cnco4)c3c2)cc(C#N)c1=O]

Step 1: 5-Bromo-1-methyl-6-oxo-1,6-dihydropyridine-3-carboxylicacid

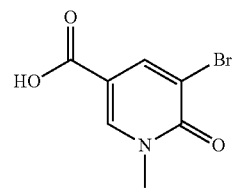

To a solution of methyl 5-bromo-1-methyl-6-oxo-1,6-dihydropyridine-3-carboxylate (200 mg, 812.82 umol) in H$_2$O (1 mL) and THF (1 mL) was added NaOH (65.02 mg, 1.63 mmol) and the mixture was stirred at 25° C. for 2 hrs. The reaction mixture was then concentrated under reduced pressure to remove solvent and then diluted with H$_2$O (10 ml) and acidified with 1 N HCl (aqueous) to pH=2. The mixture was filtered and the solid obtained was washed with 20 mL of H$_2$O and dried to afford the title compound (166 mg, 88%) as a white solid which was used without further purification. MS-ESI (m/z) calcd for C$_7$H$_{17}$BrNO$_3$ [M+H]$^+$: 232.0/244.0. Found 231.9/233.9.

Step 2: 5-Bromo-1-methyl-N-(3-(oxazol-5-yl)-1H-indazol-5-yl)-6-oxo-1,6-dihydropyridine-3-carboxamide

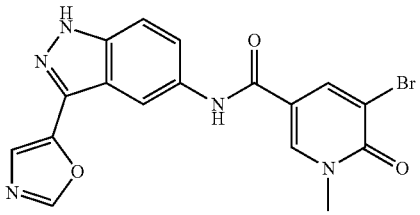 [SMILES: Cn1cc(C(=O)Nc2ccc3[nH]nc(-c4cnco4)c3c2)cc(Br)c1=O]

To a solution of 5-bromo-1-methyl-6-oxo-1,6-dihydropyridine-3-carboxylic acid (130 mg, 560.27 umol) and 3-(oxazol-5-yl)-1H-indazol-5-amine (112.16 mg, 560.27 umol) in pyridine (3 mL) was added EDCI (161.11 mg, 840.40 umol) and the mixture was stirred at 25° C. for 3 hrs. The reaction mixture was concentrated under reduced pressure to give a residue which was diluted with H$_2$O (10 mL) and filtered. The solid obtained was washed with 20 mL of H$_2$O and dried in vacuum to afford the title compound (160 mg, 69%) as a red solid which was used without further purification. MS-ESI (m/z) calcd for C$_{17}$H$_{13}$BrN$_5$O$_3$ [M+H]$^+$: 414.0/416.0. Found 413.9/415.9.

Step 3: 5-Cyano-1-methyl-N-(3-(oxazol-5-yl)-1H-indazol-5-yl)-6-oxo-1,6-dihydropyridine-3-carboxamide

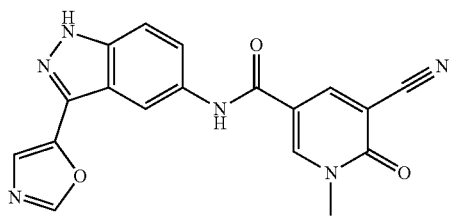 [SMILES: Cn1cc(C(=O)Nc2ccc3[nH]nc(-c4cnco4)c3c2)cc(C#N)c1=O]

A mixture of 5-bromo-1-methyl-N-(3-(oxazol-5-yl)-1H-indazol-5-yl)-6-oxo-1,6-dihydropyridine-3-carboxamide (100 mg, 241.42 umol), Zn(CN)$_2$ (56.70 mg, 482.84 umol), Zn (1.42 mg, 21.73 umol), dppf (4.02 mg, 7.24 umol), and Pd$_2$(dba)$_3$ (13.26 mg, 14.49 umol) in DMA (2 mL) was degassed and purged with N$_2$ (3×), and then the mixture was stirred at 120° C. for 2 hrs under an N$_2$ atmosphere in a microwave reactor. The reaction mixture was concentrated and purified by preparative HPLC using Method BV to afford the title compound (12.71 mg, 10%) as a yellow solid, TFA salt. $^1$H NMR (400 MHz, DMSO-d$_6$) δ 13.51 (s, 1H), 10.23 (s, 1H), 8.88 (d, J=2.43 Hz, 1H), 8.76 (d, J=2.65 Hz, 1H), 8.58 (s, 1H), 8.44 (s, 1H), 7.70-7.75 (m, 1H), 7.59-7.66 (m, 2H), 3.62 (s, 3H). MS-ESI (m/z) calc'd for C$_{18}$H$_{13}$N$_6$O$_3$ [M+H]$^+$: 361.1. Found 361.1.

Example 225: 3-Cyano-2-isopropyl-N-(3-(oxazol-5-yl)-1H-indazol-5-yl)benzamide

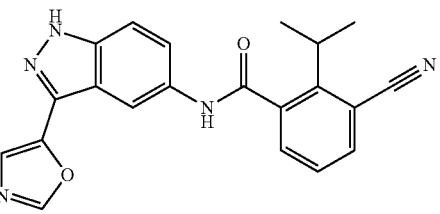

To a solution of 3-cyano-N-(3-(oxazol-5-yl)-1H-indazol-5-yl)-2-(prop-1-en-2-yl)benzamide (40 mg, 108.29 umol) in THF (6 mL) and MeOH (3 mL) was added 10% Pd/C (10 mg) under N$_2$. The suspension was degassed under vacuum and purged with H$_2$ several times. The mixture was then stirred under Hz (15 psi) at 25° C. for 1 hr. The reaction mixture was filtered and the filtrate was concentrated to give a residue. The residue was purified by preparative HPLC using Method CH to afford the title compound (5.82 mg, 14%) as a white solid. $^1$H NMR (400 MHz, DMSO-d$_6$) δ 13.51 (br s, 1H), 10.67 (s, 1H), 8.58 (d, J=7.7 Hz, 2H), 7.93 (d, J=6.8 Hz, 1H), 7.77 (d, J=7.7 Hz, 1H), 7.71-7.57 (m, 3H), 7.57-7.50 (m, 1H), 3.44-3.36 (m, 1H), 1.44 (d, J=7.1 Hz, 6H). MS-ESI (m/z) calc'd for C$_{21}$H$_{18}$N$_5$O$_2$ [M+H]$^+$: 372.1. Found 372.2.

Example 226: 5-Cyano-N-(3-(isoxazol-4-yl)-1H-indazol-5-yl)-4-methoxy-3-methylpicolinamide

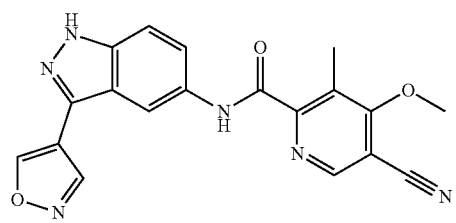 [SMILES: COc1c(C#N)cnc(C(=O)Nc2ccc3[nH]nc(-c4cnoc4)c3c2)c1C]

Prepared as described for 5-cyano-N-(7-fluoro-3-(furan-3-yl)-1H-indazol-5-yl)-3-methylpicolinamide using 5-cyano-4-methoxy-3-methylpicolinic acid in place of 5-cyano-3-methylpicolinic acid and using 3-(isoxazol-4-yl)-1H-indazol-5-amine in place of 7-fluoro-3-(furan-3-yl)-1H-indazol-5-amine to afford the title compound (22.2 mg, 30%) as a yellow solid. $^1$H NMR (400 MHz, DMSO-d$_6$) δ 13.33 (s, 1H), 10.67 (s, 1H), 9.55 (s, 1H), 9.14 (s, 1H), 8.86 (d, J=0.7 Hz, 1H), 8.38 (dd, J=1.9, 0.8 Hz, 1H), 7.78 (dd, J=9.0, 1.9 Hz, 1H), 7.60 (dd, J=9.0, 0.7 Hz, 1H), 4.27 (s, 3H), 2.41 (d, J=0.6 Hz, 3H). MS-ESI (m/z) calc'd for C$_{19}$H$_{15}$N$_6$O$_3$ [M+H]$^+$: 375.1. Found 375.2.

Example 227: 5-Cyano-3,4-dimethyl-N-(3-(thiazol-5-yl)-1H-indazol-5-yl)picolinamide

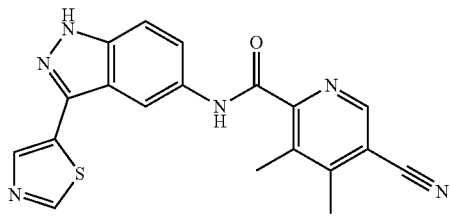 [SMILES: Cc1c(C#N)cnc(C(=O)Nc2ccc3[nH]nc(-c4cncs4)c3c2)c1C]

Prepared as described for 5-cyano-N-(7-fluoro-3-(furan-3-yl)-1H-indazol-5-yl)-3-methylpicolinamide using 5-cyano-3,4-dimethylpicolinic acid in place of 5-cyano-3-methylpicolinic acid and using 3-(thiazol-5-yl)-1H-indazol-5-amine in place of 7-fluoro-3-(furan-3-yl)-1H-indazol-5-amine to afford the title compound (22.1 mg, 30%) as a white solid. $^1$H NMR (400 MHz, DMSO-$d_6$) δ 13.41 (s, 1H), 10.77 (s, 1H), 9.15 (s, 1H), 8.90 (s, 1H), 8.61 (d, J=1.8 Hz, 1H), 8.40 (s, 1H), 7.79 (dd, J=9.0, 1.9 Hz, 1H), 7.63 (d, J=9.0 Hz, 1H), 2.56 (s, 3H), 2.47 (s, 3H). MS-ESI (m/z) calc'd for $C_{19}H_{15}N_6OS$ [M+H]$^+$: 375.1. Found 375.3.

Example 228: 4-Cyano-N-(3-(isoxazol-4-yl)-1H-indazol-5-yl)-3-methoxypicolinamide

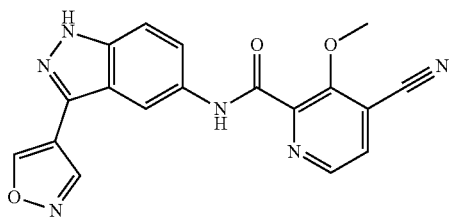 [SMILES: COc1c(C#N)ccnc1C(=O)Nc1ccc2[nH]nc(-c3cnoc3)c2c1]

A solution of 0.1 N potassium hexacyanoferrate(II) (0.87 mL, 0.090 mmol), 4-chloro-3-methoxy-N-[3-(1,2-oxazol-4-yl)-1H-indazol-5-yl]pyridine-2-carboxamide (32.0 mg, 0.090 mmol) and KOAc (4.25 mg, 0.040 mmol) were dissolved in a mixture of 1,4-dioxane (1.8 mL) and H$_2$O (0.260 mL) in a sealed microwave reactor vial. The mixture was degassed with N$_2$ for 15 minutes. Then XPhos (1.65 mg, 0,003 mmol) and XPhos-Pd-G3 (2.93 mg, 0,003 mmol) were added and the mixture was left stirring at 100° C. for 8 hrs. Water was added and the mixture was extracted with EtOAc. The organic phase was separated, dried over Na$_2$SO$_4$, filtered and concentrated to give a residue. The residue was then purified by semi-preparative HPLC using Method CX to afford the title compound (3 mg, 10%) as a yellow solid. $^1$H NMR (400 MHz, DMSO-$d_6$) δ 13.35 (s, 1H), 10.72 (s, 1H), 9.55 (s, 1H), 9.14 (s, 1H), 8.61 (d, J=4.8 Hz, 1H), 8.36 (d, J=1.8 Hz, 1H), 8.06 (d, J=4.8 Hz, 1H), 7.75 (dd, J=9.0, 1.9 Hz, 1H), 7.62 (d, J=9.0 Hz, 1H), 4.10 (s, 3H). MS-ESI (m/z) calc'd for $C_{15}H_{13}N_6O_3$ [M+H]$^+$: 361.1. Found 361.2.

Example 229: 5-Cyano-3,4-dimethyl-N-(3-(3-methylisoxazol-5-yl)-1H-indazol-5-yl)picolinamide

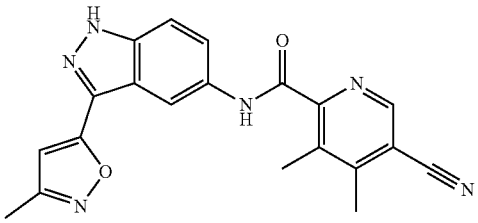 [SMILES: Cc1cc(-c2n[nH]c3ccc(NC(=O)c4ncc(C#N)c(C)c4C)cc23)on1]

Prepared as described for 5-cyano-N-(3-(isoxazol-4-yl)-1H-indazol-5-yl)-3-methylpicolinamide using (3-methylisoxazol-5-yl)boronic acid in place of isoxazole-4-boronic acid and 5-cyano-N-(3-iodo-1H-indazol-5-yl)-3,4-dimethylpicolinamide in place of 5-cyano-N-(3-iodo-1H-indazol-5-yl)-3-methylpyridine-2-carboxamide to afford the title compound (8.6 mg, 24%) as a yellow solid. $^1$H NMR (400 MHz, DMSO-$d_6$) δ 13.73 (br. s., 1H) 10.81 (s, 1H) 8.90 (s, 1H) 8.67 (d, J=1.10 Hz, 1H) 7.73-7.81 (m, 1H) 7.63-7.70 (m, 1H) 6.81 (s, 1H) 2.57 (s, 3H) 2.47 (s, 3H) 2.36 (s, 3H). MS-ESI (m/z) calc'd for $C_{20}H_{17}N_6O_2$ [M+H]$^+$: 373.1. Found 373.2.

Example 230: 5-Cyano-3,4-dimethyl-N-(3-(pyrimidin-4-yl)-1H-indazol-5-yl)picolinamide

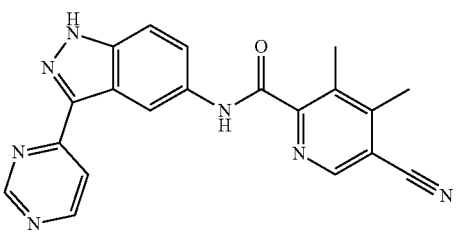 [SMILES: Cc1c(C#N)cnc(C(=O)Nc2ccc3[nH]nc(-c4ccncn4)c3c2)c1C]

Step 1: 3-Iodo-1-(tetrahydro-2H-pyran-2-yl)-1H-indazol-5-amine

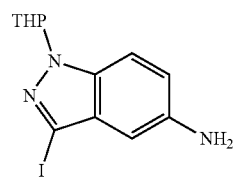

To a solution of 3-iodo-5-nitro-1-(tetrahydro-2H-pyran-2-yl)-1H-indazole (100 mg, 267.99 umol) in EtOH (2 mL) and H$_2$O (2 mL) was added Fe (74.83 mg, 1.34 mmol) and NH$_4$Cl (71.68 mg, 1.34 mmol) and the mixture was stirred at 80° C. for 2 hrs. The reaction mixture was then filtered and the filtrate was concentrated under reduced pressure to remove solvent. Then the mixture was diluted with H$_2$O (5 mL) and extracted with EtOAc (15 mL×3). The combined organic layers were dried over Na$_2$SO$_4$, filtered and concentrated under reduced pressure to afford the title compound (90 mg) as a brown gum which was used without further purification. MS-ESI (m/z) calcd for $C_{12}H_{13}IN_3O$ [M+H]$^+$: 344.0. Found 344.1.

Step 2: 5-Cyano-N-(3-iodo-1-(tetrahydro-2H-pyran-2-yl)-1H-indazol-5-yl)-3,4-dimethylpicolinamide

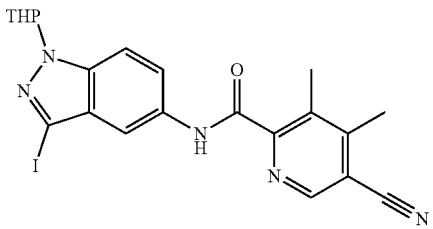

To a solution of 3-iodo-1-(tetrahydro-2H-pyran-2-yl)-1H-indazol-5-amine (90 mg, 262.27 umol) in pyridine (2 mL) was added EDCI (100.55 mg, 524.53 umol) and 5-cyano-3,4-dimethylpicolinic acid (46.20 mg, 262.27 umol) and the mixture was stirred at 20° C. for 12 hrs. The reaction mixture was concentrated under reduced pressure to remove solvent. Then the mixture was diluted with $H_2O$ (5 mL) and filtered. The solid obtained was dried under vacuum to afford the title compound (75 mg) as a brown solid which was used without further purification. MS-ESI (m/z) calcd for $C_{21}H_{21}IN_5O_2$ [M+H]$^+$: 502.1. Found 502.2

Step 3: 5-Cyano-3,4-dimethyl-N-(3-(pyrimidin-4-yl)-1-(tetrahydro-2H-pyran-2-yl)-1H-indazol-5-yl)picolinamide

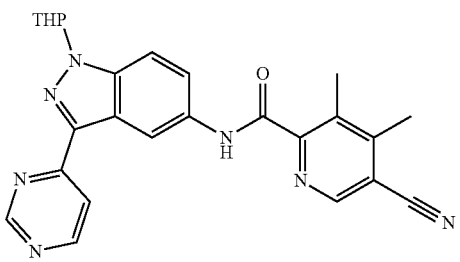

To a solution of 5-cyano-N-(3-iodo-1-(tetrahydro-2H-pyran-2-yl)-1H-indazol-5-yl)-3,4-dimethylpicolinamide (68 mg, 135.64 umol) in dioxane (2 mL) was added Pd(PPh$_3$)$_2$Cl$_2$ (9.52 mg, 13.56 umol) and 4-(tributylstannyl)pyrimidine (50.07 mg, 135.64 umol) and the mixture was stirred at 120° C. for 24 hrs under an N$_2$ atmosphere. The reaction mixture was concentrated to afford the title compound (50 mg) as a yellow solid which was used without further purification. MS-ESI (m/z) calcd for $C_{25}H_{24}N_7O_2$ [M+H]$^+$: 454.2. Found 454.1

Step 4: 5-Cyano-3,4-dimethyl-N-(3-(pyrimidin-4-yl)-1H-indazol-5-yl)picolinamide

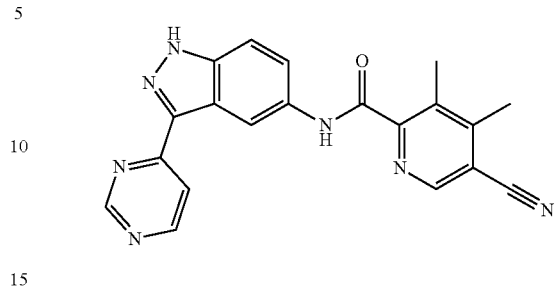

To a solution of 5-cyano-3,4-dimethyl-N-(3-(pyrimidin-4-yl)-1-(tetrahydro-2H-pyran-2-yl)-1H-indazol-5-yl)picolinamide (50 mg, 110.25 umol) in DCM (2 mL) was added TFA (1.54 g, 13.51 mmol) and the mixture was stirred at 20° C. for 3 hrs. The reaction mixture was then concentrated and purified by preparative HPLC using Method CF to afford the title compound (5.46 mg, 13%) as a pale yellow solid. $^1$H NMR (400 MHz, DMSO-d$_6$) δ 13.81 (s, 1H) 10.80 (s, 1H) 9.30 (d, J=1.10 Hz, 1H) 9.04 (d, J=0.66 Hz, 1H) 8.90 (s, 1H) 8.84 (d, J=5.29 Hz, 1H) 8.17 (dd, J=5.40, 1.21 Hz, 1H) 7.80 (dd, J=8.93, 1.87 Hz, 1H) 7.67 (d, J=9.04 Hz, 1H) 2.56 (s, 3H) 2.45 (s, 3H). MS-ESI (m/z) calc'd for $C_{20}H_{16}N_7O$ [M+H]$^+$: 370.1. Found 370.2.

Example 231: 3-Cyano-2-ethyl-6-fluoro-N-(3-(oxazol-5-yl)-1H-indazol-5-yl)benzamide

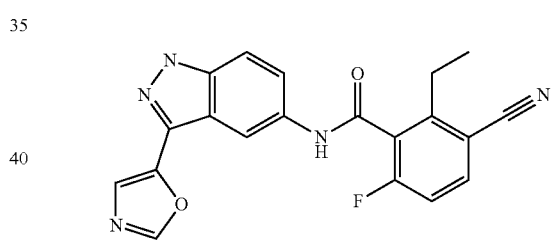

Step 1: Methyl 2-bromo-6-fluorobenzoate

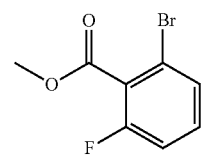

To a solution of 2-bromo-6-fluorobenzoic acid (1 g, 4.57 mmol) in MeOH (6 mL) was added H$_2$SO$_4$ (6.5 mL, 98% purity) and the mixture was stirred at 80° C. for 12 hrs. The reaction mixture was then basified with saturated aqueous Na$_2$CO$_3$ to pH=8 (40 mL) and extracted with EtOAc (15 mL 3). The combined organic layers were dried over Na$_2$SO$_4$, filtered and concentrated to afford the title compound (750 mg) as a yellow oil which was used without further purification. $^1$H NMR (400 MHz, CDCl$_3$) δ 7.40 (d, J=8 Hz, 1H), 7.29-7.26 (m, 1H), 7.08 (t, J=8.4 Hz, 1H), 3.97 (s, 3H).

Step 2: Methyl 2-fluoro-6-vinylbenzoate

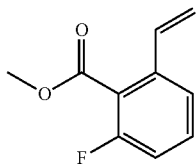

A mixture of methyl 2-bromo-6-fluorobenzoate (750 mg, 3.22 mmol), potassium trifluoro(vinyl)borate (474.22 mg, 3.54 mmol), Pd(dppf)Cl$_2$ (70.65 mg, 96.55 umol), Na$_2$CO$_3$ (1.02 g, 9.66 mmol) in dioxane (18 mL) and H$_2$O (6 mL) was degassed and purged with N$_2$ (3×), and then the mixture was stirred at 100° C. for 12 hrs under an N$_2$ atmosphere. The reaction mixture was concentrated and purified by flash silica gel chromatography (ISCO; 12 g SepaFlash column) using a 0-30% EtOAc/petroleum ether gradient eluent to afford the title compound (350 mg, 60%) as a light yellow oil. MS-ESI (m/z) calcd for C$_{10}$H$_{10}$FO$_2$ [M+H]$^+$: 181.1. Found 181.0.

Step 3: Methyl 2-ethyl-6-fluorobenzoate

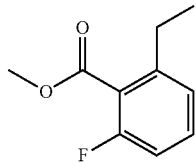

To a solution of methyl 2-fluoro-6-vinylbenzoate (350 mg, 1.94 mmol) in EtOH (15 mL) was added 10% Pd/C (1 g, 1.94 mmol). The mixture was degassed and purged with H$_2$ (3×), then it was stirred at 25° C. for 1 hr under an H$_2$ atmosphere (15 psi). The reaction mixture was filtered and the filtrate was concentrated to afford the title compound (250 mg, 71%) as a light yellow gum which was used without further purification. $^1$H NMR (400 MHz, CDCl$_3$) δ 7.27-7.22 (m, 1H), 6.97 (d, J=7.6 Hz, 1H), 6.87 (t, J=8.8 Hz, 1H), 3.86 (s, 3H), 2.66-2.60 (q, J=7.6 Hz, 2H), 1.14 (t, J=7.6 Hz, 3H).

Step 4: Methyl 3-bromo-2-ethyl-6-fluorobenzoate

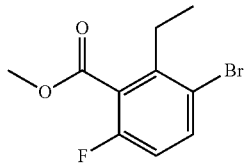

To a solution of methyl 2-ethyl-6-fluorobenzoate (250 mg, 1.37 mmol) in H$_2$SO$_4$ (4 mL, 98% purity) was added NBS (256.44 mg, 1.44 mmol) at 0° C. The mixture was stirred at 0° C. for 2 hrs and then poured into ice water (10 mL), then diluted with saturated aqueous Na$_2$CO$_3$ (20 mL) and extracted with EtOAc (8 mL×3). The combined organic phases were dried over Na$_2$SO$_4$ and concentrated under reduced pressure to give a residue. The residue was purified by flash silica gel chromatography (ISCO: 4 g SepaFlash column) using 100% petroleum ether eluent to afford the title compound (100 mg, 28%) as a yellow oil. MS-ESI (m/z) calcd for C$_{10}$H$_{11}$BrFO$_2$ [M+H]$^+$: 261.0/263.0. Found 261.0/263.0.

Step 5: 3-Bromo-2-ethyl-6-fluorobenzoic acid

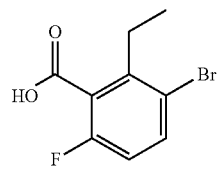

To a solution of methyl 3-bromo-2-ethyl-6-fluorobenzoate (340 mg, 1.30 mmol) in MeOH (6 mL) and H$_2$O (3 mL) was added LiOH.H$_2$O (273.23 mg, 6.51 mmol) and the mixture was stirred at 60° C. for 12 hrs. The reaction mixture was then diluted with 1M HCl to pH=4 and extracted with EtOAc (15 mL×3). The combined organic layers were dried over Na$_2$SO$_4$, filtered and concentrated under reduced pressure to afford the title compound (300 mg, 93%) as a yellow oil which was used without further purification. MS-ESI (m/z) calcd for C$_9$H$_9$BrFO$_2$ [M-H]$^-$: 245.0/247.0. Found 244.9/246.9.

Step 6: 3-Bromo-2-ethyl-6-fluoro-N-(3-(oxazol-5-yl)-1H-indazol-5-yl)benzamide

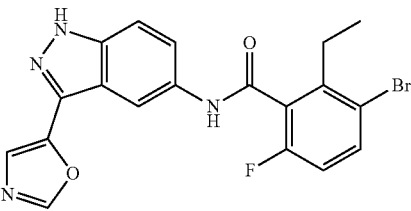 [SMILES: CCc1c(Br)ccc(F)c1C(=O)Nc1ccc2[nH]nc(-c3cnco3)c2c1]

To a solution of 3-bromo-2-ethyl-6-fluorobenzoic acid (150 mg, 607.14 umol) in pyridine (5 mL) was added EDCI (174.58 mg, 910.71 umol) and 3-(oxazol-5-yl)-1H-indazol-5-amine (121.55 mg, 607.14 umol) and the mixture was stirred at 25° C. for 12 hrs. The mixture was then concentrated and purified by flash silica gel chromatography (ISCO; 4 g SepaFlash column) using a 0-30% EtOAc/petroleum ether gradient eluent to afford the title compound (138 mg, 53%) as a yellow oil. MS-ESI (m/z) calcd for C$_{19}$H$_{15}$BrFN$_4$O$_2$ [M+H]$^+$: 429.0/431.0. Found 429.0/431.0.

Step 7: 3-Cyano-2-ethyl-6-fluoro-N-(3-(oxazol-5-yl)-1H-indazol-5-yl)benzamide

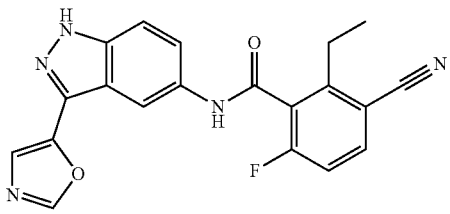 [SMILES: CCc1c(C#N)ccc(F)c1C(=O)Nc1ccc2[nH]nc(-c3cnco3)c2c1]

A mixture of 3-bromo-2-ethyl-6-fluoro-N-(3-(oxazol-5-yl)-1H-indazol-5-yl)benzamide (150 mg, 349.45 umol), Zn(CN)$_2$ (82.07 mg, 698.91 umol), Zn (2.06 mg, 31.45 umol), dppf (5.81 mg, 10.48 umol) and Pd$_2$(dba)$_3$ (19.20 mg, 20.97 umol) in DMA (3 mL) was degassed and purged with N$_2$ (3×), and then the mixture was stirred at 120° C. for 5 hrs under an N$_2$ atmosphere. The reaction was filtered and the filtrate was concentrated to give a residue. The residue was purified by preparative HPLC using Method AK to afford the title compound (5.53 mg, 3%) as a yellow solid TFA salt. $^1$H NMR (400 MHz, DMSO-d$_6$) δ 13.54 (s, 1H), 10.90 (s, 1H), 8.59 (s, 1H), 8.53 (s, 1H), 8.05 (dd, J=9.15, 5.40 Hz, 1H), 7.59-7.67 (m, 3H), 7.49 (t, J=8.71 Hz, 1H), 2.81-2.92 (m, 2H), 1.26 (t, J=7.61 Hz, 3H). MS-ESI (m/z) calc'd for C$_{20}$H$_{15}$FNO$_2$ [M+H]$^+$: 376.1. Found 376.1.

Example 232: 2-Cyano-3-ethyl-N-(3-(oxazol-5-yl)-1H-indazol-5-yl)isonicotinamide

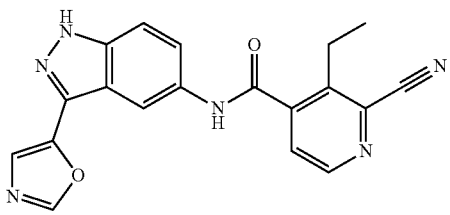 [SMILES: CCc1c(C(=O)Nc2ccc3[nH]nc(-c4cnco4)c3c2)ccnc1C#N]

Step 1: Methyl 3-bromo-2-chloroisonicotinate

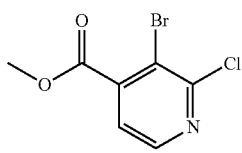

To a solution of 3-bromo-2-chloroisonicotinic acid (400 mg, 1.69 mmol) in MeOH (10 mL) was added SOCl$_2$ (1.31 g, 11.00 mmol) dropwise at 0° C.; then the mixture was stirred at 80° C. for 12 hrs. The reaction was concentrated to give a residue which was extracted with EtOAc (10 mL×3) and saturated aqueous Na$_2$CO$_3$ (10 mL). The organic layer was dried over Na$_2$SO$_4$, filtered and the filtrate was concentrated to afford the title compound (390 mg, 92%) as a brown liquid, which was used without further purification. MS-ESI (m/z) calcd for C$_7$H$_6$BrClNO$_2$ [M+H]$^+$: 249.9/251.9. Found 249.8/251.9.

Step 2: Methyl 2-chloro-3-vinylisonicotinate

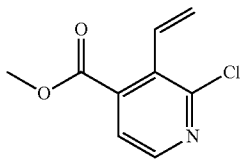

To a solution of methyl 3-bromo-2-chloroisonicotinate (340 mg, 1.36 mmol) in dioxane (5 mL) was added tributyl(vinyl)tin (473.47 mg, 1.49 mmol, 434.38 uL) and Pd(PPh$_3$)$_4$ (78.43 mg, 67.87 umol) and the mixture was stirred at 100° C. for 12 hrs under N$_2$. The procedure was repeated using 50 mg of methyl 3-bromo-2-chloroisonicotinate and the reaction mixtures were combined and concentrated. The material was purified by flash silica gel chromatography (ISCO; 4 g SepaFlash column) using a 0-9% EtOAc/petroleum ether gradient eluent to afford the title compound (227 mg, 85%) as a light yellow liquid, which was used without further purification. MS-ESI (m/z) calcd for C$_9$H$_9$ClNO$_2$ [M+H]$^+$: 198.0/200.0. Found 198.0/200.0.

Step 3: Methyl 2-chloro-3-ethylisonicotinate

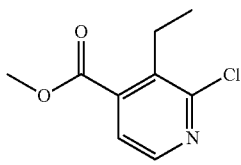

To a mixture of 10% Pd/C (200 mg) in MeOH (15 mL) was added methyl 2-chloro-3-vinylisonicotinate (200 mg, 1.01 mmol) and the mixture was stirred at 25° C. under H$_2$ at 15 psi for 30 min. The residue was purified by preparative TLC (SiO$_2$, 5:1 petroleum ether/EtOAc, R$_f$=0.51) to afford the title compound (31 mg, 15%) as a light yellow liquid. MS-ESI (m/z) calcd for C$_9$H$_{11}$ClNO$_2$ [M+H]$^+$: 200.0/202.0. Found 200.0/202.0.

Step 4: 2-Chloro-3-ethylisonicotinic acid

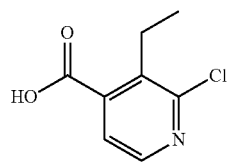

To a solution of methyl 2-chloro-3-ethylisonicotinate (31 mg, 155.28 umol) in THF (1 mL) and H$_2$O (1 mL) was added LiOH.H$_2$O (26.07 mg, 621.14 umol) and the mixture was stirred at 25° C. for 1 hr. The reaction was repeated with 8 mgs of methyl 2-chloro-3-ethylisonicotinate and the reaction mixtures were combined. The THF was removed under vacuum and the aqueous layer was acidified with 1N HCl to pH=5. The mixture was filtered and the solid was dried under vacuum to afford the title compound (16 mg) as a white solid which was used without further purification. MS-ESI (m/z) calcd for $C_8H_9ClNO_2$ [M+H]⁺: 186.0/188.0. Found 186.0/188.0.

Step 5: 2-Chloro-3-ethyl-N-(3-(oxazol-5-yl)-1H-indazol-5-yl)isonicotinamide

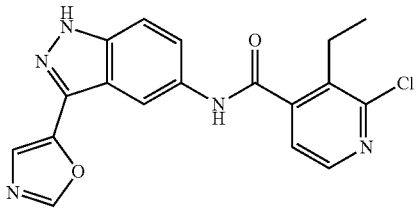 [SMILES: CCc1c(C(=O)Nc2ccc3[nH]nc(-c4cnco4)c3c2)ccnc1Cl]

To a solution of 2-chloro-3-ethylisonicotinic acid (16 mg, 86.20 umol) and EDCI (24.79 mg, 129.31 umol) in pyridine (1 mL) was added 3-(oxazol-5-yl)-1H-indazol-5-amine (17.26 mg, 86.20 umol) and then the mixture was stirred at 25° C. for 12 hrs. The reaction was then concentrated to give a residue which was extracted with EtOAc (3 mL×3) and water (3 mL). The organic layer was dried over $Na_2SO_4$, filtered and the filtrate was concentrated under vacuum to afford the title compound (25 mg) as a brown liquid, which was used without further purification. MS-ESI (m/z) calcd for $C_{15}H_{15}ClN_5O_2$[M+H]⁺: 368.1/370.1. Found 368.0/370.0.

Step 6: 2-Cyano-3-ethyl-1-N-(3-(oxazol-5-yl)-1H-indazol-5-yl)isonicotinamide

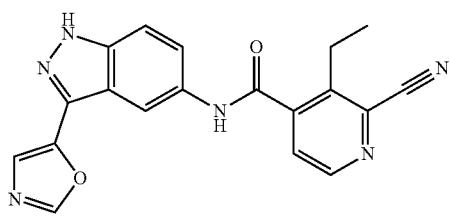

To a solution of 2-chloro-3-ethyl-N-(3-(oxazol-5-yl)-1H-indazol-5-yl)isonicotinamide (15 mg, 40.78 umol) and $Zn(CN)_2$ (4.79 mg, 40.78 umol) in DMF (1 mL) was added Zn (320.03 ug, 4.89 umol), $Pd_2(dba)_3$ (746.94 ug, 0.816 umol) and dppf (904.40 ug, 1.63 umol) and the mixture was stirred at 120° C. under $N_2$ for 2 hrs in a microwave reactor. The mixture was filtered and the filtrate was purified by preparative HPLC using Method AI to afford the title compound (2.67 mg, 13%) as a pale yellow solid, TFA salt. ¹H NMR (400 MHz, DMSO-d₆) δ 13.54 (s, 1H) 10.83 (s, 1H) 8.77 (d, J=4.85 Hz, 1H) 8.59 (s, 1H) 8.51 (s, 1H) 7.89 (d, J=4.85 Hz, 1H) 7.63 (d, J=6.84 Hz, 3H) 2.95 (q, J=7.42 Hz, 2H) 1.27 (t, J=7.50 Hz, 3H). MS-ESI (m/z) calc'd for $C_{19}H_{15}N_6O_2$ [M+H]⁺: 359.1. Found 359.1.

Example 233: (E)-5-Cyano-N-(3-(2-cyclopropylvinyl)-1H-indazol-5-yl)-3,4-dimethylpicolinamide

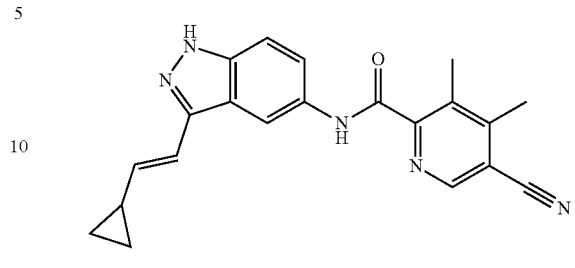

Prepared as described for 5-cyano-3,4-dimethyl-N-(3-(2-methylprop-1-en-1-yl)-1H-indazol-5-yl)picolinamide using (E)-2-(2-cyclopropylvinyl)-4,4,5,5-tetramethyl-1,3,2-dioxaborolane in place of 4,4,5,5-tetramethyl-2-(2-methylprop-1-en-1-yl)-1,3,2-dioxaborolane to afford the title compound (15.77 mg, 12%) as a pale yellow solid. ¹H NMR (400 MHz, DMSO-d₆) δ 12.86 (br s, 1H), 10.62 (s, 1H), 8.87 (s, 1H), 8.31 (s, 1H), 7.69 (br d, J=8.82 Hz, 1H), 7.47 (d, J=8.82 Hz, 1H), 6.74 (d, J=16.10 Hz, 1H), 6.03 (dd, J=16.21, 8.93 Hz, 1H), 2.54 (s, 3H), 2.43 (s, 3H), 1.63-1.73 (m, 1H), 0.84 (q, J=5.66 Hz, 2H), 0.52-0.58 (m, 2H). MS-ESI (m/z) calc'd for $C_{21}H_{20}N_5O$ [M+H]⁺: 358.2 Found 358.1.

Example 234: 3-Cyano-2-methoxy-6-methyl-N-(3-(oxazol-5-yl)-1H-indazol-5-yl)benzamide

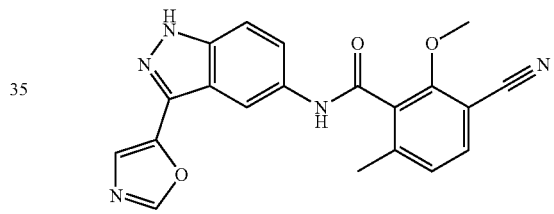

Prepared as described for 4-cyano-N-(3-(isoxazol-4-yl)-1H-indazol-5-yl)-3-methoxypicolinamide using 3-chloro-2-methoxy-6-methyl-N-(3-(oxazol-5-yl)-1H-indazol-5-yl)benzamide in place of 4-chloro-3-methoxy-N-[3-(1,2-oxazol-4-yl)-1H-indazol-5-yl]pyridine-2-carboxamide to afford the title compound (9.6 mg, 16%) as a white solid. ¹H NMR (400 MHz, DMSO-d₆) δ 13.53 (br. s., 1H) 10.67 (s, 1H) 8.60 (s, 1H) 8.56 (s, 1H) 7.80 (d, J=7.92 Hz, 1H) 7.58-7.66 (m, 3H) 7.28 (d, J=7.92 Hz, 1H) 3.99 (s, 3H) 2.39 (s, 3H). MS-ESI (m/z) calc'd for $C_{20}H_{16}N_5O$; [M+H]⁺: 374.1. Found 374.3.

Example 235: 5-Cyano-3-methyl-N-(3-(3-methylisoxazol-5-yl)-1H-indazol-5-yl)picolinamide

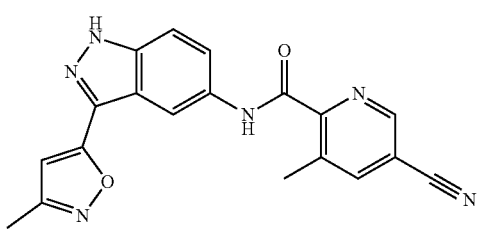

Prepared as described for 5-cyano-N-(3-(isoxazol-4-yl)-1H-indazol-5-yl)-3-methylpicolinamide using (3-methylisoxazol-5-yl)boronic acid in place of isoxazole-4-boronic acid and 5-cyano-N-(3-iodo-1H-indazol-5-yl)-3-methylpicolinamide in place of 5-cyano-N-(3-iodo-1H-indazol-5-yl)-3-methylpyridine-2-carboxamide to afford the title compound (3.4 mg, 15%) as a yellow solid. ¹H NMR (400 MHz, DMSO-d₆) δ 13.73 (br. s., 1H) 10.84 (s, 1H) 9.01 (d, J=1.32 Hz, 1H) 8.70 (d, J=1.32 Hz, 1H) 8.42 (dd, J=1.98, 0.66 Hz, 1H) 7.83 (dd, J=9.02, 1.98 Hz, 1H) 7.67 (d, J=9.24 Hz, 1H) 6.82 (s, 1H) 2.61 (s, 3H) 2.36 (s, 3H). MS-ESI (m/z) calc'd for C₁₉H₁₅N₆O₂[M+H]⁺: 359.1. Found 359.2.

Example 236: 3-Cyano-2-fluoro-N-(3-(isoxazol-4-yl)-1H-indazol-5-yl)-6-methylbenzamide

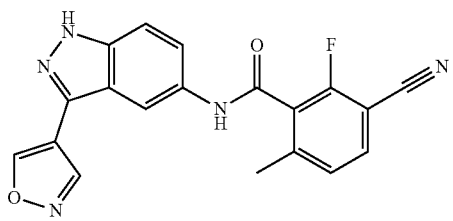 [SMILES: Cc1ccc(C#N)c(F)c1C(=O)Nc1ccc2[nH]nc(-c3cnoc3)c2c1]

Step 1: 3-Bromo-2-fluoro-N-(3-(isoxazol-4-yl)-1H-indazol-5-yl)-6-methylbenzamide

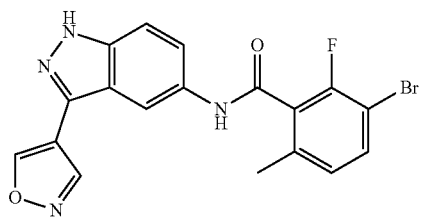

To a mixture of 3-bromo-2-fluoro-6-methylbenzoic acid (45.0 mg, 0.190 mmol), 3-(1,2-oxazol-4-yl)-1H-indazol-5-amine (42.96 mg, 0.210 mmol) and Et₃N (53.83 uL, 0.390 mmol) in MeCN (2.5 mL), was added HATU (73.43 mg, 0.190 mmol) and the mixture was stirred at r.t. for 1 hr. The reaction mixture was partitioned between H₂O and EtOAc, the phases were separated, the aqueous layer was extracted with EtOAc (2×) and the combined organic phases were washed with brine (1×), dried over Na₂SO₄ and concentrated to afford the title compound (115 mg) which was used without further purification. ¹H NMR (400 MHz, DMSO-d₆) δ 13.34 (s, 1H) 10.72 (s, 1H) 9.53 (s, 1H) 9.13 (s, 1H) 8.35 (s, 1H) 7.68-7.77 (m, 1H) 7.59-7.64 (m, 2H) 7.17 (d, J=8.36 Hz, 1H) 2.35 (s, 3H). MS-ESI (m/z) calc'd for C₁₅H₁₃BrFN₄O₂ [M+H]⁺: 415.0/417.0. Found 415.2/417.2.

Step 2: 3-Cyano-2-fluoro-N-(3-(isoxazol-4-yl)-1H-indazol-5-yl)-6-methylbenzamide

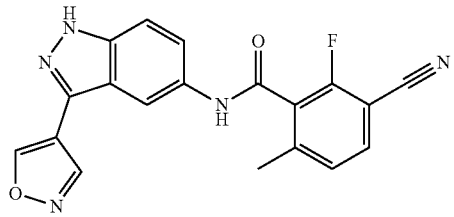 [SMILES: Cc1ccc(C#N)c(F)c1C(=O)Nc1ccc2[nH]nc(-c3cnoc3)c2c1]

Prepared as described for 4-cyano-N-(3-(isoxazol-4-yl)-1H-indazol-5-yl)-3-methoxypicolinamide using 3-bromo-2-fluoro-N-(3-(isoxazol-4-yl)-1H-indazol-5-yl)-6-methylbenzamide in place of 4-chloro-3-methoxy-N-[3-(1,2-oxazol-4-yl)-1H-indazol-5-yl]pyridine-2-carboxamide to afford the title compound (1.9 mg, 3%) as a white solid. ¹H NMR (400 MHz, DMSO-d₆) δ 13.37 (br. s., 1H) 10.80 (br. s., 1H) 9.54 (s, 1H) 9.14 (s, 1H) 8.34 (s, 1H) 7.92-8.00 (m, 1H) 7.62 (s, 2H) 7.43 (d, J=8.14 Hz, 1H) 2.47 (s, 3H). MS-ESI (m/z) calc'd for C₁₉H₁₃FN₅O₂ [M+H]⁺: 362.1. Found 362.2.

Example 237: 5-Cyano-3,4-dimethyl-N-(3-(2-methylpyrimidin-4-yl)-1H-indazol-5-yl)picolinamide

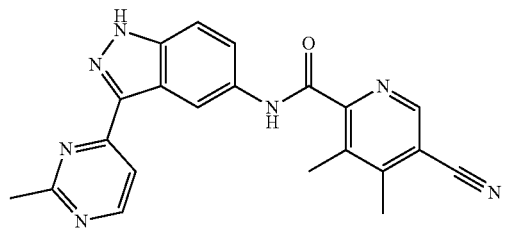 [SMILES: Cc1nccc(-c2n[nH]c3ccc(NC(=O)c4ncc(C#N)c(C)c4C)cc23)n1]

Step 1: tert-Butyl 5-[(5-cyano-3,4-dimethylpyridine-2-carbonyl)amino]-3-(2-methylpyrimidin-4-yl)indazole-1-carboxylate

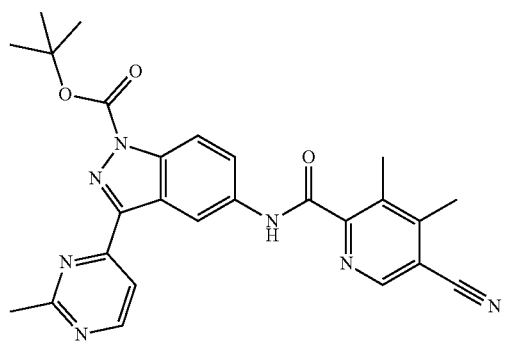

A solution of tert-butyl 5-(5-cyano-3,4-dimethylpicolinamido)-3-iodo-1H-indazole-1-carboxylate (50.0 mg, 0.100 mmol) and trimethyl-(2-methylpyrimidin-4-yl)stannane (500.0 mg, 0.510 mmol) in toluene (2 mL) was degassed with N₂ for 15 min in a microwave reactor vial. Tetrakis (triphenylphosphine)palladium(0) (11.17 mg, 0.010 mmol) was added, the vial was sealed, and the resulting mixture was heated at reflux with vigorous stirring under N₂ for 24 hrs. Then the mixture was filtered through Celite. A solution of KF in H₂O was added to the filtrate and the mixture was extracted with EtOAc (2×). The combined organic layers were dried over Na₂SO₄, filtered and concentrated under reduced pressure to afford the title compound (149 mg) which was used without further purification.

Step 2: 5-Cyano-3,4-dimethyl-N-(3-(2-methylpyrimidin-4-yl)-1H-indazol-5-yl)picolinamide

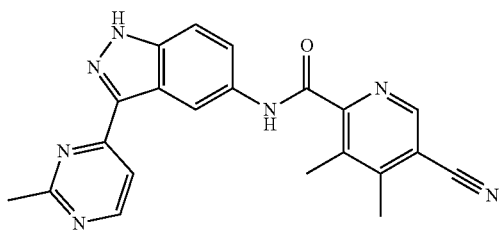 [SMILES: Cc1nccc(-c2n[nH]c3ccc(NC(=O)c4ncc(C#N)c(C)c4C)cc23)n1]

tert-Butyl 5-[(5-cyano-3,4-dimethylpyridine-2-carbonyl)amino]-3-(2-methylpyrimidin-4-yl)indazole-1-carboxylate was dissolved in DCM (1 mL) and cooled to 0° C. followed by the addition of trifluoroacetic acid (148.9 mg, 1.31 mmol). The reaction mixture stirred at r.t. for 2 hrs. A saturated aqueous solution of NaHCO₃ was added followed by DCM. The organic phase was filtered through a phase separator and concentrated. The residue was purified by silica gel column chromatography using a 20-100% EtOAc/cyclohexane gradient eluent. The isolated material was further purified by semi-preparative chiral HPLC using Method CY to afford the title compound (3.1 mg, 8% yield) as a white solid. ¹H NMR (400 MHz, DMSO-d₆) δ 13.69 (bs, 1H), 10.76 (s, 1H), 9.05 (d, J=1.9 Hz, 1H), 8.90 (s, 1H), 8.71 (d, J=5.3 Hz, 1H), 7.94 (d, J=5.3 Hz, 1H), 7.83 (dd, J=9.0, 2.0 Hz, 1H), 7.65 (d, J=8.9 Hz, 1H), 2.74 (s, 3H), 2.57 (s, 3H), 2.45 (s, 3H). MS-ESI (m/z) calc'd for C₂₁H₁₈N₇O [M+H]⁺: 384.2. Found 384.3.

Example 238: 5-Cyano-3,4-dimethyl-N-(3-(oxazol-5-yl)-1H-pyrazolo[3,4-c]pyridin-5-yl)picolinamide

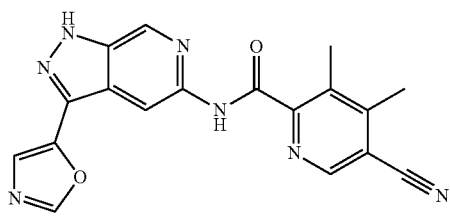 [SMILES: Cc1c(C#N)cnc(C(=O)Nc2cc3c(-c4cnco4)n[nH]c3cn2)c1C]

Step 1: 5-chloro-1H-pyrazolo[3,4-c]pyridine-3-carbaldehyde

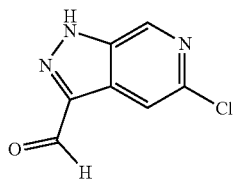 [SMILES: O=Cc1n[nH]c2cnc(Cl)cc12]

To a stirred solution of NaNO₂ (14.47 g, 209.72 mmol) in H₂O (40 mL) was slowly added HCl (2 M, 91.75 mL) dropwise at 0° C. and the reaction mixture was stirred at 0° C. for 10 min before adding DMF (60 mL). Then a solution of 5-chloro-1H-pyrazolo[3,4-c]pyridine (4 g, 26.22 mmol) in DMF (60 mL) was added at 0° C. and the reaction mixture was heated to 80° C. and stirred for 12 hrs. After cooling to 25° C., the reaction mixture was concentrated to give a residue. Saturated aqueous NaHCO₃ was added to the residue to adjust to pH=8 and the mixture was extracted with EtOAc (200 mL×3). The combined organic phases were washed with brine (200 mL×1), dried over Na₂SO₄, filtered and concentrated. The material was purified by silica gel column chromatography using a 0-33% EtOAc/petroleum ether gradient eluent to afford the title compound (800 mg, 17%) as a light yellow solid. MS-ESI (m/z) calcd for C₇H₅ClN₃O [M+H]⁺: 182.0. Found 182.0.

Step 2: 5-(5-Chloro-1H-pyrazolo[3,4-c]pyridin-3-yl)oxazole

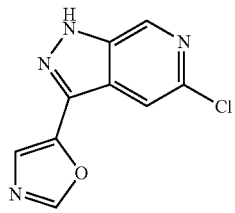 [SMILES: Clc1cc2c(-c3cnco3)n[nH]c2cn1]

To a solution of 5-chloro-1H-pyrazolo[3,4-c]pyridine-3-carbaldehyde (700 mg, 3.86 mmol) in MeOH (21 mL) was added Tos-MIC (827.92 mg, 4.24 mmol) and K₂CO₃ (1.07 g, 7.71 mmol). The mixture was then stirred at 80° C. for 30 min under an N₂ atmosphere. After cooling to 25° C., the reaction mixture was concentrated and poured into H₂O (10 mL) and extracted with EtOAc (10 mL×3). The combined organic phases were concentrated to give a residue which was purified by silica gel column chromatography using a 0-33% EtOAc/petroleum ether gradient eluent to afford the title compound (120 mg, 14%) as a yellow solid. MS-ESI (m/z) calcd for C₉H₆ClN₄O [M+H]⁺: 221.0. Found 220.9.

Step 3: 5-(5-Chloro-1-(tetrahydro-2H-pyran-2-yl)-1H-pyrazolo[3,4-c]pyridin-3-yl)oxazole

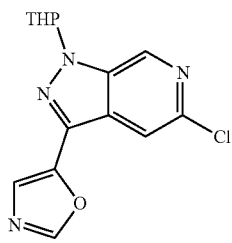

To a solution of 5-(5-chloro-1H-pyrazolo[3,4-c]pyridin-3-yl)oxazole (120 mg, 543.93 umol) in DCM (10 mL) was added 3,4-dihydro-2H-pyran (91.51 mg, 1.09 mmol, 99.46 uL) and TsOH (93.67 mg, 543.93 umol) and the reaction mixture was stirred at 50° C. for 12 hrs. After cooling to 25° C., the reaction mixture was poured into water (10 mL) and extracted with EtOAc (10 mL×3). The combined organic phases were concentrated to give a residue which was purified by silica gel column chromatography using a 0-33% EtOAc/petroleum ether gradient eluent to afford the title compound (65 mg, 39%) as a yellow oil. MS-ESI (m/z) calcd for $C_{14}H_{14}ClN_4O_2[M+H]^+$: 305.1/307.1. Found 305.1/307.1.

Step 4: N-(3-(Oxazol-5-yl)-1-(tetrahydro-2H-pyran-2-yl)-1H-pyrazolo[3,4-c]pyridin-5-yl)-1,1-diphenylmethanimine

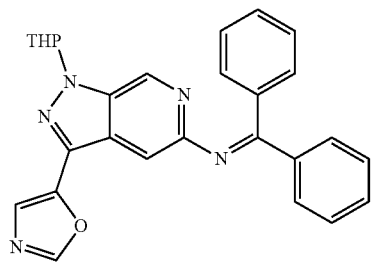

A mixture of 5-(5-chloro-1-(tetrahydro-2H-pyran-2-yl)-1H-pyrazolo[3,4-c]pyridin-3-yl)oxazole (50 mg, 164.08 umol), diphenylmethanimine (35.68 mg, 196.89 umol, 33.04 uL), BINAP (10.22 mg, 16.41 umol), tBuONa (20.50 mg, 213.30 umol) and $Pd_2(dba)_3$ (15.03 mg, 16.41 umol) in tolulene (4 mL) was degassed and purged with $N_2$ (3×), and then the mixture was stirred at 110° C. for 12 hrs under an $N_2$ atmosphere. After cooling to 25° C., the reaction mixture was poured into water (5 mL) and extracted with EtOAc (5 mL×3). The combined organic phases were concentrated to give a residue which was purified by preparative TLC (SiO$_2$, 1:1 petroleum ether/EtOAc, $R_f$=0.70) to afford the title compound (15 mg, 20%) as a yellow oil. MS-ESI (m/z) calcd for $C_{27}H_{24}N_5O_2$ [M+H]$^+$: 450.2. Found 450.2.

Step 5: 3-(Oxazol-5-yl)-1-(tetrahydro-2H-pyran-2-yl)-1H-pyrazolo[3,4-c]pyridin-5-amine

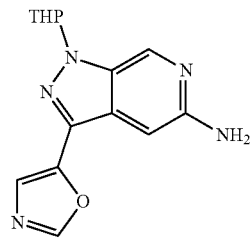

To a solution of N-(3-(oxazol-5-yl)-1-(tetrahydro-2H-pyran-2-yl)-1H-pyrazolo[3,4-c]pyridin-5-yl)-1,1-diphenylmethanimine (12 mg, 26.70 umol) in THF (1 mL) was added HCl (4 M, 6.67 uL) and the mixture was stirred at 25° C. for 30 min. After cooling to 25° C., the reaction mixture was poured into water (5 mL) and extracted with EtOAc (5 mL×3). The combined organic phases were concentrated in vacuum to afford the title compound (10 mg) as a yellow oil which was used without further purification. MS-ESI (m/z) calcd for $C_{14}H_{16}N_5O_2$ [M+H]$^+$: 286.1. Found 286.1.

Step 6: 5-Cyano-3,4-dimethyl-N-(3-(oxazol-5-yl)-1-(tetrahydro-2H-pyran-2-yl)-1H-pyrazolo[3,4-c]pyridin-5-yl)picolinamide

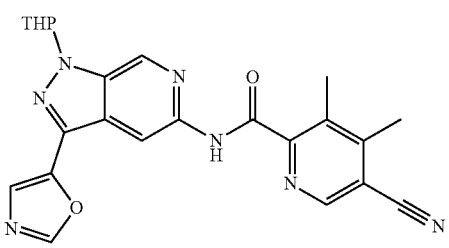

To a solution of 3-(oxazol-5-yl)-1-(tetrahydro-2H-pyran-2-yl)-1H-pyrazolo[3,4-c]pyridin-5-amine (10 mg, 35.05 umol) and 5-cyano-3,4-dimethylpicolinic acid (6.17 mg, 35.05 umol) in pyridine (2 mL) was added EDCI (20.16 mg, 105.15 umol) and the mixture was stirred at 25° C. for 2 hrs. After cooling to 25° C., the reaction mixture was poured into water (5 mL) and extracted with EtOAc (5 mL×3). The combined organic phases were concentrated in vacuum and purified by preparative TLC (SiO$_2$, 1:1 petroleum ether/EtOAc, $R_f$=0.60) to afford the title compound (10 mg, 640%) as a yellow solid. MS-ESI (m/z) calcd for $C_{23}H_{22}N_7O_3$ [M+H]$^+$: 444.2. Found 444.1.

Step 7: 5-Cyano-3,4-dimethyl-N-(3-(oxazol-5-yl)-1H-pyrazolo[3,4-c]pyridin-5-yl)picolinamide

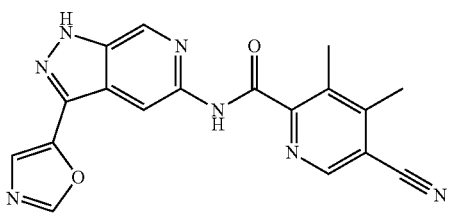 [SMILES: Cc1c(C#N)cnc(C(=O)Nc2cc3c(-c4cnco4)n[nH]c3cn2)c1C]

To a solution of 5-cyano-3,4-dimethyl-N-(3-(oxazol-5-yl)-1-(tetrahydro-2H-pyran-2-yl)-1H-pyrazolo[3,4-c]pyridin-5-yl)picolinamide (10 mg, 22.55 umol) in DCM (1 mL) was added TFA (0.5 mL) and the mixture was stirred at 25° C. for 12 hrs. The reaction mixture was concentrated to give a residue which was purified by preparative HPLC using Method CB to afford the title compound (1.95 mg, 18%) as a pale yellow solid, TFA salt. $^1$H NMR (400 MHz, DMSO-$d_6$) δ 14.08 (br s, 1H), 10.96 (s, 1H), 8.96 (s, 1H), 8.88 (s, 1H), 8.79 (s, 1H), 8.66 (s, 1H), 7.72 (s, 1H), 2.56 (s, 3H), 2.52 (br s, 3H). MS-ESI (m/z) calc'd for $C_{18}H_{14}N_7O_2$ [M+H]$^+$: 360.1. Found 360.1.

Example 239: 3-Cyano-1,4-dimethyl-N-(3-(oxazol-5-yl)-1H-indazol-5-yl)-1H-pyrazole-5-carboxamide

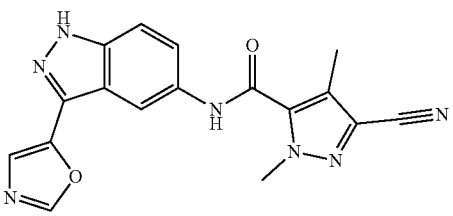 [SMILES: Cc1c(C#N)nn(C)c1C(=O)Nc1ccc2[nH]nc(-c3cnco3)c2c1]

Prepared as described for 3-cyano-N-(3-(1-(difluoromethyl)-1H-pyrazol-4-yl)-1H-indazol-5-yl)-1,4-dimethyl-1H-pyrazole-5-carboxamide using 3-(oxazol-5-yl)-1H-indazol-5-amine in place of 3-(1-(difluoromethyl)-1H-pyrazol-4-yl)-1H-indazol-5-amine to afford the title compound (13.51 mg, 9%) as a pink solid. $^1$H NMR (400 MHz, DMSO-$d_6$) δ 13.55 (s, 1H), 10.65 (s, 1H), 8.59 (s, 1H), 8.52 (s, 1H), 7.65 (s, 3H), 4.05 (s, 3H), 2.31 (s, 3H). MS-ESI (m/z) calc'd for $C_{17}H_{14}N_7O_2$ [M+H]$^+$: 348.1. Found 348.1.

Example 240: 5-Cyano-3,4-dimethyl-N-(3-(1-methyl-1H-1,2,3-triazol-4-yl)-1H-indazol-5-yl)picolinamide

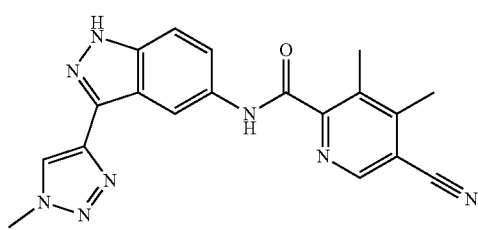 [SMILES: Cc1c(C#N)cnc(C(=O)Nc2ccc3[nH]nc(-c4cn(C)nn4)c3c2)c1C]

Step 1: 3-Bromo-5-nitro-1H-indazole

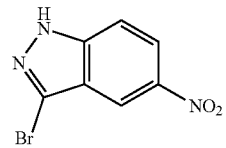 [SMILES: O=[N+]([O-])c1ccc2[nH]nc(Br)c2c1]

To a solution of 5-nitro-1H-indazole (2 g, 12.26 mmol) in AcOH (20 mL) was added Br$_2$ (5.88 g, 36.78 mmol). The mixture was stirred at 80° C. for 2 hrs. After cooling to r.t., the reaction mixture was poured into ice water (200 mL) and filtered. The solid was washed with 200 mL of H$_2$O and dried under vacuum to afford the title compound (2.9 g) as a yellow solid which was used without further purification.

Step 2: 5-Nitro-3-((trimethylsilyl)ethynyl)-1H-indazole

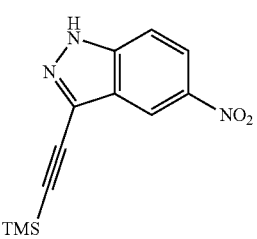 [SMILES: C[Si](C)(C)C#Cc1n[nH]c2ccc([N+](=O)[O-])cc12]

A mixture of 3-bromo-5-nitro-1H-indazole (2.7 g, 11.16 mmol), ethynyl(trimethyl)silane (3.29 g, 33.47 mmol), Et$_3$N (4.52 g, 44.62 mmol), Pd(PPh$_3$)$_4$ (1.29 g, 1.12 mmol) and CuI (106.23 mg, 557.78 umol) in THF (50 mL) was degassed and purged with N$_2$ (3×), and then the mixture was stirred at 80° C. for 3 hrs under an N$_2$ atmosphere. The reaction mixture was concentrated and purified by flash silica gel chromatography (ISCO; 40 g SepaFlash column) using a 0-12% EtOAc/petroleum ether gradient eluent to afford the title compound (1.25 g) as a yellow solid which was used without further purification. MS-ESI (m/z) calcd for $C_{12}H_{14}N_3O_2Si$ [M+H]$^+$: 260.1. Found 260.0.

Step 3: 3-Ethynyl-5-nitro-1H-indazole

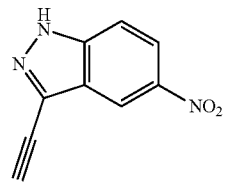

To a solution of 5-nitro-3-((trimethylsilyl)ethynyl)-1H-indazole (1.25 g, 4.82 mmol) in MeOH (12 mL) was added K$_2$CO$_3$ (2.00 g, 14.46 mmol). The reaction mixture was stirred at 25° C. for 2 hrs and concentrated. The residue was diluted with H$_2$O (20 mL) and extracted with EtOAc (10 mL×3). The combined organic layers were dried over Na$_2$SO$_4$, filtered and concentrated under reduced pressure to afford the title compound (813 mg) as a yellow solid which was used without further purification. MS-ESI (m/z) calcd for $C_9H_6N_3O_2$ [M+H]$^+$: 188.0. Found 188.0.

Step 4: 5-Nitro-3-(1-((trimethylsilyl)methyl)-1H-1,2,3-triazol-4-yl)-1H-indazole

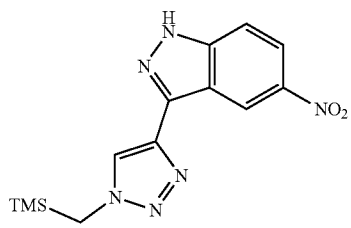 [SMILES: C[Si](C)(C)Cn1cc(-c2n[nH]c3ccc([N+](=O)[O-])cc23)nn1]

To a solution of 3-ethynyl-5-nitro-1H-indazole (400 mg, 2.14 mmol) and (azidomethyl)trimethylsilane (276.21 mg, 2.14 mmol) in DMF (15 mL) was added CuI (81.41 mg, 427.45 umol) and DIEA (276.23 mg, 2.14 mmol). The mixture was stirred at 25° C. for 12 hrs under an N$_2$ atmosphere. The reaction mixture was concentrated and purified by flash silica gel chromatography (ISCO; 20 g SepaFlash column) using a 0-30% EtOAc/petroleum ether gradient eluent to afford the title compound (232 mg, 34%) as a red solid. MS-ESI (m/z) calcd for $C_{13}H_{17}N_6O_2Si$ [M+H]$^+$: 317.1. Found 317.1.

Step 5: 3-(1-Methyl-1H-1,2,3-triazol-4-yl)-5-nitro-1H-indazole

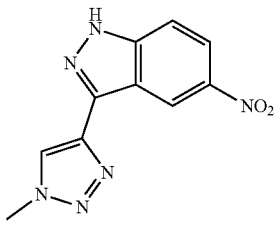 [SMILES: Cn1cc(-c2n[nH]c3ccc([N+](=O)[O-])cc23)nn1]

To a solution of 5-nitro-3-(1-((trimethylsilyl)methyl)-1H-1,2,3-triazol-4-yl)-1H-indazole (232 mg, 733.27 umol) in MeCN (3 mL) and EtOH (1.5 mL) was added CsF (222.77 mg, 1.47 mmol). The mixture was stirred at 80° C. for 2 hrs and concentrated. The residue was then diluted with H$_2$O (5 mL) and filtered. The solid was dried under vacuum to afford the title compound (97 mg) as a red solid which was used without further purification. MS-ESI (m/z) calcd for $C_{10}H_9N_6O_2$ [M+H]$^+$: 245.1. Found 245.0.

Step 6: 3-(1-Methyl-1H-1,2,3-triazol-4-yl)-1H-indazol-5-amine

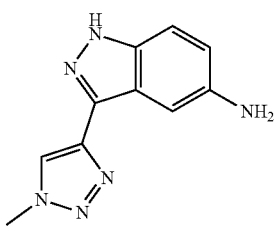

To a solution of 3-(1-methyl-1H-1,2,3-triazol-4-yl)-5-nitro-1H-indazole (97 mg, 397.20 umol) in EtOH (3 mL) was added SnCl$_2$.2H$_2$O (268.88 mg, 1.19 mmol). The mixture was then stirred at 80° C. for 2 hrs, then diluted with Na$_2$CO$_3$ (5 mL) and extracted with EtOAc (10 mL×3). The combined organic layers were dried over Na$_2$SO$_4$, filtered and concentrated under reduced pressure to afford the title compound (53 mg) as a yellow solid which was used without further purification. MS-ESI (m/z) calcd for $C_{10}H_{11}N_6$ [M+H]$^+$: 215.1. Found 215.0.

Step 7: 5-Cyano-3,4-dimethyl-N-(3-(1-methyl-1H-1,2,3-triazol-4-yl)-1H-indazol-5-yl)picolinamide

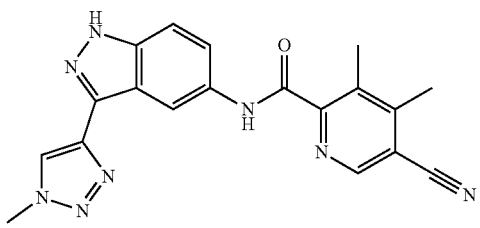 [SMILES: Cc1c(C#N)cnc(C(=O)Nc2ccc3[nH]nc(-c4cn(C)nn4)c3c2)c1C]

To a solution of 3-(1-methyl-1H-1,2,3-triazol-4-yl)-1H-indazol-5-amine (50 mg, 233.40 umol), 5-cyano-3,4-dimethylpicolinic acid (41.12 mg, 233.40 umol) in pyridine (2 mL) was added EDCI (67.11 mg, 350.10 umol). The mixture was stirred at 20° C. for 3 hrs, then concentrated and purified by preparative HPLC using Method AI to afford the title compound (11.31 mg, 10%) as a pale yellow solid. $^1$H NMR (400 MHz, DMSO-d$_6$) δ 13.20 (s, 1H), 10.72 (s, 1H), 8.88 (s, 1H), 8.81 (s, 1H), 8.50 (s, 1H), 7.71 (dd, J=1.76, 9.04 Hz, 1H), 7.57 (d, J=8.82 Hz, 1H), 4.15 (s, 3H), 2.55 (s, 3H), 2.45 (s, 3H). MS-ESI (m/z) calc'd for $C_{19}H_{17}N_8O$ [M+H]$^+$: 373.1. Found 373.1.

Example 241: 5-Cyano-3-methyl-N-(3-(1-methyl-1H-1,2,3-triazol-4-yl)-1H-indazol-5-yl)picolinamide

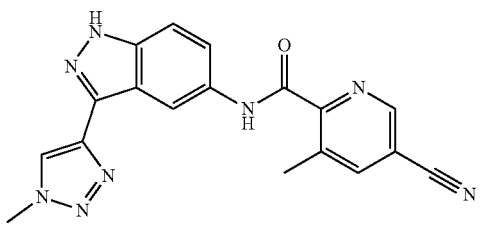 [SMILES: Cc1cc(C#N)cnc1C(=O)Nc1ccc2[nH]nc(-c3cn(C)nn3)c2c1]

Prepared as described for 5-cyano-3,4-dimethyl-N-(3-(1-methyl-1H-1,2,3-triazol-4-yl)-1H-indazol-5-yl)picolinamide using 5-cyano-3-methylpicolinic acid in place of 5-cyano-3,4-dimethylpicolinic acid to afford the title compound (20.01 mg, 18% yield) as a white solid. $^1$H NMR (400 MHz, DMSO-d$_6$) δ 13.18 (br s, 1H), 10.73 (s, 1H), 8.98 (d, J=1.47 Hz, 1H), 8.84 (d, J=1.34 Hz, 1H), 8.50 (s, 1H), 8.39 (d, J=0.98 Hz, 1H), 7.74 (dd, J=1.83, 9.05 Hz, 1H), 7.56 (d, J=8.80 Hz, 1H), 4.15 (s, 3H), 2.59 (s, 3H). MS-ESI (m/z) calc'd for $C_{18}H_{15}N_5O$ [M+H]$^+$: 359.1. Found 359.1.

Example 242: 5-Cyano-3-methyl-N-(3-(2-oxooxazol-3(2H)-yl)-1H-indazol-5-yl)picolinamide

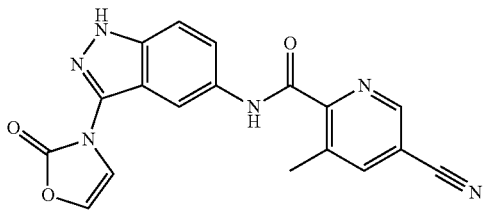 [SMILES: Cc1cc(C#N)cnc1C(=O)Nc1ccc2[nH]nc(-n3ccoc3=O)c2c1]

Step 1: 5-Nitro-1-(tetrahydro-2H-pyran-2-yl)-1H-indazol-3-amine

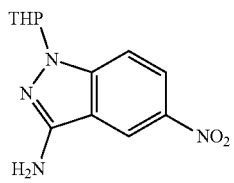

To a solution of 5-nitro-1H-indazol-3-amine (1.1 g, 6.17 mmol) in CHCl₃ (20 mL) was added MsOH (29.67 mg, 308.73 umol, 21.98 uL) and 3,4-dihydro-2H-pyran (1.56 g, 18.52 mmol, 1.69 mL). The mixture was stirred at 70° C. for 12 hrs. The reaction mixture was concentrated and purified by flash silica gel chromatography (ISCO; 20 g SepaFlash column) using a 0-21% EtOAc/petroleum ether gradient eluent to afford the title compound (280 mg, 17%) as an orange solid. MS-(ESI) (m/z) calcd for $C_{12}H_{15}N_4O_3$ (M+H)$^+$: 263.1. Found 263.0.

Step 2: 2-Hydroxy-N-(5-nitro-1-(tetrahydro-2H-pyran-2-yl)-1H-indazol-3-yl)acetamide

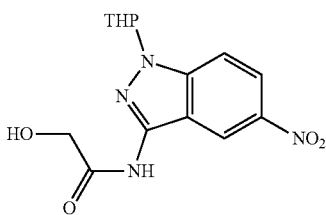

To a solution of 5-nitro-1-(tetrahydro-2H-pyran-2-yl)-1H-indazol-3-amine (170 mg, 648.20 umol) in DCM (3 mL) was added Et₃N (72.15 mg, 713.02 umol) and 2-chloro-2-oxoethyl acetate (88.50 mg, 648.20 umol). The mixture was stirred at 20° C. for 1 hr and then concentrated. THF (3 mL), H₂O (1 mL) and LiOH.H₂O (54.40 mg, 1.30 mmol) was then added and the mixture was stirred at 20° C. for 12 hrs. The reaction mixture was concentrated and purified by preparative TLC (SiO₂, 1:1 petroleum ether/EtOAc, R$_f$=0.15) to afford the title compound (50 mg, 24%) as a yellow solid. MS-(ESI) (m/z) calcd for $C_{14}H_{17}N_4O$ (M+H)$^+$: 321.1. Found 321.1.

Step 3: 3-(5-Nitro-1-(tetrahydro-2H-pyran-2-yl)-1H-indazol-3-yl)oxazolidine-2,4-dione

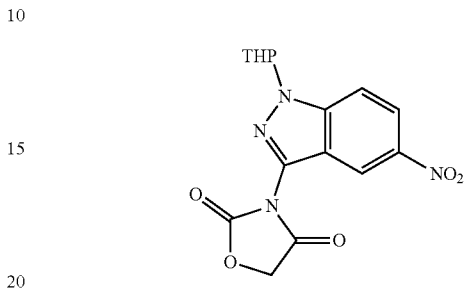

To a solution of 2-hydroxy-N-(5-nitro-1-(tetrahydro-2H-pyran-2-yl)-1H-indazol-3-yl)acetamide (50 mg, 156.10 umol) in DMF (2 mL) was added 1,1'-carbonyldiimidazole (75.94 mg, 468.31 umol). The mixture was stirred at 20° C. for 12 hrs, then diluted with H₂O (3 mL) and extracted with EtOAc (10 mL×3). The combined organic layers were dried over Na₂SO₄, filtered and concentrated under reduced pressure to give a residue. The residue was purified by preparative TLC (SiO₂, 2:1 petroleum ether/EtOAc, R$_f$=0.25) to afford the title compound (50 mg, 92%) as a yellow oil. MS-(ESI) (m/z) calcd for $C_{15}H_{15}N_4O_6$ (M+H): 347.1. Found 347.0.

Step 4: 4-Hydroxy-3-(5-nitro-1-(tetrahydro-2H-pyran-2-yl)-1H-indazol-3-yl)oxazolidin-2-one

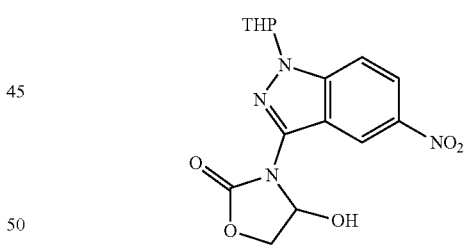

To a solution of 3-(5-nitro-1-(tetrahydro-2H-pyran-2-yl)-1H-indazol-3-yl)oxazolidine-2,4-dione (90 mg, 259.89 umol) in MeOH (2 mL) was added NaBH₄ (9.83 mg, 259.89 umol) at 0° C. The mixture was stirred at 0° C. for 1 hr, then quenched by addition of H₂O (3 mL) at 0° C. The mixture was concentrated and extracted with EtOAc (10 mL×3). The combined organic layers were dried over Na₂SO₄, filtered and concentrated under reduced pressure to give a residue. The residue was purified by preparative TLC (SiO₂, 1:1 petroleum ether/EtOAc, R$_f$=0.2) to afford the title compound (28 mg, 30%) as a yellow gum. MS-(ESI) (m/z) calcd for $C_{15}H_{17}N_4O_6$(M+H)$^+$: 349.1. Found 349.0.

Step 5: 3-(5-Nitro-1-(tetrahydro-2H-pyran-2-yl)-1H-indazol-3-yl)oxazol-2(3H)-one

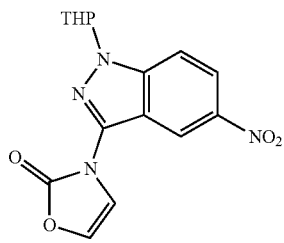

To a solution of 4-hydroxy-3-(5-nitro-1-(tetrahydro-2H-pyran-2-yl)-1H-indazol-3-yl)oxazolidin-2-one (50 mg, 143.55 umol), Et$_3$N (29.05 mg, 287.10 umol) and DMAP (1.75 mg, 14.36 umol) in DCE (2 mL) was added MsCl (246.66 mg, 2.15 mmol) at 0° C. The mixture was stirred at 65° C. for 16 hrs, quenched by addition of saturated aqueous Na$_2$CO$_3$ (1 mL) at 20° C., and then diluted with saturated NH$_4$Cl (3 mL) and extracted with EtOAc (10 mL×3). The combined organic layers were dried over Na$_2$SO$_4$, filtered and concentrated under reduced pressure to give a residue. The residue was purified by preparative TLC (SiO$_2$, 1:1 petroleum ether/EtOAc, R$_f$=0.53) to afford the title compound (30 mg, 63%) as a yellow solid. MS-(ESI) (m/z) calcd for C$_{15}$H$_{15}$N$_4$O$_5$ (M+H)$^+$: 331.1. Found 331.1.

Step 6: 3-(5-Amino-1-(tetrahydro-2H-pyran-2-yl)-1H-indazol-3-yl)oxazol-2(3H)-one

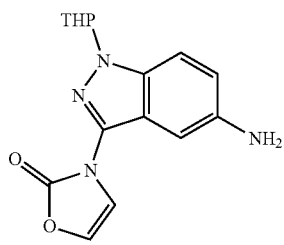

To a solution of 3-(5-nitro-1-(tetrahydro-2H-pyran-2-yl)-1H-indazol-3-yl)oxazol-2(3H)-one (30 mg, 90.83 umol) in EtOH (1 mL) and H$_2$O (0.5 mL) was added Fe (25.36 mg, 454.14 umol) and NH$_4$Cl (24.29 mg, 454.14 umol) and the mixture was stirred at 20° C. for 2 hrs. The reaction mixture was then filtered. The filtrate was concentrated under reduced pressure to afford the title compound (25 mg) as a brown solid which was used without further purification. MS-(ESI) (m/z) calcd for C$_{15}$H$_{17}$N$_4$O$_3$(M+H)$^+$: 301.1. Found 301.1.

Step 7: 5-Cyano-3-methyl-N-(3-(2-oxooxazol-3(2H)-yl)-1-(tetrahydro-2H-pyran-2-yl)-1H-indazol-5-yl)picolinamide

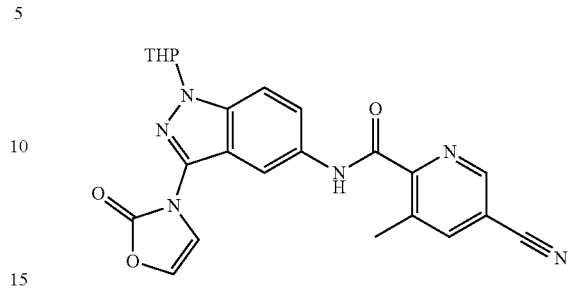

To a solution of 5-cyano-3-methylpicolinic acid (13.50 mg, 83.25 umol) and 3-(5-amino-1-(tetrahydro-2H-pyran-2-yl)-1H-indazol-3-yl)oxazol-2(3H)-one (25 mg, 83.25 umol) in pyridine (2 mL) was added EDCI (23.94 mg, 124.88 umol) and the mixture was stirred at 20° C. for 12 hrs. The reaction mixture was then concentrated to afford the title compound (35 mg) as a brown gum which was used without further purification. MS-(ESI) (m/z) calcd for C$_{23}$H$_{21}$N$_6$O$_4$ (M+H)$^+$: 445.15. Found 445.15.

Step 8: 5-Cyano-3-methyl-N-(3-(2-oxooxazol-3(2H)-yl)-1H-indazol-5-yl)picolinamide

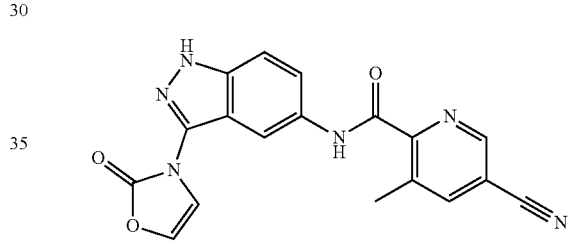

To a solution of 5-cyano-3-methyl-N-(3-(2-oxooxazol-3(2H)-yl)-1-(tetrahydro-2H-pyran-2-yl)-1H-indazol-5-yl)picolinamide (35 mg, 78.75 umol) in DCM (1 mL) was added TFA (8.98 mg, 78.75 umol) and the mixture was stirred at 20° C. for 2 hrs. The reaction mixture was concentrated and purified by preparative HPLC using Method AI to afford the title compound (1.9 mg, 5%) as a pale yellow solid. $^1$H NMR (400 MHz, DMSO-d$_6$) δ 13.28 (s, 1H) 10.77 (s, 1H) 8.98 (d, J=1.32 Hz, 1H) 8.40 (br d, J=5.07 Hz, 2H) 7.77 (dd, J=8.93, 1.43 Hz, 1H) 7.58 (d, J=9.04 Hz, 1H) 7.55 (d, J=1.98 Hz, 1H) 7.50 (d, J=1.98 Hz, 1H) 2.56 (s, 3H). MS-ESI (m/z) calc'd for C$_{15}$H$_{13}$N$_6$O$_3$ [M+H]$^+$: 361.1. Found 361.1.

Example 243: 5-Cyano-3,4-dimethyl-N-(3-(2-methylprop-1-en-1-yl)-1H-indazol-5-yl)picolinamide

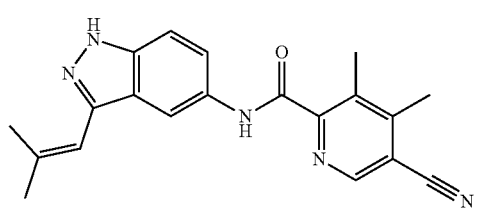 [SMILES: CC(C)=Cc1n[nH]c2ccc(NC(=O)c3ncc(C#N)c(C)c3C)cc12]

Step 1: N-(3-Bromo-1H-indazol-5-yl)-5-cyano-3,4-dimethylpicolinamide

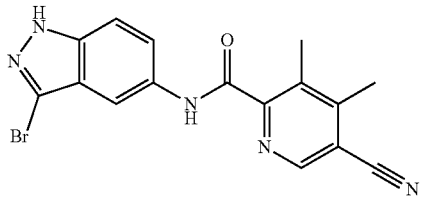

To a solution of 3-bromo-1H-indazol-5-amine (500 mg, 2.36 mmol) and 5-cyano-3,4-dimethylpicolinic acid (415.41 mg, 2.36 mmol) in DCM (15 mL) was added T3P (50 wt. % in EtOAc, 1.95 g, 3.07 mmol, 1.82 mL) at 20° C. and the reaction mixture was stirred at 30° C. for 0.5 hr. Et$_3$N (477.20 mg, 4.72 mmol, 656.40 uL) was then added and the reaction mixture was stirred at 30° C. for 1 hr. The reaction mixture was poured into H$_2$O (15 mL) and stirred at 25° C. for 0.5 hr. Then the mixture was filtered and the solid was dried to afford the title compound as a brown solid (417 mg), which was used without further purification. MS-ESI (m/z) calcd for $C_{16}H_{13}BrN_5O$ [M+H]$^+$: 370.0/372.0. Found 370.0/372.0.

Step 2: 5-Cyano-3,4-dimethyl-N-(3-(2-methylprop-1-en-1-yl)-1H-indazol-5-yl)picolinamide

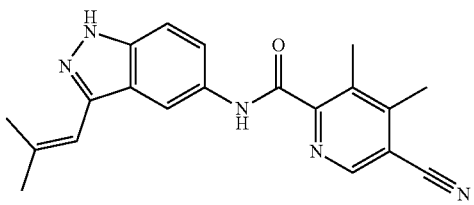 [SMILES: CC(C)=Cc1n[nH]c2ccc(NC(=O)c3ncc(C#N)c(C)c3C)cc12]

To a solution of N-(3-bromo-1H-indazol-5-yl)-5-cyano-3,4-dimethylpicolinamide (50 mg, 135.06 umol) in EtOH (1 mL) and H$_2$O (0.25 mL) was added 4,4,5,5-tetramethyl-2-(2-methylprop-1-en-1-yl)-1,3,2-dioxaborolane (73.77 mg, 405.18 umol), KOAc (66.28 mg, 675.31 umol) and Pd(Amphos)Cl$_2$ (9.56 mg, 13.51 umol) at 20° C. Then the reaction mixture was stirred at 90° C. for 12 hrs under N$_2$. The reaction mixture was filtered and concentrated and purified by preparative HPLC using Method AJ to afford the title compound (12.29 mg, 91%) as a white solid. $^1$H NMR (400 MHz, DMSO-d$_4$) δ 12.92 (s, 1H), 10.65 (s, 1H), 8.88 (s, 1H), 8.30 (s, 1H), 7.57-7.52 (m, 1H), 7.50-7.46 (m, 1H), 6.44 (s, 1H), 2.55 (s, 3H), 2.44 (s, 3H), 2.13 (s, 3H), 1.99 (s, 3H). MS-ESI (m/z) calc'd for $C_{20}H_{20}N_5O$ [M+H]$^+$: 346.2. Found 346.2.

Example 244: (E)-5-Cyano-3,4-dimethyl-N-(3-styryl-1H-indazol-5-yl)picolinamide

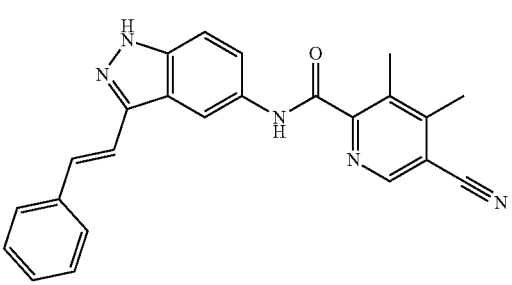 [SMILES: Cc1c(C#N)cnc(C(=O)Nc2ccc3[nH]nc(/C=C/c4ccccc4)c3c2)c1C]

Prepared as described for 5-cyano-3,4-dimethyl-N-(3-(2-methylprop-1-en-1-yl)-1H-indazol-5-yl)picolinamide using (E)-4,4,5,5-tetramethyl-2-styryl-1,3,2-dioxaborolane in place of 4,4,5,5-tetramethyl-2-(2-methylprop-1-en-1-yl)-1,3,2-dioxaborolane to afford the title compound (45.33 mg, 15%) as a yellow solid. $^1$H NMR (400 MHz, DMSO-d$_6$) δ 13.19 (s, 1H), 10.71 (s, 1H), 8.90 (s, 1H), 8.57 (s, 1H), 7.74 (d, J=9.0 Hz, 1H), 7.68 (d, J=7.5 Hz, 2H), 7.58-7.51 (m, 2H), 7.45-7.37 (m, 3H), 7.33-7.27 (m, 1H), 2.56 (s, 3H), 2.47 (s, 3H). MS-ESI (m/z) calc'd for $C_{24}H_{20}N_5O$ [M+H]$^+$: 394.2 Found 394.1.

Example 245: (E)-5-cyano-3,4-dimethyl-N-(3-(prop-1-en-1-yl)-1H-indazol-5-yl)picolinamide

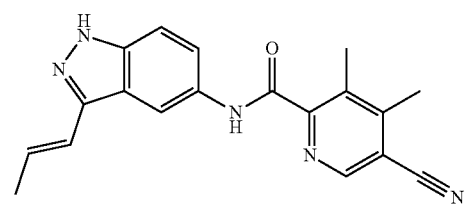 [SMILES: C/C=C/c1n[nH]c2ccc(NC(=O)c3ncc(C#N)c(C)c3C)cc12]

Prepared as described for 5-cyano-3,4-dimethyl-N-(3-(2-methylprop-1-en-1-yl)-1H-indazol-5-yl)picolinamide using (E)-4,4,5,5-tetramethyl-2-(prop-1-en-1-yl)-1,3,2-dioxaborolane in place of 4,4,5,5-tetramethyl-2-(2-methylprop-1-en-1-yl)-1,3,2-dioxaborolane to afford the title compound (127.86 mg, 55% yield) as a gray solid. $^1$H NMR (400 MHz, DMSO-d$_6$) δ 12.92 (s, 1H), 10.67 (s, 1H), 8.89 (s, 1H), 8.47 (s, 1H), 7.68-7.61 (m, 1H), 7.50 (d, J=8.9 Hz, 1H), 6.72 (dd, J=1.6, 16.1 Hz, 1H), 6.56-6.45 (m, 1H), 2.56 (s, 3H), 2.45 (s, 3H), 1.96 (dd, J=1.4, 6.5 Hz, 3H). MS-ESI (m/z) calc'd for $C_{19}H_{15}N_5O$ [M+H]$^+$: 332.1 Found 332.2.

Example 246: 4-Cyano-N-(3-(isoxazol-4-yl)-1H-indazol-5-yl)-1,3-dimethyl-1H-pyrrole-2-carboxamide and Example 247: 4-Cyano-N-(3-(isoxazol-4-yl)-1H-indazol-5-yl)-1-methyl-1H-pyrrole-2-carboxamide

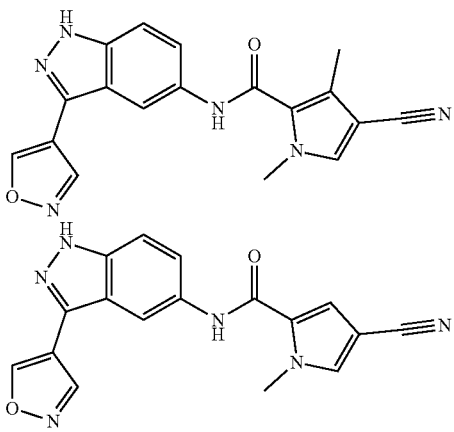

Step 1: 2-((Methylamino)methylene)malononitrile

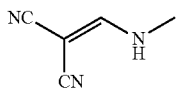

To a solution of 2-(ethoxymethylene)malononitrile (1.1 g, 9.01 mmol) in EtOH (4 mL) was added methylamine (1.03 g, 9.91 mmol, 300% in EtOH). The mixture was stirred at 25° C. for 0.5 hr. The reaction mixture was filtered and the solid was dried under vacuum to afford the title compound (760 mg) as a yellow solid which was used without further purification.

Step 2: Ethyl 3-amino-4-cyano-1-methyl-1H-pyrrole-2-carboxylate

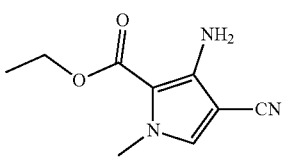

To a solution of 2-((methylamino)methylene)malononitrile (630 mg, 5.88 mmol) in DMF (4 mL) was added ethyl 2-bromoacetate (982.24 mg, 5.88 mmol) and $K_2CO_3$ (812.88 mg, 5.88 mmol). The mixture was stirred at 80° C. for 30 min. NaOEt (600.37 mg, 8.82 mmol) was then added and the mixture was stirred at 90° C. for 4.5 hrs. The reaction was filtered and the filtrate was diluted with $H_2O$ (20 mL) and extracted with EtOAc (10 mL 3). The combined organic phases were dried over $Na_2SO_4$, filtered and the filtrate was concentrated under reduced pressure to give a residue. The residue was purified by flash silica gel chromatography (ISCO; 4 g SepaFlash column) using a 0-20% EtOAc/petroleum ether gradient eluent to afford the title compound (364 mg, 32%) as a yellow solid. MS-ESI (m/z) calcd for $C_9H_{12}N_3O_2$ [M+H]$^+$: 194.1. Found 194.3.

Step 3: Ethyl 4-cyano-3-iodo-1-methyl-1H-pyrrole-2-carboxylate

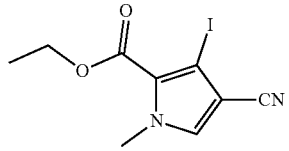

To a solution of ethyl 3-amino-4-cyano-1-methyl-1H-pyrrole-2-carboxylate (360 mg, 1.86 mmol) in MeCN (6 mL) at 25° C. was added diiodomethane (1.80 g, 6.71 mmol). The mixture was then heated to 35° C. and isopentyl nitrite (545.71 mg, 4.66 mmol) was added. The reaction mixture was then stirred at 65° C. for an additional 10 min. The reaction mixture was diluted with $H_2O$ (30 mL) and extracted with EtOAc (15 mL×3). The combined organic phases were dried over $Na_2SO_4$ and concentrated under reduced pressure to give a residue. The residue was purified by flash silica gel chromatography (ISCO; 4 g SepaFlash column) using a 0-8% EtOAc/petroleum ether gradient eluent to afford the title compound (266 mg, 47%) as a yellow solid. MS-ESI (m/z) calcd for $C_9H_{10}IN_2O_2$ [M+H]$^+$: 305.0. Found 304.9.

Step 4: Ethyl 4-Cyano-1,3-dimethyl-1H-pyrrole-2-carboxylate

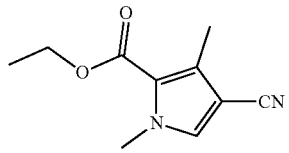

A mixture of ethyl 4-cyano-3-iodo-1-methyl-1H-pyrrole-2-carboxylate (300 mg, 986.57 umol), $K_2CO_3$ (409.06 mg, 2.96 mmol), Pd(dppf)Cl$_2$ (36.09 mg, 49.33 umol) and trimethylboroxine (247.70 mg, 1.97 mmol) in dioxane (5 mL) was degassed and purged with $N_2$ (3×), and then the mixture was stirred at 100° C. for 12 hrs under an $N_2$ atmosphere. The reaction was filtered and the filtrate was concentrated. The mixture was diluted with $H_2O$ (5 mL) and extracted with EtOAc (2 mL×3). The combined organic phases were dried over $Na_2SO_4$ and concentrated under reduced pressure to afford the title compound (200 mg) as a brown solid which was used without further purification. MS-ESI (m/z) calcd for $C_{10}H_{13}N_2O_2$[M+H]$^+$: 193.1. Found 193.1.

Step 5: 4-Cyano-1,3-dimethyl-1H-pyrrole-2-carboxylic acid

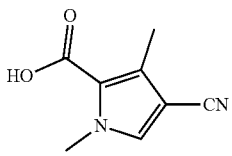

To a solution of ethyl 4-cyano-1,3-dimethyl-1H-pyrrole-2-carboxylate (80 mg, 416.20 umol) in EtOH (5 mL) was added NaOH (49.94 mg, 1.25 mmol). The reaction mixture was stirred at 25° C. for 12 hrs, then diluted with 1 M HCl to pH=4, and extracted with EtOAc (20 mL×3). The combined organic layers were dried over Na₂SO₄, filtered and concentrated under reduced pressure to afford the title compound (73 mg) as a brown solid which was used without further purification. MS-ESI (m/z) calcd for $C_8H_9N_2O_2$ [M+H]⁺: 165.1. Found 165.0.

Step 6: 4-Cyano-N-(3-(isoxazol-4-yl)-1H-indazol-5-yl)-1,3-dimethyl-1H-pyrrole-2-carboxamide and 4-Cyano-N-(3-(isoxazol-4-yl)-1H-indazol-5-yl)-1-methyl-1H-pyrrole-2-carboxamide

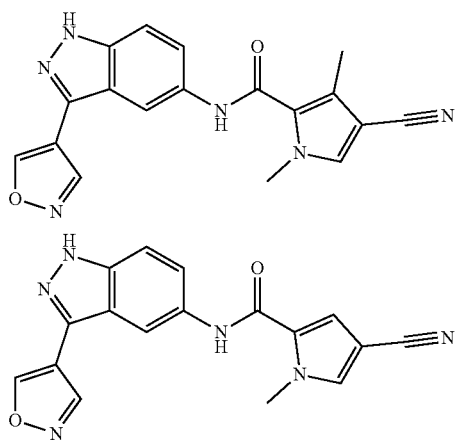

To a solution of 4-cyano-1,3-dimethyl-1H-pyrrole-2-carboxylic acid (100 mg, 609.16 umol) in pyridine (20 mL) was added EDCI (233.55 mg, 1.22 mmol) and 3-(isoxazol-4-yl)-1H-indazol-5-amine (121.95 mg, 609.16 umol). The mixture was stirred at 25° C. for 12 hrs and then concentrated. The material was purified by preparative HPLC using Method AK to afford a mixture of products. The mixture was further separated by SFC using Method AL to give two compounds. 4-cyano-N-(3-(isoxazol-4-yl)-1H-indazol-5-yl)-1,3-dimethyl-1H-pyrrole-2-carboxamide (5.69 mg, 3%) was isolated as a white solid. ¹H NMR (400 MHz, DMSO-d₆) δ 13.32 (s, 1H), 10.14 (s, 1H), 9.52 (s, 1H), 9.13 (s, 1H), 8.31 (s, 1H), 7.72 (s, 1H), 7.55-7.63 (m, 2H), 3.76 (s, 3H), 2.31 (s, 3H). MS-ESI (m/z) calc'd for $C_{18}H_{15}N_6O_2$ [M+H]⁺: 347.1 Found 347.1. A second fraction was isolated to afford 4-cyano-N-(3-(isoxazol-4-yl)-1H-indazol-5-yl)-1-methyl-1H-pyrrole-2-carboxamide (2.04 mg, 1%) as a yellow solid. ¹H NMR (400 MHz, DMSO-d₆) 13.35 (br s, 1H), 10.16 (s, 1H), 9.55-9.61 (m, 1H), 9.15 (s, 1H), 8.27 (s, 1H), 7.87 (d, J=1.38 Hz, 1H), 7.65-7.68 (m, 1H), 7.59-7.61 (m, 1H), 7.44 (d, J=1.50 Hz, 1H), 3.95 (s, 3H).). MS-ESI (m/z) calc'd for $C_{17}H_{13}N_6O_2$[M+H]⁺: 333.1 Found 333.1.

Example 248: (E)-5-Cyano-3,4-dimethyl-N-(3-(2-(pyridin-2-yl)vinyl)-1H-indazol-5-yl)picolinamide

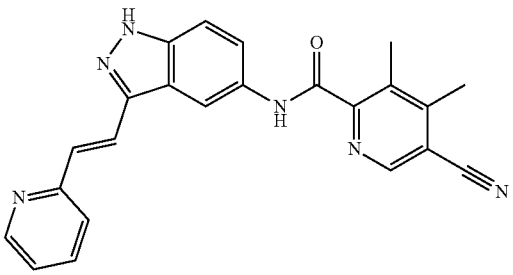 [SMILES: Cc1c(C#N)cnc(C(=O)Nc2ccc3[nH]nc(/C=C/c4ccccn4)c3c2)c1C]

Step 1: 3-Iodo-5-nitro-1H-indazole

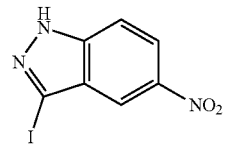

To a solution of 5-nitro-1H-indazole (5 g, 30.65 mmol) in DMF (75 mL) was added KOH (6.02 g, 107.27 mmol) and I₂ (23.34 g, 91.95 mmol). The mixture was stirred at 65° C. for 1 hr. The reaction mixture was quenched by addition of an aqueous solution of Na₂S₂O₃ (700 mL) at 20° C., and then extracted with EtOAc (150 mL×3). The combined organic layers were dried over Na₂SO₄, filtered and concentrated under reduced pressure to afford the title compound (8.86 g) as a yellow solid which was used without further purification.

Step 2: 3-Iodo-5-nitro-1-(tetrahydro-2H-pyran-2-yl)-1H-indazole

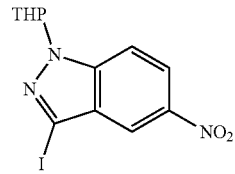

To a solution of 3-iodo-5-nitro-1H-indazole (8 g, 27.68 mmol) and 3,4-dihydro-2H-pyran (6.98 g, 83.04 mmol, 7.59 mL) in CHCl₃ (100 mL) was added MsOH (2.66 g, 27.68 mmol). The mixture was stirred at 70° C. for 12 hrs and then concentrated. The material was purified by flash silica gel chromatography (ISCO; 40 g SepaFlash column) using a 0-10% EtOAc/petroleum ether gradient eluent to afford the title compound (5.01 g, 37%) as a yellow solid. MS-ESI (m/z) calcd for $C_{12}H_{13}IN_3O_3$[M+H]⁺: 374.0. Found 373.9.

Step 3: 3-Iodo-1-(tetrahydro-2H-pyran-2-yl)-1H-indazol-5-amine

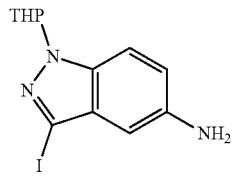

To a solution of 3-iodo-5-nitro-1-(tetrahydro-2H-pyran-2-yl)-1H-indazole (1 g, 2.68 mmol) in EtOH (24 mL) and H$_2$O (6 mL) was added Fe (748.30 mg, 13.40 mmol) and NH$_4$Cl (716.76 mg, 13.40 mmol). The mixture was stirred at 25° C. for 2 hrs and then filtered. The filtrate was concentrated under reduced pressure to remove solvent and then diluted with H$_2$O (100 mL) and extracted with EtOAc (100 mL×3). The organic phase was dried over Na$_2$SO$_4$, filtered and concentrated under reduced pressure to afford the title compound (755 mg) as a brown oil which was used without further purification. MS-ESI (m/z) calcd for C$_{12}$H$_{15}$IN$_3$O [M+H]$^+$: 344.0. Found 344.0.

Step 4: 5-Cyano-N-(3-iodo-1-(tetrahydro-2H-pyran-2-yl)-1H-indazol-5-yl)-3,4-dimethylpicolinamide

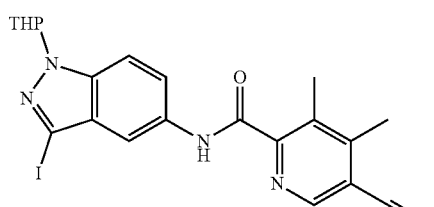

To a solution of 3-iodo-1-(tetrahydro-2H-pyran-2-yl)-1H-indazol-5-amine (200 mg, 582.81 umol), 5-cyano-3,4-dimethylpicolinic acid (102.68 mg, 582.81 umol) in pyridine (4 mL) was added EDCI (167.59 mg, 874.22 umol). The mixture was stirred at 25° C. for 12 hrs and then concentrated under reduced pressure to remove solvent. The residue was diluted with H$_2$O (5 mL) and extracted with EtOAc (5 mL×3). The combined organic layers were dried over Na$_2$SO$_4$, filtered and concentrated under reduced pressure to afford the title compound (264 mg) as a yellow solid which was used without further purification. MS-ESI (m/z) calcd for C$_{21}$H$_{21}$IN$_5$O$_2$[M+H]$^+$: 502.1. Found 502.0

Step 5: (E)-5-Cyano-3,4-dimethyl-N-(3-(2-(pyridin-2-yl)vinyl)-1-(tetrahydro-2H-pyran-2-yl)-1H-indazol-5-yl)picolinamide

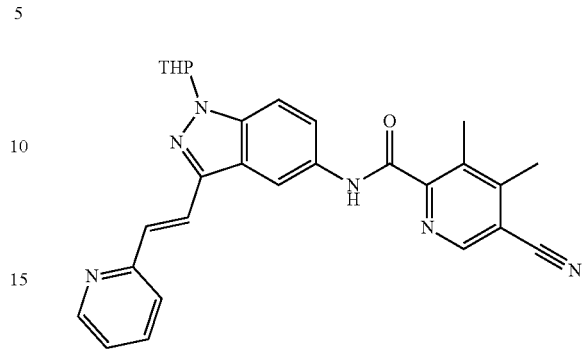

A mixture of 5-cyano-N-(3-iodo-1-(tetrahydro-2H-pyran-2-yl)-1H-indazol-5-yl)-3,4-dimethylpicolinamide (60 mg, 119.68 umol), 2-vinylpyridine (15.10 mg, 143.62 umol, 15.50 uL), Pd(OAc)$_2$ (2.69 mg, 11.97 umol), Et$_3$N (12.11 mg, 119.68 umol) and tris-o-tolylphosphane (3.64 mg, 11.97 umol) in DMF (2 mL) was degassed and purged with N$_2$ (3×). The mixture was then stirred at 120° C. for 4 hrs under an N$_2$ atmosphere in a microwave. The residue was diluted with H$_2$O (5 mL) and extracted with EtOAc (5 mL×3). The organic phase was dried over Na$_2$SO$_4$, filtered and concentrated under reduced pressure to give a residue. The residue was purified by preparative TLC (SiO$_2$, petroleum ether/EtOAc=1/1, R$_f$=0.37) to afford the title compound (37 mg, 65%) as a yellow solid. MS-ESI (m/z) calcd for C$_{28}$H$_{27}$N$_6$O$_2$[M+H]$^+$: 479.2. Found 479.2.

Step 6: (E)-5-Cyano-3,4-dimethyl-N-(3-(2-(pyridin-2-yl)vinyl)-1H-indazol-5-yl)picolinamide

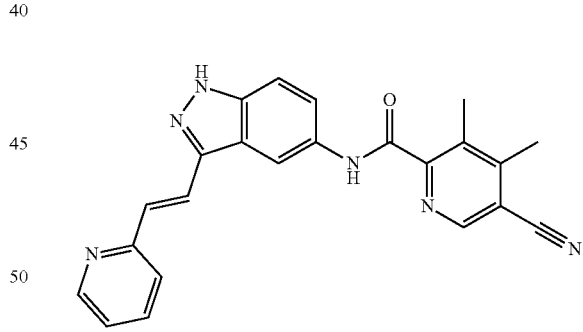

To a solution of (E)-5-cyano-3,4-dimethyl-N-(3-(2-(pyridin-2-yl)vinyl)-1-(tetrahydro-2H-pyran-2-yl)-1H-indazol-5-yl)picolinamide (37.00 mg, 77.32 umol) in DCM (2 mL) was added TFA (0.5 mL). The mixture was stirred at 25° C. for 1 hr. The reaction mixture was concentrated and purified by preparative HPLC using Method AI to afford the title compound (10.86 mg, 33%) as a yellow solid. $^1$H NMR (400 MHz, DMSO-d$_6$) δ 13.49 (br s, 1H), 10.78 (s, 1H), 8.91 (s, 1H), 8.69 (br s, 1H), 8.67 (br s, 1H), 8.05-8.13 (m, 2H), 8.00 (br s, 1H), 7.69-7.72 (m, 1H), 7.61-7.64 (m, 1H), 7.53 (br d, J=16.51 Hz, 1H), 7.45-7.50 (m, 1H), 2.57 (s, 3H), 2.48 (s, 3H). MS-ESI (m/z) calc'd for C$_{23}$H$_{19}$N$_6$O [M+H]$^+$: 395.2 Found 395.1.

Example 249: 5-Cyano-4-methoxy-N-(3-(oxazol-5-yl)-1H-indazol-5-yl)picolinamide

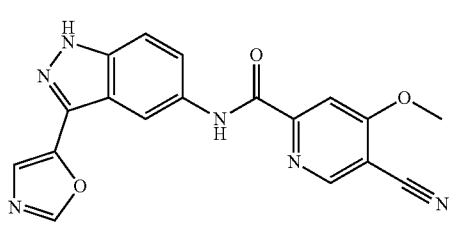 [SMILES: COc1cc(C(=O)Nc2ccc3[nH]nc(-c4cnco4)c3c2)ncc1C#N]

Step 1: 6-(1-Ethoxyvinyl)-4-methoxynicotinonitrile

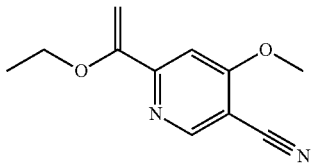

To a solution of 6-chloro-4-methoxynicotinonitrile (500 mg, 2.97 mmol) in dioxane (5 m L) was added tributyl(1-ethoxyvinyl)stannane (1.29 g, 3.56 mmol) and Pd(PPh$_3$)$_2$Cl$_2$ (208.18 mg, 296.59 umol). The mixture was stirred at 100° C. for 12 hrs under an N$_2$ atmosphere. The reaction mixture was concentrated and purified by flash silica gel chromatography (ISCO; 4 g SepaFlash column) using a 0-15% EtOAc/petroleum ether gradient eluent to afford the title compound (500 mg, 83%) as a light yellow solid. MS-ESI (m/z) calcd for C$_{11}$H$_{13}$N$_2$O$_2$ [M+H]$^+$: 205.1. Found 205.3.

Step 2: Ethyl 5-cyano-4-methoxypicolinate

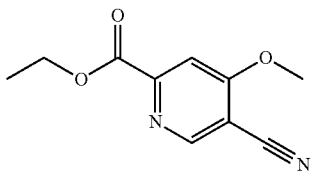

To a solution of 6-(1-ethoxyvinyl)-4-methoxynicotinonitrile (285 mg, 1.40 mmol) in dioxane (4 mL) was added NaIO$_4$ (596.98 mg, 2.79 mmol) in H$_2$O (2 mL) and KMnO$_4$ (33.08 mg, 209.33 umol). The mixture was stirred at 25° C. for 1 hr. The process was repeated using 200 mg of 6-(1-ethoxyvinyl)-4-methoxynicotinonitrile and the reaction mixtures were combined and filtered. The filtrate was diluted with saturated aqueous NaHCO$_3$ (10 mL) and extracted with EtOAc (5 mL×3). The combined organic layers were dried over Na$_2$SO$_4$, filtered and concentrated under reduced pressure to give a residue. The residue was purified by flash silica gel chromatography (ISCO; 10 g SepaFlash column) using a 0-30% EtOAc/petroleum ether gradient eluent to afford the title compound (150 mg, 52%) as a white solid. MS-ESI (m/z) calcd for C$_{10}$H$_{11}$N$_2$O$_3$[M+H]$^+$: 207.1. Found 207.0.

Step 3: 5-Cyano-4-methoxypicolinic acid

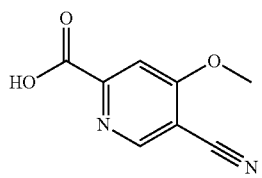

To a solution of ethyl 5-cyano-4-methoxypicolinate (100 mg, 484.97 umol) in THF (1 mL) and H$_2$O (1 mL) was added NaOH (23.28 mg, 581.97 umol) and the mixture was stirred at 20° C. for 0.5 hr. The reaction mixture was concentrated under reduced pressure to remove solvent. The residue obtained was diluted with H$_2$O (10 mL) and treated with 1 M HCl to adjust the pH to about 3. The formed solid was filtered and the solid was dried under reduced pressure to afford the title compound (70 mg) as a light yellow solid which was used without further purification. MS-ESI (m/z) calcd for C$_8$H$_7$N$_2$O$_3$[M−H]$^-$: 177.0. Found 177.0.

Step 4: 5-Cyano-4-methoxy-N-(3-(oxazol-5-yl)picolinamide

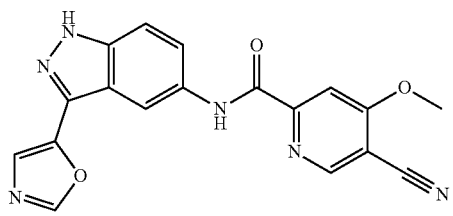 [SMILES: COc1cc(C(=O)Nc2ccc3[nH]nc(-c4cnco4)c3c2)ncc1C#N]

To a solution of 5-cyano-4-methoxypicolinic acid (70 mg, 392.94 umol) and 3-(oxazol-5-yl)-1H-indazol-5-amine (78.67 mg, 392.94 umol) in pyridine (1 mL) was added EDCI (150.65 mg, 785.88 umol) and the mixture was stirred at 20° C. for 12 hrs. The reaction mixture was concentrated under reduced pressure to remove solvent. The residue obtained was triturated in 5 mL of EtOAc and 1 mL of MeOH for 2 hrs and then the mixture was filtered and the solid was washed with EtOAc (3 mL×3). The solid was dried under reduced pressure to afford the title compound (49.92 mg, 32%) as a pale yellow solid. $^1$H NMR (400 MHz, DMSO-d$_6$) δ 13.51 (s, 1H) 10.90 (s, 1H) 9.00 (s, 1H) 8.71 (s, 1H) 8.57 (s, 1H) 7.89-8.02 (m, 2H) 7.55-7.70 (m, 2H) 4.15 (s, 3H). MS-ESI (m/z) calc'd for C$_{18}$H$_{13}$N$_6$O$_3$[M+H]$^+$: 361.1 Found 361.1.

Example 250: 5-Cyano-N-(3-(oxazol-5-yl)-1H-indazol-5-yl)-3-(prop-1-en-2-yl)picolinamide

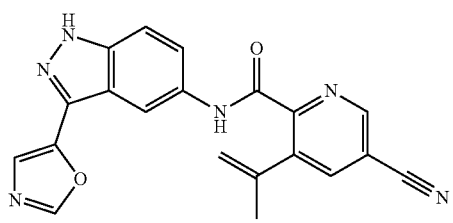 [SMILES: C=C(C)c1cc(C#N)cnc1C(=O)Nc1ccc2[nH]nc(-c3cnco3)c2c1]

Step 1: 6-Chloro-5-(prop-1-ent-2-yl)nicotinonitrile

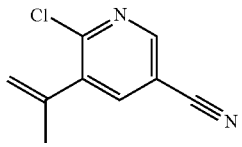

To a solution of 5-bromo-6-chloronicotinonitrile (1 g, 4.60 mmol) in EtOH (12 mL) and H$_2$O (3 mL) was added 4,4,5,5-tetramethyl-2-(prop-1-en-2-yl)-1,3,2-dioxaborolane (850.05 mg, 5.06 mmol), Pd(Amphos)Cl$_2$ (325.63 mg, 459.87 umol) and KOAc (1.35 g, 13.80 mmol) at 20° C. The mixture was stirred at 100° C. for 1.5 hrs under an N$_2$ atmosphere. The reaction mixture was concentrated and purified by flash silica gel chromatography (ISCO; 20 g SepaFlash column) using a 0-6% EtOAc/petroleum ether gradient eluent to afford the title compound (700 mg, 85%) as a pale yellow oil. MS-ESI (m/z) calcd for C$_9$H$_8$ClN$_2$ [M+H]$^+$: 179.0/181.0. Found 179.0/181.0.

Step 2: Methyl 5-cyano-3-(prop-1-en-2-yl)picolinate

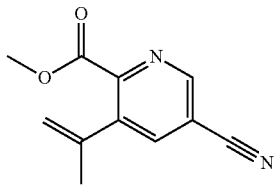

A mixture of 6-chloro-5-(prop-1-en-2-yl)nicotinonitrile (800 mg, 4.48 mmol), Pd(dppf)Cl$_2$ (327.72 mg, 447.88 umol), Et$_3$N (2.27 g, 22.39 mmol) in MeOH (10 mL) was degassed and purged with CO (3×) at 20° C., and then the mixture was stirred at 50° C. for 24 hrs under a CO atmosphere (30 psi). The reaction mixture was concentrated and purified by flash silica gel chromatography (ISCO; 20 g SepaFlash column) using a 0-9% EtOAc/petroleum ether gradient eluent to afford the title compound (430 mg, 47%) as a white oil. MS-ESI (m/z) calcd for C$_{11}$H$_{10}$N$_2$O$_2$ [M+H]$^+$: 203.1. Found 203.1.

Step 3: 5-Cyano-3-(prop-1-en-2-yl)picolinic acid

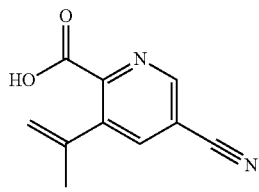

To a solution of methyl 5-cyano-3-(prop-1-en-2-yl)picolinate (30 mg, 148.36 umol) in THF (1 mL) and H$_2$O (0.5 mL) was added LiOH.H$_2$O (12.45 mg, 296.72 umol) and the mixture was stirred at 20° C. for 15 min. The reaction mixture was then adjusted to pH=3 with 2 N HCl and extracted with EtOAc (10 mL×3). The combined organic layers were dried over Na$_2$SO$_4$, filtered and concentrated under reduced pressure to afford the title compound (25 mg) as a white solid which was used without further purification. MS-ESI (m/z) calcd for C$_{10}$H$_9$N$_2$O$_2$ [M+H]$^+$: 189.1. Found 189.0.

Step 4: 5-Cyano-N-(3-(oxazol-5-yl)-1H-indazol-5-yl)-3-(prop-1-en-2-yl)picolinamide

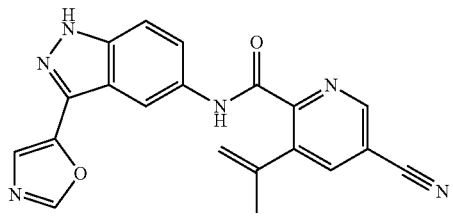 [SMILES: C=C(C)c1cc(C#N)cnc1C(=O)Nc1ccc2[nH]nc(-c3cnco3)c2c1]

To a solution of 5-cyano-3-(prop-1-en-2-yl)picolinic acid (25 mg, 132.85 umol) in pyridine (1 mL) was added EDCI (25.47 mg, 132.85 umol) and 3-(oxazol-5-yl)-1H-indazol-5-amine (26.60 mg, 132.85 umol) and the mixture was stirred at 20° C. for 12 hrs. The reaction mixture was concentrated and purified by preparative HPLC using Method AN to afford the title compound (5.45 mg, 8%) as a yellow solid TFA salt. $^1$H NMR (400 MHz, DMSO-d$_6$) δ 13.52 (s, 1H) 10.81 (s, 1H) 9.06 (d, J=1.47 Hz, 1H) 8.59 (s, 1H) 8.51 (s, 1H) 8.45 (d, J=1.47 Hz, 1H) 7.67-7.71 (m, 1H) 7.59-7.65 (m, 2H) 5.26 (s, 1H) 5.13 (s, 1H) 2.11 (s, 3H). MS-ESI (m/z) calc'd for C$_{20}$H$_{15}$N$_6$O$_2$ [M+H]$^+$: 371.1 Found 371.1.

Example 251: 5-Cyano-3-isopropyl-N-(3-(oxazol-5-yl)-1H-indazol-5-yl)picolinamide

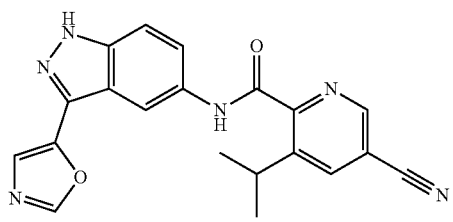 [SMILES: CC(C)c1cc(C#N)cnc1C(=O)Nc1ccc2[nH]nc(-c3cnco3)c2c1]

A mixture of 5-cyano-N-(3-(oxazol-5-yl)-1H-indazol-5-yl)-3-(prop-1-en-2-yl)picolinamide (100 mg, 270.00 umol), 10% Pd/C (100 mg) in EtOH (5 mL) was degassed and purged with H$_2$ (3×), and the mixture was stirred at 15° C. for 12 hrs under an H$_2$ atmosphere (15 psi). The reaction mixture was filtered and the filtrate was concentrated and purified by preparative HPLC using Method AO to afford the title compound (6.89 mg, 5%) as a white solid TFA salt. $^1$H NMR (400 MHz, DMSO-de) δ 13.53 (br s, 1H) 10.81 (s, 1H) 8.98 (s, 1H) 8.58 (br d, J=11.86 Hz, 3H) 7.72 (br d, J=8.68 Hz, 1H) 7.59-7.69 (m, 2H) 3.47-3.54 (m, 1H) 1.27 (br d, J=6.72 Hz, 6H). MS-ESI (m/z) calc'd for C$_{20}$H$_{17}$N$_6$O$_2$ [M+H]$^+$: 373.1 Found 373.1.

Example 252: 5-Cyano-3,4-dimethyl-N-(3-((1R)-2-phenylcyclopropyl)-1H-indazol-5-yl)picolinamide

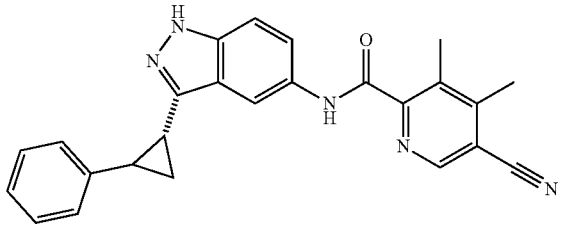

Step 1: 5-Nitro-3-((1R)-2-phenylcyclopropyl)-1-(tetrahydro-2H-pyran-2-yl)-1H-indazole

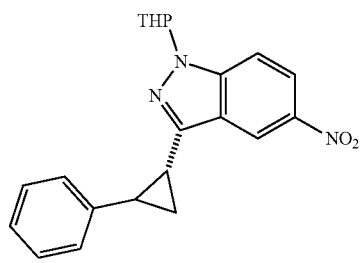

To a solution of 3-iodo-5-nitro-1-(tetrahydro-2H-pyran-2-yl)-1H-indazole (100 mg, 267.99 umol) in dioxane (2 mL) and H$_2$O (0.2 mL) was added 4,4,5,5-tetramethyl-2-((1R,2R)-2-phenylcyclopropyl)-1,3,2-dioxaborolane (65.43 mg, 267.99 umol), K$_2$CO$_3$ (111.11 mg, 803.98 umol) and Pd(dppf)Cl$_2$ (19.61 mg, 26.80 umol) at 20° C. The mixture was then stirred at 90° C. for 12 hrs under an N$_2$ atmosphere. The process was repeated using 100 mg of 3-iodo-5-nitro-1-(tetrahydro-2H-pyran-2-yl)-1H-indazole and the reaction mixtures were combined and concentrated. The material was purified by flash silica gel chromatography (ISCO; 25 g SepaFlash column) using a 0-8% EtOAc/petroleum ether gradient eluent to afford the title compound (60 mg, 80%) as a yellow solid. MS-ESI (m/z) calcd for C$_{21}$H$_{22}$N$_3$O$_3$ [M+H]$^+$: 364.2. Found 364.2.

Step 2: 3-((1R)-2-Phenylcyclopropyl)-1-(tetrahydro-2H-pyran-2-yl)-1H-indazol-5-amine

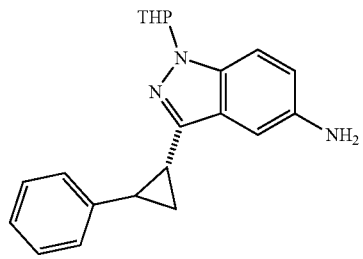

To a solution of 5-nitro-3-((1R)-2-phenylcyclopropyl)-1-(tetrahydro-2H-pyran-2-yl)-1H-indazole (60 mg, 165.10 umol) in EtOH (1 mL) and H$_2$O (0.5 mL) was added Fe (46.10 mg, 825.52 umol) and NH$_4$Cl (44.16 mg, 825.52 umol) at 20° C. and the mixture was stirred at 80° C. for 1 hr. The reaction mixture was concentrated under reduced pressure to remove solvent. The residue was diluted with saturated aqueous NaHCO$_3$ (10 mL) and extracted with EtOAc (2 mL 3). The combined organic layers were washed with brine (10 mL×1), dried over Na$_2$SO$_4$, filtered and concentrated under reduced pressure to afford the title compound (60 mg) as a brown oil which was used without further purification. MS-ESI (m/z) calcd for C$_{21}$H$_{24}$N$_3$O [M+H]$^+$: 334.2. Found 334.3.

Step 3: 5-Cyano-3,4-dimethyl-N-(3-((1R)-2-phenylcyclopropyl)-1-(tetrahydro-2H-pyran-2-yl)-1H-indazol-5-yl)picolinamide

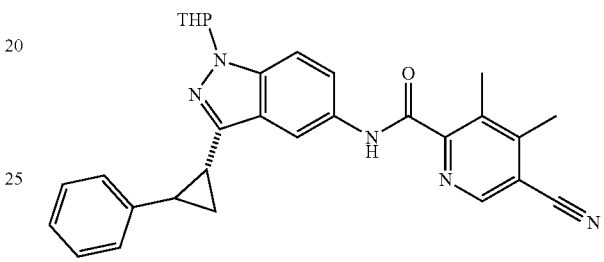

To a solution of 3-((1R)-2-phenylcyclopropyl)-1-(tetrahydro-2H-pyran-2-yl)-1H-indazol-5-amine (60 mg, 179.95 umol) in pyridine (1 mL) was added 5-cyano-3,4-dimethylpicolinic acid (31.70 mg, 179.95 umol) and EDCI (68.99 mg, 359.90 umol) at 20° C. and the mixture was stirred at 20° C. for 12 hrs. The reaction mixture was then concentrated under reduced pressure to remove solvent. The residue was diluted with H$_2$O (10 mL) and extracted with EtOAc (2 mL×3). The combined organic layers were washed with brine (5 mL), dried over Na$_2$SO$_4$, filtered and concentrated under reduced pressure to afford the title compound (100 mg) as a brown oil which was used without further purification. MS-ESI (m/z) calcd for C$_{30}$H$_3$ON$_5$O$_2$ [M+H]$^+$: 492.2. Found 492.2.

Step 4: 5-Cyano-3,4-dimethyl-N-(3-((1R)-2-phenylcyclopropyl)-1H-indazol-5-yl)picolinamide

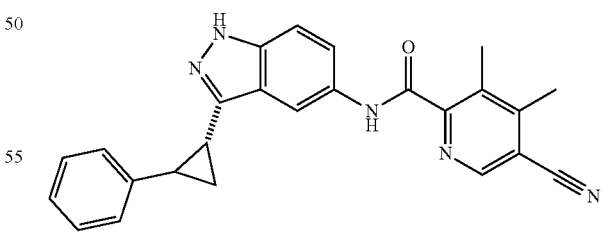

To a solution of 5-cyano-3,4-dimethyl-N-(3-((1R)-2-phenylcyclopropyl)-1-(tetrahydro-2H-pyran-2-yl)-1H-indazol-5-yl)picolinamide (100 mg, 203.42 umol) in MeOH (2 mL) and H$_2$O (0.4 mL) was added PTSA (175.15 mg, 1.02 mmol) and the mixture was stirred at 70° C. for 3 hrs. The process was repeated using 30 mg of 5-cyano-3,4-dimethyl-N-(3-((1R)-2-phenylcyclopropyl)-1-(tetrahydro-2H-pyran-2-yl)-1H-indazol-5-yl)picolinamide and the reaction mixtures were combined and concentrated under reduced pressure to remove solvent. The residue was purified by preparative HPLC using Method AP to afford the title compound (7 mg, 8%) as a light yellow solid. $^1$H NMR (400 MHz, CDCl$_3$) δ 10.06 (s, 1H) 9.69 (br s, 1H) 8.65 (s, 1H) 8.29 (s, 1H) 7.60 (dd, J=8.82, 1.67 Hz, 1H) 7.45 (d, J=8.82 Hz, 1H) 7.30-7.36 (m, 2H) 7.19-7.25 (m, 3H) 2.84 (s, 3H) 2.64 (s, 3H) 2.60 (dd, J=8.58, 5.48 Hz, 1H) 2.51-2.57 (m, 1H) 1.82 (dt, J=8.64, 5.33 Hz, 1H) 1.54 (br s, 1H). MS-ESI (m/z) calc'd for C$_{25}$H$_{22}$N$_6$O [M+H]$^+$: 408.2. Found 408.2.

Example 253: N-(3-(Azetidin-1-yl)-1H-indazol-5-yl)-5-cyano-3-methylpicolinamide

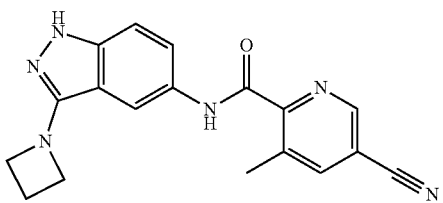 [SMILES: Cc1cc(C#N)cnc1C(=O)Nc1ccc2[nH]nc(N3CCC3)c2c1]

Step 1: 3-(Azetidin-1-yl)-5-nitro-1-(tetrahydro-2H-pyran-2-yl)-1H-indazole

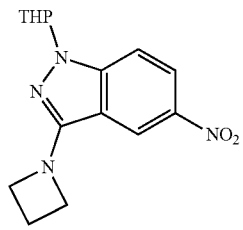

To a mixture of azetidine hydrochloride (752.16 mg, 8.04 mmol) in toluene (66 mL) was added Cs$_2$CO$_3$ (2.62 g, 8.04 mmol) and the mixture was stirred at 15° C. for 10 min. 3-Iodo-5-nitro-1-(tetrahydro-2H-pyran-2-yl)-1H-indazole (1 g, 2.68 mmol) was then added followed by BINAP (166.87 mg, 267.99 umol) and Pd$_2$(dba)$_3$ (245.40 mg, 267.99 umol). The mixture was degassed and purged with N$_2$ (3×), and stirred at 100° C. for 12 hrs under an N$_2$ atmosphere. The reaction was filtered and the filtrate was concentrated to give a residue. The residue was purified by flash silica gel chromatography (ISCO; 40 g SepaFlash column) using a 0-9% EtOAc/petroleum ether gradient eluent to afford the title compound (240 mg, 29%) as a yellow solid. MS-ESI (m/z) calcd for C$_{15}$H$_{18}$N$_4$O$_3$[M+H]$^+$: 303.1. Found 303.1.

Step 2: 3-(Azetidin-1-yl)-1-(tetrahydro-2H-pyran-2-yl)-1H-indazol-5-amine

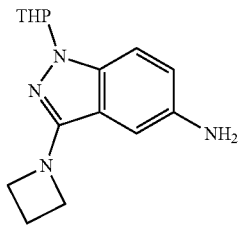

To a solution of 3-(azetidin-1-yl)-5-nitro-1-(tetrahydro-2H-pyran-2-yl)-1H-indazole (240 mg, 793.84 umol) in THF (15 mL) and H$_2$O (3 mL) was added Zn (519.09 mg, 7.94 mmol) and NH$_4$Cl (764.33 mg, 14.29 mmol) at 25° C. The mixture was stirred at 25° C. for 0.5 hr and then filtered. The filtrate was diluted with H$_2$O (40 mL) and extracted with EtOAc (30 mL×3). The combined organic phases were dried over Na$_2$SO$_4$ and concentrated to afford the title compound (190 mg) as a yellow oil which was used without further purification. MS-ESI (m/z) calcd for C$_{15}$H$_{21}$N$_4$O [M+H]$^+$: 273.2. Found 273.2.

Step 3: N-(3-(Azetidin-1-yl)-1-(tetrahydro-2H-pyran-2-yl)-1H-indazol-5-yl)-5-cyano-3-methylpicolinamide

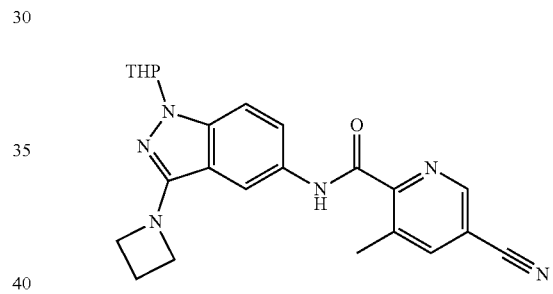

To a solution of 5-cyano-3-methylpicolinic acid (41.68 mg, 257.03 umol) in pyridine (3 mL) was added EDCI (73.91 mg, 385.54 umol) and 3-(azetidin-1-yl)-1-(tetrahydro-2H-pyran-2-yl)-1H-indazol-5-amine (70 mg, 257.03 umol) at 20° C. The mixture was stirred at 20° C. for 12 hrs and then concentrated. The mixture was diluted with H$_2$O (10 mL) and extracted with EtOAc (5 mL×4). The combined organic phases were dried over Na$_2$SO$_4$, filtered, and the filtrate was concentrated under vacuum to afford the title compound (95 mg) as a brown solid which was used without further purification. MS-ESI (m/z) calcd for C$_{23}$H$_{25}$N$_6$O$_2$ [M+H]$^+$: 417.2. Found 417.2.

Step 4: N-(3-(Azetidin-1-yl)-1H-indazol-5-yl)-5-cyano-3-methylpicolinamide

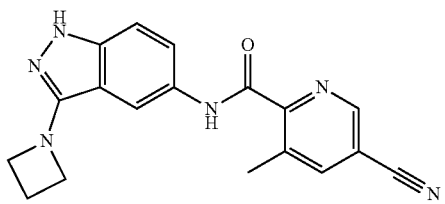 [SMILES: Cc1cc(C#N)cnc1C(=O)Nc1ccc2[nH]nc(N3CCC3)c2c1]

A solution of N-(3-(azetidin-1-yl)-1-(tetrahydro-2H-pyran-2-yl)-1H-indazol-5-yl)-5-cyano-3-methylpicolinamide (95 mg, 228.11 umol) in TFA (0.8 mL) and DCM (3 mL) was stirred at 20° C. for 6 hrs. The reaction was filtered and the filtrate was concentrated. The material was purified by preparative HPLC using Method AQ to give material of insufficient purity. The material was then further purified by preparative HPLC using Method AR to afford the title compound (6.47 mg, 6%, TFA salt) as a yellow solid. $^1$H NMR (400 MHz, DMSO-$d_6$) δ 11.79 (s, 1H), 10.59 (s, 1H), 8.97 (s, 1H), 8.39 (s, 1H), 8.07 (s, 1H), 7.63 (dd, J=8.93, 1.87 Hz, 1H), 7.29 (d, J=9.04 Hz, 1H), 4.03 (t, J=7.28 Hz, 4H), 2.57 (s, 3H), 2.38 (quin, J=7.22 Hz, 2H). MS-ESI (m/z) calc'd for $C_{18}H_{17}N_6O$ [M+H]$^+$: 333.1. Found 333.2.

Example 254: 5-Cyano-N-(3-(3,3-difluoroazetidin-1-yl)-1H-indazol-5-yl)-3-methylpicolinamide

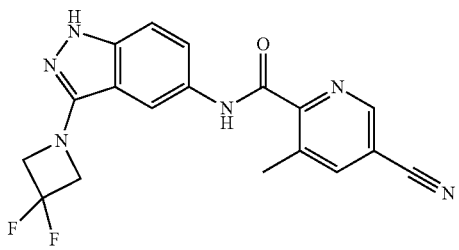 [SMILES: Cc1cc(C#N)cnc1C(=O)Nc1ccc2[nH]nc(N3CC(F)(F)C3)c2c1]

Step 1: 3-(3,3-Difluoroazetidin-1-yl)-5-nitro-1-(tetrahydro-2H-pyran-2-yl)-1H-indazole

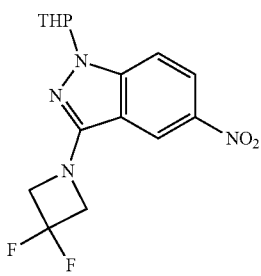

A mixture of 3-iodo-5-nitro-1-(tetrahydro-2H-pyran-2-yl)-1H-indazole (260 mg, 696.78 umol), 3,3-difluoroazetidine hydrochloride (270.77 mg, 2.09 mmol), t-BuONa (334.80 mg, 3.48 mmol), t-BuXPhos-Pd-G3 (44.21 mg, 48.77 umol) in toluene (20 mL) was degassed and purged with $N_2$ (3×), and then the mixture was stirred at 110° C. for 12 hrs under an $N_2$ atmosphere. The process was repeated with an additional 50 mg of 3-iodo-5-nitro-1-(tetrahydro-2H-pyran-2-yl)-1H-indazole and the reaction mixtures were combined and concentrated. The material was purified by flash silica gel chromatography (ISCO; 12 g SepaFlash column) using a 0-9% EtOAc/petroleum ether gradient eluent to afford the title compound (145 mg, 62%) as a yellow solid. MS-ESI (m/z) calcd for $C_{15}H_{17}F_2N_4O_3$ [M+H]$^+$: 339.1. Found 339.0.

Step 2: 5-Cyano-N-(3-(3,3-difluoroazetidin-1-yl)-1H-indazol-5-yl)-3-methylpicolinamide

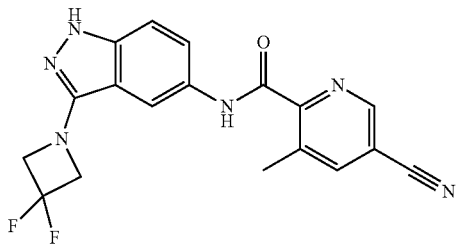 [SMILES: Cc1cc(C#N)cnc1C(=O)Nc1ccc2[nH]nc(N3CC(F)(F)C3)c2c1]

Prepared as described for N-(3-(azetidin-1-yl)-1H-indazol-5-yl)-5-cyano-3-methylpicolinamide using 3-(3,3-difluoroazetidin-1-yl)-5-nitro-1-(tetrahydro-2H-pyran-2-yl)-1H-indazole in place of 3-(azetidin-1-yl)-5-nitro-1-(tetrahydro-2H-pyran-2-yl)-1H-indazole. $^1$H NMR (400 MHz, DMSO-$d_6$) δ 12.13 (s, 1H), 10.65 (s, 1H), 8.99 (d, J=1.43 Hz, 1H), 8.40 (d, J=1.07 Hz, 1H), 8.06 (s, 1H), 7.69 (dd, J=1.79, 9.06 Hz, 1H), 7.37 (d, J=8.94 Hz, 1H), 4.49 (t, J=12.58 Hz, 4H), 2.58 (s, 3H). MS-ESI (m/z) calc'd for $C_{18}H_{15}F_2N_6O$ [M+H]$^+$: 369.1 Found 369.2.

Example 255: N-(3-(Benzyloxy)-1H-indazol-5-yl)-5-cyano-3-methylpicolinamide

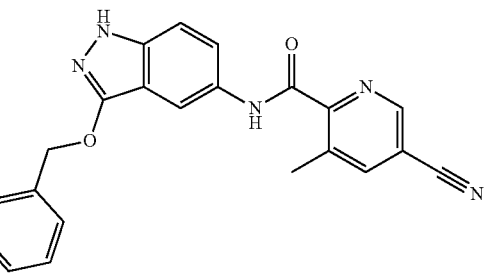

Step 1: 5-Nitro-1H-indazol-3-ol

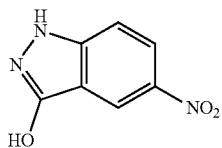 [SMILES: O=[N+]([O-])c1ccc2[nH]nc(O)c2c1]

To a solution of methyl 2-bromo-5-nitrobenzoate (1 g, 3.85 mmol) in EtOH (1.5 mL) was added $NH_2NH_2 \cdot H_2O$ (1.96 g, 38.46 mmol) at 25° C., and the mixture was stirred at 90° C. for 2 hrs. HCl (1 M, 20 mL) was added dropwise until a solid formed, then the mixture was filtered and the solid was dried under vacuum to afford the title compound (533 mg, 77%) as a brown solid, which was used without further purification. MS-ESI (m/z) calcd for $C_7H_6N_3O_3$ [M+H]$^+$: 180.0. Found 180.3.

Step 2: Ethyl 3-hydroxy-5-nitro-1H-indazole-1-carboxylate

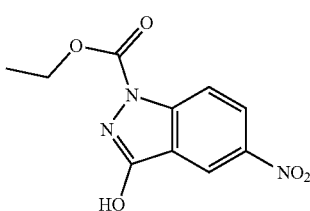 [SMILES: CCOC(=O)n1nc(O)c2cc([N+](=O)[O-])ccc21]

To a solution of 5-nitro-1H-indazol-3-ol (500 mg, 2.79 mmol) in pyridine (3 mL) was added ethyl chloroformate (348.35 mg, 3.21 mmol) at 25° C. The mixture was stirred at 70° C. for 5 hrs. Additional ethyl chloroformate (181.75 mg, 1.67 mmol) was added and stirring was continued at 70° C. for 2.5 hrs. The reaction was poured into $H_2O$ (10 mL) and extracted with EtOAc (10 mL×3). The organic layer was dried over $Na_2SO_4$, filtered and the filtrate was concentrated to give a residue. The residue was washed with EtOAc (8 mL) and filtered and the solid was dried under vacuum to afford the title compound (336 mg, 46%) as a light yellow solid, which was used without further purification. MS-ESI (m/z) calcd for $C_{10}H_{10}N_3O_5$ [M+H]$^+$: 252.1. Found 252.0.

Step 3: 3-(Benzyloxy)-5-nitro-1H-indazole

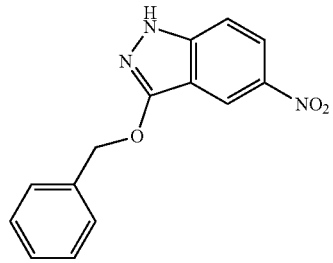 [SMILES: O=[N+]([O-])c1ccc2[nH]nc(OCc3ccccc3)c2c1]

To a solution of ethyl 3-hydroxy-5-nitro-1H-indazole-1-carboxylate (50 mg, 199.05 umol) and $K_2CO_3$ (68.77 mg, 497.62 umol) in acetone (2 mL) was added (bromomethyl)benzene (37.45 mg, 218.95 umol) at 20° C. The mixture was stirred at 70° C. for 12 hrs and then concentrated to give a residue. The residue was washed with MeOH (2 mL), and filtered. The filtrate was purified by preparative TLC (silica gel, petroleum ether/EtOAc=3/1, Rt=0.35) to afford the title compound (19 mg, 35%) as a yellow solid. MS-ESI (m/z) calcd for $C_{14}H_{11}N_3O_3$ [M+H]$^+$: 270.1. Found 270.3.

Step 4: 3-(Benzyloxy)-1H-indazol-5-amine

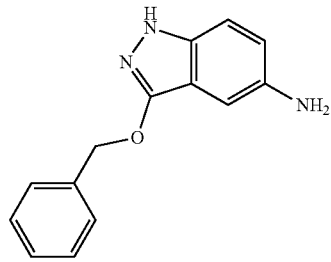 [SMILES: Nc1ccc2[nH]nc(OCc3ccccc3)c2c1]

To a solution of 3-(benzyloxy)-5-nitro-1H-indazole (19 mg, 70.57 umol) in EtOH (2 mL) and $H_2O$ (0.5 mL) was added Fe (19.70 mg, 352.83 umol) and $NH_4Cl$ (18.87 mg, 352.83 umol), then the mixture was stirred at 80° C. for 1 hr. The reaction was filtered and the filtrate was concentrated under vacuum to afford the title compound (30 mg) as a brown liquid, which was used without further purification. MS-ESI (m/z) calcd for $C_{14}H_{14}N_3O$ [M+H]$^+$: 240.1. Found 240.4.

Step 5: N-(3-(Benzyloxy)-1H-indazol-5-yl)-5-cyano-3-methylpicolinamide

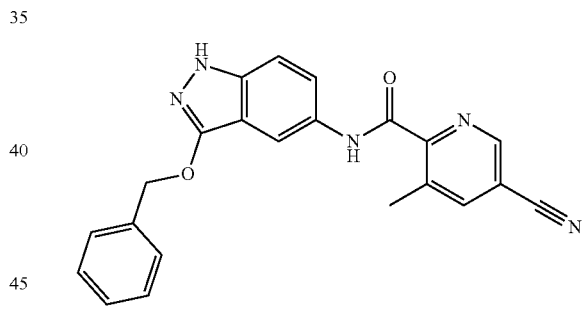

To a solution of 3-(benzyloxy)-1H-indazol-5-amine (30 mg, 125.38 umol) and 5-cyano-3-methylpicolinic acid (24.40 mg, 150.46 umol) in pyridine (1 mL) was added EDCI (36.05 mg, 188.07 umol) at 20° C. and the mixture was stirred at 20° C. for 2 hrs. The reaction mixture was then concentrated to give a residue. The residue was purified by preparative HPLC using Method AS to afford the title compound (3.83 mg, 8%) as a pale yellow solid. $^1$H NMR (400 MHz, DMSO-$d_6$) δ 11.95 (s, 1H) 10.68 (s, 1H) 8.98 (s, 1H) 8.39 (s, 1H) 8.24 (s, 1H) 7.61 (dd, J=9.04, 1.98 Hz, 1H) 7.53 (d, J=7.28 Hz, 2H) 7.32-7.44 (m, 4H) 5.40 (s, 2H) 2.56 (s, 3H). MS-ESI (m/z) calc'd for $C_{22}H_{18}N_5O_2$ [M+H]$^+$: 384.1 Found 384.2.

Example 256: 5-Cyano-3-methyl-N-(3-(oxetan-3-yl)-1H-indazol-5-yl)picolinamide

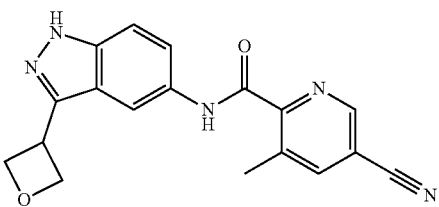 [SMILES: Cc1cc(C#N)cnc1C(=O)Nc1ccc2[nH]nc(C3COC3)c2c1]

Step 1: 3-Iodo-5-nitro-1H-indazole

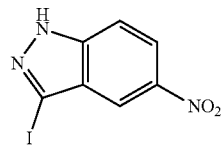

To a solution of 5-nitro-1H-indazole (2 g, 12.26 mmol) in DMF (20 mL) was added KOH (2.61 g, 46.59 mmol) and $I_2$ (6.22 g, 24.52 mmol) at 25° C. The mixture was stirred at 65° C. for 2 hrs and then poured into saturated aqueous $Na_2SO_3$ (200 mL). A yellow solid formed that was filtered, washed with $H_2O$ (100 mL×2), and dried under vacuum to afford the title compound (3.86 g) as a brown solid which was used without further purification.

Step 2: 3-Iodo-5-nitro-1-(tetrahydro-2H-pyran-2-yl)-1H-indazole

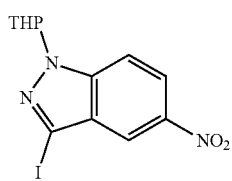

To a solution of 3-iodo-5-nitro-1H-indazole (3.8 g, 13.15 mmol) in $CHCl_3$ (40 mL) was added MsOH (126.35 mg, 1.31 mmol) and 3,4-dihydro-2H-pyran (1.69 g, 20.03 mmol) at 25° C. The mixture was stirred at 80° C. for 12 hrs and then concentrated to afford a residue. The residue was purified by flash silica gel chromatography (ISCO; 25 g SepaFlash column) using a 0-10% EtOAc/petroleum ether gradient eluent to afford the title compound (2.7 g, 55%) as a yellow solid.

Step 3: 5-Nitro-3-(oxetan-3-yl)-1-(tetrahydro-2H-pyran-2-yl)-1H-indazole

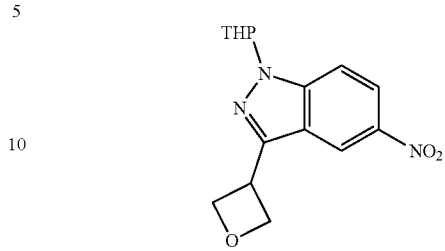

A mixture of 3-iodo-5-nitro-1-(tetrahydro-2H-pyran-2-yl)-1H-indazole (400 mg, 1.07 mmol), 3-iodooxetane (394.43 mg, 2.14 mmol), $Na_2CO_3$ (227.23 mg, 2.14 mmol), [Ir(dF(Me)ppy)$_2$(dtbbpy)]PF$_6$ (10.87 mg, 10.72 umol) and NiCl$_2$ glyme (1.18 mg, 5.36 umol), 4,4'-di-tert-butyl-2,2'-dipyridyl (1.44 mg, 5.36 umol) tris(trimethylsilyl)silane (266.56 mg, 1.07 mmol) in DME (8 mL) was degassed and purged with $N_2$ (3×), and then the mixture was stirred at 25° C. for 12 hrs under an Ar atmosphere while shining a 34 Watt, KessilWide Angle blue LED Grow Light. For similar conditions, see: Zhang, P., Le, C., MacMillian D. W. C. Silyl Radical Activation of Alkyl Halides in Metallaphotoredox Cataylis: A Unique Pathway for Cross-Electrophile Coupling. *J Am. Chem. Soc.*, 2016, 138, 8084-8087. The reaction mixture was concentrated and purified by flash silica gel chromatography (ISCO; 40 g SepaFlash column) using a 0-20% EtOAc/petroleum ether gradient eluent to afford the title compound (220 mg, 7%) as an orange solid. MS-ESI (m/z) calcd for $C_{19}H_{18}N_3O_4[M+H]^+$: 304.1. Found 304.2

Step 4: 3-(Oxetan-3-yl)-1-(tetrahydro-2H-pyran-2-yl)-1H-indazol-5-amine

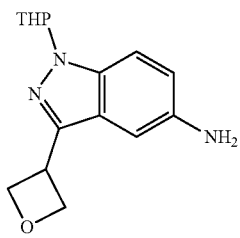

To a solution of 5-nitro-3-(oxetan-3-yl)-1-(tetrahydro-2H-pyran-2-yl)-1H-indazole (80 mg, 263.75 umol) in $H_2O$ (1 mL) and THF (5 mL) was added NH$_4$Cl (253.95 mg, 4.75 mmol) and Zn (172.47 mg, 2.64 mmol) at 20° C. and the mixture was stirred for 0.5 hr. The reaction mixture was then filtered and the filtrate was diluted with $H_2O$ (10 mL) and extracted with EtOAc (5 mL×4). The combined organic layers were dried over $Na_2SO_4$, filtered and concentrated to afford the title compound (87 mg) as a brown gum which was used without further purification. MS-ESI (m/z) calcd for $C_{19}H_{20}N_3O_2[M+H]^+$: 274.2. Found 274.1

Step 5: 5-Cyano-3-methyl-N-(3-(oxetan-3-yl)-1-(tetrahydro-2H-pyran-2-yl)-1H-indazol-5-yl)picolinamide

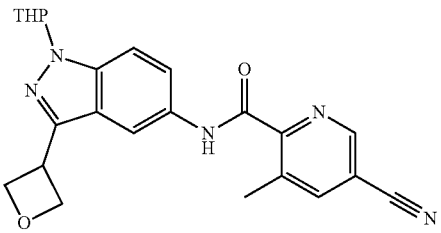

To a solution of 5-cyano-3-methylpicolinic acid (40 mg, 246.69 umol) in pyridine (3 mL) was added EDCI (70.94 mg, 370.04 umol) and 3-(oxetan-3-yl)-1-(tetrahydro-2H-pyran-2-yl)-1H-indazol-5-amine (67.43 mg, 246.69 umol). The mixture was stirred at 20° C. for 12 hrs and then concentrated to give a residue. The residue was diluted with H$_2$O (6 mL) and extracted with EtOAc (4 mL×3). The combined organic layers were dried over Na$_2$SO$_4$, filtered and concentrated to afford the title compound (100 mg) as a brown gum which was used without further purification. MS-ESI (m/z) calcd for C$_{23}$H$_{24}$N$_5$O; [M+H]$^+$: 418.2. Found 418.1

Step 6: 5-Cyano-3-methyl-N-(3-(oxetan-3-yl)-1H-indazol-5-yl)picolinamide

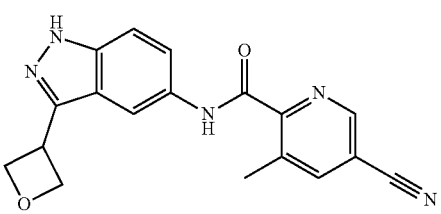 [SMILES: Cc1cc(C#N)cnc1C(=O)Nc1ccc2[nH]nc(C3COC3)c2c1]

To a solution of 5-cyano-3-methyl-N-(3-(oxetan-3-yl)-1-(tetrahydro-2H-pyran-2-yl)-1H-indazol-5-yl)picolinamide (50 mg, 119.77 umol) in DCM (3 mL) was added TFA (0.5 mL). The mixture was stirred at 15° C. for 12 hrs and then concentrated to give a residue. The residue was purified by preparative HPLC using Method AT to afford the title compound (6.22 mg, 15%) as a pale yellow solid. $^1$H NMR (400 MHz, DMSO-d$_6$) δ 12.88 (br s, 1H) 10.69 (s, 1H) 8.97 (s, 1H) 8.36 (d, J=17 Hz, 2H) 7.67 (d, J=9 Hz, 1H) 7.49 (d, J=9 Hz, 1H) 5.02 (dd, J=8, 6 Hz, 2H) 4.90 (t, J=6 Hz, 2H) 4.56-4.65 (m, 1H) 2.56 (s, 3H). MS-ESI (m/z) calc'd for C$_{18}$H$_{16}$N$_5$O$_2$ [M+H]$^+$: 334.1 Found 334.2.

Example 257: 5-Cyano-N-(3-(2,2-dimethylcyclopropyl)-1H-indazol-5-yl)-3,4-dimethylpicolinamide

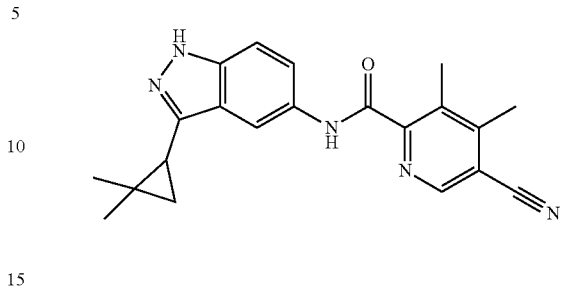

Step 1: 3-(2,2-Dimethylcyclopropyl)-5-nitro-1-(tetrahydro-2H-pyran-2-yl)-1H-indazole

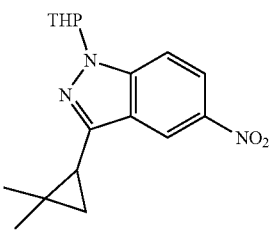

To a solution of 3-iodo-5-nitro-1-(tetrahydro-2H-pyran-2-yl)-1H-indazole (50 mg, 134.00 umol) in H$_2$O (0.5 mL) and tert-amyl alcohol (1.5 mL) was added 2-(2,2-dimethylcyclopropyl)-4,4,5,5-tetramethyl-1,3,2-dioxaborolane (26.28 mg, 134.00 umol), Cs$_2$CO$_3$ (87.32 mg, 267.99 umol) and cataCXium A-Pd-G2 (8.96 mg, 13.40 umol) at 20° C. and then the mixture was stirred at 70° C. for 12 hrs under an N$_2$ atmosphere. The reaction mixture was concentrated and purified by preparative TLC (SiO$_2$, petroleum ether/EtOAc=5/1, R$_f$=0.61) to afford the title compound (30 mg, 71%) as a yellow solid. MS-ESI (m/z) calcd for C$_{17}$H$_{22}$N$_3$O$_3$ [M+H]$^+$: 316.2. Found 316.2.

Step 2: 3-(2,2-Dimethylyclopropyl)-1-(tetrahydro-2H-pyran-2-yl)-1H-indazol-5-amine

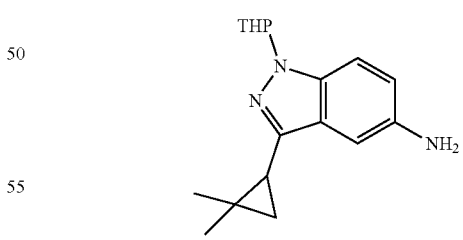

To a solution of 3-(2,2-dimethylcyclopropyl)-5-nitro-1-(tetrahydro-2H-pyran-2-yl)-1H-indazole (10 mg, 31.71 umol) in EtOH (1 mL) and H$_2$O (0.5 mL) was added Fe (17.71 mg, 317.09 umol) and NH$_4$Cl (16.96 mg, 317.09 umol) at 20° C. Then the mixture was stirred at 80° C. for 1 hr and concentrated to afford a residue. The residue was diluted with saturated aqueous NaHCO$_3$ (5 mL) and extracted with EtOAc (2 mL×3). The combined organic layers were washed with brine (5 mL), dried over Na$_2$SO$_4$, filtered and concentrated under reduced pressure to afford the title compound (20 mg) as a brown solid which was used without further purification. MS-ESI (m/z) calcd for $C_{17}H_{24}N_3O$ [M+H]$^+$: 286.2. Found 286.3.

Step 3: 5-Cyano-N-(3-(2,2-dimethylcyclopropyl)-1-(tetrahydro-2H-pyran-2-yl)-1H-indazol-5-yl)-3,4-dimethylpicolinamide

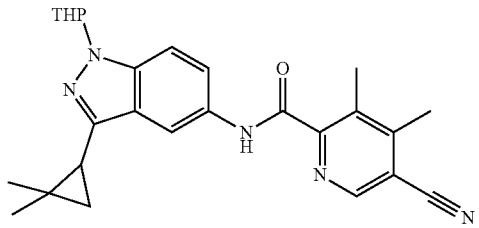

To a solution of 3-(2,2-dimethylcyclopropyl)-1-(tetrahydro-2H-pyran-2-yl)-1H-indazol-5-amine (20 mg, 70.08 umol) in pyridine (1 mL) was added 5-cyano-3,4-dimethylpicolinic acid (12.35 mg, 70.08 umol) and EDCI (26.87 mg, 140.16 umol) at 20° C. Then the mixture was stirred at 20° C. for 12 hrs and then concentrated. The residue was diluted with H$_2$O (10 mL) and extracted with EtOAc (2 mL×3). The combined organic layers were washed with brine (10 mL), dried over Na$_2$SO$_4$, filtered and concentrated under reduced pressure to afford the title compound (40 mg) as a brown solid which was used without further purification. MS-ESI (m/z) calcd for $C_{26}H_{30}N_5O_2$ [M+H]$^+$: 444.2. Found 444.3.

Step 4: 5-Cyano-N-(3-(2,2-dimethylcyclopropyl)-1H-indazol-5-yl)-3,4-dimethylpicolinamide

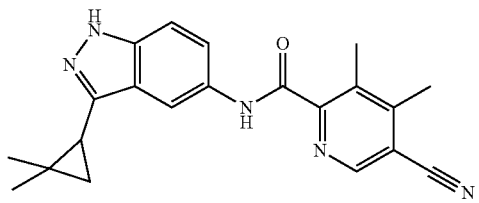 [SMILES: Cc1c(C#N)cnc(C(=O)Nc2ccc3[nH]nc(C4CC4(C)C)c3c2)c1C]

To a solution of 5-cyano-N-(3-(2,2-dimethylcyclopropyl)-1-(tetrahydro-2H-pyran-2-yl)-1H-indazol-5-yl)-3,4-dimethylpicolinamide (40 mg, 90.18 umol) in MeOH (1 mL) and H$_2$O (0.2 mL) was added PTSA (77.65 mg, 450.92 umol) at 20° C. The mixture was stirred at 70° C. for 3 hrs and concentrated. The residue was purified by preparative HPLC using Method AP to afford the title compound (10.41 mg, 21%) as a pale yellow solid. $^1$H NMR (400 MHz, CDCl$_3$) δ 10.05 (br s, 1H), 8.66 (s, 1H), 8.23 (s, 1H), 7.60 (dd, J=1.6, 8.8 Hz, 1H), 7.43 (d, J=8.8 Hz, 1H), 2.86 (s, 3H), 2.64 (s, 3H), 2.07 (dd, J=5.7, 8.5 Hz, 1H), 1.35 (s, 3H), 1.28 (t, J=5.0 Hz, 1H), 0.99 (dd, J=4.3, 8.5 Hz, 1H), 0.92 (s, 3H). MS-ESI (m/z) calc'd for $C_{21}H_{22}N_5O$ [M+H]$^+$: 360.2 Found 360.2.

Example 258: 5-Cyano-4-methoxy-6-methyl-N-(3-(oxazol-5-yl)-1H-indazol-5-yl)picolinamide

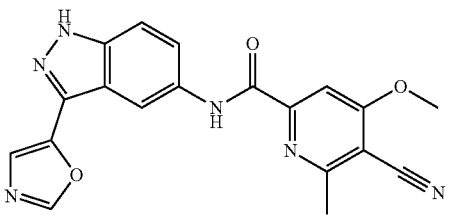 [SMILES: COc1cc(C(=O)Nc2ccc3[nH]nc(-c4cnco4)c3c2)nc(C)c1C#N]

Step 1: 4-Hydroxy-2-methyl-6-oxo-1,6-dihydropyridine-3-carbonitrile

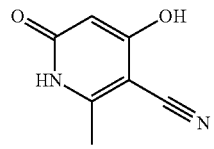

To a solution of bis(2,4,6-trichlorophenyl) malonate (3 g, 6.48 mmol) in chlorobenzene (30 mL) was added 3-aminobut-2-enenitrile (532.08 mg, 6.48 mmol) and the mixture was stirred at 130° C. for 3 hrs. The reaction mixture was then filtered and the solid was washed with toluene (5 mL) and petroleum ether (5 mL). The solid was dried to afford the title compound (540 mg) as a brown solid, which was used without further purification. MS-ESI (m/z) calcd for $C_7H_7N_2O_2$ [M+H]$^+$: 151.0. Found 151.1.

Step 2: 4,6-Dichloro-2-methylnicotinonitrile

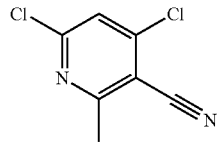

A mixture of 4-hydroxy-2-methyl-6-oxo-1,6-dihydropyridine-3-carbonitrile (540 mg, 3.60 mmol), benzyltriethylammonium chloride (1.64 g, 7.19 mmol) and POCl$_3$ (1.10 g, 7.19 mmol, 668.48 uL) in MeCN (7 mL) was degassed and purged with N$_2$ (3×) at 25° C., and then stirred at 80° C. for 12 hrs under an N$_2$ atmosphere. The reaction mixture was concentrated and quenched by the addition of 10 g of ice water. The mixture was further diluted with H$_2$O (8 mL) and adjusted to pH=7 with saturated aqueous NaHCO$_3$ and extracted with EtOAc (8 mL×3). The combined organic phases were washed with brine (8 mL×1), dried over Na$_2$SO$_4$, filtered and concentrated to afford the title compound (738 mg) as a brown solid, which was used without further purification.

Step 3: 6-Chloro-4-methoxy-2-methyl-1,6-dihydro-pyridine-3-carbonitrile

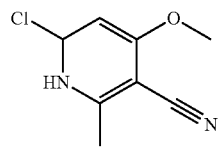

To a solution of 4,6-dichloro-2-methylnicotinonitrile (638 mg, 3.13 mmol) in MeOH (8 mL) was added MeONa (169.36 mg, 3.13 mmol). The mixture was stirred at 20° C. for 16 hrs and then concentrated to give a residue. The residue was diluted with water (8 mL) and extracted with dichloromethane (8 mL×3). The combined organic phases were washed with brine (8 mL×1), dried over $Na_2SO_4$, filtered and concentrated. The material was purified by silica gel column chromatography using a 0-20% EtOAc/petroleum ether gradient eluent to afford the title compound (190 mg, 33%) as a white solid. MS-ESI (m/z) calcd for $C_8H_8ClN_2O$ [M+H]$^+$: 183.0/185.0 Found 183.1/185.1.

Step 4: Methyl 5-cyano-4-methoxy-6-methyl-1,2-dihydropyridine-2-carboxylate

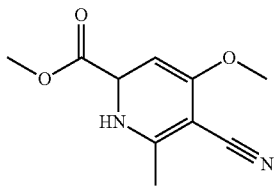

To a solution of 6-chloro-4-methoxy-2-methyl-1,6-dihydropyridine-3-carbonitrile (190 mg, 1.04 mmol) in MeOH (5 mL) was added Pd(dppf)Cl$_2$ (76.13 mg, 104.05 umol) and Et3N (315.86 mg, 3.12 mmol, 434.47 uL) under an N$_2$ atmosphere. The resulting suspension was degassed and purged with CO (3×). The mixture was then stirred under CO (50 psi) at 80° C. for 12 hrs. The mixture was then filtered and the filtrate was concentrated to afford a residue. The residue was purified by preparative TLC (SiO$_2$, petroleum ether/EtOAc=1/1, R$_f$=0.40) to afford the title compound (151 mg, 70%) as a white solid. MS-ESI (m/z) calcd for $C_{10}H_{11}N_2O_3$ [M+H]$^+$: 207.1 Found 207.2.

Step 5: 5-Cyano-4-methoxy-6-methyl-1,2-dihydropyridine-2-carboxylic acid

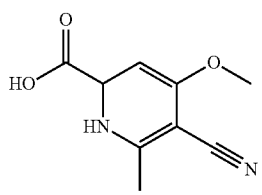

To a solution of methyl 5-cyano-4-methoxy-6-methyl-1,2-dihydropyridine-2-carboxylate (170 mg, 824.45 umol) in THF (2 mL) and H$_2$O (2 mL) was added LiOH.H$_2$O (69.19 mg, 1.65 mmol) and the mixture was stirred at 40° C. for 2 hrs. The reaction mixture was then concentrated and adjusted to pH=3 with 1 N HCl and extracted with EtOAc (4 mL×3). The combined organic phases were washed with brine (4 mL×1), dried over Na$_2$SO$_4$, filtered and concentrated to afford the title compound (98 mg) as a white solid, which was used without further purification. MS-ESI (m/z) calcd for $C_9H_9N_2O_3$ [M+H]$^+$: 193.1. Found 193.1.

Step 6: 5-Cyano-4-methoxy-6-methyl-N-(3-(oxazol-5-yl)-1H-indazol-5-yl)picolinamide

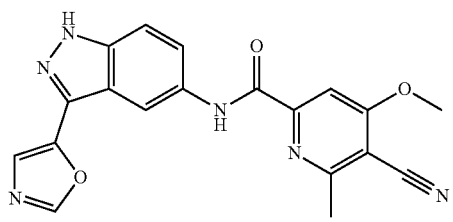 [SMILES: COc1cc(C(=O)Nc2ccc3[nH]nc(-c4cnco4)c3c2)nc(C)c1C#N]

To a solution of 5-cyano-4-methoxy-6-methyl-1,2-dihydropyridine-2-carboxylic acid (50 mg, 260.18 umol) in pyridine (3 mL) was added EDCI (99.76 mg, 520.37 umol) and 3-(oxazol-5-yl)-1H-indazol-5-amine (52.09 mg, 260.18 umol). The mixture was stirred at 20° C. for 2 hrs and then concentrated to afford a residue. The residue was purified by preparative HPLC using Method AU to afford the title compound (7.79 mg, 6%) as a pale yellow solid TFA salt. $^1$H NMR (400 MHz, DMSO-d$_6$) δ 13.54 (s, 1H), 10.72 (s, 1H), 8.65 (s, 1H), 8.58 (s, 1H), 7.93 (d, J=7.7 Hz, 1H), 7.80 (s, 1H), 7.69 (s, 1H), 7.65 (d, J=9.0 Hz, 1H), 4.12 (s, 3H), 2.77 (s, 3H). MS-ESI (m/z) calc'd for $C_{19}H_{15}N_6O_3$ [M+H]$^+$: 375.1 Found 375.1.

Example 259: tert-butyl 4-((5-(5-Cyano-3,4-dimethylpicolinamido)-1H-indazol-3-yl)methylene)piperidine-1-carboxylate

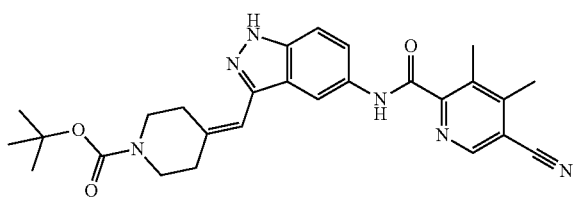 [SMILES: Cc1c(C#N)cnc(C(=O)Nc2ccc3[nH]nc(C=C4CCN(C(=O)OC(C)(C)C)CC4)c3c2)c1C]

Step 1: 3-Iodo-1H-indazol-5-amine

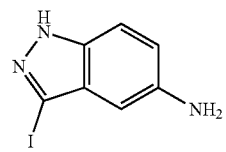

To a solution of 3-iodo-5-nitro-1H-indazole (1 g, 3.46 mmol) in H$_2$O (8 mL) and EtOH (24 mL) was added Fe (966.08 mg, 17.30 mmol) and NH₄Cl (925.36 mg, 17.30 mmol) and the mixture was stirred at 80° C. for 0.5 hr. The reaction was then filtered and the filtrate was concentrated to afford a residue. The residue was diluted with H₂O (30 mL) and extracted with EtOAc (20 mL×3). The combined organic phases were dried with Na₂SO₄, filtered, and the filtrate was concentrated to afford the title compound (850 mg) as a yellow solid which was used without further purification. MS-ESI (m/z) calcd for C₇H₇IN₃ [M+H]⁺: 259.9. Found 259.9.

Step 2: 5-Cyano-N-(3-iodo-1H-indazol-5-yl)-3,4-dimethylpicolinamide

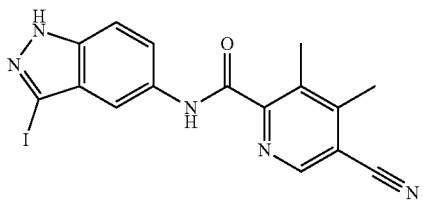 [SMILES: Cc1c(C#N)cnc(C(=O)Nc2ccc3[nH]nc(I)c3c2)c1C]

To a solution of 3-iodo-1H-indazol-5-amine (850 mg, 3.28 mmol) and 5-cyano-3,4-dimethylpicolinic acid (578.07 mg, 3.28 mmol) in pyridine (25 mL) was added EDCI (943.54 mg, 4.92 mmol). The mixture was stirred at 25° C. for 12 hrs and then concentrated to afford a residue. The residue was diluted with H₂O (10 mL) and filtered. The solid was dried under vacuum to afford the title compound (1.2 g) as a yellow solid which was used without further purification. MS-ESI (m/z) calcd for C₁₆H₁₃IN₅O [M+H]⁺: 418.0. Found 418.0.

Step 3: tert-butyl 4-((5-(5-Cyano-3,4-dimethylpicolinamido)-1H-indazol-3-yl)methylene)piperidine-1-carboxylate

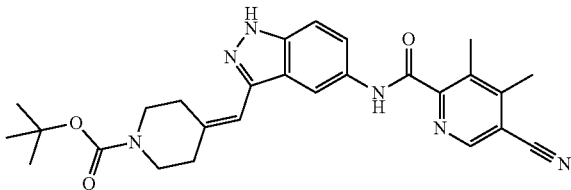 [SMILES: Cc1c(C#N)cnc(C(=O)Nc2ccc3[nH]nc(C=C4CCN(C(=O)OC(C)(C)C)CC4)c3c2)c1C]

To a solution of 5-cyano-N-(3-iodo-1H-indazol-5-yl)-3,4-dimethylpicolinamide (64.54 mg, 154.69 umol) in EtOH (4 mL) and H₂O (1 mL) was added KOAc (75.90 mg, 773.43 umol), Pd(Amphos)Cl₂ (10.95 mg, 15.47 umol) and tert-butyl 4-((4,4,5,5-tetramethyl-1,3,2-dioxaborolan-2-yl)methylene)piperidine-1-carboxylate (50 mg, 154.69 umol) at 20° C. Then the reaction mixture was stirred at 90° C. for 12 hrs under N₂. The reaction mixture was concentrated and purified by preparative HPLC using Method AV to afford the title compound (28.8 mg, 38%) as a pale yellow solid. ¹H NMR (400 MHz, DMSO-d₆) δ 12.99 (s, 1H), 10.66 (s, 1H), 8.88 (s, 1H), 8.31 (s, 1H), 7.59-7.47 (m, 2H), 6.52 (s, 1H), 3.49-3.38 (m, 4H), 2.83 (br s, 2H), 2.55 (s, 3H), 2.44 (s, 3H), 2.42-2.38 (m, 2H), 1.43 (s, 9H). MS-ESI (m/z) calc'd for C₂₇H₃₁N₆O₃ [M+H]⁺: 487.2 Found 487.3.

Example 260: 5-Cyano-3,4-dimethyl-N-(3-(piperidin-4-ylidenemethyl)-1H-indazol-5-yl)picolinamide

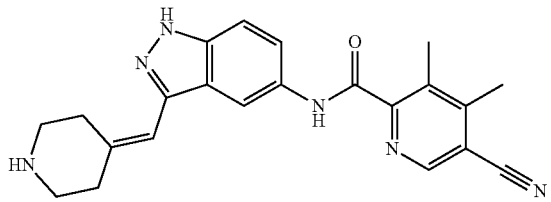 [SMILES: Cc1c(C#N)cnc(C(=O)Nc2ccc3[nH]nc(C=C4CCNCC4)c3c2)c1C]

To a solution of tert-butyl 4-((5-(5-cyano-3,4-dimethylpicolinamido)-1H-indazol-3-yl)methylene)piperidine-1-carboxylate (85 mg, 174.69 umol) in DCM (4 mL) was added TFA (1 mL). The mixture was stirred at 20° C. for 1 hr. The reaction mixture was then concentrated and purified by preparative HPLC using Method AW to afford the title compound (28.77 mg, 31%, TFA salt) as a pale yellow solid. ¹H NMR (400 MHz, DMSO-d₆) δ 13.12 (br s, 1H), 10.71 (s, 1H), 8.89 (s, 1H), 8.74 (br s, 2H), 8.40 (s, 1H), 7.53 (s, 2H), 6.64 (s, 1H), 3.24 (br s, 2H), 3.15 (br d, J=7.7 Hz, 4H), 2.65 (br t, J=5.6 Hz, 2H), 2.55 (s, 3H), 2.43 (s, 3H). MS-ESI (m/z) calc'd for C₂₂H₂₃N₆O [M+H]⁺: 387.2 Found 387.3.

Example 261: (Z)-5-Cyano-N-(3-((dihydrofuran-3(2H)-ylidene)methyl)-1H-indazol-5-yl)-3,4-dimethylpicolinamide

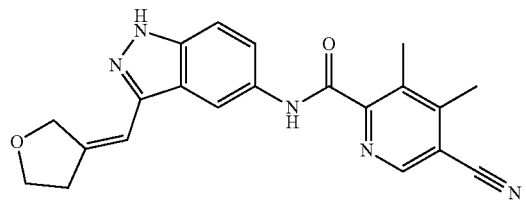 [SMILES: Cc1c(C#N)cnc(C(=O)Nc2ccc3[nH]nc(/C=C4/CCOC4)c3c2)c1C]

Step 1: (Z)-2-((Dihydrofuran-3(2H)-ylidene)methyl)-4,4,5,5-tetramethyl-1,3,2-dioxaborolane

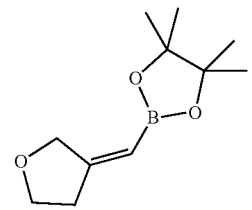

To a solution of 2,2,6,6-tetramethylpiperidine (318.18 mg, 2.25 mmol, 382.43 uL) in THF (5 mL) was added n-BuLi (2.5 M, 896.97 uL) dropwise at −30° C. over 0.5 hr under N₂. The mixture was stirred at −30° C. for 0.5 hr. Then a solution of bis(4,4,5,5-tetramethyl-1,3,2-dioxaborolan-2-yl)methane (500 mg, 1.87 mmol) in THF (5 mL) was added dropwise at −78° C. The mixture was stirred at −78° C. for 0.5 hr. Then a solution of dihydrofuran-3(2H)-one (579.89 mg, 6.74 mmol) in THF (8 mL) was added dropwise at −78° C. and the resulting mixture was stirred at 20° C. for 12 hrs under N₂. After cooling to 0° C., the reaction mixture was poured into saturated aqueous NH₄Cl (8 mL) and the mixture was stirred at 0° C. for 1 hr. The mixture was filtered and the filtrate was poured into water (10 mL) and extracted with EtOAc (10 mL×3). The combined organic phases were washed with brine (10 mL×1), dried over Na₂SO₄, filtered and concentrated in vacuum to afford the title compound (600 mg) as a brown oil, which was used without further purification.

Step 2: (Z)-5-Cyano-N-(3-((dihydrofuran-3(2H)-ylidene)methyl)-1H-indazol-5-yl)-3,4-dimethylpicolinamide

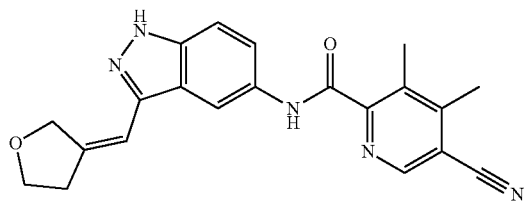 [SMILES: Cc1c(C#N)cnc(C(=O)Nc2ccc3[nH]nc(/C=C4/CCOC4)c3c2)c1C]

A mixture of N-(3-bromo-1H-indazol-5-yl)-5-cyano-3,4-dimethylpicolinamide (90 mg, 243.11 umol), (Z)-2-((dihydrofuran-3(2H)-ylidene)methyl)-4,4,5,5-tetramethyl-1,3,2-dioxaborolane (321.24 mg, 1.53 mmol), Pd(Amphos)Cl₂ (17.21 mg, 24.31 umol) and AcOK (71.58 mg, 729.33 umol) in EtOH (3 mL) and H₂O (0.75 mL) was degassed and purged with N₂ (3×), and then the mixture was stirred at 90° C. for 12 hrs under an N₂ atmosphere. The reaction mixture was concentrated, then the mixture was poured into water (6 mL) and extracted with dichloromethane (6 mL×3). The combined organic phases were washed with brine (6 mL×1), dried over Na₂SO₄, filtered and concentrated. The residue was purified by preparative HPLC using Method AI to afford the title compound (49.96 mg, 40%) as a white solid TFA salt. ¹H NMR (400 MHz, DMSO-d₆) δ 13.06 (s, 1H), 10.67 (s, 1H), 8.88 (s, 1H), 8.39 (s, 1H), 7.59-7.53 (m, 1H), 7.52-7.47 (m, 1H), 6.88-6.71 (m, 1H), 4.61 (br s, 2H), 3.84 (t, J=6.8 Hz, 2H), 2.81 (br t, J=6.1 Hz, 2H), 2.55 (s, 3H), 2.45 (s, 3H). MS-ESI (m/z) calc'd for C₂₁H₂₀N₅O₂ [M+H]⁺: 374.2 Found 374.2.

Example 262: 5-Cyano-3,4-dimethyl-N-(3-((tetrahydro-4H-pyran-4-ylidene)methyl)-1H-indazol-5-yl)picolinamide

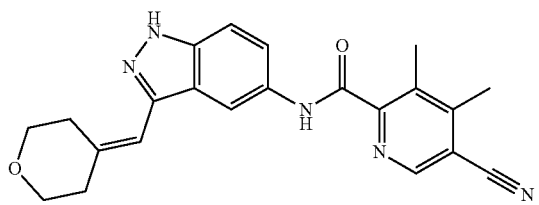 [SMILES: Cc1c(C#N)cnc(C(=O)Nc2ccc3[nH]nc(C=C4CCOCC4)c3c2)c1C]

Prepared as described for (Z)-5-cyano-N-(3-((dihydrofuran-3(2H)-ylidene)methyl)-1H-indazol-5-yl)-3,4-dimethylpicolinamide using 4,4,5,5-tetramethyl-2-((tetrahydro-4H-pyran-4-ylidene)methyl)-1,3,2-dioxaborolane in place of (Z)-2-((dihydrofuran-3(2H)-ylidene)methyl)-4,4,5,5-tetramethyl-1,3,2-dioxaborolane to afford the title compound (8.3 mg, 5%) as a pale yellow solid. ¹H NMR (400 MHz, DMSO-d₆) δ 12.97 (br s, 1H) 10.66 (s, 1H) 8.88 (s, 1H) 8.32 (s, 1H) 7.53-7.58 (m, 1H) 7.47-7.52 (m, 1H) 6.48 (s, 1H) 3.72 (t, J=5.38 Hz, 2H) 3.65 (t, J=5.44 Hz, 2H) 2.90 (br t, J=4.95 Hz, 2H) 2.55 (s, 3H) 2.42-2.47 (m, 5H). MS-ESI (m/z) calc'd for C₂₂H₂₂N₅O₂ [M+H]⁺: 388.2. Found 388.1.

Example 263: 5-Cyano-3,4-dimethyl-N-(3-(oxetan-3-ylidenemethyl)-1H-indazol-5-yl)picolinamide

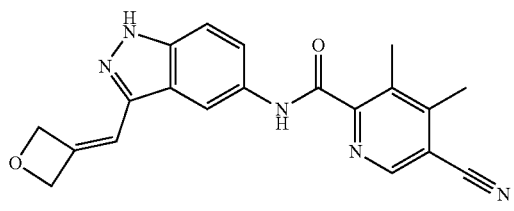 [SMILES: Cc1c(C#N)cnc(C(=O)Nc2ccc3[nH]nc(C=C4COC4)c3c2)c1C]

A mixture of 4,4,5,5-tetramethyl-2-(oxetan-3-ylidenemethyl)-1,3,2-dioxaborolane (150 mg, 765.11 umol), N-(3-bromo-1H-indazol-5-yl)-5-cyano-3,4-dimethylpicolinamide (45.03 mg, 121.64 umol), Pd(dppf)Cl₂ (4.45 mg, 6.08 umol), and K₂CO₃ (50.43 mg, 364.92 umol) in dioxane (4 mL) and H₂O (1 mL) was degassed and purged with N₂ (3×), and then the mixture was stirred at 90° C. for 12 hrs under an N₂ atmosphere. After cooling to 20° C., the reaction mixture was filtered and the filtrate was concentrated to afford a residue. The residue was purified by preparative HPLC using Method AX to afford the title compound (9 mg, 21%) as a pale yellow solid. ¹H NMR (400 MHz, MeOD) δ 8.75 (s, 1H), 8.30 (d, J=1.3 Hz, 1H), 7.62-7.56 (m, 1H), 7.54-7.49 (m, 1H), 6.58 (quin, J=2.4 Hz, 1H), 5.65 (q, J=2.9 Hz, 2H), 5.50-5.43 (m, 2H), 2.64 (s, 3H), 2.62 (s, 3H). MS-ESI (m/z) calc'd for C₂₂H₂₂N₅O₂ [M+H]⁺: 360.1. Found 360.2.

Example 264: 5-Cyano-N-(3-(methoxymethyl)-1H-indazol-5-yl)-3,4-dimethylpicolinamide

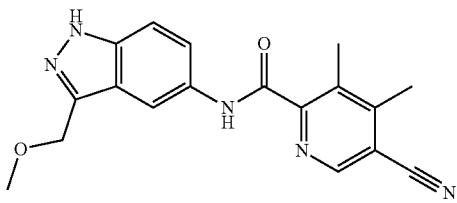 [SMILES: COCc1n[nH]c2ccc(NC(=O)c3ncc(C#N)c(C)c3C)cc12]

Step 1: 5-Nitro-1-((2-(trimethylsilyl)ethoxy)methyl)-1H-indazole-3-carbaldehyde

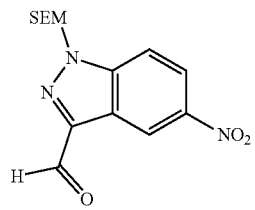

To a solution of 5-nitro-1H-indazole-3-carbaldehyde (2 g, 10.46 mmol) in THF (70 mL) was added N-cyclohexyl-N-methylcyclohexanamine (2.04 g, 10.46 mmol) and SEM-Cl (2.62 g, 15.70 mmol). The mixture was stirred at 20° C. for 12 hrs and then concentrated to afford a residue. The residue was purified by flash silica gel chromatography (ISCO; 20 g SepaFlash column) using a 0-15% EtOAc/petroleum ether gradient eluent to afford the title compound (1.34 g, 40%) as a yellow solid. MS-ESI (m/z) calcd for $C_{14}H_{20}N_3O_4Si$ $[M+H]^+$: 322.1. Found 322.1.

Step 2: (5-Nitro-1-((2-(trimethylsilyl)ethoxy)methyl)-1H-indazol-3-yl)methanol

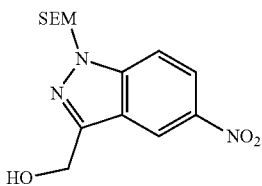 [SMILES: C[Si](C)(C)CCOCn1nc(CO)c2cc([N+](=O)[O-])ccc21]

To a solution of 5-nitro-1-((2-(trimethylsilyl)ethoxy)methyl)-1H-indazole-3-carbaldehyde (1 g, 3.11 mmol) in MeOH (25 mL) was added $NaBH_4$ (117.71 mg, 3.11 mmol) at 0° C. and the mixture was stirred at 0° C. for 0.5 hr. The reaction was quenched by addition of $H_2O$ (15 mL), then the mixture was extracted with EtOAc (30 mL×3). The combined organic layers were dried over $Na_2SO_4$, filtered and concentrated under reduced pressure to give a residue. The residue was purified by flash silica gel chromatography (ISCO; 20 g SepaFlash column) using a 0-39% EtOAc/petroleum ether gradient eluent to afford the title compound (500 mg, 50%) as a yellow oil. MS-ESI (m/z) calcd for $C_{14}H_{22}N_3O_4Si$ $[M+H]^+$: 324.1. Found 324.1.

Step 3: 3-(Methoxymethyl)-5-nitro-1-((2-(trimethylsilyl)ethoxy)methyl)-1H-indazole

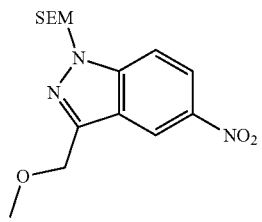 [SMILES: COCc1nn(COCC[Si](C)(C)C)c2ccc([N+](=O)[O-])cc12]

To a solution of NaH (74.20 mg, 1.86 mmol, 60% purity) in DMF (15 mL) was added a solution of (5-nitro-1-((2-(trimethylsilyl)ethoxy)methyl)-1H-indazol-3-yl)methanol (500 mg, 1.55 mmol) in DMF (10 mL) at 0° C. and the mixture was stirred at 0° C. for 1 hr. Then MeI (263.32 mg, 1.86 mmol) was added and the reaction mixture was allowed to warm to 20° C. and stirred for 1.5 hrs. The reaction was quenched by addition of $H_2O$ (20 mL), then the mixture was extracted with EtOAc (40 mL×3). The combined organic layers were dried over $Na_2SO_4$, filtered and concentrated under reduced pressure to afford the title compound (500 mg) as a yellow oil which was used without further purification. MS-ESI (m/z) calcd for $C_{15}H_{24}N_3O_4Si$ $[M+H]^+$: 338.2. Found 338.1.

Step 4: 3-(Methoxymethyl)-1-((2-(trimethylsilyl)ethoxy)methy)-1H-indazol-5-amine

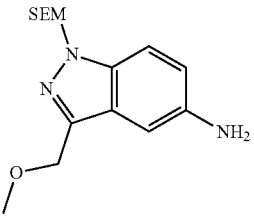 [SMILES: COCc1nn(COCC[Si](C)(C)C)c2ccc(N)cc12]

To a solution of 3-(methoxymethyl)-5-nitro-1-((2-(trimethylsilyl)ethoxy)methyl)-1H-indazole (500 mg, 1.48 mmol) in EtOH (4 mL) and $H_2O$ (0.5 mL) was added Fe (413.73 mg, 7.41 mmol) and $NH_4Cl$ (396.30 mg, 7.41 mmol). The mixture was stirred at 80° C. for 1 hr and then filtered. The filtrate was diluted with $H_2O$ (5 mL) and extracted with EtOAc (10 mL×3). The combined organic layers were dried over $Na_2SO_4$, filtered and concentrated under reduced pressure to afford the title compound (500 mg) as a brown oil which was used without further purification. MS-ESI (m/z) calcd for $C_{15}H_{25}N_3O_2Si$ $[M+H]^+$: 308.2. Found 308.1.

Step 5: 5-Cyano-N-(3-(methoxymethyl)-1-((2-(trimethylsilyl)ethoxy)methyl)-1H-indazol-5-yl)-3,4-dimethylpicolinamide

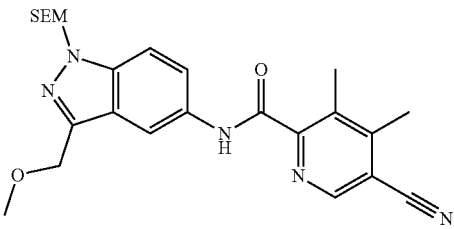 [SMILES: COCc1nn(COCC[Si](C)(C)C)c2ccc(NC(=O)c3ncc(C#N)c(C)c3C)cc12]

To a solution of 3-(methoxymethyl)-1-((2-(trimethylsilyl)ethoxy)methyl)-1H-indazol-5-amine (300 mg, 975.73 umol) in pyridine (5 mL) was added EDCI (374.10 mg, 1.95 mmol) and 5-cyano-3,4-dimethylpicolinic acid (171.90 mg, 975.73 umol). The mixture was stirred at 20° C. for 1 hr and then concentrated under reduced pressure to afford the title compound (450 mg) as a red oil which was used without further purification. MS-ESI (m/z) calcd for $C_{24}H_{31}N_5O_3Si$ $[M+H]^+$: 466.2. Found 466.2.

Step 6: 5-Cyano-N-(3-(methoxymethyl)-1H-indazol-5-yl)-3,4-dimethylpicolinamide

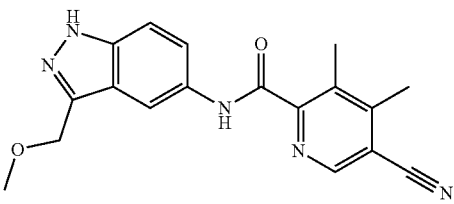 [SMILES: COCc1n[nH]c2ccc(NC(=O)c3ncc(C#N)c(C)c3C)cc12]

A solution of 5-cyano-N-(3-(methoxymethyl)-1-((2-(trimethylsilyl)ethoxy)methyl)-1H-indazol-5-yl)-3,4-dimethylpicolinamide (230 mg, 493.97 umol) in TFA (1.5 mL) was stirred at 20° C. for 12 hrs. The reaction mixture was then concentrated under reduced pressure to remove solvent. The residue was purified by preparative HPLC using Method AY to afford the title compound (18.24 mg, 10%) as a pale yellow solid. $^1$H NMR (400 MHz, DMSO-d$_6$) δ 12.97 (s, 1H) 10.67 (s, 1H) 8.88 (s, 1H) 8.33 (s, 1H) 7.58-7.62 (m, 1H) 7.49-7.53 (m, 1H) 4.72 (s, 2H) 3.29 (s, 3H) 2.54 (s, 3H) 2.43 (s, 3H). MS-ESI (m/z) calc'd for C$_{15}$H$_{18}$N$_5$O$_2$[M+H]$^+$: 336.1. Found 336.2.

Example 265: 5-Cyano-3,4-dimethyl-N-(3-(2-(trifluoromethyl)cyclopropyl)-1H-indazol-5-yl)picolinamide and Example 266: (E)-5-Cyano-3,4-dimethyl-N-(3-(3,3,3-trifluoroprop-1-en-1-yl)-1H-indazol-5-yl)picolinamide

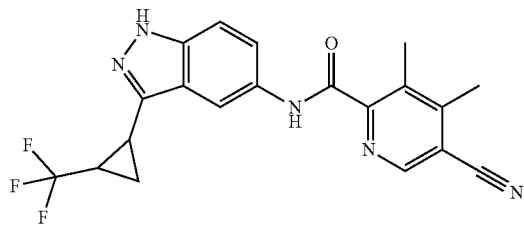

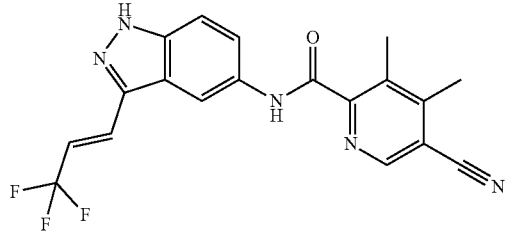

Step 1: 2-Diazo-1,1,1-trifluoroethane

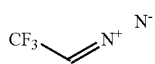

To a solution of 2,2,2-trifluoroethan-1-amine hydrochloride (25 g, 184.48 mmol, 19.84 mL) in H$_2$O (77 mL) and Et$_2$O (150 mL) was added a solution of NaNO$_2$ (14.00 g, 202.93 mmol) in H$_2$O (30 mL) at 0° C. The reaction mixture was then, warmed to 20° C. and stirred for 3 hrs. The reaction solution turned from colorless to light yellow. The phases were separated and the Et$_2$O layer was dried over Na$_2$SO$_4$, and filtered to afford the title compound (25 g) in Et$_2$O as a light yellow liquid, which was used without further purification.

Step 2: 5-Nitro-1-(tetrahydro-2H-pyran-2-yl)-3-vinyl-1H-indazole

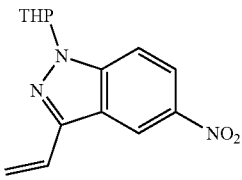

To a solution of 3-iodo-5-nitro-1-(tetrahydro-2H-pyran-2-yl)-1H-indazole (2.2 g, 5.90 mmol) and 4,4,5,5-tetramethyl-2-vinyl-1,3,2-dioxaborolane (1.09 g, 7.07 mmol, 1.20 mL) in dioxane (18 mL) and H$_2$O (3.6 mL) was added K$_3$PO$_4$ (2.50 g, 11.79 mmol) and Pd(PPh$_3$)$_4$ (510.97 mg, 442.19 umol) at 20° C. under an N$_2$ atmosphere and the mixture was stirred at 90° C. for 12 hrs. The reaction mixture was concentrated to afford a residue. The residue was purified by flash silica gel chromatography (ISCO; 12 g SepaFlash column) using a 0-6% EtOAc/petroleum ether gradient eluent to afford the title compound (2.5 g, 78%) as a pale yellow solid. MS-ESI (m/z) calcd for C$_{14}$H$_{16}$N$_3$O$_3$ [M+H]$^+$: 274.1. Found 274.1.

Step 3: 5-Nitro-1-(tetrahydro-2H-pyran-2-yl)-3-(2-(trifluoromethyl)cyclopropyl)-1H-indazole

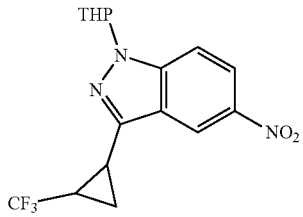

To a solution of 5-nitro-1-(tetrahydro-2H-pyran-2-yl)-3-vinyl-1H-indazole (2 g, 7.32 mmol) and Pd(OAc)$_2$ (246.45 mg, 1.10 mmol) in THF (25 mL) was added a solution of 2-diazo-1,1,1-trifluoroethane (24.16 g, 219.55 mmol) in Et$_2$O (150 mL) dropwised at 0° C. Then the reaction mixture was stirred at 20° C. for 24 hrs under N$_2$. The reaction mixture was dissolved in H$_2$O (20 mL) and the aqueous phase was extracted with EtOAc (20 mL×3). The combined organic phases were dried over Na$_2$SO$_4$, filtered and concentrated to give a residue. The residue was purified by flash silica gel chromatography (ISCO; 40 g SepaFlash column) using a 0-2% EtOAc/petroleum ether gradient eluent to afford the title compound (143 mg, 6%) as a yellow oil. MS-ESI (m/z) calcd for C$_{16}$H$_{16}$F$_3$N$_3$O$_3$ [M+H]$^+$: 356.1. Found 356.0.

Step 4: 1-(Tetrahydro-2H-pyran-2-yl)-3-(2-(trifluoromethyl)cyclopropyl)-1H-indazol-5-amine

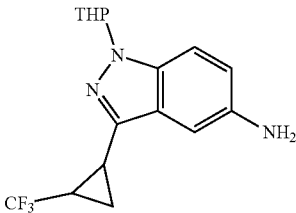

To a solution of 5-nitro-1-(tetrahydro-2H-pyran-2-yl)-3-(2-(trifluoromethyl)cyclopropyl)-1H-indazole (130 mg, 365.88 umol) in THF (12 mL) and H$_2$O (3 mL) was added NH$_4$Cl (117.43 mg, 2.20 mmol) and Zn (191.40 mg, 2.93 mmol) and the reaction mixture was stirred at 20° C. for 2 hrs. The reaction mixture was filtered and the filtrate was concentrated. The residue was dissolved into H$_2$O (10 mL) and the aqueous phase was extracted with EtOAc (10 mL×3). The combined organic phases were dried over Na$_2$SO$_4$, filtered and concentrated in vacuum to afford the title compound (130 mg) as a yellow oil, which was used without further purification. MS-ESI (m/z) calcd for C$_{16}$H$_{19}$F$_3$N$_3$O [M+H]$^+$: 326.1. Found 326.4.

Step 5: 5-Cyano-3,4-dimethyl-N-(1-(tetrahydro-2H-pyran-2-yl)-3-(2-(trifluoromethyl)cyclopropyl)-1H-indazol-5-yl picolinamide

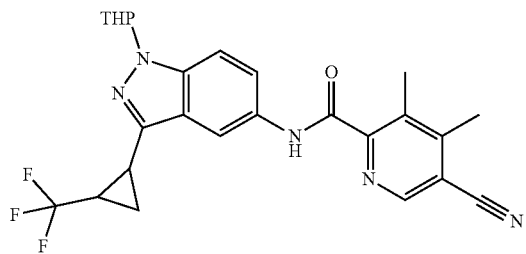

To a solution of 1-(tetrahydro-2H-pyran-2-yl)-3-(2-(trifluoromethyl)cyclopropyl)-1H-indazol-5-amine (130 mg, 399.60 umol) and 5-cyano-3,4-dimethylpicolinic acid (77.44 mg, 439.56 umol) in DCM (6 mL) was added T3P (50 wt. % in EtOAc, 381.43 mg, 599.40 umol, 356.48 uL) at 20° C. and the reaction mixture was stirred at 35° C. for 0.5 hr. Then Et$_3$N (121.31 mg, 1.20 mmol, 166.86 uL) was added and the reaction mixture was stirred at 35° C. for 2 hrs. The reaction mixture was diluted with H$_2$O (10 mL) and extracted with dichloromethane (10 mL×3). The combined organic phases were dried over Na$_2$SO$_4$, filtered and the filtrate was concentrated. The residue was purified by preparative TLC (SiO$_2$, petroleum ether/EtOAc=3/1, R$_f$=0.3) to afford the title compound (60 mg, 31%) as a yellow oil. MS-ESI (m/z) calcd for C$_{25}$H$_{25}$F$_3$N$_5$O$_2$ [M+H]$^+$: 484.2. Found 484.3.

Step 6: 5-Cyano-3,4-dimethyl-N-(3-(2-(trifluoromethyl)cyclopropyl)-1H-indazol-5-yl)picolinamide and (E)-5-Cyano-3,4-dimethyl-N-(3-(3,3,3-trifluoroprop-1-en-1-yl)-1H-indazol-5-yl)picolinamide

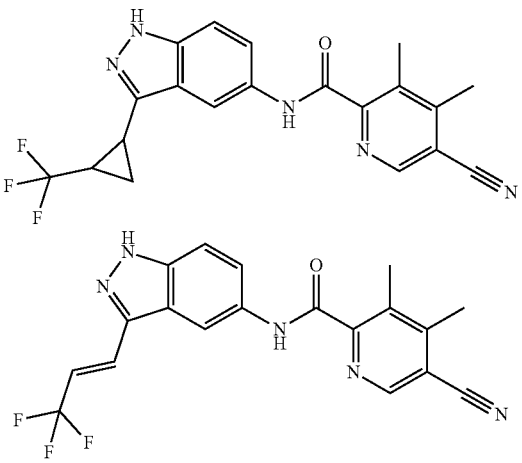

To a solution of 5-cyano-3,4-dimethyl-N-(1-(tetrahydro-2H-pyran-2-yl)-3-(2-(trifluoromethyl)cyclopropyl)-1H-indazol-5-yl)picolinamide (50 mg, 103.42 umol) in DCM (2 mL) was added TFA (770.00 mg, 6.75 mmol, 500.00 uL) and the reaction mixture was stirred at 20° C. for 12 hrs. The reaction mixture was then adjusted to pH=8 by addition of ice cold saturated aqueous NaHCO$_3$ and extracted with dichloromethane (10 mL×3). The combined organic phases were dried over Na$_2$SO$_4$, filtered and concentrated. The residue was purified by preparative HPLC using Method AZ to afford 5-cyano-N-(3-(methoxymethyl)-1H-indazol-5-yl)-3,4-dimethylpicolinamide (23.52 mg, 57%) as a pale yellow solid. $^1$H NMR (400 MHz, MeOD) δ 8.71 (s, 1H), 8.31-8.24 (m, 1H), 7.59 (dd, J=1.8, 8.9 Hz, 1H), 7.47 (d, J=8.9 Hz, 1H), 2.72-2.65 (m, 1H), 2.59 (d, J=3.4 Hz, 6H), 2.33-2.21 (m, 1H), 1.54-1.42 (m, 2H). MS-ESI (m/z) calc'd for C$_{20}$H$_{17}$F$_3$N$_5$O [M+H]$^+$: 400.1. Found 400.1. (E)-5-Cyano-3,4-dimethyl-N-(3-(3,3,3-trifluoroprop-1-en-1-yl)-1H-indazol-5-yl)picolinamide (15.59 mg, 39° %) as a pale pink solid was also isolated. $^1$H NMR (400 MHz, MeOD) δ 8.72 (s, 1H), 8.47 (d, J=1.1 Hz, 1H), 7.69 (dd, J=1.7, 8.9 Hz, 1H), 7.61-7.56 (m, 1H), 7.51 (dd, J=2.2, 16.4 Hz, 1H), 6.69 (qd, J=6.7, 16.3 Hz, 1H), 2.61 (d, J=2.8 Hz, 6H). MS-ESI (m/z) calc'd for C$_{19}$H$_{15}$F$_3$N$_5$O [M+H]$^+$: 386.1. Found 386.1.

Example 267: 5-Cyano-3,4-dimethyl-N-(3-(prop-1-en-2-yl)-1H-indazol-5-yl)picolinamide

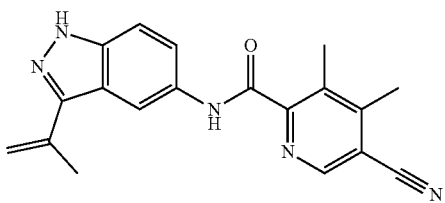 [SMILES: C=C(C)c1n[nH]c2ccc(NC(=O)c3ncc(C#N)c(C)c3C)cc12]

Step 1: 5-Nitro-3-(prop-1-en-2-yl)-1-(tetrahydro-2H-pyran-2-yl)-1H-indazole

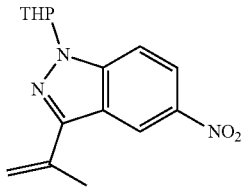

A mixture of 3-iodo-5-nitro-1-(tetrahydro-2H-pyran-2-yl)-1H-indazole (1 g, 2.68 mmol), 4,4,5,5-tetramethyl-2-(prop-1-en-2-yl)-1,3,2-dioxaborolane (495.37 mg, 2.95 mmol), Pd(dppf)Cl$_2$ (196.09 mg, 267.99 umol), K$_3$PO$_4$ (1.71 g, 8.04 mmol) in dioxane (24 mL) and H$_2$O (6 mL) at 20° C. was degassed and purged with N$_2$ (3×). The mixture was stirred at 90° C. for 4 hrs under an N$_2$ atmosphere and then concentrated to remove solvent. The residue was diluted with H$_2$O (20 mL) and extracted with EtOAc (20 mL×3). The combined organic phases were dried over Na$_2$SO$_4$, filtered and concentrated. The material was purified by flash silica gel chromatography (ISCO; 12 g SepaFlash column) using a 0-7% EtOAc/petroleum ether gradient eluent to afford the title compound (570 mg, 74%) as a yellow solid. MS-ESI (m/z) calcd for C$_{15}$H$_{18}$N$_3$O$_3$ [M+H]$^+$: 288.1. Found 288.0.

Step 2: 3-(Prop-1-en-2-yl)-1-(tetrahydro-2H-pyran-2-yl)-1H-indazol-5-anine

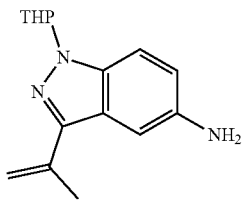

To a solution of 5-nitro-3-(prop-1-en-2-yl)-1-(tetrahydro-2H-pyran-2-yl)-1H-indazole (200 mg, 696.10 umol) in EtOH (2 mL) and H$_2$O (2 mL) was added Fe (194.37 mg, 3.48 mmol) and NH$_4$Cl (186.18 mg, 3.48 mmol) at 20° C. The mixture was stirred at 80° C. for 1 hr and then filtered. The filtrate was diluted with H$_2$O (20 mL) and extracted with EtOAc (20 mL×3). The organic phase was dried over Na$_2$SO$_4$, filtered and concentrated under reduced pressure to afford the title compound (140 mg) as a red oil which was used without further purification. MS-ESI (m/z) calcd for C$_{15}$H$_{20}$N$_3$O [M+H]$^+$: 258.2. Found 258.1.

Step 3: 5-Cyano-3,4-dimethyl-N-(3-(prop-1-en-2-yl)-1-(tetrahydro-2H-pyran-2-yl)-1H-indazol-5-yl)picolinamide

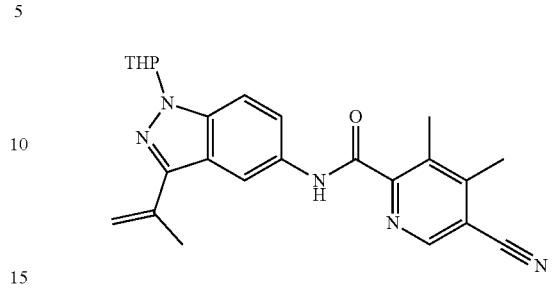

To a solution of 3-(prop-1-en-2-yl)-1-(tetrahydro-2H-pyran-2-yl)-1H-indazol-5-amine (140 mg, 544.05 umol), 5-cyano-3,4-dimethylpicolinamide (95.85 mg, 544.05 umol) in pyridine (5 mL) was added EDCI (156.44 mg, 816.07 umol). The mixture was stirred at 20° C. for 12 hrs and then concentrated to remove solvent. The reaction mixture was diluted with water (10 mL) and filtered. The solid was washed with H$_2$O (10 mL) and dried in vacuum to afford the title compound (210 mg) as a red solid which was used without further purification. MS-ESI (m/z) calcd for C$_{24}$H$_{26}$N$_5$O$_2$ [M+H]$^+$: 416.2. Found 416.1.

Step 4: 5-Cyano-3,4-dimethyl-N-(3-(prop-1-en-2-yl)-1H-indazol-5-yl)picolinamide

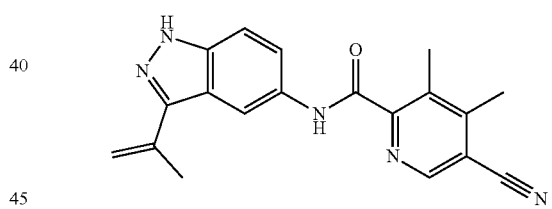

A mixture of 5-cyano-3,4-dimethyl-N-(3-(prop-1-en-2-yl)-1-(tetrahydro-2H-pyran-2-yl)-1H-indazol-5-yl)picolinamide (70 mg, 168.48 umol) in DCM (2 mL) and TFA (0.5 mL) was stirred at 20° C. for 1 hr. Saturated aqueous NaHCO$_3$ (20 mL) was then added to the reaction mixture at 0° C. and the mixture was extracted with DCM (10 m L×3). The organic phase was dried over Na$_2$SO$_4$, filtered and concentrated to give a residue. The residue was purified by preparative HPLC using Method AZ to afford the title compound (7.81 mg, 14%) as a pale yellow solid. $^1$H NMR (400 MHz, DMSO-d$_6$) δ 10.69 (br s, 1H), 8.89 (s, 1H), 8.53 (s, 1H), 7.70 (br d, J=8.80 Hz, 1H), 7.54 (d, J=8.93 Hz, 1H), 5.70 (s, 1H), 5.36 (s, 1H), 2.55 (s, 3H), 2.44 (s, 3H), 2.25 (s, 3H). MS-ESI (m/z) calc'd for C$_9$H$_{18}$N$_5$O [M+H]$^+$: 332.1. Found 332.1.

Example 268: 5-Cyano-3,4-dimethyl-N-(3-(1-methylcyclopropyl)-1H-indazol-5-yl)picolinamide

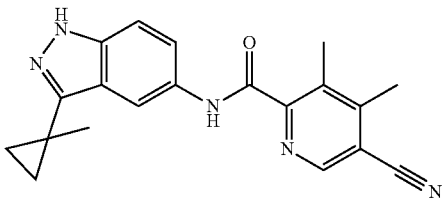 [SMILES: Cc1c(C#N)cnc(C(=O)Nc2ccc3[nH]nc(C4(C)CC4)c3c2)c1C]

Step 1:
N-Methoxy-N,1-dimethylcyclopropane-1-carboxamide

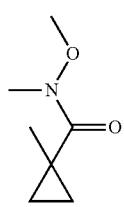

To a solution of 1-methylcyclopropane-1-carboxylic acid (3 g, 29.97 mmol) in DCM (60 mL) was added CDI (5.83 g, 35.96 mmol), the mixture was stirred at 20° C. for 2 hrs, then N-methoxymethanamine hydrochloride (3.51 g, 35.96 mmol) was added. The mixture was stirred at 20° C. for another 10 hrs and then diluted with MeOH (10 mL). The mixture was purified by flash silica gel chromatography (ISCO; 40 g SepaFlash column) using a 0-10% EtOAc/petroleum ether gradient eluent to afford the title compound (2.7 g, 63%) as a colorless oil. MS-ESI (m/z) calcd for $C_7H_{14}NO_2$ [M+H]$^+$: 144.1. Found 144.0.

Step 2: (5-Bromo-2-fluorophenyl)(1-methylcyclopropyl)methanone

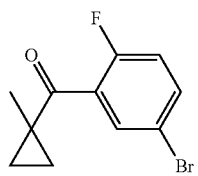

To a solution of 4-bromo-1-fluoro-2-iodobenzene (3.28 g, 10.90 mmol) in THF (50 mL) was added i-PrMgCl (2M, 7.15 mL) at 0° C. The mixture was stirred at 0° C. for 0.5 hr, then N-methoxy-N,1-dimethylcyclopropane-1-carboxamide (1.3 g, 9.08 mmol) in THF (30 mL) was added. The mixture was stirred at 20° C. for 12 hrs. The process was repeated using 500 mg of N-methoxy-N,1-dimethylcyclopropane-1-carboxamide and the combined reaction mixtures were quenched with saturated aqueous NH$_4$Cl (100 mL) and extracted with EtOAc (60 mL×3). The combined organic layers were dried over Na$_2$SO$_4$, filtered and concentrated to give a residue. The residue was purified by flash silica gel chromatography (ISCO; 40 g SepaFlash column) using 2% EtOAc/Petroleum ether as eluent to afford the title compound (1.2 g, 37%) as a colorless oil. MS-ESI (m/z) calcd for $C_{11}H_{11}BrFO$ [M+H]$^+$: 257.0/259.0. Found 256.9/259.0.

Step 3:
5-Bromo-3-(1-methylcyclopropyl)-1H-indazole

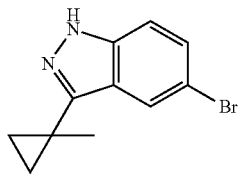

A solution of (5-bromo-2-fluorophenyl)(1-methylcyclopropyl)methanone (500 mg, 1.94 mmol) in NH$_2$NH$_2$H$_2$O (10 mL) was stirred at 100° C. for 3 hrs. The reaction mixture was diluted with H$_2$O (30 ml) and extracted with EtOAc (20 mL×5). The combined organic layers were dried over Na$_2$SO$_4$, filtered and concentrated to give a residue. The residue was purified by flash silica gel chromatography (ISCO; 4 g SepaFlash column) using a 0-9% EtOAc/petroleum ether gradient eluent to afford the title compound (300 mg, 61%) as a light yellow solid. MS-ESI (m/z) calcd for $C_{11}H_{12}BrN_2$ [M+H]$^+$: 251.0/253.0. Found 251.0/253.0.

Step 4: 5-Bromo-3-(1-methylcyclopropyl)-1-(tetrahydro-2H-pyran-2-yl)-1H-indazole

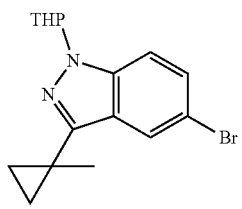

To a solution of 5-bromo-3-(1-methylcyclopropyl)-1H-indazole (230 mg, 915.89 umol) in DCM (6 mL) was added 3,4-dihydro-2H-pyran (115.56 mg, 1.37 mmol) and PTSA (15.77 mg, 91.59 umol) at 20° C. and the mixture was stirred at 45° C. for 12 hrs. The reaction mixture was concentrated and purified by flash silica gel chromatography (ISCO; 4 g SepaFlash column) using a 0-5% EtOAc/petroleum ether gradient eluent to afford the title compound (150 mg, 49%) as a light yellow gum. MS-ESI (m/z) calcd for $C_{16}H_{20}BrN_2O$ [M+H]$^+$: 335.1/337.1. Found 335.0/337.0.

Step 5: N-(3-(1-Methylcyclopropyl)-1-(tetrahydro-2H-pyran-2-yl)-1H-indazol-5-yl)-1,1-diphenylmethanimine

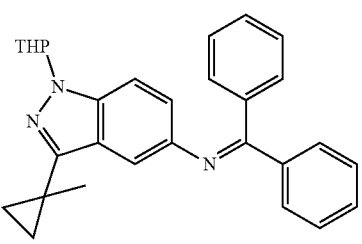

A mixture of 5-bromo-3-(1-methylcyclopropyl)-1-(tetrahydro-2H-pyran-2-yl)-1H-indazole (150 mg, 447.44 umol), diphenylmethanimine (97.31 mg, 536.93 umol), Pd$_2$(dba)$_3$ (20.49 mg, 22.37 umol), t-BuXphos (19.00 mg, 44.74 umol) and t-BuONa (86.00 mg, 894.89 umol) in toluene (4 mL) was degassed and purged with N$_2$ (3×) at 20° C. The mixture was then stirred at 100° C. for 12 hrs under an N$_2$ atmosphere and concentrated. The material was purified by flash silica gel chromatography (ISCO; 4 g SepaFlash column) using a 0-5% EtOAc/petroleum ether gradient eluent to afford the title compound (180 mg, 92%) as a yellow gum. MS-ESI (m/z) calcd for C$_{29}$H$_{30}$N$_3$O [M+H]$^+$: 436.2. Found 436.2.

Step 6: 3-(1-Methylcyclopropyl)-1-(tetrahydro-2H-pyran-2-yl)-1H-indazol-5-amine

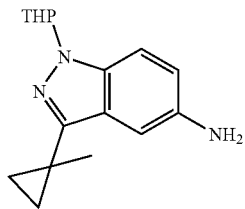

To a solution of N-(3-(1-methylcyclopropyl)-1-(tetrahydro-2H-pyran-2-yl)-1H-indazol-5-yl)-1,1-diphenylmethanimine (180 mg, 413.26 umol) in THF (4 mL) was added 1 M HCl (1.24 mL) and the mixture was stirred at 20° C. for 10 min. The reaction mixture was then basified with saturated aqueous NaHCO$_3$ to pH=7, diluted with H$_2$O (10 mL), and extracted with EtOAc (5 mL 3). The combined organic layers were dried over Na$_2$SO$_4$, filtered and concentrated to give a residue. The residue was purified by preparative TLC (SiO$_2$, petroleum ether/EtOAc=1/1, R$_f$=0.24) to afford the title compound (86 mg, 60%) as a yellow gum. MS-ESI (m/z) calcd for C$_{16}$H$_{22}$N$_3$O [M+H]$^+$: 272.2. Found 272.4.

Step 7: 5-Cyano-3,4-dimethyl-N-(3-(1-methylcyclopropyl)-1-(tetrahydro-2H-pyran-2-yl)-1H-indazol-5-yl)picolinamide

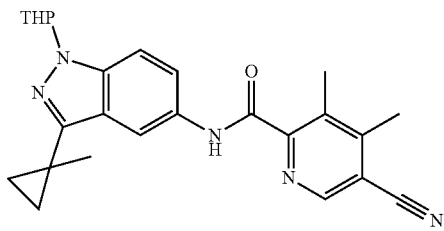

To a solution of 5-cyano-3,4-dimethylpicolinic acid (55.83 mg, 316.93 umol) in pyridine (3 mL) was added EDCI (91.13 mg, 475.39 umol) and 3-(1-methylcyclopropyl)-1-(tetrahydro-2H-pyran-2-yl)-1H-indazol-5-amine (86 mg, 316.93 umol) and the mixture was stirred at 20° C. for 2 hrs. The reaction mixture was then concentrated to give a residue. The residue was diluted with H$_2$O (10 mL) and extracted with EtOAc (5 mL×4). The combined organic layers were dried over Na$_2$SO$_4$, filtered and concentrated to afford the title compound (117 mg) as a brown solid which was used without further purification. MS-ESI (m/z) calcd for C$_{25}$H$_{21}$N$_5$O$_2$[M+H]$^+$: 430.2. Found 430.4.

Step 8: 5-Cyano-3,4-dimethyl-N-(3-(1-methylcyclopropyl)-1H-indazol-5-yl)picolinamide

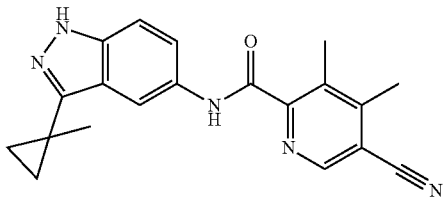 [SMILES: Cc1c(C#N)cnc(C(=O)Nc2ccc3[nH]nc(C4(C)CC4)c3c2)c1C]

To a solution of 5-cyano-3,4-dimethyl-N-(3-(1-methylcyclopropyl)-1-(tetrahydro-2H-pyran-2-yl)-1H-indazol-5-yl)picolinamide (60 mg, 139.69 umol) in DCM (2 mL) was added TFA (0.5 mL). The mixture was stirred at 20° C. for 12 hrs and then concentrated. The material was purified by preparative HPLC using Method BA to afford the title compound (21.01 mg, 33%) as a pale yellow solid TFA salt. $^1$H NMR (400 MHz, DMSO-d$_6$) δ 12.57 (br s, 1H) 10.63 (s, 1H) 8.89 (s, 1H) 8.31 (d, J=1 Hz, 1H) 7.61 (dd, J=9, 2 Hz, 1H) 7.45 (d, J=9 Hz, 1H) 2.56 (s, 3H) 2.45 (s, 3H) 1.55 (s, 3H) 1.10-1.14 (m, 2H) 0.79-0.83 (m, 2H). MS-ESI (m/z) calc'd for C$_{20}$H$_{20}$N$_5$O [M+H]$^+$: 346.2. Found 346.2.

Example 269: 5-Cyano-N-(3-(1-methoxyethyl)-1H-indazol-5-yl)-3,4-dimethylpicolinamide

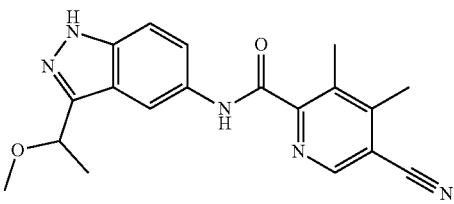 [SMILES: COC(C)c1n[nH]c2ccc(NC(=O)c3ncc(C#N)c(C)c3C)cc12]

Step 1: 3-Iodo-5-nitro-1H-indazole

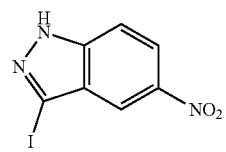 [SMILES: O=[N+]([O-])c1ccc2[nH]nc(I)c2c1]

To a solution of 5-nitro-1H-indazole (10 g, 61.30 mmol) in DMF (100 mL) was added KOH (10.32 g, 183.90 mmol) and the mixture was stirred at 20° C. for 5 min. Then 12 (31.12 g, 122.60 mmol) was added and the reaction mixture was stirred at 20° C. for 3 hrs. The reaction mixture was quenched with saturated aqueous Na$_2$SO$_3$ (100 mL), then filtered and the solid was washed with petroleum ether (100 mL) and dried to afford the title compound (15 g, 85%) as an orange solid, which was used without further purification. MS-ESI (m/z) calcd for C$_7$H$_5$IN$_3$O$_2$ [M+H]$^+$: 289.9. Found 289.9.

Step 2: 3-Iodo-5-nitro-1-((2-(trimethylsilyl)ethoxy)methyl)-1H-indazole

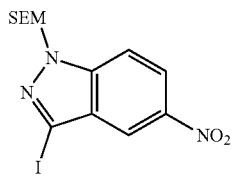 [SMILES: C[Si](C)(C)CCOCn1nc(I)c2cc([N+](=O)[O-])ccc21]

To a solution of 3-iodo-5-nitro-1H-indazole (15 g, 51.90 mmol) in THF (100 mL) was added NaH (4.15 g, 103.80 mmol, 60% purity) and the reaction mixture was stirred at 0° C. for 0.5 hr. Then SEM-Cl (12.98 g, 77.85 mmol, 13.78 mL) was added and the mixture was stirred at 20° C. for 12 hrs. The reaction mixture was poured into water (100 mL) and extracted with EtOAc (100 mL×3). The combined organic phases were washed with brine (100 mL×1), dried over anhydrous $Na_2SO_4$, filtered and concentrated. The residue was purified by silica gel column chromatography using a 0-20% EtOAc/petroleum ether gradient eluent to afford the title compound (10 g, 46%) as a yellow solid. MS-ESI (m/z) calcd for $C_{13}H_{19}IN_3O_3Si$ $[M+H]^+$: 420.0. Found 420.0.

Step 3: 3-(1-Ethoxyvinyl)-5-nitro-1-((2-(trimethylsilyl)ethoxy)methyl)-1H-indazole

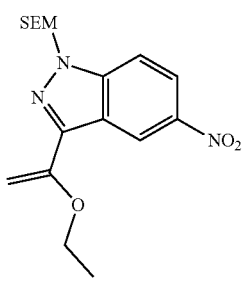 [SMILES: C=C(OCC)c1nn(COCC[Si](C)(C)C)c2ccc([N+](=O)[O-])cc12]

A mixture of 3-iodo-5-nitro-1-((2-(trimethylsilyl)ethoxy)methyl)-1H-indazole (2 g, 4.77 mmol), butyl(1-ethoxyvinyl)-X²-stannane-octane (1/1) (3.45 g, 9.54 mmol, 3.22 mL) and $Pd(PPh_3)_2Cl_2$ (334.80 mg, 477.00 umol) in dioxane (20 mL) was degassed and purged with $N_2$ (3×), and then the mixture was stirred at 100° C. for 4 hrs under $N_2$ atmosphere. The reaction mixture was concentrated and purified by silica gel column chromatography using a 0-20% EtOAc/petroleum ethergradient eluent to afford the title compound (1.7 g, 95%) as a yellow oil. MS-ESI (m/z) calcd for $C_{17}H_{26}N_3O_4Si$ $[M+H]^+$: 364.2. Found 364.1.

Step 4: 1-(5-Nitro-1-((2-(trimethylsilyl)ethoxy)methyl)-1H-indazol-3-yl)ethan-1-one

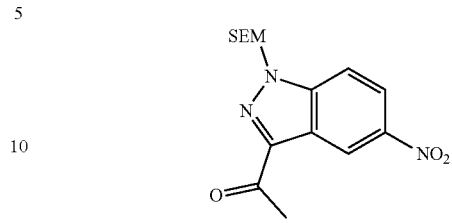

To a solution of 3-(1-ethoxyvinyl)-5-nitro-1-((2-(trimethylsilyl)ethoxy)methyl)-1H-indazole (1.7 g, 4.68 mmol) in THF (10 mL) was added HCl (1 M, 46.77 mL). The mixture was stirred at 20° C. for 0.5 hr. The reaction mixture was poured into water (10 mL). The aqueous phase was extracted with EtOAc (15 mL×3). The combined organic phases were washed with brine (15 mL×1), dried over anhydrous $Na_2SO_4$, filtered and concentrated in vacuum. The residue was purified by silica gel column chromatography using a 0-20% EtOAc/petroleum ether gradient eluent to afford the title compound (1 g, 64%) as a pink solid. MS-ESI (m/z) calcd for $C_{15}H_{22}N_3O_4Si$ $[M+H]^+$: 336.1. Found 336.1.

Step 5: 1-(5-Nitro-1-((2-(trimethylsilyl)ethoxy)methyl)-1H-indazol-3-yl)ethan-1-ol

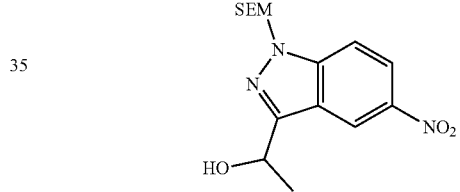

To a solution of 1-(5-nitro-1-((2-(trimethylsilyl)ethoxy)methyl)-1H-indazol-3-yl)ethan-1-one (1 g, 2.98 mmol) in MeOH (10 mL) was added $NaBH_4$ (338.36 mg, 8.94 mmol). The mixture was stirred at 20° C. for 0.5 hr. The reaction mixture was poured into water (10 mL) and extracted with EtOAc (10 mL×3). The combined organic phases were washed with brine (10 mL×1), dried over anhydrous $Na_2SO_4$, filtered and concentrated in vacuum to afford the title compound (700 mg, 70%) as a brown oil, which was used without further purification. MS-ESI (m/z) calcd for $C_{15}H_{24}N_3O_4Si$ $[M+H]^+$: 338.2. Found 338.2.

Step 6: 3-(1-Methoxyethyl)-5-nitro-1-((2-(trimethylsilyl)ethoxy)methyl)-1H-indazole

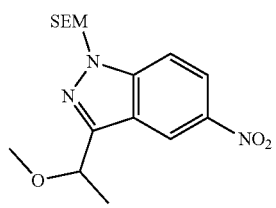 [SMILES: COC(C)c1nn(COCC[Si](C)(C)C)c2ccc(N)cc12]

To a solution of 1-(5-nitro-1-((2-(trimethylsilyl)ethoxy)methyl)-1H-indazol-3-yl)ethan-1-ol (700 mg, 2.07 mmol) in THF (5 mL) was added a 60% NaH dispersion in mineral oil (165.94 mg, 4.15 mmol) at 0° C. and the reaction mixture was stirred at 0° C. for 0.5 hr. Then MeI (588.88 mg, 4.15 mmol, 258.28 uL) was added and the mixture was stirred at 20° C. for 12 hrs. The reaction mixture was poured into water (10 mL) and extracted with EtOAc (10 mL×3). The combined organic phases were washed with brine (10 mL×1), dried over anhydrous $Na_2SO_4$, filtered and concentrated. The residue was purified by silica gel column chromatography using a 0-30% EtOAc/petroleum ether gradient eluent to afford the title compound (670 mg, 92%) as a colorless oil. MS-ESI (m/z) calcd for $C_{16}H_{26}N_3O_4Si$ $[M+H]^+$: 352.2. Found 352.0.

Step 7: 3-(1-Methoxyethyl)-1-((2-(trimethylsilyl)ethoxy)methyl)-1H-indazol-5-amine

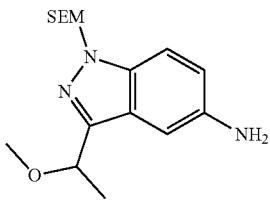

To a solution of 3-(1-methoxyethyl)-5-nitro-1-((2-(trimethylsilyl)ethoxy)methyl)-1H-indazole (670 mg, 1.91 mmol) in EtOH (10 mL) and $H_2O$ (2.5 mL) was added Fe (532.28 mg, 9.53 mmol) and $NH_4Cl$ (509.84 mg, 9.53 mmol) at 20° C. The reaction mixture was then stirred at 80° C. for 2 hrs. The mixture was filtered and the filtrate was poured into water (5 mL) and extracted with EtOAc (5 mL×3). The combined organic phases were washed with brine (5 mL×1), dried over anhydrous $Na_2SO_4$, filtered and concentrated in vacuum to afford the title compound (660 mg) as a yellow oil, which was used without further purification. MS-ESI (m/z) calcd for $C_{16}H_{28}N_3O_2Si$ $[M+H]^+$: 322.2. Found 322.2.

Step 8: 5-Cyano-N-(3-(1-methoxyethyl)-1-((2-(trimethylsilyl)ethoxy)methyl)-1H-indazol-5-yl)-3,4-dimethylpicolinamide

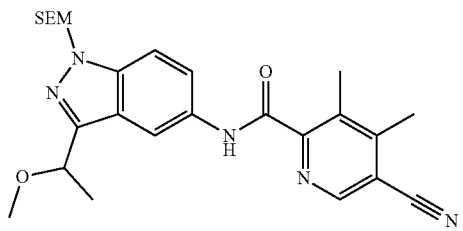 [SMILES: COC(C)c1nn(COCC[Si](C)(C)C)c2ccc(NC(=O)c3ncc(C#N)c(C)c3C)cc12]

To a solution of 3-(1-methoxyethyl)-1-((2-(trimethylsilyl)ethoxy)methyl)-1H-indazol-5-amine (660 mg, 2.05 mmol) and 5-cyano-3,4-dimethylpicolinic acid (361.67 mg, 2.05 mmol) in pyridine (3 mL) was added EDCI (787.11 mg, 4.11 mmol) and the mixture was stirred at 20° C. for 2 hrs. The reaction mixture was concentrated and the residue was diluted with water (10 mL) and extracted with EtOAc (10 mL×3). The combined organic phases were washed with brine (10 mL×1), dried over anhydrous $Na_2SO_4$, filtered and concentrated. The residue was purified by silica gel column chromatography using a 0-30% EtOAc/petroleum ether gradient eluent to afford the title compound (740 mg, 75%) as a yellow solid. MS-ESI (m/z) calcd for $C_{25}H_{34}N_5O_3Si$ $[M+H]^+$: 480.2. Found 480.3.

Step 9: 5-Cyano-N-(3-(1-methoxyethyl)-1H-indazol-5-yl)-3,4-dimethylpicolinamide

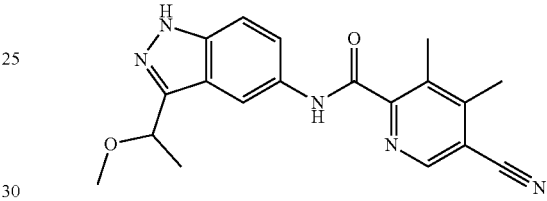

To a solution of 5-cyano-N-(3-(1-methoxyethyl)-1-((2-(trimethylsilyl)ethoxy)methyl)-1H-indazol-5-yl)-3,4-dimethylpicolinamide (300 mg, 625.46 umol) in MeOH (5 mL) was added 12 M HCl (521.22 uL) at 20° C. and the mixture was stirred at 60° C. for 12 hrs. The reaction mixture was diluted with $H_2O$ (10 mL) and adjusted to pH=8 with saturated aqueous $NaHCO_3$. The mixture was then extracted with EtOAc (10 mL×3). The combined organic phases were washed with brine (10 mL×1), dried over anhydrous $Na_2SO_4$, filtered and concentrated. The residue was purified by silica gel column chromatography using a 0-50% EtOAc/petroleum ether gradient eluent to afford material of insufficient purity. The material was then further purified by preparative HPLC using Method BB to afford the title compound (74.99 mg, 34%) as a white solid. $^1H$ NMR (400 MHz, DMSO-$d_6$) δ 12.86 (s, 1H), 10.63 (s, 1H), 8.87 (s, 1H), 8.35 (s, 1H), 7.64 (dd, J=1.9, 8.9 Hz, 1H), 7.50 (d, J=8.8 Hz, 1H), 4.73 (q, J=6.5 Hz, 1H), 3.16 (s, 3H), 2.55 (s, 3H), 2.44 (s, 3H), 1.57 (d, J=6.6 Hz, 3H). MS-ESI (m/z) calc'd for $C_{19}H_{20}N_5O_2$ $[M+H]^+$: 350.2. Found 350.2.

Example 270: 6-Chloro-5-cyano-N-(3-isopropyl-1H-indazol-5-yl)-3,4-dimethylpicolinamide

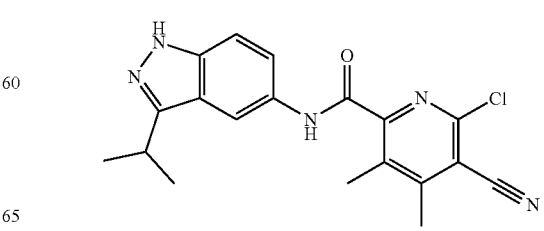

427

Step 1: 3-Bromo-1-(4-methoxybenzyl)-5-nitro-1H-indazole

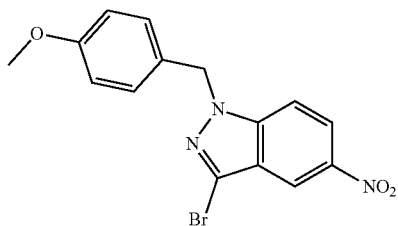 [SMILES: COc1ccc(Cn2nc(Br)c3cc([N+](=O)[O-])ccc32)cc1]

To a solution of 3-bromo-5-nitro-1H-indazole (2.42 g, 10 mmol) in DMF (10 mL) was added K₂CO₃ (4.15 g, 30 mmol) and 1-(chloromethyl)-4-methoxybenzene (2.92 mL, 20 mmol) and the mixture was stirred at 25° C. for 2 hrs. H₂O was added and the solid formed was filtered and washed with water and dried. The solid was triturated with Et₂O and dried to obtain 3-bromo-1-[(4-methoxyphenyl)methyl]-5-nitroindazole (3.57 g, 99%) as an off white solid. ¹H NMR (400 MHz, DMSO-d₆) δ 8.48 (d, J=2.1 Hz, 1H), 8.32 (dd, J=9.3, 2.2 Hz, 1H), 8.08 (d, J=9.3 Hz, 1H), 7.27 (d, J=8.7 Hz, 2H), 6.89 (d, J=8.7 Hz, 2H), 5.67 (s, 2H), 3.71 (s, 3H). MS-ESI (m/z) calc'd for $C_{15}H_{13}BrN_3O_3$ [M+H]⁺: 362.0/364.0. Found 362.0/364.0.

Step 2: 1-(4-Methoxybenzyl)-5-nitro-3-(prop-1-en-2-yl)-1H-indazole

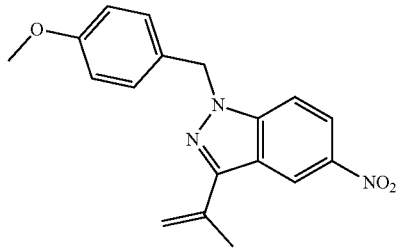 [SMILES: C=C(C)c1nn(Cc2ccc(OC)cc2)c2ccc([N+](=O)[O-])cc12]

To a solution of 3-bromo-1-(4-methoxybenzyl)-5-nitro-1H-indazole (1.09 g, 3 mmol) and 4,4,5,5-tetramethyl-2-(1-methylethenyl)-1,3,2-dioxaborolane (0.5 g, 3 mmol) in THF (12.5 mL) and H₂O (2.5 mL) was added K₂CO₃ (1.24 g, 9 mmol) and the mixture was purged with N₂ for 5 minutes. Pd(dppf)Cl₂ (0.11 g, 0.150 mmol) was added and the reaction was stirred under N₂ at 90° C. for 24 hrs. H₂O was added and the mixture was extracted with EtOAc (3×). The combined organic layers were passed through a phase separator and evaporated to obtain a brown residue which was purified by silica gel column chromatography using a 0-30% MeOH/EtOAc gradient eluent to afford the title compound (969.9 mg, 99%) as a yellow solid. ¹H NMR (400 MHz, DMSO-d₆) δ 8.81 (dd, J=2.1, 0.6 Hz, 1H), 8.25 (dd, J=9.3, 2.1 Hz, 1H), 7.96 (dd, J=9.2, 0.6 Hz, 1H), 7.25 (d, J=8.7 Hz, 2H), 6.88 (d, J=8.7 Hz, 2H), 5.89-5.82 (m, 1H), 5.67 (s, 2H), 5.50 (p, J=1.3 Hz, 1H), 3.70 (s, 3H), 2.28-2.24 (m, 3H). MS-ESI (m/z) calc'd for $C_{18}H_{18}N_3O_3$ [M+H]⁺: 324.1. Found 324.2.

428

Step 3: 3-Isopropyl-1-(4-methoxybenzyl)-1H-indazol-5-amine

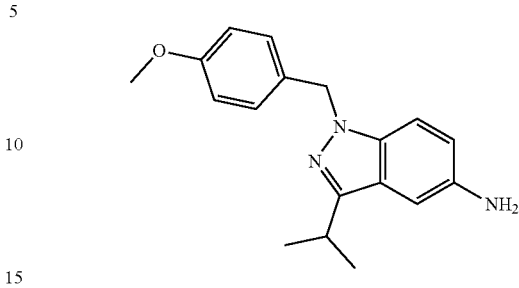

To a suspension of 1-(4-methoxybenzyl)-5-nitro-3-(prop-1-en-2-yl)-1H-indazole (969.9 mg, 3 mmol) in EtOH (30 mL) was added 10% Pd/C (319.21 mg, 0.300 mmol) and the mixture was hydrogenated at 6 bar for 4 hrs. The mixture was purified by strong cation exchange (SCX) using MeOH to wash the cartridge and NH₃/MeOH to wash out the desired product. The MeOH was evaporated under reduced pressure to afford the title compound (68 mg, 78%) as a dark solid. ¹H NMR (400 MHz, DMSO-d₆) δ 7.25 (dd, J=8.8, 0.8 Hz, 1H), 7.12 (d, J=8.7 Hz, 2H), 6.83 (d, J=8.7 Hz, 2H), 6.78 (dd, J=2.1, 0.8 Hz, 1H), 6.73 (dd, J=8.8, 2.0 Hz, 1H), 5.34 (s, 2H), 4.73 (s, 2H), 3.69 (s, 3H), 3.19 (hept, J=7.0 Hz, 1H), 1.32 (d, J=6.9 Hz, 6H). MS-ESI (m/z) calc'd for $C_{18}H_{22}N_3O$ [M+H]⁺: 296.2. Found 296.2.

Step 4: 3-Isopropyl-1H-indazol-5-amine

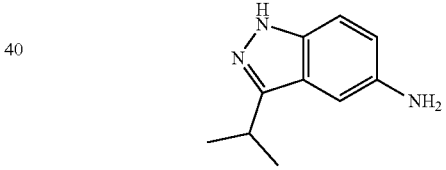

A solution of 3-isopropyl-1-(4-methoxybenzyl)-1H-indazol-5-amine (690.0 mg, 2.34 mmol) in trifluoroacetic acid (20 mL) was heated at 75° C. for 15 hrs. Analysis indicated incomplete reaction. The volume was then concentrated to ~10 mL and the solution was irradiated in a microwave reactor (I hr, 90° C., very high absorption, 3 rounds). The solvent was evaporated and the residue was taken up in MeOH. K₂CO₃ was added and the mixture was stirred at 50° C. for 24 hrs. The solvent was evaporated, the residue was taken up in H₂O, and the precipitate that formed was filtered and dried. The residue was purified by silica gel column chromatography using a 50-100% EtOAc/cyclohexane to afford the title compound (300 mg, 73%) as a beige solid. ¹H NMR (400 MHz, DMSO-d₆) δ 12.04 (s, 1H), 7.15 (dd, J=8.7, 0.8 Hz, 1H), 6.77 (d, J=1.9 Hz, 1H), 6.73 (dd, J=8.7, 2.0 Hz, 1H), 4.68 (s, 2H), 3.19 (hept, J=6.9 Hz, 1H), 1.32 (d, J=6.9 Hz, 6H). MS-ESI (m/z) calc'd for $C_{10}H_{13}N_3O$ [M+H]⁺: 176.1. Found 176.0.

Step 5: 6-Chloro-5-cyano-N-(3-isopropyl-1H-indazol-5-yl)-3,4-dimethylpicolinamide

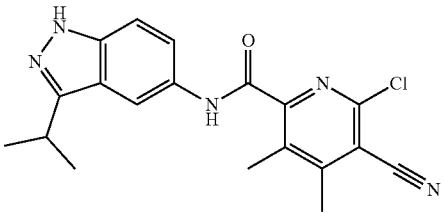 [SMILES: Cc1c(C(=O)Nc2ccc3[nH]nc(C(C)C)c3c2)nc(Cl)c(C#N)c1C]

Prepared as described for 3-chloro-5-cyano-N-(3-cyclopropyl-1H-indazol-5-yl)-4,6-dimethylpicolinamide (Example 283) using 6-chloro-5-cyano-3,4-dimethylpicolinic acid in place of 3-chloro-5-cyano-4,6-dimethylpicolinic acid and using 3-isopropyl-1H-indazol-5-amine in place of 3-cyclopropyl-1H-indazol-5-amine to afford the title compound (43 mg, 58%) as a yellow solid. $^1$H NMR (400 MHz, DMSO-$d_6$) δ 12.59 (s, 1H), 10.66 (s, 1H), 8.24 (d, J=1.9 Hz, 1H), 7.56 (dd, J=8.9, 1.9 Hz, 1H), 7.46 (d, J=8.9 Hz, 1H), 3.34 (h, J=7.0 Hz, 1H), 2.59 (s, 3H), 2.39 (s, 3H), 1.38 (d, J=6.9 Hz, 6H. MS-ESI (m/z) calc'd for $C_{19}H_{19}ClN_5O$ [M+H]$^+$: 368.1/370.1. Found 368.1/370.1.

Example 271: 6-Chloro-5-cyano-N-(3-ethyl-1H-indazol-5-yl)-3,4-dimethylpicolinamide

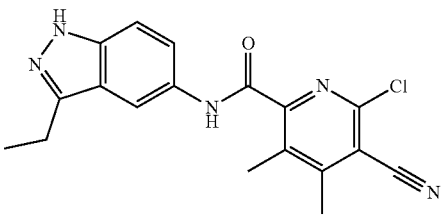

Step 1:
3-Bromo-1-(4-methoxybenzyl)-5-nitro-1H-indazole

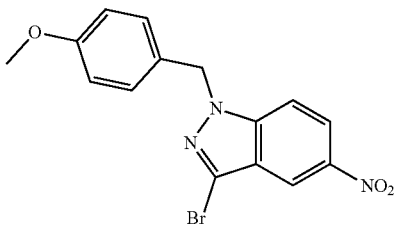 [SMILES: COc1ccc(Cn2nc(Br)c3cc([N+](=O)[O-])ccc32)cc1]

To a solution of 3-bromo-5-nitro-1H-indazole (2.42 g, 10 mmol) in DMF (10 mL) was added K$_2$CO$_3$ (4.15 g, 30 mmol) and 1-(chloromethyl)-4-methoxybenzene (2.92 mL, 20 mmol). The mixture was stirred at 25° C. for 2 hrs. H$_2$O was added and the solid that formed was filtered, washed with H$_2$O, and dried. The solid was triturated with Et$_2$O and dried to afford the title compound (3.57 g, 99%) as an off white solid. $^1$H NMR (400 MHz, DMSO-$d_6$) δ 8.48 (d, J=2.1 Hz, 1H), 8.32 (dd, J=9.3, 2.2 Hz, 1H), 8.08 (d, J=9.3 Hz, 1H), 7.27 (d, J=8.7 Hz, 2H), 6.89 (d, J=8.7 Hz, 2H), 5.67 (s, 2H), 3.71 (s, 3H). MS-ESI (m/z) calc'd for $C_{15}H_{13}BrN_3O_3$ [M+H]$^+$: 362.0/364.0. Found 362.0/364.0.

Step 2:
1-(4-Methoxybenzyl)-5-nitro-3-vinyl-1H-indazole

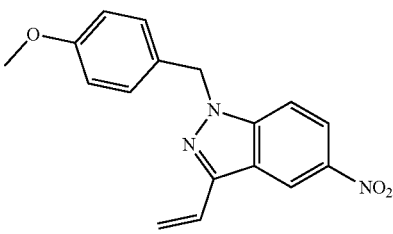 [SMILES: C=Cc1nn(Cc2ccc(OC)cc2)c2ccc([N+](=O)[O-])cc12]

To a solution of 3-bromo-1-(4-methoxybenzyl)-5-nitro-1H-indazole (1.09 g, 3 mmol) and 2-ethenyl-4,4,5,5-tetramethyl-1,3,2-dioxaborolane (0.51 mL, 3 mmol) in THF (12.5 mL)/H$_2$O (2.5 mL) was added K$_2$CO$_3$ (1.24 g, 9 mmol) and the mixture was purged with N$_2$ for 5 minutes. Pd(dppf)Cl$_2$ (0.11 g, 0.150 mmol) was added and the reaction was stirred under N$_2$ at 90° C. for 24 hours. H$_2$O was added and the mixture was extracted with EtOAc (3×). The combined organic layers were passed through a phase separator and concentrated. The residue was purified by silica gel column chromatography using a 0-30% MeOH/EtOAc gradient eluent to afford the title compound (794 mg, 86%) as an orange solid. $^1$H NMR (400 MHz, DMSO-$d_6$) δ 8.94 (dd, J=2.2, 0.6 Hz, 1H), 8.25 (dd, J=9.3, 2.1 Hz, 1H), 7.96 (dd, J=9.3, 0.6 Hz, 1H), 7.25 (d, J=8.7 Hz, 2H), 7.13 (dd, J=17.9, 11.4 Hz, 1H), 6.88 (d, J=8.7 Hz, 2H), 6.20 (dd, J=17.9, 1.1 Hz, 1H), 5.65 (s, 2H), 5.60 (dd, J=11.4, 1.1 Hz, 1H), 3.70 (s, 3H). MS-ESI (m/z) calc'd for $C_{17}H_{16}N_3O_3$ [M+H]$^+$: 310.1. Found 310.1.

Step 3:
3-Ethyl-1-(4-methoxybenzyl)-1H-indazol-5-amine

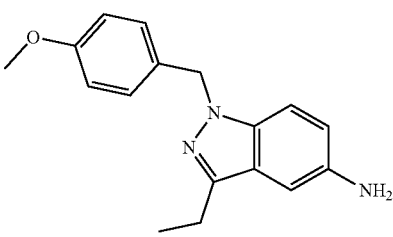 [SMILES: CCc1nn(Cc2ccc(OC)cc2)c2ccc(N)cc12]

To a suspension of 1-(4-methoxybenzyl)-5-nitro-3-vinyl-1H-indazole (794.0 mg, 2.57 mmol) in MeOH (25.67 mL) was added 10% Pd/C (273.17 mg, 0.260 mmol) and the mixture was hydrogenated at 6 bar for 1 hr. The catalyst was removed by filtration through Celite and the filtrate was purified by strong cation exchange (SCX) using MeOH to wash the cartride and NH$_3$/MeOH to wash out the desired product. The MeOH was evaporated under reduced pressure to afford the title compound (658 mg, 91%) as a red oil. $^1$H NMR (400 MHz, DMSO-$d_6$) δ 7.27 (dd, J=8.8, 0.8 Hz, 1H), 7.13 (d, J=8.6 Hz, 2H), 6.83 (d, J=8.8 Hz, 2H), 6.74 (dd, J=8.8, 2.0 Hz, 1H), 6.71 (dd, J=2.0, 0.8 Hz, 1H), 5.34 (s, 2H), 4.74 (s, 2H), 3.69 (s, 3H), 2.78 (q, J=7.6 Hz, 2H), 1.26

(t, J=7.6 Hz, 3H). MS-ESI (m/z) calc'd for C₁₇H₂₀N₃O [M+H]⁺: 282.2. Found 282.2.

Step 4: 3-Ethyl-1H-indazol-5-amine

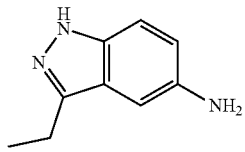

A solution of 3-ethyl-1-(4-methoxybenzyl)-1H-indazol-5-amine (658.0 mg, 2.34 mmol) in trifluoroacetic acid (10 mL) was irradiated in a microwave reactor (1 hr, 90° C.), then the mixture was diluted with MeOH. K₂CO₃ was added and the suspension was heated at 65° C. for 15 hrs. The solvent was evaporated and the residue was taken up in H₂O and extracted with EtOAc (2×). The combined organic layers were passed through a phase separator and concentrated to obtain a solid. MeOH was added, a suspension formed and the solid was filtered away. The MeOH layer was concentrated and the residue was purified by strong cation exchange (SCX) using MeOH to wash the cartridge and NH₃/MeOH to wash out the desired product. The MeOH was evaporated under reduced pressure to afford the title compound (337 mg, 89%) as a red solid. ¹H NMR (400 MHz, DMSO-d₆) δ 12.07 (s, 1H), 7.15 (dd, J=8.7, 0.9 Hz, 1H), 6.74 (dd, J=8.7, 2.0 Hz, 1H), 6.72-6.70 (m, 1H), 4.68 (s, 2H), 2.78 (q, J=7.6 Hz, 2H), 1.26 (t, J=7.6 Hz, 3H). MS-ESI (m/z) calc'd for C₉H₁₂N₃ [M+H]⁺: 162.1. Found 161.9.

Step 5: 6-Chloro-5-cyano-N-(3-ethyl-1H-indazol-5-yl)-3,4-dimethylpicolinamide

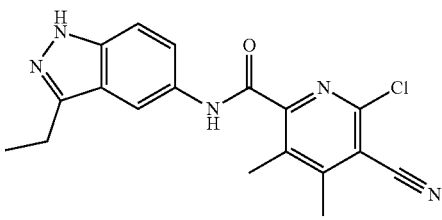

Prepared as described for 3-chloro-5-cyano-N-(3-cyclopropyl-1H-indazol-5-yl)-4,6-dimethylpicolinamide (Example 283) using 6-chloro-5-cyano-3,4-dimethylpicolinic acid in place of 3-chloro-5-cyano-4,6-dimethylpicolinic acid and using 3-ethyl-1H-indazol-5-amine in place of 3-cyclopropyl-1H-indazol-5-amine to afford the title compound (31.4 mg, 44%) as a yellow solid. ¹H NMR (400 MHz, DMSO-d₆) δ 12.62 (s, 1H), 10.67 (s, 1H), 8.20 (d, J=1.8 Hz, 1H), 7.53 (dd, J=8.9, 1.9 Hz, 1H), 7.46 (dd, J=8.8, 0.8 Hz, 1H), 2.91 (q, J=7.6 Hz, 2H), 2.59 (s, 3H), 2.39 (s, 3H), 1.32 (t, J=7.6 Hz, 3H). MS-ESI (m/z) calc'd for C₁₈H₁₇ClN₅O [M+H]⁺: 354.1/356.1. Found 354.1/356.1.

Example 272: 5-Cyano-3-methyl-N-(3-(pyridazin-4-yl)-1H-indazol-5-yl)picolinamide

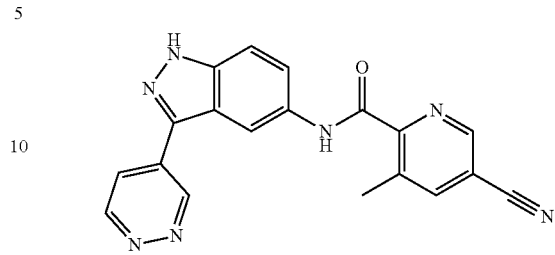

Prepared as described for 5-cyano-N-(3-(isoxazol-4-yl)-1H-indazol-5-yl)-3-methylpicolinamide using pyridazin-4-ylboronic acid in place of isoxazole-4-boronic acid and 5-cyano-N-(3-iodo-1H-indazol-5-yl)-3-methylpicolinamide in place of 5-cyano-N-(3-iodo-1H-indazol-5-yl)-3-methylpyridine-2-carboxamide to afford the title compound (6.1 mg, 12%) as a yellow solid. ¹H NMR (400 MHz, DMSO-d₆) δ 13.78 (s, 1H), 10.83 (s, 1H), 9.82 (dd, J=2.4, 1.3 Hz, 1H), 9.34 (dd, J=5.4, 1.3 Hz, 1H), 9.01 (d, J=1.9 Hz, 1H), 8.74 (d, J=1.7 Hz, 1H), 8.42 (dd, J=2.0, 0.9 Hz, 1H), 8.14 (dd, J=5.4, 2.4 Hz, 1H), 7.91 (dd, J=9.0, 1.9 Hz, 1H), 7.70 (d, J=9.0 Hz, 1H), 2.62 (s, 3H). MS-ESI (m/z) calc'd for C₁₉H₁₄N₇O [M+H]⁺: 356.1. Found 356.3.

Example 273: 5-Cyano-3-methyl-N-(3-(6-methylpyridazin-4-yl)-1H-indazol-5-yl)picolinamide

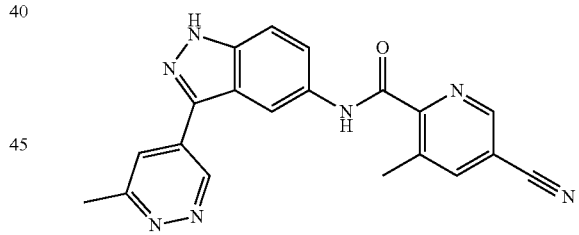

Prepared as described for 5-cyano-N-(3-(isoxazol-4-yl)-1H-indazol-5-yl)-3-methylpicolinamide using (6-methylpyridazin-4-yl)boronic acid in place of isoxazole-4-boronic acid and 5-cyano-N-(3-iodo-1H-indazol-5-yl)-3-methylpicolinamide in place of 5-cyano-N-(3-iodo-1H-indazol-5-yl)-3-methylpyridine-2-carboxamide to afford the title compound (26 mg, 47%) as a white solid. ¹H NMR (400 MHz, DMSO-d₆) δ 13.82 (s, 1H), 10.82 (s, 1H), 9.65 (d, J=2.1 Hz, 1H), 9.02 (d, J=1.9 Hz, 1H), 8.67 (d, J=1.8 Hz, 1H), 8.42 (d, J=1.9 Hz, 1H), 8.03 (d, J=2.1 Hz, 1H), 7.97 (dd, J=9.0, 1.8 Hz, 1H), 7.70 (d, J=9.0 Hz, 1H), 2.74 (s, 3H), 2.62 (s, 3H). MS-ESI (m/z) calc'd for C₂₀H₁₆N₇O [M+H]⁺: 370.1. Found 370.3.

Example 274: 3-Cyano-N-(3-methyl-1H-indazol-5-yl)-2-(prop-1-en-2-yl)benzamide

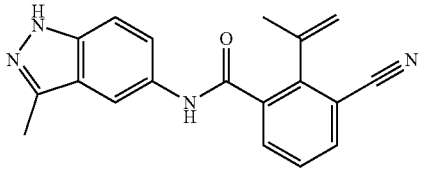

2-bromo-3-cyano-N-(3-methyl-1H-indazol-5-yl)benzamide (40.0 mg, 0.080 mmol) and 4,4,5,5-tetramethyl-2-(1-methylethenyl)-1,3,2-dioxaborolane (20.72 mg, 0.120 mmol) were dissolved in 1,4-dioxane (1 mL). Then $K_2CO_3$ (34.09 mg, 0.250 mmol) was added and the mixture was degassed with $N_2$ for 5 minutes. Tetrakis(triphenylphosphine)palladium(0) (9.5 mg, 0.010 mmol) was added and the mixture was stirred at 100° C. under $N_2$ for 6 hrs. 4,4,5,5-Tetramethyl-2-(1-methylethenyl)-1,3,2-dioxaborolane (20.72 mg, 0.120 mmol), KOAc (16.14 mg, 0.160 mmol) and water (0.250 mL) were then added and the mixture was stirred under $N_2$ for 5 min. Then Pd(amphos)$Cl_2$ (5.84 mg, 0.010 mmol) was added and the mixture was stirred under microwave irradiation at 100° C. for 30 min. The reaction mixture was partitioned between water and EtOAc. The phases were separated and the aqueous layer was extracted with EtOAc (2×). The combined organic phases were washed with brine (1×), dried over $Na_2SO_4$, and evaporated to dryness. The material was purified by silica gel column chromatography using a 0-80% EtOAc/cyclohexane gradient eluent. The residue was further purified by preparative HPLC using Method DC to afford the title compound (3 mg, 12%) as a white solid. $^1$H NMR (400 MHz, DMSO-$d_6$) δ 12.59 (s, 1H) 10.36 (s, 1H) 8.12 (s, 1H) 7.98 (dd, J=7.70, 1.32 Hz, 1H) 7.86 (dd, J=7.70, 1.10 Hz, 1H) 7.62 (t, J=7.81 Hz, 1H) 7.43 (d, J=1.10 Hz, 2H) 5.36 (t, J=1.54 Hz, 1H) 5.05 (s, 1H) 2.47 (s, 3H) 2.13 (s, 3H). MS-ESI (m/z) calc'd for $C_{19}H_{17}N_4O$ [M+H]$^+$: 317.1. Found 317.3.

Example 275: 3-Chloro-5-cyano-4,6-dimethyl-N-(3-methyl-1H-indazol-5-yl)picolinamide

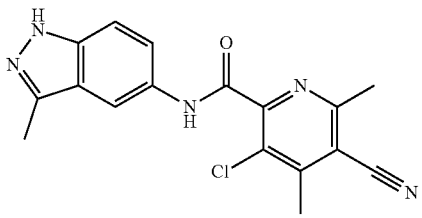 [SMILES: Cc1nc(C(=O)Nc2ccc3[nH]nc(C)c3c2)c(Cl)c(C)c1C#N]

Step 1: 2,5-Dichloro-3-cyano-4,6-dimethylpyridine 1-oxide

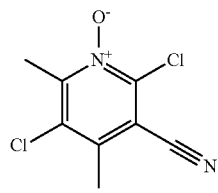

To a solution of 2,5-dichloro-4,6-dimethylpyridine-3-carbonitrile (2.01 g, 10 mmol) in trifluoroacetic acid (50 mL) was added hydrogen peroxide (3.06 mL, 30 mmol) and the mixture was stirred at 75° C. for 1 hr. The reaction was concentrated to afford the title compound (2.17 g, 99%) as a yellow oil which was used without further purification. MS-ESI (m/z) calc'd for $C_8H_7Cl_2N_2O$ [M+H]$^+$: 219.0. Found 219.0.

Step 2: 2,5-Dichloro-6-(hydroxymethyl)-4-methylnicotinonitrile

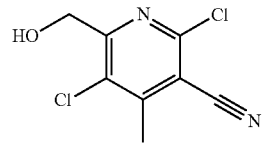

To a solution of 2,5-dichloro-3-cyano-4,6-dimethylpyridine 1-oxide (2.17 g, 10 mmol) in DCM (50 mL) was added trifluoroacetic anhydride (4.17 mL, 30 mmol) dropwise and the mixture was stirred at 25° C. for 15 hrs. The solvent was evaporated and the residue was taken up in MeOH. $K_2CO_3$ (3 g) was added and the suspension was stirred at 25° C. for 1 hr. The solvent was evaporated, the residue was taken up in $H_2O$ and extracted with DCM (3×), the combined organic layers were passed through a phase separator and concentrated to afford (1.9 g, 88%) as a yellow solid. $^1$H NMR (400 MHz, DMSO-$d_6$) δ 5.60 (t, J=6.3 Hz, 1H), 4.66 (d, J=6.3 Hz, 2H), 2.58 (s, 3H). MS-ESI (m/z) calc'd for $C_8H_7Cl_2N_2O$ [M+H]$^+$: 217.0/219.0. Found 219.0.

Step 3: 5-Chloro-6-(hydroxymethyl)-2,4-dimethylnicotinonitrile

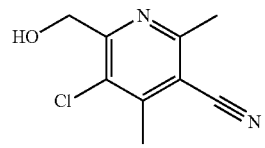

To a mixture of 2,5-dichloro-6-(hydroxymethyl)-4-methylnicotinonitrile (868.2 mg, 4 mmol), trimethylboroxine (0.56 mL, 4 mmol) and $K_2CO_3$ (552.84 mg, 4 mmol) in 1,4-dioxane (27 mL)/$H_2O$ (13 mL) was added tetrakis(triphenylphosphine)palladium(0) (462.22 mg, 0.400 mmol) and the mixture was stirred at 90° C. under $N_2$ for 15 hours. The mixture was diluted with $H_2O$ and extracted with DCM (3×). The combined organic layers were passed through a phase separator and concentrated. The residue was purified by silica gel column chromatography using a 12-100% EtOAc/cyclohexane gradient eluent to afford the title compound (120 mg, 15%) as a yellow solid. $^1$H NMR (400 MHz, DMSO-d$_6$) δ 5.35 (t, J=5.9 Hz, 1H), 4.65 (d, J=5.7 Hz, 2H), 2.66 (s, 3H), 2.54 (s, 3H). MS-ESI (m/z) calc'd for C$_9$H$_{10}$ClN$_2$O [M+H]$^+$: 197.0/199.0. Found 199.0.

Step 4: 3-Chloro-5-cyano-4,6-dimethylpicolinic acid

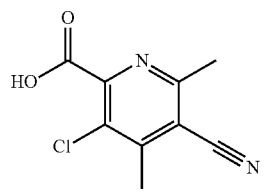

To a solution of 5-chloro-6-(hydroxymethyl)-2,4-dimethylnicotinonitrile (120.0 mg, 0.610 mmol) in acetone (5 mL) was added a solution of KMnO$_4$ (144.66 mg, 0.920 mmol) in water (1 mL) and the mixture was stirred at 25° C. for 4 hours. The solid formed was filtered and washed with acetone and water. The filtrate was concentrated to remove the acetone and the resulting aqueous layer was washed with EtOAc. The water was acidified by addition of conc. HCl and then extracted with EtOAc (3×). The combined organic layers were passed through a phase separator and concentrated to afford the title compound (98 mg, 76%) as an off white solid. $^1$H NMR (400 MHz, DMSO-d$_6$) δ 13.62 (s, 1H), 2.66 (s, 3H), 2.57 (s, 3H). MS-ESI (m/z) calc'd for C$_9$H$_8$ClN$_2$O$_2$ [M+H]$^+$: 211.0/213.0. Found 212.9.

Step 5: 3-Chloro-5-cyano-4,6-dimethyl-N-(3-methyl-1H-indazol-5-yl)picolinamide

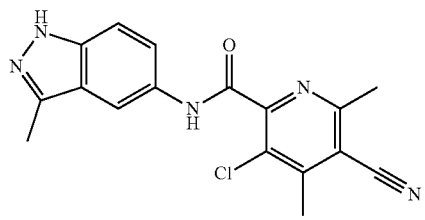 [SMILES: Cc1nc(C(=O)Nc2ccc3[nH]nc(C)c3c2)c(Cl)c(C)c1C#N]

Prepared as described for 3-chloro-5-cyano-N-(3-cyclopropyl-1H-indazol-5-yl)-4,6-dimethylpicolinamide (Example 283) using 3-chloro-5-cyano-4,6-dimethylpicolinic acid in place of 3-chloro-5-cyano-4,6-dimethylpicolinic acid and using 3-methyl-1H-indazol-5-amine in place of 3-cyclopropyl-1H-indazol-5-amine to afford the title compound (53 mg, 78%) as a yellow solid. $^1$H NMR (400 MHz, DMSO-d$_6$) δ 12.63 (s, 1H), 10.74 (s, 1H), 8.17 (s, 1H), 7.46 (s, 2H), 2.73 (s, 3H), 2.63 (s, 3H), 2.48 (s, 3H). MS-ESI (m/z) calc'd for C$_{17}$H$_{15}$ClN$_5$O [M+H]$^+$: 340.1/342.1. Found 340.1/342.1.

Example 276: 5-Cyano-N-(3-(cyclobutylidenemethyl)-1H-indazol-5-yl)-3,4-dimethylpicolinamide

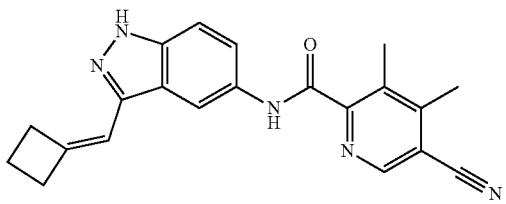 [SMILES: Cc1c(C#N)cnc(C(=O)Nc2ccc3[nH]nc(C=C4CCC4)c3c2)c1C]

Step 1: 2-(Cyclobutylidenemethyl)-4,4,5,5-tetramethyl-1,3,2-dioxaborolane

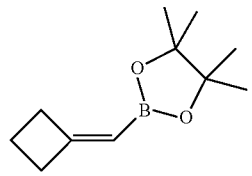

To a solution of 2,2,6,6-tetramethylpiperidine (1.21 g, 8.56 mmol, 1.45 mL) in 15 mL of dry THF was added n-BuLi (2.5 M, 3.42 mL) dropwise under an N$_2$ atmosphere at −30° C. and the mixture was stirred at −30° C. for 0.5 hr. The reaction was then cooled to −78° C. and a solution of bis(4,4,5,5-tetramethyl-1,3,2-dioxaborolan-2-yl)methane (1.91 g, 7.13 mmol) in 15 mL of dry THF was added dropwise. The reaction mixture was stirred at −78° C. for 0.5 hr and a solution of cyclobutanone (500 mg, 7.13 mmol, 533.05 uL) in 14 mL of dry THF was added dropwise. The reaction mixture was then warmed to 20° C. and stirred for an additional 12 hrs. The reaction mixture was slowly poured into 20 mL of saturated aqueous NH$_4$Cl at 0° C. and after stirring for 1 hr, the solution was diluted with H$_2$O (10 mL) and extracted with EtOAc (20 mL×3). The organic phase was dried over Na$_2$SO$_4$, filtered and concentrated under reduced pressure to afford the title compound (1.2 g) as a yellow oil which was used without further purification.

Step 2: 5-Cyano-N-(3-(cyclobutylidenemethyl)-1H-indazol-5-yl)-3,4-dimethylpicolinamide

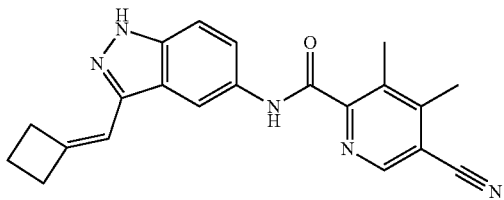 [SMILES: Cc1c(C#N)cnc(C(=O)Nc2ccc3[nH]nc(C=C4CCC4)c3c2)c1C]

A mixture of N-(3-bromo-1H-indazol-5-yl)-5-cyano-3,4-dimethylpicolinamide (100 mg, 270.12 umol), 2-(cyclobutylidenemethyl)-4,4,5,5-tetramethyl-1,3,2-dioxaborolane (314.55 mg, 1.62 mmol), AcOK (79.53 mg, 810.37 umol), and Pd(Amphos)Cl$_2$ (19.13 mg, 27.01 umol) in 4 mL of EtOH and 0.8 mL of H$_2$O was degassed and purged with N₂ (3×) at 20° C. The mixture was then stirred at 90° C. for 12 hrs under an N₂ atmosphere. The reaction mixture was concentrated and diluted with 5 mL of H₂O and extracted with EtOAc (5 mL×4). The organic phase was dried over Na₂SO₄, filtered, and the filtrate was concentrated under reduced pressure to give a residue. The residue was diluted with 1 mL of MeCN and 1 mL of DMF. Then the mixture was filtered and the solid was dried in vacuum to afford the title compound (16.14 mg, 16%) as a gray solid. ¹H NMR (400 MHz, DMSO-d₆) δ 12.89 (s, 1H), 10.64 (s, 1H), 8.88 (s, 1H), 8.30 (s, 1H), 7.54-7.59 (m, 1H), 7.45-7.50 (m, 1H), 6.39 (t, J=2.32 Hz, 1H), 3.07 (br t, J=7.89 Hz, 2H), 2.88-2.93 (m, 2H), 2.55 (s, 3H), 2.44 (s, 3H), 2.06 (quin, J=7.82 Hz, 2H). MS-ESI (m/z) calcd for $C_{21}H_{20}N_5O$ [M+H]⁺: 358.2. Found 358.1.

Example 277: 5-Cyano-3,4-dimethyl-N-(3-(2-morpholinopyridin-4-yl)-1H-indazol-5-yl)picolinamide

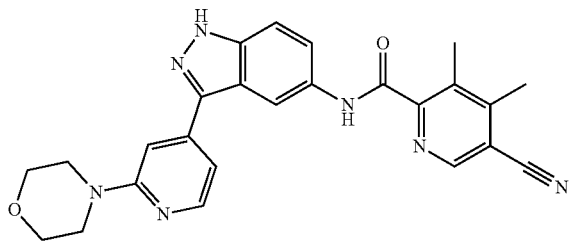 [SMILES: Cc1c(C#N)cnc(C(=O)Nc2ccc3[nH]nc(-c4ccnc(N5CCOCC5)c4)c3c2)c1C]

A mixture of N-(3-bromo-1H-indazol-5-yl)-5-cyano-3,4-dimethylpicolinamide (100 mg, 270.12 umol), (2-morpholino-4-pyridyl) boronic acid (84.29 mg, 405.18 umol), Pd(Amphos)Cl₂ (19.13 mg, 27.01 umol) and AcOK (79.53 mg, 810.37 umol) in 2 mL of EtOH and 0.4 mL of H₂O was degassed and purged with N₂ (3×) at 20° C. The mixture was stirred at 90° C. for 1 hr under an N₂ atmosphere. The reaction mixture was concentrated under reduced pressure and purified by preparative-HPLC using Method CO to afford the title compound (13.41 mg, 9%) as a white solid, TFA salt. ¹H NMR (400 MHz, DMSO-d₆) δ 13.73 (br s, 1H), 10.82 (s, 1H), 8.91 (s, 1H), 8.72 (s, 1H), 8.25 (d, 1H, J=5.7 Hz), 7.78 (dd, 1H, J=1.7, 9.0 Hz), 7.68 (d, 1H, J=9.0 Hz), 7.49 (br s, 1H), 7.38 (br d, 1H, J=5.3 Hz), 3.7-3.8 (m, 4H), 3.63 (br s, 4H), 2.56 (s, 3H), 2.45 (s, 3H). MS-ESI (m/z) calcd for $C_{25}H_{24}N_7O_2$ (M+H)⁺: 454.2. Found 454.2.

Example 278: 6-Chloro-5-cyano-3,4-dimethyl-N-(3-(2-morpholinopyridin-4-yl)-1H-indazol-5-yl)picolinamide

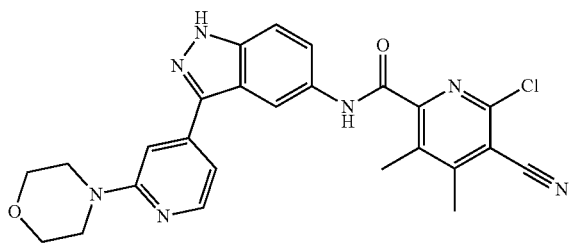 [SMILES: Cc1c(C(=O)Nc2ccc3[nH]nc(-c4ccnc(N5CCOCC5)c4)c3c2)nc(Cl)c(C#N)c1C]

Step 1: 4-(4-Bromopyridin-2-yl)morpholine

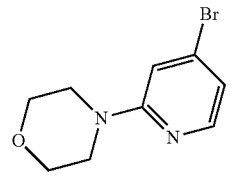 [SMILES: Brc1ccnc(N2CCOCC2)c1]

To a solution of 4-bromo-2-fluoropyridine (2 g, 11.36 mmol) in 10 mL of DMF was added morpholine (1.19 g, 13.64 mmol) and Cs₂CO₃ (7.41 g, 22.73 mmol) at 20° C. and the mixture was stirred at 100° C. for 12 hrs. The reaction mixture was diluted with 40 mL of H₂O and extracted with EtOAc (20 mL×3). The combined organic layers were dried over Na₂SO₄ and filtered. The filtrate was concentrated and purified by flash silica gel chromatography (ISCO; 12 g SepaFlash column) using a 0-8% EtOAc/petroleum ether gradient eluent to afford the title compound (2.13 g, 75%) as a white solid. MS-ESI (m/z) calcd for $C_9H_{12}BrN_2O$ [M+H]⁺: 243.0/245.0. Found 243.0/245.0.

Step 2: (2-Morpholinopyridin-4-yl)boronic acid

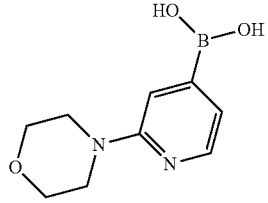 [SMILES: OB(O)c1ccnc(N2CCOCC2)c1]

A mixture of 4-(4-bromopyridin-2-yl)morpholine (1 g, 4.11 mmol), bis(pinacolato)diboron (1.25 g, 4.94 mmol), AcOK (1.01 g, 10.28 mmol), Pd(dppf)Cl₂ (300.99 mg, 411.35 umol) in 15 mL of dioxane was degassed and purged with N₂ (3×) at 20° C., and then the mixture was stirred at 80° C. for 12 hrs under an N₂ atmosphere. The mixture was filtered, the filtrate was concentrated under reduced pressure to afford the title compound (0.85 g) as black oil, which was used without further purification. MS-ESI (m/z) calcd for $C_9H_{14}BN_2O_3$ [M+H]⁺: 209.1. Found 209.2.

Step 3: 3-(2-Morpholinopyridin-4-yl)-1H-indazol-5-amine

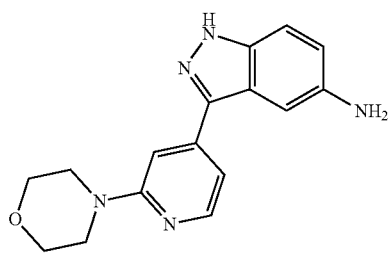 [SMILES: Nc1ccc2[nH]nc(-c3ccnc(N4CCOCC4)c3)c2c1]

A mixture of (2-morpholinopyridin-4-yl)boronic acid (235.45 mg, 1.13 mmol), 3-bromo-1H-indazol-5-amine (200 mg, 943.19 umol), Pd(Amphos)Cl$_2$ (66.78 mg, 94.32 umol), AcOK (277.69 mg, 2.83 mmol) in 2 mL of EtOH and 0.5 mL of H$_2$O was degassed and purged with N$_2$ (3×) at 20° C., and then the mixture was stirred at 100° C. for 12 hrs under a N$_2$ atmosphere. The reaction mixture was diluted with 30 mL of H$_2$O and extracted with EtOAc (40 mL×5), the combined organic layers were dried over solid Na$_2$SO$_4$, filtered, and the filtrate was concentrated under reduced pressure to give a residue. The residue was purified by preparative-TLC (SiO$_2$, petroleum ether/EtOAc=1/3, P1 Rf=0.15) to afford the title compound (58 mg, 21%) as a yellow solid. MS-ESI (m/z) calcd for C$_{16}$H$_{18}$N$_5$O [M+H]$^+$: 296.1. Found 296.1.

Step 4: 6-Chloro-5-cyano-3,4-dimethyl-N-(3-(2-morpholinopyridin-4-yl)-1H-indazol-5-yl)picolinamide

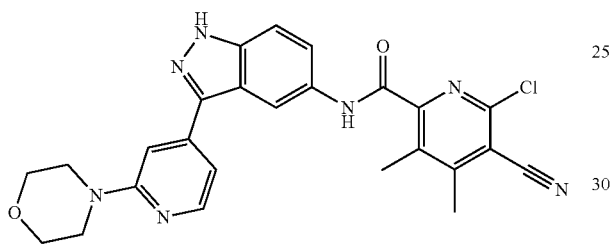

To a solution of 3-(2-morpholinopyridin-4-yl)-1H-indazol-5-amine (53 mg, 179.46 umol) in 3 mL of DCM was added 6-chloro-5-cyano-3,4-dimethylpicolinic acid (31.50 mg, 149.55 umol), Et$_3$N (45.40 mg, 448.64 umol) and T3P (50 wt % in EtOAc, 123.71 mg, 194.41 umol, 115.62 uL). The mixture was stirred at 15° C. for 12 hrs. The reaction mixture was concentrated under reduced pressure and purified by preparative-HPLC using Method AP to afford the title compound (16.48 mg, 22%) as a yellow solid. $^1$H NMR (400 MHz, DMSO-d$_6$) δ 13.50 (s, 1H) 10.82 (s, 1H) 8.62 (s, 1H) 8.29 (d, J=5 Hz, 1H) 7.70-7.77 (m, 1H) 7.62-7.68 (m, 1H) 7.30 (s, 1H) 7.25 (d, J=5 Hz, 1H) 3.69-3.79 (m, 4H) 3.49-3.59 (m, 4H) 2.60 (s, 3H) 2.40 (s, 3H). MS-(ESI) (m/z) calcd for C$_{25}$H$_{23}$ClN$_7$O$_2$ (M+H)$^+$: 488.2/490.2. Found 488.2/490.2.

Example 279: 5-Cyano-N-(3-(2-ethylpyridin-4-yl)-1H-indazol-5-yl)-3,4-dimethylpicolinamide

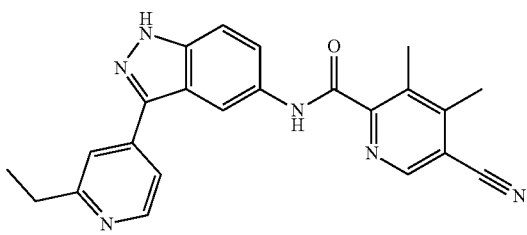 [SMILES: CCc1cc(-c2n[nH]c3ccc(NC(=O)c4ncc(C#N)c(C)c4C)cc23)ccn1]

Step 1: (2-Ethylpyridin-4-yl)boronic acid

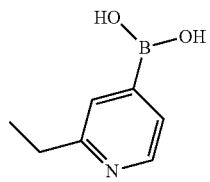

To a solution of 4-bromo-2-ethyl-pyridine (70 mg, 376.25 umol) in 1 mL of dioxane was added bis(pinacolato)diboron (114.65 mg, 451.49 umol), AcOK (111.15 mg, 1.13 mmol) and Pd(dppf)Cl$_2$ (12.39 mg, 16.93 umol) at 20° C. The mixture was degassed and purged with N$_2$ (3×), and then stirred at 80° C. for 12 hrs under an N$_2$ atmosphere. The reaction mixture was concentrated under reduced pressure to afford the title compound (50 mg) as a black solid which was used without further purification. MS-ESI (m/z) calcd for C$_7$H$_{11}$BNO$_2$ [M+H]$^+$: 152.1. Found 152.1.

Step 2: 5-Cyano-N-(3-(2-ethylpyridin-4-yl)-1H-indazol-5-yl)-3,4-dimethylpicolinamide

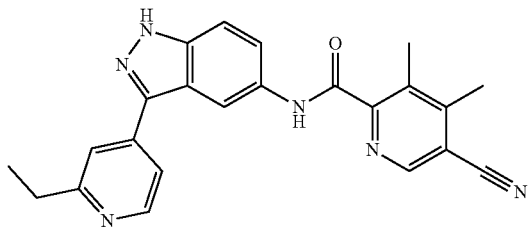 [SMILES: CCc1cc(-c2n[nH]c3ccc(NC(=O)c4ncc(C#N)c(C)c4C)cc23)ccn1]

A mixture of (2-ethyl-4-pyridyl) boronic acid (50 mg, 331.19 umol), N-(3-bromo-1H-indazol-5-yl)-5-cyano-3,4-dimethylpicolinamide (122.61 mg, 331.19 umol), AcOK (97.51 mg, 993.57 umol) and Pd(Amphos)Cl$_2$ (23.45 mg, 33.12 umol, 23.45 uL) in 2 mL of EtOH and 0.5 mL of H$_2$O was degassed and purged with N$_2$ (3×), and then the mixture was stirred at 100° C. for 2 hrs under an N$_2$ atmosphere. The reaction mixture was concentrated under reduced pressure to remove solvent and diluted with 20 mL of EtOAc. The mixture was filtered, the filtrate was concentrated and purified by preparative HPLC using Method CP to afford the title compound (25.14 mg, 15%) as a white solid TFA salt. $^1$H NMR (400 MHz, DMSO-d$_6$) δ 14.06 (br s, 1H), 10.87 (s, 1H), 8.91 (s, 1H), 8.81 (d, J=6.0 Hz, 1H), 8.77 (s, 1H), 8.24 (s, 1H), 8.17 (br d, J=5.5 Hz, 1H), 7.86-7.81 (m, 1H), 7.77-7.72 (m, 1H), 3.03 (q, J=7.5 Hz, 2H), 2.56 (s, 3H), 2.47 (s, 3H), 1.38 (t, J=7.6 Hz, 3H), MS-ESI (m/z) calcd for C$_{23}$H$_{21}$N$_6$O [M+H]$^+$: 397.2. Found 397.2.

Example 280: 5-Cyano-3,4-dimethyl-N-(3-(1-methyl-2-oxo-1,2-dihydropyridin-3-yl)-1H-indazol-5-yl)picolinamide

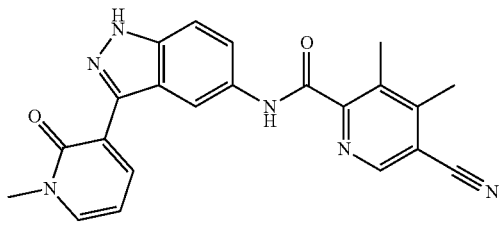 [SMILES: Cc1c(C#N)cnc(C(=O)Nc2ccc3[nH]nc(-c4cccn(C)c4=O)c3c2)c1C]

Step 1: (1-Methyl-2-oxo-1,2-dihydropyridin-3-yl)boronic acid

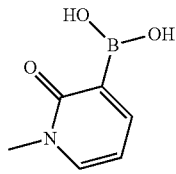

A mixture of 3-bromo-1-methyl-pyridin-2-one (70 mg, 372.30 umol), KOAc (109.61 mg, 1.12 mmol), bis(pinacolato)diboron (141.81 mg, 558.45 umol) and Pd(dppf)Cl₂.CH₂Cl₂ (15.20 mg, 18.61 umol) in 2 mL of dioxane was degassed and purged with N₂ (3×) at 20° C., and then the mixture was stirred at 100° C. for 3 hrs under an N₂ atmosphere. The reaction mixture was concentrated under reduced pressure to afford the title compound (60 mg) as a black solid, which was used without further purification. MS-ESI (m/z) calcd for C₆H₉BNO₃ [M+H]⁺: 154.1. Found 154.1.

Step 2: 5-Cyano-3,4-dimethyl-N-(3-(1-methyl-2-oxo-1,2-dihydropyridin-3-yl)-1H-indazol-5-yl)picolinamide

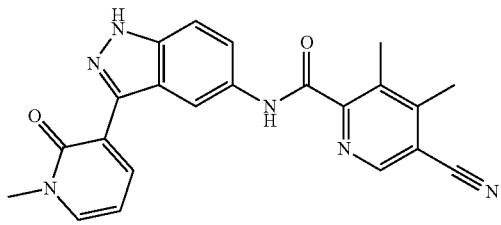 [SMILES: Cc1c(C#N)cnc(C(=O)Nc2ccc3[nH]nc(-c4cccn(C)c4=O)c3c2)c1C]

A mixture of (1-methyl-2-oxo-1,2-dihydropyridin-3-yl)boronic acid (60 mg, 392.30 umol), 5-cyano-N-(3-iodo-1H-indazol-5-yl)-3,4-dimethylpicolinamide (181.86 mg, 435.89 umol), Pd(Amphos)C₁₂ (30.86 mg, 43.59 umol, 30.86 uL) and AcOK (128.34 mg, 1.31 mmol) in 2 mL of EtOH and 0.5 mL of H₂O was degassed and purged with N₂ (3×) at 20° C., and then the mixture was stirred at 100° C. for 12 hrs under an N₂ atmosphere. The reaction mixture was concentrated under reduced pressure to remove solvent and purified by preparative HPLC using Method CQ. The material was further purified by preparative HPLC using Method CR to afford the title compound (6.38 mg, 4%) as a pale yellow solid. ¹H NMR (400 MHz, MeOD) δ 8.72 (s, 1H), 8.25 (s, 1H), 7.90 (br d, J=6.8 Hz, 1H), 7.77 (br d, J=5.7 Hz, 1H), 7.71 (br d, J=8.3 Hz, 1H), 7.55 (br d, J=8.9 Hz, 1H), 6.51 (br t, J=6.8 Hz, 1H), 3.69 (s, 3H), 2.61 (s, 3H), 2.58 (s, 3H). MS-ESI (m/z) calcd for C₂₂H₁₉N₆O₂ [M+H]⁺: 399.2. Found 399.1.

Example 281: (E)-5-Cyano-3,4-dimethyl-N-(3-(2-(pyridin-4-yl)vinyl)-1H-indazol-5-yl)picolinamide

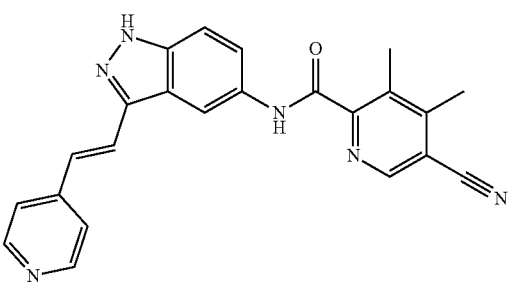 [SMILES: Cc1c(C#N)cnc(C(=O)Nc2ccc3[nH]nc(/C=C/c4ccncc4)c3c2)c1C]

Step 1: (E)-(2-(Pyridin-4-yl)vinyl)boronic acid

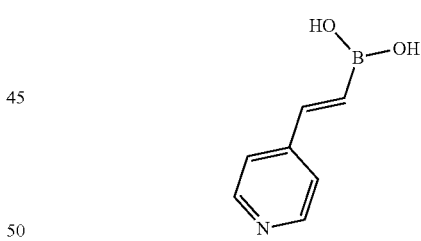

A mixture of 4-bromopyridine (0.5 g, 3.16 mmol), 4,4,5,5-tetramethyl-2-vinyl-1,3,2-dioxaborolane (536.14 mg, 3.48 mmol, 590.46 uL), tri-tert-butylphosphonium tetrafluoroborate (91.82 mg, 316.46 umol), DIPEA (818.02 mg, 6.33 mmol, 1.10 mL) and Pd₂(dba)₃ (144.90 mg, 158.23 umol) in 4 mL of toluene was degassed and purged with N₂ (3×) at 20° C., then the mixture was stirred at 100° C. for 3 hrs under an N₂ atmosphere. The mixture was filtered and the filtrate was concentrated under vacuum to afford the title compound (1 g) as a yellow oil, which was used without further purification. MS-ESI (m/z) calcd for C₇H₉BNO₂ [M+H]⁺: 150.1. Found 150.1.

Step 2: (E)-5-Cyano-3,4-dimethyl-N-(3-(2-(pyridin-4-yl)vinyl)-1H-indazol-5-yl)picolinamide

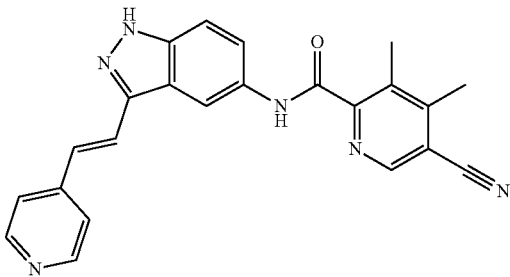 [SMILES: Cc1c(C#N)cnc(C(=O)Nc2ccc3[nH]nc(/C=C/c4ccncc4)c3c2)c1C]

A mixture of 5-cyano-N-(3-iodo-1H-indazol-5-yl)-3,4-dimethylpicolinamide (100 mg, 239.69 umol), (E)-(2-(pyridin-4-yl)vinyl)boronic acid (107.11 mg, 719.07 umol), Pd(Amphos)Cl$_2$ (16.97 mg, 23.97 umol, 16.97 uL) and AcOK (70.57 mg, 719.07 umol) in 2 mL of EtOH and 0.5 mL of H$_2$O was degassed and purged with N$_2$ (3×) at 20° C., and then the mixture was stirred at 100° C. for 12 hrs under an N$_2$ atmosphere. The reaction mixture was concentrated under reduced pressure to remove solvent and then purified by preparative-HPLC using Method CS to afford the title compound (55.35 mg, 45%) as an orange solid, TFA salt. $^1$H NMR (400 MHz, DMSO-d$_6$) δ 13.67 (br s, 1H), 10.75 (s, 1H), 8.91 (s, 1H), 8.78 (br d, J=6.1 Hz, 2H), 8.67 (s, 1H), 8.26-8.21 (m, 3H), 7.72-7.67 (m, 1H), 7.66-7.61 (m, 1H), 7.58 (d, J=16.4 Hz, 1H), 2.57 (s, 3H), 2.48 (s, 3H). MS-ESI (m/z) calcd for C$_{23}$H$_{19}$N$_6$O [M+H]$^+$: 395.2. Found 395.0.

Example 282: (E)-6-chloro-5-cyano-3,4-dimethyl-N-(3-(prop-1-en-1-yl)-1H-indazol-5-yl)picolinamide

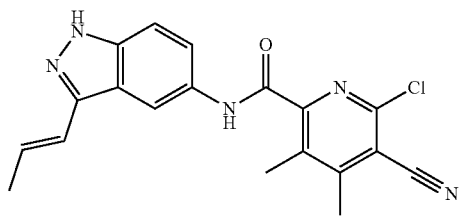 [SMILES: C/C=C/c1n[nH]c2ccc(NC(=O)c3nc(Cl)c(C#N)c(C)c3C)cc12]

Step 1: (E)-3-(prop-1-en-1-yl)-1H-indazol-5-amine

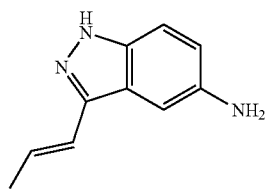

To a solution of 3-bromo-1H-indazol-5-amine (150 mg, 707.39 umol) and 4,4,5,5-tetramethyl-2-[(E)-prop-1-enyl]-1,3,2-dioxaborolane (136.70 mg, 813.50 umol) in 6 mL of EtOH and 1.5 mL of H$_2$O was added AcOK (208.27 mg, 2.12 mmol) and Pd(Amphos)Cl$_2$ (50.09 mg, 70.74 umol) at 15° C. under an N$_2$ atmosphere. Then the reaction mixture was stirred at 80° C. for 12 hrs under an N$_2$ atmosphere. The reaction mixture was concentrated and the residue was diluted with 20 mL of H$_2$O and extracted with EtOAc (15 mL×3). The combined organic phases were dried over Na$_2$SO$_4$, filtered, and the filtrate was concentrated to give a residue. The residue was purified by preparative-TLC (SiO$_2$, petroleum ether/EtOAc=0:1, R$_f$=0.43) to afford the title compound (75 mg, 13%) as a red solid. MS-(ESI) (m/z) calcd for C$_{10}$H$_{12}$N$_3$ [M+H]$^+$: 174.1. Found 174.1.

Step 2: (E)-6-Chloro-5-cyano-3,4-dimethyl-N-(3-(prop-1-en-1-yl)-1H-indazol-5-yl)picolinamide

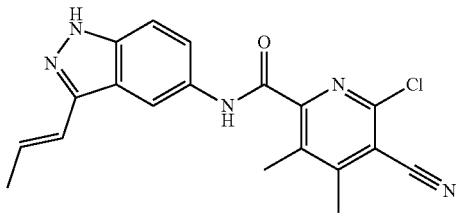 [SMILES: C/C=C/c1n[nH]c2ccc(NC(=O)c3nc(Cl)c(C#N)c(C)c3C)cc12]

To a solution of 6-chloro-5-cyano-3,4-dimethyl-pyridine-2-carboxylic acid (55 mg, 261.14 umol) and (E)-3-(prop-1-en-1-yl)-1H-indazol-5-amine (49.76 mg, 287.25 umol) in 10 mL of dry CH$_2$C$_{12}$ was added Et$_3$N (79.27 mg, 783.41 umol) and the reaction mixture was stirred at 20° C. for 0.5 hr. Then T3P (50 wt % in EtOAc, 249.27 mg, 391.71 umol, 232.96 uL) was added and the reaction mixture was stirred at 20° C. for 12 hrs. The reaction mixture was then concentrated and purified by preparative-HPLC using Method CT to afford the title compound (24.38 mg, 13%) as a pale yellow solid. $^1$H NMR (400 MHz, DMSO-d$_6$) δ 12.94 (br s, 1H), 10.71 (br s, 1H), 8.42 (s, 1H), 7.68-7.56 (m, 1H), 7.51 (br d, J=8.8 Hz, 1H), 6.72 (br d, J=16.0 Hz, 1H), 6.50 (br dd, J=6.5, 15.9 Hz, 1H), 2.59 (s, 3H), 2.39 (s, 3H), 1.95 (br d, J=6.1 Hz, 3H). MS-(ESI) (m/z) calcd for C$_{19}$H$_{17}$ClN$_5$O (M+H)$^+$: 366.1. Found 366.0.

Example 283: 3-Chloro-5-cyano-N-(3-cyclopropyl-1H-indazol-5-yl)-4,6-dimethylpicolinamide

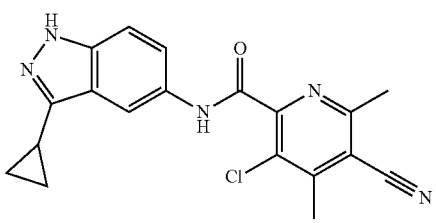 [SMILES: Cc1nc(C(=O)Nc2ccc3[nH]nc(C4CC4)c3c2)c(Cl)c(C)c1C#N]

Step 1: 2,5-Dichloro-3-cyano-4,6-dimethylpyridine 1-oxide

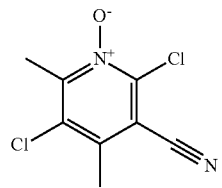

To a solution of 2,5-dichloro-4,6-dimethylpyridine-3-carbonitrile (2.01 g, 10 mmol) in trifluoroacetic acid (50 mL) was added hydrogen peroxide (3.06 mL, 30 mmol) and the mixture was stirred at 75° C. for 1 hr. The solvent was evaporated to afford the title compound (2.17 g, 99%) as a yellow oil. $^1$H NMR (400 MHz, DMSO-d$_6$) δ 2.62 (s, 3H), 2.53 (s, 3H). MS-(ESI) (m/z) calcd for $C_8H_7Cl_2N_2O$ (M+H)$^+$: 217.0/219.0. Found 217.0/219.0

Step 2: 2,5-Dichloro-6-(hydroxymethyl)-4-methylnicotinonitrile

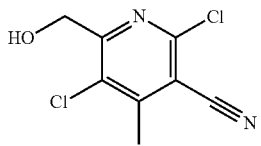

To a solution of 2,5-dichloro-3-cyano-4,6-dimethylpyridine 1-oxide (2.17 g, 10 mmol) in DCM (50 mL) was added trifluoroacetic anhydride (4.17 mL, 30 mmol) dropwise and the mixture was stirred at 25° C. for 15 hrs. The solvent was then evaporate and the residue was taken up in MeOH. K$_2$CO$_3$ (3 g) was added and the suspension was stirred at 25° C. for 1 hr. The solvent was evaporated to give a residue that was taken up in water and extracted with DCM (3×). The combined organic layers were passed through a phase separator and evaporated to afford the title compound (1.9 g, 88%) as a yellow solid. $^1$H NMR (400 MHz, DMSO-d$_6$) δ 5.60 (t, J=6.3 Hz, 1H), 4.66 (d, J=6.3 Hz, 2H), 2.58 (s, 3H). MS-(ESI) (m/z) calcd for $C_8H_7Cl_2N_2O$ (M+H)$^+$: 217.0/219.0. Found 217.0/219.0.

Step 3: 5-Chloro-6-(hydroxymethyl)-2,4-dimethylnicotinonitrile

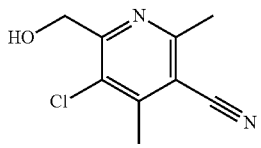

To a mixture of 2,5-dichloro-6-(hydroxymethyl)-4-methylnicotinonitrile (868.2 mg, 4 mmol), 2,4,6-trimethyl-1,3,5,2,4,6-trioxatriborinane (0.56 mL, 4 mmol) and potassium carbonate (552.84 mg, 4 mmol) in 1,4-dioxane (27 mL) and H$_2$O (13 mL) was added tetrakis(triphenylphosphine)palladium(0) (462.22 mg, 0.400 mmol) and the mixture was stirred at 90° C. under N$_2$ for 15 hrs. The mixture was diluted with water and extracted with DCM (3×), the combined organic layers were passed through a phase separator and evaporated to obtain a dark residue which was purified by silica gel column chromatography using a 50-100% EtOAc/cyclohexane gradient eluent to afford the title compound (120 mg, 15%) as a yellow solid. $^1$H NMR (400 MHz, DMSO-d$_6$) δ 5.35 (t, J=5.9 Hz, 1H), 4.65 (d, J=5.7 Hz, 2H), 2.66 (s, 3H), 2.54 (s, 3H). MS-(ESI) (m/z) calcd for $C_9H_{10}ClN_2O$ (M+H)$^+$: 197.0/199.0. Found 197.0/199.0.

Step 4: 3-Chloro-5-cyano-4,6-dimethylpicolinic acid

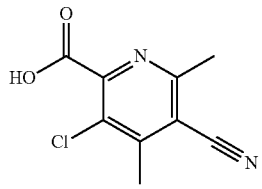

To a solution of 5-chloro-6-(hydroxymethyl)-2,4-dimethylpyridine-3-carbonitrile (120.0 mg, 0.610 mmol) in acetone (5 mL) was added a solution of potassium permanganate (144.66 mg, 0.920 mmol) in H$_2$O (1 mL) and the mixture was stirred at 25° C. for 4 hrs. A solid formed that was removed by filtration and washed with acetone and H$_2$O. The filtrate was concentrated and the resulting aqueous mixture was washed with EtOAc and then acidified by addition of conc. HCl and then extracted with EtOAc (3×). The combined organic layers were passed through a phase separator and evaporated to afford the title compound (98 mg, 76%) as an off-white solid. $^1$H NMR (400 MHz, DMSO-d$_6$) δ 13.62 (s, 1H), 2.66 (s, 3H), 2.57 (s, 3H). MS-(ESI) (m/z) calcd for $C_9H_8ClN_2O_2$(M+H)$^+$: 211.0/213.0. Found 210.9/212.9.

Step 5: 3-Chloro-5-cyano-N-(3-cyclopropyl-1H-indazol-5-yl)-4,6-dimethylpicolinamide

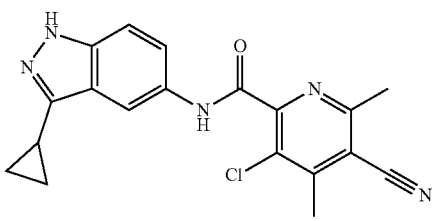 [SMILES: Cc1nc(C(=O)Nc2ccc3[nH]nc(C4CC4)c3c2)c(Cl)c(C)c1C#N]

To a mixture of 3-chloro-5-cyano-4,6-dimethylpicolinic acid (43.0 mg, 0.200 mmol), 3-cyclopropyl-1H-indazol-5-amine (35.36 mg, 0.200 mmol) and Et$_3$N (28.46 uL, 0.200 mmol) in MeCN (2.389 mL) was added HATU (77.63 mg, 0.200 mmol) and the reaction was stirred at 25° C. for 24 hours. Water was added and a solid formed that was collected by filtration and dried to give the title compound (60 mg, 80%) as a yellow solid. $^1$H NMR (400 MHz, DMSO-d$_6$) δ 12.56 (s, 1H), 10.73 (s, 1H), 8.24 (s, 1H), 7.48 (dd, J=9.0, 1.8 Hz, 1H), 7.44 (d, J=8.9 Hz, 1H), 2.73 (s, 3H), 2.63 (s, 3H), 2.21 (td, J=8.5, 4.3 Hz, 1H), 1.06-0.86 (m, 4H). MS-(ESI) (m/z) calcd for $C_{19}H_{17}ClN_5O$ (M+H)$^+$: 366.0/368.1. Found 366.1/368.2.

Example 284: 5-Cyano-N-(3-ethyl-1H-indazol-5-yl)-3-methyl-4-(trifluoromethyl)picolinamide

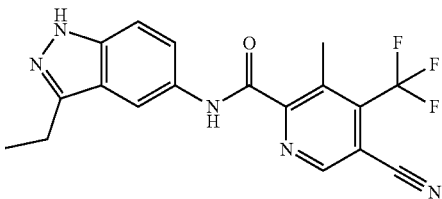 [SMILES: CCc1n[nH]c2ccc(NC(=O)c3ncc(C#N)c(C(F)(F)F)c3C)cc12]

Step 1: 6-Hydroxy-5-methyl-2-oxo-4-(trifluoroethyl)-1,2-dihydropyridine-3-carbonitrile

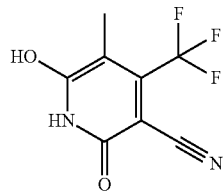

To a mixture of methyl 4,4,4-trifluoro-2-methyl-3-oxobutanoate (3.96 g, 20 mmol) and 2-cyanoacetamide (1.68 g, 20 mmol) in 1,4-dioxane (20 mL) was added Et₃N (3.07 mL, 22 mmol) and the reaction was stirred at 100° C. for 16 hrs. The solvent was evaporated and the residue was taken up in Et₂O, then decanted. The oil obtained was concentrated to afford the title compound (3.2 g, 73%) as a brown solid. $^1$H NMR (400 MHz, DMSO-$d_6$) δ 10.30 (s, 1H), 8.94 (bs, 1H), 1.87 (q, J=3.1 Hz, 3H); $^{19}$F NMR (377 MHz, DMSO-$d_6$) δ −57.47 (t, J=3.4 Hz). MS-(ESI) (m/z) calcd for $C_8H_6F_3N_2O_2$ (M+H)$^+$: 219.0. Found 219.0.

Step 2: 2,6-Dichloro-5-methyl-4-(trifluoromethyl)nicotinonitrile

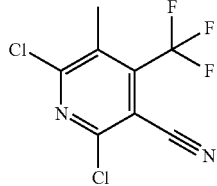

To a solution of 6-hydroxy-5-methyl-2-oxo-4-(trifluoromethyl)-1H-pyridine-3-carbonitrile (3.2 g, 14.67 mmol) in POCl₃ (20.0 mL, 213.92 mmol) was added tetraethylammonium chloride (2.43 g, 14.67 mmol) and the mixture was stirred at 100° C. for 48 hrs. The solvent was evaporated to give a residue that was taken up in water and extracted with DCM (3×). The combined organic layers were passed through a phase separator and evaporated to a black oil which was purified by silica gel column chromatography using a 0-50% DCM/cyclohexane gradient eluent to afford the title compound (1.15 g, 31%) as a white solid. $^1$H NMR (400 MHz, DMSO-$d_6$) δ 2.51 (s, 3H); $^{19}$F NMR (377 MHz, DMSO-$d_6$) δ −58.07 (q, J=2.2 Hz). MS-(ESI) (m/z) calcd for $C_8H_4Cl_2F_3N_2$ (M+H)$^+$: 255.0/257.0. Found 255.0/257.0.

Step 3: 2-Chloro-6-(furan-2-yl)-5-methyl-4-(trifluoromethyl)nicotinonitrile

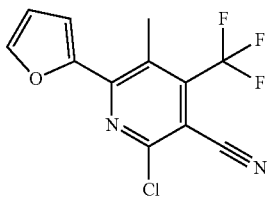 [SMILES: Cc1c(-c2ccco2)nc(Cl)c(C#N)c1C(F)(F)F]

A mixture of 2,6-dichloro-5-methyl-4-(trifluoromethyl)nicotinonitrile (1.15 g, 4.51 mmol), 2-furanylboronic acid (504.56 mg, 4.51 mmol), K₂CO₃ (1.56 g, 11.27 mmol) and tetrakis(triphenylphosphine)palladium(0) (260.55 mg, 0.230 mmol) in 1,4-dioxane (7.516 mL) and H₂O (7.516 mL) was heated at 100° C. for 3 hrs. The organic solvent was evaporated and the resulting mixture was diluted with H₂O and extracted with EtOAc (3×). The combined organic layers were passed through a phase separator and evaporated to give a purple residue which was purified by silica gel column chromatography using a 0-15% EtOAc/cyclohexane gradient eluent to afford the title compound (432 mg, 33%) as a yellow solid. $^1$H NMR (400 MHz, DMSO-$d_6$) δ 8.11 (dd, J=1.7, 0.7 Hz, 1H), 7.45 (dd, J=3.6, 0.8 Hz, 1H), 6.83 (dd, J=3.6, 1.7 Hz, 1H), 2.64 (q, J=2.1 Hz, 3H); $^{19}$F NMR (377 MHz, DMSO-$d_6$) δ-57.34 (q, J=2.0 Hz). MS-(ESI) (m/z) calcd for $C_{12}H_7ClF_3N_2O$ (M+H)$^+$: 287.0/289.0. Found 287.0/289.0.

Step 4: 6-(Furan-2-yl)-5-methyl-4-(trifluoromethyl)-1,4-dihydropyridine-3-carbonitrile

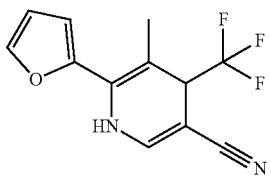 [SMILES: CC1=C(c2ccco2)NC=C(C#N)C1C(F)(F)F]

To a mixture of 2-chloro-6-(furan-2-yl)-5-methyl-4-(trifluoromethyl)pyridine-3-carbonitrile (432.0 mg, 1.51 mmol) in acetic acid (0.200 mL) and H₂O (1.8 mL) was added zinc (197.07 mg, 3.01 mmol) and the suspension was stirred at 95° C. for 3 hrs. The mixture was extracted with DCM (3×) and the combined organic layers were passed through a phase separator. The residue was concentrated and purified by silica gel column chromatography using a 2-20% EtOAc/cyclohexane gradient eluent to afford the title compound (132 mg, 30% yield) as a white solid. $^1$H NMR (400 MHz, DMSO-$d_6$) δ 10.49 (s, 1H), 7.82 (d, J=1.8 Hz, 1H), 6.76 (d, J=3.4 Hz, 1H), 6.63 (dd, J=3.5, 1.8 Hz, 1H), 4.32 (q, J=8.1 Hz, 1H), 1.94 (s, 3H). $^{19}$F NMR (377 MHz, DMSO-$d_6$) δ −72.54 (d, J=7.9 Hz). MS-(ESI) (m/z) calcd for $C_{12}H_{10}F_3N_2O$ (M+H)$^+$:255.1 Found 255.1.

Step 5: 5-Cyano-3-methyl-4-(trifluoromethyl)picolinic acid

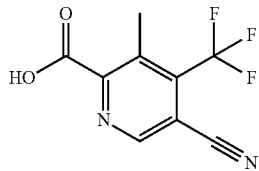 [SMILES: Cc1c(C(=O)O)ncc(C#N)c1C(F)(F)F]

To a solution of 6-(furan-2-yl)-5-methyl-4-(trifluoromethyl)-1,4-dihydropyridine-3-carbonitrile (120.0 mg, 0.470 mmol) in acetone (3.54 mL)/H$_2$O (1.18 mL) was added K$_2$CO$_3$ (130.48 mg, 0.940 mmol) and KMnO$_4$ (447.59 mg, 2.83 mmol) and the mixture was stirred at 50° C. for 2 hrs. The reaction was quenched by addition of formic acid and a solid formed that was removed by filtration. The filtrate was concentrated under reduced pressure to remove volatile organics and the remaining aqueous solution was acidified by addition of conc. HCl and then extracted with EtOAc (3×). The combined organic layers were dried over Na$_2$SO$_4$, passed through a phase separator and evaporated to afford the title compound (98 mg, 81%) as a white solid. $^1$H NMR (400 MHz, DMSO-d$_6$) δ 14.44 (s, 1H), 9.15 (s, 1H), 2.50 (s, 3H), $^{19}$F NMR (377 MHz, DMSO-d$_6$) δ −58.10. MS-(ESI) (m/z) calcd for C$_9$H$_6$F$_3$N$_2$O$_2$ (M+H)$^+$:231.0 Found 231.0.

Step 6: 5-Cyano-N-(3-ethyl-1H-indazol-5-yl)-3-methyl-4-(trifluoromethyl)picolinamide

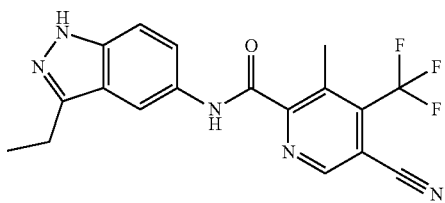 [SMILES: CCc1n[nH]c2ccc(NC(=O)c3ncc(C#N)c(C(F)(F)F)c3C)cc12]

Prepared as described for 3-chloro-5-cyano-N-(3-cyclopropyl-1H-indazol-5-yl)-4,6-dimethylpicolinamide (Example 283) using 5-cyano-3-methyl-4-(trifluoromethyl)picolinic acid in place of 3-chloro-5-cyano-4,6-dimethylpicolinic acid and using 3-ethyl-1H-indazol-5-amine in place of 3-cyclopropyl-1H-indazol-5-amine to afford the title compound (24.3 mg, 42%) as a beige solid. $^1$H NMR (400 MHz, DMSO-d$_6$) δ 12.64 (s, 1H), 10.78 (s, 1H), 9.40-9.11 (m, 1H), 8.24-8.21 (m, 1H), 7.52 (dd, J=8.9, 1.8 Hz, 1H), 7.47 (d, J=8.7 Hz, 1H), 2.91 (q, J=7.6 Hz, 2H), 2.65-2.56 (m, 3H), 1.32 (t, J=7.6 Hz, 3H). $^{19}$F NMR (377 MHz, DMSO-d$_6$) δ −57.97 (q, J=2.3 Hz). MS-ESI (m/z) calc'd for C$_{18}$H$_{15}$F$_3$N$_5$O [M+H]$^+$: 374.1. Found 374.2

Example 285: 5-Cyano-N-(3-methoxy-1H-indazol-5-yl)-3-methyl-4-(trifluoromethyl)picolinamide

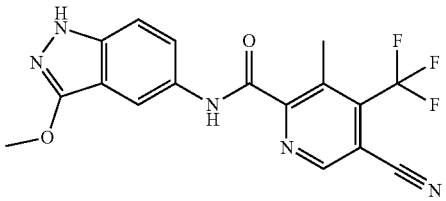 [SMILES: COc1n[nH]c2ccc(NC(=O)c3ncc(C#N)c(C(F)(F)F)c3C)cc12]

Prepared as described for 3-chloro-5-cyano-N-(3-cyclopropyl-1H-indazol-5-yl)-4,6-dimethylpicolinamide (Example 283) using 5-cyano-3-methyl-4-(trifluoromethyl)picolinic acid in place of 3-chloro-5-cyano-4,6-dimethylpicolinic acid and using 3-methoxy-1H-indazol-5-amine in place of 3-cyclopropyl-1H-indazol-5-amine to afford the title compound (16.2 mg, 28%) as a white solid. $^1$H NMR (400 MHz, DMSO-d$_6$) δ 11.93 (s, 1H), 10.80 (s, 1H), 9.43-9.09 (m, 1H), 8.13 (d, J=1.8 Hz, 1H), 7.53 (dd, J=8.9, 2.0 Hz, 1H), 7.38 (dd, J=8.9, 0.8 Hz, 1H), 4.00 (s, 3H), 2.58 (q, J=1.8 Hz, 5H). $^{19}$F NMR (377 MHz, DMSO-d$_6$) δ −57.98 (q, J=2.2 Hz). MS-ESI (m/z) calc'd for C$_{17}$H$_{13}$F$_3$N$_5$O$_2$ [M+H]$^+$: 376.1. Found 376.1.

Example 286: 5-Cyano-N-(3-cyclopropyl-1H-indazol-5-yl)-3-methyl-4-(trifluoromethyl)picolinamide

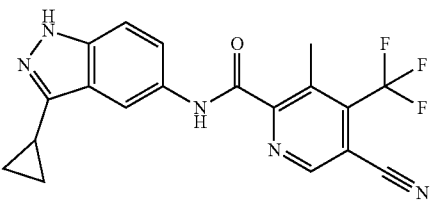 [SMILES: Cc1c(C(=O)Nc2ccc3[nH]nc(C4CC4)c3c2)ncc(C#N)c1C(F)(F)F]

Prepared as described for 3-chloro-5-cyano-N-(3-cyclopropyl-1H-indazol-5-yl)-4,6-dimethylpicolinamide (Example 283) using 5-cyano-3-methyl-4-(trifluoromethyl)picolinic acid in place of 3-chloro-5-cyano-4,6-dimethylpicolinic acid to afford the title compound (50 mg, 83%) as a yellow solid. $^1$H NMR (400 MHz, DMSO-d$_6$) δ 12.57 (s, 1H), 10.79 (s, 1H), 9.26 (s, 1H), 8.27 (d, J=1.9 Hz, 1H), 7.52 (dd, J=8.9, 1.8 Hz, 1H), 7.46 (d, J=8.9 Hz, 1H), 2.59 (q, J=2.3 Hz, 3H), 2.22 (tt, J=8.2, 5.0 Hz, 1H), 1.01-0.90 (m, 4H). $^{19}$F NMR (377 MHz, DMSO-d$_6$) δ −57.97 (q, J=2.3 Hz). MS-ESI (m/z) calc'd for C$_{19}$H$_{15}$F$_3$N$_5$O [M+H]$^+$: 386.1. Found 386.2.

Example 287: 5-Cyano-N-(3-methoxy-1H-indazol-5-yl)-3,4,6-trimethylpicolinamide

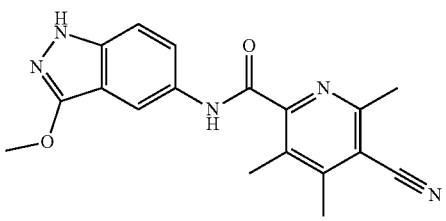 [SMILES: COc1n[nH]c2ccc(NC(=O)c3nc(C)c(C#N)c(C)c3C)cc12]

Prepared as described for 3-chloro-5-cyano-N-(3-cyclopropyl-1H-indazol-5-yl)-4,6-dimethylpicolinamide (Example 283) using 5-cyano-3,4,6-trimethylpicolinic acid in place of 3-chloro-5-cyano-4,6-dimethylpicolinic acid and using 3-methoxy-1H-indazol-5-amine in place of 3-cyclopropyl-1H-indazol-5-amine to afford the title compound (67.8 mg, 93%) as a pale yellow solid. $^1$H NMR (400 MHz, DMSO-$d_6$) δ 11.88 (s, 1H), 10.57 (s, 1H), 8.14 (d, J=1.9 Hz, 1H), 7.56 (dd, J=9.0, 2.0 Hz, 1H), 7.35 (dd, J=9.0, 0.8 Hz, 1H), 4.00 (s, 3H), 2.70 (s, 3H), 2.52 (s, 3H), 2.36 (s, 3H). MS-ESI (m/z) calc'd for $C_{18}H_{18}N_5O_2$ [M+H]$^+$: 336.1. Found 336.1.

Example 288: 5-Cyano-3-methyl-N-(3-(oxazol-5-yl)-1H-indazol-5-yl)-6-(trifluoromethyl)picolinamide

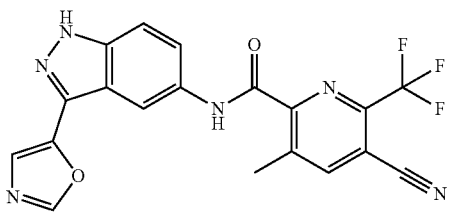 [SMILES: Cc1cc(C#N)c(C(F)(F)F)nc1C(=O)Nc1ccc2[nH]nc(-c3cnco3)c2c1]

Step 1: Methyl 5-cyano-3-methyl-6-(trifluoromethyl)picolinate

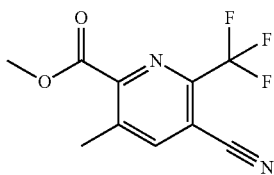 [SMILES: COC(=O)c1nc(C(F)(F)F)c(C#N)cc1C]

A solution of methyl 5-cyano-3-methylpyridine-2-carboxylate (500.0 mg, 2.84 mmol) and zinc trifluoromethanesulfinate (1881.82 mg, 5.68 mmol) in DMSO (8 mL) was cooled in ice water. The mixture was stirred vigorously while adding a 70% solution of tert-butyl hydroperoxide in H$_2$O (1.18 mL, 8.51 mmol). The solution was allowed to reach r.t. and then warmed at 50° C. for 2 hrs and then at r.t. overnight. To the mixture was added an additional 2 eq. of zinc trifluoromethanesulfinate and 3 eq of tert-butyl hydroperoxide and the reaction was stirred at 50° C. for an additional 2 hrs. The reaction mixture was partitioned between H$_2$O and EtOAc and the phases were separated. The aqueous layer was extracted with EtOAc (2×), the combined organic phases were washed with saturated aqueous NaHCO$_3$ (1×) and H$_2$O (1×), dried over Na$_2$SO$_4$ and evaporated to dryness to give a residue. The residue was purified by silica gel chromatography using a 0-30% EtOAc/cyclohexane gradient eluent to afford a mixture of 2 regioisomers: methyl 5-cyano-3-methyl-4-(trifluoromethyl)pyridine-2-carboxylate and methyl 5-cyano-3-methyl-6-(trifluoromethyl)pyridine-2-carboxylate (150 mg, 22%) in a 1:1 ratio. The isomers were separated using Method CU to afford the title compound (43.6 mg, 6%) as a white solid. $^1$H NMR (400 MHz, DMSO-$d_6$) δ 8.77 (s, 1H) 3.95 (s, 3H) 2.59 (s, 3H). MS-ESI (m/z) calc'd for $C_{10}H_8F_3N_2O_2$[M+H]$^+$: 245.1. Found 245.0.

Step 2: 5-Cyano-3-methyl-6-(trifluoromethyl)picolinic acid

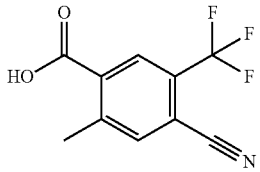 [SMILES: Cc1cc(C#N)c(C(F)(F)F)cc1C(=O)O]

To a solution of methyl 5-cyano-3-methyl-6-(trifluoromethyl)pyridine-2-carboxylate (35.0 mg, 0.140 mmol) in MeOH (3.5 mL) was added an aqueous solution of 1 N sodium hydroxide (0.14 mL, 0.140 mmol) and the mixture was stirred at r.t. for 2 hrs. The reaction mixture was concentration to afford the title compound (41 mg) which was used without further purification. $^1$H NMR (400 MHz, DMSO-$d_6$) δ 8.27 (s, 1H) 2.32 (s, 3H). MS-ESI (m/z) calc'd for $C_9H_6F_3N_2O_2$[M+H]$^+$: 231.0. Found 231.0.

Step 3: 5-Cyano-3-methyl-N-(3-(oxazol-5-yl)-1H-indazol-5-yl)-6-(trifluoromethyl)picolinamide

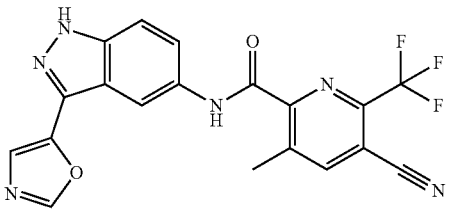 [SMILES: Cc1cc(C#N)c(C(F)(F)F)nc1C(=O)Nc1ccc2[nH]nc(-c3cnco3)c2c1]

Prepared as described for 3-chloro-5-cyano-N-(3-cyclopropyl-1H-indazol-5-yl)-4,6-dimethylpicolinamide (Example 283) using 5-cyano-3-methyl-6-(trifluoromethyl)picolinic acid in place of 3-chloro-5-cyano-4,6-dimethylpicolinic acid and using 3-(oxazol-5-yl)-1H-indazol-5-amine in place of 3-cyclopropyl-1H-indazol-5-amine to afford the title compound (24.9 mg, 37%) as a yellow solid. $^1$H NMR (400 MHz, DMSO-$d_6$) δ 13.57 (br. s., 1H) 10.82 (s, 1H) 8.78 (s, 1H) 8.59 (s, 1H) 8.54 (d, J=1.10 Hz, 1H) 7.72 (d, J=1.98 Hz, 1H) 7.64-7.68 (m, 2H) 2.62 (s, 3H). MS-ESI (m/z) calc'd for $C_{19}H_{12}F_3N_6O_2$[M+H]$^+$: 413.1. Found 413.1.

Example 289: 5-Cyano-3-methyl-N-(3-(oxazol-5-yl)-1H-indazol-5-yl)-4-(trifluoromethyl)picolinamide

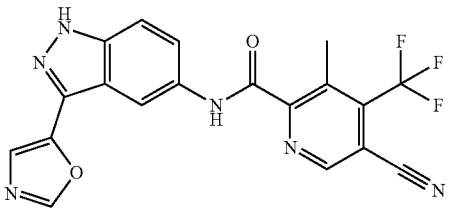 [SMILES: Cc1c(C(=O)Nc2ccc3[nH]nc(-c4cnco4)c3c2)ncc(C#N)c1C(F)(F)F]

Prepared as described for 3-chloro-5-cyano-N-(3-cyclopropyl-1H-indazol-5-yl)-4,6-dimethylpicolinamide (Example 283) using 5-cyano-3-methyl-4-(trifluoromethyl)picolinic acid in place of 3-chloro-5-cyano-4,6-dimethylpicolinic acid and using 3-(oxazol-5-yl)-1H-indazol-5-amine in place of 3-cyclopropyl-1H-indazol-5-amine to afford the title compound (7.9 mg, 18%) as a yellow solid. ¹H NMR (400 MHz, DMSO-d₆) δ 13.64 (br. s., 1H) 10.99 (br. s., 1H) 9.28 (s, 1H) 8.59-8.61 (m, 1H) 8.56 (d, J=1.10 Hz, 1H) 8.54 (s, 1H) 7.69-7.75 (m, 1H) 7.63-7.68 (m, 2H) 2.59-2.64 (m, 3H). MS-ESI (m/z) calc'd for $C_{19}H_{12}F_3N_6O_2[M+H]^+$: 413.1. Found 413.1.

Example 290: 6-Chloro-5-cyano-N-(3-cyano-1H-indazol-5-yl)-3,4-dimethylpicolinamide

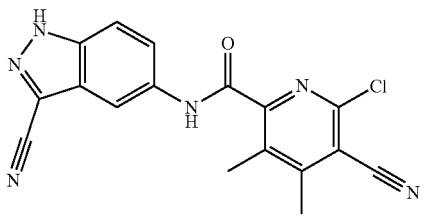 [SMILES: Cc1c(C(=O)Nc2ccc3[nH]nc(C#N)c3c2)nc(Cl)c(C#N)c1C]

Prepared as described for 3-chloro-5-cyano-N-(3-cyclopropyl-1H-indazol-5-yl)-4,6-dimethylpicolinamide (Example 283) using 6-chloro-5-cyano-3,4-dimethylpicolinic acid in place of 3-chloro-5-cyano-4,6-dimethylpicolinic acid and using 5-amino-1H-indazole-3-carbonitrile in place of 3-cyclopropyl-1H-indazol-5-amine to afford the title compound (37 mg, 56%) as a light yellow solid. ¹H NMR (400 MHz, DMSO-d₆) δ 14.37 (bs, 1H) 10.97 (s, 1H) 8.44 (d, J=1.32 Hz, 1H) 7.76-7.82 (m, 1H) 7.70 (dd, J=9.02, 1.76 Hz, 1H) 2.61 (s, 3H) 2.40 (s, 3H). MS-ESI (m/z) calc'd for $C_{17}H_{12}ClN_6O [M+H]^+$: 351.1. Found 351.0.

Example 291: 6-Chloro-5-cyano-N-(3-(difluoromethyl)-1H-indazol-5-yl)-3,4-dimethylpicolinamide

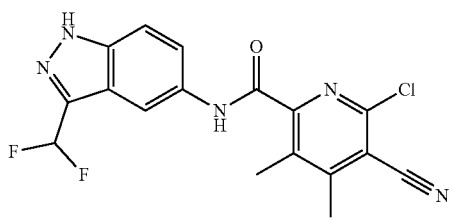

Step 1: 3-(Difluoromethyl)-1H-indazole

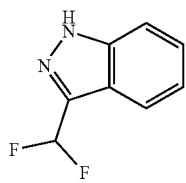

DAST (2.71 mL, 20.53 mmol) was added to a solution of 1H-indazole-3-carboxaldehyde (1.5 g, 10.26 mmol) in DCM (6 mL) at 0° C., and the mixture was stirred for 5 hrs at r.t. The reaction was cooled to 0° C. and then carefully quenched with saturated aqueous NaHCO₃. The mixture was extracted with EtOAc (3×100 mL) and the combined organic layers were washed with brine (100 mL), dried over Na₂SO₄ and concentrated to give a residue. The residue was purified by silica gel column chromatography using a 0-50% EtOAc/cyclohexane gradient eluent to afford the title compound (710 mg, 41%) as a beige solid. ¹H NMR (400 MHz, DMSO-d₆) δ 13.57 (s, 1H), 7.84 (d, J=8.2 Hz, 1H), 7.64 (d, J=8.5 Hz, 1H), 7.51-7.14 (m, 3H). MS-ESI (m/z) calc'd for $C_8H_7F_2N_2[M+H]^+$: 169.1. Found 168.9.

Step 2: 3-(Difluoromethyl)-5-nitro-1H-indazole

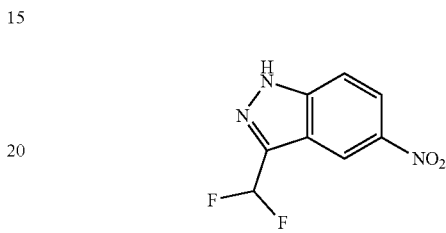

To a stirred solution of 3-(difluoromethyl)-1H-indazole (709.0 mg, 4.22 mmol) in sulfuric acid (3.0 mL, 56.28 mmol) at 0° C. was added nitric acid (1.0 mL, 22.38 mmol) and the mixture was stirred for 30 min at 0° C. The mixture was diluted with water and extracted with EtOAc (2×). The combined organic layers were washed with brine, dried over Na₂SO₄, filtered and concentrated to give a residue. The residue was purified by silica gel column chromatography using a 0-30% EtOAc/cyclohexane gradient eluent to afford the title compound (517 mg, 58%) as a beige solid. ¹H NMR (400 MHz, DMSO-d₆) δ 14.26 (s, 1H), 8.76 (d, J=2.1 Hz, 1H), 8.29 (dd, J=9.2, 2.2 Hz, 1H), 7.86 (d, J=9.2 Hz, 1H), 7.52 (t, J=53.6 Hz, 1H). MS-ESI (m/z) calc'd for $C_8H_6F_2N_3O_2 [M+H]^+$: 214.0. Found 214.0.

Step 3: 3-(Difluoromethyl)-5-nitro-1-(tetrahydro-2H-pyran-2-yl)-1H-indazole

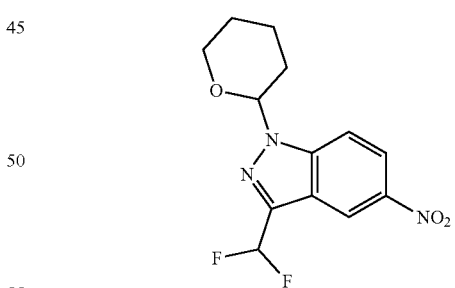

To a solution of 3-(difluoromethyl)-5-nitro-1H-indazole (300.0 mg, 1.41 mmol) and 3,4-dihydro-2H-pyran (0.18 mL, 2.11 mmol) in toluene (4 mL) was added p-toluenesulfonic acid (53.55 mg, 0.280 mmol). The reaction mixture was stirred at r.t. for 2 hrs and then at 60° C. for 30 minutes. The reaction mixture was partitioned between water (100 mL) and EtOAc (100 mL), the phases were separated, the aqueous layer was extracted with EtOAc (2×100 mL) and the combined organic phases were washed with brine (1×100 mL), dried over Na₂SO₄ and evaporated to dryness. The residue was purified by silica gel column chromatography using a 0-30% EtOAc/cyclohexane gradient eluent to afford the title compound (380 mg, 91%) as a white solid. $^1$H NMR (400 MHz, DMSO-$d_6$) δ 8.77 (d, J=2.1 Hz, 1H), 8.37 (dd, J=9.3, 2.2 Hz, 1H), 8.11 (d, J=9.3 Hz, 1H), 7.55 (t, J=53.5 Hz, 1H), 6.08 (dd, J=9.6, 2.4 Hz, 1H), 3.94-3.86 (m, 1H), 3.85-3.76 (m, 1H), 2.43-2.28 (m, 1H), 2.11-1.99 (m, 2H), 1.84-1.70 (m, 1H), 1.66-1.55 (m, 2H). MS-ESI (m/z) calc'd for $C_{13}H_{14}F_2N_3O_3$ [M+H]$^+$: 298.1. Found 298.1.

Step 4: 3-(Difluoromethyl)-1-(tetrahydro-2H-pyran-2-yl)-1H-indazol-5-amine

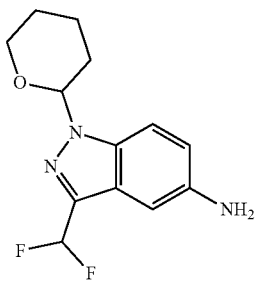 [SMILES: Nc1ccc2c(c1)c(C(F)F)nn2C1CCCCO1]

A mixture of 3-(difluoromethyl)-5-nitro-1-(tetrahydro-2H-pyran-2-yl)-1H-indazole (190.0 mg, 0.640 mmol), ammonium chloride (37.61 mg, 0.700 mmol), and iron (142.79 mg, 2.56 mmol) in 4 mL of EtOH and 4 mL of H$_2$O was heated to reflux for 1.5 hrs. The mixture was cooled and filtered through Celite. The filtrate was evaporated, and the resulting residue was taken up into EtOAc and saturated aqueous NaHCO$_3$. The phases were separated and the organic phase was dried over Na$_2$SO$_4$, filtered and concentrated under reduced pressure to afford the title compound (140 mg, 82%). MS-ESI (m/z) calc'd for $C_{13}H_{16}F_2N_3O$ [M+H]$^+$: 268.1. Found 268.1.

Step 5: 6-Chloro-5-cyano-N-(3-(difluoromethyl)-1-(tetrahydro-2?H-pyran-2-yl)-1H-indazol-5-yl)-3,4-dimethylpicolinamide

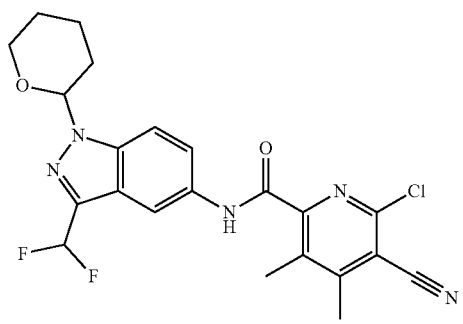 [SMILES: Cc1c(C(=O)Nc2ccc3c(c2)c(C(F)F)nn3C2CCCCO2)nc(Cl)c(C#N)c1C]

To a solution of 3-(difluoromethyl)-1-(tetrahydro-2H-pyran-2-yl)-1H-indazol-5-amine (67.0 mg, 0.250 mmol) and 6-chloro-5-cyano-3,4-dimethylpyridine-2-carboxylic acid (50.0 mg, 0.210 mmol) in MeCN (3 mL), Et$_3$N (0.04 mL, 0.310 mmol) and HATU (79.43 mg, 0.210 mmol) were added, and the resulting solution was stirred at r.t. for 2 hrs. The reaction mixture was then concentrated under reduced pressure and extracted with EtOAc (100 mL) and H$_2$O (100 mL). The organic phases were concentrated and the residue was triturated with cooled MeCN/H$_2$O and then filtered to afford the title compound (86 mg, 90%) as a pale yellow solid. $^1$H NMR (400 MHz, DMSO-$d_6$) δ 10.88 (s, 1H), 8.43 (d, J=1.9 Hz, 1H), 7.87 (d, J=9.1 Hz, 1H), 7.74 (dd, J=9.1, 1.9 Hz, 1H), 7.37 (t, J=53.8 Hz, 1H), 5.99-5.85 (m, 1H), 3.95-3.85 (m, 1H), 3.82-3.72 (m, 1H), 2.59 (s, 3H), 2.39 (s, 3H), 2.38-2.31 (m, 1H), 2.11-1.96 (m, 2H), 1.85-1.69 (m, 1H), 1.67-1.50 (m, 2H). MS-ESI (m/z) calc'd for $C_{22}H_{21}ClF_2N_5O_2$ [M+H]$^+$: 460.1. Found 460.1.

Step 6: 6-Chloro-5-Cyano-N-(3-(difluoromethyl)-1H-indazol-5-yl)-3,4-dimethylpicolinamide

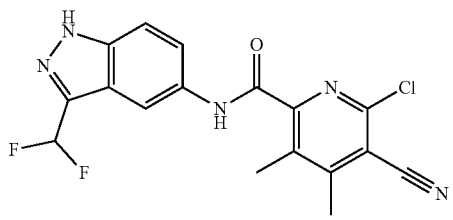 [SMILES: Cc1c(C(=O)Nc2ccc3[nH]nc(C(F)F)c3c2)nc(Cl)c(C#N)c1C]

To a solution of 6-chloro-5-cyano-N-(3-(difluoromethyl)-1-(tetrahydro-2H-pyran-2-yl)-1H-indazol-5-yl)-3,4-dimethylpicolinamide (86.0 mg, 0.190 mmol) in DCM (3 mL) was added trifluoroacetic acid (1 mL) at 0° C. and the resulting mixture was stirred at r.t. for 3 hrs. Then the reaction mixture was concentrated under reduced pressure and the residue was taken-up in DCM and washed with saturated aqueous NaHCO$_3$ and brine. The layers were separated and the organic phase was dried over Na$_2$SO$_4$, filtered and concentrated under reduced pressure to give a residue. The residue was triturated with cooled MeCN (1 mL) and H$_2$O (3 mL), filtered and the solid dried under reduced pressure at 50° C. to afford the title compound (25.9 mg, 37%) as a pale yellow solid. $^1$H NMR (400 MHz, DMSO-$d_6$) δ 13.62 (s, 1H), 10.83 (s, 1H), 8.42 (s, 1H), 7.72-7.60 (m, 1H), 7.34 (t, J=54.0 Hz, 1H), 2.60 (s, 3H), 2.39 (s, 3H). MS-ESI (m/z) calc'd for $C_{17}H_{13}ClF_2N_5O$ [M+H]$^+$: 376.1. Found 376.1.

Example 292: 5-Cyano-N-(3-(difluoromethyl)-1H-indazol-5-yl)-3,4-dimethylpicolinamide

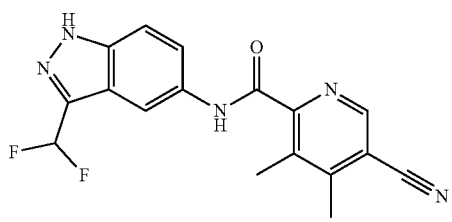 [SMILES: Cc1c(C#N)cnc(C(=O)Nc2ccc3[nH]nc(C(F)F)c3c2)c1C]

Step 1: 5-Cyano-N-(3-(difluoromethyl)-1-(tetrahydro-2H-pyran-2-yl)-1H-indazol-5-yl)-3,4-dimethylpicolinamide

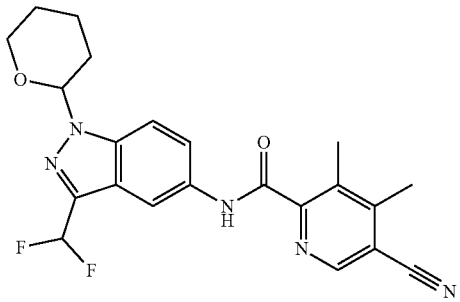 [SMILES: Cc1c(C#N)cnc(C(=O)Nc2ccc3c(c2)c(C(F)F)nn3C2CCCCO2)c1C]

To a solution of 3-(difluoromethyl)-1-(tetrahydro-2H-pyran-2-yl)-1H-indazol-5-amine (120.0 mg, 0.450 mmol) and 5-cyano-3,4-dimethylpicolinic acid (65.0 mg, 0.360 mmol) in MeCN (3 mL) was added Et$_3$N (0.08 mL, 0.540 mmol) and HATU (137.48 mg, 0.360 mmol) and the resulting mixture was stirred for 3 hrs at r.t. The reaction mixture was then concentrated under reduced pressure to give a residue that was triturated with cooled MeOH (2 mL) and then filtered. The solid was dried to afford the title compound (133 mg, 86%). $^1$H NMR (400 MHz, DMSO-d$_6$) δ 10.82 (s, 1H), 8.89 (s, 1H), 8.49 (d, 2H), 7.85 (d, J=9.1 Hz, 1H), 7.76 (dd, J=9.2, 1.9 Hz, 1H), 7.36 (t, J=53.7 Hz, 1H), 5.92 (dd, J=9.8, 2.4 Hz, 1H), 3.96-3.84 (m, 1H), 3.82-3.69 (m, 1H), 2.55 (s, 3H), 2.45 (s, 3H), 2.44-2.30 (m, 1H), 2.09-1.96 (m, 2H), 1.66-1.54 (m, 2H). MS-ESI (m/z) calc'd for C$_{22}$H$_{22}$F$_2$N$_5$O$_2$ [M+H]$^+$: 426.2. Found 426.1.

Step 2: 5-Cyano-N-(3-(difluoromethyl)-1H-indazol-5-yl)-3,4-dimethylpicolinamide

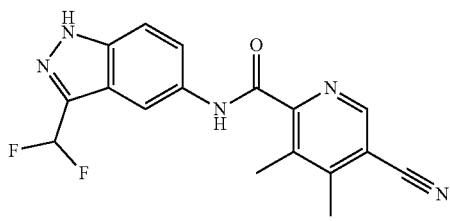 [SMILES: Cc1c(C#N)cnc(C(=O)Nc2ccc3[nH]nc(C(F)F)c3c2)c1C]

Prepared as described for 6-chloro-5-cyano-N-(3-(difluoromethyl)-1H-indazol-5-yl)-3,4-dimethylpicolinamide using 6-chloro-5-cyano-N-(3-(difluoromethyl)-1-(tetrahydro-2H-pyran-2-yl)-1H-indazol-5-yl)-3,4-dimethylpicolinamide in place of 6-chloro-5-cyano-N-(3-(difluoromethyl)-1-(tetrahydro-2H-pyran-2-yl)-1H-indazol-5-yl)-3,4-dimethylpicolinamide to afford the title compound (32.5 mg, 30%) as a pale yellow solid. $^1$H NMR (400 MHz, DMSO-d$_6$) δ 13.59 (s, 1H), 10.77 (s, 1H), 8.88 (s, 1H), 8.50-8.44 (m, 1H), 7.69 (dd, J=9.0, 1.9 Hz, 1H), 7.64 (dd, J=9.0, 0.8 Hz, 1H), 7.33 (t, J=54.0 Hz, 1H), 2.55 (s, 3H), 2.44 (s, 3H). MS-ESI (m/z) calc'd for C$_{17}$H$_{14}$F$_2$N$_5$O [M+H]$^+$: 342.1. Found 342.1.

Example 293: 6-Chloro-5-cyano-3,4-dimethyl-N-(3-(trifluoromethyl)-1H-indazol-5-yl)picolinamide

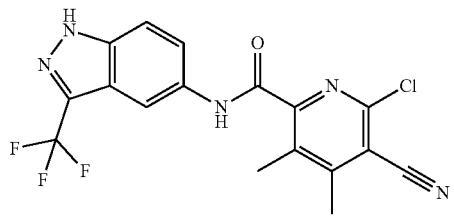 [SMILES: Cc1c(C(=O)Nc2ccc3[nH]nc(C(F)(F)F)c3c2)nc(Cl)c(C#N)c1C]

Step 1: 5-Bromo-1-(tetrahydro-2H-pyran-2-yl)-3-(trifluoromethyl)-1H-indazole

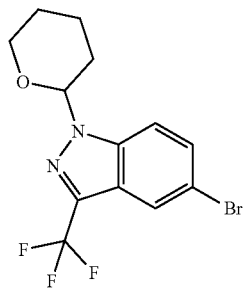 [SMILES: FC(F)(F)c1nn(C2CCCCO2)c2ccc(Br)cc12]

To a solution of 5-bromo-3-(trifluoromethyl)-1H-indazole (500.0 mg, 1.89 mmol) and 3,4-dihydro-2H-pyran (0.34 mL, 3.77 mmol) in toluene (4 mL) was added p-toluenesulfonic acid monohydrate (71.77 mg, 0.380 mmol) and the mixture was stirred at r.t. for 2 hrs and then at 60° C. for 30 minutes. The reaction mixture was partitioned between water and EtOAc and the phases were separated. The aqueous layer was extracted with EtOAc (2×) and the combined organic phases were washed with water (1×), dried over Na$_2$SO$_4$ and evaporated to dryness. The crude material was purified by silica gel column chromatography using a 0-20% EtOAc/cyclohexane gradient eluent to afford the title compound (570 mg, 87%) as a colourless oil. $^1$H NMR (400 MHz, DMSO-d$_6$) δ 8.03 (s, 1H) 7.95 (d, J=9.02 Hz, 1H) 7.75 (dd, J=9.02, 1.76 Hz, 1H) 6.05 (dd, J=9.46, 2.20 Hz, 1H) 3.85-3.96 (m, 1H) 3.72-3.84 (m, 1H) 2.26-2.41 (m, 1H) 1.97-2.09 (m, 2H) 1.69-1.84 (m, 1H) 1.61 (dt, J=8.25, 4.24 Hz, 2H). MS-ESI (m/z) calc'd for C$_{13}$H$_{13}$BrF$_2$N$_2$O [M+H]$^+$: 349.0/351.0. Found 349.0/350.9.

Step 2: 1,1-Diphenyl-N-(1-(tetrahydro-2H-pyran-2-yl)-3-(trifluoromethyl)-1H-indazol-5-yl)methanimine

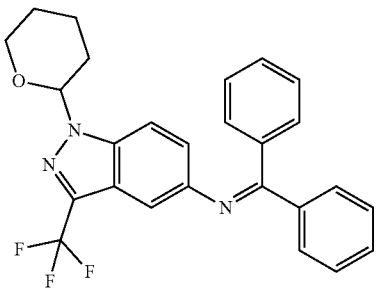 [SMILES: FC(F)(F)c1nn(C2CCCCO2)c2ccc(N=C(c3ccccc3)c3ccccc3)cc12]

To a solution of diphenylmethanimine (0.05 mL, 0.300 mmol) in toluene (2.5 mL) was added 5-bromo-1-(tetrahydro-2H-pyran-2-yl)-3-(trifluoromethyl)-1H-indazole (70.0 mg, 0.200 mmol) and sodium tert-butoxide (38.53 mg, 0.400 mmol) and the mixture was degassed and purged with $N_2$ (3×). Then racemic BINAP (37.45 mg, 0.060 mmol) and $Pd(dba)_2$ (18.36 mg, 0.020 mmol) were added and the mixture was degassed again with $N_2$ for 5 min. The reaction mixture was stirred at 80° C. overnight. The reaction mixture was partitioned between water and EtOAc. The phases were separated and the aqueous layer was extracted with EtOAc (2×) and the combined organic phases were washed with brine (1×), dried over $Na_2SO_4$ and concentrated to afford the title compound (190 mg) as a red oil. $^1$H NMR (400 MHz, DMSO-$d_6$) δ 7.59 (d, J=9.02 Hz, 1H) 6.96 (dd, J=9.02, 1.98 Hz, 1H) 6.76 (s, 1H) 5.83 (dd, J=9.68, 2.20 Hz, 1H) 5.24 (s, 2H) 3.88 (d, J=11.22 Hz, 1H) 3.67-3.80 (m, 1H) 2.23-2.40 (m, 1H) 1.91-2.10 (m, 2H) 1.68-1.82 (m, 1H) 1.53-1.63 (m, 2H). MS-ESI (m/z) calc'd for $C_{26}H_{23}F_3N_3O$ [M+H]$^+$: 450.2. Found 450.2.

Step 3: 1-(Tetrahydro-2H-pyran-2-yl)-3-(trifluoromethyl)-1H-indazol-5-amine

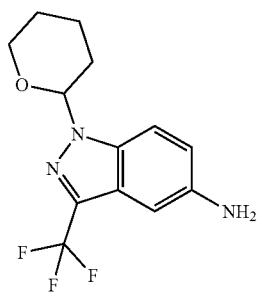 [SMILES: Nc1ccc2c(c1)c(C(F)(F)F)nn2C1CCCCO1]

1,1-Diphenyl-N-(1-(tetrahydro-2H-pyran-2-yl)-3-(trifluoromethyl)-1H-indazol-5-yl)methanimine (89.89 mg, 0.200 mmol) was dissolved in THF (2 mL) and then 1 M HCl (2.0 mL, 2 mmol) was added and the mixture was stirred at r.t. for 1 hr. The reaction mixture was partitioned between $H_2O$ and EtOAc, the phases were separated, the aqueous layer was extracted with EtOAc (2×) and the combined organic phases were washed with $H_2O$ (1×), dried over $Na_2SO_4$ and evaporated to dryness. The material was purified by silica gel column chromatography using a 0-30% EtOAc gradient eluent to afford the title compound (43 mg, 75%) as a colorless oil. $^1$H NMR (400 MHz, DMSO-$d_6$) δ 7.59 (d, J=9.02 Hz, 1H) 6.96 (dd, J=9.02, 1.98 Hz, 1H) 6.76 (s, 1H) 5.83 (dd, J=9.68, 2.20 Hz, 1H) 5.24 (s, 2H) 3.88 (d, J=11.22 Hz, 1H) 3.67-3.80 (m, 1H) 2.23-2.40 (m, 1H) 1.91-2.10 (m, 2H) 1.68-1.82 (m, 1H) 1.53-1.63 (m, 2H). MS-ESI (m/z) calc'd for $C_{13}H_{15}F_3N_3O$ [M+H]$^+$: 268.1. Found 268.1.

Step 4: 6-Chloro-5-cyano-3,4-dimethyl-N-(1-(tetrahydro-2H-pyran-2-yl)-3-(trifluoromethyl)-1H-indazol-5-yl)picolinamide

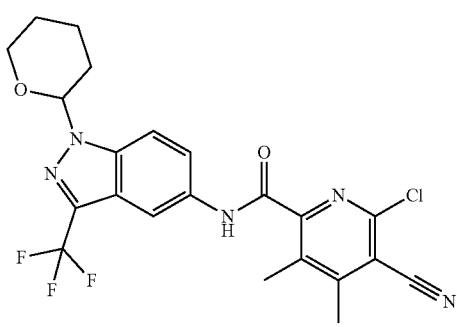 [SMILES: Cc1c(C(=O)Nc2ccc3c(c2)c(C(F)(F)F)nn3C2CCCCO2)nc(Cl)c(C#N)c1C]

To a mixture of 6-chloro-5-cyano-3,4-dimethylpicolinic acid (25.0 mg, 0.120 mmol), 1-(tetrahydro-2H-pyran-2-yl)-3-(trifluoromethyl)-1H-indazol-5-amine (40.63 mg, 0.140 mmol) and $Et_3N$ (33.09 uL, 0.240 mmol) in MeCN (2.5 mL) was added HATU (45.13 mg, 0.120 mmol) and the mixture was stirred at r.t. for 1 hr. The reaction mixture was partitioned between water and EtOAc and the phases were separated. The aqueous layer was extracted with EtOAc (2×) and the combined organic phases were washed with $H_2O$ (1×), dried over $Na_2SO_4$ and concentrated to afford the title compound (81 mg) as a yellow oil which was used without further purification. $^1$H NMR (400 MHz, DMSO-$d_6$) δ 10.96 (s, 1H) 8.41 (s, 1H) 7.96 (d, J=9.02 Hz, 1H) 7.80 (dd, J=9.24, 1.76 Hz, 1H) 6.00 (d, J=7.70 Hz, 1H) 3.84-3.97 (m, 1H) 3.68-3.82 (m, 1H) 2.59 (s, 3H) 2.39 (s, 3H) 2.30-2.38 (m, 1H) 2.00-2.11 (m, 2H) 1.76 (br. s., 1H) 1.61 (d, J=3.96 Hz, 2H). MS-ESI (m/z) calc'd for $C_{22}H_{20}ClF_3N_5O_2$ [M+H]$^+$: 478.1. Found 478.1.

Step 5: 6-Chloro-5-cyano-3,4-dimethyl-N-(3-(trifluoromethyl)-1H-indazol-5-yl)picolinamide

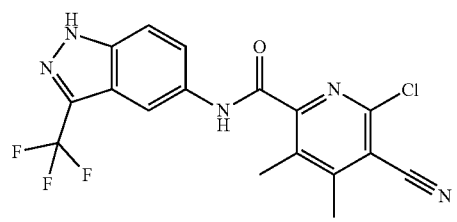 [SMILES: Cc1c(C(=O)Nc2ccc3[nH]nc(C(F)(F)F)c3c2)nc(Cl)c(C#N)c1C]

Prepared as described for 6-chloro-5-cyano-N-(3-(difluoromethyl)-1H-indazol-5-yl)-3,4-dimethylpicolinamide using 6-chloro-5-cyano-3,4-dimethyl-N-(1-(tetrahydro-2H-pyran-2-yl)-3-(trifluoromethyl)-1H-indazol-5-yl)picolinamide in place of 6-chloro-5-cyano-N-(3-(difluoromethyl)-1-(tetrahydro-2H-pyran-2-yl)-1H-indazol-5-yl)-3,4- dimethylpicolinamide to afford the title compound (26 mg, 56%) as a light yellow solid. ¹H NMR (400 MHz, DMSO-d₆) δ 14.02 (br. s., 1H) 10.90 (s, 1H) 8.40 (s, 1H) 7.74 (s, 2H) 2.60 (s, 3H) 2.40 (s, 3H). MS-ESI (m/z) calc'd for C₁₇H₁₂ClF₃N₅O [M+H]⁺: 394.0/396.1. Found 394.0/396.0.

Example 294: 5-Cyano-3-isopropyl-N-(3-methyl-1H-indazol-5-yl)picolinamide

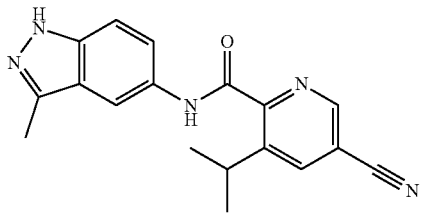 [SMILES: Cc1n[nH]c2ccc(NC(=O)c3ncc(C#N)cc3C(C)C)cc12]

To a solution of 5-cyano-N-(3-methyl-1H-indazol-5-yl)-3-(prop-1-en-2-yl)picolinamide (17.0 mg, 0.05 mmol) in a mixture of MeOH (2 mL) and EtOH (8 mL) was added 10% Pd/C (1.7 mg, 0.03 mmol) and the mixture was hydrogenated at r.t. for 3 hrs. The mixture was then filtered through Celite and the filtrate was concentrated under reduced pressure. The residue was purified by silica gel column chromatography using a 0-80% EtOAc/cyclohexane gradient eluent to afford the title compound (3.4 mg, 20%) as a pale yellow solid. ¹H NMR (400 MHz, DMSO-d₆) δ 12.62 (s, 1H), 10.66 (s, 1H), 8.97 (d, J=1.9 Hz, 1H), 8.55 (d, J=1.9 Hz, 1H), 8.24 (dd, J=1.8, 0.8 Hz, 1H), 7.52 (dd, J=8.9, 1.9 Hz, 1H), 7.45 (dd, J=8.8, 0.8 Hz, 1H), 3.47 (h, J=6.9 Hz, 1H), 2.48 (s, 3H), 1.27 (d, J=6.9 Hz, 6H). MS-ESI (m/z) calc'd for C₁₈H₁₈N₅O [M+H]⁺: 320.1. Found 320.2.

Example 295: 3-Cyano-2-isopropyl-N-(3-methyl-1H-indazol-5-yl)benzamide

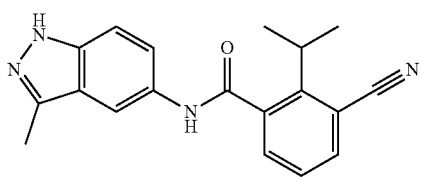 [SMILES: Cc1n[nH]c2ccc(NC(=O)c3cccc(C#N)c3C(C)C)cc12]

Prepared as described for 5-cyano-3-isopropyl-N-(3-methyl-1H-indazol-5-yl)picolinamide 3-cyano-N-(3-methyl-1H-indazol-5-yl)-2-(prop-1-en-2-yl)benzamide in place of 5-cyano-N-(3-methyl-1H-indazol-5-yl)-3-(prop-1-en-2-yl) to afford the title compound (3.8 mg, 25%) as a white solid. ¹H NMR (400 MHz, DMSO-d₆) δ 12.61 (br. s., 1H) 10.53 (s, 1H) 8.19 (s, 1H) 7.91 (dd, J=7.70, 1.32 Hz, 1H) 7.72 (dd, J=7.59, 1.43 Hz, 1H) 7.42-7.55 (m, 3H) 3.46 (signal under H2O, 1H) 2.47 (s, 3H) 1.43 (d, J=7.26 Hz, 6H). MS-ESI (m/z) calc'd for C₁₉H₁₉N₄O [M+H]⁺: 319.2. Found 319.3.

Example 296: 6-Chloro-5-cyano-3,4-dimethyl-N-(3-(methylsulfonyl)-1H-indazol-5-yl)picolinamide

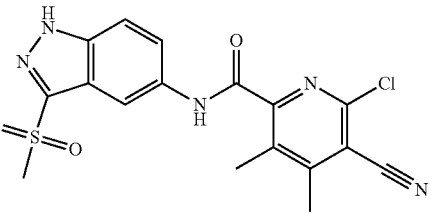

To a solution of 6-chloro-5-cyano-3,4-dimethyl-N-(3-(methylthio)-1H-indazol-5-yl)picolinamide (35.54 mg, 0.100 mmol) in DMF (12 mL) was added oxone (117.53 mg, 0.190 mmol). The reaction was stirred at r.t. overnight. The reaction was quenched with saturated aqueous NaHSO₃, followed by saturated aqueous NaHCO₃ to neutralization, and the mixture was extracted with EtOAc (100 mL×3). The combined organic layers were dried, filtered and concentrated. The residue was purified by reversed phase column chromatography using a 2-100% MeCN/H₂O (0.1% HCOOH) gradient eluent to afford the title compound (5.3 mg, 14%) as a white solid. ¹H NMR (400 MHz, DMSO-d₆) δ 10.90 (s, 1H), 8.53-8.50 (m, 1H), 7.77 (dd, J=9.1, 1.8 Hz, 1H), 7.73 (d, J=9.0 Hz, 1H), 3.33 (s, 3H), 2.59 (s, 3H), 2.39 (s, 3H). MS-ESI (m/z) calc'd for C₁₇H₁₅ClN₅O₃S [M+H]⁺: 404.1. Found 404 1.

Example 297: 5-Cyano-3,4-dimethyl-N-(3-methyl-1H-indazol-5-yl)picolinamide

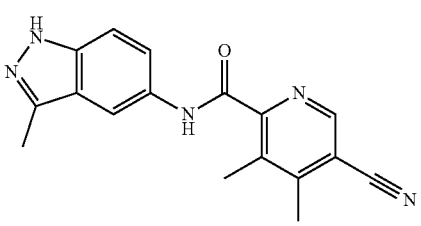 [SMILES: Cc1c(C#N)cnc(C(=O)Nc2ccc3[nH]nc(C)c3c2)c1C]

Prepared as described for 3-chloro-5-cyano-N-(3-cyclopropyl-1H-indazol-5-yl)-4,6-dimethylpicolinamide (Example 283) using 5-cyano-3,4-dimethylpicolinic acid in place of 3-chloro-5-cyano-4,6-dimethylpicolinic acid and using 3-methyl-1H-indazol-5-amine in place of 3-cyclopropyl-1H-indazol-5-amine to afford the title compound (39.7 mg, 57%) as a light yellow solid. ¹H NMR (400 MHz, DMSO-d₆) δ 12.61 (s, 1H) 10.62 (s, 1H) 8.88 (s, 1H) 8.24 (d, J=1.32 Hz, 1H) 7.51-7.58 (m, 1H) 7.42-7.48 (m, 1H) 2.56 (s, 3H) 2.48 (s, 3H) 2.45 (s, 3H). MS-ESI (m/z) calc'd for C₁₇H₁₆N₅O [M+H]⁺: 306.1. Found 306.3.

Example 298: 6-Chloro-5-cyano-3,4-dimethyl-N-(3-methyl-1H-indazol-5-yl)picolinamide

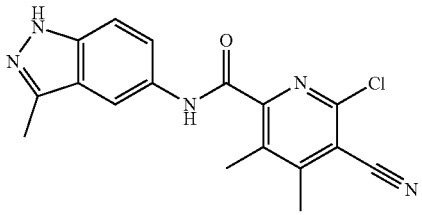 [SMILES: Cc1c(C(=O)Nc2ccc3[nH]nc(C)c3c2)nc(Cl)c(C#N)c1C]

Prepared as described for 3-chloro-5-cyano-N-(3-cyclopropyl-1H-indazol-5-yl)-4,6-dimethylpicolinamide (Example 283) using 6-chloro-5-cyano-3,4-dimethylpicolinic acid in place of 3-chloro-5-cyano-4,6-dimethylpicolinic acid and using 3-methyl-1H-indazol-5-amine in place of 3-cyclopropyl-1H-indazol-5-amine to afford the title compound (18 mg, 45%) as a yellow solid. $^1$H NMR (400 MHz, DMSO-$d_6$) δ 12.63 (s, 1H) 10.68 (s, 1H) 8.20 (s, 1H) 7.50-7.56 (m, 1H) 7.41-7.48 (m, 1H) 2.60 (s, 3H) 2.48 (s, 3H) 2.39 (s, 3H). MS-ESI (m/z) calc'd for $C_{17}H_{10}ClN_5O$ [M+H]$^+$: 340.1. Found 340.2.

Example 299: 3-Cyano-2-methoxy-6-methyl-N-(3-methyl-1H-indazol-5-yl)benzamide

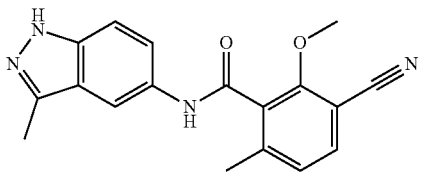 [SMILES: COc1c(C#N)ccc(C)c1C(=O)Nc1ccc2[nH]nc(C)c2c1]

Prepared as described for 3-chloro-5-cyano-N-(3-cyclopropyl-1H-indazol-5-yl)-4,6-dimethylpicolinamide (Example 283) using 3-cyano-2-methoxy-6-methylbenzoic acid in place of 3-chloro-5-cyano-4,6-dimethylpicolinic acid and using 3-methyl-1H-indazol-5-amine in place of 3-cyclopropyl-1H-indazol-5-amine to afford the title compound (22.3 mg, 28%) as a white solid. $^1$H NMR (400 MHz, DMSO-$d_6$) δ 12.60 (s, 1H) 10.52 (s, 1H) 8.20 (s, 1H) 7.79 (d, J=7.92 Hz, 1H) 7.44 (d, J=1.10 Hz, 2H) 7.23-7.30 (m, 1H) 3.98 (s, 3H) 2.48 (s, 3H) 2.38 (s, 3H). MS-ESI (m/z) calc'd for $C_{18}H_{17}N_4O_2$[M+H]$^+$: 321.1. Found 321.3.

Example 300: N-(3-Bromo-1H-indazol-5-yl)-5-cyano-3,4-dimethylpicolinamide

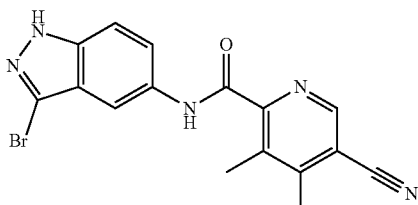

Prepared as described for 3-chloro-5-cyano-N-(3-cyclopropyl-1H-indazol-5-yl)-4,6-dimethylpicolinamide (Example 283) using 5-cyano-3,4-dimethylpicolinic acid in place of 3-chloro-5-cyano-4,6-dimethylpicolinic acid and using 3-bromo-1H-indazol-5-amine in place of 3-cyclopropyl-1H-indazol-5-amine to afford the title compound (16.5 mg, 20%) as a white solid. $^1$H NMR (400 MHz, DMSO-$d_6$) δ 13.43 (br. s., 1H) 10.80 (s, 1H) 8.89 (s, 1H) 8.24 (d, J=1.32 Hz, 1H) 7.64-7.71 (m, 1H) 7.54-7.63 (m, 1H) 2.56 (s, 3H) 2.45 (s, 3H). MS-ESI (m/z) calc'd for $C_{16}H_{13}BrN_5O$ [M+H]$^+$: 370.0/372.0. Found 370.3/372.3.

Example 301: N-(3-Chloro-1H-indazol-5-yl)-5-cyano-3,4-dimethylpicolinamide

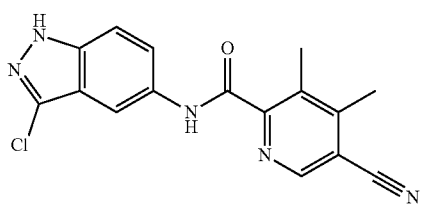 [SMILES: Cc1c(C#N)cnc(C(=O)Nc2ccc3[nH]nc(Cl)c3c2)c1C]

Prepared as described for 3-chloro-5-cyano-N-(3-cyclopropyl-1H-indazol-5-yl)-4,6-dimethylpicolinamide (Example 283) using 6-bromo-5-cyano-3,4-dimethylpicolinic acid in place of 3-chloro-5-cyano-4,6-dimethylpicolinic acid and using 3-chloro-1H-indazol-5-amine in place of 3-cyclopropyl-1H-indazol-5-amine to afford the title compound (29.2 mg, 39%) as a yellow solid. $^1$H NMR (400 MHz, DMSO-$d_4$) δ 13.29 (br. s., 1H) 10.80 (br. s., 1H) 8.89 (s, 1H) 8.26-8.34 (m, 1H) 7.63-7.70 (m, 1H) 7.53-7.61 (m, 1H) 2.56 (s, 3H) 2.45 (s, 3H). MS-ESI (m/z) calc'd for $C_{16}H_{13}ClN_5O$ [M+H]$^+$: 326.1. Found 326.2.

Example 302: 6-Bromo-5-cyano-3,4-dimethyl-N-(3-methyl-1H-indazol-5-yl)picolinamide

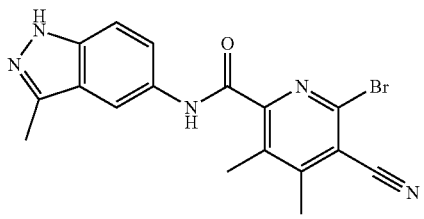 [SMILES: Cc1c(C(=O)Nc2ccc3[nH]nc(C)c3c2)nc(Br)c(C#N)c1C]

Step 1: 6-Bromo-5-cyano-3,4-dimethylpicolinic acid

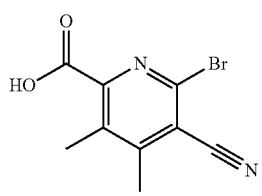

6-Chloro-5-cyano-3,4-dimethylpicolinic acid (20.0 mg, 0.090 mmol) was dissolved in 1 mL of 33% w/w HBr in acetic acid. The reaction was stirred at 100° C. for 10 minutes and concentrated to afford the title compound (22 mg, 98%) as a beige solid which was used without further purification. $^1$H NMR (400 MHz, DMSO-d$_6$) δ 14.17 (br. s., 1H) 2.55 (s, 3H) 2.31 (s, 3H). MS-ESI (m/z) calc'd for C$_9$H$_8$BrN$_2$O$_2$ [M+H]$^+$: 255.0/257.0. Found 255.0/257.0.

Step 2: 6-Bromo-5-cyano-3,4-dimethyl-N-(3-methyl-1H-indazol-5-yl)picolinamide

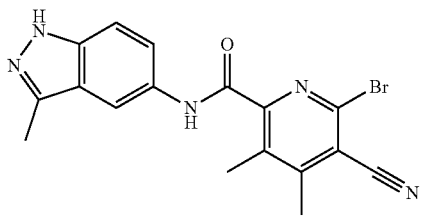

Prepared as described for 3-chloro-5-cyano-N-(3-cyclopropyl-1H-indazol-5-yl)-4,6-dimethylpicolinamide (Example 283) using 6-bromo-5-cyano-3,4-dimethylpicolinic acid in place of 3-chloro-5-cyano-4,6-dimethylpicolinic acid and using 3-methyl-1H-indazol-5-amine in place of 3-cyclopropyl-1H-indazol-5-amine to afford the title compound (23 mg, 76%) as a yellow solid. $^1$H NMR (400 MHz, DMSO-d$_6$) δ 12.63 (s, 1H) 10.67 (s, 1H) 8.19 (s, 1H) 7.50-7.56 (m, 1H) 7.44-7.49 (m, 1H) 2.60 (s, 3H) 2.48 (s, 3H) 2.36 (s, 3H). MS-ESI (m/z) calc'd for C$_{17}$H$_{15}$BrN$_5$O [M+H]$^+$: 384.0/386.0. Found 384.1/386.2.

Example 303: 6-Chloro-5-cyano-N-(3-cyclopropyl-1H-indazol-5-yl)-3,4-dimethylpicolinamide

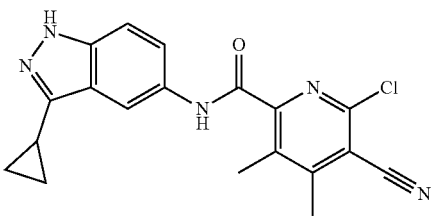 [SMILES: Cc1c(C(=O)Nc2ccc3[nH]nc(C4CC4)c3c2)nc(Cl)c(C#N)c1C]

Prepared as described for 3-chloro-5-cyano-N-(3-cyclopropyl-1H-indazol-5-yl)-4,6-dimethylpicolinamide (Example 283) using 6-chloro-5-cyano-3,4-dimethylpicolinic acid in place of 3-chloro-5-cyano-4,6-dimethylpicolinic acid to afford the title compound (16.1 mg, 53%) as a yellow solid. $^1$H NMR (400 MHz, DMSO-d$_6$) δ 12.57 (s, 1H) 10.68 (s, 1H) 8.26 (d, J=1.32 Hz, 1H) 7.49-7.59 (m, 1H) 7.40-7.49 (m, 1H) 2.60 (s, 3H) 2.40 (s, 3H) 2.17-2.27 (m, 1H) 0.97-1.03 (m, 2H) 0.91-0.96 (m, 2H). MS-ESI (m/z) calc'd for C$_{19}$H$_{17}$ClN$_5$O [M+H]$^+$: 366.1/368.0. Found 368.2.

Example 304: 5-Cyano-N-(3-cyclopropyl-1H-indazol-5-yl)-6-methoxy-3,4-dimethylpicolinamide

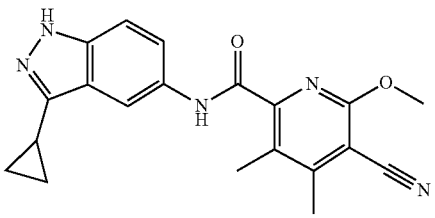

Prepared as described for 3-chloro-5-cyano-N-(3-cyclopropyl-1H-indazol-5-yl)-4,6-dimethylpicolinamide (Example 283) using 5-cyano-6-methoxy-3,4-dimethylpicolinic acid in place of 3-chloro-5-cyano-4,6-dimethylpicolinic acid to afford the title compound (11.8 mg, 40%) as a yellow solid. $^1$H NMR (400 MHz, DMSO-d$_6$) δ 12.55 (s, 1H) 10.48 (s, 1H) 8.28 (d, J=1.32 Hz, 1H) 7.55 (dd, J=9.02, 1.76 Hz, 1H) 7.44 (d, J=8.58 Hz, 1H) 4.06 (s, 3H) 2.52 (peak under DMSO signal, 3H) 2.34 (s, 3H) 2.17-2.26 (m, 1H) 0.89-1.04 (m, 4H). MS-ESI (m/z) calc'd for C$_{20}$H$_{20}$N$_5$O$_2$[M+H]$^+$: 362.2. Found 362.2.

Example 305: 5-Cyano-N-(3-cyclopropyl-1H-indazol-5-yl)-3,4,6-trimethylpicolinamide

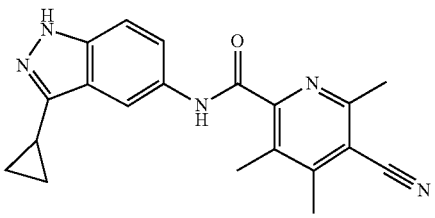

Prepared as described for 3-chloro-5-cyano-N-(3-cyclopropyl-1H-indazol-5-yl)-4,6-dimethylpicolinamide (Example 283) using 5-cyano-3,4,6-trimethylpicolinic acid in place of 3-chloro-5-cyano-4,6-dimethylpicolinic acid to afford the title compound (10.1 mg, 36%) as a yellow solid. $^1$H NMR (400 MHz, DMSO-d$_6$) δ 12.54 (s, 1H) 10.57 (s, 1H) 8.28 (s, 1H) 7.55 (dd, J=8.91, 1.87 Hz, 1H) 7.44 (d, J=8.80 Hz, 1H) 2.71 (s, 3H) 2.54 (s, 3H) 2.39 (s, 3H) 2.12-2.28 (m, 1H) 0.89-1.10 (m, 4H). MS-ESI (m/z) calc'd for C$_{20}$H$_{20}$N$_5$O [M+H]$^+$: 346.2. Found 346.3.

Example 306: 4-Chloro-5-cyano-3-methyl-N-(3-methyl-1H-indazol-5-yl)picolinamide and Example 307: 6-Chloro-5-cyano-3-methyl-N-(3-methyl-1H-indazol-5-yl)picolinamide

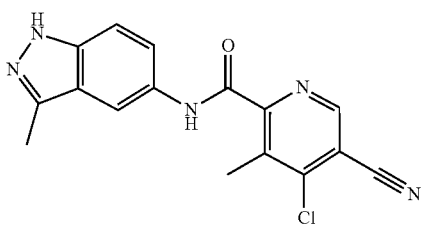

-continued

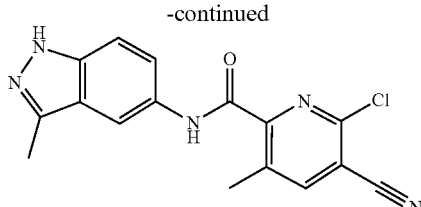

Step 1: Methyl 5-bromo-3-methylpicolinate

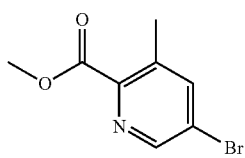

To a solution of 5-bromo-2-carboxy-3-methylpyridine (6.48 g, 30 mmol) in DMF (50 mL) was added K$_2$CO$_3$ (12.44 g, 90 mmol) and iodomethane (3.74 mL, 60 mmol) and the mixture was stirred at 80° C. for 1 hr. The mixture was poured into H$_2$O (150 mL) and stirred for 10 minutes. A solid formed that was collected by filtration and dried to afford the title compound (4.8 g, 70%) as a white solid. $^1$H NMR (400 MHz, DMSO-d$_6$) δ 8.67-8.57 (m, 1H), 8.15 (dd, J=2.2, 0.9 Hz, 1H), 3.86 (s, 3H), 2.46 (d, J=0.7 Hz, 3H). MS-ESI (m/z) calc'd for C$_8$H$_9$BrNO$_2$ [M+H]$^+$: 230.0/232.0. Found 229.9/231.9.

Step 2: Methyl 3-methyl-5-vinylpicolinate

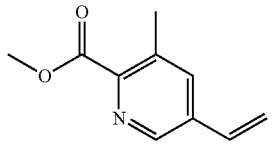

A solution of methyl 5-bromo-3-methylpyridine-2-carboxylate (4.8 g, 20.86 mmol) and tributyl(ethenyl)stannane (7.32 mL, 25.04 mmol) in 1,4-dioxane (104.32 mL) was purged with N$_2$ for 10 minutes. Bis(triphenylphosphine)palladium(I$_1$) dichloride (1.47 g, 2.09 mmol) was added and the mixture was stirred at 100° C. for 1.5 hrs. The solvent was evaporated and the residue was purified by silica gel column chromatography using a 0-50% EtOAc/cyclohexane gradient eluent to afford the title compound (3.496 g, 95%) as a yellow oil. $^1$H NMR (400 MHz, DMSO-d$_6$) δ 8.56 (d, J=2.1 Hz, 1H), 7.92 (dt, J=2.1, 0.7 Hz, 1H), 6.80 (dd, J=17.7, 11.0 Hz, 1H), 6.10 (dd, J=17.7, 0.8 Hz, 1H), 5.51 (dd, J=11.0, 0.8 Hz, 1H), 3.85 (s, 3H), 2.46 (d, J=0.6 Hz, 3H). MS-ESI (m/z) calc'd for C$_{10}$H$_{12}$NO$_2$ [M+H]$^+$: 178.1. Found 178.0.

Step 3: Methyl 5-formyl-3-methylpicolinate

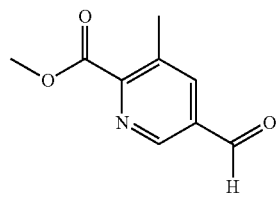

To a solution of methyl 3-methyl-5-vinylpicolinate (3.5 g, 19.73 mmol) in 1,4-dioxane (98.65 mL) was added a solution of NaIO$_4$ (8.48 g, 39.46 mmol) in H$_2$O (98.65 mL) and the mixture was stirred at 25° C. for 10 minutes. A 4% solution of osmium tetroxide in water (6.28 mL, 0.990 mmol) was added and the solution was stirred at 25° C. for 1 hr. The mixture was diluted with H$_2$O and extracted with DCM (3×). The combined organic layers were passed through a phase separator and concentrated to afford the title compound (3.535 g, 100%) as a black solid. $^1$H NMR (400 MHz, DMSO-d$_6$) δ 10.14 (s, 1H), 8.95 (d, J=1.9 Hz, 1H), 8.24 (dd, J=2.0, 0.9 Hz, 1H), 3.91 (s, 3H), 2.51 (s, 3H). MS-ESI (m/z) calc'd for C$_9$H$_{10}$NO$_3$ [M+H]$^+$: 180.1. Found 180.0.

Step 4: Methyl 5-cyano-3-methylpicolinate

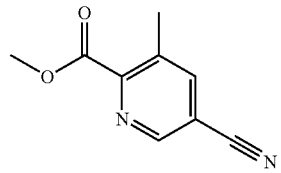

To a solution of methyl 5-formyl-3-methylpicolinate (3.54 g, 19.73 mmol) in DMSO (15 mL) was added hydroxylamine hydrochloride (1.51 g, 21.7 mmol) and the mixture was stirred at 90° C. for 1 hr. After cooling down, H$_2$O was added and the solid formed was filtered under vacuum, washed with H$_2$O and dried to afford the title compound (1.7 g, 49%) as a purple solid. $^1$H NMR (400 MHz, DMSO-d$_6$) δ 8.92 (dd, 1=1.9, 0.7 Hz, 1H), 8.39 (dd, 1=1.9, 0.8 Hz, 1H), 3.90 (s, 3H), 2.47 (d, J=0.7 Hz, 3H). MS-ESI (m/z) calc'd for C$_9$H$_9$N$_2$O$_2$ [M+H]$^+$: 177.1. Found 176.9.

Step 5: 5-Cyano-2-(methoxycarbonyl)-3-methylpyridine 1-oxide

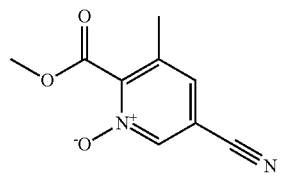

To a solution of methyl 5-cyano-3-methylpicolinate (400.0 mg, 2.27 mmol) in DCM (10 mL) was added MCPBA (783.65 mg, 4.54 mmol) and the mixture was stirred at 50° C. overnight After that another equivalent of MCPBA was added and the mixture was stirred at 50° C. for an additional 24 hrs. The solution was washed with 2M aqueous K₂CO₃ (1×) and the aqueous layer was extracted with DCM (3×). All the organic phases were combined, washed with H₂O (1×), passed through a phase separator and evaporated to dryness to obtain material that was further purified by silica gel column chromatography using a 0-100% EtOAc gradient eluent to afford the title compound (220 mg, 50%) as a white solid. ¹H NMR (400 MHz, DMSO-d₆) δ 8.88 (s, 1H) 7.85-7.93 (m, 1H) 3.94 (s, 3H) 2.25 (s, 3H).1H) 7.85-7.93 (m, 1H) 3.94 (s, 3H) 2.25 (s, 3H). MS-ESI (m/z) calc'd for C₉H₉N₂O₃[M+H]⁺: 193.1. Found 193.0.

Step 6: Methyl 6-chloro-5-cyano-3-methylpicolinate and Methyl 4-chloro-5-cyano-3-methylpicolinate

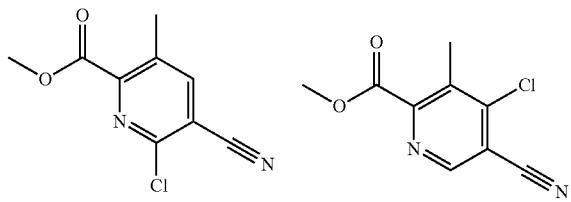

5-Cyano-2-(methoxycarbonyl)-3-methylpyridine 1-oxide (30.0 mg, 0.160 mmol) was suspended in POCl₃ (0.5 mL, 5.35 mmol) and the mixture was stirred at reflux for 1 hr. Excess POCl₃ was evaporated and the reaction mixture was partitioned between saturated aqueous NaHCO₃ and DCM. The phases were separated; the aqueous layer was extracted with DCM (2×) and the combined organic phases were washed with H₂O (1×), dried over Na₂SO₄ and evaporated to dryness to afford a 4:1 mixture (determined by NMR) respectively of the title compounds (27 mg, 82%) as a white solid. Methyl 6-chloro-5-cyano-3-methylpicolinate: ¹H NMR (400 MHz, DMSO-d₆) δ 8.58 (s, 1H) 3.92 (s, 3H) 2.48 (d, J=0.66 Hz, 3H). Methyl 4-chloro-5-cyano-3-methylpicolinate: ¹H NMR (400 MHz, DMSO-d₆) δ 9.00 (d, J=0.66 Hz, 1H) 3.94 (s, 3H) 2.47 (s, 3H). MS-ESI (m/z) calc'd for C₉H₈ClN₂O₂[M+H]⁺: 213.0. Found 213.0.

Step 7: 6-Chloro-5-cyano-3-methylpicolinic acid and 4-Chloro-5-cyano-3-methylpicolinic acid

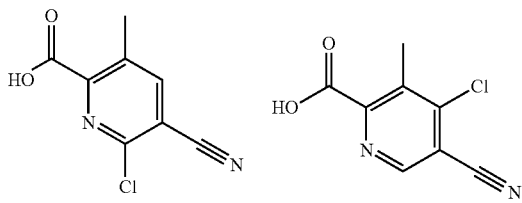

To a solution of methyl 6-chloro-5-cyano-3-methylpicolinate and methyl 4-chloro-5-cyano-3-methylpicolinate (27.0 mg, 0.130 mmol) in EtOH (1 mL) was added a solution of LiOH.H₂O (5.38 mg, 0.130 mmol) in H₂O (0.600 mL) and the resulting mixture was stirred at r.t. for 1 hr. 1 M HCl was added dropwise until pH=1 and the mixture was extracted with EtOAc (2×). The combined organic phases were washed with water (1×), dried over Na₂SO₄ and evaporated to afford a 4:1 mixture, respectively, of the title compounds (19 mg, 75%) as a white solid which was used without further purification. 6-Chloro-5-cyano-3-methylpicolinic acid: ¹H NMR (400 MHz, DMSO-d₆) δ 14.09 (br. s., 1H) 8.52 (d, J=0.66 Hz, 1H) 2.45 (s, 3H). 4-Chloro-5-cyano-3-methylpicolinic acid: ¹H NMR (400 MHz, DMSO-d₆) δ 14.09 (br. s., 1H) 8.96 (s, 1H) 2.47 (s, 3H). MS-ESI (m/z) calc'd for C₈H₆ClN₂O₂ [M+H]⁺: 197.0/199.0. Found 196.9/198.7.

Step 8: 4-Chloro-5-cyano-3-methyl-N-(3-methyl-1H-indazol-5-yl)picolinamide and 6-Chloro-5-cyano-3-methyl-N-(3-methyl-1H-indazol-5-yl)picolinamide

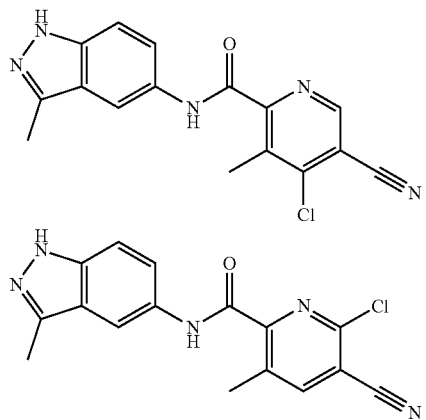

To a mixture of 6-chloro-5-cyano-3-methylpicolinic acid and 4-chloro-5-cyano-3-methylpicolinic acid (18.0 mg, 0.090 mmol), 3-methyl-1H-indazol-5-amine (16.17 mg, 0.110 mmol) and triethylamine (25.52 µL, 0.180 mmol) was added HATU (34.81 mg, 0.090 mmol) and the mixture was stirred at r.t. for 2 hrs. The reaction mixture was evaporated to dryness. The residue was purified via HPLC using Method DE to afford the title compounds. 4-Chloro-5-cyano-3-methyl-N-(3-methyl-1H-indazol-5-yl)picolinamide (2.9 mg, 10%) as a yellow solid: ¹H NMR (400 MHz, DMSO-d₆) δ 12.66 (s, 1H) 10.76 (s, 1H) 9.07 (d, J=0.66 Hz, 1H) 8.23 (d, J=1.32 Hz, 1H) 7.51-7.58 (m, 1H) 7.43-7.50 (m, 1H) 2.57 (s, 3H) 2.48 (s, 3H). MS-ESI (m/z) calc'd for C₁₆H₁₃ClN₅O [M+H]⁺: 326.1. Found 326.1. 6-Chloro-5-cyano-3-methyl-N-(3-methyl-1H-indazol-5-yl)picolinamide (8.1 mg, 27%) as a yellow solid: ¹H NMR (400 MHz, DMSO-d₆) δ 12.65 (br. s., 1H) 10.66 (s, 1H) 8.57 (s, 1H) 8.21 (d, J=1.32 Hz, 1H) 7.53-7.61 (m, 1H) 7.46 (d, J=8.80 Hz, 1H) 2.52 (peak under DMSO signal, s, 3H) 2.48 (s, 3H). MS-ESI (m/z) calc'd for C₁₆H₁₃ClN₅O [M+H]⁺: 326.1. Found 326.1.

Example 308: 6-Chloro-5-cyano-N-(3-methoxy-1H-indazol-5-yl)-3,4-dimethylpicolinamide

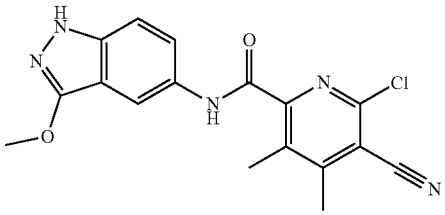 [SMILES: COc1n[nH]c2ccc(NC(=O)c3nc(Cl)c(C#N)c(C)c3C)cc12]

Prepared as described for 3-chloro-5-cyano-N-(3-cyclopropyl-1H-indazol-5-yl)-4,6-dimethylpicolinamide (Example 283) using 6-chloro-5-cyano-3,4-dimethylpicolinic acid in place of 3-chloro-5-cyano-4,6-dimethylpicolinic acid and using 3-methoxy-1H-indazol-5-amine in place of 3-cyclopropyl-1H-indazol-5-amine to afford the title compound (44 mg, 65%) as a yellow solid. $^1$H NMR (400 MHz, DMSO-$d_6$) δ 11.93 (s, 1H) 10.70 (s, 1H) 8.13 (d, J=1.98 Hz, 1H) 7.54 (dd, J=9.02, 1.98 Hz, 1H) 7.32-7.41 (m, 1H) 4.01 (s, 3H) 2.59 (s, 3H) 2.38 (s, 3H). MS-ESI (m/z) calc'd for $C_{17}H_{15}ClN_5O_2$ [M+H]$^+$: 356.1. Found 356.0.

Example 309: 3-Chloro-5-cyano-N-(3-(isoxazol-4-yl)-1H-indazol-5-yl)picolinamide

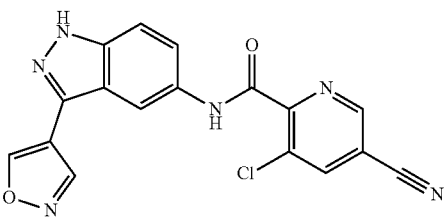 [SMILES: N#Cc1cnc(C(=O)Nc2ccc3[nH]nc(-c4cnoc4)c3c2)c(Cl)c1]

Prepared as described for 3-chloro-5-cyano-N-(3-cyclopropyl-1H-indazol-5-yl)-4,6-dimethylpicolinamide (Example 283) using 3-chloro-5-cyanopicolinic acid in place of 3-chloro-5-cyano-4,6-dimethylpicolinic acid and using 3-(isoxazol-4-yl)-1H-indazol-5-amine in place of 3-cyclopropyl-1H-indazol-5-amine to afford the title compound (9 mg, 3%) as a yellow solid. $^1$H NMR (400 MHz, DMSO-$d_6$) δ 13.38 (s, 1H), 10.88 (s, 1H), 9.55 (s, 1H), 9.19-9.09 (m, 2H), 8.83 (d, J=1.7 Hz, 1H), 8.35 (d, J=1.8 Hz, 1H), 7.70 (dd, J=8.9, 1.9 Hz, 1H), 7.63 (d, J=8.9 Hz, 1H). MS-ESI (m/z) calc'd for $C_{17}H_{10}ClN_6O_2$[M+H]$^+$: 365.1/367.1. Found 365.2/367.3.

Example 310: 5-Cyano-3-cyclopropyl-N-(3-(isoxazol-4-yl)-1H-indazol-5-yl)picolinamide

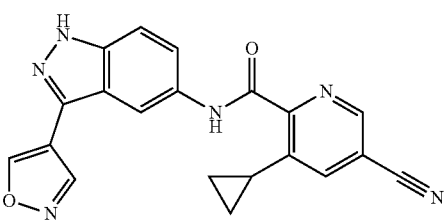 [SMILES: N#Cc1cnc(C(=O)Nc2ccc3[nH]nc(-c4cnoc4)c3c2)c(C2CC2)c1]

Prepared as described for 3-chloro-5-cyano-N-(3-cyclopropyl-1H-indazol-5-yl)-4,6-dimethylpicolinamide (Example 283) using 5-cyano-3-cyclopropylpicolinic acid in place of 3-chloro-5-cyano-4,6-dimethylpicolinic acid and using 3-(isoxazol-4-yl)-1H-indazol-5-amine in place of 3-cyclopropyl-1H-indazol-5-amine to afford the title compound (1.6 mg, 4%) as a pale yellow solid. $^1$H NMR (400 MHz, DMSO-$d_6$) δ 9.37 (s, 1H), 9.01 (s, 1H), 8.80 (d, J=1.9 Hz, 1H), 8.48 (dd, J=1.9, 0.8 Hz, 1H), 7.94 (d, J=1.9 Hz, 1H), 7.72 (dd, J=9.0, 1.9 Hz, 1H), 7.62 (dd, J=9.0, 0.8 Hz, 1H), 2.88 (td, J=8.5, 4.3 Hz, 1H), 1.21-1.17 (m, 2H), 0.91 (dd, J=5.2, 1.7 Hz, 2H). MS-ESI (m/z) calc'd for $C_{20}H_{15}N_6O_2$[M+H]$^+$: 371.1. Found 371.3.

Example 311: 5-Cyano-3-cyclopropyl-N-(3-(3-methoxyphenyl)-1H-indazol-5-yl)picolinamide

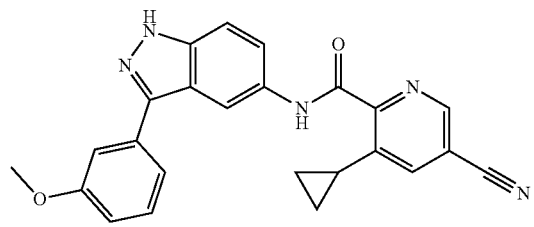 [SMILES: COc1cccc(-c2n[nH]c3ccc(NC(=O)c4ncc(C#N)cc4C4CC4)cc23)c1]

Prepared as described for 3-chloro-5-cyano-N-(3-cyclopropyl-1H-indazol-5-yl)-4,6-dimethylpicolinamide (Example 283) using 5-cyano-3-cyclopropylpicolinic acid in place of 3-chloro-5-cyano-4,6-dimethylpicolinic acid and using 3-(3-methoxyphenyl)-1H-indazol-5-amine in place of 3-cyclopropyl-1H-indazol-5-amine to afford the title compound (30.9 mg, 36%) as a yellow solid. $^1$H NMR (400 MHz, DMSO-$d_6$) δ 13.25 (s, 1H), 10.79 (s, 1H), 8.90 (d, J=1.8 Hz, 11H), 8.63 (d, J=1.8 Hz, 1H), 8.02 (d, J=1.9 Hz, 11H), 7.77 (dd, J=9.0, 1.9 Hz, 1H), 7.60 (d, J=9.0 Hz, 1H), 7.53 (dt, J=7.7, 1.3 Hz, 1H), 7.50-7.43 (m, 2H), 6.99 (ddd, J=8.1, 2.7, 1.1 Hz, 1H), 3.85 (s, 3H), 2.56-2.52 (m, 1H), 1.11-1.02 (m, 2H), 0.95-0.86 (m, 2H). MS-ESI (m/z) calc'd for $C_{24}H_{20}N_5O_2$ [M+H]$^+$: 410.2. Found 410.3.

Example 312: 5-Cyano-3-cyclopropyl-N-(3-(oxazol-5-yl)-1H-indazol-5-yl)picolinamide

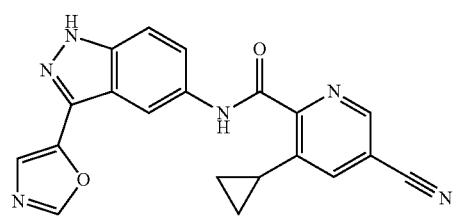 [SMILES: N#Cc1cnc(C(=O)Nc2ccc3[nH]nc(-c4cnco4)c3c2)c(C2CC2)c1]

Prepared as described for 3-chloro-5-cyano-N-(3-cyclopropyl-1H-indazol-5-yl)-4,6-dimethylpicolinamide (Example 283) using 5-cyano-3-cyclopropylpicolinic acid in place of 3-chloro-5-cyano-4,6-dimethylpicolinic acid and using 3-(oxazol-5-yl)-1H-indazol-5-amine in place of 3-cyclopropyl-1H-indazol-5-amine to afford the title compound (13.2 mg, 15%). $^1$H NMR (400 MHz, DMSO-$d_6$) δ 13.55 (s, 1H), 10.82 (s, 1H), 8.90 (d, J=1.8 Hz, 1H), 8.61 (d, J=1.8 Hz, 1H), 8.58 (s, 1H), 8.03 (d, J=1.9 Hz, 1H), 7.75 (dd, J=9.0, 1.9 Hz, 1H), 7.63 (d, J=8.6 Hz, 2H), 2.58-2.52 (m, 1H), 1.13-1.03 (m, 2H), 0.96-0.86 (m, 2H). MS-ESI (m/z) calc'd for $C_{20}H_{15}N_6O_2$ [M+H]$^+$: 371.1. Found 371.3.

Example 313: 5-Cyano-N-(3-methyl-1H-indazol-5-yl)-3-(prop-1-en-2-yl)picolinamide

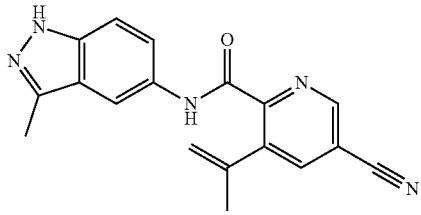 [SMILES: C=C(C)c1cc(C#N)cnc1C(=O)Nc1ccc2[nH]nc(C)c2c1]

Prepared as described for 3-chloro-5-cyano-N-(3-cyclopropyl-1H-indazol-5-yl)-4,6-dimethylpicolinamide (Example 283) using 5-cyano-3-(prop-1-en-2-yl)picolinic acid in place of 3-chloro-5-cyano-4,6-dimethylpicolinic acid and using 3-methyl-1H-indazol-5-amine in place of 3-cyclopropyl-1H-indazol-5-amine to afford the title compound (20.1 mg, 60%) as a pale yellow solid. $^1$H NMR (400 MHz, DMSO-$d_6$) δ 12.61 (s, 1H), 10.66 (s, 1H), 9.04 (d, J=1.9 Hz, 1H), 8.43 (d, J=1.9 Hz, 1H), 8.16 (dd, J=1.9, 0.8 Hz, 1H), 7.48 (dd, J=8.9, 1.9 Hz, 1H), 7.43 (dd, J=8.8, 0.8 Hz, 1H), 5.25 (t, J=1.5 Hz, 1H), 5.16-5.08 (m, 1H), 2.46 (s, 3H), 2.10 (t, J=1.2 Hz, 3H). MS-ESI (m/z) calc'd for $C_{18}H_{16}N_5O$ [M+H]$^+$: 318.1. Found 318.2.

Example 314: 5-Cyano-N-(7-fluoro-1H-indazol-5-yl)-3,4-dimethylpicolinamide and Example 315: 5-Cyano-N-(3-fluoro-1H-indazol-5-yl)-3,4-dimethylpicolinamide

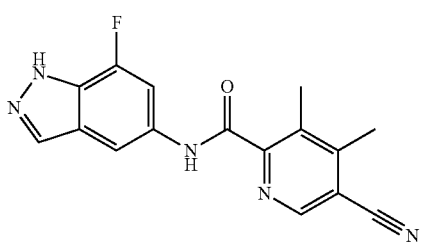

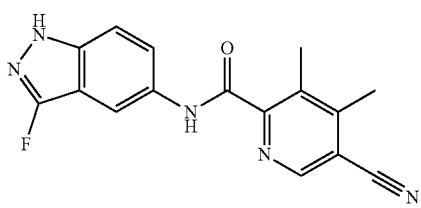

Step 1: 7-Fluoro-5-nitro-1H-indazole and 3-Fluoro-5-nitro-1H-indazole

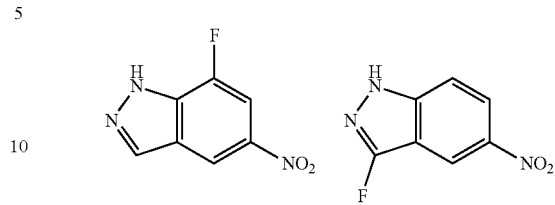

To a solution of 5-nitro-1H-indazole (300.0 mg, 1.84 mmol) in MeCN (1.24 mL) was added Selectfluor (651.49 mg, 1.84 mmol) and AcOH (1.24 mL) and the reaction mixture was heated in a microwave reactor at 150° C. for 30 min. The reaction was quenched with water and extracted with EtOAc (2×). The combined organic layers were dried over $Na_2SO_4$, filtered, and concentrated to give a residue. The residue was purified by silica gel chromatography using a 0-80% EtOAc/cyclohexane gradient eluent to afford a mixture of the title compounds (53 mg) as a white solid. Major isomer: 3-fluoro-1H-indazol-5-amine (83.3% mol/mol by NMR): $^1$H NMR (400 MHz, DMSO-$d_6$) δ 13.41 (s, 1H), 8.76 (d, J=2.2 Hz, 1H), 8.25 (dd, J=9.3, 2.2 Hz, 1H), 7.70 (dd, J=9.3, 2.2 Hz, 1H); Minor isomer: 7-fluoro-5-nitro-1H-indazole, 16.67% mol/mol by NMR. $^1$H NMR (400 MHz, DMSO-$d_6$) δ 8.74 (d, J=1.8 Hz, 1H), 8.54 (d, J=3.1 Hz, 1H), 8.07 (dd, J=10.9, 1.9 Hz, 1H). MS-ESI (m/z) calc'd for $C_7H_3FN_3O_2$[M–H]$^-$: 180.0. Found 179.9.

Step 2: 7-Fluoro-1H-indazol-5-amine and 3-Fluoro-1H-indazol-5-amine

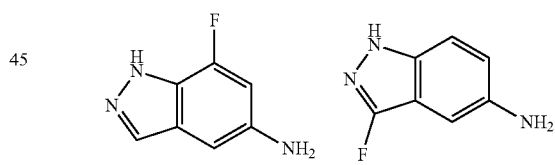

To a solution of a mixture of 3-fluoro-5-nitro-1H-indazole and 7-fluoro-5-nitro-1H-indazole (53.0 mg, 0.19 mmol) in EtOH (10 mL) was added 10% Pd/C (31.13 mg, 0.030 mmol) and the mixture was hydrogenated at r.t. for 2 hrs. The reaction was filtered through Celite, washing with MeOH, and the resulting solution was concentrated to afford a mixture of the title compounds (23 mg) which was used without further purification. Major isomer: 3-fluoro-1H-indazol-5-amine, 81.6% mol/mol by NMR. $^1$H NMR (400 MHz, DMSO-$d_6$) δ 11.96 (s, 1H), 7.17 (dd, J=9.0, 2.6 Hz, 1H), 6.85 (dd, J=8.9, 2.1 Hz, 1H), 6.59 (d, J=2.1 Hz, 1H), 4.93 (s, 2H); Minor isomer: 7-fluoro-1H-indazol-5-amine, 18.4% mol/mol by NMR. MS-ESI (m/z) calc'd for $C_7H_7FN_3$ [M+H]$^+$: 152.1. Found 152.0.

Step 3: 5-Cyano-N-(7-fluoro-1H-indazol-5-yl)-3,4-dimethylpicolinamide and 5-Cyano-N-(3-fluoro-1H-indazol-5-yl)-3,4-dimethylpicolinamide

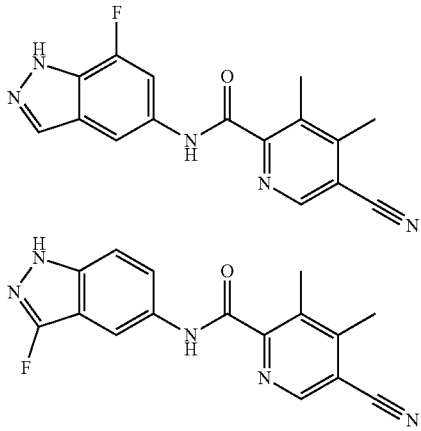

To a solution of a mixture of intermediate 1 and 2, 5-cyano-3,4-dimethylpyridine-2-carboxylic acid (20.0 mg, 0.110 mmol) and 3-fluoro-1H-indazol-5-amine; 7-fluoro-1H-indazol-5-amine (23.0 mg, 0.150 mmol) and triethylamine (0.02 mL, 0.140 mmol) in MeCN (2 mL), HATU (42.3 mg, 0.110 mmol) was added and the mixture was stirred at 25° C. for 1 hr. EtOAC and H₂O were added, the organic phase was separated, dried over Na₂SO₄, filtered and concentrate. The material obtained (54 mg) was purified by semi-preparative HPLC using Method DF to afford the title compounds. The first eluted compound, 5-cyano-N-(7-fluoro-1H-indazol-5-yl)-3,4-dimethylpicolinamide (2.2 mg, 6%) as a white solid: $^1$H NMR (400 MHz, DMSO-d$_6$) δ 13.61 (s, 1H), 10.78 (s, 1H), 8.89 (s, 1H), 8.19 (s, 1H), 8.11 (d, J=1.5 Hz, 1H), 7.58 (d, J=12.8 Hz, 1H), 2.55 (s, 3H), 2.44 (s, 3H). MS-ESI (m/z) calc'd for C$_{16}$H$_{13}$FN$_5$O [M+H]$^+$: 310.1. Found 310.2. The second eluted compound 5-cyano-N-(3-fluoro-1H-indazol-5-yl)-3,4-dimethylpicolinamide (18 mg, 52%) as a white solid: $^1$H NMR (400 MHz, DMSO-d$_6$) δ 12.54 (s, 1H), 10.77 (s, 1H), 8.88 (s, 1H), 8.32-8.18 (m, 1H), 7.66 (dd, J=9.1, 1.9 Hz, 1H), 7.50 (dd, J=9.0, 2.3 Hz, 1H), 2.55 (s, 3H), 2.43 (s, 3H). MS-ESI (m/z) calc'd for C$_{16}$H$_{13}$FN$_5$O [M+H]$^+$: 310.1. Found 310.2.

Example 316: 3-Cyano-6-fluoro-2-methyl-N-(3-methyl-1H-indazol-5-yl)benzamide

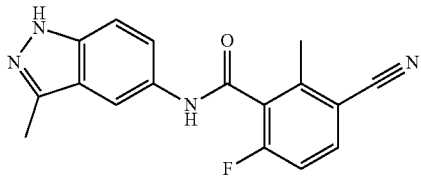 [SMILES: Cc1c(C#N)ccc(F)c1C(=O)Nc1ccc2[nH]nc(C)c2c1]

Step 1: 3-Bromo-6-fluoro-2-methyl-N-(3-methyl-1H-indazol-5-yl)benzamide

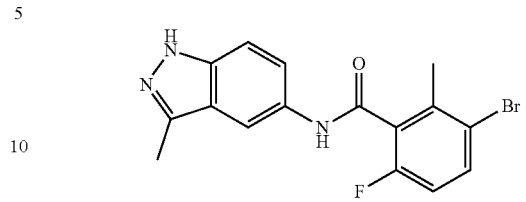

To a solution of 3-methyl-1H-indazol-5-amine (75.79 mg, 0.510 mmol), 3-bromo-6-fluoro-2-methylbenzoic acid (100.0 mg, 0.430 mmol) and Et$_3$N (0.06 mL, 0.430 mmol) in MeCN (3 mL), was added HATU (163.17 mg, 0.430 mmol) and the reaction mixture was left stirring at r.t. for 2 hrs. Water (100 mL) and EtOAc (100 mL) were added and the organic phase was separated, dried over Na$_2$SO$_4$, filtered and concentrated under reduced pressure to give a residue. The residue was purified by silica gel column chromatography using a 0-20% MeOH/DCM gradient eluent to afford the title compound (110 mg, 71%). $^1$H NMR (400 MHz, DMSO-d$_6$) δ 12.61 (s, 1H), 10.65 (s, 1H), 8.20 (t, J=1.4 Hz, 1H), 7.75 (dd, J=8.9, 5.4 Hz, 1H), 7.43 (d, J=1.0 Hz, 2H), 7.20 (t, J=8.7 Hz, 1H), 2.47 (s, 3H), 2.37 (s, 3H). MS-ESI (m/z) calc'd for C$_{16}$H$_{14}$BrFN$_3$O [M+H]$^+$: 362.0/364.0. Found 362.1/364.1.

Step 2: 3-Cyano-6-fluoro-2-methyl-N-(3-methyl-1H-indazol-5-yl)benzamide

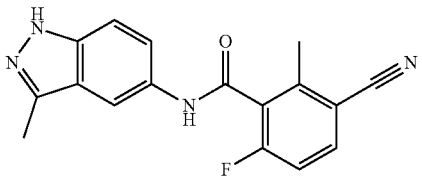 [SMILES: Cc1c(C#N)ccc(F)c1C(=O)Nc1ccc2[nH]nc(C)c2c1]

A 0.1 N aqueous solution of potassium hexacyanoferrate (II) (1.66 mL, 0.170 mmol), 3-bromo-6-fluoro-2-methyl-N-(3-methyl-1H-indazol-5-yl)benzamide (60.0 mg, 0.170 mmol) and K$_2$CO$_3$ (8.13 mg, 0.080 mmol) were dissolved in a mixture of 1,4-dioxane (2.918 mL) and H$_2$O (0.403 mL) in a sealed microwave reactor vial. The mixture was degassed with N$_2$ for 15 minutes. Then XPhos (3.16 mg, 0.010 mmol) and Xphos-Pd-G3 (5.61 mg, 0.010 mmol) were added and the mixture was stirred at 100° C. for 6 hrs. Water was added and the mixture was extracted with EtOAc. The organic phase was separated, dried over Na$_2$SO$_4$, filtered and concentrated. The solid was purified by semi-preparative HPLC using Method DD to afford the title compound (14.1 mg, 28%) as a white solid. $^1$H NMR (400 MHz, DMSO-d$_6$) δ 12.63 (s, 1H), 10.71 (s, 1H), 8.18 (t, J=1.3 Hz, 1H), 8.01 (dd, J=8.7, 5.5 Hz, 1H), 7.50-7.39 (m, 3H), 2.53 (s, 3H), 2.48 (s, 3H). MS-ESI (m/z) calc'd for C$_{17}$H$_{14}$FN$_4$O [M+H]$^+$: 309.1. Found 309.2.

Example 317: 6-Chloro-5-cyano-3,4-dimethyl-N-(3-(methylthio)-1H-indazol-5-yl)picolinamide

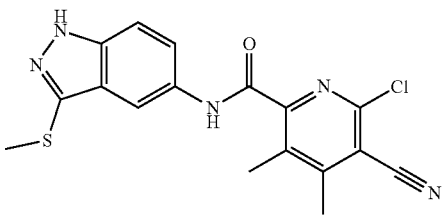

Step 1: 3-(Methylthio)-5-nitro-1H-indazole

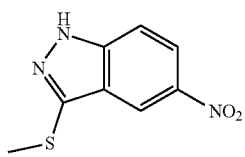

3-Iodo-5-nitro-1H-indazole (1.0 g, 3.46 mmol), sodium thiomethoxide (1.21 g, 17.3 mmol) and copper(I) iodide (65.89 mg, 0.350 mmol) were dissolved in dry DMSO (30 mL) and H$_2$O (6 mL) and the mixture was heated at 120° C. for 30 min. under microwave irradiation. The reaction mixture was diluted with saturated aqueous NaHCO$_3$ and extracted with DCM. The organic phase was dried over Na$_2$SO$_4$, filtered and evaporated under reduced pressure to give a residue. The residue was purified by silica gel column chromatography (10 g Biotage silica cartridge) using a 0-50% EtOAc/cyclohexane gradient eluent to afford the title compound (430 mg, 59%) as a yellow solid. $^1$H NMR (400 MHz, DMSO-d$_6$) δ 13.72 (s, 1H), 8.56 (dd, J=2.2, 0.6 Hz, 1H), 8.21 (dd, J=9.2, 2.2 Hz, 1H), 7.70 (dd, J=9.2, 0.7 Hz, 1H), 2.65 (s, 3H). MS-ESI (m/z) calc'd for C$_8$H$_8$N$_3$O$_2$S [M+H]$^+$: 210.1. Found 210.0.

Step 2: 3-(Methylthio)-1H-indazol-5-anine

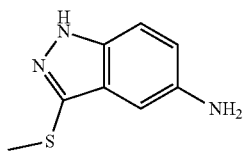

A mixture of 3-methylsulfanyl-5-nitro-1H-indazole (150.0 mg, 0.670 mmol), NH$_4$Cl (38.16 mg, 0.710 mmol), and Fe (161.24 mg, 2.89 mmol) in EtOH/H$_2$O (3 mL/3 mL) was heated to reflux for 1.5 hrs. The mixture was cooled and filtered through Celite. The filtrate was evaporated, and the resulting residue was purified by strong cation exchange (SCX) using MeOH to wash the cartride and NH$_3$/MeOH to wash out the desired product. The MeOH was evaporated under reduced pressure to afford the title compound (110 mg, 92%) as a red solid. $^1$H NMR (400 MHz, DMSO-d$_6$) δ 12.62 (s, 1H), 7.21 (d, J=8.7 Hz, 1H), 6.79 (dd, J=8.8, 2.1 Hz, 1H), 6.66 (d, J=2.0 Hz, 1H), 4.86 (s, 2H), 2.47 (s, 3H). MS-ESI (m/z) calc'd for C$_8$H$_{10}$N$_3$S [M+H]$^+$: 180.1. Found 180.0.

Step 3: 6-Chloro-5-cyano-3,4-dimethyl-N-(3-(methylthio)-1H-indazol-5-yl)picolinamide

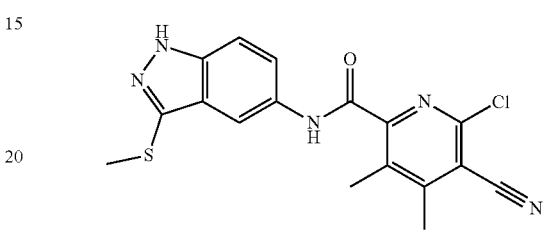

Prepared as described for 3-chloro-5-cyano-N-(3-cyclopropyl-1H-indazol-5-yl)-4,6-dimethylpicolinamide (Example 283) using 6-chloro-5-cyano-3,4-dimethylpicolinic acid in place of 3-chloro-5-cyano-4,6-dimethylpicolinic acid and using 3-(methylthio)-1H-indazol-5-amine in place of 3-cyclopropyl-1H-indazol-5-amine to afford the title compound (41.4 mg, 42%) as a white solid. $^1$H NMR (400 MHz, DMSO-d$_6$) δ 13.11 (s, 1H), 10.76 (s, 1H), 8.20 (s, 1H), 7.63-7.56 (m, 1H), 7.53 (d, J=8.9 Hz, 1H), 2.59 (s, 3H), 2.57 (s, 3H), 2.39 (s, 3H). MS-ESI (m/z) calc'd for C$_7$H$_{15}$ClN$_5$OS [M+H]$^+$: 372.1. Found 372.0.

Example 318: 3-Chloro-5-cyano-N-(3-(oxazol-5-yl)-1H-indazol-5-yl)picolinamide

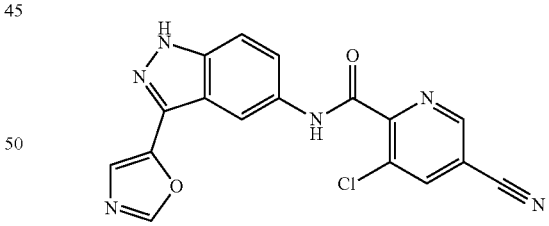

Prepared as described for 3-chloro-5-cyano-N-(3-cyclopropyl-1H-indazol-5-yl)-4,6-dimethylpicolinamide (Example 283) using 3-chloro-5-cyanopicolinic acid in place of 3-chloro-5-cyano-4,6-dimethylpicolinic acid and using 3-(oxazol-5-yl)-1H-indazol-5-amine in place of 3-cyclopropyl-1H-indazol-5-amine to afford the title compound (51 mg, 70%) as a white solid. $^1$H NMR (400 MHz, DMSO-d$_6$) δ 13.54 (s, 1H), 10.95 (s, 1H), 9.13 (d, J=1.7 Hz, 1H), 8.82 (d, J=1.8 Hz, 1H), 8.59 (s, 1H), 8.55 (dd, J=1.9, 0.9 Hz, 1H), 7.69 (dd, J=9.0, 1.8 Hz, 1H), 7.67-7.63 (m, 2H). MS-ESI (m/z) calc'd for C$_{17}$H$_{10}$ClN$_6$O$_2$[M+H]$^+$: 365.1/367.0. Found 365.1/367.1.

Example 319: 5-Cyano-N-(3-(3-(dimethylphosphoryl)phenyl)-1H-indazol-5-yl)-3-methylpicolinamide

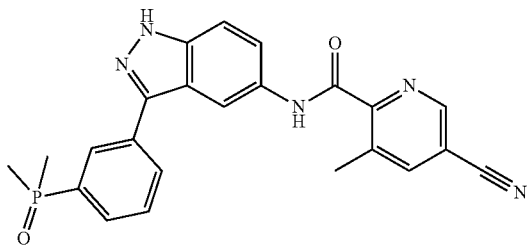 [SMILES: Cc1cc(C#N)cnc1C(=O)Nc1ccc2[nH]nc(-c3cccc(P(C)(C)=O)c3)c2c1]

Step 1: (3-Bromophenyl)dimethylphosphine oxide

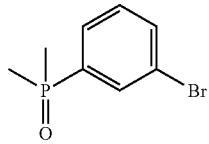

Dimethylphosphine oxide (834.0 mg, 10.69 mmol) and 1-bromo-3-iodobenzene (1.36 mL, 10.69 mmol) were dissolved in 1,4-dioxane (36 mL) and the flask was purged with N$_2$ (3×). In a separate vial, Pd(dba)$_2$ (48.92 mg, 0.050 mmol), Xantphos (61.83 mg, 0.110 mmol) and Et$_3$N (1.74 mL, 12.5 mmol) were stirred in 1,4-dioxane (4 mL) for 10 minutes to prepare a solution. This catalyst solution was added to the previous solution and left stirring at 25° C. for 24 hrs. The solvent was evaporated and the residue obtained was taken up in water and extracted with DCM, the organic layer was passed through a phase separator and evaporated to give an oil which was purified by silica gel column chromatography using a 0-10% MeOH/DCM gradient eluent to afford the title compound (1.67 g, 67%) as a clear oil. $^1$H NMR (400 MHz, DMSO-d$_6$) δ 7.93 (dt, J=11.2, 1.7 Hz, 1H), 7.83-7.72 (m, 2H), 7.49 (td, J=7.7, 3.0 Hz, 1H), 1.67 (d, J=13.5 Hz, 6H). MS-ESI (m/z) calc'd for C$_8$H$_1$BrOP [M+H]$^+$: 233.0/235.0. Found 233.0/235.0.

Step 2: Dimethyl(3-(4,4,5,5-tetramethyl-1,3,2-dioxaborolan-2-yl)phenyl)phosphine oxide

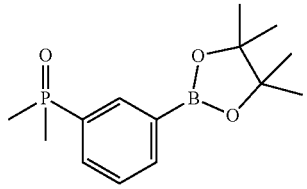

(3-Bromophenyl)dimethylphosphine oxide (0.47 g, 2 mmol), bis(pinacolato)diborane (0.68 mL, 2.6 mmol), KOAc (588.84 mg, 6 mmol) and [1,1'-bis(diphenylphosphino)ferrocene]dichloropalladium(II) (43.9 mg, 0.060 mmol) were placed in a flask that was sealed with a rubber septum. The atmosphere in the flask was purged with N$_2$ and 1,4-dioxane (20 mL) was added. The mixture was stirred at 60° C. for 24 hrs. The solvent was evaporated and the black residue obtained was purified by silica gel column chromatography using a 0-15% MeOH/DCM gradient eluent to afford the title compound (650 mg) as a yellow oil. $^1$H NMR (400 MHz, DMSO-d$_6$) δ 8.09-8.01 (m, 1H), 7.92-7.81 (m, 2H), 7.54 (td, J=7.5, 2.5 Hz, 1H), 1.64 (d, J=13.4 Hz, 6H), 1.06 (s, 12H). MS-ESI (m/z) calc'd for C$_{14}$H$_{23}$BO$_3$P [M+H]$^+$: 281.1. Found 281.2.

Step 3: (3-(5-Amino-1H-indazol-3-yl)phenyl)dimethylphosphine oxide

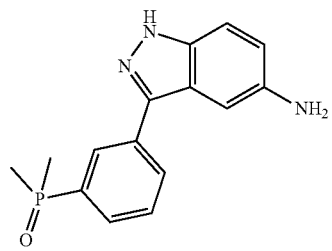 [SMILES: CP(C)(=O)c1cccc(-c2n[nH]c3ccc(N)cc23)c1]

3-Iodo-1H-indazol-5-amine (280.6 mg, 1.08 mmol) was dissolved in THF (10 mL) then a solution of tripotassium phosphate (449.12 mg, 3.25 mmol) and dimethyl(3-(4,4,5,5-tetramethyl-1,3,2-dioxaborolan-2-yl)phenyl)phosphine oxide (650.17 mg, 1.3 mmol) in H$_2$O (3 mL) was added and the mixture was degassed with N$_2$ for 15 minutes. SPhos-Pd-G2 (78.06 mg, 0.110 mmol) was added and the mixture was stirred at 80° C. under N$_2$ for 6 hrs. The organic solvent was evaporated and the mixture was diluted with H$_2$O and extracted with EtOAc (3×). The combined organic layers were passed through a phase separator and evaporated to obtain a residue which was purified by silica gel column chromatography using a 0-100% MeOH/DCM gradient eluent to afford the title compound (61 mg, 20%) as a beige solid. $^1$H NMR (400 MHz, DMSO-d$_6$) δ 12.90 (s, 1H), 8.31-8.20 (m, 1H), 8.05 (dd, J=7.7, 1.6 Hz, 1H), 7.77-7.67 (m, 1H), 7.63 (td, J=7.7, 3.1 Hz, 1H), 7.32 (d, J=8.8 Hz, 1H), 7.16-7.03 (m, 1H), 6.84 (dd, J=8.8, 2.0 Hz, 1H), 4.95 (s, 2H), 1.72 (d, J=13.3 Hz, 6H). MS-ESI (m/z) calc'd for C$_{15}$H$_{17}$N$_3$O P [M+H]$^+$: 286.1. Found 286.1.

Step 4: 5-Cyano-N-(3-(3-(dimethylphosphoryl)phenyl)-1H-indazol-5-yl)-3-methylpicolinamide

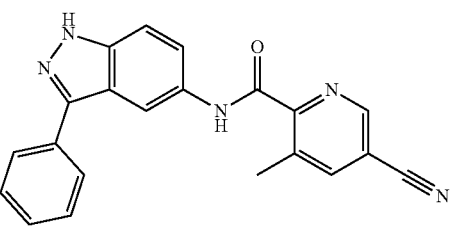

Prepared as described for 3-chloro-5-cyano-N-(3-cyclopropyl-1H-indazol-5-yl)-4,6-dimethylpicolinamide (Example 283) using 5-cyano-3-methylpicolinic acid in place of 3-chloro-5-cyano-4,6-dimethylpicolinic acid and using (3-(5-amino-1H-indazol-3-yl)phenyl)dimethylphosphine oxide in place of 3-cyclopropyl-1H-indazol-5-amine to afford the title compound (54 mg, 63%) as a yellow solid. $^1$H NMR (400 MHz, DMSO-$d_6$) δ 13.37 (s, 1H), 10.81 (s, 1H), 9.00 (d, J=2.0 Hz, 1H), 8.64-8.59 (m, 1H), 8.41 (dd, J=2.0, 0.8 Hz, 1H), 8.31 (dt, J=12.0, 1.6 Hz, 1H), 8.14-8.06 (m, 1H), 7.86-7.77 (m, 2H), 7.70 (td, J=7.6, 2.9 Hz, 1H), 7.62 (d, J=8.9 Hz, 1H), 2.58 (s, 3H), 1.74 (d, J=13.3 Hz, 6H). MS-ESI (m/z) calc'd for $C_{23}H_{21}N_5O_2P$ [M+H]$^+$: 430.1. Found 430.2.

Example 320: 6-Chloro-N-(3-chloro-1H-indazol-5-yl)-5-cyano-3,4-dimethylpicolinamide

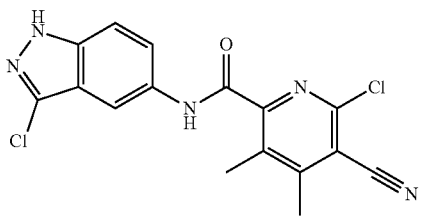 [SMILES: Cc1c(C(=O)Nc2ccc3[nH]nc(Cl)c3c2)nc(Cl)c(C#N)c1C]

Prepared as described for 3-chloro-5-cyano-N-(3-cyclopropyl-1H-indazol-5-yl)-4,6-dimethylpicolinamide (Example 283) using 6-chloro-5-cyano-3,4-dimethylpicolinic acid in place of 3-chloro-5-cyano-4,6-dimethylpicolinic acid and using 3-chloro-1H-indazol-5-amine in place of 3-cyclopropyl-1H-indazol-5-amine to afford the title compound (14 mg, 19%) as a yellow solid. $^1$H NMR (400 MHz, DMSO-$d_6$) δ 13.30 (s, 1H), 10.85 (s, 1H), 8.25 (dd, J=1.9, 0.8 Hz, 1H), 7.63 (dd, J=9.0, 1.8 Hz, 1H), 7.59 (dd, J=9.0, 0.8 Hz, 1H), 2.59 (s, 3H), 2.39 (s, 3H). MS-ESI (m/z) calc'd for $C_{16}H_{12}Cl_2N_5O$ [M+H]$^+$: 360.0/362.0. Found 360.0/362.0.

Example 321: N-(3-Chloro-1H-indazol-5-yl)-5-cyano-6-methoxy-3,4-dimethylpicolinamide

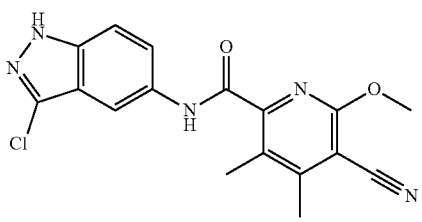 [SMILES: COc1nc(C(=O)Nc2ccc3[nH]nc(Cl)c3c2)c(C)c(C)c1C#N]

Prepared as described for 3-chloro-5-cyano-N-(3-cyclopropyl-1H-indazol-5-yl)-4,6-dimethylpicolinamide (Example 283) using 5-cyano-6-methoxy-3,4-dimethylpicolinic acid in place of 3-chloro-5-cyano-4,6-dimethylpicolinic acid and using 3-chloro-1H-indazol-5-amine in place of 3-cyclopropyl-1H-indazol-5-amine to afford the title compound (34 mg, 48%) as a yellow solid. $^1$H NMR (400 MHz, DMSO-$d_6$) δ 13.30 (s, 1H), 10.65 (s, 1H), 8.27 (s, 1H), 7.66 (dd, J=9.1, 1.9 Hz, 1H), 7.59 (d, J=8.9 Hz, 1H), 4.06 (s, 3H), 2.52 (s, 3H), 2.34 (s, 3H). MS-ESI (m/z) calc'd for $C_{17}H_{15}ClN_5O_2$ [M+H]$^+$: 356.1/358.1. Found 356.1/358.1.

Example 322: 5-Cyano-6-methoxy-3,4-dimethyl-N-(3-methyl-1H-indazol-5-yl)picolinamide

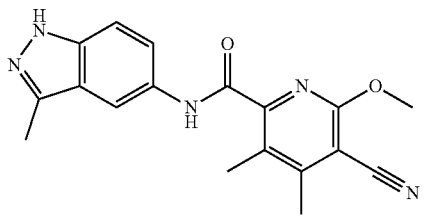 [SMILES: COc1nc(C(=O)Nc2ccc3[nH]nc(C)c3c2)c(C)c(C)c1C#N]

Prepared as described for 3-chloro-5-cyano-N-(3-cyclopropyl-1H-indazol-5-yl)-4,6-dimethylpicolinamide (Example 283) using 5-cyano-6-methoxy-3,4-dimethylpicolinic acid in place of 3-chloro-5-cyano-4,6-dimethylpicolinic acid and using 3-methyl-1H-indazol-5-amine in place of 3-cyclopropyl-1H-indazol-5-amine to afford the title compound (22.5 mg, 34%) as a yellow solid. $^1$H NMR (400 MHz, DMSO-$d_6$) δ 12.61 (s, 1H), 10.48 (s, 1H), 8.20 (dd, J=1.9, 0.8 Hz, 1H), 7.53 (dd, J=8.9, 1.9 Hz, 1H), 7.45 (dd, J=8.8, 0.8 Hz, 1H), 4.05 (s, 3H), 2.51 (s, 3H), 2.48 (s, 3H), 2.33 (s, 3H). MS-ESI (m/z) calc'd for $C_{18}H_{18}N_5O_2$ [M+H]$^+$: 336.1. Found 336.2.

Example 323: 5-cyano-3-methyl-N-(3-(3-(piperidin-1-yl)propyl)-1H-indazol-5-yl)picolinamide

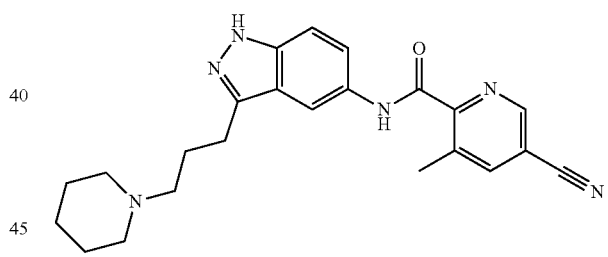

Step 1: 1-(Prop-2-yn-1-yl)piperidine

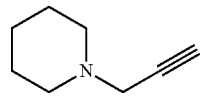

To a solution of piperidine (4.94 mL, 50 mmol) in DCM (10 mL) was added 3-bromo-1-propyne (2.38 g, 20 mmol) dropwise and the mixture was stirred at 25° C. for 15 hrs. The solvent was evaporated to give a residue that was taken up in Et$_2$O and washed with H$_2$O (3×). The organic layer was passed through a phase separator and evaporated to afford the title compound (2.33 g, 95%) as an orange oil. $^1$H NMR (400 MHz, DMSO-$d_6$) δ 3.20 (d, J=2.4 Hz, 2H), 3.08 (t, J=2.4 Hz, 1H), 2.41-2.33 (m, 4H), 1.61-1.28 (m, 6H).

Step 2: 3-(3-(Piperidin-1-yl)prop-1-yn-1-yl)-1H-indazol-5-amine

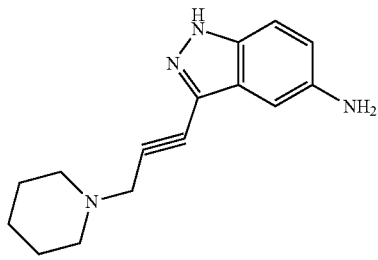 [SMILES: Nc1ccc2[nH]nc(C#CCN3CCCCC3)c2c1]

A mixture of 3-iodo-1H-indazol-5-amine (1.04 g, 4 mmol), 1-prop-2-ynylpiperidine (0.74 g, 6 mmol), bis(triphenylphosphine)palladium(II) dichloride (281.56 mg, 0.400 mmol) and copper (I) iodide (38.09 mg, 0.200 mmol) in Et$_3$N (4 mL) was heated at 90° C. for 2 hrs. The solvent was evaporated and the residue was purified by silica gel column chromatography using a 0-50% MeOH/DCM gradient eluent to afford the title compound (160 mg, 16%) as an orange oil. $^1$H NMR (400 MHz, DMSO-d$_6$) δ 12.83 (s, 1H), 7.26 (dd, J=8.7, 0.8 Hz, 1H), 6.80 (dd, J=8.8, 2.1 Hz, 1H), 6.69 (dd, J=2.1, 0.8 Hz, 1H), 4.97 (d, J=2.7 Hz, 2H), 3.54 (s, 2H), 2.64 (t, J=5.3 Hz, 2H), 1.64-1.29 (m, 8H). MS-ESI (m/z) calc'd for C$_{15}$H$_{19}$N$_4$ [M+H]$^+$: 255.2. Found 255.4.

Step 3: 1-(3-(Piperidin-1-yl)propyl)-1H-indazol-5-amine

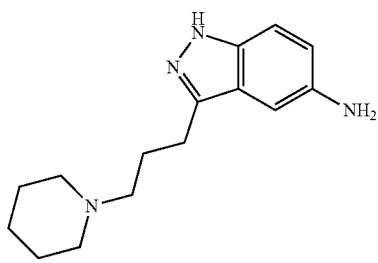 [SMILES: Nc1ccc2[nH]nc(CCCN3CCCCC3)c2c1]

To a solution of 3-(3-(piperidin-1-yl)prop-1-yn-1-yl)-1H-indazol-5-amine (160.0 mg, 0.630 mmol) in EtOH (6.291 mL) was added 10% Pd/C (66.95 mg, 0.060 mmol) and the mixture was hydrogenated at 3 bars for 24 hrs. The catalyst was removed by filtration through Celite and the filtrate evaporated to afford the title compound (116 mg, 71%) as an orange solid. $^1$H NMR (400 MHz, DMSO-d$_6$) δ 12.15 (s, 1H), 7.27-7.13 (m, 1H), 6.79-6.75 (m, 1H), 6.75-6.68 (m, 1H), 4.73 (s, 2H), 3.13-2.97 (m, 2H), 2.78 (t, J=7.4 Hz, 2H), 2.73-2.55 (m, 2H), 1.99-1.83 (m, 2H), 1.74-1.31 (m, 8H). MS-ESI (m/z) calc'd for C$_{15}$H$_{13}$N$_4$ [M+H]$^+$: 259.2. Found 259.5.

Step 4: 5-cyano-3-methyl-N-(3-(3-(piperidin-1-yl)propyl)-1H-indazol-5-yl)picolinamide

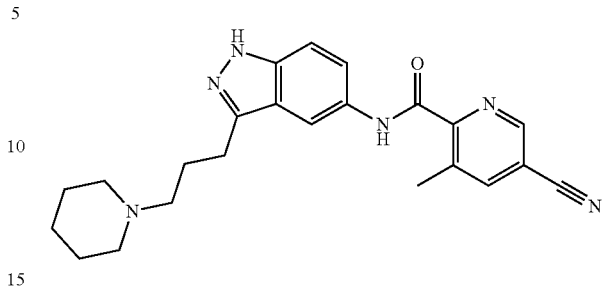

Prepared as described for 3-chloro-5-cyano-N-(3-cyclopropyl-1H-indazol-5-yl)-4,6-dimethylpicolinamide (Example 283) using 5-cyano-3-methylpicolinic acid in place of 3-chloro-5-cyano-4,6-dimethylpicolinic acid and using 1-(3-(piperidin-1-yl)propyl)-1H-indazol-5-amine in place of 3-cyclopropyl-1H-indazol-5-amine to afford the title compound (23.6 mg, 12%) as a yellow solid. $^1$H NMR (400 MHz, DMSO-d$_6$) δ 12.66 (s, 1H), 10.65 (s, 1H), 8.99 (d, J=2.1 Hz, 1H), 8.40 (dd, J=2.0, 0.9 Hz, 1H), 8.30 (dd, J=1.9, 0.7 Hz, 1H), 8.18 (s, 1H), 7.61 (dd, J=8.9, 1.9 Hz, 1H), 7.46 (dd, J=8.9, 0.7 Hz, 1H), 2.92 (t, J=7.5 Hz, 2H), 2.61-2.52 (m, 9H), 1.97 (p, J=7.7 Hz, 2H), 1.62-1.49 (m, 4H), 1.41 (p, J=5.9 Hz, 2H). MS-ESI (m/z) calc'd for C$_{23}$H$_{28}$N$_6$O$^+$ [M+H]$^+$: 404.2. Found 403.2.

Example 324: N-(3-Bromo-1H-indazol-5-yl)-6-chloro-5-cyano-3,4-dimethylpicolinamide

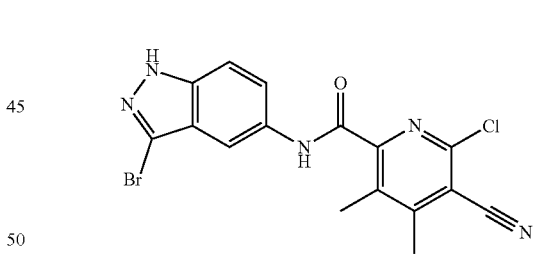

Prepared as described for 3-chloro-5-cyano-N-(3-cyclopropyl-1H-indazol-5-yl)-4,6-dimethylpicolinamide (Example 283) using 6-chloro-5-cyano-3,4-dimethylpicolinic acid in place of 3-chloro-5-cyano-4,6-dimethylpicolinic acid and using 3-bromo-1H-indazol-5-amine in place of 3-cyclopropyl-1H-indazol-5-amine to afford the title compound (55 mg, 68%) as a yellow solid. $^1$H NMR (400 MHz, DMSO-d$_6$) δ 13.44 (s, 1H), 10.85 (s, 1H), 8.20-8.17 (m, 1H), 7.64 (dd, J=9.0, 1.9 Hz, 1H), 7.59 (d, J=9.0 Hz, 1H), 2.59 (s, 3H), 2.39 (s, 3H). MS-ESI (m/z) calc'd for C$_{16}$H$_{12}$BrClN$_5$O [M+H]$^+$: 404.0/406.0. Found 404.0/406.0.

Example 325: 5-Cyano-3,4,6-trimethyl-N-(3-methyl-1H-indazol-5-yl)picolinamide

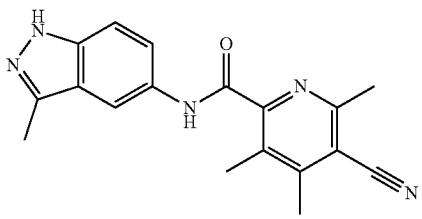 [SMILES: Cc1nc(C(=O)Nc2ccc3[nH]nc(C)c3c2)c(C)c(C)c1C#N]

Prepared as described for 3-chloro-5-cyano-N-(3-cyclopropyl-1H-indazol-5-yl)-4,6-dimethylpicolinamide (Example 283) using 5-cyano-3,4,6-trimethylpicolinic acid in place of 3-chloro-5-cyano-4,6-dimethylpicolinic acid and using 3-methyl-1H-indazol-5-amine in place of 3-cyclopropyl-1H-indazol-5-amine to afford the title compound (57 mg, 89%) as a yellow solid. $^1$H NMR (400 MHz, DMSO-$d_6$) δ 12.60 (s, 1H), 10.56 (s, 1H), 8.21 (s, 1H), 7.56-7.51 (m, 1H), 7.44 (d, J=8.8 Hz, 1H), 2.70 (s, 3H), 2.53 (s, 3H), 2.47 (s, 3H), 2.38 (s, 3H). MS-ESI (m/z) calc'd for $C_{18}H_{18}N_5O$ [M+H]$^+$: 320.1. Found 320.2.

Example 326: 3-Chloro-5-cyano-4-methyl-N-(3-methyl-1H-indazol-5-yl)picolinamide

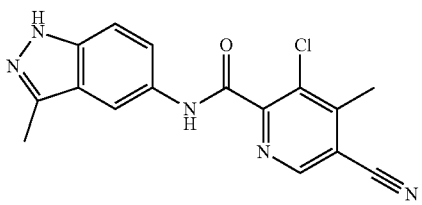 [SMILES: Cc1c(C#N)cnc(C(=O)Nc2ccc3[nH]nc(C)c3c2)c1Cl]

Step 1: 5-Chloro-4,6-dimethylnicotinonitrile

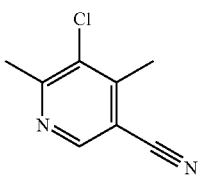

To a mixture of 2,5-dichloro-4,6-dimethylpyridine-3-carbonitrile (2.01 g, 10 mmol) in acetic acid (1 mL) and H$_2$O (9 mL) was added zinc (1.31 g, 20 mmol) and the suspension was stirred at 95° C. for 3 hrs. The mixture was extracted with DCM (3×) and the combined organic layers were passed through a phase separator and evaporated to obtain a yellow solid which was purified by silica gel column chromatography using a 2-20% EtOAc/cyclohexane gradient eluent to afford the title compound (930 mg, 56%) as a white solid. $^1$H NMR (400 MHz, DMSO-$d_6$) δ 8.78 (s, 1H), 2.64 (s, 3H), 2.54 (s, 3H). MS-ESI (m/z) calc'd for $C_8H_8ClN_2$ [M+H]$^+$: 167.0. Found 166.9.

Step 2: 3-Chloro-5-cyano-2,4-dimethylpyridine 1-oxide

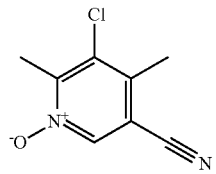

To a solution of 5-chloro-4,6-dimethylnicotinonitrile (930.0 mg, 5.58 mmol) in DCM (55.82 mL) was added MCPBA (1.38 g, 5.58 mmol) and the mixture was stirred at 25° C. for 5 hrs. The solution was washed with saturated aqueous K$_2$CO$_3$ (3×) and the aqueous layers were extracted with DCM (2×). The organic phases were combined, passed through a phase separator and concentrated to afford the title compound (970 mg, 95%) as a white solid. $^1$H NMR (400 MHz, DMSO-$d_6$) δ 8.94 (s, 1H), 2.55 (s, 3H), 2.48 (s, 3H). MS-ESI (m/z) calc'd for $C_8H_8ClN_2$ [M+H]$^+$: 183.0. Found 183.0.

Step 3: 5-Chloro-6-(hydroxymethyl)-4-methylnicotinonitrile

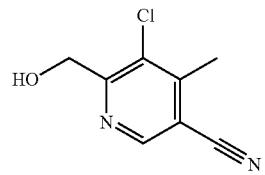

To a solution of 3-chloro-5-cyano-2,4-dimethylpyridine 1-oxide (970.0 mg, 5.31 mmol) in DCM (26.56 mL) was added trifluoroacetic anhydride (2.22 mL, 15.94 mmol) dropwise and the mixture was stirred at 25° C. for 15 hours. The solvent was evaporate and the residue was taken up in MeOH. K$_2$CO$_3$ (3 g) was added and the suspension was stirred at 25° C. for 1 hr. The solvent was evaporated and the residue was taken up in water and extracted with DCM (3×). The combined organic layers were passed through a phase separator and concentrated to afford the title compound (305 mg, 31%) as a yellow solid. $^1$H NMR (400 MHz, DMSO-$d_6$) δ 8.90 (s, 1H), 5.41 (t, J=6.1 Hz, 1H), 4.70 (d, J=6.0 Hz, 2H), 2.56 (s, 3H). MS-ESI (m/z) calc'd for $C_8H_8ClN_2$ [M+H]$^+$: 183.0. Found 182.9.

Step 4: 3-Chloro-5-Cyano-4-methylpicolinic acid

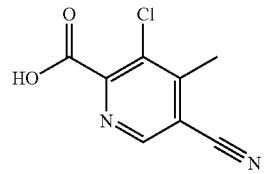

To a solution of 5-chloro-6-(hydroxymethyl)-4-methylpyridine-3-carbonitrile (305.0 mg, 1.67 mmol) in acetone (10 mL) was added a solution of KMnO$_4$ (395.92 mg, 2.51 mmol) in H₂O (5 mL) and the mixture was stirred at 25° C. for 2 hrs. The dark mixture was filtered and washed with water. The filtrate was acidified by addition of conc. HCl and then extracted with EtOAc (3×). The combined organic layers were passed through a phase separator and concentrated to afford the title compound (325 mg, 99%) as a beige solid. ¹H NMR (400 MHz, DMSO-d₆) δ 14.41 (bs, 1H), 8.93 (s, 1H), 2.59 (s, 3H). MS-ESI (m/z) calc'd for C₈H₈ClN₂O₂ [M+H]⁺: 197.0. Found 197.0.

Step 5: 3-Chloro-5-cyano-4-methyl-N-(3-methyl-1H-indazol-5-yl)picolinamide

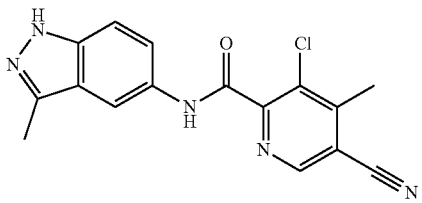 [SMILES: Cc1c(C#N)cnc(C(=O)Nc2ccc3[nH]nc(C)c3c2)c1Cl]

Prepared as described for 3-chloro-5-cyano-N-(3-cyclopropyl-1H-indazol-5-yl)-4,6-dimethylpicolinamide (Example 283) using 3-chloro-5-cyano-4-methylpicolinic acid in place of 3-chloro-5-cyano-4,6-dimethylpicolinic acid and using 3-methyl-1H-indazol-5-amine in place of 3-cyclopropyl-1H-indazol-5-amine to afford the title compound (57 mg, 89%) as a yellow solid. ¹H NMR (400 MHz, DMSO-d₆) δ 12.63 (s, 1H), 10.77 (s, 1H), 9.02 (s, 1H), 8.19 (d, J=1.4 Hz, 1H), 7.46 (d, J=1.0 Hz, 2H), 2.65 (s, 3H), 2.48 (s, 3H). MS-ESI (m/z) calc'd for C₁₆H₁₃ClN₅O [M+H]⁺: 326.1/328.1. Found 326.1/328.1.

Example 327: 5-Cyano-N-(3-cyclopropyl-1H-indazol-5-yl)-6-(difluoromethyl)-3,4-dimethylpicolinamide

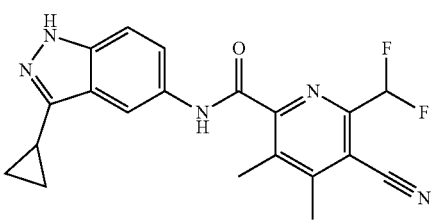 [SMILES: Cc1c(C(=O)Nc2ccc3[nH]nc(C4CC4)c3c2)nc(C(F)F)c(C#N)c1C]

Step 1: Methyl 6-chloro-5-cyano-3,4-dimethylpicolinate

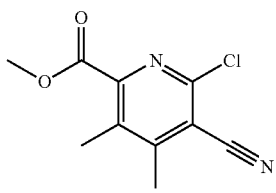

To a solution of 6-chloro-5-cyano-3,4-dimethylpyridine-2-carboxylic acid (500.0 mg, 2.09 mmol) in DMF (4.017 mL) was added potassium carbonate (866.19 mg, 6.27 mmol) and iodomethane (260.11 uL, 4.18 mmol) and then the mixture was stirred at 80° C. for 4 hrs. The reaction mixture was extracted with water (150 mL) and EtOAc (150 mL). The organic phase was separated, washed with saturated aqueous NaHCO₃, dried over Na₂SO₄, filtered and concentrated. The residue was purified by silica gel column chromatography using a 0-40% EtOAc/cyclehexane gradient eluent to afford the title compound (465 mg, 99%) as a white solid. ¹H NMR (400 MHz, DMSO-d₆) δ 3.92 (s, 3H), 2.55 (s, 3H), 2.33 (s, 3H). MS-ESI (m/z) calc'd for C₁₀H₁₀ClN₂O₂ [M+H]⁺: 225.0. Found 225.0.

Step 2: Methyl 5-cyano-3,4-dimethyl-6-vinylpicolinate

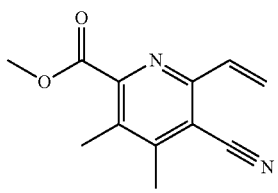 [SMILES: C=Cc1nc(C(=O)OC)c(C)c(C)c1C#N]

A microwave vial was charged with methyl 6-chloro-5-cyano-3,4-dimethylpicolinate (115.0 mg, 0.510 mmol), triphenylphosphine (4.03 mg, 0.020 mmol), tributyl(ethenyl)stannane (0.18 mL, 0.610 mmol) and toluene (3.171 mL) under N₂. The reaction mixture was degassed with N₂ for 10 min, then palladium tetrakis triphenylphosphine (5.92 mg, 0.010 mmol) was added and the mixture was heated to reflux for 3 hrs. Water (150 mL) and EtOAc (150 mL) were added, the organic phase was separated, washed with brine, dried over Na₂SO₄, filtered and concentrated under vacuum. The residue was purified by silica gel column chromatography using a 0-50% EtOAc/cyclehexane gradient eluent to afford the title compound (76 mg, 69%) as a white solid. ¹H NMR (400 MHz, chloroform-d₆) δ 7.15 (dd, J=16.9, 10.7 Hz, 1H), 6.63 (dd, J=16.9, 1.5 Hz, 1H), 5.72 (dd, J=10.7, 1.5 Hz, 1H), 3.99 (s, 3H), 2.55 (s, 3H), 2.38 (s, 3H). MS-ESI (m/z) calc'd for C₁₂H₁₃N₂O₂ [M+H]⁺: 217.1. Found 217.0.

Step 3: Methyl 5-cyano-6-formyl-3,4-dimethylpicolinate

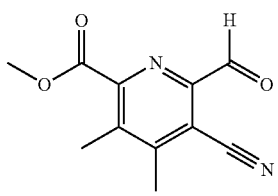 [SMILES: COC(=O)c1nc(C=O)c(C#N)c(C)c1C]

To a solution of methyl 5-cyano-3,4-dimethyl-6-vinylpicolinate (124.0 mg, 0.570 mmol) (118 mg) in 1,4-dioxane (1.751 mL) was added a solution of sodium:periodate (485.7 mg, 2.27 mmol) in H₂O (1.751 mL), then 4% tetraoxoosmium (0.18 mL, 0.030 mmol) was added and the mixture was stirred at 25° C. for 2 hrs. The suspension was diluted with H₂O and extracted with EtOAc (2×), the combined organic layers were dried over Na₂SO₄, filtered and evaporated to afford the title compound (123.8 mg, 99%) as a beige solid which was used without further purification. MS-ESI (m/z) calc'd for C₁₁H₁₁N₂O₃ [M+H]⁺: 219.1. Found 219.0.

Step 4: Methyl 5-cyano-6-(difluoromethyl)-3,4-dimethylpicolinate

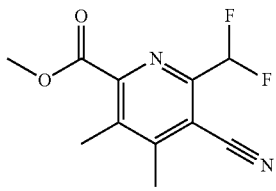 [SMILES: COC(=O)c1nc(C(F)F)c(C#N)c(C)c1C]

To a solution of methyl 5-cyano-6-formyl-3,4-dimethylpicolinate (123.8 mg, 0.570 mmol) in DCM (2.5 mL) was added DAST (0.11 mL, 0.850 mmol) dropwise at 0° C. The resulting mixture was allowed to warm to r.t., then stirred for 18 hrs. The reaction solution was quenched with saturated aqueous NaHCO₃ at 0° C. and diluted with H₂O (100 ml) and EtOAc (100 mL). The layers were separated and the organic layer was washed with brine, dried over Na₂SO₄ and concentrated to give a crude product which was purified by silica gel column chromatography using a 0-50% EtOAc/cyclohexane gradient to afford the title compound (73 mg, 54%) as a white solid. ¹H NMR (400 MHz, DMSO-d₆) δ 7.14 (t, J=53.1 Hz, 1H), 3.94 (s, 3H), 2.60 (s, 3H), 2.40 (s, 3H). MS-ESI (m/z) calc'd for C₁₁H₁₁F₂N₂O₂ [M+H]⁺: 241.1. Found 241.0.

Step 5: 5-Cyano-6-(difluoromethyl)-3,4-dimethylpicolinic acid

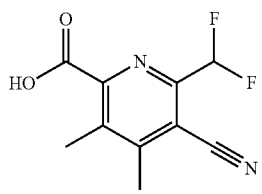 [SMILES: Cc1c(C(=O)O)nc(C(F)F)c(C#N)c1C]

To a solution of methyl 5-cyano-6-(difluoromethyl)-3,4-dimethylpicolinate (73.0 mg, 0.300 mmol) in EtOH (2.5 mL) was added a solution of LiOH·H₂O (12.75 mg, 0.300 mmol) in water (1.5 mL) and the resulting mixture was stirred at r.t. for 1 hr. 1 M HCl was added dropwise until pH 1, followed by EtOAc. The reaction mixture was partitioned between H₂O and EtOAc, the phases were separated, the aqueous layer was extracted with EtOAc (2×) and the combined organic phases dried over anhydrous Na₂SO₄, filtered and evaporated to dryness to afford the title compound (66.5 mg, 97%) as a white solid which was used without further purification. ¹H NMR (400 MHz, DMSO-d₆) δ 14.15 (s, 1H), 7.12 (t, J=53.2 Hz, 1H), 2.58 (s, 3H), 2.39 (s, 3H). MS-ESI (m/z) calc'd for C₁₀H₉F₂N₂O₂ [M+H]⁺: 227.1. Found 227.1.

Step 6: 5-Cyano-N-(3-cyclopropyl-1H-indazol-5-yl)-6-(difluoromethyl)-3,4-dimethylpicolinamide

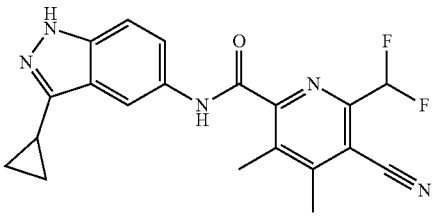 [SMILES: Cc1c(C(=O)Nc2ccc3[nH]nc(C4CC4)c3c2)nc(C(F)F)c(C#N)c1C]

To a solution of 5-cyano-6-(difluoromethyl)-3,4-dimethylpicolinic acid (36.5 mg, 0.160 mmol) and 3-cyclopropyl-1H-indazol-5-amine (30.75 mg, 0.180 mmol) and Et₃N (0.03 mL, 0.210 mmol) in MeCN (4.138 mL) was added HATU (61.36 mg, 0.160 mmol) in portions and the mixture was stirred at 25° C. for 1 hr. The reaction mixture was filtered and the solid was washed with MeCN (2×5 mL) and H₂O (2×5 mL), then dried under reduced pressure to afford the title compound (43.9 mg, 71%) as a yellow solid. ¹H NMR (400 MHz, DMSO-d₆) δ 12.56 (s, 1H), 10.69 (s, 1H), 8.26 (d, J=1.8 Hz, 1H), 7.53 (dd, J=8.9, 1.9 Hz, 1H), 7.45 (d, J=8.9 Hz, 1H), 7.19 (t, J=53.2 Hz, 1H), 2.63 (s, 3H), 2.48 (s, 3H), 2.21 (ddd, J=13.2, 8.3, 5.1 Hz, 1H), 0.98 (dt, J=8.5, 2.8 Hz, 2H), 0.93 (dt, J=5.0, 2.6 Hz, 2H). MS-ESI (m/z) calc'd for C₂₀H₁₅F₂N₅O [M+H]⁺: 382.1. Found 382.2.

Example 328: 5-Cyano-N-(3-cyclopropyl-1H-indazol-5-yl)-3,4-dimethyl-6-(trifluoromethyl)picolinamide

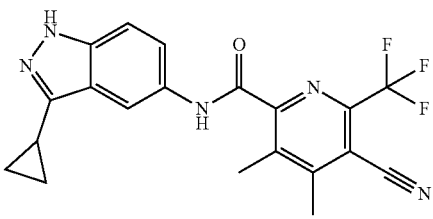 [SMILES: Cc1c(C(=O)Nc2ccc3[nH]nc(C4CC4)c3c2)nc(C(F)(F)F)c(C#N)c1C]

Step 1: Methyl 5-cyano-3,4-dimethyl-6-(trifluoromethyl)picolinate

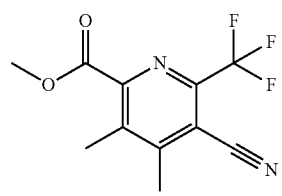 [SMILES: COC(=O)c1nc(C(F)(F)F)c(C#N)c(C)c1C]

A solution of methyl 5-cyano-3-methylpyridine-2-carboxylate (500.0 mg, 2.84 mmol) and zinc trifluoromethanesulfinate (1881.82 mg, 5.68 mmol) in DMSO (8 mL) was cooled in an ice water bath. The mixture was stirred vigorously while adding a 70% aqueous solution of tert-butyl hydroperoxide (1.18 mL, 8.51 mmol). The solution was allowed to reach r.t. and then warmed at 50° C. for 2 h. An additional 2 eq. of trifluoromethanesulfinate and 3 eq. of t-BuOOH were added and stirring was continued at 50° C. for 2 hrs. The reaction mixture was partitioned between H₂O and EtOAc and the phases were separated. The aqueous layer was extracted with EtOAc (2×) and the combined organic phases were washed with saturated aqueous NaHCO₃ (1×) and H₂O (1×), dried over Na₂SO₄ and evaporated to dryness. The residue was purified by silica gel column chromatography using a 0-40% EtOAc/cyclohexane gradient eluent to afford the title compound (100 mg, 20%) as a colorless oil. ¹H NMR (400 MHz, DMSO-d₆) δ 3.96 (s, 3H) 2.64 (s, 3H) 2.45 (s, 3H). MS-ESI (m/z) calc'd for C₁₉H₁₀F₃N₂O₂ [M+H]⁺: 259.1. Found 259.1.

Step 2:
5-Cyano-3,4-dimethyl-6-(trifluoromethyl)picolinic acid

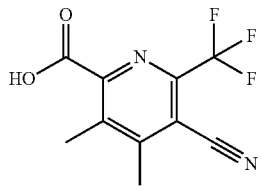 [SMILES: Cc1c(C(=O)O)nc(C(F)(F)F)c(C#N)c1C]

To a solution of methyl 5-cyano-3,4-dimethyl-6-(trifluoromethyl)picolinate (100.0 mg, 0.390 mmol) in MeOH (5 mL) was added a 1 N aqueous solution of NaOH (0.39 mL, 0.390 mmol) and the mixture was stirred at r.t. for 2 hrs. Volatiles were removed under reduced pressure to afford the title compound (105 mg) as a white solid which was used without further purification. ¹H NMR (400 MHz, DMSO-d₆) δ 2.50 (s, 3H) 2.26 (s, 3H). MS-ESI (m/z) calc'd for C₁₀H₈F₃N₂O₂ [M+H]⁺: 245.1. Found 244.9.

Step 3: 5-Cyano-N-(3-cyclopropyl-1H-indazol-5-yl)-3,4-dimethyl-6 (trifluoromethyl)picolinamide

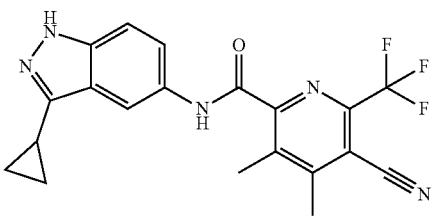 [SMILES: Cc1c(C(=O)Nc2ccc3[nH]nc(C4CC4)c3c2)nc(C(F)(F)F)c(C#N)c1C]

To a mixture of 5-cyano-3,4-dimethyl-6-(trifluoromethyl) picolinic acid (47.12 mg, 0.190 mmol), 3-cyclopropyl-1H-indazol-5-amine (40.12 mg, 0.230 mmol) and Et₃N (53.8 uL, 0.390 mmol) in MeCN (2.5 mL) was added HATU (73.38 mg, 0.190 mmol) and the mixture was stirred at r.t. for 1 hr. Then 0.5 mL of 1 N aqueous NaOH were added and the mixture was stirred at r.t. for 30 min. The reaction mixture was partitioned between H₂O and EtOAc and the phases were separated. The aqueous layer was extracted with EtOAc (2×) and the combined organic phases were washed with H₂O (1×), dried over Na₂SO₄ and evaporated to dryness. The residue was purified by preparative HPLC using Method DG to afford the title compound (38.2 mg, 50%) as a yellow solid. ¹H NMR (400 MHz, DMSO-d₆) δ 12.58 (s, 1H) 10.72 (s, 1H) 8.23-8.32 (m, 1H) 7.50-7.56 (m, 1H) 7.43-7.49 (m, 1H) 2.68 (s, 3H) 2.49 (s, 3H) 2.18-2.28 (m, 1H) 0.91-1.05 (m, 4H). MS-ESI (m/z) calc'd for C₂₀H₁₇F₃N₅O [M+H]⁺: 400.1. Found 400.2.

Example 329: 6-Bromo-5-cyano-N-(3-methoxy-1H-indazol-5-yl)-3,4-dimethylpicolinamide

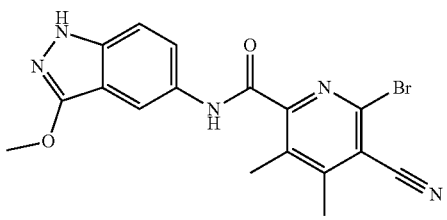 [SMILES: COc1n[nH]c2ccc(NC(=O)c3nc(Br)c(C#N)c(C)c3C)cc12]

Step 1: 6-Bromo-5-cyano-3,4-dimethylpicolinic acid

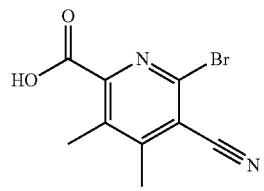

6-Chloro-5-cyano-3,4-dimethylpyridine-2-carboxylic acid (50.0 mg, 0.240 mmol) was dissolved in 1 mL of HBr (33% w/w in AcOH) and the reaction was stirred at 100° C. for 10 minutes. The reaction mixture was concentrated under reduced pressure and residual acetic acid was removed by co-evaporation with MeCN to afford the title compound (70 mg) as a beige solid which was used without further purification. ¹H NMR (400 MHz, DMSO-d₆) δ 2.55 (s, 3H) 2.31 (s, 3H). MS-ESI (m/z) calc'd for C₉H₈BrN₂O₂ [M+H]⁺: 255.0/257.0. Found 255.0/257.0.

Step 2: 6-Bromo-5-cyano-N-(3-methoxy-1H-indazol-5-yl)-3,4-dimethylpicolinamide

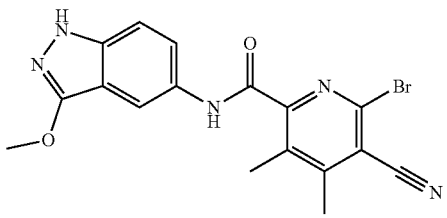 [SMILES: COc1n[nH]c2ccc(NC(=O)c3nc(Br)c(C#N)c(C)c3C)cc12]

To a mixture of 6-bromo-5-cyano-3,4-dimethylpicolinic acid (30.0 mg, 0.120 mmol), 3-methoxy-1H-indazol-5-amine (23.03 mg, 0.140 mmol) and Et₃N (32.79 uL, 0.240 mmol) in MeCN (2.5 mL) was added HATU (44.72 mg, 0.120 mmol) and the mixture was stirred at r.t. for 1 hr. The reaction mixture was partitioned between H₂O and EtOAc and the phases were separated. The aqueous layer was extracted with EtOAc (2×) and the combined organic phases were washed with H₂O (1×), dried over Na₂SO₄ and evaporated to dryness. The residue was purified by preparative HPLC using Method DH to afford the title compound (29.2 mg, 62%) as a yellow solid. ¹H NMR (400 MHz, DMSO-d₆) δ 11.92 (s, 1H) 10.69 (s, 1H) 8.12 (d, J=1.98 Hz, 1H) 7.54 (dd, J=9.02, 1.98 Hz, 1H) 7.37 (d, J=8.80 Hz, 1H) 4.01 (s, 3H) 2.59 (s, 3H) 2.35 (s, 3H). MS-ESI (m/z) calc'd for C₁₇H₁₅BrN₅O₂ [M+H]⁺: 400.0/402.0. Found 400.2/402.1.

Example 330: 6-Bromo-5-cyano-N-(3-cyclopropyl-1H-indazol-5-yl)-3,4-dimethylpicolinamide

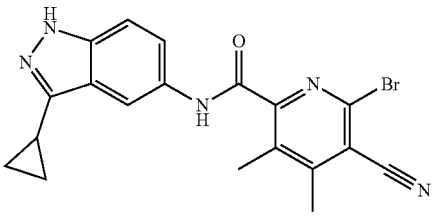 [SMILES: Cc1c(C(=O)Nc2ccc3[nH]nc(C4CC4)c3c2)nc(Br)c(C#N)c1C]

To a mixture of 6-bromo-5-cyano-3,4-dimethylpicolinic acid (30.1 mg, 0.120 mmol), 3-cyclopropyl-1H-indazol-5-amine (24.53 mg, 0.140 mmol) and triethylamine (32.89 uL, 0.240 mmol) in MeCN (2.5 mL) was added HATU (44.87 mg, 0.120 mmol) and the mixture was stirred at r.t. for 1 hr. The reaction mixture was partitioned between H₂O and EtOAc and the phases were separated. The aqueous layer was extracted with EtOAc (2×) and the combined organic phases were washed with water (1×), dried over Na₂SO₄ and evaporated to dryness. The residue was purified by preparative HPLC using Method DI to afford the title compound (35.1 mg, 73%) as a yellow solid. ¹H NMR (400 MHz, DMSO-d₆) δ 12.57 (s, 1H) 10.67 (s, 1H) 8.25 (d, J=1.54 Hz, 1H) 7.50-7.56 (m, 1H) 7.43-7.48 (m, 1H) 2.60 (s, 3H) 2.37 (s, 3H) 2.18-2.27 (m, 1H) 0.90-1.04 (m, 4H). MS-ESI (m/z) calc'd for C₁₉H₁₇BrN₅O [M+H]⁺: 410.1/412.1. Found 410.2/412.2.

Example 331: 3,6-Dichloro-5-cyano-N-(3-cyclopropyl-1H-indazol-5-yl)-4-methylpicolinamide

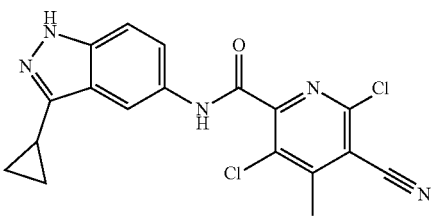 [SMILES: Cc1c(Cl)c(C(=O)Nc2ccc3[nH]nc(C4CC4)c3c2)nc(Cl)c1C#N]

Step 1: 2,5-Dichloro-3-cyano-4,6-dimethylpyridine 1-oxide

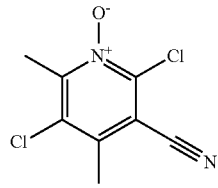

To a solution of 2,5-dichloro-4,6-dimethylpyridine-3-carbonitrile (2.01 g, 10 mmol) in trifluoroacetic acid (50 mL) was added hydrogen peroxide (3.06 mL, 30 mmol) and the mixture was stirred at 75° C. for 1 hr. The solvent was evaporated to afford the title compound (2.17 g, 99%) as a yellow oil which was used without further purification. ¹H NMR (400 MHz, DMSO-d₆) δ 2.62 (s, 3H), 2.53 (s, 3H). MS-ESI (m/z) calc'd for C₈H₇Cl₂N₂O [M+H]⁺: 217.0/219.0. Found 217.0/219.0.

Step 2: 2,5-Dichloro-6-(hydroxymethyl)-4-methylnicotinonitrile

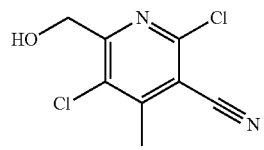

To a solution of 2,5-dichloro-3-cyano-4,6-dimethylpyridine 1-oxide (2.17 g, 10 mmol) in DCM (50 mL) was added trifluoroacetic anhydride (4.17 mL, 30 mmol) dropwise and the mixture was stirred at 25° C. for 15 hrs. The solvent was evaporated and the residue was taken up in MeOH. K₂CO₃ (3 g) was added and the suspension was stirred at 25° C. for 1 hr. The solvent was evaporated and the residue was taken up in water and extracted with DCM (3×). The combined organic layers were passed through a phase separator and evaporated to afford the title compound (1.9 g, 88%) as a yellow solid. ¹H NMR (400 MHz, DMSO-d₆) δ 5.60 (t, J=6.3 Hz, 1H), 4.66 (d, J=6.3 Hz, 2H), 2.58 (s, 3H). MS-ESI (m/z) calc'd for C₈H₇Cl₂N₂O [M+H]⁺: 217.0/219.0. Found 217.0/219.0.

Step 3: 3,6-Dichloro-5-cyano-4-methylpicolinic acid

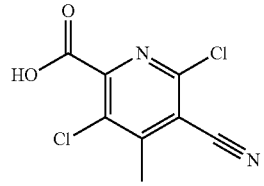

To a solution of 2,5-dichloro-6-(hydroxymethyl)-4-methylpyridine-3-carbonitrile (1.0 g, 4.61 mmol) in acetone (23.91 mL) was added a solution of KMnO₄ (0.97 g, 6.13 mmol) in H₂O (23.91 mL) and the mixture was stirred at 25° C. for 1 hr. The solid was filtered and the filtrate was evaporated to remove the organic solvent. The pH was adjusted to 1 by addition of conc. HCl and the suspension was extracted with EtOAc (3×). The combined organic layers were dried over Na₂SO₄, then passed through a phase separator and evaporated to afford the title compound (800 mg, 75%) as a yellow solid. ¹H NMR (400 MHz, DMSO-d₆) δ 14.83 (s, 1H), 2.62 (s, 3H). MS-ESI (m/z) calc'd for C₈H₅Cl₂N₂O₂ [M+H]⁺: 231.0/233.0. Found 231.0/232.9.

Step 4: 3,6-Dichloro-5-cyano-N-(3-cyclopropyl-1H-indazol-5-yl)-4-methylpicolinamide

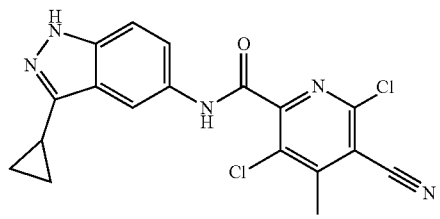 [SMILES: Cc1c(Cl)c(C(=O)Nc2ccc3[nH]nc(C4CC4)c3c2)nc(Cl)c1C#N]

To a mixture of 3,6-dichloro-5-cyano-4-methylpicolinic acid (46.21 mg, 0.200 mmol), 3-cyclopropyl-1H-indazol-5-amine (37.25 mg, 0.200 mmol) and Et₃N (27.88 uL, 0.200 mmol) in MeCN (2 mL) was added HATU (76.05 mg, 0.200 mmol) and the reaction was stirred at 25° C. for 2 hrs. Water was added and a solid formed that was collected by filtration and purified by silica gel column chromatography using a 0-50% EtOAc/cyclohexane gradient eluent to afford the title compound (44.5 mg, 58% yield) as a yellow solid. ¹H NMR (400 MHz, DMSO-d₆) δ 12.59 (s, 1H), 10.85 (s, 1H), 8.22 (s, 1H), 7.57-7.39 (m, 2H), 2.68 (s, 3H), 2.22 (ddd, J=13.4, 8.3, 5.1 Hz, 1H), 0.98 (dt, J=8.3, 2.7 Hz, 2H), 0.93 (dt, J=5.1, 2.7 Hz, 2H). MS-ESI (m/z) calc'd for C₁₈H₁₄Cl₂N₅O [M+H]⁺: 386.1/388.1. Found 386.1/388.2.

Example 332: 5-Cyano-N-(3-cyclopropyl-1H-indazol-5-yl)-3,4-dimethyl-6-vinylpicolinamide

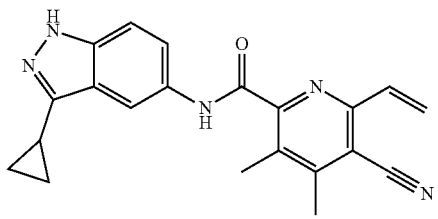 [SMILES: C=Cc1nc(C(=O)Nc2ccc3[nH]nc(C4CC4)c3c2)c(C)c(C)c1C#N]

Step 1: 5-Cyano-3,4-dimethyl-6-vinylpicolinic acid

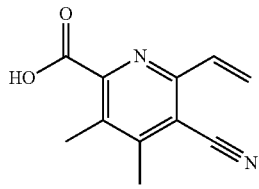

To a solution of methyl 5-cyano-6-ethenyl-3,4-dimethylpyridine-2-carboxylate (130.0 mg, 0.600 mmol) in EtOH (4.682 mL) was added a solution of LiOH.H₂O (25.23 mg, 0.600 mmol) in water (2.809 mL) and the resulting mixture was stirred at r.t. for 1 hr. 1M aqueous HCl was added dropwise until pH=1 and the mixture was extracted with EtOAc. The phases were separated and the combined organic phases were washed with H₂O (1×), dried over Na₂SO₄ and evaporated to dryness to afford the title compound (19 mg, 75%) as a white solid which was used without further purification. MS-ESI (m/z) calc'd for C₁₁H₁₁N₂O₂ [M+H]⁺: 203.1. Found 203.3

Step 2: 5-Cyano-N-(3-cyclopropyl-1H-indazol-5-yl)-3,4-dimethyl-6-vinylpicolinamide

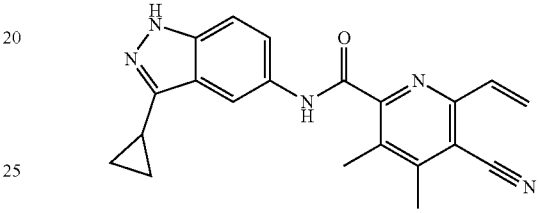

To a solution of 5-cyano-3,4-dimethyl-6-vinylpicolinic acid (70.0 mg, 0.350 mmol), 3-cyclopropyl-1H-indazol-5-amine (70.92 mg, 0.380 mmol) and Et₃N (0.06 mL, 0.450 mmol) in MeCN (9.07 mL) was added HATU (131.63 mg, 0.350 mmol) in portions and the mixture was stirred at 25° C. for 1 hr. The reaction mixture was filtered and the solid was washed with MeCN (2×5 mL) and H₂O (2×5 mL), then dried under reduced pressure to afford the title compound (107 mg, 86%) as a pale yellow solid. ¹H NMR (400 MHz, DMSO-d₆) δ 12.54 (s, 1H), 10.61 (s, 1H), 8.29 (d, J=1.8 Hz, 1H), 7.55 (dd, J=8.9, 1.9 Hz, 1H), 7.44 (d, J=8.9 Hz, 1H), 7.13 (dd, J=16.8, 10.6 Hz, 1H), 6.64 (dd, J=16.8, 1.8 Hz, 1H), 5.81 (dd, J=10.7, 1.9 Hz, 1H), 2.55 (s, 3H), 2.41 (s, 3H), 2.27-2.15 (m, 1H), 1.02-0.96 (m, 2H), 0.96-0.90 (m, 2H). MS-ESI (m/z) calc'd for C₂₁H₂₀N₅O [M+H]⁺: 358.2. Found 358.2.

Example 333: 5-Cyano-N-(3-cyclopropyl-1H-indazol-5-yl)-6-ethyl-3,4-dimethylpicolinamide

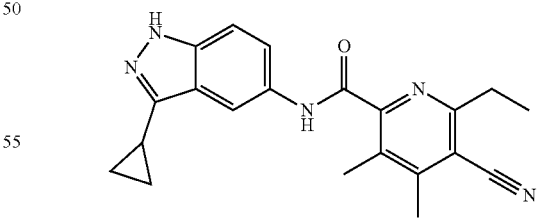

To a suspension of 5-cyano-N-(3-cyclopropyl-1H-indazol-5-yl)-3,4-dimethyl-6-vinylpicolinamide (70.0 mg, 0.200 mmol) in EtOH (2 mL) was added 10% Pd/C (7.0 mg, 0.070 mmol) and the mixture was hydrogenated at r.t. and 1 atm for 4 hrs. The mixture was filtered through Celite and the filtrate was concentrated under reduced pressure to afford the title compound (55.6 mg, 79%) as a pale yellow solid which was used without further purification. ¹H NMR (400

MHz, DMSO-d$_6$) δ 12.54 (s, 1H), 10.52 (s, 1H), 8.28 (d, 1H), 7.54 (dd, J=8.9, 1.9 Hz, 1H), 7.43 (d, J=8.9 Hz, 1H), 3.00 (q, J=7.5 Hz, 2H), 2.54 (s, 3H), 2.39 (s, 3H), 2.27-2.16 (m, 1H), 1.32 (t, J=7.6 Hz, 3H), 1.06-0.86 (m, 4H). MS-ESI (m/z) calc'd for C$_{21}$H$_{22}$N$_5$O [M+H]$^+$: 360.2. Found 360.3.

Example 334: 5-Cyano-6-cyclopropyl-N-(3-cyclopropyl-1H-indazol-5-yl)-3,4-dimethylpicolinamide

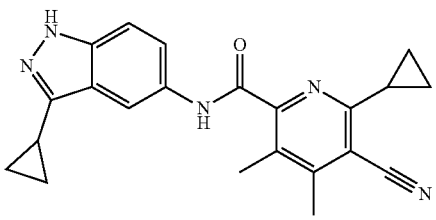 [SMILES: Cc1c(C(=O)Nc2ccc3[nH]nc(C4CC4)c3c2)nc(C2CC2)c(C#N)c1C]

Step 1: Methyl 5-cyano-6-cyclopropyl-3,4-dimethylpicolinate

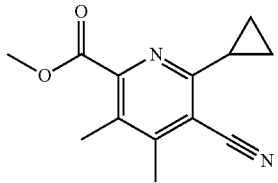 [SMILES: COC(=O)c1nc(C2CC2)c(C#N)c(C)c1C]

A mixture of methyl 6-chloro-5-cyano-3,4-dimethylpyridine-2-carboxylate (150.0 mg, 0.670 mmol), cyclopropylboronic acid (172.08 mg, 2 mmol), K$_2$CO$_3$ (138.43 mg, 1 mmol) and tetrakis(triphenylphosphine)palladium(0) (77.16 mg, 0.070 mmol) in 1,4-dioxane (2.7 mL) was degassed with N$_2$ and then stirred in a closed microwave vial at 110° C. overnight. The mixture was allowed to cool to r.t., diluted with water, and extracted with EtOAc. The organic layer was washed with brine, dried over Na$_2$SO$_4$, filtered, and the concentrated under reduced pressure to give a residue. The residue was purified by silica gel column chromatography using a 0-30% EtOAc/cyclohexane gradient eluent to afford the title compound (142 mg, 92%) as a white solid. $^1$H NMR (400 MHz, DMSO-d$_6$) δ 3.88 (s, 3H), 2.49 (s, 3H), 2.38 (tt, J=8.0, 4.6 Hz, 1H), 2.23 (s, 3H), 1.11 (dt, J=8.0, 3.2 Hz, 2H), 0.99 (dt, J=4.6, 3.1 Hz, 2H). MS-ESI (m/z) calc'd for C$_{13}$H$_{15}$N$_2$O$_2$[M+H]$^+$: 231.1. Found 231.1.

Step 2: 5-Cyano-6-cyclopropyl-3,4-dimethylpicolinic acid

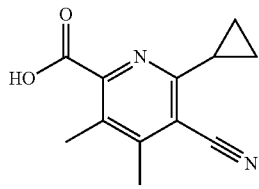 [SMILES: Cc1c(C(=O)O)nc(C2CC2)c(C#N)c1C]

To a solution of methyl 5-cyano-6-cyclopropyl-3,4-dimethylpicolinate (142.0 mg, 0.620 mmol) in EtOH (4.818 mL) was added a solution of LiOH.H$_2$O (25.88 mg, 0.620 mmol) in H$_2$O (2.891 mL) and the resulting mixture was stirred at r.t. for 1 hr. 1M aqueous HCl was added dropwise until pH=1. The reaction mixture was partitioned between H$_2$O and EtOAc, the phases were separated, the aqueous layer was extracted with EtOAc (2×). The combined organic phases were washed with H$_2$O (1×), dried over Na$_2$SO$_4$ and evaporated to dryness to afford the title compound (19 mg, 75%) as a white solid. $^1$H NMR (400 MHz, DMSO-d$_6$) δ 13.69 (s, 1H), 2.47 (s, 3H), 2.41-2.32 (m, 1H), 2.24 (s, 3H), 1.14-1.07 (m, 2H), 1.04-0.97 (m, 2H). MS-ESI (m/z) calc'd for C$_{12}$H$_{13}$N$_2$O$_2$ [M+H]$^+$: 217.1. Found 217.1.

Step 3: 5-Cyano-6-cyclopropyl-N-(3-cyclopropyl-1H-indazol-5-yl)-3,4-dimethylpicolinamide

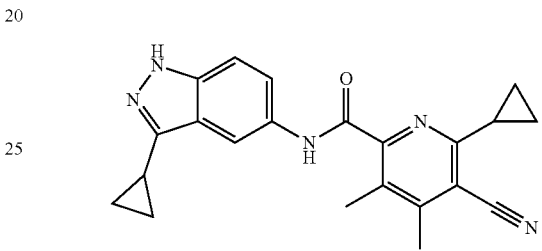

To a solution of 5-cyano-6-cyclopropyl-3,4-dimethylpicolinic acid (40.0 mg, 0.180 mmol) and 3-cyclopropyl-1H-indazol-5-amine (37.9 mg, 0.200 mmol) and Et$_3$N (0.03 mL, 0.240 mmol) in MeCN (4.535 mL) was added HATU (70.33 mg, 0.180 mmol) in portions and the mixture was stirred at 25° C. for 1 hr. The reaction mixture was filtered and the solid was washed with MeCN (2×5 mL) and H$_2$O (2×5 mL), then dried under reduced pressure to afford the title compound (42.2 mg, 61%) as a pale yellow solid. $^1$H NMR (400 MHz, DMSO-d$_6$) δ 12.53 (s, 1H), 10.37 (s, 1H), 8.26 (s, 1H), 7.51 (d, J=8.8 Hz, 1H), 7.43 (d, J=8.9 Hz, 1H), 2.53 (s, 3H), 2.45-2.37 (m, 1H), 2.34 (s, 3H), 2.26-2.16 (m, 1H), 1.22-1.07 (m, 4H), 1.04-0.86 (m, 4H). MS-ESI (m/z) calc'd for C$_{22}$H$_{22}$N$_5$O [M+H]$^+$: 372.2. Found 372.2.

Example 335: 5-Cyano-N-(3-(1-cyclopropyl-1H-pyrazol-4-yl)-1H-indazol-5-yl)-3,4-dimethylpicolinamide

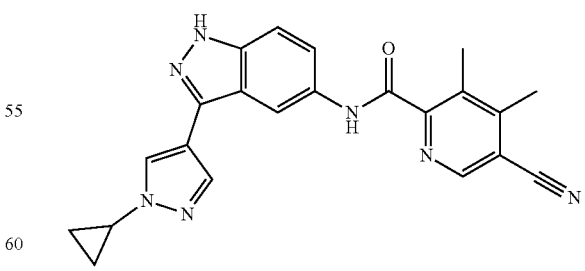

A mixture of 1-cyclopropyl-4-(4,4,5,5-tetramethyl-1,3,2-dioxaborolan-2-yl)-1H-pyrazole (100 mg, 427.16 umol), 5-cyano-N-(3-iodo-1H-indazol-5-yl)-3,4-dimethylpicolinamide (137.09 mg, 328.59 umol), Pd(Amphos)Cl$_2$ (23.27 mg, 32.86 umol, 23.27 uL) and AcOK (96.75 mg, 985.76 umol)

in 10 mL of EtOH and 2.5 mL of H$_2$O was degassed and purged with N$_2$ (3×) at 20° C., and then the mixture was stirred at 100° C. for 12 hrs under an N$_2$ atmosphere. The reaction mixture was concentrated under reduced pressure to give a residue. The residue was purified by preparative HPLC using Method DJ to afford the title compound (22.19 mg, 17%) as a light yellow solid. $^1$H NMR (400 MHz, DMSO-d$_6$) δ 12.96 (br s, 1H), 10.66 (s, 1H), 8.90 (s, 1H), 8.38 (s, 1H), 8.25 (s, 1H), 7.90 (s, 1H), 7.75 (d, J=8.11 Hz, 1H), 7.53 (d, J=8.82 Hz, 1H), 3.84 (tt, J=3.78, 7.36 Hz, 1H), 2.56 (s, 3H), 2.47 (s, 3H), 1.12-1.16 (m, 2H), 0.98-1.04 (m, 2H). MS-(ESI) (m/z) calcd for C$_{22}$H$_{20}$N$_7$O (M+H)$^+$: 398.2. Found 398.2.

Example A. LRRK2 Kinase Activity

LRRK2 kinase activity was measured using a LanthaScreen™ Kinase Activity Assay from ThermoFisher Scientific. Recombinant wild type or G2019S-LRRK2 protein (Life Technologies, PR8604B or PV4881, respectively), was incubated with a fluorescein-labeled peptide substrate called LRRKtide that is based upon ezrin/radixin/moesin (ERM) (Life Technologies, PV4901) in the presence of ATP and serially diluted compound. After an incubation period of 1 hr, the phosphotransferase activity was stopped and a terbium-labelled anti-pERM antibody (Life Technologies, PV4899) was added to detect the phosphorylation of LRRKtide by measuring the time resolved-Forster resonant energy transfer (TR-FRET) signal from the terbium label on the antibody to the fluorescein tag on LRRKtide, expressed as the 520 nm/495 nm emission ratio. Compound-dependent inhibition of the TR-FRET signal was used to generate a concentration-response curve for IC$_{50}$ determination.

The assay was carried out under the following protocol conditions: 1 mM compound in DMSO was serially diluted 1:3, 11 points in DMSO with a Biomek FX and 0.1 µL of the diluted compound was subsequently stamped into the assay plate (384-well format Lumitrac 200, Greiner, 781075) with an Echo Labcyte such that the final compound concentration in the assay was 10 µM to 169 µM. Subsequently, 5 µL of 2× kinase solution (2.9 nM final concentration) was added to the assay plate in assay buffer composed of 50 mM Tris pH 8.5 (Sigma, T6791), 5 mM MgCl$_2$ (Fluka, 63020), 1 mM EGTA (Sigma, E3889), 0.01% BRIJ-35 (Sigma, P1254) and 2 mM DTT. The reaction was started by addition of 2×ATP/LRRKtide solution in assay buffer such that the final concentration was 400 nM LRRKtide and 25 µM ATP. After 60 min incubation at room temperature, the reaction was stopped by addition of 10 µL of 2× stop solution containing a final concentration of 2 nM anti-pERM antibody and 10 mM EDTA. After a 30 min incubation at RT, the TR-FRET signal was measured on a Wallac 2104 EnVision multilabel reader at an excitation wavelength of 340 nm and reading emission at 520 nm and 495 nm. The ratio of the 520 nm and 495 nm emission was used to analyze the data.

The Results of the LRRK2 kinase activity assay are shown in Table A-1 and Table A-2. Data is displayed as follows: + is IC$_{50}$≤100 nM; ++ is 100 nM<IC$_{50}$≤1,000 nM; and +++ is 1,000 nM<IC$_{50}$≤10,000 nM.

TABLE A-I

| | LRRK2 Kinase Activity Assay | |
|---|---|---|
| Example No. | LRRK2 WT IC$_{50}$ (nM) | LRRK2 G2019S IC$_{50}$ (nM) |
| 1 | + | + |
| 2 | + | + |
| 3 | + | + |
| 4 | + | + |
| 5 | + | + |
| 6 | + | + |
| 7 | + | + |
| 8 | ++ | + |
| 9 | ++ | + |
| 10 | + | + |
| 11 | ++ | + |
| 12 | ++ | + |
| 13 | ++ | + |
| 14 | ++ | + |
| 15 | ++ | + |
| 16 | ++ | + |
| 17 | + | + |
| 18 | + | + |
| 19 | + | + |
| 20 | ++ | + |
| 21 | + | + |
| 22 | + | + |
| 23 | ++ | + |
| 24 | ++ | ++ |
| 25 | ++ | ++ |
| 26 | ++ | + |
| 27 | ++ | + |
| 28 | ++ | + |
| 29 | ++ | + |
| 30 | ++ | + |
| 31 | ++ | + |
| 32 | ++ | + |
| 33 | + | + |
| 34 | + | + |
| 35 | >10,000 | ++ |
| 36 | >10,000 | + |
| 37 | ++ | + |
| 38 | ++ | + |
| 39 | +++ | +++ |
| 40 | ++ | + |
| 41 | ++ | + |
| 42 | ++ | + |
| 43 | ++ | + |
| 44 | + | + |
| 45 | + | + |
| 46 | ++ | + |
| 47 | ++ | + |
| 48 | ++ | + |
| 49 | ++ | + |
| 50 | ++ | + |
| 51 | ++ | + |
| 52 | ++ | + |
| 53 | ++ | + |
| 54 | +++ | ++ |
| 55 | ++ | + |
| 56 | ++ | + |
| 57 | + | + |
| 58 | ++ | + |
| 59 | ++ | + |
| 60 | +++ | ++ |
| 61 | ++ | + |
| 62 | ++ | + |
| 63 | ++ | + |
| 64 | ++ | + |
| 65 | + | + |
| 66 | ++ | ++ |
| 67 | + | + |
| 68 | ++ | + |
| 69 | ++ | + |
| 70 | ++ | + |
| 71 | ++ | + |
| 72 | + | + |
| 73 | ++ | + |
| 74 | + | + |
| 75 | + | + |
| 76 | + | + |
| 77 | + | + |
| 78 | ++ | + |
| 79 | ++ | ++ |

TABLE A-1-continued

| Example No. | LRRK2 WT IC$_{50}$ (nM) | LRRK2 G2019S IC$_{50}$ (nM) |
|---|---|---|
| 80 | +++ | ++ |
| 81 | + | + |
| 82 | + | + |
| 83 | ++ | + |
| 84 | ++ | + |
| 85 | +++ | + |
| 86 | + | + |
| 87 | ++ | + |
| 88 | +++ | ++ |
| 89 | + | + |
| 90 | + | + |
| 91 | + | + |
| 92 | ++ | + |
| 93 | ++ | ++ |
| 94 | ++ | + |
| 95 | + | + |
| 96 | ++ | ++ |
| 97 | ++ | + |
| 98 | >10,000 | +++ |
| 99 | +++ | ++ |
| 100 | + | + |

TABLE A-2

| Example No. | LRRK2 WT IC50 (nM) | LRRK2 G2019S IC50 (nM) |
|---|---|---|
| 101 | ++ | + |
| 102 | ++ | + |
| 103 | + | + |
| 104 | ++ | ++ |
| 105 | ++ | + |
| 106 | +++ | + |
| 107 | ++ | ++ |
| 108 | ++ | + |
| 109 | ++ | + |
| 110 | ++ | + |
| 111 | ++ | + |
| 112 | ++ | ++ |
| 113 | ++ | + |
| 114 | +++ | ++ |
| 115 | + | + |
| 116 | +++ | ++ |
| 117 | ++ | + |
| 118 | + | + |
| 119 | ++ | + |
| 120 | + | + |
| 121 | ++ | + |
| 122 | + | + |
| 123 | ++ | + |
| 124 | + | + |
| 125 | ++ | ++ |
| 126 | ++ | + |
| 127 | + | + |
| 128 | + | + |
| 129 | + | + |
| 130 | + | + |
| 131 | ++ | + |
| 132 | + | + |
| 133 | ++ | + |
| 134 | + | + |
| 135 | +++ | ++ |
| 136 | +++ | ++ |
| 137 | + | + |
| 138 | + | + |
| 139 | +++ | + |
| 140 | + | + |
| 141 | + | + |
| 142 | ++ | + |
| 143 | ++ | + |
| 144 | + | + |
| 145 | + | + |

TABLE A-2-continued

| Example No. | LRRK2 WT IC50 (nM) | LRRK2 G2019S IC50 (nM) |
|---|---|---|
| 146 | ++ | + |
| 147 | + | + |
| 148 | + | + |
| 149 | ++ | + |
| 150 | ++ | ++ |
| 151 | ++ | + |
| 152 | +++ | ++ |
| 153 | +++ | ++ |
| 154 | ++ | + |
| 155 | +++ | + |
| 156 | ++ | ++ |
| 157 | + | + |
| 158 | + | + |
| 159 | + | + |
| 160 | + | + |
| 161 | +++ | ++ |
| 162 | ++ | + |
| 163 | + | + |
| 164 | + | + |
| 165 | + | + |
| 166 | + | + |
| 167 | + | + |
| 168 | + | + |
| 169 | + | + |
| 170 | ++ | + |
| 171 | + | + |
| 172 | + | + |
| 173 | + | + |
| 174 | + | + |
| 175 | + | + |
| 176 | + | + |
| 177 | + | + |
| 178 | + | + |
| 179 | + | + |
| 180 | ++ | ++ |
| 181 | + | + |
| 182 | ++ | + |
| 183 | + | + |
| 184 | + | + |
| 185 | + | + |
| 186 | + | + |
| 187 | + | + |
| 188 | + | + |
| 189 | + | + |
| 190 | + | + |
| 191 | + | + |
| 192 | + | + |
| 193 | + | + |
| 194 | ++ | + |
| 195 | + | + |
| 196 | ++ | + |
| 197 | ++ | + |
| 198 | ++ | + |
| 199 | + | + |
| 200 | + | + |
| 201 | + | + |
| 202 | + | + |
| 203 | + | + |
| 204 | ++ | + |
| 205 | + | + |
| 206 | +++ | + |
| 207 | + | + |
| 208 | + | + |
| 209 | + | + |
| 210 | + | + |
| 211 | + | + |
| 212 | + | + |
| 213 | + | + |
| 214 | + | + |
| 215 | + | + |
| 216 | + | + |
| 217 | + | + |
| 218 | +++ | + |
| 219 | + | + |
| 220 | + | + |
| 221 | + | + |
| 222 | + | + |

TABLE A-2-continued

| Example No. | LRRK2 WT IC50 (nM) | LRRK2 G2019S IC50 (nM) |
|---|---|---|
| 223 | +++ | + |
| 224 | + | + |
| 225 | + | + |
| 226 | + | + |
| 227 | + | + |
| 228 | ++ | + |
| 229 | + | + |
| 230 | ++ | + |
| 231 | + | + |
| 232 | + | + |
| 233 | + | + |
| 234 | + | + |
| 235 | + | + |
| 236 | + | + |
| 237 | + | + |
| 238 | ++ | + |
| 239 | + | ++ |
| 240 | ++ | + |
| 241 | ++ | ++ |
| 242 | +++ | + |
| 243 | ++ | + |
| 244 | + | + |
| 245 | ++ | + |
| 246 | + | + |
| 247 | + | + |
| 248 | + | + |
| 249 | ++ | + |
| 250 | + | + |
| 251 | ++ | + |
| 252 | ++ | + |
| 253 | +++ | ++ |
| 254 | +++ | ++ |
| 255 | ++ | + |
| 256 | +++ | +++ |
| 257 | +++ | +++ |
| 258 | +++ | + |
| 259 | >10,000 | >10,000 |
| 260 | >10,000 | +++ |
| 261 | +++ | + |
| 262 | +++ | +++ |
| 263 | +++ | ++ |
| 264 | +++ | ++ |
| 265 | +++ | ++ |
| 266 | ++ | + |
| 267 | ++ | + |
| 268 | +++ | ++ |
| 269 | >10,000 | +++ |
| 270 | + | + |
| 271 | + | + |
| 272 | ++ | + |
| 273 | ++ | + |
| 274 | +++ | + |
| 275 | ++ | + |
| 276 | ++ | + |
| 277 | + | + |
| 278 | + | + |
| 279 | + | + |
| 280 | +++ | +++ |
| 281 | + | + |
| 282 | + | + |
| 283 | ++ | + |
| 284 | +++ | + |
| 285 | +++ | + |
| 286 | +++ | + |
| 287 | ++ | + |
| 288 | + | + |
| 289 | + | + |
| 290 | + | + |
| 291 | + | + |
| 292 | +++ | ++ |
| 293 | + | + |
| 294 | +++ | ++ |
| 295 | ++ | + |
| 296 | ++ | + |
| 297 | ++ | + |
| 298 | + | + |
| 299 | ++ | + |
| 300 | ++ | + |
| 301 | +++ | + |
| 302 | + | + |
| 303 | + | + |
| 304 | + | + |
| 305 | ++ | + |
| 306 | ++ | + |
| 307 | ++ | + |
| 308 | + | + |
| 309 | + | + |
| 310 | ++ | + |
| 311 | ++ | + |
| 312 | ++ | + |
| 313 | +++ | ++ |
| 314 | +++ | ++ |
| 315 | +++ | + |
| 316 | ++ | + |
| 317 | + | + |
| 318 | + | + |
| 319 | ++ | + |
| 320 | + | + |
| 321 | ++ | + |
| 322 | + | + |
| 323 | >10,000 | >10,000 |
| 324 | + | + |
| 325 | +++ | + |
| 326 | ++ | + |
| 327 | + | + |
| 328 | + | + |
| 329 | + | + |
| 330 | + | + |
| 331 | + | + |
| 332 | ++ | + |
| 333 | ++ | + |
| 334 | ++ | + |
| 335 | + | + |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound which is 5-cyano-N-(3-(1-(difluoromethyl)-1H-pyrazol-4-yl)-1H-indazol-5-yl)-3,4-dimethylpicolinamide, or a pharmaceutically acceptable salt thereof.

2. The compound of claim 1, wherein the compound is 5-cyano-N-(3-(1-(difluoromethyl)-1H-pyrazol-4-yl)-1H-indazol-5-yl)-3,4-dimethylpicolinamide.

3. A pharmaceutical composition comprising a compound of claim 1, or a pharmaceutically acceptable salt thereof, and at least one pharmaceutically acceptable carrier.

4. A method for treating a neurodegenerative disease in a patient, said method comprising: administering to the patient a therapeutically effective amount of the compound of claim 1, or a pharmaceutically acceptable salt thereof.

5. The method of claim 4, wherein said neurodegenerative disease is selected from Parkinson's disease, Parkinson disease with dementia, Parkinson's associated risk syndrome, dementia with Lewy bodies, Lewy body variant of Alzheimer's disease, combined Parkinson's disease and Alzheimer's disease, multiple system atrophy, striatonigral degeneration, olivopontocerebellar atrophy, and Shy-Drager syndrome.

6. The method of claim 4, wherein said neurodegenerative disease is Parkinson's disease.

7. A compound which is 5-cyano-3,4-dimethyl-N-(3-(oxazol-5-yl)-1H-indazol-5-yl)picolinamide, or a pharmaceutically acceptable salt thereof.

8. The compound of claim 7, wherein the compound is 5-cyano-3,4-dimethyl-N-(3-(oxazol-5-yl)-1H-indazol-5-yl)picolinamide.

9. A pharmaceutical composition comprising a compound of claim 7, or a pharmaceutically acceptable salt thereof, and at least one pharmaceutically acceptable carrier.

10. A method for treating a neurodegenerative disease in a patient, said method comprising: administering to the patient a therapeutically effective amount of the compound of claim 7, or a pharmaceutically acceptable salt thereof.

11. The method of claim 10, wherein said neurodegenerative disease is selected from Parkinson's disease, Parkinson disease with dementia, Parkinson's associated risk syndrome, dementia with Lewy bodies, Lewy body variant of Alzheimer's disease, combined Parkinson's disease and Alzheimer's disease, multiple system atrophy, striatonigral degeneration, olivopontocerebellar atrophy, and Shy-Drager syndrome.

12. The method of claim 10, wherein said neurodegenerative disease is Parkinson's disease.

13. A compound which is 6-chloro-5-cyano-N-(3-methoxy-1H-indazol-5-yl)-3,4-dimethylpicolinamide, or a pharmaceutically acceptable salt thereof.

14. The compound of claim 13, wherein the compound is 6-chloro-5-cyano-N-(3-methoxy-1H-indazol-5-yl)-3,4-dimethylpicolinamide.

15. A pharmaceutical composition comprising a compound of claim 13, or a pharmaceutically acceptable salt thereof, and at least one pharmaceutically acceptable carrier.

16. A method for treating a neurodegenerative disease in a patient, said method comprising: administering to the patient a therapeutically effective amount of the compound of claim 13, or a pharmaceutically acceptable salt thereof.

17. The method of claim 16, wherein said neurodegenerative disease is selected from Parkinson's disease, Parkinson disease with dementia, Parkinson's associated risk syndrome, dementia with Lewy bodies, Lewy body variant of Alzheimer's disease, combined Parkinson's disease and Alzheimer's disease, multiple system atrophy, striatonigral degeneration, olivopontocerebellar atrophy, and Shy-Drager syndrome.

18. The method of claim 16, wherein said neurodegenerative disease is Parkinson's disease.

* * * * *